United States Patent
Cheng et al.

(10) Patent No.: US 7,211,423 B2
(45) Date of Patent: May 1, 2007

(54) ACETYL COA CARBOXYLASE 2 SEQUENCES AND METHODS

(75) Inventors: Dong Cheng, Furlong, PA (US); John N. Feder, Belle Meade, NJ (US); Luping Chen, Newtown, PA (US); Ching-Hsuen Chu, Bridgewater, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 11/186,999

(22) Filed: Jul. 21, 2005

(65) Prior Publication Data

US 2006/0019364 A1  Jan. 26, 2006

Related U.S. Application Data

(60) Provisional application No. 60/590,948, filed on Jul. 23, 2004.

(51) Int. Cl.
| | |
|---|---|
| *C12N 9/10* | (2006.01) |
| *C12N 15/70* | (2006.01) |
| *C12N 1/20* | (2006.01) |
| *C12N 5/16* | (2006.01) |
| *C12Q 1/68* | (2006.01) |
| *C12P 21/06* | (2006.01) |
| *C07H 21/04* | (2006.01) |

(52) U.S. Cl. ............................ 435/193; 435/6; 435/325; 435/69.1; 435/183; 435/320.1; 435/252.3; 435/23.2

(58) Field of Classification Search ................ 435/193, 435/6, 320.1, 252.3, 325, 69.1; 536/23.2
See application file for complete search history.

(56) References Cited

FOREIGN PATENT DOCUMENTS

WO WO02/079441 * 10/2002

OTHER PUBLICATIONS

Abu-Elbeiga, et al., "The subcellular localization of acetyl-CoA carboxylase 2", PNAS, vol. 97(4), pp. 1444-1449 (2000).
Beaty, et al., "Acetyl Coenzyme A Carboxylase", J. Biol. Chem., vol. 257(2), pp. 924-929 (1982).
Ha, et al., "Cloning of human acetyl-CoA carboxylase-β and its unique features", PNAS, vol. 93, pp. 11466-11470 (1996).
Tanabe, et al., "[1] Acetyl-CoA Carboxylase from Rat Liver", Methods Enzymol., vol. 71, pp. 5-16 (1981).
NCBI Entrez Accession No. NM_053922 (gi:16758803), Rubink, et al., Oct. 17, 2005.

* cited by examiner

*Primary Examiner*—Manjunath N. Rao
*Assistant Examiner*—Iqbal Chowdhury
(74) *Attorney, Agent, or Firm*—Brian C. Carey

(57) ABSTRACT

The present invention relates generally to novel nucleotide and amino acid sequences, and more particularly to novel human acetyl CoA carboxylase 2 (ACC2) and rat ACC2 sequences. The sequences provided herein can be expressed in a recombinant format. Methods of isolating the ACC2 sequence are also provided, which can be employed to isolate any ACC sequence. The ACC2 sequences can be employed in therapeutic applications to diagnose or treat a condition associated with ACC2. The invention also relates to the identification of modulators of ACC activity using the recombinant human ACC2 enzyme as the screening target.

7 Claims, 51 Drawing Sheets

FIG. 1A

| | | | | | | | | | | | | | | | | |
|---|---|---|---|---|---|---|---|---|---|---|---|---|---|---|---|---|
| atg | gtc | ttg | ctt | ctt | tgt | cta | tct | cgt | ctg | att | ttc | tcc | tgt | ctg | acc | 48 |
| Met | Val | Leu | Leu | Leu | Cys | Leu | Ser | Arg | Leu | Ile | Phe | Ser | Cys | Leu | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttt | tcc | tgg | tta | aaa | atc | tgg | ggg | aaa | atg | acg | gac | tcc | aag | ccg | atc | 96 |
| Phe | Ser | Trp | Leu | Lys | Ile | Trp | Gly | Lys | Met | Thr | Asp | Ser | Lys | Pro | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | aag | agt | aaa | tca | gaa | gca | aac | ctc | atc | ccg | agc | cag | gag | ccc | ttt | 144 |
| Thr | Lys | Ser | Lys | Ser | Glu | Ala | Asn | Leu | Ile | Pro | Ser | Gln | Glu | Pro | Phe | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | gcc | tct | gat | aac | tca | ggg | gag | aca | ccg | cag | aga | aat | ggg | gag | ggc | 192 |
| Pro | Ala | Ser | Asp | Asn | Ser | Gly | Glu | Thr | Pro | Gln | Arg | Asn | Gly | Glu | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| cac | act | ctg | ccc | aag | aca | ccc | agc | cag | gcc | gag | cca | gcc | tcc | cac | aaa | 240 |
| His | Thr | Leu | Pro | Lys | Thr | Pro | Ser | Gln | Ala | Glu | Pro | Ala | Ser | His | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | ccc | aaa | gat | gcc | ggt | cgg | cgg | aga | aac | tcc | cta | cca | ccc | tcc | cac | 288 |
| Gly | Pro | Lys | Asp | Ala | Gly | Arg | Arg | Arg | Asn | Ser | Leu | Pro | Pro | Ser | His | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | aag | ccc | cca | aga | aac | ccc | ctt | tct | tcc | agt | gac | gca | gca | ccc | tcc | 336 |
| Gln | Lys | Pro | Pro | Arg | Asn | Pro | Leu | Ser | Ser | Ser | Asp | Ala | Ala | Pro | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| cca | gag | ctt | caa | gcc | aac | ggg | act | ggg | aca | caa | ggt | ctg | gag | gcc | aca | 384 |
| Pro | Glu | Leu | Gln | Ala | Asn | Gly | Thr | Gly | Thr | Gln | Gly | Leu | Glu | Ala | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| gat | acc | aat | ggc | ctg | tcc | tcc | tca | gcc | agg | ccc | cag | ggc | cag | caa | gct | 432 |
| Asp | Thr | Asn | Gly | Leu | Ser | Ser | Ser | Ala | Arg | Pro | Gln | Gly | Gln | Gln | Ala | |
| | | 130 | | | | | 135 | | | | | 140 | | | | |

| | | | | | | | | | | | | | | | | |
|---|---|---|---|---|---|---|---|---|---|---|---|---|---|---|---|---|
| ggc | tcc | ccc | tcc | aaa | gaa | gac | aag | aag | cag | gca | aac | atc | aag | agg | cag | 480 |
| Gly | Ser | Pro | Ser | Lys | Glu | Asp | Lys | Lys | Gln | Ala | Asn | Ile | Lys | Arg | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctg | atg | acc | aac | ttc | atc | ctg | ggc | tct | ttt | gat | gac | tac | tcc | tct | gac | 528 |
| Leu | Met | Thr | Asn | Phe | Ile | Leu | Gly | Ser | Phe | Asp | Asp | Tyr | Ser | Ser | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | gac | tct | gtt | gct | ggc | tca | tct | cgt | gag | tct | acc | cgg | aag | ggc | agc | 576 |
| Glu | Asp | Ser | Val | Ala | Gly | Ser | Ser | Arg | Glu | Ser | Thr | Arg | Lys | Gly | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| cgg | gcc | agc | ttg | ggg | gcc | ctg | tcc | cta | gag | gct | tat | ctg | acc | aca | ggt | 624 |
| Arg | Ala | Ser | Leu | Gly | Ala | Leu | Ser | Leu | Glu | Ala | Tyr | Leu | Thr | Thr | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| gaa | gct | gag | acc | cgc | gtc | ccc | act | atg | agg | ccg | agc | atg | tcg | gga | ctc | 672 |
| Glu | Ala | Glu | Thr | Arg | Val | Pro | Thr | Met | Arg | Pro | Ser | Met | Ser | Gly | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| cac | ctg | gtg | aag | agg | gga | cgg | gaa | cac | aag | aag | ctg | gac | ctg | cac | aga | 720 |
| His | Leu | Val | Lys | Arg | Gly | Arg | Glu | His | Lys | Lys | Leu | Asp | Leu | His | Arg | |
| 225 | | | | | 230 | | | | | 235 | | | | | 240 | |

FIG. 1B

```
gac ttt acc gtg gct tct ccc gct gag ttt gtc aca cgc ttt ggg ggg          768
Asp Phe Thr Val Ala Ser Pro Ala Glu Phe Val Thr Arg Phe Gly Gly
            245                 250                 255 gat cgg gtc atc gag aag gtg ctt att gcc aac aac ggg att gcc gcc          816
Asp Arg Val Ile Glu Lys Val Leu Ile Ala Asn Asn Gly Ile Ala Ala
            260                 265                 270 gtg aag tgc atg cgc tcc atc cgc agg tgg gcc tat gag atg ttc cgc          864
Val Lys Cys Met Arg Ser Ile Arg Arg Trp Ala Tyr Glu Met Phe Arg
            275                 280                 285 aac gag cgg gcc atc cgg ttt gtt gtg atg gtg acc ccc gag gac ctt          912
Asn Glu Arg Ala Ile Arg Phe Val Val Met Val Thr Pro Glu Asp Leu
            290                 295                 300 aag gcc aac gca gag tac atc aag atg gcg gat cat tac gtc ccc gtc          960
Lys Ala Asn Ala Glu Tyr Ile Lys Met Ala Asp His Tyr Val Pro Val
305                 310                 315                 320 cca gga ggg ccc aat aac aac aac tat gcc aac gtg gag ctg att gtg         1008
Pro Gly Gly Pro Asn Asn Asn Asn Tyr Ala Asn Val Glu Leu Ile Val
            325                 330                 335 gac att gcc aag aga atc ccc gtg cag gcg gtg tgg gct ggc tgg ggc         1056
Asp Ile Ala Lys Arg Ile Pro Val Gln Ala Val Trp Ala Gly Trp Gly
            340                 345                 350 cat gct tca gaa aac cct aaa ctt ccg gag ctg ctg tgc aag aat gga         1104
His Ala Ser Glu Asn Pro Lys Leu Pro Glu Leu Leu Cys Lys Asn Gly
            355                 360                 365 gtt gct ttc tta ggc cct ccc agt gag gcc atg tgg gcc tta gga gat         1152
Val Ala Phe Leu Gly Pro Pro Ser Glu Ala Met Trp Ala Leu Gly Asp
            370                 375                 380 aag atc gcc tcc acc gtt gtc gcc cag acg cta cag gtc cca acc ctg         1200
Lys Ile Ala Ser Thr Val Val Ala Gln Thr Leu Gln Val Pro Thr Leu
385                 390                 395                 400 ccc tgg agt gga agc ggc ctg aca gtg gag tgg aca gaa gat gat ctg         1248
Pro Trp Ser Gly Ser Gly Leu Thr Val Glu Trp Thr Glu Asp Asp Leu
            405                 410                 415 cag cag gga aaa aga atc agt gtc cca gaa gat gtt tat gac aag ggt         1296
Gln Gln Gly Lys Arg Ile Ser Val Pro Glu Asp Val Tyr Asp Lys Gly
            420                 425                 430 tgc gtg aaa gac gta gat gag ggc ttg gag gca gca gaa aga att ggt         1344
Cys Val Lys Asp Val Asp Glu Gly Leu Glu Ala Ala Glu Arg Ile Gly
            435                 440                 445 ttt cca ttg atg atc aaa gct tct gaa ggt ggc ggg ggg aag gga atc         1392
Phe Pro Leu Met Ile Lys Ala Ser Glu Gly Gly Gly Gly Lys Gly Ile
450                 455                 460 cgg aag gct gag agt gcg gag gac ttc ccg atc ctt ttc aga caa gta         1440
Arg Lys Ala Glu Ser Ala Glu Asp Phe Pro Ile Leu Phe Arg Gln Val
465                 470                 475                 480
```

FIG. 1C

```
cag agt gag atc cca ggc tcg ccc atc ttt ctc atg aag ctg gcc cag      1488
Gln Ser Glu Ile Pro Gly Ser Pro Ile Phe Leu Met Lys Leu Ala Gln
            485                 490                 495 cac gcc cgt cac ctg gaa gtt cag atc ctc gct gac cag tat ggg aat      1536
His Ala Arg His Leu Glu Val Gln Ile Leu Ala Asp Gln Tyr Gly Asn
            500                 505                 510 gct gtg tct ctg ttt ggt cgc gac tgc tcc atc cag cgg cgg cat cag      1584
Ala Val Ser Leu Phe Gly Arg Asp Cys Ser Ile Gln Arg Arg His Gln
            515                 520                 525 aag atc gtt gag gaa gca ccg gcc acc atc gcc ccg ctg gcc ata ttc      1632
Lys Ile Val Glu Glu Ala Pro Ala Thr Ile Ala Pro Leu Ala Ile Phe
            530                 535                 540 gag ttc atg gag cag tgt gcc atc cgc ctg gcc aag acc gtg ggc tat      1680
Glu Phe Met Glu Gln Cys Ala Ile Arg Leu Ala Lys Thr Val Gly Tyr
545                 550                 555                 560 gtg agt gca ggg aca gtg gaa tac ctc tat agt cag gat ggc agc ttc      1728
Val Ser Ala Gly Thr Val Glu Tyr Leu Tyr Ser Gln Asp Gly Ser Phe
            565                 570                 575 cac ttc ttg gag ctg aat cct cgc ttg cag gtg gaa cat ccc tgc aca      1776
His Phe Leu Glu Leu Asn Pro Arg Leu Gln Val Glu His Pro Cys Thr
            580                 585                 590 gaa atg att gct gac gtt aat ctg ccg gcc gcc cag cta cag atc gcc      1824
Glu Met Ile Ala Asp Val Asn Leu Pro Ala Ala Gln Leu Gln Ile Ala
            595                 600                 605 atg ggc gtg cca ctg cac cgg ctg aag gat atc cgg ctt ctg tat gga      1872
Met Gly Val Pro Leu His Arg Leu Lys Asp Ile Arg Leu Leu Tyr Gly
            610                 615                 620 gag tca cca tgg gga gtg act ccc att tct ttt gaa acc ccc tca aac      1920
Glu Ser Pro Trp Gly Val Thr Pro Ile Ser Phe Glu Thr Pro Ser Asn
625                 630                 635                 640 cct ccc ctc gcc cga ggc cac gtc att gcc gcc aga atc acc agc gaa      1968
Pro Pro Leu Ala Arg Gly His Val Ile Ala Ala Arg Ile Thr Ser Glu
            645                 650                 655 aac cca gac gag ggt ttt aag ccg agc tcc ggg act gtc cag gaa ctg      2016
Asn Pro Asp Glu Gly Phe Lys Pro Ser Ser Gly Thr Val Gln Glu Leu
            660                 665                 670 aat ttc cgg agc agc aag aac gtg tgg ggt tac ttc agc gtg gcc gct      2064
Asn Phe Arg Ser Ser Lys Asn Val Trp Gly Tyr Phe Ser Val Ala Ala
            675                 680                 685 act gga ggc ctg cac gag ttt gcg gat tcc caa ttt ggg cac tgc ttc      2112
Thr Gly Gly Leu His Glu Phe Ala Asp Ser Gln Phe Gly His Cys Phe
            690                 695                 700 tcc tgg gga gag aac cgg gaa gag gcc att tcg aac atg gtg gtg gct      2160
Ser Trp Gly Glu Asn Arg Glu Glu Ala Ile Ser Asn Met Val Val Ala
705                 710                 715                 720
```

FIG. 1D

```
ttg aag gaa ctg tcc atc cga ggt gac ttt agg act acc gtg gaa tac        2208
Leu Lys Glu Leu Ser Ile Arg Gly Asp Phe Arg Thr Thr Val Glu Tyr
            725                 730                 735 ctc att aac ctc ctg gag acc gag agc ttc cag aac aac gac atc gac        2256
Leu Ile Asn Leu Leu Glu Thr Glu Ser Phe Gln Asn Asn Asp Ile Asp
            740                 745                 750 acc ggg tgg ttg gac tac ctc att gct gag aaa gtg cag gcg gag aaa        2304
Thr Gly Trp Leu Asp Tyr Leu Ile Ala Glu Lys Val Gln Ala Glu Lys
            755                 760                 765 ccg gat atc atg ctt ggg gtg gta tgc ggg gcc ttg aac gtg gcc gat        2352
Pro Asp Ile Met Leu Gly Val Val Cys Gly Ala Leu Asn Val Ala Asp
770                 775                 780 gcg atg ttc aga acg tgc atg aca gat ttc tta cac tcc ctg gaa agg        2400
Ala Met Phe Arg Thr Cys Met Thr Asp Phe Leu His Ser Leu Glu Arg
785                 790                 795                 800 ggc cag gtc ctc cca gcg gat tca cta ctg aac ctt gta gat gtg gaa        2448
Gly Gln Val Leu Pro Ala Asp Ser Leu Leu Asn Leu Val Asp Val Glu
            805                 810                 815 tta att tac gga ggt gtt aag tac att ctc aag gtg gcc cgg cag tct        2496
Leu Ile Tyr Gly Gly Val Lys Tyr Ile Leu Lys Val Ala Arg Gln Ser
            820                 825                 830 ctg acc atg ttc gtt ctc atc atg aat ggc tgc cac atc gag att gat        2544
Leu Thr Met Phe Val Leu Ile Met Asn Gly Cys His Ile Glu Ile Asp
            835                 840                 845 gcc cac cgg ctg aat gat ggg ggg ctc ctg ctc tcc tac aat ggg aac        2592
Ala His Arg Leu Asn Asp Gly Gly Leu Leu Leu Ser Tyr Asn Gly Asn
850                 855                 860 agc tac acc acc tac atg aag gaa gag gtt gac agt tac cga att acc        2640
Ser Tyr Thr Thr Tyr Met Lys Glu Glu Val Asp Ser Tyr Arg Ile Thr
865                 870                 875                 880 atc ggc aat aag acg tgt gtg ttt gag aag gag aac gat cct aca gtc        2688
Ile Gly Asn Lys Thr Cys Val Phe Glu Lys Glu Asn Asp Pro Thr Val
            885                 890                 895 ctg aga tcc ccc tcg gct ggg aag ctg aca cag tac aca gtg gag gat        2736
Leu Arg Ser Pro Ser Ala Gly Lys Leu Thr Gln Tyr Thr Val Glu Asp
            900                 905                 910 ggg ggc cac gtt gag gct ggg agc agc tac gct gag atg gag gtg atg        2784
Gly Gly His Val Glu Ala Gly Ser Ser Tyr Ala Glu Met Glu Val Met
            915                 920                 925 aag atg atc atg acc ctg aac gtt cag gaa aga ggc cgg gtg aag tac        2832
Lys Met Ile Met Thr Leu Asn Val Gln Glu Arg Gly Arg Val Lys Tyr
930                 935                 940 atc aag cgt cca ggt gcc gtg ctg gaa gca ggc tgc gtg gtg gcc agg        2880
Ile Lys Arg Pro Gly Ala Val Leu Glu Ala Gly Cys Val Val Ala Arg
945                 950                 955                 960
```

FIG. 1E

```
ctg gag ctc gat gac cct tct aaa gtc cac ccg gct gaa ccg ttc aca    2928
Leu Glu Leu Asp Asp Pro Ser Lys Val His Pro Ala Glu Pro Phe Thr
                965                 970                 975 gga gaa ctc cct gcc cag cag aca ctg ccc atc ctc gga gag aaa ctg    2976
Gly Glu Leu Pro Ala Gln Gln Thr Leu Pro Ile Leu Gly Glu Lys Leu
                980                 985                 990 cac cag gtc ttc cac agc gtc ctg gaa aac ctc acc aac gtc atg agt    3024
His Gln Val Phe His Ser Val Leu Glu Asn Leu Thr Asn Val Met Ser
            995                 1000                1005 ggc ttt tgt ctg cca gag ccc gtt ttt agc ata aag ctg aag gag        3069
Gly Phe Cys Leu Pro Glu Pro Val Phe Ser Ile Lys Leu Lys Glu
    1010                1015                1020 tgg gtg cag aag ctc atg atg acc ctc cgg cac ccg tca ctg ccg        3114
Trp Val Gln Lys Leu Met Met Thr Leu Arg His Pro Ser Leu Pro
    1025                1030                1035 ctg ctg gag ctg cag gag atc atg acc agc gtg gca ggc cgc atc        3159
Leu Leu Glu Leu Gln Glu Ile Met Thr Ser Val Ala Gly Arg Ile
    1040                1045                1050 ccc gcc cct gtg gag aag tct gtc cgc agg gtg atg gcc cag tat        3204
Pro Ala Pro Val Glu Lys Ser Val Arg Arg Val Met Ala Gln Tyr
    1055                1060                1065 gcc agc aac atc acc tcg gtg ctg tgc cag ttc ccc agc cag cag        3249
Ala Ser Asn Ile Thr Ser Val Leu Cys Gln Phe Pro Ser Gln Gln
    1070                1075                1080 ata gcc acc atc ctg gac tgc cat gca gcc acc ctg cag cgg aag        3294
Ile Ala Thr Ile Leu Asp Cys His Ala Ala Thr Leu Gln Arg Lys
    1085                1090                1095 gct gat cga gag gtc ttc ttc atc aac acc cag agc atc gtg cag        3339
Ala Asp Arg Glu Val Phe Phe Ile Asn Thr Gln Ser Ile Val Gln
    1100                1105                1110 ttg gtc cag aga tac cgc agc ggg atc cgc ggc tat atg aaa aca        3384
Leu Val Gln Arg Tyr Arg Ser Gly Ile Arg Gly Tyr Met Lys Thr
    1115                1120                1125 gtg gtg ttg gat ctc ctg aga aga tac ttg cgt gtt gag cac cat        3429
Val Val Leu Asp Leu Leu Arg Arg Tyr Leu Arg Val Glu His His
    1130                1135                1140 ttt cag caa gcc cac tac gac aag tgt gtg ata aac ctc agg gag        3474
Phe Gln Gln Ala His Tyr Asp Lys Cys Val Ile Asn Leu Arg Glu
    1145                1150                1155 cag ttc aag cca gac atg tcc cag gtg ctg gac tgc atc ttc tcc        3519
Gln Phe Lys Pro Asp Met Ser Gln Val Leu Asp Cys Ile Phe Ser
    1160                1165                1170 cac gca cag gtg gcc aag aag aac cag ctg gtg atc atg ttg atc        3564
His Ala Gln Val Ala Lys Lys Asn Gln Leu Val Ile Met Leu Ile
    1175                1180                1185
```

FIG. 1F

```
gat gag ctg tgt ggc cca gac cct tcc ctg tcg gac gag ctg atc          3609
Asp Glu Leu Cys Gly Pro Asp Pro Ser Leu Ser Asp Glu Leu Ile
    1190            1195                1200 tcc atc ctc aac gag ctc act cag ctg agc aaa agc gag cac tgc          3654
Ser Ile Leu Asn Glu Leu Thr Gln Leu Ser Lys Ser Glu His Cys
    1205            1210                1215 aaa gtg gcc ctc aga gcc cgg cag atc ctg att gcc tcc cac ctc          3699
Lys Val Ala Leu Arg Ala Arg Gln Ile Leu Ile Ala Ser His Leu
    1220            1225                1230 ccc tcc tac gag ctg cgg cat aac cag gtg gag tcc att ttc ctg          3744
Pro Ser Tyr Glu Leu Arg His Asn Gln Val Glu Ser Ile Phe Leu
    1235            1240                1245 tct gcc att gac atg tac ggc cac cag ttc tgc ccc gag aac ctc          3789
Ser Ala Ile Asp Met Tyr Gly His Gln Phe Cys Pro Glu Asn Leu
    1250            1255                1260 aag aaa tta ata ctt tcg gaa aca acc atc ttc gac gtc ctg cct          3834
Lys Lys Leu Ile Leu Ser Glu Thr Thr Ile Phe Asp Val Leu Pro
    1265            1270                1275 act ttc ttc tat cac gca aac aaa gtc gtg tgc atg gcg tcc ttg          3879
Thr Phe Phe Tyr His Ala Asn Lys Val Val Cys Met Ala Ser Leu
    1280            1285                1290 gag gtt tac gtg cgg agg ggc tac atc gcc tat gag tta aac agc          3924
Glu Val Tyr Val Arg Arg Gly Tyr Ile Ala Tyr Glu Leu Asn Ser
    1295            1300                1305 ctg cag cac cgg cag ctc ccg gac ggc acc tgc gtg gta gaa ttc          3969
Leu Gln His Arg Gln Leu Pro Asp Gly Thr Cys Val Val Glu Phe
    1310            1315                1320 cag ttc atg ctg ccg tcc tcc cac cca aac cgg atg acc gtg ccc          4014
Gln Phe Met Leu Pro Ser Ser His Pro Asn Arg Met Thr Val Pro
    1325            1330                1335 atc agc atc acc aac cct gac ctg ctg agg cac agc aca gag ctc          4059
Ile Ser Ile Thr Asn Pro Asp Leu Leu Arg His Ser Thr Glu Leu
    1340            1345                1350 ttc atg gac agc ggc ttc tcc cca ctg tgc cag cgc atg gga gcc          4104
Phe Met Asp Ser Gly Phe Ser Pro Leu Cys Gln Arg Met Gly Ala
    1355            1360                1365 atg gta gcc ttc agg aga ttc gag gac ttc acc aga aat ttt gat          4149
Met Val Ala Phe Arg Arg Phe Glu Asp Phe Thr Arg Asn Phe Asp
    1370            1375                1380 gaa gtc atc tct tgc ttc gcc aac gtg ccc aaa gac acc ccc ctc          4194
Glu Val Ile Ser Cys Phe Ala Asn Val Pro Lys Asp Thr Pro Leu
    1385            1390                1395 ttc agc gag gcc cgc acc tcc cta tac tcc gag gat gac tgc aag          4239
Phe Ser Glu Ala Arg Thr Ser Leu Tyr Ser Glu Asp Asp Cys Lys
    1400            1405                1410
```

FIG. 1G

```
agc ctc aga gaa gag ccc atc cac att ctg aat gtg tcc atc cag      4284
Ser Leu Arg Glu Glu Pro Ile His Ile Leu Asn Val Ser Ile Gln
    1415                1420                1425 tgt gca gac cac ctg gag gat gag gca ctg gtg ccg att tta cgg      4329
Cys Ala Asp His Leu Glu Asp Glu Ala Leu Val Pro Ile Leu Arg
    1430                1435                1440 aca ttc gta cag tcc aag aaa aat atc ctt gtg gat tat gga ctc      4374
Thr Phe Val Gln Ser Lys Lys Asn Ile Leu Val Asp Tyr Gly Leu
    1445                1450                1455 cga cga atc aca ttc ttg att gcc caa gag aaa gaa ttt ccc aag      4419
Arg Arg Ile Thr Phe Leu Ile Ala Gln Glu Lys Glu Phe Pro Lys
    1460                1465                1470 ttt ttc aca ttc aga gca aga gat gag ttt gca gaa gat cgc att      4464
Phe Phe Thr Phe Arg Ala Arg Asp Glu Phe Ala Glu Asp Arg Ile
    1475                1480                1485 tac cgt cac ttg gaa cct gcc ctg gcc ttc cag ctg gaa ctc aac      4509
Tyr Arg His Leu Glu Pro Ala Leu Ala Phe Gln Leu Glu Leu Asn
    1490                1495                1500 cgg atg cgt aac ttc gat ctg acc gcc gtg ccc tgt gcc aac cac      4554
Arg Met Arg Asn Phe Asp Leu Thr Ala Val Pro Cys Ala Asn His
    1505                1510                1515 aag atg cac ctt tac ctg ggt gct gcc aag gtg aag gaa ggt gtg      4599
Lys Met His Leu Tyr Leu Gly Ala Ala Lys Val Lys Glu Gly Val
    1520                1525                1530 gaa gtg acg gac cat agg ttc ttc atc cgc gcc atc atc agg cac      4644
Glu Val Thr Asp His Arg Phe Phe Ile Arg Ala Ile Ile Arg His
    1535                1540                1545 tct gac ctg atc aca aag gaa gcc tcc ttc gaa tac ctg cag aac      4689
Ser Asp Leu Ile Thr Lys Glu Ala Ser Phe Glu Tyr Leu Gln Asn
    1550                1555                1560 gag ggt gag cgg ctg ctc ctg gag gcc atg gac gag ctg gag gtg      4734
Glu Gly Glu Arg Leu Leu Leu Glu Ala Met Asp Glu Leu Glu Val
    1565                1570                1575 gcg ttc aat aac acc agc gtg cgc acc gac tgc aac cac atc ttc      4779
Ala Phe Asn Asn Thr Ser Val Arg Thr Asp Cys Asn His Ile Phe
    1580                1585                1590 ctc aac ttc gtg ccc act gtc atc atg gac ccc ttc aag atc gag      4824
Leu Asn Phe Val Pro Thr Val Ile Met Asp Pro Phe Lys Ile Glu
    1595                1600                1605 gag tcc gtg cgc tac atg gtt atg cgc tac ggc agc cgg ctg tgg      4869
Glu Ser Val Arg Tyr Met Val Met Arg Tyr Gly Ser Arg Leu Trp
    1610                1615                1620 aaa ctc cgt gtg cta cag gct gag gtc aag atc aac atc cgc cag      4914
Lys Leu Arg Val Leu Gln Ala Glu Val Lys Ile Asn Ile Arg Gln
    1625                1630                1635
```

FIG. 1H

```
acc acc acc ggc agt gcc gtt ccc atc cgc ctg ttc atc acc aat        4959
Thr Thr Thr Gly Ser Ala Val Pro Ile Arg Leu Phe Ile Thr Asn
    1640            1645                1650 gag tcg ggc tac tac ctg gac atc agc ctc tac aaa gaa gtg act        5004
Glu Ser Gly Tyr Tyr Leu Asp Ile Ser Leu Tyr Lys Glu Val Thr
    1655            1660                1665 gac tcc aga tct gga aat atc atg ttt cac tcc ttc ggc aac aag        5049
Asp Ser Arg Ser Gly Asn Ile Met Phe His Ser Phe Gly Asn Lys
    1670            1675                1680 caa ggg ccc cag cac ggg atg ctg atc aat act ccc tac gtc acc        5094
Gln Gly Pro Gln His Gly Met Leu Ile Asn Thr Pro Tyr Val Thr
    1685            1690                1695 aag gat ctg ctc cag gcc aag cga ttc cag gcc cag acc ctg gga        5139
Lys Asp Leu Leu Gln Ala Lys Arg Phe Gln Ala Gln Thr Leu Gly
    1700            1705                1710 acc acc tac atc tat gac ttc ccg gaa atg ttc agg cag gct ctc        5184
Thr Thr Tyr Ile Tyr Asp Phe Pro Glu Met Phe Arg Gln Ala Leu
    1715            1720                1725 ttt aaa ctg tgg ggc tcc cca gac aag tat ccc aaa gac atc ctg        5229
Phe Lys Leu Trp Gly Ser Pro Asp Lys Tyr Pro Lys Asp Ile Leu
    1730            1735                1740 aca tac act gaa tta gtg ttg gac tct cag ggc cag ctg gtg gag        5274
Thr Tyr Thr Glu Leu Val Leu Asp Ser Gln Gly Gln Leu Val Glu
    1745            1750                1755 atg aac cga ctt cct ggt gga aat gag gtg ggc atg gtg gcc ttc        5319
Met Asn Arg Leu Pro Gly Gly Asn Glu Val Gly Met Val Ala Phe
    1760            1765                1770 aaa atg agg ttt aag acc cag gag tac ccg gaa gga cgg gat gtg        5364
Lys Met Arg Phe Lys Thr Gln Glu Tyr Pro Glu Gly Arg Asp Val
    1775            1780                1785 atc gtc atc ggc aat gac atc acc ttt cgc att gga tcc ttt ggc        5409
Ile Val Ile Gly Asn Asp Ile Thr Phe Arg Ile Gly Ser Phe Gly
    1790            1795                1800 cct gga gag gac ctt ctg tac ctg cgg gca tcc gag atg gcc cgg        5454
Pro Gly Glu Asp Leu Leu Tyr Leu Arg Ala Ser Glu Met Ala Arg
    1805            1810                1815 gca gag ggc att ccc aaa att tac gtg gca gcc aac agt ggc gcc        5499
Ala Glu Gly Ile Pro Lys Ile Tyr Val Ala Ala Asn Ser Gly Ala
    1820            1825                1830 cgt att ggc atg gca gag gag atc aaa cac atg ttc cac gtg gct        5544
Arg Ile Gly Met Ala Glu Glu Ile Lys His Met Phe His Val Ala
    1835            1840                1845 tgg gtg gac cca gaa gac ccc cac aaa gga ttt aaa tac ctg tac        5589
Trp Val Asp Pro Glu Asp Pro His Lys Gly Phe Lys Tyr Leu Tyr
    1850            1855                1860
```

FIG. 1I

```
ctg act ccc caa gac tac acc aga atc agc tcc ctg aac tcc gtc         5634
Leu Thr Pro Gln Asp Tyr Thr Arg Ile Ser Ser Leu Asn Ser Val
    1865            1870                1875 cac tgt aaa cac atc gag gaa gga gga gag tcc aga tac atg atc         5679
His Cys Lys His Ile Glu Glu Gly Gly Glu Ser Arg Tyr Met Ile
    1880            1885                1890 acg gat atc atc ggg aag gat gat ggc ttg ggc gtg gag aat ctg         5724
Thr Asp Ile Ile Gly Lys Asp Asp Gly Leu Gly Val Glu Asn Leu
    1895            1900                1905 agg ggc tca ggc atg att gct ggg gag tcc tct ctg gct tac gaa         5769
Arg Gly Ser Gly Met Ile Ala Gly Glu Ser Ser Leu Ala Tyr Glu
    1910            1915                1920 gag atc gtc acc att agc ttg gtg acc tgc cga gcc att ggg att         5814
Glu Ile Val Thr Ile Ser Leu Val Thr Cys Arg Ala Ile Gly Ile
    1925            1930                1935 ggg gcc tac ttg gtg agg ctg ggc cag cga gtg atc cag gtg gag         5859
Gly Ala Tyr Leu Val Arg Leu Gly Gln Arg Val Ile Gln Val Glu
    1940            1945                1950 aat tcc cac atc atc ctc aca gga gca agt gct ctc aac aag gtc         5904
Asn Ser His Ile Ile Leu Thr Gly Ala Ser Ala Leu Asn Lys Val
    1955            1960                1965 ctg gga aga gag gtc tac aca tcc aac aac cag ctg ggt ggc gtt         5949
Leu Gly Arg Glu Val Tyr Thr Ser Asn Asn Gln Leu Gly Gly Val
    1970            1975                1980 cag atc atg cat tac aat ggt gtc tcc cac atc acc gtg cca gat         5994
Gln Ile Met His Tyr Asn Gly Val Ser His Ile Thr Val Pro Asp
    1985            1990                1995 gac ttt gag ggg gtt tat acc atc ctg gag tgg ctg tcc tat atg         6039
Asp Phe Glu Gly Val Tyr Thr Ile Leu Glu Trp Leu Ser Tyr Met
    2000            2005                2010 cca aag gat aat cac agc cct gtc cct atc atc aca ccc act gac         6084
Pro Lys Asp Asn His Ser Pro Val Pro Ile Ile Thr Pro Thr Asp
    2015            2020                2025 ccc att gac aga gaa att gaa ttc ctc cca tcc aga gct ccc tac         6129
Pro Ile Asp Arg Glu Ile Glu Phe Leu Pro Ser Arg Ala Pro Tyr
    2030            2035                2040 gac ccc cgg tgg atg ctt gca gga agg cct cac cca act ctg aag         6174
Asp Pro Arg Trp Met Leu Ala Gly Arg Pro His Pro Thr Leu Lys
    2045            2050                2055 gga acg tgg cag agc gga ttc ttt gac cac ggc agt ttc aag gaa         6219
Gly Thr Trp Gln Ser Gly Phe Phe Asp His Gly Ser Phe Lys Glu
    2060            2065                2070 atc atg gca ccc tgg gcg cag acc gtg gtg aca gga cga gca agg         6264
Ile Met Ala Pro Trp Ala Gln Thr Val Val Thr Gly Arg Ala Arg
    2075            2080                2085
```

FIG. 1J

| | | | | | | | | | | | | | | | |
|---|---|---|---|---|---|---|---|---|---|---|---|---|---|---|---|
| ctt | ggg | ggg | att | ccc | gtg | gga | gtg | att | gct | gtg | gag | aca | cgg | act | 6309 |
| Leu | Gly | Gly | Ile | Pro | Val | Gly | Val | Ile | Ala | Val | Glu | Thr | Arg | Thr | |
| | 2090 | | | | 2095 | | | | | 2100 | | | | | |
| gtg | gag | gtg | gca | gtc | cct | gca | gac | cct | gcc | aac | ctg | gat | tct | gag | 6354 |
| Val | Glu | Val | Ala | Val | Pro | Ala | Asp | Pro | Ala | Asn | Leu | Asp | Ser | Glu | |
| | 2105 | | | | 2110 | | | | | 2115 | | | | | |
| gcc | aag | ata | att | cag | cag | gca | gga | cag | gtg | tgg | ttc | cca | gac | tca | 6399 |
| Ala | Lys | Ile | Ile | Gln | Gln | Ala | Gly | Gln | Val | Trp | Phe | Pro | Asp | Ser | |
| | 2120 | | | | 2125 | | | | | 2130 | | | | | |
| gcc | tac | aaa | acc | gcc | cag | gcc | atc | aag | gac | ttc | aac | cgg | gag | aag | 6444 |
| Ala | Tyr | Lys | Thr | Ala | Gln | Ala | Ile | Lys | Asp | Phe | Asn | Arg | Glu | Lys | |
| | 2135 | | | | 2140 | | | | | 2145 | | | | | |
| ttg | ccc | ctg | atg | atc | ttt | gcc | aac | tgg | agg | ggg | ttc | tcc | ggt | ggc | 6489 |
| Leu | Pro | Leu | Met | Ile | Phe | Ala | Asn | Trp | Arg | Gly | Phe | Ser | Gly | Gly | |
| | 2150 | | | | 2155 | | | | | 2160 | | | | | |
| atg | aaa | gac | atg | tat | gac | cag | gtg | ctg | aag | ttt | gga | gcc | tac | atc | 6534 |
| Met | Lys | Asp | Met | Tyr | Asp | Gln | Val | Leu | Lys | Phe | Gly | Ala | Tyr | Ile | |
| | 2165 | | | | 2170 | | | | | 2175 | | | | | |
| gtg | gac | ggc | ctt | aga | caa | tac | aaa | cag | ccc | atc | ctg | atc | tat | atc | 6579 |
| Val | Asp | Gly | Leu | Arg | Gln | Tyr | Lys | Gln | Pro | Ile | Leu | Ile | Tyr | Ile | |
| | 2180 | | | | 2185 | | | | | 2190 | | | | | |
| ccg | ccc | tat | gcg | gag | ctc | cgg | gga | ggc | tcc | tgg | gtg | gtc | ata | gat | 6624 |
| Pro | Pro | Tyr | Ala | Glu | Leu | Arg | Gly | Gly | Ser | Trp | Val | Val | Ile | Asp | |
| | 2195 | | | | 2200 | | | | | 2205 | | | | | |
| gcc | acc | atc | aac | ccg | ctg | tgc | ata | gaa | atg | tat | gca | gac | aaa | gag | 6669 |
| Ala | Thr | Ile | Asn | Pro | Leu | Cys | Ile | Glu | Met | Tyr | Ala | Asp | Lys | Glu | |
| | 2210 | | | | 2215 | | | | | 2220 | | | | | |
| agc | agg | ggt | ggt | gtt | ctg | gaa | cca | gag | ggg | aca | gtg | gag | att | aag | 6714 |
| Ser | Arg | Gly | Gly | Val | Leu | Glu | Pro | Glu | Gly | Thr | Val | Glu | Ile | Lys | |
| | 2225 | | | | 2230 | | | | | 2235 | | | | | |
| ttc | cga | aag | aaa | gat | ctg | ata | aag | tcc | atg | aga | agg | atc | gat | cca | 6759 |
| Phe | Arg | Lys | Lys | Asp | Leu | Ile | Lys | Ser | Met | Arg | Arg | Ile | Asp | Pro | |
| | 2240 | | | | 2245 | | | | | 2250 | | | | | |
| gct | tac | aag | aag | ctc | atg | gaa | cag | cta | ggg | gaa | cct | gat | ctc | tcc | 6804 |
| Ala | Tyr | Lys | Lys | Leu | Met | Glu | Gln | Leu | Gly | Glu | Pro | Asp | Leu | Ser | |
| | 2255 | | | | 2260 | | | | | 2265 | | | | | |
| gac | aag | gac | cga | aag | gac | ctg | gag | ggc | cgg | cta | aag | gct | cgc | gag | 6849 |
| Asp | Lys | Asp | Arg | Lys | Asp | Leu | Glu | Gly | Arg | Leu | Lys | Ala | Arg | Glu | |
| | 2270 | | | | 2275 | | | | | 2280 | | | | | |
| gac | ctg | ctg | ctc | ccc | atc | tac | cac | cag | gtg | gcg | gtg | cag | ttc | gcc | 6894 |
| Asp | Leu | Leu | Leu | Pro | Ile | Tyr | His | Gln | Val | Ala | Val | Gln | Phe | Ala | |
| | 2285 | | | | 2290 | | | | | 2295 | | | | | |
| gac | ttc | cat | gac | aca | ccc | ggc | cgg | atg | ctg | gag | aag | ggc | gtc | ata | 6939 |
| Asp | Phe | His | Asp | Thr | Pro | Gly | Arg | Met | Leu | Glu | Lys | Gly | Val | Ile | |
| | 2300 | | | | 2305 | | | | | 2310 | | | | | |

FIG. 1K

```
tct gac atc ctg gag tgg aag acc gca cgc acc ttc ctg tat tgg      6984
Ser Asp Ile Leu Glu Trp Lys Thr Ala Arg Thr Phe Leu Tyr Trp
    2315                2320                2325 cgt ctg cgc cgc ctc ctc ctg gag gac cag gtc aag cag gag atc      7029
Arg Leu Arg Arg Leu Leu Leu Glu Asp Gln Val Lys Gln Glu Ile
    2330                2335                2340 ctg cag gcc agc ggg gag ctg agt cac gtg cat atc cag tcc atg      7074
Leu Gln Ala Ser Gly Glu Leu Ser His Val His Ile Gln Ser Met
    2345                2350                2355 ctg cgt cgc tgg ttc gtg gag acg gag ggg gct gtc aag gcc tac      7119
Leu Arg Arg Trp Phe Val Glu Thr Glu Gly Ala Val Lys Ala Tyr
    2360                2365                2370 ttg tgg gac aac aac cag gtg gtt gtg cag tgg ctg gaa cag cac      7164
Leu Trp Asp Asn Asn Gln Val Val Val Gln Trp Leu Glu Gln His
    2375                2380                2385 tgg cag gca ggg gat ggc ccg cgc tcc acc atc cgt gag aac atc      7209
Trp Gln Ala Gly Asp Gly Pro Arg Ser Thr Ile Arg Glu Asn Ile
    2390                2395                2400 acg tac ctg aag cac gac tct gtc ctc aag acc atc cga ggc ctg      7254
Thr Tyr Leu Lys His Asp Ser Val Leu Lys Thr Ile Arg Gly Leu
    2405                2410                2415 gtt gaa gaa aac ccc gag gtg gcc gtg gac tgt gtg ata tac ctg      7299
Val Glu Glu Asn Pro Glu Val Ala Val Asp Cys Val Ile Tyr Leu
    2420                2425                2430 agc cag cac atc agc cca gct gag cgg gcg cag gtc gtt cac ctg      7344
Ser Gln His Ile Ser Pro Ala Glu Arg Ala Gln Val Val His Leu
    2435                2440                2445 ctg tct acc atg gac agc ccg gcc tcc acc tga                      7377
Leu Ser Thr Met Asp Ser Pro Ala Ser Thr
    2450                2455
```

FIG. 2A

```
tcccttgaca ggttgtctga atg gtc ttg ctt ctc ttt ctg act tgc ctg gtt    53
                     Met Val Leu Leu Leu Phe Leu Thr Cys Leu Val
                      1               5                      10 ttc tcc tgc ctg acc att tcc tgg tta aaa atc tgg ggg aag atg aca     101
Phe Ser Cys Leu Thr Ile Ser Trp Leu Lys Ile Trp Gly Lys Met Thr
            15                  20                  25 gac tcg aag ccg ctc agc aac agt aag gtg gat gca agc ctc ctt tcg     149
Asp Ser Lys Pro Leu Ser Asn Ser Lys Val Asp Ala Ser Leu Leu Ser
            30                  35                  40 agc aag gag gag tcc ttt tca gcc tcg gac cag tca gag gag cat ggc     197
Ser Lys Glu Glu Ser Phe Ser Ala Ser Asp Gln Ser Glu Glu His Gly
        45                  50                  55 gac tgc agc tgt ccg ttg aca act cct gac cag gag gag ctg gcc tcc     245
Asp Cys Ser Cys Pro Leu Thr Thr Pro Asp Gln Glu Glu Leu Ala Ser
60                  65                  70                  75 cac gga ggt cct gta gat gcc agt cag cag agg aac tct gtg cca agc     293
His Gly Gly Pro Val Asp Ala Ser Gln Gln Arg Asn Ser Val Pro Ser
                80                  85                  90 tca cac cag aag cct ccg agg aac cca cta tct tcc aat gac acc tgt     341
Ser His Gln Lys Pro Pro Arg Asn Pro Leu Ser Ser Asn Asp Thr Cys
            95                 100                 105 tcc tcc cca gaa ctc caa acc aac ggg gta gca gcc cct ggc tca gag     389
Ser Ser Pro Glu Leu Gln Thr Asn Gly Val Ala Ala Pro Gly Ser Glu
            110                 115                 120 gtt cca gaa gcc aac ggg ttg cct ttc cca gcc agg cct cag acc cag     437
Val Pro Glu Ala Asn Gly Leu Pro Phe Pro Ala Arg Pro Gln Thr Gln
        125                 130                 135 aga acg gga tcc ccc act agg gag gac aag aag cag gca cac atc aag     485
Arg Thr Gly Ser Pro Thr Arg Glu Asp Lys Lys Gln Ala His Ile Lys
140                 145                 150                 155 agg cag ctg atg acc agc ttt atc ctg ggc tcc ctc gat gac aac tcc     533
Arg Gln Leu Met Thr Ser Phe Ile Leu Gly Ser Leu Asp Asp Asn Ser
                160                 165                 170 tct gac gag gac cct agt gct agc tcc ttc cag acc tcc tct cgg aag     581
Ser Asp Glu Asp Pro Ser Ala Ser Ser Phe Gln Thr Ser Ser Arg Lys
            175                 180                 185 ggc agc agg gct agc ctg ggc acc ctg tcc cag gag gct gca ttg aac     629
Gly Ser Arg Ala Ser Leu Gly Thr Leu Ser Gln Glu Ala Ala Leu Asn
            190                 195                 200 aca gct gat cct gag tct cac aca cct act atg agg ccc agc atg tct     677
Thr Ala Asp Pro Glu Ser His Thr Pro Thr Met Arg Pro Ser Met Ser
        205                 210                 215 gga ctc cat ctg gtg aag aga ggc cgt gaa cac aag aaa ctg gac ctg     725
Gly Leu His Leu Val Lys Arg Gly Arg Glu His Lys Lys Leu Asp Leu
220                 225                 230                 235
```

FIG. 2B

| | | | | | | | | | | | | | | | | |
|---|---|---|---|---|---|---|---|---|---|---|---|---|---|---|---|---|
| cac | aga | gat | ttc | act | gta | gct | tcc | cca | gcc | gaa | ttt | gtc | acc | cgc | ttt | 773 |
| His | Arg | Asp | Phe | Thr | Val | Ala | Ser | Pro | Ala | Glu | Phe | Val | Thr | Arg | Phe | |
| | | | | 240 | | | | 245 | | | | | 250 | | | |

| | | | | | | | | | | | | | | | | |
|---|---|---|---|---|---|---|---|---|---|---|---|---|---|---|---|---|
| gga | ggc | aac | agg | gtt | atc | gag | acg | gtg | ctc | atc | gcc | aat | aat | ggt | atc | 821 |
| Gly | Gly | Asn | Arg | Val | Ile | Glu | Thr | Val | Leu | Ile | Ala | Asn | Asn | Gly | Ile | |
| | | | 255 | | | | | 260 | | | | | 265 | | | |

| | | | | | | | | | | | | | | | | |
|---|---|---|---|---|---|---|---|---|---|---|---|---|---|---|---|---|
| gct | gcg | gtc | aag | tgt | atg | cgc | tcc | atc | cgc | cgc | tgg | gcc | tat | gag | atg | 869 |
| Ala | Ala | Val | Lys | Cys | Met | Arg | Ser | Ile | Arg | Arg | Trp | Ala | Tyr | Glu | Met | |
| | | 270 | | | | | 275 | | | | | 280 | | | | |

| | | | | | | | | | | | | | | | | |
|---|---|---|---|---|---|---|---|---|---|---|---|---|---|---|---|---|
| ttc | cgt | aat | gaa | cgc | gcc | atc | cgg | ttt | gtg | gtt | atg | gtg | aca | ccc | gag | 917 |
| Phe | Arg | Asn | Glu | Arg | Ala | Ile | Arg | Phe | Val | Val | Met | Val | Thr | Pro | Glu | |
| | 285 | | | | | 290 | | | | | 295 | | | | | |

| | | | | | | | | | | | | | | | | |
|---|---|---|---|---|---|---|---|---|---|---|---|---|---|---|---|---|
| gat | ctt | aag | gcc | aac | gca | gag | tac | atc | aag | atg | gcg | gac | cag | tac | gtt | 965 |
| Asp | Leu | Lys | Ala | Asn | Ala | Glu | Tyr | Ile | Lys | Met | Ala | Asp | Gln | Tyr | Val | |
| 300 | | | | | 305 | | | | | 310 | | | | | 315 | |

| | | | | | | | | | | | | | | | | |
|---|---|---|---|---|---|---|---|---|---|---|---|---|---|---|---|---|
| ccg | gtc | cca | gga | gga | ccc | aat | aat | aac | aac | tac | gcc | aac | gtt | gag | ctg | 1013 |
| Pro | Val | Pro | Gly | Gly | Pro | Asn | Asn | Asn | Asn | Tyr | Ala | Asn | Val | Glu | Leu | |
| | | | 320 | | | | | 325 | | | | | 330 | | | |

| | | | | | | | | | | | | | | | | |
|---|---|---|---|---|---|---|---|---|---|---|---|---|---|---|---|---|
| atc | ata | gac | att | gcc | aag | aga | atc | cct | gtg | cag | gcc | gtg | tgg | gct | ggc | 1061 |
| Ile | Ile | Asp | Ile | Ala | Lys | Arg | Ile | Pro | Val | Gln | Ala | Val | Trp | Ala | Gly | |
| | | | 335 | | | | | 340 | | | | | 345 | | | |

| | | | | | | | | | | | | | | | | |
|---|---|---|---|---|---|---|---|---|---|---|---|---|---|---|---|---|
| tgg | ggc | cac | gct | tcg | gaa | aac | ccc | aaa | ctt | cca | gag | cta | ctg | tgc | aag | 1109 |
| Trp | Gly | His | Ala | Ser | Glu | Asn | Pro | Lys | Leu | Pro | Glu | Leu | Leu | Cys | Lys | |
| | | 350 | | | | | 355 | | | | | 360 | | | | |

| | | | | | | | | | | | | | | | | |
|---|---|---|---|---|---|---|---|---|---|---|---|---|---|---|---|---|
| cac | gag | att | gct | ttc | cta | ggt | ccc | ccg | agt | gag | gcc | atg | tgg | gcc | ctg | 1157 |
| His | Glu | Ile | Ala | Phe | Leu | Gly | Pro | Pro | Ser | Glu | Ala | Met | Trp | Ala | Leu | |
| | 365 | | | | | 370 | | | | | 375 | | | | | |

| | | | | | | | | | | | | | | | | |
|---|---|---|---|---|---|---|---|---|---|---|---|---|---|---|---|---|
| gga | gac | aag | atc | tcc | tcc | acc | att | gta | gcc | cag | aca | ttg | cag | atc | cca | 1205 |
| Gly | Asp | Lys | Ile | Ser | Ser | Thr | Ile | Val | Ala | Gln | Thr | Leu | Gln | Ile | Pro | |
| 380 | | | | | 385 | | | | | 390 | | | | | 395 | |

| | | | | | | | | | | | | | | | | |
|---|---|---|---|---|---|---|---|---|---|---|---|---|---|---|---|---|
| act | cta | ccc | tgg | agc | gga | agc | ggt | ctc | aca | gtg | gag | tgg | acg | gag | gac | 1253 |
| Thr | Leu | Pro | Trp | Ser | Gly | Ser | Gly | Leu | Thr | Val | Glu | Trp | Thr | Glu | Asp | |
| | | | | 400 | | | | | 405 | | | | | 410 | | |

| | | | | | | | | | | | | | | | | |
|---|---|---|---|---|---|---|---|---|---|---|---|---|---|---|---|---|
| agc | cag | cat | cag | ggc | aaa | tgc | atc | agc | gtc | ccg | gaa | gac | gtt | tat | gaa | 1301 |
| Ser | Gln | His | Gln | Gly | Lys | Cys | Ile | Ser | Val | Pro | Glu | Asp | Val | Tyr | Glu | |
| | | | 415 | | | | | 420 | | | | | 425 | | | |

| | | | | | | | | | | | | | | | | |
|---|---|---|---|---|---|---|---|---|---|---|---|---|---|---|---|---|
| caa | ggc | tgt | gtg | aga | gat | gtg | gac | gaa | ggc | ttg | cag | gca | gca | gaa | aaa | 1349 |
| Gln | Gly | Cys | Val | Arg | Asp | Val | Asp | Glu | Gly | Leu | Gln | Ala | Ala | Glu | Lys | |
| | | 430 | | | | | 435 | | | | | 440 | | | | |

| | | | | | | | | | | | | | | | | |
|---|---|---|---|---|---|---|---|---|---|---|---|---|---|---|---|---|
| gta | gga | ttt | cct | ctg | atg | atc | aaa | gcc | tct | gaa | ggt | gga | gga | ggg | aaa | 1397 |
| Val | Gly | Phe | Pro | Leu | Met | Ile | Lys | Ala | Ser | Glu | Gly | Gly | Gly | Gly | Lys | |
| | 445 | | | | | 450 | | | | | 455 | | | | | |

| | | | | | | | | | | | | | | | | |
|---|---|---|---|---|---|---|---|---|---|---|---|---|---|---|---|---|
| gga | atc | cgc | agg | gct | gag | agt | gca | gag | gac | ttc | ccg | atg | ctt | ttc | aga | 1445 |
| Gly | Ile | Arg | Arg | Ala | Glu | Ser | Ala | Glu | Asp | Phe | Pro | Met | Leu | Phe | Arg | |
| 460 | | | | | 465 | | | | | 470 | | | | | 475 | |

FIG. 2C

```
cag gtg cag agt gag atc ccg ggc tcg ccc atc ttt ctc atg aag ctg       1493
Gln Val Gln Ser Glu Ile Pro Gly Ser Pro Ile Phe Leu Met Lys Leu
            480                 485                 490 gcc cag aat gct cgg cac ttg gag gtc cag gtc ttg gca gat cag tat       1541
Ala Gln Asn Ala Arg His Leu Glu Val Gln Val Leu Ala Asp Gln Tyr
            495                 500                 505 ggg aac gca gtg tcc ctg ttt gga cga gac tgc tcc atc cag agg cgg       1589
Gly Asn Ala Val Ser Leu Phe Gly Arg Asp Cys Ser Ile Gln Arg Arg
            510                 515                 520 cac cag aag atc att gag gag gct ccg gcc acc atc gct gct ccg gct       1637
His Gln Lys Ile Ile Glu Glu Ala Pro Ala Thr Ile Ala Ala Pro Ala
    525                 530                 535 gtg ttt gag ttc atg gaa cag tgt gcc gtc ctc ctg gcc aag act gtg       1685
Val Phe Glu Phe Met Glu Gln Cys Ala Val Leu Leu Ala Lys Thr Val
540                 545                 550                 555 ggt tat gtg agc gcg gga acc gtg gag tac cta tac agc cag gat ggc       1733
Gly Tyr Val Ser Ala Gly Thr Val Glu Tyr Leu Tyr Ser Gln Asp Gly
                560                 565                 570 agc ttt cac ttc ttg gag ctg aac cca cgc ctg cag gtg gaa cat ccc       1781
Ser Phe His Phe Leu Glu Leu Asn Pro Arg Leu Gln Val Glu His Pro
                575                 580                 585 tgc act gaa atg atc gca gat gtc aac ctg ccc gct gca cag tta cag       1829
Cys Thr Glu Met Ile Ala Asp Val Asn Leu Pro Ala Ala Gln Leu Gln
                590                 595                 600 atc gcc atg ggc gtg ccc ctg cac cgg ctg aag gac ata cgg ctt ctg       1877
Ile Ala Met Gly Val Pro Leu His Arg Leu Lys Asp Ile Arg Leu Leu
            605                 610                 615 tac gga gag tcc ccc tgg gga gtg acc ccc gtt tct ttt gag acc cct       1925
Tyr Gly Glu Ser Pro Trp Gly Val Thr Pro Val Ser Phe Glu Thr Pro
620                 625                 630                 635 ttg agc cct ccc att gcc cga ggc cat gtc att gca gcc agg atc acc       1973
Leu Ser Pro Pro Ile Ala Arg Gly His Val Ile Ala Ala Arg Ile Thr
                640                 645                 650 agc gaa aac cca gac gag ggc ttt aag cca agc tca ggg aca gtg cag       2021
Ser Glu Asn Pro Asp Glu Gly Phe Lys Pro Ser Ser Gly Thr Val Gln
                655                 660                 665 gag ctg aac ttc cgc agc aac aag aac gtg tgg ggt tac ttc agc gtg       2069
Glu Leu Asn Phe Arg Ser Asn Lys Asn Val Trp Gly Tyr Phe Ser Val
            670                 675                 680 gcc gct gct ggg ggc ttg cac gag ttt gcc gat tcc cag ttt ggg cac       2117
Ala Ala Ala Gly Gly Leu His Glu Phe Ala Asp Ser Gln Phe Gly His
            685                 690                 695 tgc ttc tcc tgg ggc gag aac cgt gaa gag gct att tcg aac atg gtg       2165
Cys Phe Ser Trp Gly Glu Asn Arg Glu Glu Ala Ile Ser Asn Met Val
700                 705                 710                 715
```

FIG. 2D

```
gtg gct ttg aaa gaa ctg tct atc cgg ggt gac ttc cgg acc acc gtg       2213
Val Ala Leu Lys Glu Leu Ser Ile Arg Gly Asp Phe Arg Thr Thr Val
            720             725             730 gaa tat ctc gtc aac ctt ctg gag acg gag agc ttc cag aac aat gat       2261
Glu Tyr Leu Val Asn Leu Leu Glu Thr Glu Ser Phe Gln Asn Asn Asp
            735             740             745 atc gac acg ggg tgg ctg gac cac ctc atc gct cag cgg gtg cag gca       2309
Ile Asp Thr Gly Trp Leu Asp His Leu Ile Ala Gln Arg Val Gln Ala
            750             755             760 gag aag ccg gac atc atg ctc ggg gtg gtg tgt ggg gcc ttg aac gtg       2357
Glu Lys Pro Asp Ile Met Leu Gly Val Val Cys Gly Ala Leu Asn Val
            765             770             775 gca gac gcg atg ttc aga acc tgt atg acg gaa ttc ctg cat tcc ttg       2405
Ala Asp Ala Met Phe Arg Thr Cys Met Thr Glu Phe Leu His Ser Leu
780             785             790             795 gaa agg ggt cag gtc ctc ccg gct gat tct ctg ctg aac atc gtg gac       2453
Glu Arg Gly Gln Val Leu Pro Ala Asp Ser Leu Leu Asn Ile Val Asp
            800             805             810 gtt gag ttg att tac gga ggc atc aaa tat gtt ctc aag gtg gcc cgg       2501
Val Glu Leu Ile Tyr Gly Gly Ile Lys Tyr Val Leu Lys Val Ala Arg
            815             820             825 cag tcc ctg acc atg ttt gtc ctc atc atg aat ggt tgc cac atc gag       2549
Gln Ser Leu Thr Met Phe Val Leu Ile Met Asn Gly Cys His Ile Glu
            830             835             840 atc gat gcc cac cgg ctg aac gat ggg ggc ctg ctc ctg tcc tac aat       2597
Ile Asp Ala His Arg Leu Asn Asp Gly Gly Leu Leu Leu Ser Tyr Asn
            845             850             855 ggt agc agt tac act aca tac atg aag gaa gag gtg gac agt tac cgg       2645
Gly Ser Ser Tyr Thr Thr Tyr Met Lys Glu Glu Val Asp Ser Tyr Arg
860             865             870             875 atc act atc ggc aat aag aca tgc gtg ttt gaa aag gaa aac gac ccc       2693
Ile Thr Ile Gly Asn Lys Thr Cys Val Phe Glu Lys Glu Asn Asp Pro
            880             885             890 acc gtc ctg aga tcc ccc tcg gct ggg aag ctg atg cag tac acg gtg       2741
Thr Val Leu Arg Ser Pro Ser Ala Gly Lys Leu Met Gln Tyr Thr Val
            895             900             905 gag gat ggc cag cac gtg gaa gtc ggg agc agc tat gct gag atg gag       2789
Glu Asp Gly Gln His Val Glu Val Gly Ser Ser Tyr Ala Glu Met Glu
            910             915             920 gtg atg aag atg atc atg acc ctg aac gtg caa gag agc ggc cgg gtg       2837
Val Met Lys Met Ile Met Thr Leu Asn Val Gln Glu Ser Gly Arg Val
            925             930             935 aag tac atc aag cga cca ggg gcg gta ttg gag gct ggc tgc gtg gtg       2885
Lys Tyr Ile Lys Arg Pro Gly Ala Val Leu Glu Ala Gly Cys Val Val
940             945             950             955
```

FIG. 2E

```
gca aag cta gaa ctc gat gac cct tca aaa gtg cac gcg gca cag ccg    2933
Ala Lys Leu Glu Leu Asp Asp Pro Ser Lys Val His Ala Ala Gln Pro
            960                 965                 970 ttc aca ggg gag ctc ccc gcc cag cag act ctg ccc atc ctc ggg gag    2981
Phe Thr Gly Glu Leu Pro Ala Gln Gln Thr Leu Pro Ile Leu Gly Glu
        975                 980                 985 agg ctg cat cag gtg ttc cac agc gtc ttg gaa aat ctg  acc aat gtc   3029
Arg Leu His Gln Val Phe His Ser Val Leu Glu Asn Leu  Thr Asn Val
        990                 995             1000 atg aat ggc tac tgc ctg ccc  gag ccc ttc ttc agc  atg aag ctg      3074
Met Asn Gly Tyr Cys Leu Pro  Glu Pro Phe Phe Ser  Met Lys Leu
        1005                1010                1015 aag gac tgg gtg gag aag ctc  atg atg act ctc cgg  cat ccc tcc      3119
Lys Asp Trp Val Glu Lys Leu  Met Met Thr Leu Arg  His Pro Ser
        1020                1025                1030 cta cct ctg ctg gag ctg cag  gag atc atg acc agc  gtg gca ggc      3164
Leu Pro Leu Leu Glu Leu Gln  Glu Ile Met Thr Ser  Val Ala Gly
        1035                1040                1045 cgc atc ccg gtt ccg gtg gag  aag gca gtc cgc agg  gtg atg gcg      3209
Arg Ile Pro Val Pro Val Glu  Lys Ala Val Arg Arg  Val Met Ala
        1050                1055                1060 cag tac gcc agc aac atc act  tcg gtg ctc tgc cag  ttc ccc agc      3254
Gln Tyr Ala Ser Asn Ile Thr  Ser Val Leu Cys Gln  Phe Pro Ser
        1065                1070                1075 cag cag ata gcc acc atc ctg  gac tgc cac gcc gcc  acc ctg cag      3299
Gln Gln Ile Ala Thr Ile Leu  Asp Cys His Ala Ala  Thr Leu Gln
        1080                1085                1090 cgt aag gtg gac cga gag gcc  ttc ttc atg aac aca  cag agc atc      3344
Arg Lys Val Asp Arg Glu Ala  Phe Phe Met Asn Thr  Gln Ser Ile
        1095                1100                1105 gtg cag ctg atc cag aga tac  cgc agt ggg acc cgt  ggc tac atg      3389
Val Gln Leu Ile Gln Arg Tyr  Arg Ser Gly Thr Arg  Gly Tyr Met
        1110                1115                1120 aag gct gtg gtg cta gac ctc  ctg agg aga tat ctg  aac gtg gag      3434
Lys Ala Val Val Leu Asp Leu  Leu Arg Arg Tyr Leu  Asn Val Glu
        1125                1130                1135 cat cat ttc cag caa gcc cac  tat gac aag tgt gtg  atc aac ctg      3479
His His Phe Gln Gln Ala His  Tyr Asp Lys Cys Val  Ile Asn Leu
        1140                1145                1150 agg gag cag ttc aag ccg gac  atg act cgg gtg ctg  gac tgc atc      3524
Arg Glu Gln Phe Lys Pro Asp  Met Thr Arg Val Leu  Asp Cys Ile
        1155                1160                1165 ttc tca cac tca caa gtg gcc  aag aag aac cag ctg  gtg acc atg      3569
Phe Ser His Ser Gln Val Ala  Lys Lys Asn Gln Leu  Val Thr Met
        1170                1175                1180
```

FIG. 2F

```
ttg ata gat gag ctg tgt ggc  cca gac ccc acc ctg  tca gaa gag      3614
Leu Ile Asp Glu Leu Cys Gly  Pro Asp Pro Thr Leu  Ser Glu Glu
    1185            1190                 1195 ctg acc tcc atc ctc aag gaa  ctc acg cag ttg agc  agg agt gag      3659
Leu Thr Ser Ile Leu Lys Glu  Leu Thr Gln Leu Ser  Arg Ser Glu
    1200            1205                 1210 cac tgc aag gtg gcc ctc aga  gcc agg cag gtc ctg  att gcc tct      3704
His Cys Lys Val Ala Leu Arg  Ala Arg Gln Val Leu  Ile Ala Ser
    1215            1220                 1225 cac ctc ccc tcc tac gag ctg  cgg cac aac cag gtg  gag tcc atc      3749
His Leu Pro Ser Tyr Glu Leu  Arg His Asn Gln Val  Glu Ser Ile
    1230            1235                 1240 ttc ctg tca gcc att gac atg  tat ggc cac cag ttc  tgc ccg gaa      3794
Phe Leu Ser Ala Ile Asp Met  Tyr Gly His Gln Phe  Cys Pro Glu
    1245            1250                 1255 aac ctc aag aaa cta ata ctt  tcg gaa acg acc ata  ttc gat gtc      3839
Asn Leu Lys Lys Leu Ile Leu  Ser Glu Thr Thr Ile  Phe Asp Val
    1260            1265                 1270 ctg ccc act ttc ttc tat cac  gct aac aag gtc gtc  tgt atg gcg      3884
Leu Pro Thr Phe Phe Tyr His  Ala Asn Lys Val Val  Cys Met Ala
    1275            1280                 1285 tcc ctg gag gtt tat gtg agg  aga ggt tac atc gcc  tac gag tta      3929
Ser Leu Glu Val Tyr Val Arg  Arg Gly Tyr Ile Ala  Tyr Glu Leu
    1290            1295                 1300 aac agc cta cag cac cgg gag  ctc cct gac ggc acc  tgc gtg gtg      3974
Asn Ser Leu Gln His Arg Glu  Leu Pro Asp Gly Thr  Cys Val Val
    1305            1310                 1315 gag ttc cag ttc atg ctg ccg  tct tcc cac ccc aac  cgg atg gcc      4019
Glu Phe Gln Phe Met Leu Pro  Ser Ser His Pro Asn  Arg Met Ala
    1320            1325                 1330 atg ccc atc aat gtc tct gac  cct gac ctg ctg aga  cac agt aag      4064
Met Pro Ile Asn Val Ser Asp  Pro Asp Leu Leu Arg  His Ser Lys
    1335            1340                 1345 gaa ctc ttc atg gac agt ggc  ttc tcc cca ctg tgc  cag cgg atg      4109
Glu Leu Phe Met Asp Ser Gly  Phe Ser Pro Leu Cys  Gln Arg Met
    1350            1355                 1360 ggg gcc atg gtg gcc ttc agg  aga ttt gag gag ttc  acc agg aac      4154
Gly Ala Met Val Ala Phe Arg  Arg Phe Glu Glu Phe  Thr Arg Asn
    1365            1370                 1375 ttc gat gaa gtc atc tcc tgc  ttt gcc aac gtg cct  aca gac act      4199
Phe Asp Glu Val Ile Ser Cys  Phe Ala Asn Val Pro  Thr Asp Thr
    1380            1385                 1390 cct ctc ttc agt aag gcg tgc  act tcc ctc tac tca  gag gag gac      4244
Pro Leu Phe Ser Lys Ala Cys  Thr Ser Leu Tyr Ser  Glu Glu Asp
    1395            1400                 1405
```

FIG. 2G

```
agc aag agc ctt caa gag gag ccc atc cac atc ctg aat gtg gcc    4289
Ser Lys Ser Leu Gln Glu Glu Pro Ile His Ile Leu Asn Val Ala
    1410            1415                1420 atc cag tgc gcc gac cac atg gag gac gag aga ctg gtg ccg gtt    4334
Ile Gln Cys Ala Asp His Met Glu Asp Glu Arg Leu Val Pro Val
    1425            1430                1435 ttc cgt gcc ttt gta cag tcc aag aaa cac atc ctt gtg gat tac    4379
Phe Arg Ala Phe Val Gln Ser Lys Lys His Ile Leu Val Asp Tyr
    1440            1445                1450 gga ctg cga aga atc aca ttc ctt atc gcc caa gag aga gaa ttt    4424
Gly Leu Arg Arg Ile Thr Phe Leu Ile Ala Gln Glu Arg Glu Phe
    1455            1460                1465 ccc aag ttc ttc acg ttc aga gcg aga gat gag ttt gca gaa gac    4469
Pro Lys Phe Phe Thr Phe Arg Ala Arg Asp Glu Phe Ala Glu Asp
    1470            1475                1480 cgg att tac cgc cac ttg gag ccg gcc ctg gcc ttc cag ctg gag    4514
Arg Ile Tyr Arg His Leu Glu Pro Ala Leu Ala Phe Gln Leu Glu
    1485            1490                1495 ctg agc cgg atg cgc aac ttt gac ctg acg gcc gtg ccc tgt gcc    4559
Leu Ser Arg Met Arg Asn Phe Asp Leu Thr Ala Val Pro Cys Ala
    1500            1505                1510 aac cat aag atg cat ctt tac ctg gga gcc gcc aag gtg aag gaa    4604
Asn His Lys Met His Leu Tyr Leu Gly Ala Ala Lys Val Lys Glu
    1515            1520                1525 ggg ctg gag gtg act gac cac agg ttc ttc atc cga gcc atc ata    4649
Gly Leu Glu Val Thr Asp His Arg Phe Phe Ile Arg Ala Ile Ile
    1530            1535                1540 agg cac tca gac ctg atc acc aag gaa gcc tcc ttc gag tac ctg    4694
Arg His Ser Asp Leu Ile Thr Lys Glu Ala Ser Phe Glu Tyr Leu
    1545            1550                1555 cag aat gaa ggg gag cgg ctg ctg gaa gcc atg gat gag ctg        4739
Gln Asn Glu Gly Glu Arg Leu Leu Leu Glu Ala Met Asp Glu Leu
    1560            1565                1570 gag gtg gcg ttc aac aac acc agc gtg cgc act gac tgc aac cac    4784
Glu Val Ala Phe Asn Asn Thr Ser Val Arg Thr Asp Cys Asn His
    1575            1580                1585 atc ttc ctc aac ttc gtg ccc acg gtc atc atg gac cca ctc aag    4829
Ile Phe Leu Asn Phe Val Pro Thr Val Ile Met Asp Pro Leu Lys
    1590            1595                1600 atc gag gag tcg gtg cgt gcc atg gtc atg cgt tac ggc agt cgg    4874
Ile Glu Glu Ser Val Arg Ala Met Val Met Arg Tyr Gly Ser Arg
    1605            1610                1615 ctg tgg aag ctc cgt gtg ctg cag gca gaa gtt aag atc aac atc    4919
Leu Trp Lys Leu Arg Val Leu Gln Ala Glu Val Lys Ile Asn Ile
    1620            1625                1630
```

FIG. 2H

```
cgt cag acg acc tcg gac tgc gcc gtc ccc att cgc ctc ttc atc    4964
Arg Gln Thr Thr Ser Asp Cys Ala Val Pro Ile Arg Leu Phe Ile
    1635            1640            1645 acc aac gag tcc ggc tac tac ctg gac atc agc ctc tac aaa gaa    5009
Thr Asn Glu Ser Gly Tyr Tyr Leu Asp Ile Ser Leu Tyr Lys Glu
    1650            1655            1660 gtg acc gac tcc aga tcc gga aac atc atg ttt cat tcc ttc ggc    5054
Val Thr Asp Ser Arg Ser Gly Asn Ile Met Phe His Ser Phe Gly
    1665            1670            1675 aac aaa caa ggg agc ctg cac ggg atg ctg atc aac acg ccc tac    5099
Asn Lys Gln Gly Ser Leu His Gly Met Leu Ile Asn Thr Pro Tyr
    1680            1685            1690 gtc acc aag gat ctg ctc caa gcc aag cga ttc cag gcg cag tcc    5144
Val Thr Lys Asp Leu Leu Gln Ala Lys Arg Phe Gln Ala Gln Ser
    1695            1700            1705 ctg ggg acc acc tat gtg tac gac ttc cca gag atg ttc agg cag    5189
Leu Gly Thr Thr Tyr Val Tyr Asp Phe Pro Glu Met Phe Arg Gln
    1710            1715            1720 gct ctc ttt aaa ttg tgg ggc tcc cca gag aag tac ccc aaa gat    5234
Ala Leu Phe Lys Leu Trp Gly Ser Pro Glu Lys Tyr Pro Lys Asp
    1725            1730            1735 atc ctg aca tac aca gag ctg gtg ttg gac tcc cag ggc cag ctg    5279
Ile Leu Thr Tyr Thr Glu Leu Val Leu Asp Ser Gln Gly Gln Leu
    1740            1745            1750 gtg gag atg aac cgg ctt cct ggt tgt aac gag gtg ggc atg gtg    5324
Val Glu Met Asn Arg Leu Pro Gly Cys Asn Glu Val Gly Met Val
    1755            1760            1765 gtt ttc aaa atg agg ttc aag acc ccg gag tat cca gaa ggc cgg    5369
Val Phe Lys Met Arg Phe Lys Thr Pro Glu Tyr Pro Glu Gly Arg
    1770            1775            1780 gac act atc gtc atc ggc aac gac att acc ttc caa atc ggc tct    5414
Asp Thr Ile Val Ile Gly Asn Asp Ile Thr Phe Gln Ile Gly Ser
    1785            1790            1795 ttc ggc ata gga gag gac ttc ctg tat cta cgg gca tcg gag atg    5459
Phe Gly Ile Gly Glu Asp Phe Leu Tyr Leu Arg Ala Ser Glu Met
    1800            1805            1810 gcc cgg aca gag ggc atc ccc caa atc tat ctg gca gcc aac agc    5504
Ala Arg Thr Glu Gly Ile Pro Gln Ile Tyr Leu Ala Ala Asn Ser
    1815            1820            1825 ggg gcc cgt atg ggc ctg tcc gag gag atc aag cag ata ttc caa    5549
Gly Ala Arg Met Gly Leu Ser Glu Glu Ile Lys Gln Ile Phe Gln
    1830            1835            1840 gtg gca tgg gtg gac cct gag gat ccc tac aaa gga ttt aga tac    5594
Val Ala Trp Val Asp Pro Glu Asp Pro Tyr Lys Gly Phe Arg Tyr
    1845            1850            1855
```

FIG. 2I

```
ctg tac ctg acg ccc caa gac tac acc cag atc agc tcc cag aac        5639
Leu Tyr Leu Thr Pro Gln Asp Tyr Thr Gln Ile Ser Ser Gln Asn
    1860              1865                  1870 tcc gtg cac tgc aaa cac atc gag gac gaa ggc gag tcc agg tat        5684
Ser Val His Cys Lys His Ile Glu Asp Glu Gly Glu Ser Arg Tyr
    1875              1880                  1885 gtc atc gtt gat gtc atc ggg aag gac agc agc ctg ggt gtg gag        5729
Val Ile Val Asp Val Ile Gly Lys Asp Ser Ser Leu Gly Val Glu
    1890              1895                  1900 aac ctg cgg ggc tcg ggc atg att gca gga gag gct tct ctg gct        5774
Asn Leu Arg Gly Ser Gly Met Ile Ala Gly Glu Ala Ser Leu Ala
    1905              1910                  1915 tac gaa aaa aat gtc acc atc agc atg gtg acc tgc cgc gcc atc        5819
Tyr Glu Lys Asn Val Thr Ile Ser Met Val Thr Cys Arg Ala Ile
    1920              1925                  1930 gga atc ggg gct tac ctg gtg agg ctg ggc cag cgg gtg atc cag        5864
Gly Ile Gly Ala Tyr Leu Val Arg Leu Gly Gln Arg Val Ile Gln
    1935              1940                  1945 gtg gaa aac tcc cac atc atc ctc acg gga gcc ggt gct ctc aac        5909
Val Glu Asn Ser His Ile Ile Leu Thr Gly Ala Gly Ala Leu Asn
    1950              1955                  1960 aag gtc ctg gga aga gag gtc tac aca tcc aac aac caa ctg ggc        5954
Lys Val Leu Gly Arg Glu Val Tyr Thr Ser Asn Asn Gln Leu Gly
    1965              1970                  1975 ggt gtg cag atc atg cac acc aac ggg gtc tcc cac gtc acg gtg        5999
Gly Val Gln Ile Met His Thr Asn Gly Val Ser His Val Thr Val
    1980              1985                  1990 cca gat gac ttc gag ggg gtc tgc acc att ctg gaa tgg ctg tca        6044
Pro Asp Asp Phe Glu Gly Val Cys Thr Ile Leu Glu Trp Leu Ser
    1995              2000                  2005 tat ata cca aag gac aat caa agc cca gtc ccc atc atc act cct        6089
Tyr Ile Pro Lys Asp Asn Gln Ser Pro Val Pro Ile Ile Thr Pro
    2010              2015                  2020 tct gac ccc atc gac agg gaa att gaa ttc acc cca acc aaa gct        6134
Ser Asp Pro Ile Asp Arg Glu Ile Glu Phe Thr Pro Thr Lys Ala
    2025              2030                  2035 ccc tat gac ccc agg tgg ctg ctt gca ggg agg cct cac cca act        6179
Pro Tyr Asp Pro Arg Trp Leu Leu Ala Gly Arg Pro His Pro Thr
    2040              2045                  2050 ctg aag ggg acc tgg cag agt gga ttc ttc gac cat ggc agt ttc        6224
Leu Lys Gly Thr Trp Gln Ser Gly Phe Phe Asp His Gly Ser Phe
    2055              2060                  2065 aag gaa atc atg gca ccc tgg gcc cag acc gtg gtg act gga cga        6269
Lys Glu Ile Met Ala Pro Trp Ala Gln Thr Val Val Thr Gly Arg
    2070              2075                  2080
```

FIG. 2J

```
gca agg ctg ggg ggc atc cct gta ggg gtg att gcc gtg gag act    6314
Ala Arg Leu Gly Gly Ile Pro Val Gly Val Ile Ala Val Glu Thr
    2085            2090            2095 cgg tct gtg gag gtg gct gtc cct gct gac cct gcc aac ttg gat    6359
Arg Ser Val Glu Val Ala Val Pro Ala Asp Pro Ala Asn Leu Asp
    2100            2105            2110 tct gag gcc aag atc atc cag cag gca ggc cag gtg tgg ttc ccg    6404
Ser Glu Ala Lys Ile Ile Gln Gln Ala Gly Gln Val Trp Phe Pro
    2115            2120            2125 gac tct gcc ttc aag acg gct cag gtc atc agg gac ttc aac cag    6449
Asp Ser Ala Phe Lys Thr Ala Gln Val Ile Arg Asp Phe Asn Gln
    2130            2135            2140 gag cat ctg cct ctc atg atc ttt gcc aac tgg aga ggc ttc tcg    6494
Glu His Leu Pro Leu Met Ile Phe Ala Asn Trp Arg Gly Phe Ser
    2145            2150            2155 ggt ggc atg aaa gac atg tac gag cag atg ctg aag ttt ggc gcc    6539
Gly Gly Met Lys Asp Met Tyr Glu Gln Met Leu Lys Phe Gly Ala
    2160            2165            2170 tac atc gtg gac agt ctc cgt ctg ttc aag cag cca gtt ctc atc    6584
Tyr Ile Val Asp Ser Leu Arg Leu Phe Lys Gln Pro Val Leu Ile
    2175            2180            2185 tat atc cct cct ggt gcc gaa ctc cga ggg ggc gcc tgg gtt gtc    6629
Tyr Ile Pro Pro Gly Ala Glu Leu Arg Gly Gly Ala Trp Val Val
    2190            2195            2200 ctc gac tcc agc atc aac ccc ctg tgc ata gag atg tac gca gac    6674
Leu Asp Ser Ser Ile Asn Pro Leu Cys Ile Glu Met Tyr Ala Asp
    2205            2210            2215 aaa gag agc agg ggg ggt gtc ctg gag ccc gag ggc act gtg gag    6719
Lys Glu Ser Arg Gly Gly Val Leu Glu Pro Glu Gly Thr Val Glu
    2220            2225            2230 att aag ttc cgg aag aaa gat ttg gtg aag acc ata agg agg att    6764
Ile Lys Phe Arg Lys Lys Asp Leu Val Lys Thr Ile Arg Arg Ile
    2235            2240            2245 gac cca gtg tgc aag aaa ctc ctg ggg cag ctg ggg aca gcc cag    6809
Asp Pro Val Cys Lys Lys Leu Leu Gly Gln Leu Gly Thr Ala Gln
    2250            2255            2260 ctc cct gac aag gac cgg aaa gag ctg gag agc cag ctg aag gcc    6854
Leu Pro Asp Lys Asp Arg Lys Glu Leu Glu Ser Gln Leu Lys Ala
    2265            2270            2275 cgg gag gac ctg ctg ctc ccc atc tac cac cag gtg gca gtg cag    6899
Arg Glu Asp Leu Leu Leu Pro Ile Tyr His Gln Val Ala Val Gln
    2280            2285            2290 ttc gcc gac ctg cat gac acg ccg ggc cac atg ctg gag aag gga    6944
Phe Ala Asp Leu His Asp Thr Pro Gly His Met Leu Glu Lys Gly
    2295            2300            2305
```

FIG. 2K

```
atc att tct gat gtg ctg gag tgg aag acc aca cgt acc tac ttc      6989
Ile Ile Ser Asp Val Leu Glu Trp Lys Thr Thr Arg Thr Tyr Phe
    2310            2315            2320 tac tgg agg ctg cgc cgg ctg ctg ctg gag gca cag gtg aag cag      7034
Tyr Trp Arg Leu Arg Arg Leu Leu Leu Glu Ala Gln Val Lys Gln
    2325            2330            2335 gag att ctg cga gcc agc cct gag ctg agc cat gag cac acg cag      7079
Glu Ile Leu Arg Ala Ser Pro Glu Leu Ser His Glu His Thr Gln
    2340            2345            2350 tcc atg ctg cga cgc tgg ttt gtg gag acc gag ggc gcc gtc aag      7124
Ser Met Leu Arg Arg Trp Phe Val Glu Thr Glu Gly Ala Val Lys
    2355            2360            2365 gcc tac ctg tgg gac agc aac cag gtg gta gtc cag tgg ctg gaa      7169
Ala Tyr Leu Trp Asp Ser Asn Gln Val Val Val Gln Trp Leu Glu
    2370            2375            2380 cag cac tgg tca gcc agg gac aac ctg cgt tcc act atc cga gag      7214
Gln His Trp Ser Ala Arg Asp Asn Leu Arg Ser Thr Ile Arg Glu
    2385            2390            2395 aac atc aat tat ctg aag cgg gac tct gtc ctc aag acc atc caa      7259
Asn Ile Asn Tyr Leu Lys Arg Asp Ser Val Leu Lys Thr Ile Gln
    2400            2405            2410 agc cta gtt caa gaa cac cca gag gcg acc atg gac tgt gtg gca      7304
Ser Leu Val Gln Glu His Pro Glu Ala Thr Met Asp Cys Val Ala
    2415            2420            2425 tac ctg agc cag cac ctc acg ccc gct gag cag atg cag gtg gtt      7349
Tyr Leu Ser Gln His Leu Thr Pro Ala Glu Gln Met Gln Val Val
    2430            2435            2440 cag ctg ctg tct acc acg gag agc cca gct tcc cac tga              7388
Gln Leu Leu Ser Thr Thr Glu Ser Pro Ala Ser His
    2445            2450            2455
```

FIG. 3A

```
AB004329    ATGGTCTTGCTTCTCTTTCTGACTTACCTGGTTTTCTCCTGCCTGACCATTTCCTGGTTA
BMS         ATGGTCTTGCTTCTCTTTCTGACTTGCCTGGTTTTCTCCTGCCTGACCATTTCCTGGTTA
            ************************* **********************************

AB004329    AAAATCTGGGGAAGATGACAGACTCGAGGCCGCTCAGCAACAGTAAGGTGGATGCAAGC
BMS         AAAATCTGGGGAAGATGACAGACTCGAAGCCGCTCAGCAACAGTAAGGTGGATGCAAGC
            *************************** ********************************

AB004329    CTCCTTCCGAGCAAGGAGGAGTCTTTT---GCCTCGGACCAGTCAGAGGAGCATGGCGAC
BMS         CTCCTTTCGAGCAAGGAGGAGTCCTTTTCAGCCTCGGACCAGTCAGAGGAGCATGGCGAC
            ****** **************** ***   ******************************

AB004329    TGCAGCTGTCCGTTGACAACTCCTGACCAGGAGGAGCTGGCCTCCCACGGAGGTCCTGTA
BMS         TGCAGCTGTCCGTTGACAACTCCTGACCAGGAGGAGCTGGCCTCCCACGGAGGTCCTGTA
            ************************************************************

AB004329    GATGCCAGTCAGCAGAGGAACTCTGTACCAACCTCACACCAGAAGCCTCCGAGGAACCCA
BMS         GATGCCAGTCAGCAGAGGAACTCTGTGCCAAGCTCACACCAGAAGCCTCCGAGGAACCCA
            ************************** **** ****************************

AB004329    CTATCTTCCAATGACACCTGTTCCTCCCCAGAACTCCAAACCAACGGGGTAGCAGCACCT
BMS         CTATCTTCCAATGACACCTGTTCCTCCCCAGAACTCCAAACCAACGGGGTAGCAGCCCCT
            ******************************************************** ***

AB004329    GGCTCAGAGGTTCCAGAAGCCAACGGGTTGCCTTTCCCAGCCAGGCCTCAGACCCAGAGA
BMS         GGCTCAGAGGTTCCAGAAGCCAACGGGTTGCCTTTCCCAGCCAGGCCTCAGACCCAGAGA
            ************************************************************

AB004329    ACGGGATCCCCCACTAGGGAGGACAAGAAGCAGGCACCCATCAAGAGGCAGCTGATGACC
BMS         ACGGGATCCCCCACTAGGGAGGACAAGAAGCAGGCACACATCAAGAGGCAGCTGATGACC
            ************************************ ***********************

AB004329    AGCTTTATCCTGGGCTCCCTCGATGACAACTCCTCTGACGAGGACCCTAGTTCTAACTCC
BMS         AGCTTTATCCTGGGCTCCCTCGATGACAACTCCTCTGACGAGGACCCTAGTGCTAGCTCC
            *************************************************** *** ****

AB004329    TTTCAGACCTCCTCTCGGAAGGGCAGCAGGGATAGCCTGGGCACCTGTTCCCAGGAGGCT
BMS         TTCCAGACCTCCTCTCGGAAGGGCAGCAGGGCTAGCCTGGGCACCCTGTCCCAGGAGGCT
            ** ****************************  ************  *** **********

AB004329    GCATTGAACACAGCTGATCCTGAGTCTCACACACCTACTATGAGGCCCAGCATGTCTGGA
BMS         GCATTGAACACAGCTGATCCTGAGTCTCACACACCTACTATGAGGCCCAGCATGTCTGGA
            ************************************************************

AB004329    CTCCATCTGGTGAAGAGAGGCCGTGAACACAAGAAACTGGACCTGCACAGAGATTTCACT
BMS         CTCCATCTGGTGAAGAGAGGCCGTGAACACAAGAAACTGGACCTGCACAGAGATTTCACT
            ************************************************************

AB004329    GTAGCTTCCCCAGCCGAATTTGTCACCCGCTTTGGAGGCAACAGGGTTATCGAGACGGTG
BMS         GTAGCTTCCCCAGCCGAATTTGTCACCCGCTTTGGAGGCAACAGGGTTATCGAGACGGTG
            ************************************************************

AB004329    CTCATCGCCAATAATGGTATCGCTGCGGTCAAGTGGATGCGCTCCATCCGCCGCTGGGCC
BMS         CTCATCGCCAATAATGGTATCGCTGCGGTCAAGTGTATGCGCTCCATCCGCCGCTGGGCC
            *********************************** ************************

AB004329    TATGAGATGTTCCGTAATGAACGCGCTATCCGGTTTGTGGTTATGGTGACACCCGAGGAT
BMS         TATGAGATGTTCCGTAATGAACGCGCCATCCGGTTTGTGGTTATGGTGACACCCGAGGAT
            ************************** *********************************
```

FIG. 3B

```
AB004329    CTTAAGGCCAACGCAGAGTACTACAAGATGGCGGACCCAGTAC-TTCCGGTCCCAGGAGG
BMS         CTTAAGGCCAACGCAGAGTACATCAAGATGGCGGACC-AGTACGTTCCGGTCCCAGGAGG
            *********************  ************* **** ******************

AB004329    ACCCAATAATAACAACTACGCCAACGTTGAGCTGATCATAGACATTGCCAAGAGAATCCC
BMS         ACCCAATAATAACAACTACGCCAACGTTGAGCTGATCATAGACATTGCCAAGAGAATCCC
            ************************************************************

AB004329    TGTGCAGGCCGTGTGGGCTGGCTGGGGCCACGCTTCGGAAAACCCCAAACTTCCAGAGCT
BMS         TGTGCAGGCCGTGTGGGCTGGCTGGGGCCACGCTTCGGAAAACCCCAAACTTCCAGAGCT
            ************************************************************

AB004329    ACTGTGCAAGCACGGGATTGCTTTTCTAGGTCCCC-GAGTGAGGCCAATGTTGGGCCTGG
BMS         ACTGTGCAAGCACGAGATTGCTTTCCTAGGTCCCCCGAGTGAGGCCA-TGTGGGCCCTGG
            ************** ******** *********** *********** *** ***** **

AB004329    GAGACAGGCTCTCCTCCACCATTGTAGCCCAGACATTGCAGATCCCAACTCTACCCTGGA
BMS         GAGACAAGATCTCCTCCACCATTGTAGCCCAGACATTGCAGATCCCAACTCTACCCTGGA
            ****** * ***************************************************

AB004329    GCGGAAGCGGTCTCACAGTGGAGTGGACGGAGGACAGCCAGCATCAGGGCAAATGCATCA
BMS         GCGGAAGCGGTCTCACAGTGGAGTGGACGGAGGACAGCCAGCATCAGGGCAAATGCATCA
            ************************************************************

AB004329    GCGTCACGGAAGACGTTTATGAACAAGGCTGTGTGAGAGATGTGGACGAAGGCTTGCAGG
BMS         GCGTCCCGGAAGACGTTTATGAACAAGGCTGTGTGAGAGATGTGGACGAAGGCTTGCAGG
            *****  *****************************************************

AB004329    CAGCAGAAAAAGTAGGATTTCCTCTGATGATCAAAGCCTCTGAAGGTGGAGGAGGGAAAG
BMS         CAGCAGAAAAAGTAGGATTTCCTCTGATGATCAAAGCCTCTGAAGGTGGAGGAGGGAAAG
            ************************************************************

AB004329    GAATCCGGCAGGCTGAGAGTGCAGAGGACTTCCCATGCTTTTTCAGACAGGTGCAGAGTG
BMS         GAATCCGCAGGGCTGAGAGTGCAGAGGACTTCCCGATGCTTTTTCAGACAGGTGCAGAGTG
            *******  *********************** *  *****************

AB004329    AGATCCCGGGCTCGCCCATCTTTCTCATGAAGCTGGCCCAGAATGCCCGGCACTTGGAGG
BMS         AGATCCCGGGCTCGCCCATCTTTCTCATGAAGCTGGCCCAGAATGCTCGGCACTTGGAGG
            ********************************************** *************

AB004329    TCCAGGTCTTGGCAGATCAGTATGGGAACGCAGTGTCCCTGTTTGGACGAGACTGCTCCA
BMS         TCCAGGTCTTGGCAGATCAGTATGGGAACGCAGTGTCCCTGTTTGGACGAGACTGCTCCA
            ************************************************************

AB004329    TCCAGAGGCGGCACCAGAAGATCATTGAGGAGGCTCCGGCCAACATCGCTGCTCCGGCTG
BMS         TCCAGAGGCGGCACCAGAAGATCATTGAGGAGGCTCCGGCCACCATCGCTGCTCCGGCTG
            ***************************************** ******************

AB004329    TGTTTGAGTTCATGGAACAGTGTGCCGTCCTCCTGGCCAAGACTGTGGTTTATGTGAGCG
BMS         TGTTTGAGTTCATGGAACAGTGTGCCGTCCTCCTGGCCAAGACTGTGGGTTATGTGAGCG
            ************************************************ ***********

AB004329    CGGGAACCGTGGGGTACCTATACAGCCAGGATGGCAGCTTTCACTTCTTGGAGCTGAACC
BMS         CGGGAACCGTGGAGTACCTATACAGCCAGGATGGCAGCTTTCACTTCTTGGAGCTGAACC
            ************ ***********************************************

AB004329    CACGCCTGCAGGTGGAACATCCCTGCACTGAAATGATTGCAGATGTCAACCTGCCCGCTG
BMS         CACGCCTGCAGGTGGAACATCCCTGCACTGAAATGATCGCAGATGTCAACCTGCCCGCTG
            ************************************* **********************
```

FIG. 3C

```
AB004329    CACAGTTACAGATCGCCATGGGCGTGCCCCTGCACCGGCTGAAGGACATACGGCTTCTGT
BMS         CACAGTTACAGATCGCCATGGGCGTGCCCCTGCACCGGCTGAAGGACATACGGCTTCTGT
            ************************************************************

AB004329    ACGGAGAGTCCCCCTGGGGAGTGACCCCCGTTTCTTTTGAGACCCCTTTGAGCCCTCCCA
BMS         ACGGAGAGTCCCCCTGGGGAGTGACCCCCGTTTCTTTTGAGACCCCTTTGAGCCCTCCCA
            ************************************************************

AB004329    TTGCCCGAGGCCATGTCATTGCAGCCAGGATCACCAGCGAAAACCCAGACGAGGCCTTTA
BMS         TTGCCCGAGGCCATGTCATTGCAGCCAGGATCACCAGCGAAAACCCAGACGAGGGCTTTA
            ****************************************************** ****

AB004329    AGCCAAGCTCAGGGACAGTACAGGAGCTGAACTTCCGCAGCAACAAGAACGTGTGGGGTT
BMS         AGCCAAGCTCAGGGACAGTGCAGGAGCTGAACTTCCGCAGCAACAAGAACGTGTGGGGTT
            ******************* ****************************************

AB004329    ACTTCAGCGTGGCCGCTGCTGGAGGCTTGCACGAGTTTCCGATTTCCCAGTTTGGGCACT
BMS         ACTTCAGCGTGGCCGCTGCTGGGGGCTTGCACGAGTTTGCCGATTCCCAGTTTGGGCACT
            **********************  **************  *****  *************

AB004329    GCTTCTCCTGGGGCGAGAACCAGGAAGAGGCTATTTCGAACATGGTGGTGGCTTTGAAAG
BMS         GCTTCTCCTGGGGCGAGAACCGTGAAGAGGCTATTTCGAACATGGTGGTGGCTTTGAAAG
            ********************* **************************************

AB004329    AACTGTCTATCCGGGGTGACTTCCGGACCACCGTGGAATATCTCGTCAACCTTCTGGAGA
BMS         AACTGTCTATCCGGGGTGACTTCCGGACCACCGTGGAATATCTCGTCAACCTTCTGGAGA
            ************************************************************

AB004329    CGGAGAGCTTACAGAACAATGATATCGACACGGGGTGGCTGGACCACCTCATCGCTCAGC
BMS         CGGAGAGCTTCCAGAACAATGATATCGACACGGGGTGGCTGGACCACCTCATCGCTCAGC
            ********** *************************************************

AB004329    GGGTGCAGGCAGAGAAGCCGGACATCATGCTCGGGGTGGTGTTTGGGGCCTTGAACGTGG
BMS         GGGTGCAGGCAGAGAAGCCGGACATCATGCTCGGGGTGGTGTGTGGGGCCTTGAACGTGG
            *****************************************  ****************

AB004329    CAGACGCAATGTTCAGAACCTGTATTACGGAATTCCTGCATTCCTTGGAAAGGGGTCAGG
BMS         CAGACGCGATGTTCAGAACCTGTATGACGGAATTCCTGCATTCCTTGGAAAGGGGTCAGG
            ******* ***************** **********************************

AB004329    TCCTCCCGGCTGATTCTCTGCTGAACATCGTGGACGTTGAATTGATTTACGGAGGCATCA
BMS         TCCTCCCGGCTGATTCTCTGCTGAACATCGTGGACGTTGAGTTGATTTACGGAGGCATCA
            **************************************** *******************

AB004329    AATATGTTCTCAAGGTGGCCCGGCAGTCCCTGACCATGTTTGTCCTCATCATGAATGGTT
BMS         AATATGTTCTCAAGGTGGCCCGGCAGTCCCTGACCATGTTTGTCCTCATCATGAATGGTT
            ************************************************************

AB004329    GCCACATCGAGATCGATGCCCACCGGCCGAACGATGGGGGCCTGCTCCTGTCCTACAATG
BMS         GCCACATCGAGATCGATGCCCACCGGCTGAACGATGGGGGCCTGCTCCTGTCCTACAATG
            *************************** ********************************

AB004329    GTAGCAGTTACACTACATACATGAAGGAAGAGGTGGACAGTTACCGGATCACTATCGGCA
BMS         GTAGCAGTTACACTACATACATGAAGGAAGAGGTGGACAGTTACCGGATCACTATCGGCA
            ************************************************************

AB004329    ATAAGACATGCGTGTTTGAAAAGGAAAACGACCCCACCGTCCTGAGATCCCCCTCGGCTG
BMS         ATAAGACATGCGTGTTTGAAAAGGAAAACGACCCCACCGTCCTGAGATCCCCCTCGGCTG
            ************************************************************
```

FIG. 3D

```
AB004329    GGAAGCTGATGCAGTACACGGTGGAGGATGGCCAGCACGTGGAAGTCGGGAGCAGCTATG
BMS         GGAAGCTGATGCAGTACACGGTGGAGGATGGCCAGCACGTGGAAGTCGGGAGCAGCTATG
            ************************************************************

AB004329    CTGAGATGGAGGTGATGAAGATGATCATGACCCTGAACGTGCAAGAGAGCGGCCGGGTGA
BMS         CTGAGATGGAGGTGATGAAGATGATCATGACCCTGAACGTGCAAGAGAGCGGCCGGGTGA
            ************************************************************

AB004329    ACTACATCAAGCGACCAGGGGCGGTATTGGAGGCTGGCTGCGTGGTGGCAAAGCTAGAAC
BMS         AGTACATCAAGCGACCAGGGGCGGTATTGGAGGCTGGCTGCGTGGTGGCAAAGCTAGAAC
            * **********************************************************

AB004329    TCGATGACCCTTCAAAAGTGCACGCGGCACAGCCGTTCACAGGGGAGCTCCCCGCCCAGC
BMS         TCGATGACCCTTCAAAAGTGCACGCGGCACAGCCGTTCACAGGGGAGCTCCCCGCCCAGC
            ************************************************************

AB004329    AGACTCTGCCCATCCTCGGGGAGAGGCTGCATCAGGTGTTCCACAGCGTCTTGGAAAATC
BMS         AGACTCTGCCCATCCTCGGGGAGAGGCTGCATCAGGTGTTCCACAGCGTCTTGGAAAATC
            ************************************************************

AB004329    TGACCAATGTCATGAATGGCTACTGCCTGCCCGAGCCCTTCTTCAGCATGAAGCTGAAGG
BMS         TGACCAATGTCATGAATGGCTACTGCCTGCCCGAGCCCTTCTTCAGCATGAAGCTGAAGG
            ************************************************************

AB004329    ACTGGGTGGAGAAGCCCATGATGACTCTCCGGCATCCCTCCCTACCTCTGCTGGAGCTGC
BMS         ACTGGGTGGAGAAGCTCATGATGACTCTCCGGCATCCCTCCCTACCTCTGCTGGAGCTGC
            *************** ********************************************

AB004329    AGGAGATCATGACCAGCGTGGCAGACCGCATCCCGGTTCCGGTGGAGAAGGCAGTCCGCA
BMS         AGGAGATCATGACCAGCGTGGCAGGCCGCATCCCGGTTCCGGTGGAGAAGGCAGTCCGCA
            ************************ ***********************************

AB004329    GGGTGTTTGCGCAGGACGCCAGCAACATCACTTCGGTGCTCTGCCAGTTCCCCAGCCAGC
BMS         GGGTGATGGCGCAGTACGCCAGCAACATCACTTCGGTGCTCTGCCAGTTCCCCAGCCAGC
            ***** * ****** *********************************************

AB004329    AGATAGCCACCATCCTGGACTGCCACGCCGCCACCCTGCAGCGTAAGGTGGACCGAGAGG
BMS         AGATAGCCACCATCCTGGACTGCCACGCCGCCACCCTGCAGCGTAAGGTGGACCGAGAGG
            ************************************************************

AB004329    CCTTCTTCATGAACACACAGAGCATCGTGCAGCTGATCCAGAGATACCGCAGTGGGACCC
BMS         CCTTCTTCATGAACACACAGAGCATCGTGCAGCTGATCCAGAGATACCGCAGTGGGACCC
            ************************************************************

AB004329    GTGGCATCATGAAGGCTGTGGTGCTAGACCTCCTGAGGAGATATCTGAACGTGGAGCATC
BMS         GTGGCTACATGAAGGCTGTGGTGCTAGACCTCCTGAGGAGATATCTGAACGTGGAGCATC
            *****  *****************************************************

AB004329    ATTTCCAGCAAGCCCACTATGACAAGTGTGTGATCAACCTGAGGGAGCAGTTCAAGGCGG
BMS         ATTTCCAGCAAGCCCACTATGACAAGTGTGTGATCAACCTGAGGGAGCAGTTCAAGCCGG
            ******************************************************** ***

AB004329    ACATGACTCGGGTGCTGGACTGCATCTTCTCACACTCACAAGTGGCCAAGAAGAACCAGC
BMS         ACATGACTCGGGTGCTGGACTGCATCTTCTCACACTCACAAGTGGCCAAGAAGAACCAGC
            ************************************************************

AB004329    TGGTGACCATGTTGATAGATGAGCTGTGTGGCCCAGACCCCACCCTGTCAGAAGAGCTGA
BMS         TGGTGACCATGTTGATAGATGAGCTGTGTGGCCCAGACCCCACCCTGTCAGAAGAGCTGA
            ************************************************************
```

FIG. 3E

| | |
|---|---|
| AB004329 | CCTCCATCCTCAAGGAACTCACGCAGTTGAGCAGGAGTGAGCACTGCAAGGTGGCCCTCA |
| BMS | CCTCCATCCTCAAGGAACTCACGCAGTTGAGCAGGAGTGAGCACTGCAAGGTGGCCCTCA |
| | ************************************************************ |
| | |
| AB004329 | GAGCCAGGCAGGTCCTGATTGCCTCTCACCTCCCCTCCTACGAGCTGCGGCACAACCAGG |
| BMS | GAGCCAGGCAGGTCCTGATTGCCTCTCACCTCCCCTCCTACGAGCTGCGGCACAACCAGG |
| | ************************************************************ |
| | |
| AB004329 | TGGAGTC-ATCTTCCTGTCAGCCATTGACATGTAATGGCCACCAGTTCTGCCCGGAAAAC |
| BMS | TGGAGTCCATCTTCCTGTCAGCCATTGACATGTA-TGGCCACCAGTTCTGCCCGGAAAAC |
| | ******* ************************** ************************* |
| | |
| AB004329 | CTCAAGAAACTAATACTTTCGGAAACGACCATATTCGATGTCCTGCCCACTTTCTTCTAT |
| BMS | CTCAAGAAACTAATACTTTCGGAAACGACCATATTCGATGTCCTGCCCACTTTCTTCTAT |
| | ************************************************************ |
| | |
| AB004329 | CACGCTAACAAGGTCGTCTGTATGGCGTCCCTGGAGGTTTATGTGAGGAGAGGTTACATC |
| BMS | CACGCTAACAAGGTCGTCTGTATGGCGTCCCTGGAGGTTTATGTGAGGAGAGGTTACATC |
| | ************************************************************ |
| | |
| AB004329 | GCCTACGAGTTAAACAGCCTACAGCACCGGGAGCTCCCTGACGGCACCTGCGTGGTGGAG |
| BMS | GCCTACGAGTTAAACAGCCTACAGCACCGGGAGCTCCCTGACGGCACCTGCGTGGTGGAG |
| | ************************************************************ |
| | |
| AB004329 | TTCCAGTTCATGCTGCCGTCTTCCCACCCCAACCGGATGGCCATGCCCATCAATGTCTCT |
| BMS | TTCCAGTTCATGCTGCCGTCTTCCCACCCCAACCGGATGGCCATGCCCATCAATGTCTCT |
| | ************************************************************ |
| | |
| AB004329 | GACCCTGACCTGCTGAGACACAGTAAGGAACTCTTCATGGACAGTGGCTTCTCCCCACTG |
| BMS | GACCCTGACCTGCTGAGACACAGTAAGGAACTCTTCATGGACAGTGGCTTCTCCCCACTG |
| | ************************************************************ |
| | |
| AB004329 | TGTCACCAGCGGATGGGGGCCATGGTGGCCTTCAGGAGATTTGAGGAGTTCACCAGGAAC |
| BMS | TG---CCAGCGGATGGGGGCCATGGTGGCCTTCAGGAGATTTGAGGAGTTCACCAGGAAC |
| | **   ******************************************************* |
| | |
| AB004329 | TTCGATGAAGTCATCTCCTGCTTTGCCAACGTGCCTACAGACACTCCTCTCTTCAGTAAG |
| BMS | TTCGATGAAGTCATCTCCTGCTTTGCCAACGTGCCTACAGACACTCCTCTCTTCAGTAAG |
| | ************************************************************ |
| | |
| AB004329 | GCGTGCACTTCCCTCTACTCAGAGGAGGACAGCAAGAGCCTTCAAGAGGAGCCCATCCAC |
| BMS | GCGTGCACTTCCCTCTACTCAGAGGAGGACAGCAAGAGCCTTCAAGAGGAGCCCATCCAC |
| | ************************************************************ |
| | |
| AB004329 | ATCCTGAATGTGGCCATCCAGTGCGCCGACCACATGGAGGACGAGAGACTGGTGCCGGTT |
| BMS | ATCCTGAATGTGGCCATCCAGTGCGCCGACCACATGGAGGACGAGAGACTGGTGCCGGTT |
| | ************************************************************ |
| | |
| AB004329 | TTCCGTGCCTTTGTACAGTCCAAGAAACACATCCTTGTGGATTACGGACTGCGAAGAATC |
| BMS | TTCCGTGCCTTTGTACAGTCCAAGAAACACATCCTTGTGGATTACGGACTGCGAAGAATC |
| | ************************************************************ |
| | |
| AB004329 | ACATTCCTTATCGCCCAAGAGAAGGAATTTCCCAAGTTCTTCACGTTCAGAGCGAGAGAT |
| BMS | ACATTCCTTATCGCCCAAGAGAGAGAATTTCCCAAGTTCTTCACGTTCAGAGCGAGAGAT |
| | *********************  ************************************* |
| | |
| AB004329 | GAGTTTGCAGAAGACCGGATTTACCGCCACTTGGAGCCGGGCCTGGCCTTCCAGCTGGAG |
| BMS | GAGTTTGCAGAAGACCGGATTTACCGCCACTTGGAGCCGGCCCTGGCCTTCCAGCTGGAG |
| | **************************************** ****************** |

FIG. 3F

```
AB004329    CTGAGCCGGATGCGCAACTTTGACTTGACGGCCGTGCCCTGTGCCAACCATAAGATGCAT
BMS         CTGAGCCGGATGCGCAACTTTGACCTGACGGCCGTGCCCTGTGCCAACCATAAGATGCAT
            ************************ ***********************************

AB004329    CTTTACCTGGGAGCCGCCAAGGTGAAGGAAGGGCTGGAGGTGACTGACCACAGGTTCTTC
BMS         CTTTACCTGGGAGCCGCCAAGGTGAAGGAAGGGCTGGAGGTGACTGACCACAGGTTCTTC
            ************************************************************

AB004329    ATCCGAGCCATCATAAGGCACTCAGACCTGATCACCAAGGAAGCCTCCTTCGAGTACCTG
BMS         ATCCGAGCCATCATAAGGCACTCAGACCTGATCACCAAGGAAGCCTCCTTCGAGTACCTG
            ************************************************************

AB004329    CAGAATGAAGGGGAGCGGCTGCTGCTGGAAGCCATGGACGAGCTGGAGGTGGCGTTCAAC
BMS         CAGAATGAAGGGGAGCGGCTGCTGCTGGAAGCCATGGACGAGCTGGAGGTGGCGTTCAAC
            ************************************************************

AB004329    AACACCAGCGTGCGCACTGACTGCAACCACATCTTCCTCAACTTCGTGCCCACGTCATC
BMS         AACACCAGCGTGCGCACTGACTGCAACCACATCTTCCTCAACTTCGTGCCCACGGTCATC
            ****************************************************  ******

AB004329    ATGGACCCACTCAAGATCGAGGAGTCGGTGCGTGCCATGGTCATGCGTTACGGCAGTCGG
BMS         ATGGACCCACTCAAGATCGAGGAGTCGGTGCGTGCCATGGTCATGCGTTACGGCAGTCGG
            ************************************************************

AB004329    CTGTGGAAGCTCCGTGTGCTGCAGGCACAAGTTAAGATCAACATCCGTCAGACGACCTCG
BMS         CTGTGGAAGCTCCGTGTGCTGCAGGCAGAAGTTAAGATCAACATCCGTCAGACGACCTCG
            *************************** ********************************

AB004329    GACTGCGCCGTCCCCATTCGCCTCTTCATCACCAACGAGTCCGGCTACTACCTGGACATC
BMS         GACTGCGCCGTCCCCATTCGCCTCTTCATCACCAACGAGTCCGGCTACTACCTGGACATC
            ************************************************************

AB004329    AGCCTCTACAAAGAAGTGACCGACTCCAGATCCGGAAACATCATGTTTCATTCCTTCGGC
BMS         AGCCTCTACAAAGAAGTGACCGACTCCAGATCCGGAAACATCATGTTTCATTCCTTCGGC
            ************************************************************

AB004329    AACAAACAAGGGAGCCTGCACGGGATGCTGATCAACACGCCCTACGTCACCAAGGATCTG
BMS         AACAAACAAGGGAGCCTGCACGGGATGCTGATCAACACGCCCTACGTCACCAAGGATCTG
            ************************************************************

AB004329    CTCCAAGCCAAGCGATTCCAGGCGCAGTCCCTGGGGACCACCTATGTGTACGACTTCCCA
BMS         CTCCAAGCCAAGCGATTCCAGGCGCAGTCCCTGGGGACCACCTATGTGTACGACTTCCCA
            ************************************************************

AB004329    GAGATGTTCAGGCAGGCTCTCTTTAAATTGTGGGGCTCCCCAGAGAAGTACGGGCCCGAT
BMS         GAGATGTTCAGGCAGGCTCTCTTTAAATTGTGGGGCTCCCCAGAGAAGTACCCCAAAGAT
            ***************************************************   ***

AB004329    ATCCTGACATACACAGAGCTGGTGTTGGACTCCCAGGGCCAGCTGGTGGAGATGAACCGG
BMS         ATCCTGACATACACAGAGCTGGTGTTGGACTCCCAGGGCCAGCTGGTGGAGATGAACCGG
            ************************************************************

AB004329    CTTCCTGGTTGTAACGAGGTGGGCATGGTGGTTTTCAAAATGAGGTTCAAGACCCCGGAG
BMS         CTTCCTGGTTGTAACGAGGTGGGCATGGTGGTTTTCAAAATGAGGTTCAAGACCCCGGAG
            ************************************************************

AB004329    TATCCAGAAGGCCGGGACACTATCGTCATCGGCAACGACATTACCTTCCAAATCGGCTCT
BMS         TATCCAGAAGGCCGGGACACTATCGTCATCGGCAACGACATTACCTTCCAAATCGGCTCT
            ************************************************************
```

FIG. 3G

```
AB004329    TTCGGCATAGGAGAGGACTTCCTGTATCTACGGGCATCGGAGATGGCCCGGACAGAGGGC
BMS         TTCGGCATAGGAGAGGACTTCCTGTATCTACGGGCATCGGAGATGGCCCGGACAGAGGGC
            ************************************************************

AB004329    ATCCCCCAAATCTATCTGGCAGCCAACAGCGGCGCCGTATTGGGCCTGTCCGAGGAGATC
BMS         ATCCCCCAAATCTATCTGGCAGCCAACAGCGGGGCCCGTATGGGCCTGTCCGAGGAGATC
            ******************************** ***    *******************

AB004329    AAGCAGATATTCCAAGTGGCATGGGTGGACCCTGAGGATCCCTACAAAGGATTTAGATAC
BMS         AAGCAGATATTCCAAGTGGCATGGGTGGACCCTGAGGATCCCTACAAAGGATTTAGATAC
            ************************************************************

AB004329    CTGTACCTGTACCTGACGCCCCAAGACTACACCCAGATCAGCTCCCAGAACTCCGTGCAC
BMS         CTGTA------CCTGACGCCCCAAGACTACACCCAGATCAGCTCCCAGAACTCCGTGCAC
            *****      *************************************************

AB004329    TGCAAACACATCGAGGACGAAGGCGAGTC-AGGTAT--TATCGTTGATGTCATCGGGAAG
BMS         TGCAAACACATCGAGGACGAAGGCGAGTCCAGGTATGTCATCGTTGATGTCATCGGGAAG
            ***************************** ******  *********************

AB004329    GACAGCAGCCTGGGTGTGGAGAACCTGCGGGGCTCGGGCATGATTGCAGGAGAGGCTTCT
BMS         GACAGCAGCCTGGGTGTGGAGAACCTGCGGGGCTCGGGCATGATTGCAGGAGAGGCTTCT
            ************************************************************

AB004329    CTGGCTTACGAAAAAAATGTCACCATCAGCATGGTCGACTGCCGCGCCATCGGAATCGGG
BMS         CTGGCTTACGAAAAAAATGTCACCATCAGCATGGTGACCTGCCGCGCCATCGGAATCGGG
            ***********************************   **********************

AB004329    GCTTACCTGGTGAGGCTGGGCCAGCGGGTGATCCAGGTGGAAAACTCCCACATCATCCTC
BMS         GCTTACCTGGTGAGGCTGGGCCAGCGGGTGATCCAGGTGGAAAACTCCCACATCATCCTC
            ************************************************************

AB004329    ACGGGAGCCGGTGCTCTCAACAAGGTTCTGGGAAGAGAGGTCTACACATCCAACAACCAA
BMS         ACGGGAGCCGGTGCTCTCAACAAGGTCCTGGGAAGAGAGGTCTACACATCCAACAACCAA
            ************************** *********************************

AB004329    CTGGGCGGTGTGCAGATCATGCACACCAACGGGGTCTCCCACGTCACGGTGCCAGATGAC
BMS         CTGGGCGGTGTGCAGATCATGCACACCAACGGGGTCTCCCACGTCACGGTGCCAGATGAC
            ************************************************************

AB004329    TTCGAGGGGGTCTGCACCATTCTGGAATGGCTGTCATATATACCAAAGGACAATCAAAGC
BMS         TTCGAGGGGGTCTGCACCATTCTGGAATGGCTGTCATATATACCAAAGGACAATCAAAGC
            ************************************************************

AB004329    CCAGTCCCCATCATCACTCCTTCTGACCCCATCGACAGGGAAATTGAATTCACCCCAACC
BMS         CCAGTCCCCATCATCACTCCTTCTGACCCCATCGACAGGGAAATTGAATTCACCCCAACC
            ************************************************************

AB004329    AAAGCTCCCTATGACCCCAGGTGGCTGCTGGCAGGGAGGCCTCACCCAACTCTGAAGGGG
BMS         AAAGCTCCCTATGACCCCAGGTGGCTGCTGGCAGGGAGGCCTCACCCAACTCTGAAGGGG
            ************************************************************

AB004329    ACCTGGCAGAGTGGATTCTTCGACCATGGCAGTTTCAAGGAAATCATGGCACCCTGGGAC
BMS         ACCTGGCAGAGTGGATTCTTCGACCATGGCAGTTTCAAGGAAATCATGGCACCCTGGGCC
            ********************************************************* *

AB004329    CAGACTGTGGTGACTGGACGAGCAAGGCTGGGGGGCATCCCTGTAGGGGTGATTGCCGTG
BMS         CAGACTGTGGTGACTGGACGAGCAAGGCTGGGGGGCATCCCTGTAGGGGTGATTGCCGTG
            ************************************************************
```

FIG. 3H

```
AB004329    GAGACTCGGTCTGTGGAGGTGGCTGTCCCTGCTCACCCAGCCAACTTGGATTCTGAGGCC
BMS         GAGACTCGGTCTGTGGAGGTGGCTGTCCCTGCTGACCCTGCCAACTTGGATTCTGAGGCC
            ******************************** **** **********************

AB004329    AAGATCATCCAGCAGGCAGGCCAGGTGTGGTTCCCGGACTCTGCCTTCAAGACGGCTCAG
BMS         AAGATCATCCAGCAGGCAGGCCAGGTGTGGTTCCCGGACTCTGCCTTCAAGACGGCTCAG
            ************************************************************

AB004329    GTCATCAGGGACTTCAACCAGGAGCATCTGCTTCTCATGATCTTTGCTAACTGGAGAGGC
BMS         GTCATCAGGGACTTCAACCAGGAGCATCTGCCTCTCATGATCTTTGCTAACTGGAGAGGC
            ******************************* ****************************

AB004329    TTCTCGGGCGGCATGAAAGACATGTCCGAGCAGATGCTGAAGTTTGGCGCCTACATCGTG
BMS         TTCTCGGGCGGCATGAAAGACATGTACGAGCAGATGCTGAAGTTTGGCGCCTACATCGTG
            ************************* **********************************

AB004329    GACAGTCTCCGTCTGTCCAAGCAGCCAGTCCTCATCTATATCCCTCCCGGTGCCGAACTC
BMS         GACAGTCTCCGTCTGTTCAAGCAGCCAGTTCTCATCTATATCCCTCCCGGTGCCGAACTC
            **************** ************ ******************************

AB004329    CGAGGGGGCTCCTGGGTTGTCCTCGACTCCAGCATCAACCCCCTGTGCATAGAGATGTAC
BMS         CGAGGGGGCGCCTGGGTTGTCCTCGACTCCAGCATCAACCCCCTGTGCATAGAGATGTAC
            ********* **************************************************

AB004329    GCAGACAAAGAGAGCAGGGGGGGTGTTCTGGAGCCCGAGGGCACTGTGGAGATTAAGTTC
BMS         GCAGACAAAGAGAGCAGGGGGGGTGTCCTGGAGCCCGAGGGCACTGTGGAGATTAAGTTC
            ************************** *********************************

AB004329    CGGAAGAAAGATTTGGTGAAGACCATAAGGAGGATTGACCCAGTGTGCAAGAAACTCCTG
BMS         CGGAAGAAAGATTTGGTGAAGACCATAAGGAGGATTGACCCAGTGTGCAAGAAACTCCTG
            ************************************************************

AB004329    GAACCAGCTGGGGACA-CCCAGCTCCCTGACAAGGACCGGAAAGAGCTGGAGAGCCAGCT
BMS         GGGC-AGCTGGGGACAGCCCAGCTCCCTGACAAGGACCGGAAAGAGCTGGAGAGCCAGCT
            *   * **********  ******************************************

AB004329    GAAGGCCCGGGAGGACCTGCTGCTCCCCATCTACCACCAGGTGGCAGTGCAGTTCGCCGA
BMS         GAAGGCCCGGGAGGACCTGCTGCTCCCCATCTACCACCAGGTGGCAGTGCAGTTCGCCGA
            ************************************************************

AB004329    CCTGCATGACACGCCGGGCCACATGCTGAAGAAGGGAATCATTTCTGATGTCCTGGAGTG
BMS         CCTGCATGACACGCCGGGCCACATGCTGGAGAAGGGAATCATTTCTGATGTCTGGAGTG
            **************************** *********************** *******

AB004329    GAAGACCACACGTACTTACTTCTACTGGAGGCTGCGCCGGCTGCTGCTGGAGGCACAGGT
BMS         GAAGACCACACGTACCTACTTCTACTGGAGGCTGCGCCGGCTGCTGCTGGAGGCACAGGT
            *************** ********************************************

AB004329    GAAGCAGGAGATTCTGCGAGCCAGCCCTGAGCTGAGCCATGAGCACACGCAGTCCATGCT
BMS         GAAGCAGGAGATTCTGCGAGCCAGCCCTGAGCTGAGCCATGAGCACACGCAGTCCATGCT
            ************************************************************

AB004329    GCGACGCTGGTTTGTGGAGACCGAGGGCGCCGTCAAGGCCTACCTGTGGGACAGCAACCA
BMS         GCGACGCTGGTTTGTGGAGACCGAGGGCGCCGTCAAGGCCTACCTGTGGGACAGCAACCA
            ************************************************************

AB004329    GGTGGTAGTCCAGTGGCTGGAACAGCACTGGTCAGCCAGGGACAACCTGCGTTCCACTAT
BMS         GGTGGTAGTCCAGTGGCTGGAACAGCACTGGTCAGCCAGGGACAACCTGCGTTCCACTAT
            ************************************************************
```

FIG. 3I

```
AB004329    CCGAGAGAACCTCAATTATCTGAAGCGGGACTCTGTCCTCAAGACCATCCAAAGCCTAGT
BMS         CCGAGAGAACATCAATTATCTGAAGCGGGACTCTGTCCTCAAGACCATCCAAAGCCTAGT
            ********* **************************************************

AB004329    TCAAGAACACCCAGAGGCGACCATGGGACTGTGTGG-ATACCTGAGCCAGCACCTCACGC
BMS         TCAAGAACACCCAGAGGCGACCATGG-ACTGTGTGGCATACCTGAGCCAGCACCTCACGC
            ************************* ********  ************************

AB004329    CCGCTGAGCAGATGCAGGTGGTTCAGCTGCTGTCGACCACGGAGAGCCCAGCTTCCCACT
BMS         CCGCTGAGCAGATGCAGGTGGTTCAGCTGCTGTCTACCACGGAGAGCCCAGCTTCCCACT
            ********************************** *************************

AB004329    GA----------------------------------------------------------
BMS         GA
            **
```

FIG. 4A

```
AB004329    MVLLLFLTYLVFSCLTISWLKIWGKMTDSRPLSNSKVDASLLPSKEESF-ASDQSEEHGD
BMS_ratACC2 MVLLLFLTCLVFSCLTISWLKIWGKMTDSKPLSNSKVDASLLSSKEESFSASDQSEEHGD
            ******* ********************:***********.****** **********

AB004329    CSCPLTTPDQEELASHGGPVDASQQRNSVPTSHQKPPRNPLSSNDTCSSPELQTNGVAAP
BMS_ratACC2 CSCPLTTPDQEELASHGGPVDASQQRNSVPSSHQKPPRNPLSSNDTCSSPELQTNGVAAP
            ******************************:*****************************

AB004329    GSEVPEANGLPFPARPQTQRTGSPTREDKKQAPIKRQLMTSFILGSLDDNSSDEDPSSNS
BMS_ratACC2 GSEVPEANGLPFPARPQTQRTGSPTREDKKQAHIKRQLMTSFILGSLDDNSSDEDPSASS
            ******************************* ***********************:.*

AB004329    FQTSSRKGSRDSLGTCSQEAALNTADPESHTPTMRPSMSGLHLVKRGREHKKLDLHRDFT
BMS_ratACC2 FQTSSRKGSRASLGTLSQEAALNTADPESHTPTMRPSMSGLHLVKRGREHKKLDLHRDFT
            ********** **** ********************************************

AB004329    VASPAEFVTRFGGNRVIETVLIANNGIAAVKWMRSIRRWAYEMFRNERAIRFVVMVTPED
BMS_ratACC2 VASPAEFVTRFGGNRVIETVLIANNGIAAVKCMRSIRRWAYEMFRNERAIRFVVMVTPED
            ****************************** *****************************

AB004329    LKANAEYYKMADPVLPVPGGPNNNNYANVELIIDIAKRIPVQAVWAGWGHASENPKLPEL
BMS_ratACC2 LKANAEYIKMADQYVPVPGGPNNNNYANVELIIDIAKRIPVQAVWAGWGHASENPKLPEL
            ******* **** :**********************************************

AB004329    LCKHGIAFLGPRVRPMLGLGDRLSSTIVAQTLQIPTLPWSGSGLTVEWTEDSQHQGKCIS
BMS_ratACC2 LCKHEIAFLGPPSEAMWALGDKISSTIVAQTLQIPTLPWSGSGLTVEWTEDSQHQGKCIS
            **** ******   ..*  .***::***********************************

AB004329    VTEDVYEQGCVRDVDEGLQAAEKVGFPLMIKASEGGGGKGIRQAESAEDFPCFFRQVQSE
BMS_ratACC2 VPEDVYEQGCVRDVDEGLQAAEKVGFPLMIKASEGGGGKGIRRAESAEDFPMLFRQVQSE
            *.****************************************:*******  :******

AB004329    IPGSPIFLMKLAQNARHLEVQVLADQYGNAVSLFGRDCSIQRRHQKIIEEAPANIAAPAV
BMS_ratACC2 IPGSPIFLMKLAQNARHLEVQVLADQYGNAVSLFGRDCSIQRRHQKIIEEAPATIAAPAV
            *****************************************************.******

AB004329    FEFMEQCAVLLAKTVVYVSAGTVGYLYSQDGSFHFLELNPRLQVEHPCTEMIADVNLPAA
BMS_ratACC2 FEFMEQCAVLLAKTVGYVSAGTVEYLYSQDGSFHFLELNPRLQVEHPCTEMIADVNLPAA
            *************** ****** *************************************

AB004329    QLQIAMGVPLHRLKDIRLLYGESPWGVTPVSFETPLSPPIARGHVIAARITSENPDEAFK
BMS_ratACC2 QLQIAMGVPLHRLKDIRLLYGESPWGVTPVSFETPLSPPIARGHVIAARITSENPDEGFK
            ********************************************************.**

AB004329    PSSGTVQELNFRSNKNVWGYFSVAAAGGLHEFPISQFGHCFSWGENQEEAISNMVVALKE
BMS_ratACC2 PSSGTVQELNFRSNKNVWGYFSVAAAGGLHEFADSQFGHCFSWGENREEAISNMVVALKE
            ******************************* .************:*************

AB004329    LSIRGDFRTTVEYLVNLLETESLQNNDIDTGWLDHLIAQRVQAEKPDIMLGVVFGALNVA
BMS_ratACC2 LSIRGDFRTTVEYLVNLLETESFQNNDIDTGWLDHLIAQRVQAEKPDIMLGVVCGALNVA
            **********************:***************************** ******

AB004329    DAMFRTCITEFLHSLERGQVLPADSLLNIVDVELIYGGIKYVLKVARQSLTMFVLIMNGC
BMS_ratACC2 DAMFRTCMTEFLHSLERGQVLPADSLLNIVDVELIYGGIKYVLKVARQSLTMFVLIMNGC
            *******:****************************************************

AB004329    HIEIDAHRPNDGGLLLSYNGSSYTTYMKEEVDSYRITIGNKTCVFEKENDPTVLRSPSAG
BMS_ratACC2 HIEIDAHRLNDGGLLLSYNGSSYTTYMKEEVDSYRITIGNKTCVFEKENDPTVLRSPSAG
            ******** ****************************************************
```

FIG. 4B

```
AB004329      KLMQYTVEDGQHVEVGSSYAEMEVMKMIMTLNVQESGRVNYIKRPGAVLEAGCVVAKLEL
BMS_ratACC2   KLMQYTVEDGQHVEVGSSYAEMEVMKMIMTLNVQESGRVKYIKRPGAVLEAGCVVAKLEL
              **************************************:*********************

AB004329      DDPSKVHAAQPFTGELPAQQTLPILGERLHQVFHSVLENLTNVMNGYCLPEPFFSMKLKD
BMS_ratACC2   DDPSKVHAAQPFTGELPAQQTLPILGERLHQVFHSVLENLTNVMNGYCLPEPFFSMKLKD
              ************************************************************

AB004329      WVEKPMMTLRHPSLPLLELQEIMTSVADRIPVPVEKAVRRVFAQDASNITSVLCQFPSQQ
BMS_ratACC2   WVEKLMMTLRHPSLPLLELQEIMTSVAGRIPVPVEKAVRRVMAQYASNITSVLCQFPSQQ
              ****  ********************** .**********:**  ***************

AB004329      IATILDCHAATLQRKVDREAFFMNTQSIVQLIQRYRSGTRGIMKAVVLDLLRRYLNVEHH
BMS_ratACC2   IATILDCHAATLQRKVDREAFFMNTQSIVQLIQRYRSGTRGYMKAVVLDLLRRYLNVEHH
              ***************************************** *****************

AB004329      FQQAHYDKCVINLREQFKADMTRVLDCIFSHSQVAKKNQLVTMLIDELCGPDPTLSEELT
BMS_ratACC2   FQQAHYDKCVINLREQFKPDMTRVLDCIFSHSQVAKKNQLVTMLIDELCGPDPTLSEELT
              ******************.*****************************************

AB004329      SILKELTQLSRSEHCKVALRARQVLIASHLPSYELRHNQVESSSCQPLTCNGHQFCPENL
BMS_ratACC2   SILKELTQLSRSEHCKVALRARQVLIASHLPSYELRHNQVESIFLSAIDMYGHQFCPENL
              ******************************************   ..:   *********

AB004329      KKLILSETTIFDVLPTFFYHANKVVCMASLEVYVRRGYIAYELNSLQHRELPDGTCVVEF
BMS_ratACC2   KKLILSETTIFDVLPTFFYHANKVVCMASLEVYVRRGYIAYELNSLQHRELPDGTCVVEF
              ************************************************************

AB004329      QFMLPSSHPNRMAMPINVSDPDLLRHSKELFMDSGFSPLCHQRMGAMVAFRRFEEFTRNF
BMS_ratACC2   QFMLPSSHPNRMAMPINVSDPDLLRHSKELFMDSGFSPLC-QRMGAMVAFRRFEEFTRNF
              *************************************** *******************

AB004329      DEVISCFANVPTDTPLFSKACTSLYSEEDSKSLQEEPIHILNVAIQCADHMEDERLVPVF
BMS_ratACC2   DEVISCFANVPTDTPLFSKACTSLYSEEDSKSLQEEPIHILNVAIQCADHMEDERLVPVF
              ************************************************************

AB004329      RAFVQSKKHILVDYGLRRITFLIAQEKEFPKFFTFRARDEFAEDRIYRHLEPGLAFQLEL
BMS_ratACC2   RAFVQSKKHILVDYGLRRITFLIAQEREFPKFFTFRARDEFAEDRIYRHLEPALAFQLEL
              *************************:************************.********

AB004329      SRMRNFDLTAVPCANHKMHLYLGAAKVKEGLEVTDHRFFIRAIIRHSDLITKEASFEYLQ
BMS_ratACC2   SRMRNFDLTAVPCANHKMHLYLGAAKVKEGLEVTDHRFFIRAIIRHSDLITKEASFEYLQ
              ************************************************************

AB004329      NEGERLLLEAMDELEVAFNNTSVRTDCNHIFLNFVAHVIMDPLKIEESVRAMVMRYGSRL
BMS_ratACC2   NEGERLLLEAMDELEVAFNNTSVRTDCNHIFLNFVPTVIMDPLKIEESVRAMVMRYGSRL
              ***********************************. ***********************

AB004329      WKLRVLQAQVKINIRQTTSDCAVPIRLFITNESGYYLDISLYKEVTDSRSGNIMFHSFGN
BMS_ratACC2   WKLRVLQAEVKINIRQTTSDCAVPIRLFITNESGYYLDISLYKEVTDSRSGNIMFHSFGN
              ********:***************************************************

AB004329      KQGSLHGMLINTPYVTKDLLQAKRFQAQSLGTTYVYDFPEMFRQALFKLWGSPEKYGPDI
BMS_ratACC2   KQGSLHGMLINTPYVTKDLLQAKRFQAQSLGTTYVYDFPEMFRQALFKLWGSPEKYPKDI
              ******************************************************** **

AB004329      LTYTELVLDSQGQLVEMNRLPGCNEVGMVVFKMRFKTPEYPEGRDTIVIGNDITFQIGSF
BMS_ratACC2   LTYTELVLDSQGQLVEMNRLPGCNEVGMVVFKMRFKTPEYPEGRDTIVIGNDITFQIGSF
              ************************************************************
```

FIG. 4C

```
AB004329    GIGEDFLYLRASEMARTEGIPQIYLAANSGAVLGLSEEIKQIFQVAWVDPEDPYKGFRYL
BMS_ratACC2 GIGEDFLYLRASEMARTEGIPQIYLAANSGARMGLSEEIKQIFQVAWVDPEDPYKGFR--
            ******************************:**************************

AB004329    YLYLTPQDYTQISSQNSVHCKHIEDEGES-GIIVDVIGKDSSLGVENLRGSGMIAGEASL
BMS_ratACC2 YLYLTPQDYTQISSQNSVHCKHIEDEGESRYVIVDVIGKDSSLGVENLRGSGMIAGEASL
            *****************************  :***************************

AB004329    AYEKNVTISMVDCRAIGIGAYLVRLGQRVIQVENSHIILTGAGALNKVLGREVYTSNNQL
BMS_ratACC2 AYEKNVTISMVTCRAIGIGAYLVRLGQRVIQVENSHIILTGAGALNKVLGREVYTSNNQL
            *********** ************************************************

AB004329    GGVQIMHTNGVSHVTVPDDFEGVCTILEWLSYIPKDNQSPVPIITPSDPIDREIEFTPTK
BMS_ratACC2 GGVQIMHTNGVSHVTVPDDFEGVCTILEWLSYIPKDNQSPVPIITPSDPIDREIEFTPTK
            ************************************************************

AB004329    APYDPRWLLAGRPHPTLKGTWQSGFFDHGSFKEIMAPWDQTVVTGRARLGGIPVGVIAVE
BMS_ratACC2 APYDPRWLLAGRPHPTLKGTWQSGFFDHGSFKEIMAPWAQTVVTGRARLGGIPVGVIAVE
            ************************************** *********************

AB004329    TRSVEVAVPAHPANLDSEAKIIQQAGQVWFPDSAFKTAQVIRDFNQEHLLLMIFANWRGF
BMS_ratACC2 TRSVEVAVPADPANLDSEAKIIQQAGQVWFPDSAFKTAQVIRDFNQEHLPLMIFANWRGF
            **********.***********************************  **********

AB004329    SGGMKDMSEQMLKFGAYIVDSLRLSKQPVLIYIPPGAELRGGSWVVLDSSINPLCIEMYA
BMS_ratACC2 SGGMKDMYEQMLKFGAYIVDSLRLFKQPVLIYIPPGAELRGGAWVVLDSSINPLCIEMYA
            ******* **************** *****************:*****************

AB004329    DKESRGGVLEPEGTVEIKFRKKDLVKTIRRIDPVCKKLLEPAGDTQLPDKDRKELESQLK
BMS_ratACC2 DKESRGGVLEPEGTVEIKFRKKDLVKTIRRIDPVCKKLLGQLGTAQLPDKDRKELESQLK
            ***************************************   *  :*************

AB004329    AREDLLLPIYHQVAVQFADLHDTPGHMLKKGIISDVLEWKTTRTYFYWRLRRLLLEAQVK
BMS_ratACC2 AREDLLLPIYHQVAVQFADLHDTPGHMLEKGIISDVLEWKTTRTYFYWRLRRLLLEAQVK
            ***************************:********************************

AB004329    QEILRASPELSHEHTQSMLRRWFVETEGAVKAYLWDSNQVVVQWLEQHWSARDNLRSTIR
BMS_ratACC2 QEILRASPELSHEHTQSMLRRWFVETEGAVKAYLWDSNQVVVQWLEQHWSARDNLRSTIR
            ************************************************************

AB004329    ENLNYLKRDSVLKTIQSLVQEHPEATMGLCGYLSQHLTPAEQMQVVQLLSTTESPASH
BMS_ratACC2 ENINYLKRDSVLKTIQSLVQEHPEATMDCVAYLSQHLTPAEQMQVVQLLSTTESPASH
            **:***********************   .*****************************
```

FIG. 5A

```
ratACC2_C7    TCCCTTGACAGGTTGTCTGAATGGTCTTGCTTCTCTTTCTGACTTGCCTGGTTTTCTCCT
RatACC2       ------------------ATGGTCTTGCTTCTCTTTCTGACTTGCCTGGTTTTCTCCT
                                ****************************************** ratACC2_C7    GCCTGACCATTTCCTGGTTAAAAATCTGGGGGAAGATGACAGACTCGAAGCCGCTCAGCA
RatACC2       GCCTGACCATTTCCTGGTTAAAAATCTGGGGGAAGATGACAGACTCGAAGCCGCTCAGCA
              ************************************************************ ratACC2_C7    ACAGTAAGGTGGATGCAAGCCTCCTTTCGAGCAAGGAGGAGTCCTTTTCAGCCTCGGACC
RatACC2       ACAGTAAGGTGGATGCAAGCCTCCTTTCGAGCAAGGAGGAGTCCTTTTCAGCCTCGGACC
              ************************************************************ ratACC2_C7    AGTCAGAGGAGCATGGCGACTGCAGCTGTCCGTTGACAACTCCTGACCAGGAGGAGCTGG
RatACC2       AGTCAGAGGAGCATGGCGACTGCAGCTGTCCGTTGACAACTCCTGACCAGGAGGAGCTGG
              ************************************************************ ratACC2_C7    CCTCCCACGGAGGTCCTGTAGATGCCAGTCAGCAGAGGAACTCTGTGCCAAGCTCACACC
RatACC2       CCTCCCACGGAGGTCCTGTAGATGCCAGTCAGCAGAGGAACTCTGTGCCAAGCTCACACC
              ************************************************************ ratACC2_C7    AGAAGCCTCCGAGGAACCCACTATCTTCCAATGACACCTGTTCCTCCCCAGAACTCCAAA
RatACC2       AGAAGCCTCCGAGGAACCCACTATCTTCCAATGACACCTGTTCCTCCCCAGAACTCCAAA
              ************************************************************ ratACC2_C7    CCAACGGGGTAGCAGCCCCTGGCTCAGAGGTTCCAGAAGCCAACGGGTTGCCTTTCCCAG
RatACC2       CCAACGGGGTAGCAGCCCCTGGCTCAGAGGTTCCAGAAGCCAACGGGTTGCCTTTCCCAG
              ************************************************************ ratACC2_C7    CCAGGCCTCAGACCCAGAGAACGGGATCCCCCACTAGGGAGGACAAGAAGCAGGCACACA
RatACC2       CCAGGCCTCAGACCCAGAGAACGGGATCCCCCACTAGGGAGGACAAGAAGCAGGCACACA
              ************************************************************ ratACC2_C7    TCAAGAGGCAGCTGATGACCAGCTTTATCCTGGGCTCCCTCGATGACAACTCCTCTGACG
RatACC2       TCAAGAGGCAGCTGATGACCAGCTTTATCCTGGGCTCCCTCGATGACAACTCCTCTGACG
              ************************************************************ ratACC2_C7    AGGACCCTAGTGCTAGCTCCTTCCAGACCTCCTCTCGGAAGGGCAGCAGGGCTAGCCTGG
RatACC2       AGGACCCTAGTGCTAGCTCCTTCCAGACCTCCTCTCGGAAGGGCAGCAGGGCTAGCCTGG
              ************************************************************ ratACC2_C7    GCACCCTGTCCCAGGAGGCTGCATTGAACACAGCTGATCCTGAGTCTCACACACCTACTA
RatACC2       GCACCCTGTCCCAGGAGGCTGCATTGAACACAGCTGATCCTGAGTCTCACACACCTACTA
              ************************************************************ ratACC2_C7    TGAGGCCCAGCATGTCTGGACTCCATCTGGTGAAGAGAGGCCGTGAACACAAGAAACTGG
RatACC2       TGAGGCCCAGCATGTCTGGACTCCATCTGGTGAAGAGAGGCCGTGAACACAAGAAACTGG
              ************************************************************ ratACC2_C7    ACCTGCACAGAGATTTCACTGTAGCTTCCCCAGCCGAATTTGTCACCCGCTTTGGAGGCA
RatACC2       ACCTGCACAGAGATTTCACTGTAGCTTCCCCAGCCGAATTTGTCACCCGCTTTGGAGGCA
              ************************************************************ ratACC2_C7    ACAGGGTTATCGAGACGGTGCTCATCGCCAATAATGGTATCGCTGCGGTCAAGTGTATGC
RatACC2       ACAGGGTTATCGAGACGGTGCTCATCGCCAATAATGGTATCGCTGCGGTCAAGTGTATGC
              ************************************************************ ratACC2_C7    GCTCCATCCGCCGCTGGGCCTATGAGATGTTCCGTAATGAACGCGCCATCCGGTTTGTGG
RatACC2       GCTCCATCCGCCGCTGGGCCTATGAGATGTTCCGTAATGAACGCGCCATCCGGTTTGTGG
              ************************************************************
```

FIG. 5B

```
ratACC2_C7    TTATGGTGACACCCGAGGATCTTAAGGCCAACGCAGAGTACATCAAGATGGCGGACCAGT
RatACC2       TTATGGTGACACCCGAGGATCTTAAGGCCAACGCAGAGTACATCAAGATGGCGGACCAGT
              ************************************************************ ratACC2_C7    ACGTTCCGGTCCCAGGAGGACCCAATAATAACAACTACGCCAACGTTGAGCTGATCATAG
RatACC2       ACGTTCCGGTCCCAGGAGGACCCAATAATAACAACTACGCCAACGTTGAGCTGATCATAG
              ************************************************************ ratACC2_C7    ACATTGCCAAGAGAATCCCTGTGCAGGCCGTGTGGGCTGGCTGGGGCCACGCTTCGGAAA
RatACC2       ACATTGCCAAGAGAATCCCTGTGCAGGCCGTGTGGGCTGGCTGGGGCCACGCTTCGGAAA
              ************************************************************ ratACC2_C7    ACCCCAAACTTCCAGAGCTACTGTGCAAGCACGAGATTGCTTTCCTAGGTCCCCCGAGTG
RatACC2       ACCCCAAACTTCCAGAGCTACTGTGCAAGCACGAGATTGCTTTCCTAGGTCCCCCGAGTG
              ************************************************************ ratACC2_C7    AGGCCATGTGGGCCCTGGGAGACAAGATCTCCTCCACCATTGTAGCCCAGACATTGCAGA
RatACC2       AGGCCATGTGGGCCCTGGGAGACAAGATCTCCTCCACCATTGTAGCCCAGACATTGCAGA
              ************************************************************ ratACC2_C7    TCCCAACTCTACCCTGGAGCGGAAGCGGTCTCACAGTGGAGTGGACGGAGGACAGCCAGC
RatACC2       TCCCAACTCTACCCTGGAGCGGAAGCGGTCTCACAGTGGAGTGGACGGAGGACAGCCAGC
              ************************************************************ ratACC2_C7    ATCAGGGCAAATGCATCAGCGTCCCGGAAGACGTTTATGAACAAGGCTGTGTGAGAGATG
RatACC2       ATCAGGGCAAATGCATCAGCGTCCCGGAAGACGTTTATGAACAAGGCTGTGTGAGAGATG
              ************************************************************ ratACC2_C7    TGGACGAAGGCTTGCAGGCAGCAGAAAAAGTAGGATTTCCTCTGATGATCAAAGCCTCTG
RatACC2       TGGACGAAGGCTTGCAGGCAGCAGAAAAAGTAGGATTTCCTCTGATGATCAAAGCCTCTG
              ************************************************************ ratACC2_C7    AAGGTGGAGGAGGGAAAGGAATCCGCAGGGCTGAGAGTGCAGAGGACTTCCCGATGCTTT
RatACC2       AAGGTGGAGGAGGGAAAGGAATCCGCAGGGCTGAGAGTGCAGAGGACTTCCCGATGCTTT
              ************************************************************ ratACC2_C7    TCAGACAGGTGCAGAGTGAGATCCCGGGCTCGCCCATCTTTCTCATGAAGCTGGCCCAGA
RatACC2       TCAGACAGGTGCAGAGTGAGATCCCGGGCTCGCCCATCTTTCTCATGAAGCTGGCCCAGA
              ************************************************************ ratACC2_C7    ATGCTCGGCACTTGGAGGTCCAGGTCTTGGCAGATCAGTATGGGAACGCAGTGTCCCTGT
RatACC2       ATGCTCGGCACTTGGAGGTCCAGGTCTTGGCAGATCAGTATGGGAACGCAGTGTCCCTGT
              ************************************************************ ratACC2_C7    TTGGACGAGACTGCTCCATCCAGAGGCGGCACCAGAAGATCATTGAGGAGGCTCCGGCCA
RatACC2       TTGGACGAGACTGCTCCATCCAGAGGCGGCACCAGAAGATCATTGAGGAGGCTCCGGCCA
              ************************************************************ ratACC2_C7    CCATCGCTGCTCCGGCTGTGTTTGAGTTCATGGAACAGTGTGCCGTCCTCCTGGCCAAGA
RatACC2       CCATCGCTGCTCCGGCTGTGTTTGAGTTCATGGAACAGTGTGCCGTCCTCCTGGCCAAGA
              ************************************************************ ratACC2_C7    CTGTGGGTTATGTGAGCGCGGGAACCGTGGAGTACCTATACAGCCAGGATGGCAGCTTTC
RatACC2       CTGTGGGTTATGTGAGCGCGGGAACCGTGGAGTACCTATACAGCCAGGATGGCAGCTTTC
              ************************************************************ ratACC2_C7    ACTTCTTGGAGCTGAACCCACGCCTGCAGGTGGAACATCCCTGCACTGAAATGATCGCAG
RatACC2       ACTTCTTGGAGCTGAACCCACGCCTGCAGGTGGAACATCCCTGCACTGAAATGATCGCAG
              ************************************************************
```

FIG. 5C

```
ratACC2_C7    ATGTCAACCTGCCCGCTGCACAGTTACAGATCGCCATGGGCGTGCCCCTGCACCGGCTGA
RatACC2       ATGTCAACCTGCCCGCTGCACAGTTACAGATCGCCATGGGCGTGCCCCTGCACCGGCTGA
              ************************************************************ ratACC2_C7    AGGACATACGGCTTCTGTACGGAGAGTCCCCCTGGGGAGTGACCCCCGTTTCTTTTGAGA
RatACC2       AGGACATACGGCTTCTGTACGGAGAGTCCCCCTGGGGAGTGACCCCCGTTTCTTTTGAGA
              ************************************************************ ratACC2_C7    CCCCTTTGAGCCCTCCCATTGCCCGAGGCCATGTCATTGCAGCCAGGATCACCAGCGAAA
RatACC2       CCCCTTTGAGCCCTCCCATTGCCCGAGGCCATGTCATTGCAGCCAGGATCACCAGCGAAA
              ************************************************************ ratACC2_C7    ACCCAGACGAGGGCTTTAAGCCAAGCTCAGGGACAGTGCAGGAGCTGAACTTCCGCAGCA
RatACC2       ACCCAGACGAGGGCTTTAAGCCAAGCTCAGGGACAGTGCAGGAGCTGAACTTCCGCAGCA
              ************************************************************ ratACC2_C7    ACAAGAACGTGTGGGGTTACTTCAGCGTGGCCGCTGCTGGGGGCTTGCACGAGTTTGCCG
RatACC2       ACAAGAACGTGTGGGGTTACTTCAGCGTGGCCGCTGCTGGGGGCTTGCACGAGTTTGCCG
              ************************************************************ ratACC2_C7    ATTCCCAGTTTGGGCACTGCTTCTCCTGGGGCGAGAACCGTGAAGAGGCTATTTCGAACA
RatACC2       ATTCCCAGTTTGGGCACTGCTTCTCCTGGGGCGAGAACCGTGAAGAGGCTATTTCGAACA
              ************************************************************ ratACC2_C7    TGGTGGTGGCTTTGAAAGAACTGTCTATCCGGGGTGACTTCCGGACCACCGTGGAATATC
RatACC2       TGGTGGTGGCTTTGAAAGAACTGTCTATCCGGGGTGACTTCCGGACCACCGTGGAATATC
              ************************************************************ ratACC2_C7    TCGTCAACCTTCTGGAGACGGAGAGCTTCCAGAACAATGATATCGACACGGGGTGGCTGG
RatACC2       TCGTCAACCTTCTGGAGACGGAGAGCTTCCAGAACAATGATATCGACACGGGGTGGCTGG
              ************************************************************ ratACC2_C7    ACCACCTCATCGCTCAGCGGGTGCAGGCAGAGAAGCCGGACATCATGCTCGGGGTGGTGT
RatACC2       ACCACCTCATCGCTCAGCGGGTGCAGGCAGAGAAGCCGGACATCATGCTCGGGGTGGTGT
              ************************************************************ ratACC2_C7    GTGGGGCCTTGAACGTGGCAGACGCGATGTTCAGAACCTGTATGACGGAATTCCTGCATT
RatACC2       GTGGGGCCTTGAACGTGGCAGACGCGATGTTCAGAACCTGTATGACGGAATTCCTGCATT
              ************************************************************ ratACC2_C7    CCTTGGAAAGGGGTCAGGTCCTCCCGGCTGATTCTCTGCTGAACATCGTGGACGTTGAGT
RatACC2       CCTTGGAAAGGGGTCAGGTCCTCCCGGCTGATTCTCTGCTGAACATCGTGGACGTTGAGT
              ************************************************************ ratACC2_C7    TGATTTACGGAGGCATCAAATATGTTCTCAAGGTGGCCCGGCAGTCCCTGACCATGTTTG
RatACC2       TGATTTACGGAGGCATCAAATATGTTCTCAAGGTGGCCCGGCAGTCCCTGACCATGTTTG
              ************************************************************ ratACC2_C7    TCCTCATCATGAATGGTTGCCACATCGAGATCGATGCCCACCGGCTGAACGATGGGGGCC
RatACC2       TCCTCATCATGAATGGTTGCCACATCGAGATCGATGCCCACCGGCTGAACGATGGGGGCC
              ************************************************************ ratACC2_C7    TGCTCCTGTCCTACAATGGTAGCAGTTACACTACATACATGAAGGAAGAGGTGGACAGTT
RatACC2       TGCTCCTGTCCTACAATGGTAGCAGTTACACTACATACATGAAGGAAGAGGTGGACAGTT
              ************************************************************ ratACC2_C7    ACCGGATCACTATCGGCAATAAGACATGCGTGTTTGAAAAGGAAAACGACCCCACCGTCC
RatACC2       ACCGGATCACTATCGGCAATAAGACATGCGTGTTTGAAAAGGAAAACGACCCCACCGTCC
              ************************************************************
```

FIG. 5D

```
ratACC2_C7   TGAGATCCCCCTCGGCTGGGAAGCTGATGCAGTACACGGTGGAGGATGGCCAGCACGTGG
RatACC2      TGAGATCCCCCTCGGCTGGGAAGCTGATGCAGTACACGGTGGAGGATGGCCAGCACGTGG
             ************************************************************ ratACC2_C7   AAGTCGGGAGCAGCTATGCTGAGATGGAGGTGATGAAGATGATCATGACCCTGAACGTGC
RatACC2      AAGTCGGGAGCAGCTATGCTGAGATGGAGGTGATGAAGATGATCATGACCCTGAACGTGC
             ************************************************************ ratACC2_C7   AAGAGAGCGGCCGGGTGAAGTACATCAAGCGACCAGGGGCGGTATTGGAGGCTGGCTGCG
RatACC2      AAGAGAGCGGCCGGGTGAAGTACATCAAGCGACCAGGGGCGGTATTGGAGGCTGGCTGCG
             ************************************************************ ratACC2_C7   TGGTGGCAAAGCTAGAACTCGATGACCCTTCAAAAGTGCACGCGGCACAGCCGTTCACAG
RatACC2      TGGTGGCAAAGCTAGAACTCGATGACCCTTCAAAAGTGCACGCGGCACAGCCGTTCACAG
             ************************************************************ ratACC2_C7   GGGAGCTCCCCGCCCAGCAGACTCTGCCCATCCTCGGGGAGAGGCTGCATCAGGTGTTCC
RatACC2      GGGAGCTCCCCGCCCAGCAGACTCTGCCCATCCTCGGGGAGAGGCTGCATCAGGTGTTCC
             ************************************************************ ratACC2_C7   ACAGCGTCTTGGAAAATCTGACCAATGTCATGAATGGCTACTGCCTGCCCGAGCCCTTCT
RatACC2      ACAGCGTCTTGGAAAATCTGACCAATGTCATGAATGGCTACTGCCTGCCCGAGCCCTTCT
             ************************************************************ ratACC2_C7   TCAGCATGAAGCTGAAGGACTGGGTGGAGAAGCTCATGATGACTCTCCGGCATCCCTCCC
RatACC2      TCAGCATGAAGCTGAAGGACTGGGTGGAGAAGCTCATGATGACTCTCCGGCATCCCTCCC
             ************************************************************ ratACC2_C7   TACCTCTGCTGGAGCTGCAGGAGATCATGACCAGCGTGGCAGGCCGCATCCCGGTTCCGG
RatACC2      TACCTCTGCTGGAGCTGCAGGAGATCATGACCAGCGTGGCAGGCCGCATCCCGGTTCCGG
             ************************************************************ ratACC2_C7   TGGAGAAGGCAGTCCGCAGGGTGATGGCGCAGTACGCCAGCAACATCACTTCGGTGCTCT
RatACC2      TGGAGAAGGCAGTCCGCAGGGTGATGGCGCAGTACGCCAGCAACATCACTTCGGTGCTCT
             ************************************************************ ratACC2_C7   GCCAGTTCCCCAGCCAGCAGATAGCCACCATCCTGGACTGCCACGCCGCCACCCTGCAGC
RatACC2      GCCAGTTCCCCAGCCAGCAGATAGCCACCATCCTGGACTGCCACGCCGCCACCCTGCAGC
             ************************************************************ ratACC2_C7   GTAAGGTGGACCGAGAGGCCTTCTTCATGAACACACAGAGCATCGTGCAGCTGATCCAGA
RatACC2      GTAAGGTGGACCGAGAGGCCTTCTTCATGAACACACAGAGCATCGTGCAGCTGATCCAGA
             ************************************************************ ratACC2_C7   GATACCGCAGTGGGACCCGTGGCTACATGAAGGCTGTGGTGCTAGACCTCCTGAGGAGAT
RatACC2      GATACCGCAGTGGGACCCGTGGCTACATGAAGGCTGTGGTGCTAGACCTCCTGAGGAGAT
             ************************************************************ ratACC2_C7   ATCTGAACGTGGAGCATCATTTCCAGCAAGCCCACTATGACAAGTGTGTGATCAACCTGA
RatACC2      ATCTGAACGTGGAGCATCATTTCCAGCAAGCCCACTATGACAAGTGTGTGATCAACCTGA
             ************************************************************ ratACC2_C7   GGGAGCAGTTCAAGCCGGACATGACTCGGGTGCTGGACTGCATCTTCTCACACTCACAAG
RatACC2      GGGAGCAGTTCAAGCCGGACATGACTCGGGTGCTGGACTGCATCTTCTCACACTCACAAG
             ************************************************************ ratACC2_C7   TGGCCAAGAAGAACCAGCTGGTGACCATGTTGATAGATGAGCTGTGTGGCCCAGACCCCA
RatACC2      TGGCCAAGAAGAACCAGCTGGTGACCATGTTGATAGATGAGCTGTGTGGCCCAGACCCCA
             ************************************************************
```

FIG. 5E

```
ratACC2_C7    CCCTGTCAGAAGAGCTGACCTCCATCCTCAAGGAACTCACGCAGTTGAGCAGGAGTGAGC
RatACC2       CCCTGTCAGAAGAGCTGACCTCCATCCTCAAGGAACTCACGCAGTTGAGCAGGAGTGAGC
              ************************************************************ ratACC2_C7    ACTGCAAGGTGGCCCTCAGAGCCAGGCAGGTCCTGATTGCCTCTCACCTCCCCTCCTACG
RatACC2       ACTGCAAGGTGGCCCTCAGAGCCAGGCAGGTCCTGATTGCCTCTCACCTCCCCTCCTACG
              ************************************************************ ratACC2_C7    AGCTGCGGCACAACCAGGTGGAGTCCATCTTCCTGTCAGCCATTGACATGTATGGCCACC
RatACC2       AGCTGCGGCACAACCAGGTGGAGTCCATCTTCCTGTCAGCCATTGACATGTATGGCCACC
              ************************************************************ ratACC2_C7    AGTTCTGCCCGGAAAACCTCAAGAAACTAATACTTTCGGAAACGACCATATTCGATGTCC
RatACC2       AGTTCTGCCCGGAAAACCTCAAGAAACTAATACTTTCGGAAACGACCATATTCGATGTCC
              ************************************************************ ratACC2_C7    TGCCCACTTTCTTCTATCACGCTAACAAGGTCGTCTGTATGGCGTCCCTGGAGGTTTATG
RatACC2       TGCCCACTTTCTTCTATCACGCTAACAAGGTCGTCTGTATGGCGTCCCTGGAGGTTTATG
              ************************************************************ ratACC2_C7    TGAGGAGAGGTTACATCGCCTACGAGTTAAACAGCCTACAGCACCGGGAGCTCCCTGACG
RatACC2       TGAGGAGAGGTTACATCGCCTACGAGTTAAACAGCCTACAGCACCGGGAGCTCCCTGACG
              ************************************************************ ratACC2_C7    GCACCTGCGTGGTGGAGTTCCAGTTCATGCTGCCGTCTTCCCACCCCAACCGGATGGCCA
RatACC2       GCACCTGCGTGGTGGAGTTCCAGTTCATGCTGCCGTCTTCCCACCCCAACCGGATGGCCA
              ************************************************************ ratACC2_C7    TGCCCATCAATGTCTCTGACCCTGACCTGCTGAGACACAGTAAGGAACTCTTCATGGACA
RatACC2       TGCCCATCAATGTCTCTGACCCTGACCTGCTGAGACACAGTAAGGAACTCTTCATGGACA
              ************************************************************ ratACC2_C7    GTGGCTTCTCCCCACTGTGCCAGCGGATGGGGGCCATGGTGGCCTTCAGGAGATTTGAGG
RatACC2       GTGGCTTCTCCCCACTGTGCCAGCGGATGGGGGCCATGGTGGCCTTCAGGAGATTTGAGG
              ************************************************************ ratACC2_C7    AGTTCACCAGGAACTTCGATGAAGTCATCTCCTGCTTTGCCAACGTGCCTACAGACACTC
RatACC2       AGTTCACCAGGAACTTCGATGAAGTCATCTCCTGCTTTGCCAACGTGCCTACAGACACTC
              ************************************************************ ratACC2_C7    CTCTCTTCAGTAAGGCGTGCACTTCCCTCTACTCAGAGGAGGACAGCAAGAGCCTTCAAG
RatACC2       CTCTCTTCAGTAAGGCGTGCACTTCCCTCTACTCAGAGGAGGACAGCAAGAGCCTTCAAG
              ************************************************************ ratACC2_C7    AGGAGCCCATCCACATCCTGAATGTGGCCATCCAGTGCGCCGACCACATGGAGGACGAGA
RatACC2       AGGAGCCCATCCACATCCTGAATGTGGCCATCCAGTGCGCCGACCACATGGAGGACGAGA
              ************************************************************ ratACC2_C7    GACTGGTGCCGGTTTTCCGTGCCTTTGTACAGTCCAAGAAACACATCCTTGTGGATTACG
RatACC2       GACTGGTGCCGGTTTTCCGTGCCTTTGTACAGTCCAAGAAACACATCCTTGTGGATTACG
              ************************************************************ ratACC2_C7    GACTGCGAAGAATCACATTCCTTATCGCCCAAGAGAGAGAATTTCCCAAGTTCTTCACGT
RatACC2       GACTGCGAAGAATCACATTCCTTATCGCCCAAGAGAGAGAATTTCCCAAGTTCTTCACGT
              ************************************************************ ratACC2_C7    TCAGAGCGAGAGATGAGTTTGCAGAAGACCGGATTTACCGCCACTTGGAGCCGGCCCTGG
RatACC2       TCAGAGCGAGAGATGAGTTTGCAGAAGACCGGATTTACCGCCACTTGGAGCCGGCCCTGG
              ************************************************************
```

FIG. 5F

```
ratACC2_C7    CCTTCCAGCTGGAGCTGAGCCGGATGCGCAACTTTGACCTGACGGCCGTGCCCTGTGCCA
RatACC2       CCTTCCAGCTGGAGCTGAGCCGGATGCGCAACTTTGACCTGACGGCCGTGCCCTGTGCCA
              ************************************************************ ratACC2_C7    ACCATAAGATGCATCTTTACCTGGGAGCCGCCAAGGTGAAGGAAGGGCTGGAGGTGACTG
RatACC2       ACCATAAGATGCATCTTTACCTGGGAGCCGCCAAGGTGAAGGAAGGGCTGGAGGTGACTG
              ************************************************************ ratACC2_C7    ACCACAGGTTCTTCATCCGAGCCATCATAAGGCACTCAGACCTGATCACCAAGGAAGCCT
RatACC2       ACCACAGGTTCTTCATCCGAGCCATCATAAGGCACTCAGACCTGATCACCAAGGAAGCCT
              ************************************************************ ratACC2_C7    CCTTCGAGTACCTGCAGAATGAAGGGGAGCGGCTGCTGCTGGAAGCCATGGATGAGCTGG
RatACC2       CCTTCGAGTACCTGCAGAATGAAGGGGAGCGGCTGCTGCTGGAAGCCATGGACGAGCTGG
              ************************************************* **** ratACC2_C7    AGGTGGCGTTCAACAACACCAGCGTGCGCACTGACTGCAACCACATCTTCCTCAACTTCG
RatACC2       AGGTGGCGTTCAACAACACCAGCGTGCGCACTGACTGCAACCACATCTTCCTCAACTTCG
              ************************************************************ ratACC2_C7    TGCCCACGGTCATCATGGACCCACTCAAGATCGAGGAGTCGGTGCGTGCCATGGTCATGC
RatACC2       TGCCCACGGTCATCATGGACCCACTCAAGATCGAGGAGTCGGTGCGTGCCATGGTCATGC
              ************************************************************ ratACC2_C7    GTTACGGCAGTCGGCTGTGGAAGCTCCGTGTGCTGCAGGCAGAAGTTAAGATCAACATCC
RatACC2       GTTACGGCAGTCGGCTGTGGAAGCTCCGTGTGCTGCAGGCAGAAGTTAAGATCAACATCC
              ************************************************************ ratACC2_C7    GTCAGACGACCTCGGACTGCGCCGTCCCCATTCGCCTCTTCATCACCAACGAGTCCGGCT
RatACC2       GTCAGACGACCTCGGACTGCGCCGTCCCCATTCGCCTCTTCATCACCAACGAGTCCGGCT
              ************************************************************ ratACC2_C7    ACTACCTGGACATCAGCCTCTACAAAGAAGTGACCGACTCCAGATCCGGAAACATCATGT
RatACC2       ACTACCTGGACATCAGCCTCTACAAAGAAGTGACCGACTCCAGATCCGGAAACATCATGT
              ************************************************************ ratACC2_C7    TTCATTCCTTCGGCAACAAACAAGGGAGCCTGCACGGGATGCTGATCAACACGCCCTACG
RatACC2       TTCATTCCTTCGGCAACAAACAAGGGAGCCTGCACGGGATGCTGATCAACACGCCCTACG
              ************************************************************ ratACC2_C7    TCACCAAGGATCTGCTCCAAGCCAAGCGATTCCAGGCGCAGTCCCTGGGGACCACCTATG
RatACC2       TCACCAAGGATCTGCTCCAAGCCAAGCGATTCCAGGCGCAGTCCCTGGGGACCACCTATG
              ************************************************************ ratACC2_C7    TGTACGACTTCCCAGAGATGTTCAGGCAGGCTCTCTTTAAATTGTGGGGCTCCCCAGAGA
RatACC2       TGTACGACTTCCCAGAGATGTTCAGGCAGGCTCTCTTTAAATTGTGGGGCTCCCCAGAGA
              ************************************************************ ratACC2_C7    AGTACCCCAAAGATATCCTGACATACACAGAGCTGGTGTTGGACTCCCAGGGCCAGCTGG
RatACC2       AGTACCCCAAAGATATCCTGACATACACAGAGCTGGTGTTGGACTCCCAGGGCCAGCTGG
              ************************************************************ ratACC2_C7    TGGAGATGAACCGGCTTCCTGGTTGTAACGAGGTGGGCATGGTGGTTTTCAAAATGAGGT
RatACC2       TGGAGATGAACCGGCTTCCTGGTTGTAACGAGGTGGGCATGGTGGTTTTCAAAATGAGGT
              ************************************************************ ratACC2_C7    TCAAGACCCCGGAGTATCCAGAAGGCCGGGACACTATCGTCATCGGCAACGACATTACCT
RatACC2       TCAAGACCCCGGAGTATCCAGAAGGCCGGGACACTATCGTCATCGGCAACGACATTACCT
              ************************************************************
```

FIG. 5G

```
ratACC2_C7    TCCAAATCGGCTCTTTCGGCATAGGAGAGGACTTCCTGTATCTACGGGCATCGGAGATGG
RatACC2       TCCAAATCGGCTCTTTCGGCATAGGAGAGGACTTCCTGTATCTACGGGCATCGGAGATGG
              ************************************************************ ratACC2_C7    CCCGGACAGAGGGCATCCCCCAAATCTATCTGGCAGCCAACAGCGGGGCCCGTATGGGCC
RatACC2       CCCGGACAGAGGGCATCCCCCAAATCTATCTGGCAGCCAACAGCGGGGCCCGTATGGGCC
              ************************************************************ ratACC2_C7    TGTCCGAGGAGATCAAGCAGATATTCCAAGTGGCATGGGTGGACCCTGAGGATCCCTACA
RatACC2       TGTCCGAGGAGATCAAGCAGATATTCCAAGTGGCATGGGTGGACCCTGAGGATCCCTACA
              ************************************************************ ratACC2_C7    AAGGATTTAGATACCTGTACCTGACGCCCCAAGACTACACCCAGATCAGCTCCCAGAACT
RatACC2       AAGGATTTAGATACCTGTACCTGACGCCCCAAGACTACACCCAGATCAGCTCCCAGAACT
              ************************************************************ ratACC2_C7    CCGTGCACTGCAAACACATCGAGGACGAAGGCGAGTCCAGGTATGTCATCGTTGATGTCA
RatACC2       CCGTGCACTGCAAACACATCGAGGACGAAGGCGAGTCCAGGTATGTCATCGTTGATGTCA
              ************************************************************ ratACC2_C7    TCGGGAAGGACAGCAGCCTGGGTGTGGAGAACCTGCGGGGCTCGGGCATGATTGCAGGAG
RatACC2       TCGGGAAGGACAGCAGCCTGGGTGTGGAGAACCTGCGGGGCTCGGGCATGATTGCAGGAG
              ************************************************************ ratACC2_C7    AGGCTTCTCTGGCTTACGAAAAAAATGTCACCATCAGCATGGTGACCTGCCGCGCCATCG
RatACC2       AGGCTTCTCTGGCTTACGAAAAAAATGTCACCATCAGCATGGTGACCTGCCGCGCCATCG
              ************************************************************ ratACC2_C7    GAATCGGGGCTTACCTGGTGAGGCTGGGCCAGCGGGTGATCCAGGTGGAAAACTCCCACA
RatACC2       GAATCGGGGCTTACCTGGTGAGGCTGGGCCAGCGGGTGATCCAGGTGGAAAACTCCCACA
              ************************************************************ ratACC2_C7    TCATCCTCACGGGAGCCGGTGCTCTCAACAAGGTCCTGGGAAGAGAGGTCTACACATCCA
RatACC2       TCATCCTCACGGGAGCCGGTGCTCTCAACAAGGTCCTGGGAAGAGAGGTCTACACATCCA
              ************************************************************ ratACC2_C7    ACAACCAACTGGGCGGTGTGCAGATCATGCACACCAACGGGGTCTCCCACGTCACGGTGC
RatACC2       ACAACCAACTGGGCGGTGTGCAGATCATGCACACCAACGGGGTCTCCCACGTCACGGTGC
              ************************************************************ ratACC2_C7    CAGATGACTTCGAGGGGGTCTGCACCATTCTGGAATGGCTGTCATATATACCAAAGGACA
RatACC2       CAGATGACTTCGAGGGGGTCTGCACCATTCTGGAATGGCTGTCATATATACCAAAGGACA
              ************************************************************ ratACC2_C7    ATCAAAGCCCAGTCCCCATCATCACTCCTTCTGACCCCATCGACAGGGAAATTGAATTCA
RatACC2       ATCAAAGCCCAGTCCCCATCATCACTCCTTCTGACCCCATCGACAGGGAAATTGAATTCA
              ************************************************************ ratACC2_C7    CCCCAACCAAAGCTCCCTATGACCCCAGGTGGCTGCTTGCAGGGAGGCCTCACCCAACTC
RatACC2       CCCCAACCAAAGCTCCCTATGACCCCAGGTGGCTGCTGGCAGGGAGGCCTCACCCAACTC
              **********************************     ***************** ratACC2_C7    TGAAGGGGACCTGGCAGAGTGGATTCTTCGACCATGGCAGTTTCAAGGAAATCATGGCAC
RatACC2       TGAAGGGGACCTGGCAGAGTGGATTCTTCGACCATGGCAGTTTCAAGGAAATCATGGCAC
              ************************************************************ ratACC2_C7    CCTGGGCCCAGACCGTGGTGACTGGACGAGCAAGGCTGGGGGGCATCCCTGTAGGGGTGA
RatACC2       CCTGGGCCCAGACTGTGGTGACTGGACGAGCAAGGCTGGGGGGCATCCCTGTAGGGGTGA
              ************* **********************************************
```

FIG. 5H

```
ratACC2_C7    TTGCCGTGGAGACTCGGTCTGTGGAGGTGGCTGTCCCTGCTGACCCTGCCAACTTGGATT
RatACC2       TTGCCGTGGAGACTCGGTCTGTGGAGGTGGCTGTCCCTGCTGACCCTGCCAACTTGGATT
              ************************************************************ ratACC2_C7    CTGAGGCCAAGATCATCCAGCAGGCAGGCCAGGTGTGGTTCCCGGACTCTGCCTTCAAGA
RatACC2       CTGAGGCCAAGATCATCCAGCAGGCAGGCCAGGTGTGGTTCCCGGACTCTGCCTTCAAGA
              ************************************************************ ratACC2_C7    CGGCTCAGGTCATCAGGGACTTCAACCAGGAGCATCTGCCTCTCATGATCTTTGCCAACT
RatACC2       CGGCTCAGGTCATCAGGGACTTCAACCAGGAGCATCTGCCTCTCATGATCTTTGCTAACT
              ***************************************************** ** ratACC2_C7    GGAGAGGCTTCTCGGGTGGCATGAAAGACATGTACGAGCAGATGCTGAAGTTTGGCGCCT
RatACC2       GGAGAGGCTTCTCGGGCGGCATGAAAGACATGTACGAGCAGATGCTGAAGTTTGGCGCCT
              ************** ***************************************** ratACC2_C7    ACATCGTGGACAGTCTCCGTCTGTTCAAGCAGCCAGTTCTCATCTATATCCCTCCTGGTG
RatACC2       ACATCGTGGACAGTCTCCGTCTGTTCAAGCAGCCAGTTCTCATCTATATCCCTCCCGGTG
              ***************************************************** ** ratACC2_C7    CCGAACTCCGAGGGGGCGCCTGGGTTGTCCTCGACTCCAGCATCAACCCCCTGTGCATAG
RatACC2       CCGAACTCCGAGGGGGCGCCTGGGTTGTCCTCGACTCCAGCATCAACCCCCTGTGCATAG
              ************************************************************ ratACC2_C7    AGATGTACGCAGACAAAGAGAGCAGGGGGGGTGTCCTGGAGCCCGAGGGCACTGTGGAGA
RatACC2       AGATGTACGCAGACAAAGAGAGCAGGGGGGGTGTCCTGGAGCCCGAGGGCACTGTGGAGA
              ************************************************************ ratACC2_C7    TTAAGTTCCGGAAGAAAGATTTGGTGAAGACCATAAGGAGGATTGACCCAGTGTGCAAGA
RatACC2       TTAAGTTCCGGAAGAAAGATTTGGTGAAGACCATAAGGAGGATTGACCCAGTGTGCAAGA
              ************************************************************ ratACC2_C7    AACTCCTGGGGCAGCTGGGGACAGCCCAGCTCCCTGACAAGGACCGGAAAGAGCTGGAGA
RatACC2       AACTCCTGGGGCAGCTGGGGACAGCCCAGCTCCCTGACAAGGACCGGAAAGAGCTGGAGA
              ************************************************************ ratACC2_C7    GCCAGCTGAAGGCCCGGGAGGACCTGCTGCTCCCCATCTACCACCAGGTGGCAGTGCAGT
RatACC2       GCCAGCTGAAGGCCCGGGAGGACCTGCTGCTCCCCATCTACCACCAGGTGGCAGTGCAGT
              ************************************************************ ratACC2_C7    TCGCCGACCTGCATGACACGCCGGGCCACATGCTGGAGAAGGGAATCATTTCTGATGTGC
RatACC2       TCGCCGACCTGCATGACACGCCGGGCCACATGCTGGAGAAGGGAATCATTTCTGATGTGC
              ************************************************************ ratACC2_C7    TGGAGTGGAAGACCACACGTACCTACTTCTACTGGAGGCTGCGCCGGCTGCTGCTGGAGG
RatACC2       TGGAGTGGAAGACCACACGTACCTACTTCTACTGGAGGCTGCGCCGGCTGCTGCTGGAGG
              ************************************************************ ratACC2_C7    CACAGGTGAAGCAGGAGATTCTGCGAGCCAGCCCTGAGCTGAGCCATGAGCACACGCAGT
RatACC2       CACAGGTGAAGCAGGAGATTCTGCGAGCCAGCCCTGAGCTGAGCCATGAGCACACGCAGT
              ************************************************************ ratACC2_C7    CCATGCTGCGACGCTGGTTTGTGGAGACCGAGGGCGCCGTCAAGGCCTACCTGTGGGACA
RatACC2       CCATGCTGCGACGCTGGTTTGTGGAGACCGAGGGCGCCGTCAAGGCCTACCTGTGGGACA
              ************************************************************ ratACC2_C7    GCAACCAGGTGGTAGTCCAGTGGCTGGAACAGCACTGGTCAGCCAGGGACAACCTGCGTT
RatACC2       GCAACCAGGTGGTAGTCCAGTGGCTGGAACAGCACTGGTCAGCCAGGGACAACCTGCGTT
              ************************************************************
```

FIG. 5I

```
ratACC2_C7    CCACTATCCGAGAGAACATCAATTATCTGAAGCGGGACTCTGTCCTCAAGACCATCCAAA
RatACC2       CCACTATCCGAGAGAACATCAATTATCTGAAGCGGGACTCTGTCCTCAAGACCATCCAAA
              ************************************************************ ratACC2_C7    GCCTAGTTCAAGAACACCCAGAGGCGACCATGGACTGTGTGGCATACCTGAGCCAGCACC
RatACC2       GCCTAGTTCAAGAACACCCAGAGGCGACCATGGACTGTGTGGCATACCTGAGCCAGCACC
              ************************************************************ ratACC2_C7    TCACGCCCGCTGAGCAGATGCAGGTGGTTCAGCTGCTGTCTACCACGGAGAGCCCAGCTT
RatACC2       TCACGCCCGCTGAGCAGATGCAGGTGGTTCAGCTGCTGTCTACCACGGAGAGCCCAGCTT
              ************************************************************ ratACC2_C7    CCCACTGA----------------------------------------------------
RatACC2       CCCACTGAGCAACCCTGGCCATCCCCAGGACCCTGGACGGTGGGAATGGCCGCGCAGCAG
              ******** ratACC2_C7    ------------------------------------------------------
RatACC2       GCCTTCGCAGTACGCCAGGACTAATTTTGGGAAAACTGGAGCTACAGCGGC
```

FIG. 11
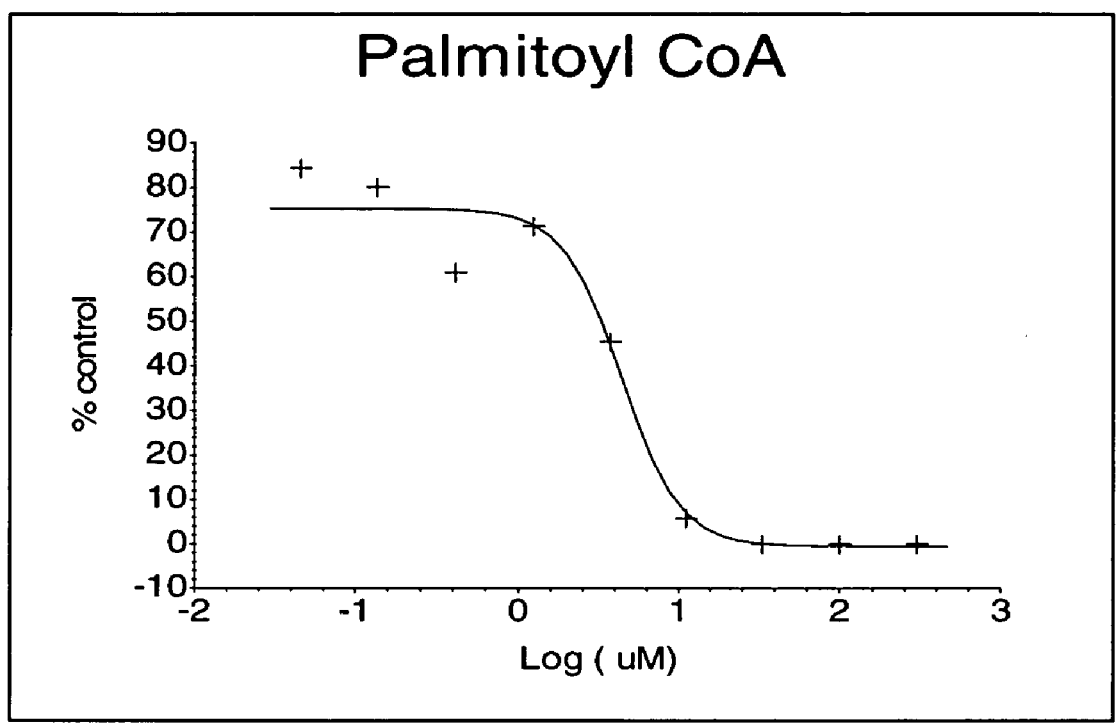
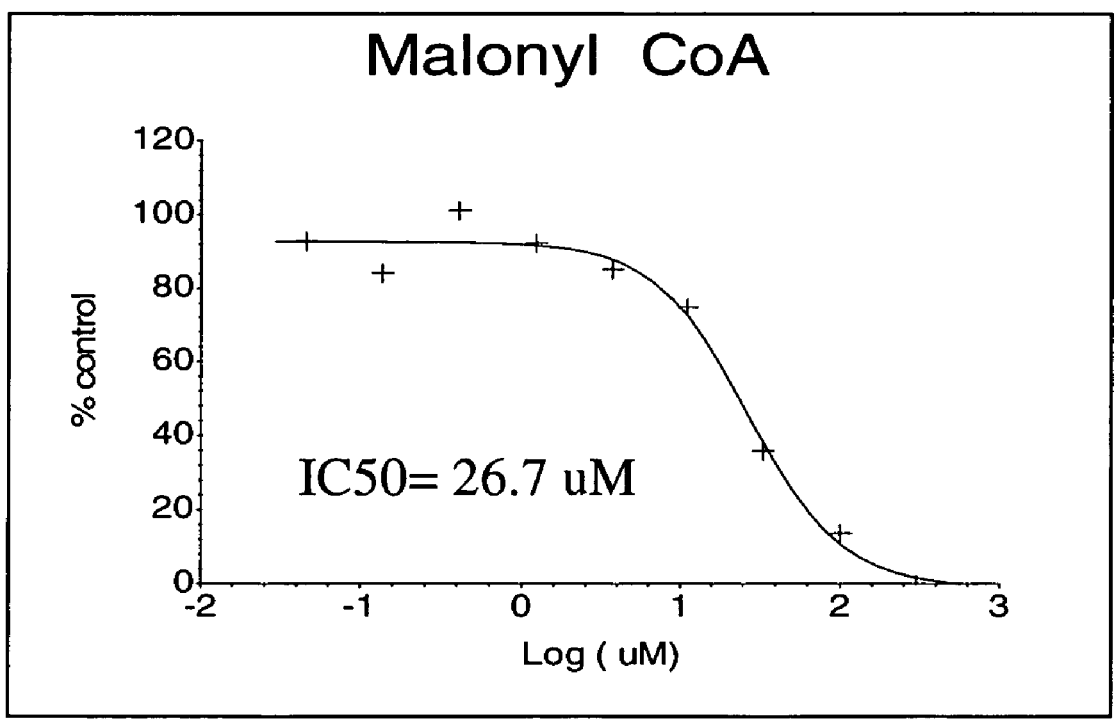

ACETYL COA CARBOXYLASE 2 SEQUENCES AND METHODS

This application claims benefit to provisional application U.S. Ser. No. 60/590,948 filed Jul. 23, 2004; under 35 U.S.C. 119(e). The entire teachings of the referenced application are incorporated herein by reference.

FIELD OF THE INVENTION

The present invention provides novel polynucleotides encoding human and rat Acetyl CoA Carboxylase 2 ("ACC2") polypeptides, fragments and homologues thereof. Vectors, host cells, antibodies, and recombinant and synthetic methods for producing the ACC2 polypeptides are provided. The invention also relates to diagnostic and therapeutic methods for applying the ACC2 polypeptides to the diagnosis, treatment, and/or prevention of various diseases and/or disorders related to these polypeptides, including obesity. The invention further relates to screening methods for identifying agonists and antagonists of the polynucleotides and polypeptides of the present invention.

BACKGROUND OF THE INVENTION

Acetyl CoA carboxylase (ACC) is the rate-determining enzyme of fatty acid biosynthesis in plants and animals. ACC is a biotin containing enzyme which catalyzes the carboxylation of acetyl CoA to form malonyl CoA in a two-step reaction (Beaty & Lane, (1982). *J. Biol. Chem.* 257:924–929). The first step is the ATP-dependent carboxylation of biotin covalently linked to the enzyme. In the second step, a carboxyltransferase step, the carboxyl group is transferred to the substrate, acetyl CoA, to form malonyl CoA. Citrate is a potent allosteric activator of ACC. Malonyl CoA is the C2 donor for de novo synthesis of long chain fatty acids.

In mammals, there are two subtypes of ACC, ACC1 and ACC2. ACC1 is mainly localized in lipogenic tissues such as adipose tissue and liver, where fatty acids are synthesized. ACC2 is found primarily in non-lipogenic tissues such as skeletal muscle and heart muscle, although some is also found in liver. Malonyl CoA allosterically inhibits carnitine palmitoyl transferase 1 (CPT1), which is a critical enzyme to transfer the long chain fatty acid into the mitochondria for β-oxidation. Because ACC2 is co-localized with CPT-1, the primary role of malonyl CoA that is synthesized by ACC2 has been suggested to regulate the rate of β-oxidation.

ACC is a potential target in metabolic diseases for the treatment of metabolic syndrome including obesity, insulin resistance and dyslipidemia. Increased rates of muscle fatty acid oxidation, a reduced fat content and a reduction in total body fat were observed in ACC-2 knock-out mice (Abu-Elheiga et al., (2001) *Science* 291:2613–2616; Abu-Elheiga et al., (2003) *Proc. Natl. Acad. Sci. USA.* 100:10207–10212). Harwood et al. reported that ACC inhibitors caused reduction in fatty acid synthesis, increase in fatty acid oxidation, and reduction of respiratory quotient in rats (Harwood et al., (2003) *J. Biol. Chem.* 278:37099–37111). Chronic dosing of these compounds resulted in the reduction of whole body fat mass and improvement of insulin sensitivity (Harwood et al., (2003) *J. Biol. Chem.* 278:37099–37111). These observations further validated the enzyme as a drug target.

Several human ACC2 and rat ACC2 nucleotide and amino acid sequences have been published (see, e.g., *Human ACC2*: GenBank Accession No. NM_001093 (SEQ ID NOs:1 and 2) and GenBank Accession No. AC007637 (SEQ ID NOs:3 and 4); *Rat ACC2*: GenBank Accession No. NM_053922 (SEQ ID NOs:7 and 8) and GenBank Accession No. AB004329 (SEQ ID NOs:9 and 10)). It was found, however, that for each species, each of the published amino acid and/or nucleotide sequences was different from one another by one or more residues. More specifically, it was found that the nucleotide sequences of human ACC2 and rat ACC2 contain non-silent mutations that introduce substitutions into several of the published encoded amino acid sequences of these enzymes.

In order to identify the most effective modulators of human ACC2 and rat ACC2, accurate nucleotide and amino acid sequences are required. Therefore, what is needed to advance research on human and rat ACC2 is an accurate amino acid sequence for these enzymes, as well as the encoding nucleotide sequences. The present invention solves this and other problems.

SUMMARY OF THE INVENTION

The present invention discloses an isolated nucleic acid molecule encoding a human ACC2 polypeptide. In one embodiment the nucleic acid molecule comprises a polynucleotide having a nucleotide sequence selected from the group consisting of: (a) a polynucleotide encoding an ACC2 polypeptide comprising SEQ ID NO:12; (b) an isolated polynucleotide encoding a human ACC2 polypeptide comprising amino acids 2 to 2458 of SEQ ID NO:12 minus the start methionine; (c) an isolated polynucleotide encoding a human ACC2 polypeptide comprising amino acids 1 to 2458 of SEQ ID NO:12 including the start codon; (d) an isolated polynucleotide encoding the ACC2 polypeptide encoded by the cDNA clone contained in ATCC Deposit No: PTA-6054; and (e) a polynucleotide capable of hybridizing under stringent conditions to the polynucleotide specified in (a)–(d), wherein the polynucleotide does not hybridize under stringent conditions to a nucleic acid molecule having a nucleotide sequence of only A residues or of only T residues. The isolated nucleic acid molecule can comprise, for example, the nucleotide sequence of SEQ ID NO:11. In additional aspects, the present invention also relates to a polynucleotide that is complementary to the isolated nucleic acid molecule, a vector comprising the isolated nucleic acid molecule and a host cell, which can be a mammalian host cell, comprising the vector.

Also disclosed is a method of making an isolated ACC2 polypeptide. In one embodiment the method comprises: (a) culturing the recombinant host cell under conditions such that the polypeptide is expressed; and (b) recovering the polypeptide.

In another aspect, the present invention describes an isolated ACC2 polypeptide. In one embodiment the polypeptide comprises an amino acid sequence selected from the group consisting of: (a) a polypeptide comprising SEQ ID NO:12; (b) a polypeptide comprising amino acids 2 to 2458 of SEQ ID NO:12, wherein amino acids 2 to 2458 comprise a polypeptide of SEQ ID NO:12 minus the start methionine; and (c) a polypeptide comprising amino acids 1 to 2458 of SEQ ID NO:12. In another embodiment, the polypeptide comprises two or more sequential amino acid deletions from one or both of: (a) the COOH-terminus of the polypeptide; and (b) the NH$_2$-terminus of the polypeptide.

A method of identifying a compound that modulates the activity of the ACC2 polypeptide is also disclosed and forms another aspect of the present invention. In one embodiment, the method comprises: (a) determining the activity of the polypeptide of Claim 8 in the absence of a test compound; (b) determining the activity of the polypeptide in the presence of a test compound; and (c) comparing the activity of the polypeptide in the presence of the test compound with the activity of the polypeptide in the absence of the test compound, wherein a change in the activity of the polypeptide in the presence of the test compound relative to the activity of the polypeptide in the absence of the test compound indicates that the compound that modulates the activity of the polypeptide.

An isolated antibody which specifically binds to the ACC2 polypeptide is additionally disclosed. In various embodiments, the antibody is selected from the group consisting of a chimeric antibody, a single chain antibody, a Fab fragment, and a humanized antibody.

The present invention also relates to an isolated nucleic acid molecule encoding a rat ACC2 polypeptide. In one embodiment the isolated nucleic acid molecule comprises a polynucleotide having a nucleotide sequence selected from the group consisting of: (a) a polynucleotide encoding an ACC2 polypeptide comprising SEQ ID NO:14; (b) an isolated polynucleotide encoding a rat ACC2 polypeptide comprising amino acids 2 to 2458 of SEQ ID NO:14 minus the start methionine; (c) an isolated polynucleotide encoding a rat ACC2 polypeptide comprising amino acids 1 to 2458 of SEQ ID NO:14 including the start codon; (d) the cDNA of ATCC Deposit No. PTA-6054; and (e) a polynucleotide capable of hybridizing under stringent conditions to the polynucleotide specified in (a)–(d), wherein the polynucleotide does not hybridize under stringent conditions to a nucleic acid molecule having a nucleotide sequence of only A residues or of only T residues.

In on embodiment, the isolated nucleic acid molecule comprises the nucleotide sequence of SEQ ID NO:13. In additional aspects, the present invention comprises a polynucleotide that is complementary to the isolated nucleic acid molecule, a vector comprising the isolated nucleic acid molecule and a host cell, which can be a mammalian host cell, comprising the vector.

The present invention also relates to a method of making an isolated ACC2 polypeptide. In one embodiment the method comprises: (a) culturing a recombinant host cell under conditions such that the polypeptide is expressed; and (b) recovering the polypeptide.

In another aspect, the present invention relates to an isolated ACC2 polypeptide. In one embodiment, the polypeptide comprises an amino acid sequence selected from the group consisting of: (a) a polypeptide comprising SEQ ID NO:14; (b) a polypeptide comprising amino acids 2 to 2455 of SEQ ID NO:14, wherein amino acids 2 to 2455 comprise a polypeptide of SEQ ID NO:14 minus the start methionine; and (c) a polypeptide comprising amino acids 1 to 2455 of SEQ ID NO:14. In another embodiment, the polypeptide comprises two or more sequential amino acid deletions from one or both of: (a) the COOH-terminus of the polypeptide; and (b) the $NH_2$-terminus of the polypeptide.

A method of identifying a compound that modulates the activity of the ACC2 polypeptide is also disclosed and forms another aspect of the present invention. In one embodiment, the method comprises: (a) determining the activity of the polypeptide of Claim 8 in the absence of a test compound; (b) determining the activity of the polypeptide in the presence of a test compound; and (c) comparing the activity of the polypeptide in the presence of the test compound with the activity of the polypeptide in the absence of the test compound, wherein a change in the activity of the polypeptide in the presence of the test compound relative to the activity of the polypeptide in the absence of the test compound indicates that the compound that modulates the activity of the polypeptide.

An isolated antibody that specifically binds to the ACC2 polypeptide is disclosed. In various embodiments, the antibody is selected from the group consisting of a chimeric antibody, a single chain antibody, a Fab fragment, and a humanized antibody.

A method of isolating an ACC polypeptide is additionally disclosed. In one embodiment, the method comprises: (a) contacting crude lysate derived from a cell or tissue expressing an ACC polypeptide with an antibody to form a complex comprising an antibody and an ACC; (b) washing the complex with a buffer comprising 0.5 M NaCl; and (c) contacting the complex with an eluting ligand. The antibody can comprise an IgG antibody, and in one embodiment, can be, for example, a c-Myc-5 IgG antibody and the eluting ligand can be a myc peptide. The myc peptide can comprise the amino acid sequence of SEQ ID NO:16. In another example, the IgG antibody is an anti-FLAG IgG antibody. Further, the antibody can be bound to a substrate. The method can be employed to isolate any ACC polypeptide, such as an ACC1 or ACC2 polypeptide.

Additionally, a polynucleotide capable of inhibiting the expression of an ACC2 gene comprising a polynucleotide sequence selected from the group consisting of SEQ ID NOs:11 and 13 by antisense inhibition is disclosed, as well as a method of inhibiting ACC2 gene expression comprising introducing an antisense polynucleotide into a cell or tissue that expresses an ACC2 gene, thereby inhibiting the expression of the gene in the cell or tissue by antisense inhibition.

A polynucleotide capable of inhibiting the expression of an ACC2 gene comprising a polynucleotide sequence selected from the group consisting of SEQ ID NOs:11 and 13 by RNA inhibition is disclosed, as well as a method of inhibiting ACC2 gene expression comprising introducing an RNAi polynucleotide into a cell or tissue that expresses an ACC2 gene, thereby inhibiting the expression of the gene in the cell or tissue by RNA inhibition.

In another aspect, the present invention discloses an isolated polypeptide comprising an ACC2 polypeptide encoded by the cDNA deposited as ATCC Accession No. PTA-6054.

In yet a further aspect, the present invention discloses a method of increasing the activity of a human ACC2 polypeptide. In one embodiment, the method comprises generating an enhanced ACC2 polypeptide comprising: (a) a phenylalanine residue at position 254, (b) a glutamine residue at position 346, (c) a threonine residue at position 565, (d) an asparagine at position 841, (e) a valine residue at position 1103, (f) a cysteine residue at position 1259, (g) an alanine residue at position 1526, and (h) an isoleucine residue at position 1717, wherein the human ACC2 polypeptide does not comprise SEQ ID NO:12 and wherein the enhanced ACC2 polypeptide has an enzymatic activity level that is greater than the enzymatic activity level of an ACC2 polypeptide that does not contain the indicated residues at the indicated positions. In various aspects, the human ACC2 polypeptide sequence is selected from the group consisting of SEQ ID NOs:2,4 and 6.

BRIEF DESCRIPTION OF THE DRAWINGS

FIGS. 1A–1K depicts a polynucleotide (SEQ ID NO:11) and encoded ACC2 amino acid sequence (SEQ ID NO:12) of a human ACC2 of the present invention identified as described herein.

FIGS. 2A–2K depicts a polynucleotide (SEQ ID NO:13) and encoded ACC2 amino acid sequence (SEQ ID NO:14) of a rat ACC2 identified as described herein.

FIGS. 3A–3I is an alignment of a published rat nucleotide ACC2 sequence (SEQ ID NO:9) with a rat ACC2-encoding sequence consensus sequence of the present invention (SEQ ID NO:13). In the figure, "AB004329" represents the nucleic acide sequence of GenBank Accession No. AB004329 and "BMS" represents a rat ACC2-encoding sequence of the present invention.

FIGS. 4A–4C is an alignment of a published rat amino acid ACC2 sequence (SEQ ID NO:10) with a rat ACC2-encoding sequence consensus sequence of the present invention (SEQ ID NO:14). In the figure, "AB004329" represents the amino acid sequence of GenBank Accession No. AB004329 and "BMS_ratACC2" represents the amino acid sequence of a rat ACC2 sequence of the present invention.

FIGS. 5A–5I is an alignment of a cloned rat ACC2 nucleotide sequence of the present invention (SEQ ID NO:13) with a sequence derived from PCR products generated in consensus sequencing (SEQ ID NO:15). In the figure, "ratACC2_C7" represents the cloned rat ACC2 nucleotide sequence and "RatACC2" represents the nucleotide sequence derived from PCR products generated in consensus sequencing.

FIG. 11 is a series of two plots depicting the concentration dependent inhibition of a recombinant human ACC2 of the present invention by the known inhibitors of ACC enzymes palmitoyl CoA and malonyl CoA; each plot is labeled according to inhibitor.

DETAILED DESCRIPTION OF THE INVENTION

Figure 6A:
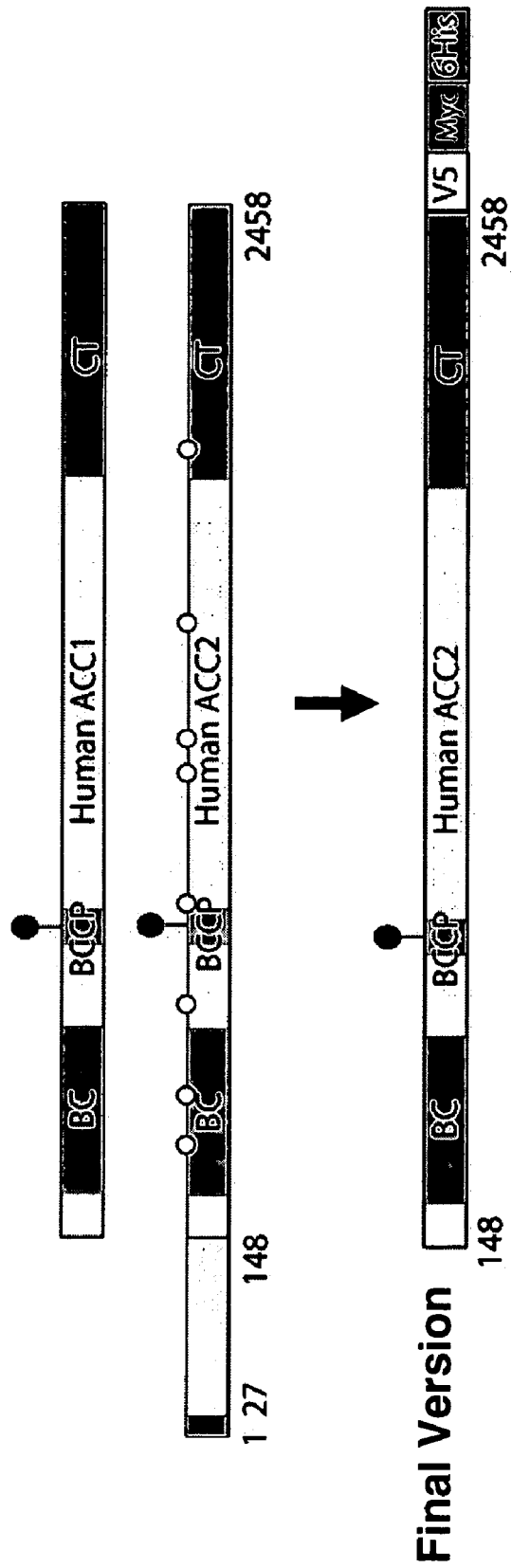
FIG. 6A is a schematic drawing for comparison of primary structure of human ACC1 versus ACC2 and the final version construct of human ACC2 which was used for expression in the current invention; BC represents the biotin carboxylase domain, BCCP represents the biotin carboxyl carrier protein domain, CT represents the carboxyltransferase domain, filled circles denote the biotin group, open circles denote the discrepancies of amino acids between pYES-human-ACC2 (designated as Mt) versus the wild type human ACC2 (designated as WT), V5, Myc, 6His represent three tags fused in frame to the human ACC2 sequence at the COOH-terminus and the numbers presented below the bar denote the amino acid numbers predicted by the full length human ACC2 cDNA.

The present invention relates to novel nucleotide sequences encoding human and rat ACC2 proteins and to the novel proteins themselves. The invention also relates to uses of the novel sequences for identifying modulators of ACC and for treating conditions associated with undesired ACC activity. The novel sequences of the present invention are consensus sequences that were identified, cloned and sequenced based on published versions of the human and rat ACC2 sequences.

A human ACC2 polynucleotide sequence of the present invention is set forth in FIG. 1 (SEQ ID NO:11), and a rat ACC2 polynucleotide of the present invention is set forth in FIG. 2 (SEQ ID NO:13). The human sequence was deposited with ATCC on Jun. 8, 2004 and has been assigned Deposit Number PTA-6054. A human ACC2 polypeptide sequence of the present invention is set forth in FIG. 1 (SEQ ID NO:12), and a rat ACC2 polypeptide of the present invention is set forth in FIG. 2 (SEQ ID NO:14). Based on the established physiological function of ACC2, these novel sequences represents an important target for the treatment of obesity, diabetes and related disease states.

I. Definitions

All scientific and technical terms used in this application have meanings commonly used in the art unless otherwise specified. As used in this application, the following words or phrases have the meanings specified.

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or less (e.g., ±15%, ±10%, ±7%, ±5%, ±4%, ±3%, ±2%, ±1, or ±0.1%) from the specified amount, as such variations are appropriate.

As used herein, unless clearly specified otherwise explicitly or by context, the terms "ACC2" and "ACC2 of the present invention" are used interchangeably and mean an acetyl CoA carboxylase polypeptide comprising SEQ ID NOs:12 or 14, which can be encoded by a polynucleotide sequence comprising the nucleic acid sequence of SEQ ID NO:11 (human ACC2) or SEQ ID NO:13 (rat ACC2). The terms also encompass variants, such as, but not limited to, polynucleotides that are not identical to SEQ ID NOs:11 and 13, due to degeneracy in the genetic code, but still code for an ACC2 polypeptide.

The terms "ACC2" and "ACC2 of the present invention" whether referring to a rat or a human sequence, encompasses sequences comprising one or more conservative substitutions in the ACC2 amino acid sequences of SEQ ID NOs:12 and 14. The substitution can be naturally occurring or introduced by man. In a conservative substitution, the replacement group will have approximately the same size, shape, hydrophobicity and charge as the original group. A table disclosing some representative, but non-limiting properties that can be used as a guide when identifying or generating a conservative mutation follows:

| Representative Conservative Amino Acid Substitutions | |
|---|---|
| Amino Acid Property | Amino Acid |
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions are shown in the following table:

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, .beta.-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

As used herein, the term "agonist," and grammatical derivations thereof, refer to an agent that initiates, supplements or potentiates the bioactivity of a functional ACC2 gene or protein, or that supplements or potentiates the bioactivity of a naturally occurring or engineered functional ACC2 gene or protein. An agonist can be a ligand. Further, an agonist can act by preventing an antagonist from acting on a given protein.

As used herein, the terms "amino acid," "amino acid residue" and "residue" are used interchangeably and mean any of the twenty naturally occurring amino acids. An amino acid is formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide (e.g., enzymatic activity). $NH_2$ refers to the free amino group present at the amino terminus of a polypeptide. COOH refers to the free carboxy group present at the carboxy terminus of a polypeptide. In addition, the phrases "amino acid" and "amino acid residue" are broadly defined to include modified and unusual amino acids.

As used herein, the term "antagonist," and grammatical derivations thereof, means an agent that decreases or inhibits the bioactivity of a functional ACC2 gene or protein, or that decreases or inhibits the bioactivity of a naturally occurring or engineered ACC2 gene or protein. An antagonist can be a ligand. Further, an antagonist can act by preventing an agonist from acting on a given protein.

As used herein, the term "antibody" means polyclonal, monoclonal, antibody fragments (e.g., a Fab fragment) and antibody derivatives. The term encompasses antibodies prepared by recombinant techniques, such as chimeric or humanized antibodies, as well as single chain or bispecific antibodies. The term specifically encompasses antibodies that bind to an epitope, or a portion thereof, of a polypeptide that is described in the present disclosure.

As used herein, the terms "antigen" and "epitope," which are well understood in the art, mean all or a portion of a macromolecule that is specifically recognized by a component of the immune system, e.g., an antibody or a T-cell antigen receptor. An epitope is a region of an antigen. As used herein, the term "antigen" encompasses antigenic epitopes, e.g., fragments of an antigen that are antigenic epitopes.

As used herein, the term "associates specifically," and grammatical derivations thereof, means an interaction between a first moiety (e.g. a modulator, such as an agonist or an antagonist) and a second moiety (e.g., an ACC2 polypeptide or fragment thereof) that occurs preferentially to an interaction the first or second moiety and any other moieties present. For example, an antibody is presented with a variety of antigens, but only binds to a particular antigen. In this example, the antibody "specifically associates" with the particular antigen.

As used herein, the term "biological activity" means any activity that a biological molecule normally exhibits in vivo. For example, when the biological molecule is ACC2, representative biological activities can include the catalytic carboxylation of biotin covalently bound to ACC2 polypeptide in an ATP-dependent manner, the catalytic formation of malonyl CoA as a result of transfer of carboxyl group to acetyl CoA, and the binding of citrate.

As used herein, the term "biological sample" means any biological sample obtained from an organism, body fluids, cell line, tissue culture. A biological sample can be a body fluid (for example, sputum, amniotic fluid, urine, saliva, breast milk, secretions, interstitial fluid, blood, serum, spinal fluid, etc.) or other tissue source. Methods for obtaining tissue biopsies and body fluids from organisms are known to those of ordinary skill in the art. Where the biological sample is to include mRNA, a tissue biopsy is a preferred source.

As used herein the term "complementary" means a nucleic acid sequence that is base paired, or is capable of base-pairing, according to the standard Watson-Crick complementarity rules. These rules generally hold that guanine pairs with cytosine (G:C) and adenine pairs with either thymine (A:T) in the case of DNA, or adenine pairs with uracil (A:U) in the case of RNA.

As used herein, the term "hybridize" means the process by which a polynucleotide strand anneals with a complementary strand through base pairing under defined hybridization conditions. Specific hybridization is an indication that two nucleic acid sequences share a high degree of complementarity.

As used herein, the terms "isolated" and "purified" are used interchangeably and refer to material (e.g., a nucleic acid or a polypeptide) removed from its original environment (e.g., the natural environment, if it is naturally occurring), and thus is altered "by the hand of man" from its natural state. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide and/or protein sequences of the present invention; such sequences are excluded from the scope of the present invention.

As used herein the term "modulate," and grammatical derivations thereof, refer to an increase, decrease, or other alteration of any and/or all chemical and/or biological activities or properties mediated by a given DNA sequence, RNA sequence, polypeptide, peptide or molecule. The definition of "modulator" as used herein encompasses agonists and/or antagonists of a particular activity or protein.

The term "modulate" refers to both upregulation (i.e., activation or stimulation) and downregulation (i.e. inhibition or suppression).

As used herein, the term "stringent hybridization conditions," in the context of nucleic acid hybridization experiments such as southern and northern blot analysis, means a set of conditions under which single stranded nucleic acid sequences are unlikely to hybridize to one another unless there is substantial complementarity between the sequences. Stringent hybridization conditions can be both sequence-and environment-dependent. Longer sequences hybridize specifically at higher temperatures. An extensive guide to the hybridization of nucleic acids is found, for example, in Tijssen, (1993) *Laboratory Techniques in Biochemistry and Molecular Biology-Hybridization with Nucleic Acid Probes*, part I, chapter 2, Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

Stringency Conditions

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C.; 1xSSC - or - 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC - or - 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC - or - 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC - or - 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC - or - 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC - or - 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC - or - 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC - or - 42° C.; 6xSSC, 50% formamide | 55° C.; 2xSSC |

-continued

| Stringency Condition | Polynucleotide Hybrid± | Hybrid Length (bp)‡ | Hybridization Temperature and Buffer† | Wash Temperature and Buffer† |
|---|---|---|---|---|
| P | DNA:RNA | <50 | Tp*; 6xSSC | Tp*; 6xSSC |
| Q | RNA:RNA | > or equal to 50 | 60° C.; 4xSSC - or - 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MEGALIGN program of the DNA*Star suite of programs, etc).
†SSPE (1xSSPE is 0.15 M NaCl, 10 mM NaH2PO4, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete. The hybridizations and washes may additionally include 5x Denhardt's reagent, 0.5–1.0% SDS, 100 µg/ml denatured, fragmented salmon sperm DNA, 0.5% sodium pyrophosphate, and up to 50% formamide.
*Tb - Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6 ($\log_{10}$[Na$^+$]) + 0.41 (% G + C) − (600/N), where N is the number of bases in the hybrid, and [Na$^+$] is the concentration of sodium ions in the hybridization buffer ([Na$^+$] for 1xSSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook et al., *Molecular Cloning: A Laboratory Manual*, 3$^{rd}$ ed., Cold Spring Harbor Press, Cold Spring Harbor (2001), and *Current Protocols in Molecular Biology*, 1995, F. M., Ausubel et al., eds, John Wiley and Sons, Inc., which are hereby incorporated by reference herein.

As used herein, the term "vector" means a replicon, such as plasmid, phage or cosmid, to which another DNA segment may be attached so as to bring about the replication of the attached segment.

II. ACC2 Polypeptides of the Present Invention

ACC2 polypeptides that form aspects of the present invention are presented in FIGS. 1 and 2 and in SEQ ID NOs:12 and 14. These sequences represent human and rat genomic ACC2 polypeptide sequences. Although several human and rat ACC2 sequences have been published (see, e.g., *Human ACC2*: GenBank Accession No. NM_001093 (SEQ ID NOs:1 and 2), GenBank Accession No. AC007637 (SEQ ID NOs:3 and 4) and the sequence of pYES-human ACC2, (SEQ ID NOs:5 and 6); Rat ACC2: GenBank Accession No. NM_053922 (SEQ ID NOs:7 and 8) and GenBank Accession No. AB004329 (SEQ ID NOs:9 and 10)), there are discrepancies between these sequences. Consequently, the present inventors re-evaluated the published human and rat ACC2 sequences, which lead to the identification of the ACC2 sequences of the present invention.

Based on the identified discrepancies in the published sequences, it was speculated that these discrepancies may represent inadvertent mutations introduced during a cloning or sequencing process. The positions at which residues differ between the published human and rat sequences were also identified. In the human ACC2 amino acid consensus sequence of the present invention, these positions are occupied by R at position 9, P at position 111, A at position 127, F at position 254, Q at position 345, V at position 347, AGWG at positions of 349–352, P at position 450, T at position 565, H at position 614, E at position 656, E at position 671, ET at position 742–743, E at position 799, N at position 841, V at position 1025, V at position 1064, V at position 1103, C at position 1259, R at position 1480, A at position 1526, R at position 1547, I at position 1717, G at position 1821, I at position 2141, PPYA at position 2194–2197, and K at position 2242. In the rat ACC2 amino acid consensus sequence of the present invention, these positions in the sequence are occupied by residues C at position 9, K at position 30, S at position 42, S at position 50, S at position 91, H at position 153, A at position 178, S at position 179, A at position 191, L at position 196, C at position 272, I at position 308, QYV at position 313–315, E at position 365, PSEA at position 372–375, WA at position 377–378, KI at position 382–383, P at position 422, R at position 463, ML at position 472–473, T at position 534, G at position 556, E at position 563, G at position 658, AD at position 693–694, R at position 707, F at position 742, C at position 774, M at position 788, L at position 849, K at position 940, L at position 1025, G at position 1048, M at position 1062, Y at position 1065, Y at position 1122, P at position 1159, IFLSAIDMY at position 1243–1251, R at position 1467, A at position 1493, PT at position 1596–1597, E at position 1629, PK at position 1737–1738, RM at position 1832–1833, RYV at position 1890–1892, T at position 1932, A at position 2079, D at position 2111, P at position 2150, Y at position 2168, F at position 2185, A at position 2203, GQL at position 2260–2262, TA at position 2264–2265, E at position 2309, I at position 2403, and DCVA at position 2428–2431. Details regarding the analysis of the published ACC2 sequences and the generation of the human and rat ACC2 polypeptide sequences of the present invention are provided in the accompanying Examples. Methods of isolating and using the polypeptides are also provided.

Although the ACC2 polypeptide sequences of SEQ ID NOs:12 and 14 form an aspect of the present invention, the polypeptides of the present invention are not limited to the precise sequences provided in the Sequence Listing. In other aspects of the present invention, variant polypeptides, and polypeptides comprising non-standard amino acids, can be generated using techniques known to those of ordinary skill in the art.

The polypeptides of the present invention can comprise non-standard amino acids, namely amino acids other than the 20 gene-encoded amino acids. Such polypeptides can be generated by natural processes, such as by posttranslational processing, or by chemical modification techniques which are well known in the art. Such modifications are described in basic texts and in more detailed monographs, as well as in the pertinent research literature. Modifications can occur anywhere in a polypeptide, including the peptide backbone, the amino acid side-chains and the amino or carboxyl termini.

A given polypeptide can contain many types of modifications. Polypeptides can be branched, for example, as a result of ubiquitination, and they can be cyclic, with or without branching. Cyclic, branched, and branched cyclic polypeptides can result from posttranslation natural processes or can be made by employing synthetic methods known to those of ordinary skill in the art. Representative modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. Tags to facilitate purification can also be added (see, e.g., Creighton, *Proteins-Structures and Molecular Properties*, 2nd ed., W. H. Freeman, New York (1992); *Posttranslational Covalent Modification of Proteins*, (Johnson, ed.), Academic Press, New York, (1984); Seifter & Englard, Method Enzymol. 182:626–646 (1990)).

The ACC2 polypeptides of the present invention, and variants, fragments and serial deletions thereof, can be produced by any method known in the art for the synthesis of polypeptides, for example, by chemical synthesis, by the recombinant expression techniques described herein or by purification from a biological source, such as tissue, as described herein. For example, methods that are well known to those skilled in the art can be used to construct expression vectors containing a partial or the entire native or mutated ACC2 polypeptide coding sequence and appropriate transcriptional/translational control signals. These methods include in vitro recombinant DNA techniques, as described herein, synthetic techniques and in vivo recombination/genetic recombination.

III. Polynucleotides of the Present Invention

ACC2 polynucleotides that form aspects of the present invention are presented in FIGS. 1 and 2 and in SEQ ID NOs:11 and 13. In the case of human ACC2, the present inventors have found discrepancies between the published sequences and the sequences of the present invention and have reconciled these differences in the ACC2 nucleotide and polypeptode sequences of the present invention.

The present inventors have identified discrepancies between the published ACC2 sequences. These residue may comprise inadvertant mutations introduced by the cloning process. In the human ACC2 sequence of the present invention, these positions in the sequence are occupied by R at position 9, P at position 111, A at position 127, F at position 254, Q at position 345, V at position 347, AGWG at positions of 349–352, P at position 450, T at position 565, H at position 614, E at position 656, E at position 671, ET at position 742–743, E at position 799, N at position 841, V at position 1025, V at position 1064, V at position 1103, C at position 1259, R at position 1480, A at position 1526, R at position 1547, I at position 1717, G at position 1821, I at position 2141, PPYA at position 2194–2197, and K at position 2242. In the rat ACC2 sequence of the present invention, these positions in the sequence are occupied by C at position 9, K at position 30, S at position 42, S at position 50, S at position 91, H at position 153, A at position 178, S at position 179, A at position 191, L at position 196, C at position 272, I at position 308, QYV at position 313–315, E at position 365, PSEA at position 372–375, WA at position 377–378, KI at position 382–383, P at position 422, R at position 463, ML at position 472–473, T at position 534, G at position 556, E at position 563, G at position 658, AD at position 693–694, R at position 707, F at position 742, C at position 774, M at position 788, L at position 849, K at position 940, L at position 1025, G at position 1048, M at position 1062, Y at position 1065, Y at position 1122, P at position 1159, IFLSAIDMY at position 1243–1251, R at position 1467, A at position 1493, PT at position 1596–1597, E at position 1629, PK at position 1737–1738, RM at position 1832–1833, RYV at position 1890–1892, T at position 1932, A at position 2079, D at position 2111, P at position 2150, Y at position 2168, F at position 2185, A at position 2203, GQL at position 2260–2262, TA at position 2264–2265, E at position 2309, I at position 2403, and DCVA at position 2428–2431. Details regarding the generation of the human and rat ACC2 sequences of the present invention are provided in the accompanying Examples.

In one aspect of the present invention, isolated polynucleotides encoding a polypeptide comprising the amino acid sequence of human ACC2 (SEQ ID NO:12) and rat ACC2 (SEQ ID NO:14) is disclosed. Examples of such polynucleotides are presented in FIGS. 1 and 2 and in SEQ ID NOs:11 and 13, which encode human and .rat ACC2 proteins, respectively. In another aspect of the present invention, the nucleotide sequence of the cDNA insert of the plasmid deposited with the ATCC as Accession Number PTA-6054 on Jun. 8, 2004, and complements thereof, are disclosed.

The present invention encompasses complements of the ACC2-encoding polynucleotides of the present invention.

As explained herein, a complementary sequence is a nucleotide sequence that it can hybridize to a polynucleotide sequence of the present invention to form a stable duplex. Sequences that are complementary to an ACC2 polynucleotide sequence of the present invention can be readily identified using the sequences provided in SEQ ID NOs:11 and 13 as templates. Thus, the present invention encompasses not only polynucleotide sequences encoding the ACC2 proteins of the present invention, but complements of these sequences as well.

As used herein, a "polynucleotide" of the present invention includes the polynucleotides disclosed herein and in the Sequence Listing, as well as those polynucleotides capable of hybridizing, under stringent hybridization conditions, to the polynucleotide sequences of SEQ ID NOs:11 and 13, the complement thereof, or the cDNA within the clone deposited with the ATCC. "Stringent hybridization conditions" are described herein.

A polynucleotide which hybridizes only to polyA+ sequences (such as any 3' terminal polyA+ tract of a cDNA shown in the sequence listing), or to a complementary stretch of T (or U) residues, is not included in the definition of "polynucleotide," since such a polynucleotide would hybridize to any nucleic acid molecule containing a poly (A) stretch or the complement thereof (e.g., almost any double-stranded cDNA clone generated using oligo dT as a primer).

The polynucleotides of the present invention can comprise any polyribonucleotide or polydeoxribonucleotide, which can be unmodified RNA or DNA or modified RNA or DNA. For example, polynucleotides can comprise single- and double-stranded DNA, DNA that is a mixture of single- and double-stranded regions, single-and double-stranded RNA, and RNA that is mixture of single-and double-stranded regions, hybrid molecules comprising DNA and RNA that may be single-stranded or, more typically, double-stranded or a mixture of single-and double-stranded regions. In addition, the polynucleotide can comprise triple-stranded regions comprising RNA, DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polynucleotides of the present invention are useful as probes for the identification and isolation of full-length cDNAs and/or genomic DNA which correspond to the polynucleotides of the present invention, as probes to hybridize to and discover novel, related DNA sequences, as probes for positional cloning of a sequence of the present invention or a related sequence, as probe to "subtract-out" known sequences in the process of discovering other novel polynucleotides, as probes to quantify polynucleotide expression, and as probes for microarrays.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Details regarding the generation of the human and rat ACC2 sequences of the present invention are provided herein and in the accompanying Examples.

IV. Fragments

The present invention encompasses fragments of the polynucleotides encoding ACC2 proteins of the present invention. As used herein, the term "fragment" means a polynucleotide sequence that is shorter than an ACC2-encoding polynucleotide sequence of the present invention (e.g., SEQ ID NOs:11 and 13), but retains a region comprising the contiguous sequence of the polynucleotide from which the fragment is derived. A fragment of an ACC2 nucleotide sequence can encode a biologically active portion of an ACC2 protein, or it can be a fragment that can be used as a hybridization probe or as a primer. Nucleic acid molecules that are fragments of an ACC2-encoding polynucleotide can comprise any number of nucleotides up to the number of nucleotides present in a full-length ACC2-encoding polynucleotide sequence of the present invention.

The term "fragment," therefore, includes any contiguous sequence not disclosed prior to the present invention, but excludes sequences known prior to the present invention. More particularly, if an isolated fragment is disclosed prior to the present invention, that fragment is not encompassed by the present invention.

A fragment of an ACC2-encoding polynucleotide sequence can, but need not, encode a biologically active ACC2. For example a fragment of an ACC2-encoding polynucleotide sequence of the present invention can be employed as a probe or as a primer, in which case, these fragments will not encode a biologically active protein. On the other hand, a truncated form of an ACC2-encoding polynucleotide sequence of the present invention may encode a biologically active protein, yet be referred to as a fragment. Both biologically active and non-biologically active sequences are within the scope of the claims of the present invention.

Polypeptide fragments also form aspects of the present invention. A polypeptide fragment of the present invention can comprise any number of amino acids up to the full length of an ACC2 amino acid sequence of the present invention. Polypeptide fragments of the present invention include truncations of any length up to, but excluding, a full length ACC2 polypeptide of the present invention. As discussed herein, a polypeptide fragment of the present invention excludes sequences known prior to the present invention. Thus, an isolated fragment that was described prior to the present invention, is not encompassed by the present invention.

A polypeptide fragment can be, for example, an epitope, which can be employed to raise antibodies against an ACC2 polypeptide of the present invention, as described herein and as generally known to those of ordinary skill in the art. Fragments can, but need not, include a biologically active segment of an ACC2 protein of the present invention. Other applications for the polypeptide fragments of the present invention will be apparent to those of ordinary skill in the art.

A polypeptide fragment of the present invention can comprise an ACC2 sequence of the present invention from which serial deletions from the $NH_2$- or COOH-terminus, or both the $NH_2$- and COOH-terminus have been made. Such a fragment will comprise a variable number of contiguous amino acids of an ACC2 polypeptide of the present invention, but will be shorter in sequence than a full-length ACC2 polypeptide of the present invention.

V. Variants

In a further aspect of the present invention, the polypeptides and polynucleotides of the present invention encompass sequences that are variants of the ACC2 polypeptide and ACC2-encoding polynucleotide sequences disclosed herein. As used herein, a "variant polynucleotide" is a polynucleotide or polypeptide differing from the polynucleotide or polypeptide of the present invention, but retaining essential properties thereof. Generally, variants are similar, and, over many regions, identical to the polynucleotide or polypeptide of the present invention. "Variants" of the polynucleotide sequences of the present invention include sequences that encode an ACC2 protein of the present invention, but differ conservatively because of the degeneracy of the genetic code. These naturally occurring variants can be identified using standard methodology, such as polymerase chain reaction (PCR), hybridization and sequencing techniques.

A variant can comprise alterations in the coding regions, non-coding regions, or both regions of an ACC2-encoding polynucleotide sequence For example, a variant can comprise alterations that produce silent substitutions, additions, or deletions, but do not alter the properties or activities of the encoded polypeptide. As noted, nucleotide variants produced by silent substitutions due to the degeneracy of the genetic code are within the scope of the claims. Moreover, a variant can comprise any number of amino acid substitutions, for example 1, 2, 3, 4, 5, 7, 8, 10, or more amino acids can be substituted, deleted, or added in any combination are also within the scope of the claims. Preferably, a variant of the present invention retains the amino acids identified as different from published ACC2 sequences (i.e., R at position 9, P at position 111, A at position 127, F at position 254, Q at position 345, V at position 347, AGWG at positions of 349–352, P at position 450, T at position 565, H at position 614, E at position 656, E at position 671, ET at position 742–743, E at position 799, N at position 841, V at position 1025, V at position 1064, V at position 1103, C at position 1259, R at position 1480, A at position 1526, R at position 1547, I at position 1717, G at position 1821, I at position 2141, PPYA at position 2194–2197, and K at position 2242 in the human sequence and C at position 9, K at position 30, S at position 42, S at position 50, S at position 91, H at position 153, A at position 178, S at position 179, A at position 191, L at position 196, C at position 272, I at position 308, QYV at position 313–315, E at position 365, PSEA at position 372–375, WA at position 377–378, KI at position 382–383, P at position 422, R at position 463, ML at position 472–473, T at position 534, G at position 556, E at position 563, G at position 658, AD at position 693–694, R at position 707, F at position 742, C at position 774, M at position 788, L at position 849, K at position 940, L at position 1025, G at position 1048, M at position 1062, Y at position 1065, Y at position 1122, P at position 1159, IFLSAIDMY at position 1243–1251, R at position 1467, A at position 1493, PT at position 1596–1597, E at position 1629, PK at position 1737–1738, RM at position 1832–1833, RYV at position 1890–1892, T at position 1932, A at position 2079, D at position 2111, P at position 2150, Y at position 2168, F at position 2185, A at position 2203, GQL at position 2260–2262, TA at position 2264–2265, E at position 2309, I at position 2403, and DCVA at position 2428–2431).

Naturally occurring variants are called "allelic variants," and refer to one of several alternate forms of a gene occupying a given locus on a chromosome of an organism. These allelic variants can vary at either the polynucleotide and/or polypeptide level and are within the scope of the present invention. Alternatively, non-naturally occurring variants may be produced by mutagenesis techniques or by direct synthesis. Nucleic acid molecules corresponding to natural allelic variants and homologues of the ACC2 cDNA of the preent invention can be isolated based on their identity to the polynucleotides disclosed herein using the cDNA, or a portion thereof, as a hybridization probe according to standard hybridization techniques under stringent hybridization conditions as described herein.

Using known methods of protein engineering and recombinant DNA technology, variants can be generated to alter a characteristic of the polypeptides of the present invention, such as molecular weight or antigenic response. For example, a variant can have one or more altered characteristics while retaining other characteristics. For example, one or more amino acids can be deleted from the $NH_2$-terminus or COOH-terminus of the protein (as described herein), which will alter the molecular weight of the protein, and might alter the immunologic response profile of the variant and/or the preferred purification protocol for the variant, but might not substantially alter the enzymatic activity of the variant.

Even if deleting one or more amino acids from the $NH_2$-terminus or COOH-terminus of a polypeptide results in modification or loss of one or more biological functions, other biological activities might still be retained. For example, the ability of a deletion variant to induce and/or to bind antibodies which recognize the protein will likely be retained when less than the majority of the residues of the protein are removed from the $NH_2$-terminus or COOH-terminus. Whether a particular polypeptide lacking $NH_2$- or COOH-terminal residues of a protein retains such immunogenic activities can readily be determined by routine methods described herein and otherwise known in the art.

Thus, the present invention encompasses polypeptide variants that show varying degrees of biological activity. Such variants include deletions, insertions, inversions, repeats, and substitutions selected according to general rules known in the art so as have little effect on activity.

Various methods for making phenotypically silent amino acid substitutions are known. For example, by comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

In another example, standard mutagenesis methods can be employed to introduce amino acid changes at specific positions of a cloned gene to identify regions critical for protein function. For example, site directed mutagenesis or alanine-scanning mutagenesis (introduction of single alanine mutations at every residue in the molecule) can be employed. The resulting mutant molecules can then be tested for biological activity.

Thus, the present invention encompasses, but is not limited to, conservative amino acid substitutions introduced into the ACC2 polypeptides of the present invention. Particular examples of conservative amino acid substitutions are presented herein.

In addition to conservative amino acid substitution, variants of the present invention include, but are not limited to: (i) substitutions with one or more of the non-conserved amino acid residues, where the substituted amino acid residues may or may not be one encoded by the genetic code, or (ii) substitution with one or more amino acid residues having a substituent group, (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, a leader or secretory sequence, or a sequence facilitating purification.

Methods of introducing coding and non-coding mutations into a sequence are known in the art and can be readily employed in the present invention to generate polypeptide and polynucleotide variants (see, e.g., Sambrook et al. and Creighton).

VI. Recombinant Expression of ACC2 Sequences

In one aspect of the present invention, the ACC2 enzymes of the present invention can be expressed recombinantly. Thus, in accordance with the present invention, conventional molecular biology, microbiology, recombinant DNA and protein chemistry techniques known to those of ordinary skill of the art can be employed to produce a DNA sequence encoding an ACC2 polypeptide, in addition to the guidance provided herein. Such techniques are explained fully in the relevant literature (see, e.g., Sambrook Sambrook et al., *Molecular Cloning: A Laboratory Manual*, $3_{rd}$ ed., Cold Spring Harbor Press, Cold Spring Harbor (2001); Glover, *DNA Cloning: A Practical Approach*, ($2^{nd}$ ed.) IRL Press, New York, USA (1995); Gait, *Oligonucleotide Synthesis: A Practical Approach*, IRL Press, New York, USA (1984); Hames & Higgins, *Protein Expression: A Practical Approach*, Oxford University Press, New York, USA, (1999); Bickerstaff, *Immobilization of Cells And Enzymes*, Humana Press, Totowa, N.J., USA (1997); Perbal, *A Practical Guide To Molecular Cloning* ($2^{nd}$ ed.) Wiley, New York, N.Y., USA (1988); *Current Protocols in Molecular Biology*, (Ausubel et al., eds.), Greene Publishing Associates and Wiley-Interscience, New York (2002); Ausubel, *Short Protocols in Molecular Biology: A Compendium of Methods from Current Protocols in Molecular Biology*, ($4^{th}$ ed.) John Wiley & Sons, New York, N.Y., USA (1999)). A DNA sequence encoding an ACC2 polypeptide of the present invention (including variants, analogs, and functional equivalents), can be prepared by various molecular biology methods known in the art.

Recombinant expression of an ACC2 polypeptide of the present invention, or a fragment, variant or analog thereof, (e.g., a human or a rat ACC2 polypeptide), requires the construction of an expression vector comprising a polynucleotide that encodes the protein of interest. Once a polynucleotide encoding an ACC2 protein of the present invention has been obtained, a vector for the production of the ACC2 polypeptide can be produced by recombinant DNA technology using techniques known in the art. Methods for preparing a protein by expressing a polynucleotide containing an ACC2-encoding nucleotide sequence are known in the art and described herein.

Methods known to those of ordinary skill in the art can be used to construct an expression vector comprising an ACC2 coding sequence and appropriate transcriptional and translational control signals. These methods include, for example, in vitro recombinant DNA techniques, synthetic techniques, and in vivo genetic recombination. The present invention, thus, encompasses replicable vectors comprising an ACC2-encoding nucleotide sequence of the present invention, which may be operably linked to a promoter.

The expression vector can then be transferred to a host cell by conventional techniques and the transfected cells are then cultured under appropriate conditions to produce an ACC2 polypeptide of the present invention. Thus, the present invention also comprises host cells containing a polynucleotide encoding an ACC2 polypeptide of the present invention operably linked to a heterologous promoter.

A variety of host-expression vector systems can be employed to express an ACC2 polypeptide of the present invention. Such host-expression systems represent vehicles by which a coding sequence of interest can be produced and subsequently purified, but also represent cells that may, when transformed or transfected with the appropriate nucleotide coding sequences, express an ACC2 polypeptide of the present invention in situ. These include but are not limited to microorganisms such as bacteria (e.g., *E. coli, B. subtilis*) transformed with recombinant bacteriophage DNA, plasmid DNA or cosmid DNA expression vectors containing ACC2 coding sequences; yeast (e.g., *Saccharomyces, Pichia*) transformed with recombinant yeast expression vectors containing ACC2 coding sequences; insect cell systems infected with recombinant virus expression vectors (e.g., baculovirus) containing ACC2 coding sequences; plant cell systems infected with recombinant virus expression vectors (e.g., cauliflower mosaic virus, (CaMV); tobacco mosaic virus, (TMV)) or transformed with recombinant plasmid expression vectors (e.g., Ti plasmid) containing ACC2 coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Under some conditions it might be desirable that bacterial cells such as *Escherichia coli*, or eukaryotic cells be used for the expression of a recombinant ACC2 polypeptide.

In bacterial systems, a number of expression vectors can be advantageously employed, depending upon the use intended for the ACC2 polypeptide being expressed. For example, when a large quantity of such a protein is to be produced, for example for the generation of a pharmaceutical composition comprising an ACC2 polypeptide, vectors that direct the expression of high levels of fusion protein products that are readily purified can be desirable. pGEX vectors can also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or Factor Xa protease cleavage sites so that the cloned target gene product can be released from the GST moiety.

In an insect system, *Autographa californica* nuclear polyhedrosis virus (AcNPV) can be used as a vector to express foreign genes. The virus grows in *Spodoptera frugiperda* cells. The ACC2 polypeptide coding sequence may be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the ACC2 polypeptide coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the ACC2 protein in infected hosts (see, e.g., Logan & Shenk, (1984) *Proc. Natl. Acad. Sci. U.S.A.* 81:355–359). Specific initiation signals may also be required for efficient translation of inserted ACC2 coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be from a variety of origins, both natural and synthetic. The efficiency of expression can be enhanced by the inclusion of appropriate transcription enhancer elements, transcription terminators, etc. (see, e.g., Bittner et al., (1987) *Method Enzymol.* 153:51–544).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be employed.

For long-term, high-yield production of recombinant proteins, stable expression is preferred. For example, cell lines that stably express the ACC2 polypeptide can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express an ACC2 polypeptide. Such engineered cell lines may be particularly useful in screening and evaluation of compounds that interact directly or indirectly with the ACC2 polypeptide.

A number of selection systems can be employed in the recombinant expression of an ACC2 polypeptide of the present invention. For example, the herpes simplex virus thymidine kinase (Wigler et al., (1977) *Cell* 11:223), hypoxanthine-guanine phosphoribosyltransferase (Szybalska & Szybalski, (1992) *Proc. Natl. Acad. Sci. U.S.A.* 48:202), and adenine phosphoribosyltransferase (Lowy et al., (1980) *Cell* 22:817) genes can be employed in tk-, hgprt- or aprt-cells, respectively. Additionally, anti-metabolite resistance can be used as the basis of selection for the following genes: dhfr, which confers resistance to methotrexate (Wigler et al., (1980) *Proc. Natl. Acad. Sci. U.S.A.* 77:357; O'Hare et al., (1981) *Proc. Natl. Acad. Sci. U.S.A.* 78:1527); gpt, which confers resistance to mycophenolic acid (Mulligan & Berg, (1981) *Proc. Natl. Acad. Sci. U.S.A.* 78:2072); neo, which confers resistance to the aminoglycoside G-418 (*Clinical Pharmacy* 12:488–505; Wu & Wu, (1991) *Biotherapy* 3:87–95; Tolstoshev, (1993) *Ann. Rev. Pharmacol. Toxicol.* 32:573–596; Mulligan, (1993) *Science* 260:926–932; and Morgan & Anderson, (1993) *Ann. Rev. Biochem.* 62:191–217; *TIB TECH* 11(5):155–215, May, 1993); and hygro, which confers resistance to hygromycin (Santerre et al., (1984) *Gene* 30:147), to provide just a few examples.

Methods known in the art of recombinant DNA technology can be applied to select the desired recombinant clone, and such methods are described, for example, in *Current Protocols in Molecular Biology*, (Ausubel et al., eds.), Greene Publishing Associates and Wiley-Interscience, New York (2002); Kriegler, *Gene Transfer and Expression A Laboratory Manual*, Stockton Press, New York, N.Y., USA (1990); *Current Protocols in Human Genetics*, (Dracopoli et al., eds.), John Wiley & Sons, New York, N.Y., USA (1994), Chapters 12 and 13; and Colberre-Garapin et al., (1981) *J. Mol. Biol.* 150:1.

The expression levels of an ACC2 polypeptide can be increased in several different ways, for example by vector amplification (for a review of this technique, see e.g., Bebbington & Hentschel, in *DNA Cloning*, vol. 3, Academic Press, New York (1987)). When a marker in the vector system expressing an ACC2 polypeptide is amplifiable, an increase in the level of inhibitor present in culture of host cell will increase the number of copies of the marker gene. Since the amplified region is associated with the ACC2 gene, production of ACC2 protein will also increase.

Once an ACC2 polypeptide of the present invention has been produced by a cell, tissue, animal, or has been chemically synthesized, or recombinantly expressed, it can be purified by any method known in the art for purification of a polypeptide, for example, by chromatography (e.g., ion exchange, affinity, particularly by affinity for the specific antigen after Protein A, and sizing column chromatography), centrifugation, differential solubility, or by any other standard technique for the purification of proteins. In addition, the ACC2 polypeptides of the present invention, or fragments thereof, can be fused to heterologous polypeptide sequences described herein or otherwise known in the art, to facilitate purification (e.g., a His tag). Another aspect of the present invention relates to the purification of ACC polypeptides, which is not limited to ACC2 polypeptides, is described herein and can be employed to generate an isolated ACC2 polypeptide.

VII. Isolation of ACC Polypeptides

The ACC2 polypeptides of the present invention can be isolated from any suitable source, for example from cells recombinantly or endogenously expressing the protein or from tissues such as rat livers and/or rat heart muscle. ACC2 can be isolated from a biological sample using standard protein purification methodology known to those of the art (see, e.g., Janson, *Protein Purification: Principles, High Resolution Methods, and Applications*, ($2^{nd}$ed.) Wiley, N.Y., (1997); Rosenberg, *Protein Analysis and Purification: Benchtop Techniques*, Birkhauser, Boston, (1996); Walker, *The Protein Protocols Handbook*, Humana Press, Totowa, N.J., (1996); Doonan, *Protein Purification Protocols*, Humana Press, Totowa, N.J., (1996); Scopes, *Protein Purification: Principles and Practice*, Springer-Verlag, N.Y., (1994); Harris, *Protein Purification Methods: A Practical Approach*, IRL Press, New York, (1989)). Guidance in the isolation of an ACC and/or FAS is provided herein, for example in the Examples (see, e.g., Example 9). Other methods of purifying active ACC will be known to those of skill in the art and any such methods can be employed in the present invention.

In one aspect of the present invention, a method of isolating an ACC polypeptide is provided. This purification method is exemplified in the context of ACC2, but the method can be employed to isolate any ACC (e.g., ACC1 or ACC2) polypeptide. In one embodiment, the method comprises a single step IgG mediated affinity column. The IgG mediated affinity column can comprise an anti-myc IgG. Anti-Myc-IgG, especially c-Myc-5 IgG, has been characterized (Hillman et al., (2001) *Protein Expression and Purification* 23, 359–368) and can be readily prepared as described by Hillman et al. (Hillman et al., (2001) *Protein Expression and Purification* 23, 359–368).

In one embodiment of the method, total crude homogenized tissue or cell cytosolic lysates, for example lysates derived from ACC virus infected Sf9 cells or any other transfected cell, are loaded on a c-Myc-5 IgG column. The loading can be accomplished by overnight incubation, although the precise loading procedure employed can depend on a variety of factors, such as volume of lysate and whether any other pre-column purification procedures were performed (e.g., a preliminary precipitation, etc.). Such considerations will be known to those of ordinary skill in the art upon considering the present disclosure.

The bound protein can then extensive washed with high salt buffer. A buffer comprising 0.5 M NaCl, for example can be employed. One purpose of this high salt wash is to remove a fraction of the proteins present in the crude lysate; accordingly, the concentration and composition of salt employed in the wash can vary.

Following the salt wash, the proteins that remain bound to the column can be eluted with an elution ligand. For example, when an anti-myc IgG antibody is employed, the elution ligand can be a peptide comprising a myc peptide (EQKLISEEDL; SEQ ID NO:16), which can comprise various modifications, such capping of the NH$_2$-or COOH-terminal, which eliminate charges. The elution of the ACC protein from the column can be performed stepwise, for example in a series of steps (e.g., 1, 2, 5, 7, 10 or more steps). Additional suitable elution ligands can be employed and can depend, in part, on the nature of the IgG employed in the method. In another example, when an anti-FLAG IgG is employed the elution ligand can comprise a FLAG peptide, which comprises the core sequence DYKD (SEQ ID NO:33) and is commercially available as a peptide having the sequence DYKDDDDK (SEQ ID NO:34).

The presence of ACC in the eluent of each step can be confirmed by immunological techniques and/or by simply running the eluent on an SDS PAGE gel and identifying the molecular weight of the eluted protein. Additionally, the identity of the eluted protein can be confirmed by an enzymatic assay, such as that described herein (see also U.S. Patent Application Ser. No. 60/558,015, incorporated herein by reference in its entirety) or an assay known in the art (see, e.g., Waite & Wakil, (1962) *J. Biol. Chem.* 237:2750–2757, Tanabe et al., (1981) *Methods Enzymol.* 71 Pt C, 5–16; Wakil et al., (1959) *Biochim. Biophys. Acta* 34:227–233, also incorporated herein by reference). The eluent from each step can be evaluated separately and the active fractions can subsequently be pooled. Pooled protein can be stored in buffer or in a lyophilized form.

VIII. Methods of Assaying for ACC2 Catalytic Activity

The activity of the ACC2 polypeptides of the present invention can be determined using a variety of ACC2 activity assays. Some representative assays are described herein below.

A $CO_2$-fixation assay is an ACC assay that can be employed in the present invention. In this assay, [$^{14}C$]—NaHCO$_3$, acetyl CoA, Mg-ATP, citrate and ACC are incubated at 37° C.; the reaction mixture is quenched with acid at the end of the reaction, and subsequently heated to remove bicarbonate as $^{14}CO_2$. Scintillant is then added and the acid-stable malonyl CoA remaining in the vial is counted in a scintillation counter (see Waite & Wakil, (1962) *J. Biol. Chem.* 237:2750–2757 and Tanabe et al., (1981) *Methods Enzymol.* 71 Pt C, 5–16).

The continuous ATP regeneration-coupled spectrophotometric assay is another ACC2 assay that can be employed in the present invention. In this assay, the ADP generated in the ACC enzyme reaction is converted to ATP by a pyruvate kinase/lactate dehydrogenase coupled enzyme system, and NADH disappearance is followed at 340 nm spectrophotometrically or fluorometrically (see Tanabe et al., (1981) *Methods Enzymol.* 71 Pt C, 5–16). The ATP-regeneration system is very sensitive to the presence of ATPases.

Yet another form of ACC assay is an ACC/FAS coupled assay. In the ACC reaction, malonyl CoA is formed from acetyl CoA. Malonyl CoA can then be used as a substrate for FAS with NADPH as the cofactor. The reaction can be monitored by the rate of utilization of NADPH spectrophotometrically (see Wakil et al., (1959) *Biochim. Biophys. Acta* 34:227–233).

Another method of assaying ACC2 enzymatic activity that can be employed in the present invention is described in U.S. Patent Application Ser. No. 60/558,015. In one embodiment of this assay, the method comprises: (a) contacting an enzyme mix comprising ACC and FAS, optionally comprising one or more of bicarbonate, Mg, ATP, NADPH and an ACC effector, with a solid support comprising a scintillant and a linking moiety; (b) incubating the enzyme mix with an acetyl CoA mix comprising radiolabeled acetyl CoA, optionally comprising one or more of bicarbonate, Mg, ATP, NADPH and an ACC effector, under suitable reaction conditions, for a desired incubation time; and (c) detecting scintillation signal, wherein scintillation signal is indicative of ACC catalytic activity.

IX. Transgenic Animals

The preparation of a transgenic non-human animal that expresses an ACC2-encoding sequence of the present invention is within the scope of the present invention. A preferred transgenic animal is a mouse.

Techniques for the preparation of transgenic animals are known in the art. Representative techniques are described in the literature and will be known to those of ordinary skill in the art. Some representative techniques are described, for example, in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species).

In one method for the preparation of a transgenic mouse, cloned recombinant or synthetic DNA sequences or DNA segments encoding a human ACC2 gene product are injected into fertilized mouse eggs. The injected eggs are implanted in pseudo pregnant females and are grown to term to provide transgenic mice whose cells express a human or rat ACC2 gene product.

X. Antibodies

In another aspect, the present invention relates to antibodies that specifically recognize the ACC2 proteins of the present invention. Such antibodies can be employed in a range of applications. By way of non-limiting example, antibodies of the present invention can be used to purify, detect, and/or target the polypeptides of the present invention, including both in vitro and in vivo diagnostic and therapeutic methods. For example, antibodies can be employed in immunoassays for qualitatively and/or quantitatively measuring levels of the polypeptides of the present invention in biological samples (see, e.g., Harlow & Lane., Antibodies: A Laboratory Manual, Cold Spring Harbor Laboratory Press, 2nd ed. (1988), incorporated by reference herein in its entirety).

Antibodies of the present invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, encompasses immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The terms "antibody" (Ab) and "monoclonal antibody" (Mab) encompasses intact molecules, as well as, antibody fragments (such as, for example, Fab and F(ab')2 fragments) which are capable of specifically binding to a given protein. Fab and F(ab')2 fragments lack the Fc fragment of intact antibody, often clear more rapidly from the circulation of the animal or plant, and may have less non-specific tissue binding than an intact antibody. Thus, in some situations these fragments are preferred, as well as the products of a Fab or other immunoglobulin expression library.

Antibodies of the present invention include chimeric, single chain, and humanized antibodies. For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; Boulianne et al., Nature 312:643 (1984); and Neuberger et al., Nature 314:268 (1985), which are incorporated herein by reference in their entirety.

A humanized antibody, which is a form of chimeric antibody, comprises a portion of an antibody molecule from non-human species that binds the desired antigen, and can comprise one or more complementarity determining regions (CDRs) from the non-human species, and a framework region from a human immunoglobulin molecule. Often, framework residues in the human framework region(s) will be substituted with the corresponding residue from the CDR donor antibody to alter, and often improve, antigen binding. These framework substitutions can be identified by methods well known in the art, e.g., by modeling of the interactions of the CDR and framework residues to identify framework residues important for antigen binding and sequence comparison to identify unusual framework residues at particular positions (see, e.g., Riechmann et al., Nature 332:323 (1988)). Antibodies can be humanized using a variety of techniques known in the art including, for example, CDR-grafting (U.S. Pat. Nos. 5,225,539; 5,530,101; and 5,585,089), veneering or resurfacing (Padlan, Mol. Immunol. 28(4/5):489–498 (1991); Studnicka et al., Prot. Engineering 7(6):805–814 (1994); Roguska. et al., Proc. Natl. Acad. Sci. U.S.A. 91:969–973 (1994)), and chain shuffling (U.S. Pat. No. 5,565,332). In some cases, a humanized antibody comprises one or more amino acid residues introduced from a source that is non-human. Methods of humanizing antibodies are known in the art; for example, humanization can be performed essentially as described in Jones et al., Nature 321:522–525 (1986); Reichmann et al., Nature 332:323–327 (1988); and Verhoeyen et al., Science 239:1534–1536 (1988), namely by substituting rodent CDRs or CDR sequences for the corresponding sequences of a human antibody. Accordingly, such "humanized" antibodies are chimeric antibodies.

In general, a humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also comprises at least a portion of an immunoglobulin constant region (Fc), typically that of a human immunoglobulin (Jones et al., Nature 321:522–525 (1986); Reichmann et al., Nature 332:323–327 (1988); and Presta, Curr. Op. Struct. Biol. 2:593–596 (1992).

Completely human antibodies are particularly desirable for therapeutic treatment of human patients. Human antibodies can be made by a variety of methods known in the art, including phage display methods using antibody libraries derived from human immunoglobulin sequences. The techniques of Cole et al., and Boerder et al., are also available for the preparation of human monoclonal antibodies (Cole et al., Monoclonal Antibodies and Cancer Therapy, Alan R. Liss, New York (1985); and Boerner et al., J. Immunol. 147(1): 86–95 (1991)).

Human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region may be introduced into mouse embryonic stem cells in addition to human heavy and light chain genes. The mouse heavy and light chain immunoglobulin genes can be rendered non-functional separately or simultaneously with the introduction of human immunoglobulin loci by homologous recombination. The modified embryonic stem cells are then expanded and microinjected into blastocysts to produce chimeric mice. The chimeric mice are then bred to produce homozygous offspring which express human antibodies.

The transgenic mice can be immunized in the normal fashion with a selected antigen, e.g., all or a portion of an ACC2 polypeptide of the present invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg & Huszar, *Int. Rev. Immunol.* 13:65–93 (1995).

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in Marks et al., *Biotechnol.* 10:779–783 (1992); Lonberg et al., *Nature* 368:856–859 (1994); Fishwild et al., *Nature Biotechnol.* 14:845–51 (1996); Neuberger, *Nature Biotechnol.* 14:826 (1996); and Lonberg & Huszer, *Intern. Rev. Immunol.* 13:65–93 (1995).

In general, a humanized antibody comprises substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody optimally can also comprise at least a portion of an immunoglobulin constant region (Fc), typically that of a human immunoglobulin.

The antibodies of the present invention can comprise monoclonal antibodies. Monoclonal antibodies can be prepared using hybridoma methods, such as those described by Kohler & Milstein, *Nature,* 256:495 (1975) and Harlow et al., *Antibodies: A Laboratory Manual*, Cold Spring Harbor Laboratory Press, 2$^{nd}$ ed. (1988); additional methods are known to those of ordinary skill in the art. Other examples of methods which may be employed for producing monoclonal antibodies includes, but are not limited to, the human B-cell hybridoma technique (Cole et al., 1983, *Proc. Natl. Acad. Sci. U.S.A.* 80:2026–2030 (1983)), and the EBV-hybridoma technique (Cole et al., *Monoclonal Antibodies And Cancer Therapy*, Alan R. Liss, New York, pp. 77–96 (1985)). Such antibodies may be of any immunoglobulin class including IgG, IgM, IgE, IgA, IgD and any subclass thereof. The hybridoma producing a mAb of this invention can be cultivated in vitro or in vivo. Production of high titers of mAbs in vivo makes this a preferred method of production in some situations.

It is generally desirable that immortalized cell lines fuse efficiently, support stable high level expression of antibody by the selected antibody-producing cells, and are sensitive to a medium such as HAT medium. Generally, methods of preparing antibodies are known in the art and can be employed in the present invention to raise antibodies against an ACC2 polypeptide of the present invention.

XI. Antisense and RNAi Methods

The present invention encompasses antisense nucleic acid molecules, i.e., molecules that are complementary to a coding strand of a double-stranded cDNA molecule (i.e., a sense strand) encoding an ACC2 protein of the present invention or a sequence that is complementary to an mRNA sequence. An antisense nucleic acid of the invention comprises a sequence that is complementary to at least a portion of an RNA transcript of a gene of interest. Absolute complementarity is not required. The ability to hybridize depends on both the degree of complementarity and the length of the antisense nucleic acid. Generally, the larger the hybridizing nucleic acid, the more base mismatches with a polynucleotide sequence of the present invention it can contain and still form a stable multiplex structure (e.g., a duplex or triplex). One of ordinary skill in the art can readily ascertain a tolerable degree of mismatch by employing standard procedures to determine the melting point of the hybridized complex. Antisense nucleic acids are preferably at least six nucleotides in length, and more preferably 6 to about 50 nucleotides in length. In specific embodiments, an antisense oligonucleotide comprises at least 10 nucleotides, at least 17 nucleotides, at least 25 nucleotides or at least 50 nucleotides.

Antisense sequences of the invention can be chemically synthesized by standard methods known in the art (see, e.g., Stein et al., *Nucl. Acids Res.* 16:3209 (1988) and Sarin et al., *Proc. Natl. Acad. Sci. U.S.A.* 85:7448–7451 (1988), or by employing an automated DNA synthesizer, many of which are commercially available. An antisense sequence of the present invention can be chemically synthesized using naturally occurring nucleotides or variously modified nucleotides designed to increase the biological stability of the molecules or to increase the physical stability of the multiplex formed between the antisense and sense nucleic acids, including, but not limited to, phosphorothioate derivatives and acridine substituted nucleotides.

Antisense sequences can also be prepared in vivo, again by employing techniques known to those of ordinary skill in the art. For example, an antisense sequence can be produced biologically using an expression vector into which a nucleic acid has been subcloned in an antisense orientation (i.e., RNA transcribed from the inserted nucleic acid will be of an antisense orientation to a target nucleic acid of interest).

An antisense nucleic acid can be complementary to an entire coding strand of the present invention, or to only a portion thereof, e.g., all or part of the protein coding region. An antisense sequence can also be complementary to a noncoding region of the coding strand of a nucleotide sequence encoding an ACC2 polypeptide. For example, an antisense sequence can be complementary to the region surrounding the translation start site of ACC2 mRNA. By employing the polynucleotide sequences encoding the ACC2 polypeptides provided herein, an antisense sequence of the present invention can be readily designed based on standard base pairing rules.

The antisense sequences of the present invention can also be used in therapeutic applications to reduce or eliminate ACC2 activity in vivo. When used therapeutically, antisense sequences of the present invention are typically administered to a subject or generated in situ such that they hybridize with or bind to cellular mRNA and/or genomic DNA encoding a GPCR-like protein to thereby inhibit expression of the protein, e.g., by inhibiting transcription and/or translation. An example of a route of administration of antisense nucleic acid molecules of the invention includes direct injection at a tissue site. In other examples, antisense nucleic acid molecules can be modified to target selected cells and then administered systemically. For example, antisense molecules can be linked to peptides or antibodies to form a complex that specifically binds to receptors or antigens expressed on a selected cell surface.

An antisense sequence of the present invention can comprise DNA or RNA and can be used to control gene expression via the formation of multiplexes or via traditional antisense methodology. Antisense techniques are discussed, for example, in Okano, *J. Neurochem.* 56:560 (1991) and in *Oligodeoxynucleotides as Antisense Inhibitors of Gene Expression*, CRC Press, Boca Raton (1988). Triple helix formation optimally results in a shut-off of RNA transcription from DNA, while antisense RNA hybridization blocks translation of an mRNA molecule into polypeptide. Both methods have previously been demonstrated to be effective in model systems, and the information disclosed herein can be used to design antisense or triple helix polynucleotides in an effort to treat or prevent disease.

RNA interference (RNAi) reagents form another aspect of the present invention. RNAi is a process by which a target gene can be specifically silenced. The RNAi process is activated when a double-stranded RNA molecule of greater than about 19 duplex nucleotides (referred to herein interchangeably as dsRNA and "RNAi reagent") enters a cell, which causes the degradation of not only the invading dsRNA molecule itself, but also single-stranded RNAs of identical sequences, including endogenous mRNAs. As such, RNAi is a powerful tool in the development of highly specific RNA-based gene-silencing therapeutics, an aspect of the present invention. Thus, in one aspect of the present invention, RNA interference (RNAi) methodologies can be employed to selective inhibit the expression of a target gene in a vertebrate, which can form an element of a therapeutic regimen.

RNAi reagents of the present invention can be obtained using any of a number of techniques known to those of ordinary skill in the art. Generally, production of RNAi reagents can be carried out by chemical synthetic methods or by recombinant nucleic acid techniques. Methods of preparing a dsRNA are described, for example, in Ausubel et al., *Current Protocols in Molecular Biology* (Supplement 56), John Wiley & Sons, New York (2001); Sambrook et al., *Molecular Cloning: A Laboratory Manual*, 3$^{rd}$ ed., Cold Spring Harbor Press, Cold Spring Harbor (2001); and can be employed in the present invention. For example, RNA can be transcribed from PCR products, followed by gel purification. Standard procedures known in the art for in vitro transcription of RNA from PCR templates. For example, dsRNA can be synthesized using a PCR template and the Ambion T7 MEGASCRIPT, or other similar, kit (Austin, Tex.); the RNA can be subsequently precipitated with LiCl and resuspended in a buffer solution.

An RNAi reagent of the present invention can be both partially or completely double-stranded. Generally, an RNAi reagent of the present invention encompasses fragments of at least 18, at least 19, at least 20, at least 21, at least 22, at least 23, at least 24, at least 25, at least 30, at least 35, at least 40, at least 45, and at least 50 or more nucleotides per strand. An RNAi reagent can also comprise 3' overhangs of at least 1, at least 2, at least 3, or at least 4 nucleotides. Broadly, an RNAi reagent of the present invention can be of any length desired by the user as long as the ability to inhibit target gene expression is preserved.

An RNAi reagent of the present invention can include modifications to the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA can be modified to include at least one of an nitrogen or sulfur heteroatom. Other modifications that can be desirable under certain conditions will be known to those of ordinary skill in the art. Modifications in RNA structure can be tailored to allow specific genetic inhibition while avoiding a general response to dsRNA.

An RNAi reagent of the present invention, can also be synthesized in vitro (see, e.g., Fire et al., *Nature* 391: 806–811 (1998); Montgomery et al., *Proc. Natl Acad Sci U.S.A.* 95:15502–15507; Tabara et al., *Science* 282:430–431 (1998)). Additionally, commercially available polynucleotide synthesizers can be employed to prepare an RNAi reagent.

At least two ways can be employed to achieve siRNA-mediated gene silencing. First, siRNAs can be synthesized in vitro and introduced into cells to transiently suppress gene expression, for example as a component of a therapeutic regimen. Synthetic RNAi reagents provide an easy and efficient way to achieve RNAi. Using synthetic 21 base pair duplexes, sequence specific gene silencing can be achieved in mammalian cells. These RNAi reagents can specifically suppress targeted gene translation in mammalian cells without activation of DNA-dependent protein kinase (PKR) by longer dsRNA, which may result in non-specific repression of translation of many proteins.

Additionally, RNAi reagents can be expressed in vivo from vectors. This approach can be used to stably express RNAi reagents in cells or transgenic animals. In one embodiment, RNAi reagent expression vectors are engineered to drive transcription from polymerase III (pol III) transcription units. The Pol III expression vectors can also be used to create transgenic mice that express siRNA.

In another embodiment, siRNAs can be expressed in a tissue-specific manner. In this approach, long double-stranded RNAs (dsRNAs) are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific (pol III) promoters to create tissue-specific knock-down mice.

An antisense sequence or RNAi reagent of the present invention can be administered as part of a therapeutic regimen in which repression of ACC2 expression is desired. In this application, the antisense sequence or RNAi reagent can be administered as a component of a buffered solution, or it can be administered as a component of a pharmaceutical composition, as described herein.

XII. ACC2 Modulators and Screening Methods

The present invention broadly encompasses modulators of ACC2 and methods of identifying such modulators. As used herein, the term "modulator" means a compound that can act as an agonist or an antagonist. An ACC2 modulator can be employed in the various methods of the present invention, for example as a component of a therapeutic regimen. Such modulators can comprise for example, one, or a combination of, a polypeptide of variable length (including antibodies and fusion proteins) or a small molecule.

A modulator of the present invention can comprise any type of chemical entity, such as a protein of any size, a small molecule or an antibody. Just as there is no limitation on whether a modulator augments or inhibits ACC2 or ACC2-mediated activity, there is no limitation on the mechanism by which a modulator of ACC2 achieves such an effect. For example, a modulator might block a ligand from associating with an ACC2 polypeptide. In another case, a modulator might inhibit an ACC2 polypeptide from associating with another polypeptide. In yet another case, a modulator might facilitate the association of an ACC2 polypeptide with another polypeptide expressed.

General methods of identifying modulators are known in the art and can be employed in the present invention. Such methods will employ a polypeptide or polynucleotide sequence of the present invention (e.g., SEQ ID NOs:11–14) as a target.

The ACC2 polypeptides and/or peptides of the present invention, or immunogenic fragments or oligopeptides thereof, can be used for screening therapeutic drugs or test compounds in a variety of drug screening techniques. The fragment employed in such a screening assay can be free in solution, affixed to a solid support, borne on a cell surface, or located intracellularly. The reduction or abolition of the formation of binding complexes between an ACC2 protein of the present invention and a test agent can be measured. Thus, the present invention provides a method for screening or assessing one or a plurality of test compounds for their ability to specifically bind an ACC2 polypeptide, or a bindable peptide fragment thereof, of the present invention, comprising providing a plurality of compounds, combining an ACC2 polypeptide, or a bindable peptide fragment thereof, with each of a plurality of test compounds for a time sufficient to allow binding under suitable conditions and detecting binding of the ACC2 polypeptide or peptide to each of the plurality of test compounds, thereby identifying the compounds that specifically bind to the ACC2 polypeptide or peptide.

Methods of identifying compounds that modulate the activity of the ACC2 polypeptides and/or peptides are provided in an aspect of the present invention and, in one embodiment, comprise combining a potential or candidate compound or drug modulator of ACC2 biological activity with an ACC2 polypeptide or peptide, for example, an ACC2 amino acid sequence as set forth in SEQ ID NOs:12 and 14, and measuring an effect of the candidate compound or drug modulator on the biological activity of the ACC2 polypeptide or peptide. Such measurable effects include, for example, physical binding interaction; the ability to cleave a suitable substrate; effects on native and cloned ACC2-expressing cell line; and effects of modulators or other ACC2-mediated physiological measures.

Another method of identifying compounds that modulate the biological activity of an ACC2 polypeptide of the present invention comprises combining a potential or test compound or drug modulator of ACC2 biological activity with a host cell that expresses an ACC2 polypeptide and measuring an effect of the test compound or drug modulator on the biological activity of the ACC2 polypeptide. The host cell can also be capable of being induced to express the ACC2 polypeptide, e.g., via inducible expression.

The physiological effects of a given test compound on an ACC2 polypeptide can also be measured. Thus, cellular assays for particular ACC2 modulators can comprise either direct measurement or quantification of the physical biological activity of the ACC2 polypeptide, or they can be measurement or quantification of a physiological effect. Such methods preferably employ an ACC2 polypeptide as described herein, or an overexpressed recombinant ACC2 polypeptide in suitable host cells comprising an expression vector as described herein, wherein the ACC2 polypeptide is expressed, overexpressed, or undergoes upregulated expression.

Another aspect of the present invention encompasses a method of screening for a compound that is capable of modulating the biological activity of an ACC2 polypeptide and comprises providing a host cell containing an expression vector harboring a nucleic acid sequence encoding a ACC2 polypeptide, or a functional peptide or portion thereof, determining the biological activity of the expressed ACC2 polypeptide in the absence of a test compound; contacting the cell with the test compound and determining the biological activity of the expressed ACC2 polypeptide in the presence of the test compound. In such a method, a difference between the activity of the ACC2 polypeptide in the presence of the test compound and in the absence of the test compound indicates a modulating effect of the compound.

Any chemical compound can be employed as a test compound in the assays of the present invention. Compounds tested as ACC2 modulators can be any small chemical compound, or biological entity (e.g., protein, sugar, nucleic acid, lipid). Test compounds will typically be small chemical molecules. Generally, compounds employed as potential modulators can be capable of dissolution in aqueous or organic (e.g., DMSO-based) solutions. The assays of the present invention can be employed to screen large chemical libraries by automating the assay steps and providing compounds from any convenient source. Assays can be run in parallel, for example, in microtiter formats on microtiter plates in robotic assays. Test compounds can be purchased from a supplier or synthesized by appropriate methods known to those of ordinary skill in the art.

High throughput screening methodologies are suitable for the detection of modulators of the ACC2 polynucleotides and polypeptides described herein. Such high throughput screening methods can involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as lead compounds, or can themselves be used as potential or actual therapeutics.

The present invention, therefore, provides methods of screening for drugs or any other agents which affect activities mediated by the ACC2 polypeptides of the present invention. In one embodiment, these methods comprise contacting a test compound with a polypeptide of the present invention, or a fragment thereof, and assaying for the presence of a complex between the agent and the polypeptide or a fragment thereof, the presence of which can be determined using methods well known to those of ordinary skill in the art.

Thus, the use of the ACC2 polypeptides of the present invention, or the polynucleotides encoding these polypeptides, to screen for molecules which modify the activities of the ACC2 polypeptides of the present invention form an aspect of the present invention. One embodiment of such a method comprises contacting an ACC2 polypeptide of the present invention with a test compound(s) suspected of having modulatory (e.g., antagonist or agonist) activity, and then assaying the activity of the polypeptide following binding.

In another aspect of the present invention, therapeutic compounds can be screened by employing the an ACC2 polypeptide of the present invention, or binding fragments thereof, in any of a variety of drug screening techniques. The polypeptide or fragment employed in such a test can be affixed to a solid support, expressed on a cell surface, free in solution, or located intracellularly. One method of drug screening employs eukaryotic or prokaryotic host cells which are stably transformed with recombinant nucleic acids expressing the polypeptide or fragment. Drugs are screened against such transformed cells in competitive binding assays. One can measure, for example, the formation of complexes between the agent being tested and a polypeptide of the present invention.

XIII. Diagnostic/Prognostic Assays and Kits

The present invention encompasses diagnostic/prognostic assays and kits. Such assays and kits can be employed to detect the presence, absence and/or expression level of an ACC2 polypeptide of the present invention. The assays and kits of the present invention can also be employed to identify or predict the presence of an adverse condition associated with ACC2, such as obesity or diabetes, or the likelihood that a subject will acquire such a condition. Non-limiting examples diagnostic methods and kits that can be employed in the present invention are provided.

Increased or decreased expression of an ACC2 gene in a subject affected with a certain condition, such as obesity or diabetes, both of which are known to be associated with ACC2, as compared to unaffected organisms can be assessed using the ACC2-endoding polynucleotides of the present invention. For example, altered expression, chromosomal rearrangement, or the presence of a mutation can be used as a diagnostic or prognostic marker for the presence of or predisposition to diabetes or obesity. These diagnostic applications can employ an ACC2 polynucleotide of the present invention.

Thus, the present invention provides a diagnostic method useful for the diagnosis of a disorder or condition. In one embodiment, the method involves measuring the expression level of an ACC2 polynucleotide of the present invention in cells, tissue or body fluid from an organism and comparing the measured gene expression level with a standard level of ACC2 polynucleotide expression, whereby an increase or decrease in the gene expression level compared to the standard is indicative of a disorder.

As used herein, the phrase "measuring the expression level of a polynucleotide of the present invention" means making qualitative, quantitative and estimated measurements of (a) the degree to which an ACC2 polypeptide of the present invention is expressed, or (b) the level of the mRNA encoding an ACC2 polypeptide in a first biological sample, either directly (e.g., by determining or estimating absolute protein level or mRNA level) or relatively (e.g., by comparing the polypeptide level in the first biological sample to the polypeptide level or mRNA level in a second biological sample). In one embodiment, the polypeptide level or mRNA level in the first biological sample is measured or estimated and compared to a standard polypeptide level or mRNA level, wherein the standard is taken from a second biological sample obtained from an individual not having the disorder or determined not to have the disorder by averaging levels from a population of organisms not having a disorder. Once a standard polypeptide level or mRNA level is known, it can be used repeatedly as a standard for comparison.

The method(s) provided herein can be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, a gene chip comprising an ACC2 polynucleotide of the present invention can be employed to identify polymorphisms between reference ACC2 polynucleotide sequences, and ACC2 polynucleotides isolated from a test subject. The knowledge of such polymorphisms (i.e. their location, as well as, their existence) can be beneficial in identifying disease loci for an ACC2-associated disorder.

In addition to various detection and purification applications, the anti-ACC2 antibodies of the present invention can also be employed in diagnostic and prognostic applications. For example, such antibodies can be employed to monitor protein levels in tissue as part of a clinical testing procedure, e.g., to, for example, determine the efficacy of a given treatment regimen. Detection can be facilitated by coupling the antibody to a detectable substance.

Continuing, labeled antibodies, and derivatives and analogs thereof, that specifically bind to an ACC2 polypeptide of the present invention can be used to detect, diagnose, or monitor diseases, disorders, and/or conditions associated with the aberrant expression and/or activity of an ACC2 polypeptide of the present invention. Antibodies of the invention can be used to assay ACC2 levels in a biological sample using classical immunohistological methods known to those of ordinary skill in the art. Other antibody-based methods useful for detecting protein gene expression include immunoassays, such as the enzyme linked immunosorbent assay (ELISA) and the radioimmunoassay (RIA).

Examples of detectable lables include various enzymes, prosthetic groups, fluorescent materials, luminescent materials, bioluminescent materials, and radioactive materials. Examples of enzymes suitable for use as a label include horseradish peroxidase, alkaline phosphatase, β-galactosidase, or acetylcholinesterase; examples of prosthetic group complexes suitable for use as a label include streptavidin/biotin and avidin/biotin; examples of fluorescent materials suitable for use as a label include umbelliferone, fluorescein, fluorescein isothiocyanate, rhodamine, dichlorotriazinylamine fluorescein, dansyl chloride or phycoerythrin; an example of a luminescent material suitable for use as a label includes luminol; examples of bioluminescent materials suitable for use as a label include luciferase, luciferin, and aequorin; and examples of suitable radioactive material include $^{125}$I, $^{131}$I, $^{35}$S, or $^{3}$H.

In one aspect, the present invention provides for the detection of aberrant expression of an ACC2 polypeptide of the present invention, comprising (a) assaying the expression of the ACC2 polypeptide in cells or body fluid of an individual using one or more antibodies specific to the ACC2 polypeptide; and (b) comparing the level of gene expression with a standard gene expression level, wherein an increase or decrease in the assayed polypeptide gene expression level compared to the standard expression level is indicative of aberrant expression.

The present invention also provides a diagnostic assay for diagnosing a disorder. In one embodiment the assay comprises (a) assaying the expression of an ACC2 polypeptide of the present invention in cells or body fluid of an individual using one or more antibodies specific to the ACC2 polypeptide; and (b) comparing the level of gene expression with a standard gene expression level, whereby an increase or decrease in the assayed ACC2 polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

The methods described herein can furthermore be utilized as diagnostic or prognostic assays to identify subjects having or at risk of developing a disease or disorder associated with an ACC2 protein, ACC2 nucleic acid expression, or ACC2 activity. Prognostic assays can be used for prognostic or predictive purposes to thereby prophylactically treat an individual prior to the onset of a disorder characterized by or associated with an ACC2 protein, ACC2 nucleic acid expression, or ACC2 activity.

In another aspect, the present invention provides a diagnostic method in which a test sample is obtained from a subject, and an ACC2 protein or nucleic acid (e.g., mRNA, genomic DNA) is detected, wherein the presence of an ACC2 protein or nucleic acid is diagnostic for a subject having or at risk of developing a disease or disorder associated with aberrant ACC2 expression or activity.

The present invention also provides a method of detecting genetic lesions or mutations in an ACC2 gene, thereby determining if a subject with the lesioned gene is at risk for an ACC2-related disorder. In one embodiment, the method comprises detecting, in a biological sample obtained from a subject, the presence or absence of a genetic mutation characterized by an alteration affecting the integrity of a gene encoding an ACC2-protein, or the misexpression of an ACC2 gene. For example, such genetic mutations can be detected by determining the presence or absence of at least one of: (1) a deletion of one or more nucleotides from an ACC2 gene; (2) an addition of one or more nucleotides to an ACC2 gene; (3) a substitution of one or more nucleotides in an ACC2 gene; (4) a chromosomal rearrangement of an ACC2 gene; (5) an alteration in the level of a messenger RNA transcript of an ACC2 gene; (6) an aberrant modification of an ACC2 gene, such as of the methylation pattern of the genomic DNA; (7) the presence of a non-wild-type splicing pattern of a messenger RNA transcript of an ACC2 gene; (8) an undesirable level of an ACC2 protein; (9) an allelic loss of an ACC2-like gene; and (10) an inappropriate post-translational modification of a GPCR-like-protein. There are a large number of assay techniques known in the art that can be used for detecting mutations in an ACC2 gene The present invention also encompasses kits for detecting the presence of ACC2 proteins in a biological sample (a test sample). Such kits can be used to determine if a subject is suffering from or is at increased risk of developing a disorder associated with aberrant expression of ACC2 protein (e.g., diabetes). For example, a kit can comprise a labeled compound or agent capable of detecting an ACC2 protein or mRNA in a biological sample and means for determining the amount of an ACC2 protein in the sample (e.g., an anti-ACC2 antibody or an oligonucleotide probe that binds to DNA encoding an ACC2 protein, e.g., SEQ ID NOs:12 and 14). A kit can also include instructions for interrerpreting observed results and/or steps for performing the assay.

For antibody-based kits, a kit can comprise, for example: (1) a first antibody, optionally attached to a solid support, that binds an ACC2 polypeptide of the present invention; and, optionally, (2) a second, different antibody that binds an ACC2 polypeptide of the present invention or the first antibody and is conjugated to a detectable label. For oligonucleotide-based kits, a kit can comprise, for example: (1) an oligonucleotide, optionally a detectably labeled oligonucleotide, that hybridizes to an ACC2 polynucleotide sequence of the present invention, or (2) a pair of primers useful for amplifying an ACC2 polynucleotide.

Depending on the nature of the kit, a kit of the present invention can also comprise other components, such as a buffering agent, a preservative, or a protein stabilizing agent. The kit can also comprise components that facilitate the detection of the label. The kit can also contain a control sample or a series of control samples that can be assayed and compared to the test sample contained. A diagnosic kit of the present invention can also comprise instructions to assist the user in performing the diagnostic test and/or interpreting the results of the diagnostic test.

XIV. Pharmaceutical Compositions

An ACC2 polypeptide of the present invention, with or without a therapeutic agent conjugated to it, can be administered alone or in combination with a another biologically active moiety, including a small molecule, and can be used as a therapeutic. Additionally, modulators of the ACC2 polypeptides of the present invention form another aspect of the invention.

The present invention provides pharmaceutical compositions. Such compositions comprise a therapeutically effective amount of an ACC2 polypeptide or an ACC2 modulator of the present invention, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water and water-based formulations are desirable carriers when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences*, (Gennaro, ed.) 20th ed., Mack Publishing, Easton, Pa., USA (2000). Such compositions will contain a therapeutically effective amount of the modulator, for example in purified form, together with a suitable amount of carrier so as to provide the form for proper administration to the subject. The formulation should suit the mode of administration.

In one embodiment, a composition is formulated in accordance with routine procedures as a pharmaceutical composition adapted for intravenous administration to human beings. Typically, compositions for intravenous administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where a composition is to be administered by infusion, it can be dispensed with an infusion bottle containing sterile pharmaceutical grade water or saline. Where a composition is administered by injection, an ampule of sterile water for injection or saline can be provided so that the ingredients may be mixed prior to administration.

The amount of ACC2 polypeptide or ACC2 modulator that will be effective in the treatment, inhibition and prevention of a disease or disorder associated with aberrant expression and/or activity of an ACC2 polypeptide of the present invention can be determined by standard clinical techniques. In addition, in vitro assays may optionally be employed to help identify optimal dosage ranges. The precise dose to be employed in the formulation will also depend on the route of administration, and the nature of the disease or disorder, and can be decided according to the judgment of the practitioner and each subject's circumstances. Effective doses can be extrapolated from dose-response curves derived from in vitro or animal model test systems.

A pharmaceutical composition can be administered in conjunction with a pharmaceutically acceptable carrier, diluent, or excipient, to achieve any of the above-described therapeutic uses and effects. Such pharmaceutical compositions can comprise agonists, antagonists, activators or inhibitors. The compositions can be administered alone, or in combination with at least one other agent or reagent, such as a stabilizing compound, which can be administered in any sterile, biocompatible pharmaceutical carrier, including, but not limited to, saline, buffered saline, dextrose, and water. The compositions can be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients, the pharmaceutical compositions can contain pharmaceutically acceptable/physiologically suitable carriers or excipients comprising auxiliaries which facilitate processing of the active compounds into preparations that can be used pharmaceutically. Further details on techniques for formulation and administration are provided in *Remington's Pharmaceutical Sciences*, (Gennaro, ed.) 20th ed., Mack Publishing, Easton, Pa., USA (2000).

The present invention also provides a pharmaceutical pack or kit comprising one or more containers filled with one or more of the ingredients of the pharmaceutical compositions of the present invention. Optionally a notice can be associated with such container(s) in the form prescribed by a governmental agency regulating the manufacture, use or sale of pharmaceuticals or biological products, which notice reflects approval by the agency of manufacture, use or sale for human administration. Such a notice can also provide guidance on how to use the pack or kit.

XV. Method of Increasing ACC2 Enzymatic Activity

In yet another aspect of the present invention, a method of increasing the activity of a human ACC2 polypeptide is disclosed. In one embodiment, the method comprises generating an enhanced ACC2 polypeptide comprising (a) a phenylalanine residue at position 254, (b) a glutamine residue at position 346, (c) a threonine residue at position 565, (d) an asparagine at position 841, (e) a valine residue at position 1103, (f) a cysteine residue at position 1259, (g) an alanine residue at position 1526, and (h) an isoleucine residue at position 1717, wherein the human ACC2 polypeptide does not comprise SEQ ID NO:12 and wherein the enhanced ACC2 polypeptide has an enzymatic activity level that is greater than the enzymatic activity level of an ACC2 polypeptide that does not contain the indicated residues at the indicated positions.

The present inventors have identified eight amino acids which, when mutated to the residues described herein, impart increased activity to ACC2. Although the ACCC2 sequences of the present invention include point mutations differentiating the ACC2 sequences of the present invention from the published sequences, this group of mutations includes a core group of eight mutations, which are believed to affect the activity of the mutated enzyme. More particularly, when the noted residues of an ACC2 sequence other than that of SEQ ID NO:12 are replaced with (a) F at position 254, (b) Q at position 346, (c) T at position 565, (d) N at position 841, (e) V at position 1103, (f) C at position 1259, (g) A at position 1526, and (h) I at position 1717, a concurrent >200-fold increase in activity is observed.

Consistent with the observations disclosed herein (see, e.g., Example 9), a method of increasing ACC2 enzymatic activity is provided. In one embodiment the method comprises introducing eight point mutations into an ACC2 sequence other than the sequence of SEQ ID NO:12. The mutations introduced are (a) F at position 254, (b) Q at position 346, (c) T at position 565, (d) N at position 841, (e) V at position 1103, (f) C at position 1259, (g) A at position 1526, and (h) I at position 1717. Additional mutations can, but need not, be introduced.

It is possible that one or more residues may be present in a published ACC2 sequence at the noted position(s). In this case, less than the eight mutations can be introduced, with the proviso that the final form of the mutated ACC2 sequence comprises the noted eight mutations. After mutations have been made, the activity of the resultant mutant can be determined as described herein and can be compared to an activity measurement made before any mutations were introduced.

The ACC2 sequence can comprise any known ACC2 sequence, such as the ACC2 sequences of SEQ ID NOs:2, 4 or 6. When there is a residue other than one of the specified eight residues at the corresponding position in the ACC2 sequence, a point mutation can be introduced into the ACC2 sequence to conform the residues and positions with the eight residue/position combinations indicated herein. Such mutations can be introduced using standard methodology, such as that provided herein.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Identification of Human ACC2 Amino Acid Sequence

To identify the wild type human ACC2 amino acid sequences, the following three amino acid sequences were compared: 1) the sequence of pYES-human-ACC2 (purchased from Dr. Ki-Han Kim, Purdue University), 2) the coding region of human ACC2 predicted by human genomic contig AC007637 (defined by 12q24 BAC RCPI11-443D10; Roswell Park Cancer Institute Human BAC Library, complete sequence), and 3) Genbank ACC2 sequence (NM_001093; Ha et al., (1996) *Proc. Natl. Acad. Sci. USA* 93:11466–11470). The multiple sequence alignment was performed with ClustalW algorithm in VectorNTI program. The result of the comparison revealed that there are multiple discrepancies among these three sequences. Specifically, in amino acid sequences predicted by genomic contig AC007637, the descripancies are C at position 9, G at position 347, G at positions of 349–352, V at position 2141; in amino acid sequences described in Genbank Accession No. NM_001093, the discripances are H at position 111, V at position 127, S at position 450, R at position 614, K at position 656, V at position 671, KI at position 742–743, K at position 799, A at position 1025, A at position 1064, A at position 1480, G at position 1547, A at position 1821, RPMR at position 2194–2197, E at position 2242; in amino acid sequences as predicted by pYES-human-ACC2, the discrepancies are Y at position 254, R at position 345, A at position 565, Y at position 841, A at position 1103, R at position 1259, V at position 1526, V at position 1717. The consensus of amino acid sequences among pYES-human-ACC2, Genbank Accession No. NM_001093 and human genome contig AC007637 is defined as the wild type human ACC2 amino acid sequence (SEQ ID NO:12). Specifiaclly the amino acids need to be R at position 9, P at position 111, A at position 127, F at position 254, Q at position 345, V at position 347, AGWG at positions of 349–352, P at position 450, T at position 565, H at position 614, E at position 656, E at position 671, ET at position 742–743, E at position 799, N at position 841, V at position 1025, V at position 1064, V at position 1103, C at position 1259, R at position 1480, A at position 1526, R at position 1547, I at position 1717, G at position 1821, I at position 2141, PPYA at position 2194–2197, K at position 2242.

Example 2

Identification of Rat ACC2 Amino Acid Sequence

Initially the published sequences for both genes were used to design primers to amplify overlapping fragments. Two different clones for each fragment were sequenced and aligned using ClustalW algorithm in VectorNTI program with the published sequences (SEQ ID NOs:7 and 9; GenBank Accession Nos. NM_053922 and AB004329, respectively). Using a consensus sequence built from this comparison, the consensus translation was then aligned with the published rat ACC2 sequence (SEQ ID NO:9, FIGS. 3 and 4) and the sequence of human ACC2 (SEQ ID NO:2) was employed to guide decisions surrounding ambiguous regions, providing a refined consensus sequence. This refined consensus sequence was then compared to the rat genomic ACC2 region and provided an identical match (FIG. 5).

Materials for Examples 3 to 5

Expression vectors pBlueBac4.5/V5-His, pcDNA4/N5-His a Bac-N-Blue Transfection kit, and monoclonal anti-V5 antibody was obtained from Invitrogen; goat anti-mouse horseradish peroxidase (HRP)-conjugated antibody was obtained from BioRad; streptavidin conjugated with HRP was obtained from Pierce; COMPLETE® protease inhibitor cocktail tablets and FuGene 6 transfection reagent was obtained from Roche Molecular Biochemicals; TALON™ resin was obtained from BD Biosciences; oligonucleotide primers were obtained from Sigma-Genosys; a LA-PCR kit and a ligation kit was obtained from Panvera Corporation; a QUIKCHANGE® multi site-directed mutagenesis kit was obtained from Stratagene; human emryonic kidney (HEK) 293 cells and insect Sf9 cells were obtained from ATCC; [$^{14}$C]—NaHCO$_3$ (45 mCi/mmol, 1 mCi/m) was obtained from NEN Life Science Products, Inc. C-Myc peptide (Ac-EQKLISEEDL-OH; SEQ ID NO:16) was synthesized.

Example 3

Construction of Human ACC2 Expression Vectors

To construct pBlueBac-human-ACC2, a ~7.5 kb fragment of a Kpn I/Xho I double digestion of pYES-human-ACC2 (purchased from Dr. Ki-Han Kim, Purdue University; SEQ ID NO: 5) was ligated with a pBlueBac4.5 vector digested with same set of restriction enzymes.

To create a V5-His tag at human ACC2 COOH-terminus, a PCR reaction was carried out using the following set of primers: forward: 5'-TCCTGTATTGGCGTCTGCGCCGC-3' (SEQ ID NO:17), reverse: 5'-CGAATTCACGGTGGAG-GCCGGGCTGTC-3' (SEQ ID NO:18), and with pYES-human-ACC2 as the template. The resultant ~490 bp product was digested with Esp3 I and EcoR I which is ligated with pBlueBac4.5/V5-His that was digested with Esp3 I and EcoR I. The resultant plasmid was designated pBlueBac-human-ACC2-V5-His.

To construct mammalian expression construct, pBlueBac-human-ACC2-V5-His was digested with Kpn I and Age I. The resultant ~7.5 kb fragment was ligated with pcDNA4/V5-His that was digested with the same set of enzymes. The resulting plasmid was designated pcDNA-human-ACC2-V5-His.

To delete the NH$_2$-terminus 148 amino acid of human ACC2, a PCR reaction was carried out using the following set of primers: forward: 5'-GGCCGAAGCCGGTACCGC-CATGGGCAAAGAAGACAAGAAGCAGGCAAACAT-CAAGAGGCAGCTG-3', (SEQ ID NO:19), reverse: 5'-CGTCTGGGCGACAACGGTGGA-3' (SEQ ID NO:20), and with pcDNA-human-ACC2-V5-His as the template. The PCR product was digested with ACC65 I and Sfi I and ligated with the ~12.5 kb digestion product of pcDNA-human-ACC2-V5-His with the same set of enzymes. The resultant plasmid was designated pcDNA-human-ACC2-Delta148-V5-His.

To insert myc tag between V5- and His-tags at the COOH terminus, a PCR reaction was carried out using the following set of primers: forward: 5'-TCCTGTATTGGCGTCTGCGC-CGC-3' (SEQ ID NO:21), reverse: 5'-GGCCGAAGCCAC-CGGTGCCCAGATCCTCTTCTGAGATGAGTTTTTGT-TCGCCCGTAGAATCGAGACCGAGGAGAG-3' (SEQ ID NO:22), and with pcDNA-human-ACC2-Delta-V5-His as the template. The PCR product was digested with Esp3 I and with Age I, which was ligated with the ~14 kb digestion product of pcDNA-human-ACC2-Delta148-V5-His generated by digestion with the same set of enzymes. The resultant plasmid was designated pcDNA-human-ACC2-Delta148-V5-Myc-His.

To conduct site-directed mutagenesis in order to create a version that contains all the amino acids as predicted by wild type sequence (SEQ ID NO:12), two intermediate plasmids were constructed. First, pBlueScrip-ACC2-N and pBlueScript-ACC2-C were constructed. pBlueScrip-ACC2-N was constructed by ligation of ~3.4 kb ACC65 I/Sac II digestion product of pcDNA-human-ACC2-Delta148-V5-Myc-His with ~3.0 kb ACC65 I/Sac II digestion product of pBlueScript II. pBlueScript-ACC2-C was constructed by ligation of the ~4.0 kb Sac II/Pme I digestion product of pcDNA-human-ACC2-Delta148-V5-Myc-His with ~3.0 kb Sac II/Pme I digestion product of pBlueScript II.

In order to change the discrepancies found in pYes-human-ACC2 that reside in the 5'-3.4 kb portion, mutagenesis was conducted using pBlueScript-ACC2-N as the template, using the following primers:

```
5'-CGATCCCCCCCAAAGCGTGTGACAAA-3',      (SEQ ID NO:23)

5'-CCACACCGCCTGCACGGGGATTC-3',         (SEQ ID NO:24)

5'-GAGGTATTCCACTGTCCCTGCACTCAC-3'v,    (SEQ ID NO:25)

5'-CGATGTGGCAGCCATTCATGATGAGAACG-3',   (SEQ ID NO:26)
and (SEQ ID NO:27)
5'-TGTTGATGAAGAAGACCTCTCGATCAGCCT-3',
``` using a QUIKCHANGE multi site-directed mutagenesis kit according to the manufacturer's instructions. Sequencing experiments were conducted to identify clones that bear all the desired changes without introducing undesired changes. The resulting clone was designated pBlueScript-ACC2-N-WT.

In order to change the discrepancies found in pYes-human-ACC2 that resides in the 3'-4.0 kb portion, mutagenesis was conducted using pBlueScript-ACC2-C as the template, using the following primers:

```
5'-GTTCTCGGGGCAGAACTGGTGGC-3',         (SEQ ID NO:28)

5'-CCTTCACCTTGGCAGCACCCAGGTAAAG-3',    (SEQ ID NO:29)
and

5'-GGGAAGTCATAGATGTAGGTGGTTCCC-3',     (SEQ ID NO:30)
``` using QUIKCHANGE multi site-directed mutagenesis kit according to the manufacturer's instructions. Sequencing experiments were conducted to identify clones that bear all the desired changes without introducing undesired changes. The resulting clone was designated pBlueScript-ACC2-C-WT.

To reconstruct the expression vector containing all the wild type amino acid sequences, a ligation was conducted to join the following three components: the ACC65 I/Age I digestion product of pcDNA4/V5-His, the ~3.4 kb ACC65 I/Sac II digestion product of pBlueScript-ACC2-N-WT, and the ~4.0 kb Sac II/Age I digestion product of pBlueScript-ACC2-C-WT. The resulting plasmid was designated pcDNA-human-ACC2-Delta148-V5-Myc-His-WT.

To construct a baculoviral vector comprising the final version human ACC2, the Kpn I/Age I digestion product of pBlueBac4.5/V5-His and the Kpn I/Age I digestion product of pcDNA-human-ACC2-Delta148-V5-Myc-His-WT were ligated. The resultant plasmid was designated as pBlueBac-human-ACC2-Delta148-V5-Myc-His-WT.

Example 4

Purification of Recombinant Human ACC2 by Anti-Myc Affinity Column

Affinity chromatography using c-Myc-5 monoclonal IgG column and was carried out essentially according to Hillman et al (Hillman et al., (2001) *Protein Expression and Purification* 23:359–368), with several modifications. Pellets of HEK-293 cells or Sf9 cells that were either transiently transfected with a human ACC2 expression vector or infected with a recombinant human ACC2 baculovirus were lysed in 5× cell pellet volume of Buffer A (225 mM mannitol, 75 mM sucrose, 10 mM Tris/HCl. pH 7.5, 0.05 mM EDTA, 1× complete protease inhibitor cocktail, 0.5 mM PMSF) with sonication for 10 seconds. The broken cells were centrifuged for 10 minutes at 2000×g. NaCl concentration of supernatant was raised to ~500 mM with addition of 1/10 volume of 5 M NaCl. The cell lysates were then further centrifuged for 30 minutes at 10,000×g at 4° C. The supernatants of the second centrifugation were incubated with 3 ml resin coupled with c-Myc-5 IgG (density: 3 mg IgG/ml resin), which was pre-equilibrated with Buffer B (100 mM Tris/HCl, pH 7.5, 0.5 M NaCl, 1 mM EDTA, 10% glycerol) overnight at 4° C. The incubated resin was then packed in a column and washed with Buffer B extensively (~200 ml) until O.D.280 reached baseline. After the wash, an aliquot of 1 ml Buffer C (Buffer B containing 1 mM myc peptide) was carefully applied to the column. Once Buffer C completely entered the column bed, column was plugged and incubated for 15 minutes at 4° C. After the incubation, the eluate was collected via gravity. This elution procedure was repeated twelve times. The elution fractions were then subjected to analyses by coomassie stain, immunoblot and ACC enzymatic assays. Peak fractions were pooled and stored at −80° C. for further study.

Example 5

ACC Enzyme Activity Assay

ACC enzymatic assays were carried out essentially according to Tanabe et al. (Tanabe et al., (1981) *Methods Enzymol.* 71 Pt C, 5–16) with modifications. In 7 ml glass scintillation vials, either fractions of recombinant human ACC2 eluted from the affinity column or ~0.25 µg of pooled purified ACC2 were mixed with 120 µl Buffer D (50 mM Hepes, pH 7.5, 10 mM MgCl2, 10 mM tripotassium citrate, 0.1 mM DTT, 100 µ/ml BSA) that contains either 4 mM ATP, 250 µM acetyl CoA or at various concentrations as indicated in the figures. Aliquots of 30 µl of 25 mM KH[$^{14}$C]O$_3$ (specific activity 1.3 µCi/µmol, final KH[$^{14}$C]O$_3$, concentration 5 mM) was then added to the mixture to initiate the reaction which was carried out for 10 min at 37° C. At the end, the reactions were quenched with 50 µl 2 N HCl and the vials were heated for 2 hours at 80° C. to remove excess bicarbonate as $^{14}$CO$_2$. Scintillant was then added and the acid-stable malonyl CoA remaining in the vial was counted in a scintillation counter. ACC specific activities were expressed as nmol/min/mg protein.

Example 6

Immunoblot Analyses of Insect Sf9 Cells Expressing Human ACC2

FIG. 1A is a schematic diagram depicting the primary structure of the form of human ACC2 that is expressed in one aspect of the present invention. In order to increase the solubility of recombinant human ACC2, the first 27 hydrophobic amino acids and the following stretch of amino acids (from 27 to 148) were deleted. This stretch of sequence has been shown to facilitate the attachment of ACC2 with mitochondria (Abu-Elheiga et al., (2000) *Proc. Nat. Acad. Sci. USA* 97:1444) Since these sequences are not present in ACC1 enzyme (Ha et al., (1996) *Proc. Natl. Acad. Sc. USA* 93:11466–11470), it was deemed plausible that they are not essential for the catalytic activity. It was also predicted that deleting the mitochondria attachment sequence would also minimize docking too much over-expressed recombinant protein to the mitochondria and thereby prevent a potential detriment to the host cells.

In order to facilitate the identification and purification of the recombinant enzyme, three consecutive tags were fused to the COOH-terminus end of the enzyme, namely V5 and myc epitope-tags, and a 6× His tag.

To ensure the fidelity of coding sequence in the recombinant human ACC2, the amino acid sequences of pYES-human-ACC2, the coding region of human ACC2 predicted by human genomic contig AC007637 and Genbank ACC2 sequence (NM_001093) (Ha et al., (1996) *Proc. Natl. Acad. Sci. USA* 93:11466–11470) were compared. The result of the comparison revealed that there are multiple discrepancies among these three sequences. Specifically, in amino acid sequences predicted by genomic contig AC007637, the descripancies are C at position 9, G at position 347, G at positions of 349–352, V at position 2141; in amino acid sequences described in Genbank Accession No. NM_001093, the discripances are H at position 111, V at position 127, S at position 450, R at position 614, K at position 656, V at position 671, KI at position 742–743, K at position 799, A at position 1025, A at position 1064, A at position 1480, G at position 1547, A at position 1821, RPMR at position 2194–2197, E at position 2242; in amino acid sequences as predicted by pYES-human-ACC2, the discrepancies are Y at position 254, R at position 345, A at position 565, Y at position 841, A at position 1103, R at position 1259, V at position 1526, V at position 1717. The consensus of amino acid sequences among pYES-human-ACC2, Genbank Accession No. NM_001093 and human genome contig AC007637 is defined as the wild type human ACC2 amino acid sequence (SEQ ID NO:12). Specifiaclly the amino acids need to be R at position 9, P at position 111, A at position 127, F at position 254, Q at position 345, V at position 347, AGWG at positions of 349–352, P at position 450, T at position 565, H at position 614, E at position 656, E at position 671, ET at position 742–743, E at position 799, N at position 841, V at position 1025, V at position 1064, V at position 1103, C at position 1259, R at position 1480, A at position 1526, R at position 1547, I at position 1717, G at position 1821, I at position 2141, PPYA at position 2194–2197, K at position 2242. The discrepancies in the human Genomic contig were attributed to the presence of a sequencing error or polymorphism, and the discrepancies in pYES-human-ACC2 and Genbank Accession No. NM_001093 were attributed to the mutations possibly introduced by a PCR reaction during the cloning (Ha et al., (1996) *Proc. Natl. Acad. Sci. USA* 93:11466–11470).

In pYES-human-ACC2, there were eight single amino acid discrepancies identified, as compared to the designated wild type human ACC2 sequence. The discrepancies are distributed throughout the entire coding region and correspond to the following mutations: F254Y, Q345R, T565A, N841Y, V1103A, C1259R, V1526A, I171V At the nucleotide level, in all cases, single nucleotide changes were identified. In order to test the possibility that these eight point mutations might change the protein's stability or, alternatively, might change ACC enzyme activity, these amino acids were systematically changed to the wild type sequence. FIG. 6A depicts the number and location of the identified discrepancies.

Activity assays indicated that these eight point mutations decrease the activity of the protein.

Figure 6B:
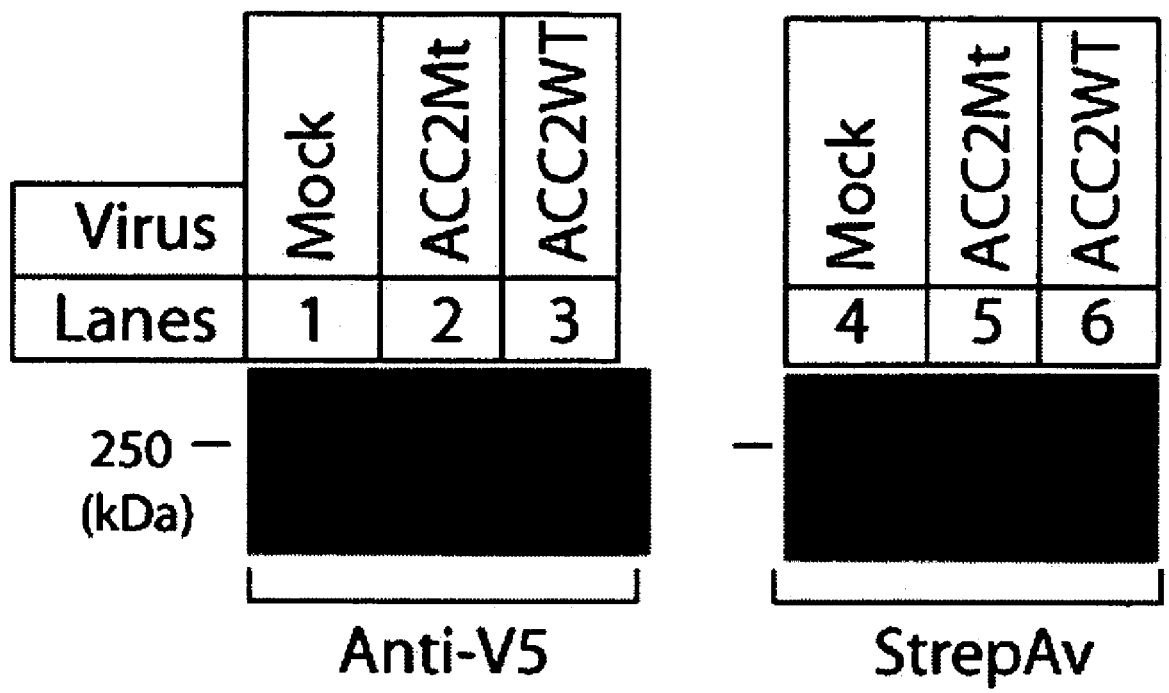
FIG. 6B is an autoradiograph depicting the results of blot analyses of total cell extracts from Sf9 cells that are infected with either wild type baculovirus as Mock control, or with ACC2Mt and ACC2WT recombinant virus respectively; the blots were probed with anti-V5 IgG (left panel) or with Streptavidin-HRP-conjugated (right panel) respectively.

FIG. 6B demonstrates ACC2 protein expression levels, which were generated using immunoblot analyses. Probed with anti-V5 IgG antibodies (V5 is a common epitope present in both ACC2Mt (containing the original eight mutations found in pYES-human-ACC2) and ACC2WT)), it was found that ACC2WT is more stable than ACC2Mt. This result was reproduced when lysates were probed with Streptavidin-conjugated-with-HRP, which detects the biotin group on ACC. Further, there is a detectable signal in Mock-infected Sf9 cells at the same molecular mass, indicating there is substantial endogenous insect cell ACC enzyme present (FIG. 6B).

Example 7

Performance of Recombinant Human ACC2 on Monomeric Avidin Column

Figure 7:
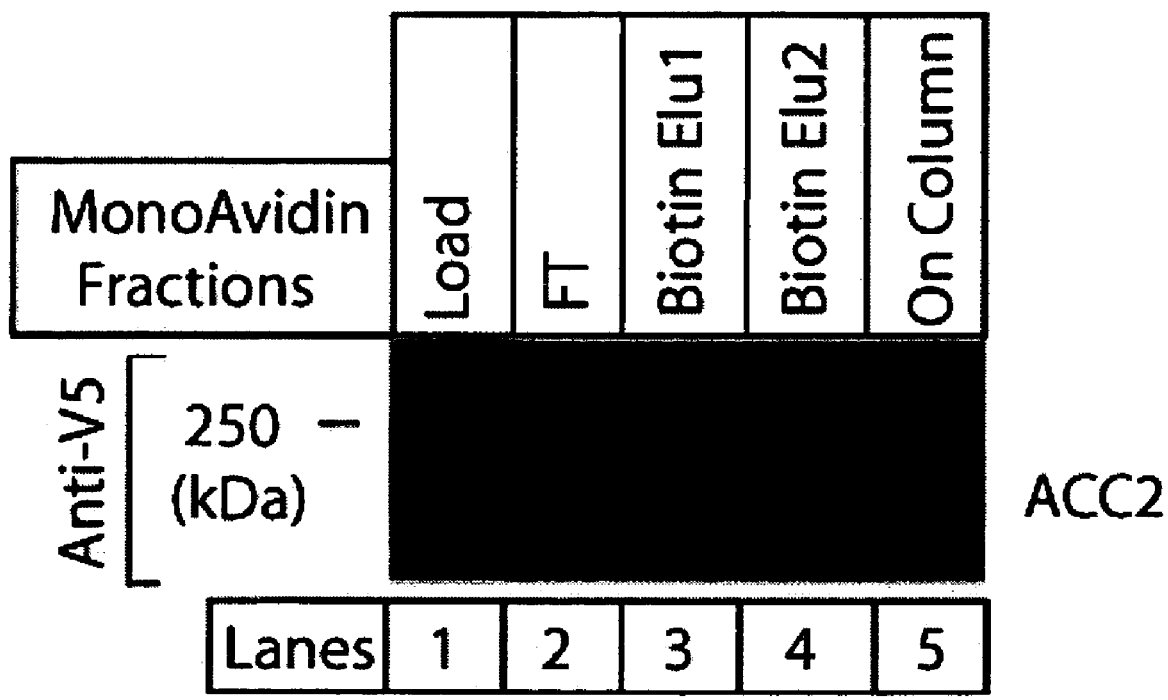
FIG. 7 is an autoradiograph depicting the results of a chromatographic separation of recombinant human ACC2 on monomeric avidin column.

Biotinylation of ACC is an indispensable protein modification for its enzymatic function. To investigate the level of biotinylation of the recombinant human ACC2, lysates derived from cells expressing human ACC2 were loaded on monomeric avidin column. The column was washed and was then eluted with 0.2 mM biotin for 3 hours (Elu1, lane 3), which was followed by another overnight elution (Elu2, lane 4). Aliquots from the flow-through from the loading step (FT), two steps of elution, and materials remained in the column after two steps of biotin-elution (eluted by boiling in SDS loading buffer) were quantitatively loaded on SDS-PAGE and blot-analyzed with anti-V5 IgG. Almost no recombinant human ACC2 was detected in the flow-through fraction, whereas there was a quantitative recovery for human ACC2 bound to the avidin column. This indicates that nearly all the recombinant human ACC2 is properly biotinylated (FIG. 7).

Example 8

Performance of Human ACC2 on TALON Resin

The observation that the recombinant human ACC2 cannot be eluted from a monomeric avidin column via competition with a high concentration of biotin suggests that in some situations this may not be a preferred method of purifying the recombinant human ACC2 of the present invention. Additionally, multiple attempts to purify that recombinant ACC2 enzyme using conventional protein purification methods (including ammonium sulfate precipitation, gel-filtration, ion-exchange chromatography) did not provide the desired level of separation of these two types of ACC enzymes. Lastly, the observation that there is endogenous insect ACC enzyme in the host cells (FIG. 6B, lane 4), suggested that it might be advantageous to employ an affinity tag that is capable of differentiating the recombinant enzyme from the endogenous ACC.

Figure 8:
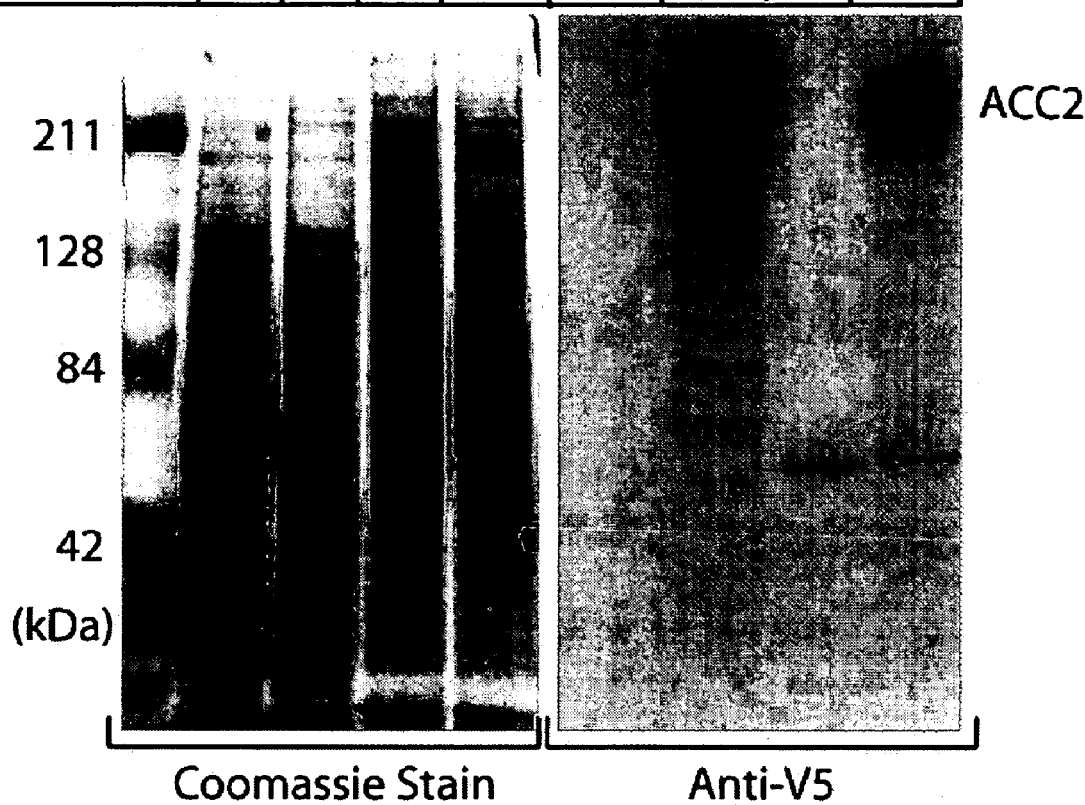
FIG. 8 is a photograph (left panel) and an autoradiograph (right panel) depicting the results of a chromatographic separation of total Sf9 cell lysates and recombinant human ACC2 on TALON resin assayed by coomassie stain (left panel) or by anti-V5 immunoblot analysis (right panel).

The first affinity tag that was employed was TALON resin (Clontech, Palo Alto, Calif.), which can be used to purify recombinant poly-His-tagged proteins (Bush et al., (1991) *J. Biol. Chem.* 266:13811–13814). FIG. 8 depicts a comparison of binding for the total lysates and recombinant human ACC2. The results suggest that there is an amount of non-specific binding of host cell proteins to the TALON resin, particularly those proteins with high molecular mass (FIG. 8, lanes 1 to 4). Probing specifically for human ACC2 indicates a loss of signal in the Eluate fraction as compared with the Load fraction (FIG. 8, lanes 6 and 8). ACC activity measurement revealed that there is a small increase in ACC specific activity before and after the sample was applied to the TALON column. These results indicated that a 6XHis-tag might not be desirable in all situations for the isolation of recombinant human ACC2 from the host cell lystates.

Example 9

Purification of Recombinant Human ACC2 with Anti-Myc-IgG

It was hypothesized that a preferred affinity column for purifying human recombinant human ACC2 would have a high enough affinity to absorb the protein (e.g., higher than Kd ~$10^{-3}$ M, the affinity reported by the manufacturer for the TALON-PolyHis resin) and to allow stringent washing condition, yet have a low enough affinity for the protein to be eluted (e.g., smaller than Kd of ~$10^{-15}$ M, the avidin-biotin affinity; Hiller et al. (1987) *Biochem. J.* 248:167–171). Antibody-antigen interactions, for example, fall into this category. An anti-Myc-IgG antibody was therefore selected for investigation. c-Myc-5 IgG has been extensively characterized (see, e.g., Hillman et al., (2001) *Protein Expres. Purif.* 23:359–368).

Figure 9A:
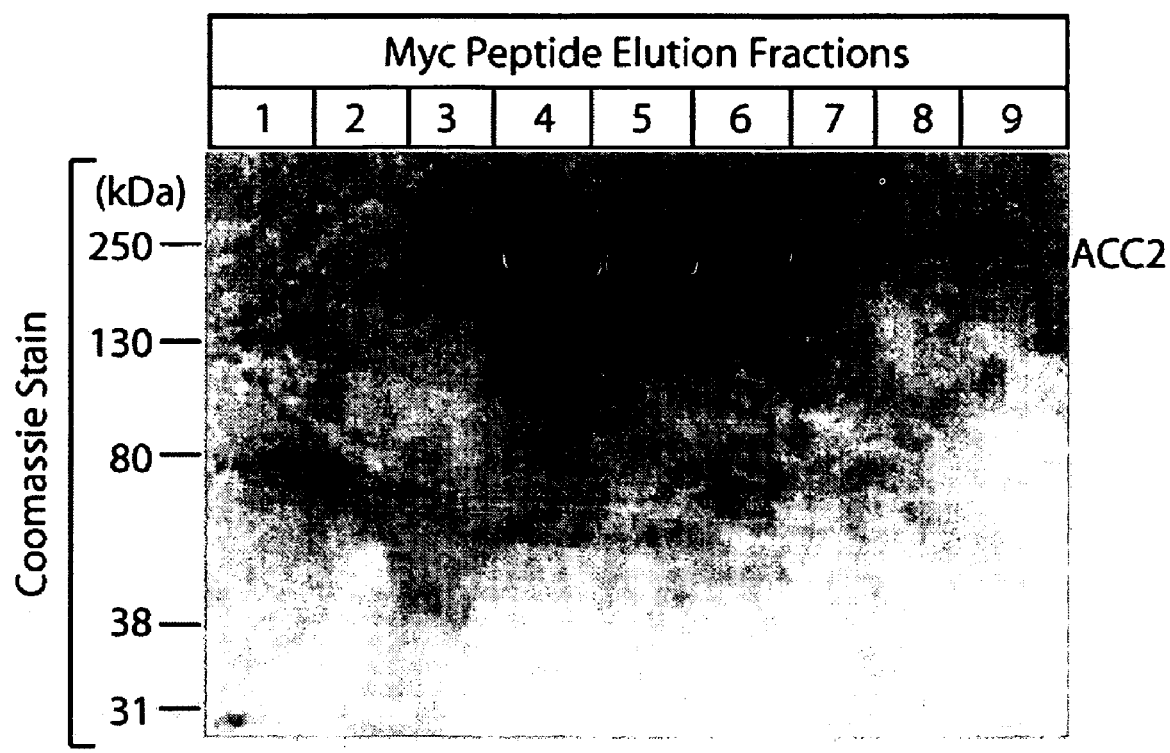
FIG. 9A is a photograph depicting the results of a chromatographic separation of a recombinant human ACC2 of the present invention on a c-Myc-5 affinity column; fractions eluted from the column by myc peptide (SEQ ID NO:16) were assayed with coomassie stain.
Figure 9B:
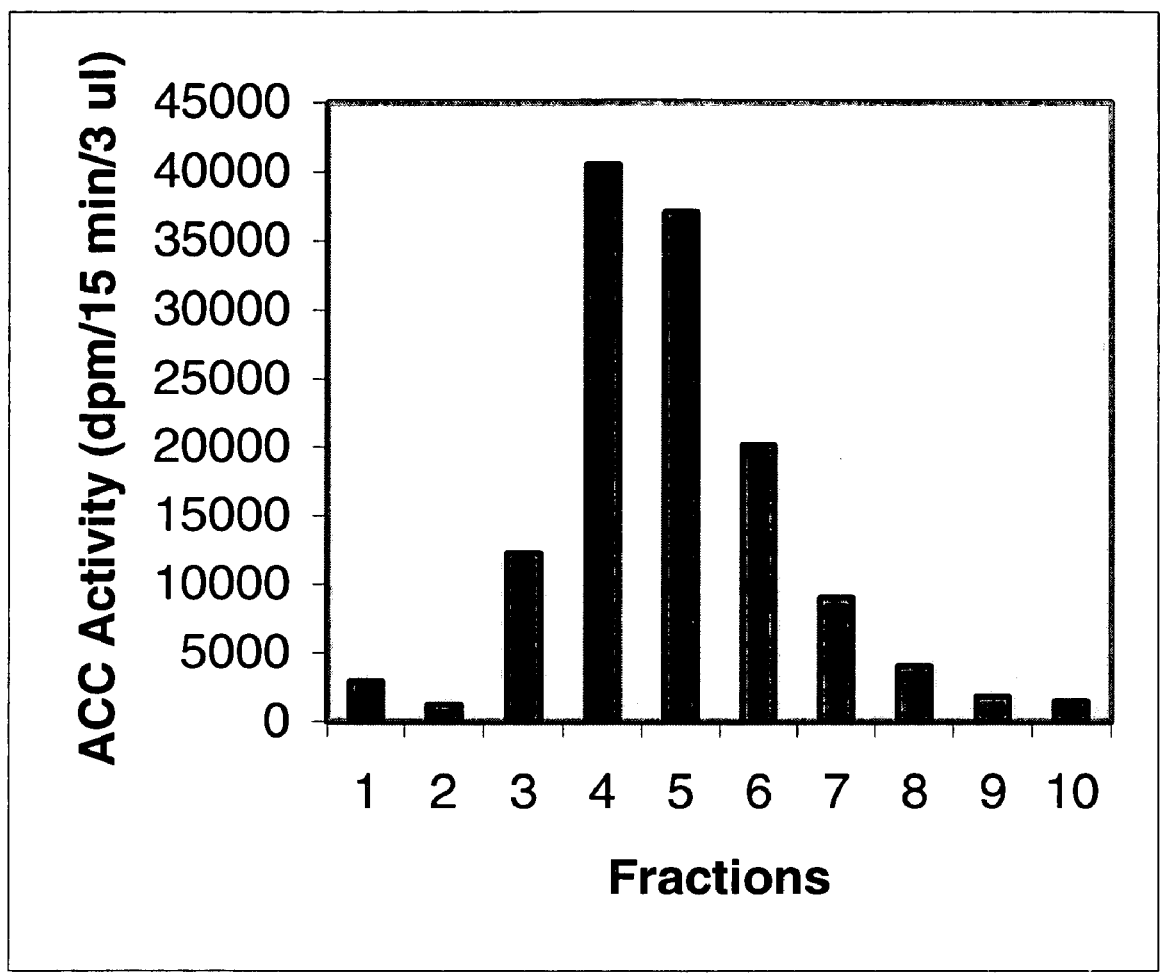
FIG. 9B is a bar graph depicting the results of a chromatographic separation of a recombinant human ACC2 of the present invention on a c-Myc-5 affinity column; fractions eluted from the column by myc peptide (SEQ ID NO:16) were assayed with ACC activity measurement.

FIGS. 9A and 9B depict the purification of human ACC2 using a c-Myc-5 IgG column. Total crude cell cytosolic lysates derived from 1 liter of human ACC2 virus infected Sf9 cells were loaded on a 3-ml c-Myc-5 IgG column by overnight incubation. The bound protein was then extensive washed with high salt buffer (0.5 M NaCl). The most tightly bound proteins were then eluted with 1 mM myc peptide (Ac-EQKLISEEDL-OH; SEQ ID NO:16) in 10 steps. The protein peak of the eluate resided at fraction 4 and 5 as a single ~250 kDa protein band (FIG. 9A). This protein was recognized by anti-V5 and Streptavidin-conjugated-with-HRP in blot analyses, indicating that the purified band is recombinant human ACC2. In a parallel ACC enzymatic measurement, ACC activity peaks were found in the same fractions as those identified in the coomassie stain assay (compare FIGS. 9A and 9B).

The active fractions were then pooled. A quantitative ACC enzyme assay indicated that the pooled enzyme has a specific activity of 500 nmol/min/mg. The yield from 1 liter Sf9 cell culture was ~2 mg protein. The recovery of total activity was 80%.

In order to address whether human-ACC2-Mt is different at enzymatic level as compared with human-ACC2-WT, human-ACC2-Mt was purified in the same way as described above. In addition to the lower yield, in ACC enzyme assays human-ACC2-Mt was not observed to contain measurable activity, indicating that one or several amino acids that were identified as discrepant between pYES-human-ACC2 and the wild type ACC2 sequence is critical for ACC enzyme activity.

Example 10

Determination of Kinetic Parameters for Recombinant Human ACC2

In order to detect recombinant human ACC2 activity in one in vitro assay (see, e.g., U.S. Patent Application Ser. No. 60/558,015, incorporated herein by reference), acetyl CoA, ATP, bicarbonate are preferably present. It was found that in the absence of any one of these compounds, no activity was detected. In addition, the presence of the known effector citrate was found to be required for the detection of ACC2 activity in the assay employed. The $K_m$ for the substrates, acetyl CoA, ATP and bicarbonate and the $K_{act}$ for the effector citrate were determined by assaying ACC activity at various concentrations of one reagent and saturating concentrations of all the others at 37° C.

Figure 10:
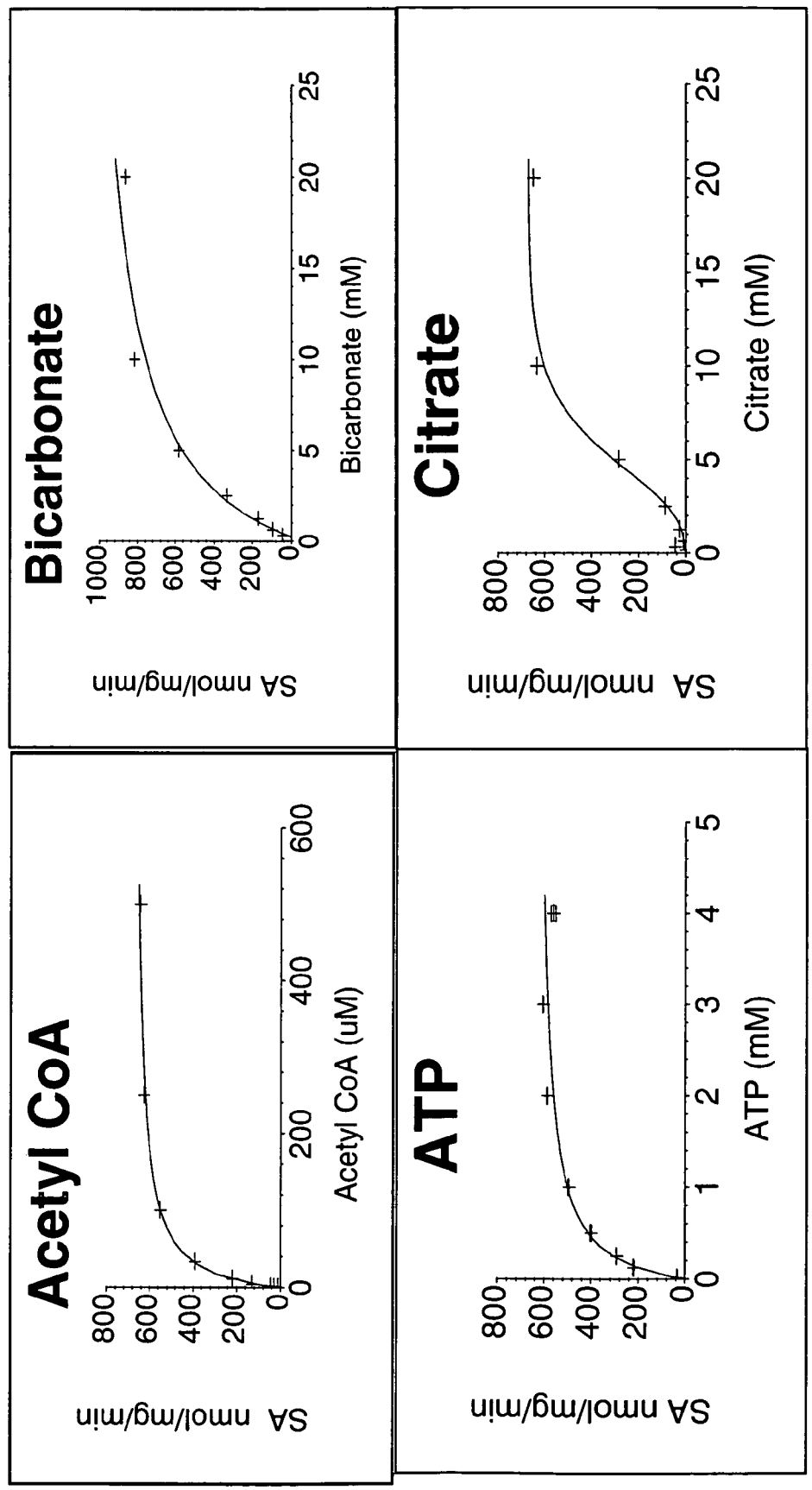
FIG. 10 is a series of four plots depicting the concentration dependence of a recombinant human ACC2 of the present invention on the substrates acetyl CoA, bicarbonate, ATP and its effector citrate; each plot is labeled according to substrate.

FIG. 10 comprises plots depicting the concentration dependence of acetyl CoA, ATP, biocarbonate and citrate. Table 1 summarizes the $K_m$ and $K_{act}$ value for the recombinant human ACC2 as compared with literature values of rat ACC enzymes.

TABLE 1

Kinetic Parameters of Recombinant Human ACC2

|  |  | Recombinant Human ACC2 | Literature Values* Rat ACC1 | Literature Values* Rat ACC2 |
|---|---|---|---|---|
| Km | Acetyl CoA (uM) | 23 | 22 | 32 |
|  | ATP (uM) | 270 | 110 | 58 |
|  | HCO$_3^-$ (mM) | 5 | 2.7 | 2.3 |
| Kact | Citrate (mM) | 1.8 | 3 | 2.1 |

(*literature value are from Trumble et al., (1995) Eur. J. Biochem. 231: 192–198)

Example 11

Effect of Known Inhibitors for Recombinant Human ACC2

FIG. 11 comprises two plots depicting the concentration dependent inhibition of recombinant human ACC2 by known inhibitors such as palmitoyl CoA and malonyl CoA. The $IC_{50}$ for these two agents was determined to be 4.4 μM and 26.7 μM for palmitoyl CoA and malonyl CoA, respectively. For comparison, the literature $IC_{50}$ values of palmitoyl CoA and malonyl CoA for rat ACC2 enzyme are 2.2 μM and 10.6 μM (Trumble et al., (1995) *Eur. J. Biochem.* 231, 192–198).

REFERENCES

The references cited herein are incorporated herein by reference to the extent that they supplement, explain, provide a background for or teach methodology, techniques and/or compositions employed herein. All cited patents, including patent applications, and publications referred to in this application are herein expressly incorporated by reference. Also expressly incorporated herein by reference are the contents of all citations of GenBank accession numbers, LocusID, and other computer database listings, as well as the contents of any Sequence Listing associated herewith.

While the invention has been described in connection with specific embodiments, it will be understood that the invention encompasses further modifications including variations, uses, and adaptations of the invention that follow the principles of the invention. Furthermore, the foregoing description is for purposes of illustration.

---

What is claimed is:

1. An isolated nucleic acid molecule comprising a polynucleotide having a nucleotide sequence selected from the group consisting of:
   (a) a polynucleotide encoding an acetyl-CoA carboxylase (ACC2) polypeptide comprising SEQ ID NO:13;
   (b) an isolated polynucleotide encoding a human ACC2 polypeptide comprising amino acids 2 to 2458 of SEQ ID NO:13;
   (c) an isolated polynucleotide including the start codon encoding a human ACC2 polypeptide comprising amino acids 1 to 2458 of SEQ ID NO:13 including the start codon; and
   (d) an isolated polynucleotide encoding the ACC2 polypeptide encoded by the cDNA clone contained in ATCC Deposit No: PTA-6054.

2. The isolated nucleic acid molecule of claim 1, wherein the isolated nucleic acid molecule comprises the nucleotide sequence of SEQ ID NO:12.

3. An ISOLATED polynucleotide that is FULLY complementary to the isolated nucleic acid molecule of claim 1.

4. A vector comprising the isolated nucleic acid molecule of claim 1.

5. An isolated host cell comprising the vector of claim 4.

6. The host cell of claim 5, wherein the host cell is a mammalian host cell.

7. A method of making an isolated polypeptide comprising:
   (a) culturing the recombinant host cell of claim 5 under conditions such that the polypeptide is expressed; and
   (b) recovering the polypeptide.

* * * * *

SEQUENCE LISTING

<160> NUMBER OF SEQ ID NOS: 34

<210> SEQ ID NO 1
<211> LENGTH: 7452
<212> TYPE: DNA
<213> ORGANISM: Homo sapiens
<220> FEATURE:
<221> NAME/KEY: CDS
<222> LOCATION: (1)..(7452)

<400> SEQUENCE: 1

```
atg gtc ttg ctt ctt tgt cta tct tgt ctg att ttc tcc tgt ctg acc      48
Met Val Leu Leu Leu Cys Leu Ser Cys Leu Ile Phe Ser Cys Leu Thr
1               5                   10                  15 ttt tcc tgg tta aaa atc tgg gag aaa atg acg gac tcc aag ccg atc      96
Phe Ser Trp Leu Lys Ile Trp Glu Lys Met Thr Asp Ser Lys Pro Ile
            20                  25                  30 acc aag agt aaa tca gaa gca aac ctc atc ccg agc cag gag ccc ttt     144
Thr Lys Ser Lys Ser Glu Ala Asn Leu Ile Pro Ser Gln Glu Pro Phe
        35                  40                  45 cca gcc tct gat aac tca ggg gag aca ccg cag aga aat ggg gag ggc     192
Pro Ala Ser Asp Asn Ser Gly Glu Thr Pro Gln Arg Asn Gly Glu Gly
    50                  55                  60 cac act ctg cac aaa gac acc cag cca ggc cga gcc cag cct ccc aca     240
His Thr Leu His Lys Asp Thr Gln Pro Gly Arg Ala Gln Pro Pro Thr
65                  70                  75                  80 aag gcc caa aga tcc ggt cgg cgg aga aac tcc cta cca ccc tcc cgc     288
Lys Ala Gln Arg Ser Gly Arg Arg Arg Asn Ser Leu Pro Pro Ser Arg
                85                  90                  95 cag aag ccc cca aga aac ccc ctt tct tcc agt gac gca gca ccc tcc     336
Gln Lys Pro Pro Arg Asn Pro Leu Ser Ser Ser Asp Ala Ala Pro Ser
            100                 105                 110 cca gag ctt caa gcc aac ggg act ggg aca caa ggt ctg gag gcc aca     384
Pro Glu Leu Gln Ala Asn Gly Thr Gly Thr Gln Gly Leu Glu Ala Thr
        115                 120                 125 gat acc aat ggc ctg tcc tcc tca gcc agg ccc cag ggc agc aag ctg     432
Asp Thr Asn Gly Leu Ser Ser Ser Ala Arg Pro Gln Gly Ser Lys Leu
    130                 135                 140 gtc ccc tcc aaa gaa gac aag aag cag gca aac atc aag agg cag ctg     480
Val Pro Ser Lys Glu Asp Lys Lys Gln Ala Asn Ile Lys Arg Gln Leu
145                 150                 155                 160 atg acc aac ttc atc ctg ggc tct ttt gat gac tac tcc tcc gac gag     528
Met Thr Asn Phe Ile Leu Gly Ser Phe Asp Asp Tyr Ser Ser Asp Glu
                165                 170                 175 gac tct gtt gct ggc tca tct cgt gag tct acc cgg aag ggc agc cgg     576
Asp Ser Val Ala Gly Ser Ser Arg Glu Ser Thr Arg Lys Gly Ser Arg
            180                 185                 190 gcc agc ttg ggg gcc ctg tcc ctg gag gct tat ctg acc aca ggt gaa     624
Ala Ser Leu Gly Ala Leu Ser Leu Glu Ala Tyr Leu Thr Thr Gly Glu
        195                 200                 205 gct gag acc cgc gtc ccc act atg agg ccg agc atg tcg gga ctc cac     672
Ala Glu Thr Arg Val Pro Thr Met Arg Pro Ser Met Ser Gly Leu His
    210                 215                 220 ctg gtg aag agg gga cgg gaa cac aag aag ctg gac ctg cac aga gac     720
Leu Val Lys Arg Gly Arg Glu His Lys Lys Leu Asp Leu His Arg Asp
225                 230                 235                 240
```

-continued

| | | |
|---|---|---|
| ttt acc gtg gct tct ccc gct gag ttt gtc aca cgc ttt ggg ggg gat<br>Phe Thr Val Ala Ser Pro Ala Glu Phe Val Thr Arg Phe Gly Gly Asp<br>245 250 255 | | 768 |
| cgg gtc atc gag aag gtg ctt att gcc aac aac ggg att gcc gct gtg<br>Arg Val Ile Glu Lys Val Leu Ile Ala Asn Asn Gly Ile Ala Ala Val<br>260 265 270 | | 816 |
| aag tgc atg cgc tcc atc cgc agg tgg gcc tat gag atg ttc cgc aac<br>Lys Cys Met Arg Ser Ile Arg Arg Trp Ala Tyr Glu Met Phe Arg Asn<br>275 280 285 | | 864 |
| gag cgg gcc atc cgg ttt gtt cgc atg gtg acc ccc gag gac ctt aag<br>Glu Arg Ala Ile Arg Phe Val Arg Met Val Thr Pro Glu Asp Leu Lys<br>290 295 300 | | 912 |
| gcc aac gca gag tac atc aag atg gcg gat cat tac ggg ccc gcc cca<br>Ala Asn Ala Glu Tyr Ile Lys Met Ala Asp His Tyr Gly Pro Ala Pro<br>305 310 315 320 | | 960 |
| gga ggg ccc aat aac aac aac tat gcc aac gtg gag ctg att gtg gac<br>Gly Gly Pro Asn Asn Asn Asn Tyr Ala Asn Val Glu Leu Ile Val Asp<br>325 330 335 | | 1008 |
| att gcc aag aga atc ccg ttg cag gcg gtg tgg gct ggc tgg ggc cat<br>Ile Ala Lys Arg Ile Pro Leu Gln Ala Val Trp Ala Gly Trp Gly His<br>340 345 350 | | 1056 |
| gct tta gaa aac cct aaa ctt ccg gag ctg ctg tgc aag aat gga gtt<br>Ala Leu Glu Asn Pro Lys Leu Pro Glu Leu Leu Cys Lys Asn Gly Val<br>355 360 365 | | 1104 |
| gct ttc tta ggc cct ccc agg ttg agg cca atg gtg ggt cta gga gat<br>Ala Phe Leu Gly Pro Pro Arg Leu Arg Pro Met Val Gly Leu Gly Asp<br>370 375 380 | | 1152 |
| aag atc gcc tcc acc gtt gtc gcc cag acg cta cag gtc cca acc ctg<br>Lys Ile Ala Ser Thr Val Val Ala Gln Thr Leu Gln Val Pro Thr Leu<br>385 390 395 400 | | 1200 |
| ccc agg agt gga agc gcc ctg aca gtg gag tgg aca gaa gat gat ctg<br>Pro Arg Ser Gly Ser Ala Leu Thr Val Glu Trp Thr Glu Asp Asp Leu<br>405 410 415 | | 1248 |
| cag cag gga aaa aga atc agt gtc cca gaa gat gtt tat gac aag ggt<br>Gln Gln Gly Lys Arg Ile Ser Val Pro Glu Asp Val Tyr Asp Lys Gly<br>420 425 430 | | 1296 |
| tgc gtg aaa gac gta gat gag ggc ttg gag gca gca gaa aga att ggt<br>Cys Val Lys Asp Val Asp Glu Gly Leu Glu Ala Ala Glu Arg Ile Gly<br>435 440 445 | | 1344 |
| ttt cca ttg atg atc aaa gct tct gaa ggt ggc gga ggg aag gga atc<br>Phe Pro Leu Met Ile Lys Ala Ser Glu Gly Gly Gly Gly Lys Gly Ile<br>450 455 460 | | 1392 |
| cgg gaa act gag agt gcg gag gac ttc ccg atc ctt ttc aga caa gta<br>Arg Glu Thr Glu Ser Ala Glu Asp Phe Pro Ile Leu Phe Arg Gln Val<br>465 470 475 480 | | 1440 |
| cag agt gag atc cca ggc tcg ccc atc ttt ctc atg aag ctg gcc cag<br>Gln Ser Glu Ile Pro Gly Ser Pro Ile Phe Leu Met Lys Leu Ala Gln<br>485 490 495 | | 1488 |
| cac gcc cgt cac ctg gaa gtt cag atc ctc gct gac cag tat ggg aat<br>His Ala Arg His Leu Glu Val Gln Ile Leu Ala Asp Gln Tyr Gly Asn<br>500 505 510 | | 1536 |
| gct gtg tct ctg ttt ggt cgc gac tgc tcc atc cag cgg cgg cat cag<br>Ala Val Ser Leu Phe Gly Arg Asp Cys Ser Ile Gln Arg Arg His Gln<br>515 520 525 | | 1584 |
| aag atc gtt gag gaa gca ccg gcc acc atc gcg ccg ctg gcc ata ttc<br>Lys Ile Val Glu Glu Ala Pro Ala Thr Ile Ala Pro Leu Ala Ile Phe<br>530 535 540 | | 1632 |
| gag ttc atg gag cag tgt gcc att cgc ctg gcc aag acc gtg ggc tat<br>Glu Phe Met Glu Gln Cys Ala Ile Arg Leu Ala Lys Thr Val Gly Tyr | | 1680 |

```
                    -continued 545                 550                 555                 560
gtg agt gca ggg aca gtg aaa tac ctc tat agt cag gat ggt agc ttc    1728
Val Ser Ala Gly Thr Val Glu Tyr Leu Tyr Ser Gln Asp Gly Ser Phe
                565                 570                 575 cac ttc ttg gag ctg aat cct cgc ttg cag gtg gaa cat ccc tgc aca    1776
His Phe Leu Glu Leu Asn Pro Arg Leu Gln Val Glu His Pro Cys Thr
            580                 585                 590 gaa atg att gct gac gtt aat ctg ccg gcc gcc cag cta cag atc gcc    1824
Glu Met Ile Ala Asp Val Asn Leu Pro Ala Ala Gln Leu Gln Ile Ala
        595                 600                 605 atg ggt gcc cca ctg cac cgg ctg aaa gat atc cgg ctt ctg tat gga    1872
Met Gly Ala Pro Leu His Arg Leu Lys Asp Ile Arg Leu Leu Tyr Gly
    610                 615                 620 gag tca ccc tgg gga gac tcc cca att tct ttt gaa aac tca gct cat    1920
Glu Ser Pro Trp Gly Asp Ser Pro Ile Ser Phe Glu Asn Ser Ala His
625                 630                 635                 640 ctc ccc tgc ccc cga ggc cac gtc att gcc acc aga atc acc agc gaa    1968
Leu Pro Cys Pro Arg Gly His Val Ile Ala Thr Arg Ile Thr Ser Glu
                645                 650                 655 aac cca gac gag ggt ttt aag ccg agc tcc ggg act gtc cag gaa ctg    2016
Asn Pro Asp Glu Gly Phe Lys Pro Ser Ser Gly Thr Val Gln Glu Leu
            660                 665                 670 aat ttc cgg agc agc aag aac gtc tgg ggt tac ttc acg gtg gcc gct    2064
Asn Phe Arg Ser Ser Lys Asn Val Trp Gly Tyr Phe Thr Val Ala Ala
        675                 680                 685 act gga ggc ctg cac gag ttt gcg att tcc cag ttt ggg cac tgc ttc    2112
Thr Gly Gly Leu His Glu Phe Ala Ile Ser Gln Phe Gly His Cys Phe
    690                 695                 700 tcc tgg gga gag aac cgg aaa gag gcc att tcg aac atg gtg gtg gct    2160
Ser Trp Gly Glu Asn Arg Lys Glu Ala Ile Ser Asn Met Val Val Ala
705                 710                 715                 720 ttg aag gaa ctg tcc ctc cga ggc gac ttt agg act acc gtg gaa tac    2208
Leu Lys Glu Leu Ser Leu Arg Gly Asp Phe Arg Thr Thr Val Glu Tyr
                725                 730                 735 ctc att aac ctc ctg gag acc gag agc ttc cag aac aac tac atc gac    2256
Leu Ile Asn Leu Leu Glu Thr Glu Ser Phe Gln Asn Asn Tyr Ile Asp
            740                 745                 750 acc ggg tgg ttg gac tac ctc att gct gag aaa gtg caa aag aaa ccg    2304
Thr Gly Trp Leu Asp Tyr Leu Ile Ala Glu Lys Val Gln Lys Lys Pro
        755                 760                 765 aat atc atg ctt ggg gtg gta tgc ggg gcc ctt gaa cgt gga gat gcg    2352
Asn Ile Met Leu Gly Val Val Cys Gly Ala Leu Glu Arg Gly Asp Ala
    770                 775                 780 atg ttc aga acg tgc atg aca gat ttc tta cac tcc ctg gaa agg ggc    2400
Met Phe Arg Thr Cys Met Thr Asp Phe Leu His Ser Leu Glu Arg Gly
785                 790                 795                 800 cag gtc ctc cca gcg gat tca cta ctg aac ctc gta gat gtg gaa tta    2448
Gln Val Leu Pro Ala Asp Ser Leu Leu Asn Leu Val Asp Val Glu Leu
                805                 810                 815 att tac gag ggt gta aag tac att cta aag gtg acc cgg cag tct ctg    2496
Ile Tyr Glu Gly Val Lys Tyr Ile Leu Lys Val Thr Arg Gln Ser Leu
            820                 825                 830 acc atg ttc gtt ctc atc atg aat ggc tgc cac atc gag att gat gcc    2544
Thr Met Phe Val Leu Ile Met Asn Gly Cys His Ile Glu Ile Asp Ala
        835                 840                 845 cac cgg ctg aat gat ggg ggg ctc ctc tcc tac aat ggg aac agc        2592
His Arg Leu Asn Asp Gly Gly Leu Leu Ser Tyr Asn Gly Asn Ser
    850                 855                 860 tac acc acc tac atg aag gaa gag gtt gac agt tac cgt acc atc ggc    2640
Tyr Thr Thr Tyr Met Lys Glu Glu Val Asp Ser Tyr Arg Thr Ile Gly
```

| | |
|---|---|
| Tyr Thr Thr Tyr Met Lys Glu Glu Val Asp Ser Tyr Arg Thr Ile Gly<br>865                   870                 875                 880 | |
| aat aag acg tgt gtt ttt gag aag gag aac gat cct aca gtc ctg aga<br>Asn Lys Thr Cys Val Phe Glu Lys Glu Asn Asp Pro Thr Val Leu Arg<br>                         885                 890                 895 | 2688 |
| tcc ccc tcg gct ggg aag ctg aca cag atc aca gtg gag gat ggg ggc<br>Ser Pro Ser Ala Gly Lys Leu Thr Gln Ile Thr Val Glu Asp Gly Gly<br>          900                 905                 910 | 2736 |
| cac gtt gag gct ggg aga cgc tac gct gag atg gag gtg atg aag atg<br>His Val Glu Ala Gly Arg Arg Tyr Ala Glu Met Glu Val Met Lys Met<br>          915                 920                 925 | 2784 |
| atc atg acc ctg aac gtt cag gaa aga ggc cgg gtg aag tac atc aag<br>Ile Met Thr Leu Asn Val Gln Glu Arg Gly Arg Val Lys Tyr Ile Lys<br>     930                 935                 940 | 2832 |
| cgt cca ggt gcg gtg ctg gaa gca ggc tgc gtg gtg gcc agg ctg gag<br>Arg Pro Gly Ala Val Leu Glu Ala Gly Cys Val Val Ala Arg Leu Glu<br>945                 950                 955                 960 | 2880 |
| ctc gat gac cct tct aaa gtc cac ccg gct gaa ccg ttc aca gga gaa<br>Leu Asp Asp Pro Ser Lys Val His Pro Ala Glu Pro Phe Thr Gly Glu<br>                         965                 970                 975 | 2928 |
| ctc cct gcc cag cag aac act gcc gac ctc gga aag aaa ctg cac agg<br>Leu Pro Ala Gln Gln Asn Thr Ala Asp Leu Gly Lys Lys Leu His Arg<br>          980                 985                 990 | 2976 |
| gtc ttc cac agc gtc ctg gga agc ctc acc aac gtc atg agt ggc ttt<br>Val Phe His Ser Val Leu Gly Ser Leu Thr Asn Val Met Ser Gly Phe<br>     995                 1000                1005 | 3024 |
| tgt ctg cca gag ccg ttt ttt agc ata aag ctg aag gag tgg gtg<br>Cys Leu Pro Glu Pro Phe Phe Ser Ile Lys Leu Lys Glu Trp Val<br>     1010                1015                1020 | 3069 |
| cag aag ctc atg atg acc ctc cgg cac ccg tca ctg ctg ctg gac<br>Gln Lys Leu Met Met Thr Leu Arg His Pro Ser Leu Leu Leu Asp<br>     1025                1030                1035 | 3114 |
| gtg cag gag atc atg acc agt cgt gca ggc cgc atc ccc ccc cct<br>Val Gln Glu Ile Met Thr Ser Arg Ala Gly Arg Ile Pro Pro Pro<br>     1040                1045                1050 | 3159 |
| gtt gag aag tct gtc cgc aag gtg atg gcc cag tat gcc agc aac<br>Val Glu Lys Ser Val Arg Lys Val Met Ala Gln Tyr Ala Ser Asn<br>     1055                1060                1065 | 3204 |
| atc acc tcg gtg ctg tgc cag ttc ccc agc cag cag ata gcc acc<br>Ile Thr Ser Val Leu Cys Gln Phe Pro Ser Gln Gln Ile Ala Thr<br>     1070                1075                1080 | 3249 |
| atc ctg gac tgc cat gca gcc acc ctg cag cgg aag gct gat cga<br>Ile Leu Asp Cys His Ala Ala Thr Leu Gln Arg Lys Ala Asp Arg<br>     1085                1090                1095 | 3294 |
| gag gtc ttc ttc atc aac acc cag agc atg gtg cag ttg gtc cag<br>Glu Val Phe Phe Ile Asn Thr Gln Ser Met Val Gln Leu Val Gln<br>     1100                1105                1110 | 3339 |
| agg tac cga agt gga atc cgc ggt cat atg aaa aca gtg gtg atc<br>Arg Tyr Arg Ser Gly Ile Arg Gly His Met Lys Thr Val Val Ile<br>     1115                1120                1125 | 3384 |
| gat ctc ttg aga aga tac ttg cgt gtt gag acc att ttc ggc aag<br>Asp Leu Leu Arg Arg Tyr Leu Arg Val Glu Thr Ile Phe Gly Lys<br>     1130                1135                1140 | 3429 |
| gca aga gat gct gat gcc aac tcc agt ggg atg gtg ggg ggc gtg<br>Ala Arg Asp Ala Asp Ala Asn Ser Ser Gly Met Val Gly Gly Val<br>     1145                1150                1155 | 3474 |
| agg agc ctg agc ttt acc tct gtg tgg gtg gtt ttg tct ccc cca<br>Arg Ser Leu Ser Phe Thr Ser Val Trp Val Val Leu Ser Pro Pro<br>     1160                1165                1170 | 3519 |

```
gcc cac tac gac aag tgt gtg ata aac ctc agg gaa cag ttc aag    3564
Ala His Tyr Asp Lys Cys Val Ile Asn Leu Arg Glu Gln Phe Lys
    1175            1180                1185 cca gac atg tcc cag gtg ctg gac tgc atc ttc tcc cac gca cag    3609
Pro Asp Met Ser Gln Val Leu Asp Cys Ile Phe Ser His Ala Gln
1190            1195                1200 gtg acc aag aag aac cag ctg gtg atc atg ttg atc gat gag ctg    3654
Val Thr Lys Lys Asn Gln Leu Val Ile Met Leu Ile Asp Glu Leu
    1205            1210                1215 tgt ggc cca gac cct tcc ctg tcg gac gag ctg atc tcc atc ctc    3699
Cys Gly Pro Asp Pro Ser Leu Ser Asp Glu Leu Ile Ser Ile Leu
    1220            1225                1230 aac gag ctc act cag ctg agc aaa agc gag cac tgc aaa gtg gcc    3744
Asn Glu Leu Thr Gln Leu Ser Lys Ser Glu His Cys Lys Val Ala
    1235            1240                1245 ctc aga gcc cgg cag atc ctg atc gcc tcc ccc tcc tac gag ctg    3789
Leu Arg Ala Arg Gln Ile Leu Ile Ala Ser Pro Ser Tyr Glu Leu
    1250            1255                1260 cgg cat aac cag gtg gag tcc att ttc ctg tct gcc att gac atg    3834
Arg His Asn Gln Val Glu Ser Ile Phe Leu Ser Ala Ile Asp Met
    1265            1270                1275 tac ggc cac cag ttc tgc ccc gag aac ctc cag aaa tta ata ctt    3879
Tyr Gly His Gln Phe Cys Pro Glu Asn Leu Gln Lys Leu Ile Leu
    1280            1285                1290 tcg gaa aca acc atc ttc gac gtc ctg aat act ttc ttc tat cac    3924
Ser Glu Thr Thr Ile Phe Asp Val Leu Asn Thr Phe Phe Tyr His
    1295            1300                1305 gca aac aaa gtc gtg tgc atg gcg tcc ttg gag gtt tac gtg ggg    3969
Ala Asn Lys Val Val Cys Met Ala Ser Leu Glu Val Tyr Val Gly
    1310            1315                1320 ggg gct tac atc gcc tat gtg tta aac agc ctg cag cac cgg cag    4014
Gly Ala Tyr Ile Ala Tyr Val Leu Asn Ser Leu Gln His Arg Gln
    1325            1330                1335 ctc ccg gac ggc acc tgc gtg gta gaa ttc cag ttc atg ctg ccg    4059
Leu Pro Asp Gly Thr Cys Val Val Glu Phe Gln Phe Met Leu Pro
    1340            1345                1350 tcc tcc cac cca aac cgg atg acc gtg ccc atc agc atc acc aac    4104
Ser Ser His Pro Asn Arg Met Thr Val Pro Ile Ser Ile Thr Asn
    1355            1360                1365 cct gac ctg ctg agg cac acg aca gag ctc ttc atg gac agc ggc    4149
Pro Asp Leu Leu Arg His Thr Thr Glu Leu Phe Met Asp Ser Gly
    1370            1375                1380 ttc tcc cca ctg tgc cag cgc atg gga gcc atg gta gcc ttc agg    4194
Phe Ser Pro Leu Cys Gln Arg Met Gly Ala Met Val Ala Phe Arg
    1385            1390                1395 aga ttc gag gac ttc acc aga aat ttt gat gaa gtc atc tct tgc    4239
Arg Phe Glu Asp Phe Thr Arg Asn Phe Asp Glu Val Ile Ser Cys
    1400            1405                1410 ttc gcc aac gtg cca aaa gac ccc ccc ctc ttc agc gag gcc cgc    4284
Phe Ala Asn Val Pro Lys Asp Pro Pro Leu Phe Ser Glu Ala Arg
    1415            1420                1425 acc tcc cta tac tcc gag gat gac tgc aag agc ctc aga gaa gag    4329
Thr Ser Leu Tyr Ser Glu Asp Asp Cys Lys Ser Leu Arg Glu Glu
    1430            1435                1440 ccc atc cac att ctg aat gtg tcc atc cag tgt gcg gac cac ctg    4374
Pro Ile His Ile Leu Asn Val Ser Ile Gln Cys Ala Asp His Leu
    1445            1450                1455 gag gat gag gca ctg gtg ccg att tta cgt aca ttc gta cag tcc    4419
Glu Asp Glu Ala Leu Val Pro Ile Leu Arg Thr Phe Val Gln Ser
    1460            1465                1470
```

```
aag aaa aat atc ctt gtg gat tat gga ctc cga cga atc cca ttc        4464
Lys Lys Asn Ile Leu Val Asp Tyr Gly Leu Arg Arg Ile Pro Phe
    1475                1480                1485 ttg att gcc caa gag aaa gaa ttt ccc aag ttt ttc aca ttc aga        4509
Leu Ile Ala Gln Glu Lys Glu Phe Pro Lys Phe Phe Thr Phe Arg
    1490                1495                1500 gca aga gat gag ttt gca gaa gat cgc att tac cgt cac ttg gaa        4554
Ala Arg Asp Glu Phe Ala Glu Asp Arg Ile Tyr Arg His Leu Glu
    1505                1510                1515 cct gcc ctg gct ttc cag ctg gaa ctc aac cgg atg cgt aac ttc        4599
Pro Ala Leu Ala Phe Gln Leu Glu Leu Asn Arg Met Arg Asn Phe
    1520                1525                1530 gat ctg acc gcc gtg ccc tgt gcc aac cac aag atg cac ctt tac        4644
Asp Leu Thr Ala Val Pro Cys Ala Asn His Lys Met His Leu Tyr
    1535                1540                1545 ctg ggt gct gcc aag gtg gaa gga agg tat gaa gtg acg gac cat        4689
Leu Gly Ala Ala Lys Val Glu Gly Arg Tyr Glu Val Thr Asp His
    1550                1555                1560 agg ttc ttc atc cgt gcc atc atc agg cac tct gac ctg atc aca        4734
Arg Phe Phe Ile Arg Ala Ile Ile Arg His Ser Asp Leu Ile Thr
    1565                1570                1575 aag gaa gcc tcc ttc gaa tac ctg cag aac gag ggt gag cgg ctg        4779
Lys Glu Ala Ser Phe Glu Tyr Leu Gln Asn Glu Gly Glu Arg Leu
    1580                1585                1590 ctc ctg gag gcc atg gac gag ctg gag gtg gcg ttc aat aac acc        4824
Leu Leu Glu Ala Met Asp Glu Leu Glu Val Ala Phe Asn Asn Thr
    1595                1600                1605 aac gtg cgc acc gac tgc aac cac atc ttc ctc aac ttc gtg ccc        4869
Asn Val Arg Thr Asp Cys Asn His Ile Phe Leu Asn Phe Val Pro
    1610                1615                1620 act gtc atc atg gac ccc aac aag atc gag gag tcc gtg cgc tac        4914
Thr Val Ile Met Asp Pro Asn Lys Ile Glu Glu Ser Val Arg Tyr
    1625                1630                1635 atg gtt atg cgc tac ggc agc cgg ctg tgg aaa ctc cgt gtg cta        4959
Met Val Met Arg Tyr Gly Ser Arg Leu Trp Lys Leu Arg Val Leu
    1640                1645                1650 cag gct gag gtc aag atc aac atc cgc cag acc acc acc ggc agt        5004
Gln Ala Glu Val Lys Ile Asn Ile Arg Gln Thr Thr Thr Gly Ser
    1655                1660                1665 gcc gtt ccc atc cgc ctg ttc atc acc aat gag tcg ggc tac tac        5049
Ala Val Pro Ile Arg Leu Phe Ile Thr Asn Glu Ser Gly Tyr Tyr
    1670                1675                1680 ctg gac atc agc ctc tac aaa gaa gtg act gac tcc aga tct gga        5094
Leu Asp Ile Ser Leu Tyr Lys Glu Val Thr Asp Ser Arg Ser Gly
    1685                1690                1695 aat atc atg ttt cac tcc ttc ggc aac aag caa ggg ccc cag cac        5139
Asn Ile Met Phe His Ser Phe Gly Asn Lys Gln Gly Pro Gln His
    1700                1705                1710 ggg atg ctg atc aat act ccc tac gtc acc aag gat ctg ctc cag        5184
Gly Met Leu Ile Asn Thr Pro Tyr Val Thr Lys Asp Leu Leu Gln
    1715                1720                1725 gcc aag cga ttc cag gcc cag acc ctg gga acc acc tac atc tat        5229
Ala Lys Arg Phe Gln Ala Gln Thr Leu Gly Thr Thr Tyr Ile Tyr
    1730                1735                1740 gac ttc ccg gaa atg ttc agg cag gct ctc ttt aaa ctg tgg ggc        5274
Asp Phe Pro Glu Met Phe Arg Gln Ala Leu Phe Lys Leu Trp Gly
    1745                1750                1755 tcc cca gac aag tat ccc aaa gac atc ctg aca tac act gaa tta        5319
Ser Pro Asp Lys Tyr Pro Lys Asp Ile Leu Thr Tyr Thr Glu Leu
```

```
                    1760                1765                1770
gtg ttg gac tct cag ggc cag ctg gtg gag atg aac cga ctt cct     5364
Val Leu Asp Ser Gln Gly Gln Leu Val Glu Met Asn Arg Leu Pro
        1775                1780                1785 ggt gga aat gag gtg ggc atg gtg gcc ttc aaa atg agg ttt aag     5409
Gly Gly Asn Glu Val Gly Met Val Ala Phe Lys Met Arg Phe Lys
        1790                1795                1800 acc cag gag tac ccg gaa gga cgg gat gtg atc gtc atc ggc aat     5454
Thr Gln Glu Tyr Pro Glu Gly Arg Asp Val Ile Val Ile Gly Asn
        1805                1810                1815 gac atc acc ttt cgc att gga tcc ttt ggc cct gga gag gac ctt     5499
Asp Ile Thr Phe Arg Ile Gly Ser Phe Gly Pro Gly Glu Asp Leu
        1820                1825                1830 ctg tac ctg cgg gca tcc gag atg gcc cgg gca gag gcg att ccc     5544
Leu Tyr Leu Arg Ala Ser Glu Met Ala Arg Ala Glu Ala Ile Pro
        1835                1840                1845 aaa att tac gtg gca gcc aac agt ggc gcc cgt att ggc atg gca     5589
Lys Ile Tyr Val Ala Ala Asn Ser Gly Ala Arg Ile Gly Met Ala
        1850                1855                1860 gag gag atc aaa cac atg ttc cac gtg gct tgg gtg gac cca gaa     5634
Glu Glu Ile Lys His Met Phe His Val Ala Trp Val Asp Pro Glu
        1865                1870                1875 gac ccc cac aaa gga ttt aaa tac ctg tac ctg act ccc caa gac     5679
Asp Pro His Lys Gly Phe Lys Tyr Leu Tyr Leu Thr Pro Gln Asp
        1880                1885                1890 tac acc aga atc agc tcc ctg aac tcc gtc cac tgt aaa cac atc     5724
Tyr Thr Arg Ile Ser Ser Leu Asn Ser Val His Cys Lys His Ile
        1895                1900                1905 gag gaa gga gga gag tcc aga tac atg atc acg gat atc atc ggg     5769
Glu Glu Gly Gly Glu Ser Arg Tyr Met Ile Thr Asp Ile Ile Gly
        1910                1915                1920 aag gat gat ggc ttg ggc gtg gag aat ctg agg ggc tca ggc atg     5814
Lys Asp Asp Gly Leu Gly Val Glu Asn Leu Arg Gly Ser Gly Met
        1925                1930                1935 att gct ggg gag tcc tct ctg gct tac gaa gag atc gtc acc att     5859
Ile Ala Gly Glu Ser Ser Leu Ala Tyr Glu Glu Ile Val Thr Ile
        1940                1945                1950 agc ttg gtg acc tgc cga gcc att ggg att ggg gcc tac ttg gtg     5904
Ser Leu Val Thr Cys Arg Ala Ile Gly Ile Gly Ala Tyr Leu Val
        1955                1960                1965 agg ctg ggc cag cga gtg atc cag gtg gag aat tcc cac atc atc     5949
Arg Leu Gly Gln Arg Val Ile Gln Val Glu Asn Ser His Ile Ile
        1970                1975                1980 ctc aca gga gca agt gct ctc aac aag gtc ctg gga aga gag gtc     5994
Leu Thr Gly Ala Ser Ala Leu Asn Lys Val Leu Gly Arg Glu Val
        1985                1990                1995 tac aca tcc aac aac cag ctg ggt ggc gtt cag atc atg cat tac     6039
Tyr Thr Ser Asn Asn Gln Leu Gly Gly Val Gln Ile Met His Tyr
        2000                2005                2010 aat ggt gtc tcc cac atc acc gtg cca gat gac ttt gag ggg gtt     6084
Asn Gly Val Ser His Ile Thr Val Pro Asp Asp Phe Glu Gly Val
        2015                2020                2025 tat acc atc ctg gag tgg ctg tcc tat atg cca aag gat aat cac     6129
Tyr Thr Ile Leu Glu Trp Leu Ser Tyr Met Pro Lys Asp Asn His
        2030                2035                2040 agc cct gtc cct atc atc aca ccc act gac ccc att gac aga gaa     6174
Ser Pro Val Pro Ile Ile Thr Pro Thr Asp Pro Ile Asp Arg Glu
        2045                2050                2055 att gaa ttc ctc cca tcc aga gct ccc tac gac ccc cgg tgg atg     6219
```

```
                                                        -continued

Ile Glu Phe Leu Pro Ser Arg Ala Pro Tyr Asp Pro Arg Trp Met
    2060                2065                2070 ctt gca gga agg cct cac cca act ctg aag gga acg tgg cag agc      6264
Leu Ala Gly Arg Pro His Pro Thr Leu Lys Gly Thr Trp Gln Ser
    2075                2080                2085 gga ttc ttt gac cac ggc agt ttc aag gaa atc atg gca ccc tgg      6309
Gly Phe Phe Asp His Gly Ser Phe Lys Glu Ile Met Ala Pro Trp
    2090                2095                2100 gcg cag acc gtg gtg aca gga cga gca agg ctt ggg ggg att ccc      6354
Ala Gln Thr Val Val Thr Gly Arg Ala Arg Leu Gly Gly Ile Pro
    2105                2110                2115 gtg gga gtg att gct gtg gag aca cgg act gtg gag gtg gca gtc      6399
Val Gly Val Ile Ala Val Glu Thr Arg Thr Val Glu Val Ala Val
    2120                2125                2130 cct gca gac cct gcc aac ctg gat tct gag gcc aag ata att cag      6444
Pro Ala Asp Pro Ala Asn Leu Asp Ser Glu Ala Lys Ile Ile Gln
    2135                2140                2145 cag gca gga cag gtg tgg ttc cca gac tca gcc tac aaa acc gcc      6489
Gln Ala Gly Gln Val Trp Phe Pro Asp Ser Ala Tyr Lys Thr Ala
    2150                2155                2160 cag gcc atc aag gac ttc aac cgg gag aag ttg ccc ctg atg atc      6534
Gln Ala Ile Lys Asp Phe Asn Arg Glu Lys Leu Pro Leu Met Ile
    2165                2170                2175 ttt gcc aac tgg agg ggg ttc tcc ggt ggc atg aaa gac atg tat      6579
Phe Ala Asn Trp Arg Gly Phe Ser Gly Gly Met Lys Asp Met Tyr
    2180                2185                2190 gac cag gtg ctg aag ttt gga gcc tac atc gtg gac ggc ctt aga      6624
Asp Gln Val Leu Lys Phe Gly Ala Tyr Ile Val Asp Gly Leu Arg
    2195                2200                2205 caa tac aaa cag ccc atc ctg atc tat atc cgc cct atg cgg gag      6669
Gln Tyr Lys Gln Pro Ile Leu Ile Tyr Ile Arg Pro Met Arg Glu
    2210                2215                2220 ctc cgg gga ggc tcc tgg gtg gtc ata gat gcc acc atc aac ccg      6714
Leu Arg Gly Gly Ser Trp Val Val Ile Asp Ala Thr Ile Asn Pro
    2225                2230                2235 ctg tgc ata gaa atg tat gca gac aaa gag agc agg ggt ggt gtt      6759
Leu Cys Ile Glu Met Tyr Ala Asp Lys Glu Ser Arg Gly Gly Val
    2240                2245                2250 ctg gaa cca gag ggg aca gtg gag att aag ttc cga aag gaa gat      6804
Leu Glu Pro Glu Gly Thr Val Glu Ile Lys Phe Arg Lys Glu Asp
    2255                2260                2265 ctg ata aag tcc atg aga agg atc gat cca gct tac aag aag ctc      6849
Leu Ile Lys Ser Met Arg Arg Ile Asp Pro Ala Tyr Lys Lys Leu
    2270                2275                2280 atg gaa cag cta ggg gaa cct gat ctc tcc gac aag gac cga aag      6894
Met Glu Gln Leu Gly Glu Pro Asp Leu Ser Asp Lys Asp Arg Lys
    2285                2290                2295 gac ctg gag ggc cgg cta aag gct cgc gag gac ctg ctc ctc ccc      6939
Asp Leu Glu Gly Arg Leu Lys Ala Arg Glu Asp Leu Leu Leu Pro
    2300                2305                2310 atc tac cac cag gtg gcg gtg cag ttc gcc gac ttc cat gac aca      6984
Ile Tyr His Gln Val Ala Val Gln Phe Ala Asp Phe His Asp Thr
    2315                2320                2325 ccc ggc cgg atg ctg gag aag ggc gtc ata tct gac atc ctg gag      7029
Pro Gly Arg Met Leu Glu Lys Gly Val Ile Ser Asp Ile Leu Glu
    2330                2335                2340 tgg aag acc gca cgc acc ttc ctg tat tgg cgt ctg cgc cgc ctc      7074
Trp Lys Thr Ala Arg Thr Phe Leu Tyr Trp Arg Leu Arg Arg Leu
    2345                2350                2355
```

| | | | | | | | | | | | | | | |
|---|---|---|---|---|---|---|---|---|---|---|---|---|---|---|
| ctc | ctg | gag | gac | cag | gtc | aag | cag | gag | atc | ctg | cag | gcc | agc | ggg | 7119 |
| Leu | Leu | Glu | Asp | Gln | Val | Lys | Gln | Glu | Ile | Leu | Gln | Ala | Ser | Gly | |
| | 2360 | | | | 2365 | | | | | 2370 | | | | | |
| gag | ctg | agt | cac | gtg | cat | atc | cag | tcc | atg | ctg | cgt | cgc | tgg | ttc | 7164 |
| Glu | Leu | Ser | His | Val | His | Ile | Gln | Ser | Met | Leu | Arg | Arg | Trp | Phe | |
| 2375 | | | | | 2380 | | | | | 2385 | | | | | |
| gtg | gag | acg | gag | ggg | gct | gtc | aag | gcc | tac | ttg | tgg | gac | aac | aac | 7209 |
| Val | Glu | Thr | Glu | Gly | Ala | Val | Lys | Ala | Tyr | Leu | Trp | Asp | Asn | Asn | |
| 2390 | | | | | 2395 | | | | | 2400 | | | | | |
| cag | gtg | gtt | gtg | cag | tgg | ctg | gaa | cag | cac | tgg | cag | gca | ggg | gat | 7254 |
| Gln | Val | Val | Val | Gln | Trp | Leu | Glu | Gln | His | Trp | Gln | Ala | Gly | Asp | |
| 2405 | | | | | 2410 | | | | | 2415 | | | | | |
| ggc | ccg | cgc | tcc | acc | atc | cgt | gag | aac | atc | acg | tac | ctg | aag | cac | 7299 |
| Gly | Pro | Arg | Ser | Thr | Ile | Arg | Glu | Asn | Ile | Thr | Tyr | Leu | Lys | His | |
| | 2420 | | | | 2425 | | | | | 2430 | | | | | |
| gac | tct | gtc | ctc | aag | acc | atc | cga | ggc | ctg | gtt | gaa | gaa | aac | ccc | 7344 |
| Asp | Ser | Val | Leu | Lys | Thr | Ile | Arg | Gly | Leu | Val | Glu | Glu | Asn | Pro | |
| 2435 | | | | | 2440 | | | | | 2445 | | | | | |
| gag | gtg | gcc | gtg | gac | tgt | gtg | ata | tac | ctg | agc | cag | cac | atc | agc | 7389 |
| Glu | Val | Ala | Val | Asp | Cys | Val | Ile | Tyr | Leu | Ser | Gln | His | Ile | Ser | |
| 2450 | | | | | 2455 | | | | | 2460 | | | | | |
| cca | gct | gag | cgg | gcg | cag | gtc | gtt | cac | ctg | ctg | tct | acc | atg | gac | 7434 |
| Pro | Ala | Glu | Arg | Ala | Gln | Val | Val | His | Leu | Leu | Ser | Thr | Met | Asp | |
| 2465 | | | | | 2470 | | | | | 2475 | | | | | |
| agc | ccg | gcc | tcc | acc | tga | | | | | | | | | | 7452 |
| Ser | Pro | Ala | Ser | Thr | | | | | | | | | | | |
| | 2480 | | | | | | | | | | | | | | |

<210> SEQ ID NO 2
<211> LENGTH: 2483
<212> TYPE: PRT
<213> ORGANISM: Homo sapiens

<400> SEQUENCE: 2

Met Val Leu Leu Leu Cys Leu Ser Cys Leu Ile Phe Ser Cys Leu Thr
1               5                   10                  15

Phe Ser Trp Leu Lys Ile Trp Glu Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu His Lys Asp Thr Gln Pro Gly Arg Ala Gln Pro Pro Thr
65                  70                  75                  80

Lys Ala Gln Arg Ser Gly Arg Arg Arg Asn Ser Leu Pro Pro Ser Arg
                85                  90                  95

Gln Lys Pro Pro Arg Asn Pro Leu Ser Ser Ser Asp Ala Ala Pro Ser
            100                 105                 110

Pro Glu Leu Gln Ala Asn Gly Thr Gly Thr Gln Gly Leu Glu Ala Thr
        115                 120                 125

Asp Thr Asn Gly Leu Ser Ser Ser Ala Arg Pro Gln Gly Ser Lys Leu
    130                 135                 140

Val Pro Ser Lys Glu Asp Lys Lys Gln Ala Asn Ile Lys Arg Gln Leu
145                 150                 155                 160

Met Thr Asn Phe Ile Leu Gly Ser Phe Asp Asp Tyr Ser Ser Asp Glu
                165                 170                 175

Asp Ser Val Ala Gly Ser Ser Arg Glu Ser Thr Arg Lys Gly Ser Arg
            180                 185                 190

```
Ala Ser Leu Gly Ala Leu Ser Leu Glu Ala Tyr Leu Thr Thr Gly Glu
        195                 200                 205

Ala Glu Thr Arg Val Pro Thr Met Arg Pro Ser Met Ser Gly Leu His
    210                 215                 220

Leu Val Lys Arg Gly Arg Glu His Lys Lys Leu Asp Leu His Arg Asp
225                 230                 235                 240

Phe Thr Val Ala Ser Pro Ala Glu Phe Val Thr Arg Phe Gly Gly Asp
            245                 250                 255

Arg Val Ile Glu Lys Val Leu Ile Ala Asn Asn Gly Ile Ala Ala Val
        260                 265                 270

Lys Cys Met Arg Ser Ile Arg Arg Trp Ala Tyr Glu Met Phe Arg Asn
    275                 280                 285

Glu Arg Ala Ile Arg Phe Val Arg Met Val Thr Pro Glu Asp Leu Lys
    290                 295                 300

Ala Asn Ala Glu Tyr Ile Lys Met Ala Asp His Tyr Gly Pro Ala Pro
305                 310                 315                 320

Gly Gly Pro Asn Asn Asn Asn Tyr Ala Asn Val Glu Leu Ile Val Asp
            325                 330                 335

Ile Ala Lys Arg Ile Pro Leu Gln Ala Val Trp Ala Gly Trp Gly His
        340                 345                 350

Ala Leu Glu Asn Pro Lys Leu Pro Glu Leu Leu Cys Lys Asn Gly Val
        355                 360                 365

Ala Phe Leu Gly Pro Pro Arg Leu Arg Pro Met Val Gly Leu Gly Asp
    370                 375                 380

Lys Ile Ala Ser Thr Val Val Ala Gln Thr Leu Gln Val Pro Thr Leu
385                 390                 395                 400

Pro Arg Ser Gly Ser Ala Leu Thr Val Glu Trp Thr Glu Asp Asp Leu
            405                 410                 415

Gln Gln Gly Lys Arg Ile Ser Val Pro Glu Asp Val Tyr Asp Lys Gly
        420                 425                 430

Cys Val Lys Asp Val Asp Glu Gly Leu Glu Ala Ala Glu Arg Ile Gly
    435                 440                 445

Phe Pro Leu Met Ile Lys Ala Ser Glu Gly Gly Gly Gly Lys Gly Ile
    450                 455                 460

Arg Glu Thr Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
            485                 490                 495

His Ala Arg His Leu Glu Val Gln Ile Leu Ala Asp Gln Tyr Gly Asn
        500                 505                 510

Ala Val Ser Leu Phe Gly Arg Asp Cys Ser Ile Gln Arg Arg His Gln
        515                 520                 525

Lys Ile Val Glu Glu Ala Pro Ala Thr Ile Ala Pro Leu Ala Ile Phe
    530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
            565                 570                 575

His Phe Leu Glu Leu Asn Pro Arg Leu Gln Val Glu His Pro Cys Thr
        580                 585                 590

Glu Met Ile Ala Asp Val Asn Leu Pro Ala Ala Gln Leu Gln Ile Ala
    595                 600                 605
```

-continued

```
Met Gly Ala Pro Leu His Arg Leu Lys Asp Ile Arg Leu Leu Tyr Gly
610                 615                 620
Glu Ser Pro Trp Gly Asp Ser Pro Ile Ser Phe Glu Asn Ser Ala His
625                 630                 635                 640
Leu Pro Cys Pro Arg Gly His Val Ile Ala Thr Arg Ile Thr Ser Glu
                645                 650                 655
Asn Pro Asp Glu Gly Phe Lys Pro Ser Ser Gly Thr Val Gln Glu Leu
                660                 665                 670
Asn Phe Arg Ser Ser Lys Asn Val Trp Gly Tyr Phe Thr Val Ala Ala
                675                 680                 685
Thr Gly Gly Leu His Glu Phe Ala Ile Ser Gln Phe Gly His Cys Phe
690                 695                 700
Ser Trp Gly Glu Asn Arg Lys Glu Ala Ile Ser Asn Met Val Val Ala
705                 710                 715                 720
Leu Lys Glu Leu Ser Leu Arg Gly Asp Phe Arg Thr Thr Val Glu Tyr
                725                 730                 735
Leu Ile Asn Leu Leu Glu Thr Glu Ser Phe Gln Asn Asn Tyr Ile Asp
                740                 745                 750
Thr Gly Trp Leu Asp Tyr Leu Ile Ala Glu Lys Val Gln Lys Lys Pro
                755                 760                 765
Asn Ile Met Leu Gly Val Val Cys Gly Ala Leu Glu Arg Gly Asp Ala
770                 775                 780
Met Phe Arg Thr Cys Met Thr Asp Phe Leu His Ser Leu Glu Arg Gly
785                 790                 795                 800
Gln Val Leu Pro Ala Asp Ser Leu Leu Asn Leu Val Asp Val Glu Leu
                805                 810                 815
Ile Tyr Glu Gly Val Lys Tyr Ile Leu Lys Val Thr Arg Gln Ser Leu
                820                 825                 830
Thr Met Phe Val Leu Ile Met Asn Gly Cys His Ile Glu Ile Asp Ala
                835                 840                 845
His Arg Leu Asn Asp Gly Gly Leu Leu Ser Tyr Asn Gly Asn Ser
850                 855                 860
Tyr Thr Thr Tyr Met Lys Glu Glu Val Asp Ser Tyr Arg Thr Ile Gly
865                 870                 875                 880
Asn Lys Thr Cys Val Phe Glu Lys Glu Asn Asp Pro Thr Val Leu Arg
                885                 890                 895
Ser Pro Ser Ala Gly Lys Leu Thr Gln Ile Thr Val Glu Asp Gly Gly
                900                 905                 910
His Val Glu Ala Gly Arg Arg Tyr Ala Glu Met Glu Val Met Lys Met
                915                 920                 925
Ile Met Thr Leu Asn Val Gln Glu Arg Gly Arg Val Lys Tyr Ile Lys
930                 935                 940
Arg Pro Gly Ala Val Leu Glu Ala Gly Cys Val Val Ala Arg Leu Glu
945                 950                 955                 960
Leu Asp Asp Pro Ser Lys Val His Pro Ala Glu Pro Phe Thr Gly Glu
                965                 970                 975
Leu Pro Ala Gln Gln Asn Thr Ala Asp Leu Gly Lys Lys Leu His Arg
                980                 985                 990
Val Phe His Ser Val Leu Gly Ser Leu Thr Asn Val Met Ser Gly Phe
                995                 1000                1005
Cys Leu Pro Glu Pro Phe Phe Ser Ile Lys Leu Lys Glu Trp Val
    1010                1015                1020
Gln Lys Leu Met Met Thr Leu Arg His Pro Ser Leu Leu Leu Asp
```

-continued

```
                1025                1030                1035
Val Gln Glu Ile Met Thr Ser Arg Ala Gly Arg Ile Pro Pro Pro
    1040                1045                1050
Val Glu Lys Ser Val Arg Lys Val Met Ala Gln Tyr Ala Ser Asn
    1055                1060                1065
Ile Thr Ser Val Leu Cys Gln Phe Pro Ser Gln Ile Ala Thr
    1070                1075                1080
Ile Leu Asp Cys His Ala Ala Thr Leu Gln Arg Lys Ala Asp Arg
    1085                1090                1095
Glu Val Phe Phe Ile Asn Thr Gln Ser Met Val Gln Leu Val Gln
    1100                1105                1110
Arg Tyr Arg Ser Gly Ile Arg Gly His Met Lys Thr Val Val Ile
    1115                1120                1125
Asp Leu Leu Arg Arg Tyr Leu Arg Val Glu Thr Ile Phe Gly Lys
    1130                1135                1140
Ala Arg Asp Ala Asp Ala Asn Ser Ser Gly Met Val Gly Gly Val
    1145                1150                1155
Arg Ser Leu Ser Phe Thr Ser Val Trp Val Val Leu Ser Pro Pro
    1160                1165                1170
Ala His Tyr Asp Lys Cys Val Ile Asn Leu Arg Glu Gln Phe Lys
    1175                1180                1185
Pro Asp Met Ser Gln Val Leu Asp Cys Ile Phe Ser His Ala Gln
    1190                1195                1200
Val Thr Lys Lys Asn Gln Leu Val Ile Met Leu Ile Asp Glu Leu
    1205                1210                1215
Cys Gly Pro Asp Pro Ser Leu Ser Asp Glu Leu Ile Ser Ile Leu
    1220                1225                1230
Asn Glu Leu Thr Gln Leu Ser Lys Ser Glu His Cys Lys Val Ala
    1235                1240                1245
Leu Arg Ala Arg Gln Ile Leu Ile Ala Ser Pro Ser Tyr Glu Leu
    1250                1255                1260
Arg His Asn Gln Val Glu Ser Ile Phe Leu Ser Ala Ile Asp Met
    1265                1270                1275
Tyr Gly His Gln Phe Cys Pro Glu Asn Leu Gln Lys Leu Ile Leu
    1280                1285                1290
Ser Glu Thr Thr Ile Phe Asp Val Leu Asn Thr Phe Phe Tyr His
    1295                1300                1305
Ala Asn Lys Val Val Cys Met Ala Ser Leu Glu Val Tyr Val Gly
    1310                1315                1320
Gly Ala Tyr Ile Ala Tyr Val Leu Asn Ser Leu Gln His Arg Gln
    1325                1330                1335
Leu Pro Asp Gly Thr Cys Val Val Glu Phe Gln Phe Met Leu Pro
    1340                1345                1350
Ser Ser His Pro Asn Arg Met Thr Val Pro Ile Ser Ile Thr Asn
    1355                1360                1365
Pro Asp Leu Leu Arg His Thr Thr Glu Leu Phe Met Asp Ser Gly
    1370                1375                1380
Phe Ser Pro Leu Cys Gln Arg Met Gly Ala Met Val Ala Phe Arg
    1385                1390                1395
Arg Phe Glu Asp Phe Thr Arg Asn Phe Asp Glu Val Ile Ser Cys
    1400                1405                1410
Phe Ala Asn Val Pro Lys Asp Pro Pro Leu Phe Ser Glu Ala Arg
    1415                1420                1425
```

-continued

```
Thr Ser Leu Tyr Ser Glu Asp Asp Cys Lys Ser Leu Arg Glu Glu
    1430            1435                1440

Pro Ile His Ile Leu Asn Val Ser Ile Gln Cys Ala Asp His Leu
    1445            1450                1455

Glu Asp Glu Ala Leu Val Pro Ile Leu Arg Thr Phe Val Gln Ser
    1460            1465                1470

Lys Lys Asn Ile Leu Val Asp Tyr Gly Leu Arg Arg Ile Pro Phe
    1475            1480                1485

Leu Ile Ala Gln Glu Lys Glu Phe Pro Lys Phe Phe Thr Phe Arg
    1490            1495                1500

Ala Arg Asp Glu Phe Ala Glu Asp Arg Ile Tyr Arg His Leu Glu
    1505            1510                1515

Pro Ala Leu Ala Phe Gln Leu Glu Leu Asn Arg Met Arg Asn Phe
    1520            1525                1530

Asp Leu Thr Ala Val Pro Cys Ala Asn His Lys Met His Leu Tyr
    1535            1540                1545

Leu Gly Ala Ala Lys Val Glu Gly Arg Tyr Glu Val Thr Asp His
    1550            1555                1560

Arg Phe Phe Ile Arg Ala Ile Ile Arg His Ser Asp Leu Ile Thr
    1565            1570                1575

Lys Glu Ala Ser Phe Glu Tyr Leu Gln Asn Glu Gly Glu Arg Leu
    1580            1585                1590

Leu Leu Glu Ala Met Asp Glu Leu Glu Val Ala Phe Asn Asn Thr
    1595            1600                1605

Asn Val Arg Thr Asp Cys Asn His Ile Phe Leu Asn Phe Val Pro
    1610            1615                1620

Thr Val Ile Met Asp Pro Asn Lys Ile Glu Glu Ser Val Arg Tyr
    1625            1630                1635

Met Val Met Arg Tyr Gly Ser Arg Leu Trp Lys Leu Arg Val Leu
    1640            1645                1650

Gln Ala Glu Val Lys Ile Asn Ile Arg Gln Thr Thr Thr Gly Ser
    1655            1660                1665

Ala Val Pro Ile Arg Leu Phe Ile Thr Asn Glu Ser Gly Tyr Tyr
    1670            1675                1680

Leu Asp Ile Ser Leu Tyr Lys Glu Val Thr Asp Ser Arg Ser Gly
    1685            1690                1695

Asn Ile Met Phe His Ser Phe Gly Asn Lys Gln Gly Pro Gln His
    1700            1705                1710

Gly Met Leu Ile Asn Thr Pro Tyr Val Thr Lys Asp Leu Leu Gln
    1715            1720                1725

Ala Lys Arg Phe Gln Ala Gln Thr Leu Gly Thr Thr Tyr Ile Tyr
    1730            1735                1740

Asp Phe Pro Glu Met Phe Arg Gln Ala Leu Phe Lys Leu Trp Gly
    1745            1750                1755

Ser Pro Asp Lys Tyr Pro Lys Asp Ile Leu Thr Tyr Thr Glu Leu
    1760            1765                1770

Val Leu Asp Ser Gln Gly Gln Leu Val Glu Met Asn Arg Leu Pro
    1775            1780                1785

Gly Gly Asn Glu Val Gly Met Val Ala Phe Lys Met Arg Phe Lys
    1790            1795                1800

Thr Gln Glu Tyr Pro Glu Gly Arg Asp Val Ile Val Ile Gly Asn
    1805            1810                1815
```

-continued

```
Asp Ile Thr Phe Arg Ile Gly Ser Phe Pro Gly Glu Asp Leu
1820            1825            1830

Leu Tyr Leu Arg Ala Ser Glu Met Ala Arg Ala Glu Ala Ile Pro
1835            1840            1845

Lys Ile Tyr Val Ala Ala Asn Ser Gly Ala Arg Ile Gly Met Ala
1850            1855            1860

Glu Glu Ile Lys His Met Phe His Val Ala Trp Val Asp Pro Glu
1865            1870            1875

Asp Pro His Lys Gly Phe Lys Tyr Leu Tyr Leu Thr Pro Gln Asp
1880            1885            1890

Tyr Thr Arg Ile Ser Ser Leu Asn Ser Val His Cys Lys His Ile
1895            1900            1905

Glu Glu Gly Gly Glu Ser Arg Tyr Met Ile Thr Asp Ile Ile Gly
1910            1915            1920

Lys Asp Asp Gly Leu Gly Val Glu Asn Leu Arg Gly Ser Gly Met
1925            1930            1935

Ile Ala Gly Glu Ser Ser Leu Ala Tyr Glu Glu Ile Val Thr Ile
1940            1945            1950

Ser Leu Val Thr Cys Arg Ala Ile Gly Ile Gly Ala Tyr Leu Val
1955            1960            1965

Arg Leu Gly Gln Arg Val Ile Gln Val Glu Asn Ser His Ile Ile
1970            1975            1980

Leu Thr Gly Ala Ser Ala Leu Asn Lys Val Leu Gly Arg Glu Val
1985            1990            1995

Tyr Thr Ser Asn Asn Gln Leu Gly Gly Val Gln Ile Met His Tyr
2000            2005            2010

Asn Gly Val Ser His Ile Thr Val Pro Asp Asp Phe Glu Gly Val
2015            2020            2025

Tyr Thr Ile Leu Glu Trp Leu Ser Tyr Met Pro Lys Asp Asn His
2030            2035            2040

Ser Pro Val Pro Ile Ile Thr Pro Thr Asp Pro Ile Asp Arg Glu
2045            2050            2055

Ile Glu Phe Leu Pro Ser Arg Ala Pro Tyr Asp Pro Arg Trp Met
2060            2065            2070

Leu Ala Gly Arg Pro His Pro Thr Leu Lys Gly Thr Trp Gln Ser
2075            2080            2085

Gly Phe Phe Asp His Gly Ser Phe Lys Glu Ile Met Ala Pro Trp
2090            2095            2100

Ala Gln Thr Val Val Thr Gly Arg Ala Arg Leu Gly Gly Ile Pro
2105            2110            2115

Val Gly Val Ile Ala Val Glu Thr Arg Thr Val Glu Val Ala Val
2120            2125            2130

Pro Ala Asp Pro Ala Asn Leu Asp Ser Glu Ala Lys Ile Ile Gln
2135            2140            2145

Gln Ala Gly Gln Val Trp Phe Pro Asp Ser Ala Tyr Lys Thr Ala
2150            2155            2160

Gln Ala Ile Lys Asp Phe Asn Arg Glu Lys Leu Pro Leu Met Ile
2165            2170            2175

Phe Ala Asn Trp Arg Gly Phe Ser Gly Gly Met Lys Asp Met Tyr
2180            2185            2190

Asp Gln Val Leu Lys Phe Gly Ala Tyr Ile Val Asp Gly Leu Arg
2195            2200            2205

Gln Tyr Lys Gln Pro Ile Leu Ile Tyr Ile Arg Pro Met Arg Glu
```

-continued

```
                            2210                2215                2220
Leu Arg Gly Gly Ser Trp Val Val Ile Asp Ala Thr Ile Asn Pro
    2225                2230                2235

Leu Cys Ile Glu Met Tyr Ala Asp Lys Glu Ser Arg Gly Gly Val
    2240                2245                2250

Leu Glu Pro Glu Gly Thr Val Glu Ile Lys Phe Arg Lys Glu Asp
    2255                2260                2265

Leu Ile Lys Ser Met Arg Arg Ile Asp Pro Ala Tyr Lys Lys Leu
    2270                2275                2280

Met Glu Gln Leu Gly Glu Pro Asp Leu Ser Asp Lys Asp Arg Lys
    2285                2290                2295

Asp Leu Glu Gly Arg Leu Lys Ala Arg Glu Asp Leu Leu Leu Pro
    2300                2305                2310

Ile Tyr His Gln Val Ala Val Gln Phe Ala Asp Phe His Asp Thr
    2315                2320                2325

Pro Gly Arg Met Leu Glu Lys Gly Val Ile Ser Asp Ile Leu Glu
    2330                2335                2340

Trp Lys Thr Ala Arg Thr Phe Leu Tyr Trp Arg Leu Arg Arg Leu
    2345                2350                2355

Leu Leu Glu Asp Gln Val Lys Gln Glu Ile Leu Gln Ala Ser Gly
    2360                2365                2370

Glu Leu Ser His Val His Ile Gln Ser Met Leu Arg Arg Trp Phe
    2375                2380                2385

Val Glu Thr Glu Gly Ala Val Lys Ala Tyr Leu Trp Asp Asn Asn
    2390                2395                2400

Gln Val Val Val Gln Trp Leu Glu Gln His Trp Gln Ala Gly Asp
    2405                2410                2415

Gly Pro Arg Ser Thr Ile Arg Glu Asn Ile Thr Tyr Leu Lys His
    2420                2425                2430

Asp Ser Val Leu Lys Thr Ile Arg Gly Leu Val Glu Glu Asn Pro
    2435                2440                2445

Glu Val Ala Val Asp Cys Val Ile Tyr Leu Ser Gln His Ile Ser
    2450                2455                2460

Pro Ala Glu Arg Ala Gln Val Val His Leu Leu Ser Thr Met Asp
    2465                2470                2475

Ser Pro Ala Ser Thr
    2480

<210> SEQ ID NO 3
<211> LENGTH: 7368
<212> TYPE: DNA
<213> ORGANISM: Homo sapiens
<220> FEATURE:
<221> NAME/KEY: CDS
<222> LOCATION: (1)..(7368)

<400> SEQUENCE: 3 atg gtc ttg ctt ctt tgt cta tct tgt ctg att ttc tcc tgt ctg acc      48
Met Val Leu Leu Leu Cys Leu Ser Cys Leu Ile Phe Ser Cys Leu Thr
1               5                  10                  15 ttt tcc tgg tta aaa atc tgg ggg aaa atg acg gac tcc aag ccg atc      96
Phe Ser Trp Leu Lys Ile Trp Gly Lys Met Thr Asp Ser Lys Pro Ile
            20                  25                  30 acc aag agt aaa tca gaa gca aac ctc atc ccg agc cag gag ccc ttt     144
Thr Lys Ser Lys Ser Glu Ala Asn Leu Ile Pro Ser Gln Glu Pro Phe
        35                  40                  45
```

```
cca gcc tct gat aac tca ggg gag aca ccg cag aga aat ggg gag ggc      192
Pro Ala Ser Asp Asn Ser Gly Glu Thr Pro Gln Arg Asn Gly Glu Gly
 50              55                  60 cac act ctg ccc aag aca ccc agc cag gcc gag cca gcc tcc cac aaa      240
His Thr Leu Pro Lys Thr Pro Ser Gln Ala Glu Pro Ala Ser His Lys
 65              70                  75                  80 ggc ccc aaa gat gcc ggt cgg cgg aga aac tcc cta cca ccc tcc cac      288
Gly Pro Lys Asp Ala Gly Arg Arg Arg Asn Ser Leu Pro Pro Ser His
                 85                  90                  95 cag aag ccc cca aga aac ccc ctt tct tcc agt gac gca gca ccc tcc      336
Gln Lys Pro Pro Arg Asn Pro Leu Ser Ser Ser Asp Ala Ala Pro Ser
                100                 105                 110 cca gag ctt caa gcc aac ggg act ggg aca caa ggt ctg gag gcc aca      384
Pro Glu Leu Gln Ala Asn Gly Thr Gly Thr Gln Gly Leu Glu Ala Thr
            115                 120                 125 gat acc aat ggc ctg tcc tcc tca gcc agg ccc cag ggc cag caa gct      432
Asp Thr Asn Gly Leu Ser Ser Ser Ala Arg Pro Gln Gly Gln Gln Ala
130                 135                 140 ggc tcc ccc tcc aaa gaa gac aag aag cag gca aac atc aag agg cag      480
Gly Ser Pro Ser Lys Glu Asp Lys Lys Gln Ala Asn Ile Lys Arg Gln
145                 150                 155                 160 ctg atg acc aac ttc atc ctg ggc tct ttt gat gac tac tcc tcc gac      528
Leu Met Thr Asn Phe Ile Leu Gly Ser Phe Asp Asp Tyr Ser Ser Asp
                165                 170                 175 gag gac tct gtt gct ggc tca tct cgt gag tct acc cgg aag ggc agc      576
Glu Asp Ser Val Ala Gly Ser Ser Arg Glu Ser Thr Arg Lys Gly Ser
                180                 185                 190 cgg gcc agc ttg ggg gcc ctg tcc ctg gag gct tat ctg acc aca ggt      624
Arg Ala Ser Leu Gly Ala Leu Ser Leu Glu Ala Tyr Leu Thr Thr Gly
            195                 200                 205 gaa gct gag acc cgc gtc ccc act atg agg ccg agc atg tcg gga ctc      672
Glu Ala Glu Thr Arg Val Pro Thr Met Arg Pro Ser Met Ser Gly Leu
210                 215                 220 cac ctg gtg aag agg gga cgg gaa cac aag aag ctg gac ctg cac aga      720
His Leu Val Lys Arg Gly Arg Glu His Lys Lys Leu Asp Leu His Arg
225                 230                 235                 240 gac ttt acc gtg gct tct ccc gct gag ttt gtc aca cgc ttt ggg ggg      768
Asp Phe Thr Val Ala Ser Pro Ala Glu Phe Val Thr Arg Phe Gly Gly
                245                 250                 255 gat cgg gtc atc gag aag gtg ctt att gcc aac aac ggg att gcc gcc      816
Asp Arg Val Ile Glu Lys Val Leu Ile Ala Asn Asn Gly Ile Ala Ala
                260                 265                 270 gtg aag tgc atg cgc tcc atc cgc agg tgg gcc tat gag atg ttc cgc      864
Val Lys Cys Met Arg Ser Ile Arg Arg Trp Ala Tyr Glu Met Phe Arg
            275                 280                 285 aac gag cgg gcc atc cgg ttt gtt gtg atg gtg acc ccc gag gac ctt      912
Asn Glu Arg Ala Ile Arg Phe Val Val Met Val Thr Pro Glu Asp Leu
290                 295                 300 aag gcc aac gca gag tac atc aag atg gcg gat cat tac gtc ccc gtc      960
Lys Ala Asn Ala Glu Tyr Ile Lys Met Ala Asp His Tyr Val Pro Val
305                 310                 315                 320 cca gga ggg ccc aat aac aac aac tat gcc aac gtg gag ctg att gtg     1008
Pro Gly Gly Pro Asn Asn Asn Asn Tyr Ala Asn Val Glu Leu Ile Val
                325                 330                 335 gac att gcc aag aga atc ccc gtg cag gct ggc tgg ggc cat gct tca     1056
Asp Ile Ala Lys Arg Ile Pro Val Gln Ala Gly Trp Gly His Ala Ser
                340                 345                 350 gaa aac cct aaa ctt ccg gag ctg ctg tgc aag aat gga gtt gct ttc     1104
Glu Asn Pro Lys Leu Pro Glu Leu Leu Cys Lys Asn Gly Val Ala Phe
            355                 360                 365
```

-continued

| | |
|---|---|
| tta ggc cct ccc agt gag gcc atg tgg gcc tta gga gat aag atc gcc<br>Leu Gly Pro Pro Ser Glu Ala Met Trp Ala Leu Gly Asp Lys Ile Ala<br>370                                   375                           380 | 1152 |
| tcc acc gtt gtc gcc cag acg cta cag gtc cca acc ctg ccc tgg agt<br>Ser Thr Val Val Ala Gln Thr Leu Gln Val Pro Thr Leu Pro Trp Ser<br>385                                   390                          395                   400 | 1200 |
| gga agc ggc ctg aca gtg gag tgg aca gaa gat gat ctg cag cag gga<br>Gly Ser Gly Leu Thr Val Glu Trp Thr Glu Asp Asp Leu Gln Gln Gly<br>                                 405                          410                          415 | 1248 |
| aaa aga atc agt gtc cca gaa gat gtt tat gac aag ggt tgc gtg aaa<br>Lys Arg Ile Ser Val Pro Glu Asp Val Tyr Asp Lys Gly Cys Val Lys<br>                       420                          425                          430 | 1296 |
| gac gta gat gag ggc ttg gag gca gca gaa aga att ggt ttt cca ttg<br>Asp Val Asp Glu Gly Leu Glu Ala Ala Glu Arg Ile Gly Phe Pro Leu<br>                                 435                          440                          445 | 1344 |
| atg atc aaa gct tct gaa ggt ggc gga ggg aag gga atc cgg aag gct<br>Met Ile Lys Ala Ser Glu Gly Gly Gly Gly Lys Gly Ile Arg Lys Ala<br>450                                   455                           460 | 1392 |
| gag agt gcg gag gac ttc ccg atc ctt ttc aga caa gta cag agt gag<br>Glu Ser Ala Glu Asp Phe Pro Ile Leu Phe Arg Gln Val Gln Ser Glu<br>465                                   470                          475                         480 | 1440 |
| atc cca ggc tcg ccc atc ttt ctc atg aag ctg gcc cag cac gcc cgt<br>Ile Pro Gly Ser Pro Ile Phe Leu Met Lys Leu Ala Gln His Ala Arg<br>                                 485                          490                          495 | 1488 |
| cac ctg gaa gtt cag atc ctc gct gac cag tat ggg aat gct gtg tct<br>His Leu Glu Val Gln Ile Leu Ala Asp Gln Tyr Gly Asn Ala Val Ser<br>                       500                          505                          510 | 1536 |
| ctg ttt ggt cgc gac tgc tcc atc cag cgg cgg cat cag aag atc gtt<br>Leu Phe Gly Arg Asp Cys Ser Ile Gln Arg Arg His Gln Lys Ile Val<br>                       515                          520                          525 | 1584 |
| gag gaa gca ccg gcc acc atc gcc ccg ctg gcc ata ttc gag ttc atg<br>Glu Glu Ala Pro Ala Thr Ile Ala Pro Leu Ala Ile Phe Glu Phe Met<br>530                                   535                           540 | 1632 |
| gag cag tgt gcc atc cgc ctg gcc aag acc gtg ggc tat gtg agt gca<br>Glu Gln Cys Ala Ile Arg Leu Ala Lys Thr Val Gly Tyr Val Ser Ala<br>545                                   550                          555                         560 | 1680 |
| ggg aca gtg gaa tac ctc tat agt cag gat ggc agc ttc cac ttc ttg<br>Gly Thr Val Glu Tyr Leu Tyr Ser Gln Asp Gly Ser Phe His Phe Leu<br>                                 565                          570                          575 | 1728 |
| gag ctg aat cct cgc ttg cag gtg gaa cat ccc tgc aca gaa atg att<br>Glu Leu Asn Pro Arg Leu Gln Val Glu His Pro Cys Thr Glu Met Ile<br>                       580                          585                          590 | 1776 |
| gct gat gtt aat ctg ccg gcc gcc cag cta cag atc gcc atg ggc gtg<br>Ala Asp Val Asn Leu Pro Ala Ala Gln Leu Gln Ile Ala Met Gly Val<br>                       595                          600                          605 | 1824 |
| cca ctg cac cgg ctg aag gat atc cgg ctt ctg tat gga gag tca cca<br>Pro Leu His Arg Leu Lys Asp Ile Arg Leu Leu Tyr Gly Glu Ser Pro<br>610                                   615                           620 | 1872 |
| tgg gga gtg act ccc att tct ttt gaa acc ccc tca aac cct ccc ctc<br>Trp Gly Val Thr Pro Ile Ser Phe Glu Thr Pro Ser Asn Pro Pro Leu<br>625                                   630                          635                         640 | 1920 |
| gcc cga ggc cac gtc att gcc gcc aga atc acc agc gaa aac cca gac<br>Ala Arg Gly His Val Ile Ala Ala Arg Ile Thr Ser Glu Asn Pro Asp<br>                                 645                          650                          655 | 1968 |
| gag ggt ttt aag ccg agc tcc ggg act gtc cag gaa ctg aat ttc cgg<br>Glu Gly Phe Lys Pro Ser Ser Gly Thr Val Gln Glu Leu Asn Phe Arg<br>                       660                          665                          670 | 2016 |
| agc agc aag aac gtg tgg ggt tac ttc agc gtg gcc gct act gga ggc<br>Ser Ser Lys Asn Val Trp Gly Tyr Phe Ser Val Ala Ala Thr Gly Gly | 2064 |

-continued

```
                675                 680                 685
ctg cac gag ttt gcg gat tcc caa ttt ggg cac tgc ttc tcc tgg gga      2112
Leu His Glu Phe Ala Asp Ser Gln Phe Gly His Cys Phe Ser Trp Gly
        690                 695                 700 gag aac cgg gaa gag gcc att tcg aac atg gtg gtg gct ttg aag gaa      2160
Glu Asn Arg Glu Glu Ala Ile Ser Asn Met Val Val Ala Leu Lys Glu
705                 710                 715                 720 ctg tcc atc cga ggc gac ttt agg act acc gtg gaa tac ctc att aac      2208
Leu Ser Ile Arg Gly Asp Phe Arg Thr Thr Val Glu Tyr Leu Ile Asn
                725                 730                 735 ctc ctg gag acc gag agc ttc cag aac aac gac atc gac acc ggg tgg      2256
Leu Leu Glu Thr Glu Ser Phe Gln Asn Asn Asp Ile Asp Thr Gly Trp
            740                 745                 750 ttg gac tac ctc att gct gag aaa gtg cag gcg gag aaa ccg gat atc      2304
Leu Asp Tyr Leu Ile Ala Glu Lys Val Gln Ala Glu Lys Pro Asp Ile
        755                 760                 765 atg ctt ggg gtg gta tgc ggg gcc ttg aac gtg gcc gat gcg atg ttc      2352
Met Leu Gly Val Val Cys Gly Ala Leu Asn Val Ala Asp Ala Met Phe
    770                 775                 780 aga acg tgc atg aca gat ttt tta cac tcc ctg gaa agg ggc cag gtc      2400
Arg Thr Cys Met Thr Asp Phe Leu His Ser Leu Glu Arg Gly Gln Val
785                 790                 795                 800 ctc cca gcg gat tca cta ctg aac ctc gta gat gtg gaa tta att tac      2448
Leu Pro Ala Asp Ser Leu Leu Asn Leu Val Asp Val Glu Leu Ile Tyr
                805                 810                 815 gga ggt gtt aag tac att ctc aag gtg gcc cgg cag tct ctg acc atg      2496
Gly Gly Val Lys Tyr Ile Leu Lys Val Ala Arg Gln Ser Leu Thr Met
            820                 825                 830 ttc gtt ctc atc atg aat ggc tgc cac atc gag att gat gcc cac cgg      2544
Phe Val Leu Ile Met Asn Gly Cys His Ile Glu Ile Asp Ala His Arg
        835                 840                 845 ctg aat gat ggg ggg ctc ctc tcc tac aat ggg aac agc tac acc      2592
Leu Asn Asp Gly Gly Leu Leu Ser Tyr Asn Gly Asn Ser Tyr Thr
    850                 855                 860 acc tac atg aag gaa gag gtt gac agt tac cga att acc atc ggc aat      2640
Thr Tyr Met Lys Glu Glu Val Asp Ser Tyr Arg Ile Thr Ile Gly Asn
865                 870                 875                 880 aag acg tgt gtg ttt gag aag gag aac gat cct aca gtc ctg aga tcc      2688
Lys Thr Cys Val Phe Glu Lys Glu Asn Asp Pro Thr Val Leu Arg Ser
                885                 890                 895 ccc tcg gct ggg aag ctg aca cag tac aca gtg gag gat ggg ggc cac      2736
Pro Ser Ala Gly Lys Leu Thr Gln Tyr Thr Val Glu Asp Gly Gly His
            900                 905                 910 gtt gag gct ggg agc agc tac gct gag atg gag gtg atg aag atg atc      2784
Val Glu Ala Gly Ser Ser Tyr Ala Glu Met Glu Val Met Lys Met Ile
        915                 920                 925 atg acc ctg aac gtt cag gaa aga ggc cgg gtg aag tac atc aag cgt      2832
Met Thr Leu Asn Val Gln Glu Arg Gly Arg Val Lys Tyr Ile Lys Arg
    930                 935                 940 cca ggt gcc gtg ctg gaa gca ggc tgc gtg gtg gcc agg ctg gag ctc      2880
Pro Gly Ala Val Leu Glu Ala Gly Cys Val Val Ala Arg Leu Glu Leu
945                 950                 955                 960 gat gac cct tct aaa gtc cac ccg gct gaa ccg ttc aca gga gaa ctc      2928
Asp Asp Pro Ser Lys Val His Pro Ala Glu Pro Phe Thr Gly Glu Leu
                965                 970                 975 cct gcc cag cag aca ctg ccc atc ctc gga gag aaa ctg cac cag gtc      2976
Pro Ala Gln Gln Thr Leu Pro Ile Leu Gly Glu Lys Leu His Gln Val
            980                 985                 990 ttc cac agc gtc ctg gaa aac ctc  acc aac gtc atg agt  ggc ttt tgt    3024
```

```
                    -continued

Phe His Ser Val Leu Glu Asn Leu  Thr Asn Val Met Ser  Gly Phe Cys
        995                 1000                 1005 ctg cca gag ccc gtt ttt agc ata aag ctg aag gag tgg gtg cag        3069
Leu Pro Glu Pro Val Phe Ser Ile Lys Leu Lys Glu Trp Val Gln
    1010            1015                1020 aag ctc atg atg acc ctc cgg cac ccg tca ctg ccg ctg ctg gag        3114
Lys Leu Met Met Thr Leu Arg His Pro Ser Leu Pro Leu Leu Glu
    1025            1030                1035 ctg cag gag atc atg acc agc gtg gca ggc cgc atc ccc gcc cct        3159
Leu Gln Glu Ile Met Thr Ser Val Ala Gly Arg Ile Pro Ala Pro
    1040            1045                1050 gtg gag aag tct gtc cgc agg gtg atg gcc cag tat gcc agc aac        3204
Val Glu Lys Ser Val Arg Arg Val Met Ala Gln Tyr Ala Ser Asn
    1055            1060                1065 atc acc tcg gtg ctg tgc cag ttc ccc agc cag cag ata gcc acc        3249
Ile Thr Ser Val Leu Cys Gln Phe Pro Ser Gln Gln Ile Ala Thr
    1070            1075                1080 atc ctg gac tgc cat gca gcc acc ctg cag cgg aag gct gat cga        3294
Ile Leu Asp Cys His Ala Ala Thr Leu Gln Arg Lys Ala Asp Arg
    1085            1090                1095 gag gtc ttc ttc atc aac acc cag agc atc gtg cag ttg gtc cag        3339
Glu Val Phe Phe Ile Asn Thr Gln Ser Ile Val Gln Leu Val Gln
    1100            1105                1110 aga tac cgc agc ggg atc cgc ggc tat atg aaa aca gtg gtg ttg        3384
Arg Tyr Arg Ser Gly Ile Arg Gly Tyr Met Lys Thr Val Val Leu
    1115            1120                1125 gat ctc ctg aga aga tac ttg cgt gtt gag cac cat ttt cag caa        3429
Asp Leu Leu Arg Arg Tyr Leu Arg Val Glu His His Phe Gln Gln
    1130            1135                1140 gcc cac tac gac aag tgt gtg ata aac ctc agg gag cag ttc aag        3474
Ala His Tyr Asp Lys Cys Val Ile Asn Leu Arg Glu Gln Phe Lys
    1145            1150                1155 cca gac atg tcc cag gtg ctg gac tgc atc ttc tcc cac gca cag        3519
Pro Asp Met Ser Gln Val Leu Asp Cys Ile Phe Ser His Ala Gln
    1160            1165                1170 gtg gcc aag aag aac cag ctg gtg atc atg ttg atc gat gag ctg        3564
Val Ala Lys Lys Asn Gln Leu Val Ile Met Leu Ile Asp Glu Leu
    1175            1180                1185 tgt ggc cca gac cct tcc ctg tcg gac gag ctg atc tcc atc ctc        3609
Cys Gly Pro Asp Pro Ser Leu Ser Asp Glu Leu Ile Ser Ile Leu
    1190            1195                1200 aac gag ctc act cag ctg agc aaa agc gag cac tgc aaa gtg gcc        3654
Asn Glu Leu Thr Gln Leu Ser Lys Ser Glu His Cys Lys Val Ala
    1205            1210                1215 ctc aga gcc cgg cag atc ctg att gcc tcc cac ctc ccc tcc tac        3699
Leu Arg Ala Arg Gln Ile Leu Ile Ala Ser His Leu Pro Ser Tyr
    1220            1225                1230 gag ctg cgg cat aac cag gtg gag tcc att ttc ctg tct gcc att        3744
Glu Leu Arg His Asn Gln Val Glu Ser Ile Phe Leu Ser Ala Ile
    1235            1240                1245 gac atg tac ggc cac cag ttc tgc ccc gag aac ctc aag aaa tta        3789
Asp Met Tyr Gly His Gln Phe Cys Pro Glu Asn Leu Lys Lys Leu
    1250            1255                1260 ata ctt tcg gaa aca acc atc ttc gac gtc ctg cct act ttc ttc        3834
Ile Leu Ser Glu Thr Thr Ile Phe Asp Val Leu Pro Thr Phe Phe
    1265            1270                1275 tat cac gca aac aaa gtc gtg tgc atg gcg tcc ttg gag gtt tac        3879
Tyr His Ala Asn Lys Val Val Cys Met Ala Ser Leu Glu Val Tyr
    1280            1285                1290
```

```
gtg cgg agg ggc tac atc gcc tat gag tta aac agc ctg cag cac        3924
Val Arg Arg Gly Tyr Ile Ala Tyr Glu Leu Asn Ser Leu Gln His
    1295                1300                1305 cgg cag ctc ccg gac ggc acc tgc gtg gta gaa ttc cag ttc atg        3969
Arg Gln Leu Pro Asp Gly Thr Cys Val Val Glu Phe Gln Phe Met
    1310                1315                1320 ctg ccg tcc tcc cac cca aac cgg atg acc gtg ccc atc agc atc        4014
Leu Pro Ser Ser His Pro Asn Arg Met Thr Val Pro Ile Ser Ile
    1325                1330                1335 acc aac cct gac ctg ctg agg cac agc aca gag ctc ttc atg gac        4059
Thr Asn Pro Asp Leu Leu Arg His Ser Thr Glu Leu Phe Met Asp
    1340                1345                1350 agc ggc ttc tcc cca ctg tgc cag cgc atg gga gcc atg gta gcc        4104
Ser Gly Phe Ser Pro Leu Cys Gln Arg Met Gly Ala Met Val Ala
    1355                1360                1365 ttc agg aga ttc gag gac ttc acc aga aat ttt gat gaa gtc atc        4149
Phe Arg Arg Phe Glu Asp Phe Thr Arg Asn Phe Asp Glu Val Ile
    1370                1375                1380 tct tgc ttc gcc aac gtg ccc aaa gac acc ccc ctc ttc agc gag        4194
Ser Cys Phe Ala Asn Val Pro Lys Asp Thr Pro Leu Phe Ser Glu
    1385                1390                1395 gcc cgc acc tcc cta tac tcc gag gat gac tgc aag agc ctc aga        4239
Ala Arg Thr Ser Leu Tyr Ser Glu Asp Asp Cys Lys Ser Leu Arg
    1400                1405                1410 gaa gag ccc atc cac att ctg aat gtg tcc atc cag tgt gca gac        4284
Glu Glu Pro Ile His Ile Leu Asn Val Ser Ile Gln Cys Ala Asp
    1415                1420                1425 cac ctg gag gat gag gca ctg gtg ccg att tta cgg aca ttc gta        4329
His Leu Glu Asp Glu Ala Leu Val Pro Ile Leu Arg Thr Phe Val
    1430                1435                1440 cag tcc aag aaa aat atc ctt gtg gat tat gga ctc cga cga atc        4374
Gln Ser Lys Lys Asn Ile Leu Val Asp Tyr Gly Leu Arg Arg Ile
    1445                1450                1455 aca ttc ttg att gcc caa gag aaa gaa ttt ccc aag ttt ttc aca        4419
Thr Phe Leu Ile Ala Gln Glu Lys Glu Phe Pro Lys Phe Phe Thr
    1460                1465                1470 ttc aga gca aga gat gag ttt gca gaa gat cgc att tac cgt cac        4464
Phe Arg Ala Arg Asp Glu Phe Ala Glu Asp Arg Ile Tyr Arg His
    1475                1480                1485 ttg gaa cct gcc ctg gcc ttc cag ctg gaa ctt aac cgg atg cgt        4509
Leu Glu Pro Ala Leu Ala Phe Gln Leu Glu Leu Asn Arg Met Arg
    1490                1495                1500 aac ttc gat ctg acc gcc gtg ccc tgt gcc aac cac aag atg cac        4554
Asn Phe Asp Leu Thr Ala Val Pro Cys Ala Asn His Lys Met His
    1505                1510                1515 ctt tac ctg ggt gct gcc aag gtg aag gaa ggt gtg gaa gtg acg        4599
Leu Tyr Leu Gly Ala Ala Lys Val Lys Glu Gly Val Glu Val Thr
    1520                1525                1530 gac cat agg ttc ttc atc cgc gcc atc atc agg cac tct gac ctg        4644
Asp His Arg Phe Phe Ile Arg Ala Ile Ile Arg His Ser Asp Leu
    1535                1540                1545 atc aca aag gaa gcc tcc ttc gaa tac ctg cag aac gag ggt gag        4689
Ile Thr Lys Glu Ala Ser Phe Glu Tyr Leu Gln Asn Glu Gly Glu
    1550                1555                1560 cgg ctg ctc ctg gag gcc atg gac gag ctg gag gtg gcg ttc aat        4734
Arg Leu Leu Leu Glu Ala Met Asp Glu Leu Glu Val Ala Phe Asn
    1565                1570                1575 aac acc agc gtg cgc acc gac tgc aac cac atc ttc ctc aac ttc        4779
Asn Thr Ser Val Arg Thr Asp Cys Asn His Ile Phe Leu Asn Phe
    1580                1585                1590
```

|  |  |
|---|---|
| gtg ccc act gtc atc atg gac ccc ttc aag atc gag gag tcc gtg<br>Val Pro Thr Val Ile Met Asp Pro Phe Lys Ile Glu Glu Ser Val<br>1595                   1600                  1605 | 4824 |
| cgc tac atg gtt atg cgc tac ggc agc cgg ctg tgg aaa ctc cgt<br>Arg Tyr Met Val Met Arg Tyr Gly Ser Arg Leu Trp Lys Leu Arg<br>1610                     1615                  1620 | 4869 |
| gtg cta cag gct gag gtc aag atc aac atc cgc cag acc acc acc<br>Val Leu Gln Ala Glu Val Lys Ile Asn Ile Arg Gln Thr Thr Thr<br>1625                     1630                  1635 | 4914 |
| ggc agt gcc gtt ccc atc cgc ctg ttc atc acc aat gag tcg ggc<br>Gly Ser Ala Val Pro Ile Arg Leu Phe Ile Thr Asn Glu Ser Gly<br>1640                     1645                  1650 | 4959 |
| tac tac ctg gac atc agc ctc tac aaa gaa gtg act gac tcc aga<br>Tyr Tyr Leu Asp Ile Ser Leu Tyr Lys Glu Val Thr Asp Ser Arg<br>1655                     1660                  1665 | 5004 |
| tct gga aat atc atg ttt cac tcc ttc ggc aac aag caa ggg ccc<br>Ser Gly Asn Ile Met Phe His Ser Phe Gly Asn Lys Gln Gly Pro<br>1670                     1675                  1680 | 5049 |
| cag cac ggg atg ctg atc aat act ccc tac gtc acc aag gat ctg<br>Gln His Gly Met Leu Ile Asn Thr Pro Tyr Val Thr Lys Asp Leu<br>1685                     1690                  1695 | 5094 |
| ctc cag gcc aag cga ttc cag gcc cag acc ctg gga acc acc tac<br>Leu Gln Ala Lys Arg Phe Gln Ala Gln Thr Leu Gly Thr Thr Tyr<br>1700                     1705                  1710 | 5139 |
| atc tat gac ttc ccg gaa atg ttc agg cag gct ctc ttt aaa ctg<br>Ile Tyr Asp Phe Pro Glu Met Phe Arg Gln Ala Leu Phe Lys Leu<br>1715                     1720                  1725 | 5184 |
| tgg ggc tcc cca gac aag tat ccc aaa gac atc ctg aca tac act<br>Trp Gly Ser Pro Asp Lys Tyr Pro Lys Asp Ile Leu Thr Tyr Thr<br>1730                     1735                  1740 | 5229 |
| gaa tta gtg ttg gac tct cag ggc cag ctg gtg gag atg aac cga<br>Glu Leu Val Leu Asp Ser Gln Gly Gln Leu Val Glu Met Asn Arg<br>1745                     1750                  1755 | 5274 |
| ctt cct ggt gga aat gag gtg ggc atg gtg gcc ttc aaa atg agg<br>Leu Pro Gly Gly Asn Glu Val Gly Met Val Ala Phe Lys Met Arg<br>1760                     1765                  1770 | 5319 |
| ttt aag acc cag gag tac ccg gaa gga cgg gat gtg atc gtc atc<br>Phe Lys Thr Gln Glu Tyr Pro Glu Gly Arg Asp Val Ile Val Ile<br>1775                     1780                  1785 | 5364 |
| ggc aat gac atc acc ttt cgc att gga tcc ttt ggc cct gga gag<br>Gly Asn Asp Ile Thr Phe Arg Ile Gly Ser Phe Gly Pro Gly Glu<br>1790                     1795                  1800 | 5409 |
| gac ctt ctg tac ctg cgg gca tcc gag atg gcc cgg gca gag ggc<br>Asp Leu Leu Tyr Leu Arg Ala Ser Glu Met Ala Arg Ala Glu Gly<br>1805                     1810                  1815 | 5454 |
| att ccc aaa att tac gtg gca gcc aac agt ggc gcc cgt att ggc<br>Ile Pro Lys Ile Tyr Val Ala Ala Asn Ser Gly Ala Arg Ile Gly<br>1820                     1825                  1830 | 5499 |
| atg gca gag gag atc aaa cac atg ttc cac gtg gct tgg gtg gac<br>Met Ala Glu Glu Ile Lys His Met Phe His Val Ala Trp Val Asp<br>1835                     1840                  1845 | 5544 |
| cca gaa gac ccc cac aaa gga ttt aaa tac ctg tac ctg act ccc<br>Pro Glu Asp Pro His Lys Gly Phe Lys Tyr Leu Tyr Leu Thr Pro<br>1850                     1855                  1860 | 5589 |
| caa gac tac acc aga atc agc tcc ctg aac tcc gtc cac tgt aaa<br>Gln Asp Tyr Thr Arg Ile Ser Ser Leu Asn Ser Val His Cys Lys<br>1865                     1870                  1875 | 5634 |
| cac atc gag gaa gga gga gag tcc aga tac atg atc acg gat atc<br>His Ile Glu Glu Gly Gly Glu Ser Arg Tyr Met Ile Thr Asp Ile | 5679 |

```
                1880                    1885                    1890
atc ggg aag gat gat ggc ttg ggc gtg gag aat ctg agg ggc tca       5724
Ile Gly Lys Asp Asp Gly Leu Gly Val Glu Asn Leu Arg Gly Ser
    1895                    1900                    1905 ggc atg att gct ggg gag tcc tct ctg gct tac gaa gag atc gtc       5769
Gly Met Ile Ala Gly Glu Ser Ser Leu Ala Tyr Glu Glu Ile Val
    1910                    1915                    1920 acc att agc ttg gtg acc tgc cga gcc att ggg att ggg gcc tac       5814
Thr Ile Ser Leu Val Thr Cys Arg Ala Ile Gly Ile Gly Ala Tyr
    1925                    1930                    1935 ttg gtg agg ctg ggc cag cga gtg atc cag gtg gag aat tcc cac       5859
Leu Val Arg Leu Gly Gln Arg Val Ile Gln Val Glu Asn Ser His
    1940                    1945                    1950 atc atc ctc aca gga gca agt gct ctc aac aag gtc ctg gga aga       5904
Ile Ile Leu Thr Gly Ala Ser Ala Leu Asn Lys Val Leu Gly Arg
    1955                    1960                    1965 gag gtc tac aca tcc aac aac cag ctg ggt ggc gtt cag atc atg       5949
Glu Val Tyr Thr Ser Asn Asn Gln Leu Gly Gly Val Gln Ile Met
    1970                    1975                    1980 cat tac aat ggt gtc tcc cac atc acc gtg cca gat gac ttt gag       5994
His Tyr Asn Gly Val Ser His Ile Thr Val Pro Asp Asp Phe Glu
    1985                    1990                    1995 ggg gtt tat acc atc ctg gag tgg ctg tcc tat atg cca aag gat       6039
Gly Val Tyr Thr Ile Leu Glu Trp Leu Ser Tyr Met Pro Lys Asp
    2000                    2005                    2010 aat cac agc cct gtc cct atc atc aca ccc act gac ccc att gac       6084
Asn His Ser Pro Val Pro Ile Ile Thr Pro Thr Asp Pro Ile Asp
    2015                    2020                    2025 aga gaa att gaa ttc ctc cca tcc aga gct ccc tac gac ccc cgg       6129
Arg Glu Ile Glu Phe Leu Pro Ser Arg Ala Pro Tyr Asp Pro Arg
    2030                    2035                    2040 tgg atg ctt gca gga agg cct cac cca act ctg aag gga acg tgg       6174
Trp Met Leu Ala Gly Arg Pro His Pro Thr Leu Lys Gly Thr Trp
    2045                    2050                    2055 cag agc gga ttc ttt gac cac ggc agt ttc aag gaa atc atg gca       6219
Gln Ser Gly Phe Phe Asp His Gly Ser Phe Lys Glu Ile Met Ala
    2060                    2065                    2070 ccc tgg gcg cag acc gtg gtg aca gga cga gca agg ctt ggg ggg       6264
Pro Trp Ala Gln Thr Val Val Thr Gly Arg Ala Arg Leu Gly Gly
    2075                    2080                    2085 att ccc gtg gga gtg att gct gtg gag aca cgg act gtg gag gtg       6309
Ile Pro Val Gly Val Ile Ala Val Glu Thr Arg Thr Val Glu Val
    2090                    2095                    2100 gca gtc cct gca gac cct gcc aac ctg gat tct gag gcc aag ata       6354
Ala Val Pro Ala Asp Pro Ala Asn Leu Asp Ser Glu Ala Lys Ile
    2105                    2110                    2115 att cag cag gca gga cag gtg tgg ttc cca gac tca gcc tac aaa       6399
Ile Gln Gln Ala Gly Gln Val Trp Phe Pro Asp Ser Ala Tyr Lys
    2120                    2125                    2130 acc gcc cag gcc gtc aag gac ttc aac cgg gag aag ttg ccc ctg       6444
Thr Ala Gln Ala Val Lys Asp Phe Asn Arg Glu Lys Leu Pro Leu
    2135                    2140                    2145 atg atc ttt gcc aac tgg agg ggg ttc tcc ggt ggc atg aaa gac       6489
Met Ile Phe Ala Asn Trp Arg Gly Phe Ser Gly Gly Met Lys Asp
    2150                    2155                    2160 atg tat gac cag gtg ctg aag ttt gga gcc tac atc gtg gac ggc       6534
Met Tyr Asp Gln Val Leu Lys Phe Gly Ala Tyr Ile Val Asp Gly
    2165                    2170                    2175 ctt aga caa tac aaa cag ccc atc ctg atc tat atc ccg ccc tat       6579
```

```
                Leu Arg Gln Tyr Lys Gln Pro Ile Leu Ile Tyr Ile Pro Pro Tyr
                    2180            2185                2190 gcg gag ctc cgg gga ggc tcc tgg gtg gtc ata gat gcc acc atc              6624
Ala Glu Leu Arg Gly Gly Ser Trp Val Val Ile Asp Ala Thr Ile
    2195            2200                2205 aac ccg ctg tgc ata gaa atg tat gca gac aaa gag agc agg ggt              6669
Asn Pro Leu Cys Ile Glu Met Tyr Ala Asp Lys Glu Ser Arg Gly
    2210            2215                2220 ggt gtt ctg gaa cca gag ggg aca gtg gag att aag ttc cga aag              6714
Gly Val Leu Glu Pro Glu Gly Thr Val Glu Ile Lys Phe Arg Lys
    2225            2230                2235 aaa gat ctg ata aag tcc atg aga agg atc gat cca gct tac aag              6759
Lys Asp Leu Ile Lys Ser Met Arg Arg Ile Asp Pro Ala Tyr Lys
    2240            2245                2250 aag ctc atg gaa cag cta ggg gaa cct gat ctc tcc gac aag gac              6804
Lys Leu Met Glu Gln Leu Gly Glu Pro Asp Leu Ser Asp Lys Asp
    2255            2260                2265 cga aag gac ctg gag ggc cgg cta aag gct cgc gag gac ctg ctg              6849
Arg Lys Asp Leu Glu Gly Arg Leu Lys Ala Arg Glu Asp Leu Leu
    2270            2275                2280 ctc ccc atc tac cac cag gtg gcg gtg cag ttc gcc gac ttc cat              6894
Leu Pro Ile Tyr His Gln Val Ala Val Gln Phe Ala Asp Phe His
    2285            2290                2295 gac aca ccc ggc cgg atg ctg gag aag ggc gtc ata tct gac atc              6939
Asp Thr Pro Gly Arg Met Leu Glu Lys Gly Val Ile Ser Asp Ile
    2300            2305                2310 ctg gag tgg aag acc gca cgc acc ttc ctg tat tgg cgt ctg cgc              6984
Leu Glu Trp Lys Thr Ala Arg Thr Phe Leu Tyr Trp Arg Leu Arg
    2315            2320                2325 cgc ctc ctc ctg gag gac cag gtc aag cag gag atc ctg cag gcc              7029
Arg Leu Leu Leu Glu Asp Gln Val Lys Gln Glu Ile Leu Gln Ala
    2330            2335                2340 agc ggg gag ctg agt cac gtg cat atc cag tcc atg ctg cgt cgc              7074
Ser Gly Glu Leu Ser His Val His Ile Gln Ser Met Leu Arg Arg
    2345            2350                2355 tgg ttc gtg gag acg gag ggg gct gtc aag gcc tac ttg tgg gac              7119
Trp Phe Val Glu Thr Glu Gly Ala Val Lys Ala Tyr Leu Trp Asp
    2360            2365                2370 aac aac cag gtg gtt gtg cag tgg ctg gaa cag cac tgg cag gca              7164
Asn Asn Gln Val Val Val Gln Trp Leu Glu Gln His Trp Gln Ala
    2375            2380                2385 ggg gat ggc ccg cgc tcc acc atc cgt gag aac atc acg tac ctg              7209
Gly Asp Gly Pro Arg Ser Thr Ile Arg Glu Asn Ile Thr Tyr Leu
    2390            2395                2400 aag cac gac tct gtc ctc aag acc atc cga ggc ctg gtt gaa gaa              7254
Lys His Asp Ser Val Leu Lys Thr Ile Arg Gly Leu Val Glu Glu
    2405            2410                2415 aac ccc gag gtg gcc gtg gac tgt gtg ata tac ctg agc cag cac              7299
Asn Pro Glu Val Ala Val Asp Cys Val Ile Tyr Leu Ser Gln His
    2420            2425                2430 atc agc cca gct gag cgg gcg cag gtc gtt cac ctg ctg tct acc              7344
Ile Ser Pro Ala Glu Arg Ala Gln Val Val His Leu Leu Ser Thr
    2435            2440                2445 atg gac agc ccg gcc tcc acc tga                                          7368
Met Asp Ser Pro Ala Ser Thr
    2450            2455

<210> SEQ ID NO 4
<211> LENGTH: 2455
<212> TYPE: PRT
```

-continued

<213> ORGANISM: Homo sapiens

<400> SEQUENCE: 4

| | | | | | | | | | | | | | | |
|---|---|---|---|---|---|---|---|---|---|---|---|---|---|---|
| Met | Val | Leu | Leu | Leu | Cys | Leu | Ser | Cys | Leu | Ile | Phe | Ser | Cys | Leu | Thr |
| 1 | | | | 5 | | | | | 10 | | | | | 15 | |
| Phe | Ser | Trp | Leu | Lys | Ile | Trp | Gly | Lys | Met | Thr | Asp | Ser | Lys | Pro | Ile |
| | | | 20 | | | | | 25 | | | | | 30 | | |
| Thr | Lys | Ser | Lys | Ser | Glu | Ala | Asn | Leu | Ile | Pro | Ser | Gln | Glu | Pro | Phe |
| | | 35 | | | | | 40 | | | | | 45 | | | |
| Pro | Ala | Ser | Asp | Asn | Ser | Gly | Glu | Thr | Pro | Gln | Arg | Asn | Gly | Glu | Gly |
| 50 | | | | | 55 | | | | | 60 | | | | | |
| His | Thr | Leu | Pro | Lys | Thr | Pro | Ser | Gln | Ala | Glu | Pro | Ala | Ser | His | Lys |
| 65 | | | | | 70 | | | | | 75 | | | | | 80 |
| Gly | Pro | Lys | Asp | Ala | Gly | Arg | Arg | Arg | Asn | Ser | Leu | Pro | Pro | Ser | His |
| | | | | 85 | | | | | 90 | | | | | 95 | |
| Gln | Lys | Pro | Pro | Arg | Asn | Pro | Leu | Ser | Ser | Ser | Asp | Ala | Ala | Pro | Ser |
| | | | 100 | | | | | 105 | | | | | 110 | | |
| Pro | Glu | Leu | Gln | Ala | Asn | Gly | Thr | Gly | Thr | Gln | Gly | Leu | Glu | Ala | Thr |
| | | | 115 | | | | | 120 | | | | | 125 | | |
| Asp | Thr | Asn | Gly | Leu | Ser | Ser | Ser | Ala | Arg | Pro | Gln | Gly | Gln | Gln | Ala |
| | 130 | | | | | 135 | | | | | 140 | | | | |
| Gly | Ser | Pro | Ser | Lys | Glu | Asp | Lys | Lys | Gln | Ala | Asn | Ile | Lys | Arg | Gln |
| 145 | | | | | 150 | | | | | 155 | | | | | 160 |
| Leu | Met | Thr | Asn | Phe | Ile | Leu | Gly | Ser | Phe | Asp | Asp | Tyr | Ser | Ser | Asp |
| | | | | 165 | | | | | 170 | | | | | 175 | |
| Glu | Asp | Ser | Val | Ala | Gly | Ser | Ser | Arg | Glu | Ser | Thr | Arg | Lys | Gly | Ser |
| | | | 180 | | | | | 185 | | | | | 190 | | |
| Arg | Ala | Ser | Leu | Gly | Ala | Leu | Ser | Leu | Glu | Ala | Tyr | Leu | Thr | Thr | Gly |
| | | 195 | | | | | 200 | | | | | 205 | | | |
| Glu | Ala | Glu | Thr | Arg | Val | Pro | Thr | Met | Arg | Pro | Ser | Met | Ser | Gly | Leu |
| 210 | | | | | 215 | | | | | 220 | | | | | |
| His | Leu | Val | Lys | Arg | Gly | Arg | Glu | His | Lys | Lys | Leu | Asp | Leu | His | Arg |
| 225 | | | | | 230 | | | | | 235 | | | | | 240 |
| Asp | Phe | Thr | Val | Ala | Ser | Pro | Ala | Glu | Phe | Val | Thr | Arg | Phe | Gly | Gly |
| | | | | 245 | | | | | 250 | | | | | 255 | |
| Asp | Arg | Val | Ile | Glu | Lys | Val | Leu | Ile | Ala | Asn | Asn | Gly | Ile | Ala | Ala |
| | | | 260 | | | | | 265 | | | | | 270 | | |
| Val | Lys | Cys | Met | Arg | Ser | Ile | Arg | Arg | Trp | Ala | Tyr | Glu | Met | Phe | Arg |
| | | 275 | | | | | 280 | | | | | 285 | | | |
| Asn | Glu | Arg | Ala | Ile | Arg | Phe | Val | Val | Met | Val | Thr | Pro | Glu | Asp | Leu |
| 290 | | | | | 295 | | | | | 300 | | | | | |
| Lys | Ala | Asn | Ala | Glu | Tyr | Ile | Lys | Met | Ala | Asp | His | Tyr | Val | Pro | Val |
| 305 | | | | | 310 | | | | | 315 | | | | | 320 |
| Pro | Gly | Gly | Pro | Asn | Asn | Asn | Tyr | Ala | Asn | Val | Glu | Leu | Ile | Val |
| | | | | 325 | | | | | 330 | | | | | 335 | |
| Asp | Ile | Ala | Lys | Arg | Ile | Pro | Val | Gln | Ala | Gly | Trp | Gly | His | Ala | Ser |
| | | | 340 | | | | | 345 | | | | | 350 | | |
| Glu | Asn | Pro | Lys | Leu | Pro | Glu | Leu | Leu | Cys | Lys | Asn | Gly | Val | Ala | Phe |
| | | 355 | | | | | 360 | | | | | 365 | | | |
| Leu | Gly | Pro | Pro | Ser | Glu | Ala | Met | Trp | Ala | Leu | Gly | Asp | Lys | Ile | Ala |
| | 370 | | | | | 375 | | | | | 380 | | | | |
| Ser | Thr | Val | Val | Ala | Gln | Thr | Leu | Gln | Val | Pro | Thr | Leu | Pro | Trp | Ser |
| 385 | | | | | 390 | | | | | 395 | | | | | 400 |

```
Gly Ser Gly Leu Thr Val Glu Trp Thr Glu Asp Leu Gln Gln Gly
            405                 410                 415

Lys Arg Ile Ser Val Pro Glu Asp Val Tyr Asp Lys Gly Cys Val Lys
            420                 425                 430

Asp Val Asp Glu Gly Leu Glu Ala Ala Glu Arg Ile Gly Phe Pro Leu
            435                 440                 445

Met Ile Lys Ala Ser Glu Gly Gly Gly Lys Gly Ile Arg Lys Ala
450                 455                 460

Glu Ser Ala Glu Asp Phe Pro Ile Leu Phe Arg Gln Val Gln Ser Glu
465                 470                 475                 480

Ile Pro Gly Ser Pro Ile Phe Leu Met Lys Leu Ala Gln His Ala Arg
                485                 490                 495

His Leu Glu Val Gln Ile Leu Ala Asp Gln Tyr Gly Asn Ala Val Ser
            500                 505                 510

Leu Phe Gly Arg Asp Cys Ser Ile Gln Arg His Gln Lys Ile Val
            515                 520                 525

Glu Glu Ala Pro Ala Thr Ile Ala Pro Leu Ala Ile Phe Glu Phe Met
530                 535                 540

Glu Gln Cys Ala Ile Arg Leu Ala Lys Thr Val Gly Tyr Val Ser Ala
545                 550                 555                 560

Gly Thr Val Glu Tyr Leu Tyr Ser Gln Asp Gly Ser Phe His Phe Leu
            565                 570                 575

Glu Leu Asn Pro Arg Leu Gln Val Glu His Pro Cys Thr Glu Met Ile
            580                 585                 590

Ala Asp Val Asn Leu Pro Ala Ala Gln Leu Gln Ile Ala Met Gly Val
            595                 600                 605

Pro Leu His Arg Leu Lys Asp Ile Arg Leu Leu Tyr Gly Glu Ser Pro
            610                 615                 620

Trp Gly Val Thr Pro Ile Ser Phe Glu Thr Pro Ser Asn Pro Pro Leu
625                 630                 635                 640

Ala Arg Gly His Val Ile Ala Ala Arg Ile Thr Ser Glu Asn Pro Asp
                645                 650                 655

Glu Gly Phe Lys Pro Ser Ser Gly Thr Val Gln Glu Leu Asn Phe Arg
            660                 665                 670

Ser Ser Lys Asn Val Trp Gly Tyr Phe Ser Val Ala Ala Thr Gly Gly
            675                 680                 685

Leu His Glu Phe Ala Asp Ser Gln Phe Gly His Cys Phe Ser Trp Gly
    690                 695                 700

Glu Asn Arg Glu Glu Ala Ile Ser Asn Met Val Val Ala Leu Lys Glu
705                 710                 715                 720

Leu Ser Ile Arg Gly Asp Phe Arg Thr Thr Val Glu Tyr Leu Ile Asn
            725                 730                 735

Leu Leu Glu Thr Glu Ser Phe Gln Asn Asn Asp Ile Asp Thr Gly Trp
            740                 745                 750

Leu Asp Tyr Leu Ile Ala Glu Lys Val Gln Ala Glu Lys Pro Asp Ile
        755                 760                 765

Met Leu Gly Val Val Cys Gly Ala Leu Asn Val Ala Asp Ala Met Phe
            770                 775                 780

Arg Thr Cys Met Thr Asp Phe Leu His Ser Leu Glu Arg Gly Gln Val
785                 790                 795                 800

Leu Pro Ala Asp Ser Leu Leu Asn Leu Val Asp Val Glu Leu Ile Tyr
                805                 810                 815

Gly Gly Val Lys Tyr Ile Leu Lys Val Ala Arg Gln Ser Leu Thr Met
```

-continued

```
                  820             825             830
Phe Val Leu Ile Met Asn Gly Cys His Ile Glu Ile Asp Ala His Arg
            835             840             845
Leu Asn Asp Gly Gly Leu Leu Leu Ser Tyr Asn Gly Asn Ser Tyr Thr
        850             855             860
Thr Tyr Met Lys Glu Glu Val Asp Ser Tyr Arg Ile Thr Ile Gly Asn
865             870             875             880
Lys Thr Cys Val Phe Glu Lys Glu Asn Asp Pro Thr Val Leu Arg Ser
                885             890             895
Pro Ser Ala Gly Lys Leu Thr Gln Tyr Thr Val Glu Asp Gly Gly His
            900             905             910
Val Glu Ala Gly Ser Ser Tyr Ala Glu Met Glu Val Met Lys Met Ile
        915             920             925
Met Thr Leu Asn Val Gln Glu Arg Gly Arg Val Lys Tyr Ile Lys Arg
    930             935             940
Pro Gly Ala Val Leu Glu Ala Gly Cys Val Val Ala Arg Leu Glu Leu
945             950             955             960
Asp Asp Pro Ser Lys Val His Pro Ala Glu Pro Phe Thr Gly Glu Leu
                965             970             975
Pro Ala Gln Gln Thr Leu Pro Ile Leu Gly Glu Lys Leu His Gln Val
            980             985             990
Phe His Ser Val Leu Glu Asn Leu  Thr Asn Val Met Ser  Gly Phe Cys
        995              1000             1005
Leu Pro Glu Pro Val Phe Ser  Ile Lys Leu Lys Glu  Trp Val Gln
    1010             1015             1020
Lys Leu Met Met Thr Leu Arg  His Pro Ser Leu Pro  Leu Leu Glu
    1025             1030             1035
Leu Gln Glu Ile Met Thr Ser  Val Ala Gly Arg Ile  Pro Ala Pro
    1040             1045             1050
Val Glu Lys Ser Val Arg Arg  Val Met Ala Gln Tyr  Ala Ser Asn
    1055             1060             1065
Ile Thr Ser Val Leu Cys Gln  Phe Pro Ser Gln Gln  Ile Ala Thr
    1070             1075             1080
Ile Leu Asp Cys His Ala Ala  Thr Leu Gln Arg Lys  Ala Asp Arg
    1085             1090             1095
Glu Val Phe Phe Ile Asn Thr  Gln Ser Ile Val Gln  Leu Val Gln
    1100             1105             1110
Arg Tyr Arg Ser Gly Ile Arg  Gly Tyr Met Lys Thr  Val Val Leu
    1115             1120             1125
Asp Leu Leu Arg Arg Tyr Leu  Arg Val Glu His His  Phe Gln Gln
    1130             1135             1140
Ala His Tyr Asp Lys Cys Val  Ile Asn Leu Arg Glu  Gln Phe Lys
    1145             1150             1155
Pro Asp Met Ser Gln Val Leu  Asp Cys Ile Phe Ser  His Ala Gln
    1160             1165             1170
Val Ala Lys Lys Asn Gln Leu  Val Ile Met Leu Ile  Asp Glu Leu
    1175             1180             1185
Cys Gly Pro Asp Pro Ser Leu  Ser Asp Glu Leu Ile  Ser Ile Leu
    1190             1195             1200
Asn Glu Leu Thr Gln Leu Ser  Lys Ser Glu His Cys  Lys Val Ala
    1205             1210             1215
Leu Arg Ala Arg Gln Ile Leu  Ile Ala Ser His Leu  Pro Ser Tyr
    1220             1225             1230
```

-continued

```
Glu Leu Arg His Asn Gln Val Glu Ser Ile Phe Leu Ser Ala Ile
1235                1240                1245

Asp Met Tyr Gly His Gln Phe Cys Pro Glu Asn Leu Lys Lys Leu
1250                1255                1260

Ile Leu Ser Glu Thr Thr Ile Phe Asp Val Leu Pro Thr Phe Phe
1265                1270                1275

Tyr His Ala Asn Lys Val Val Cys Met Ala Ser Leu Glu Val Tyr
1280                1285                1290

Val Arg Arg Gly Tyr Ile Ala Tyr Glu Leu Asn Ser Leu Gln His
1295                1300                1305

Arg Gln Leu Pro Asp Gly Thr Cys Val Val Glu Phe Gln Phe Met
1310                1315                1320

Leu Pro Ser Ser His Pro Asn Arg Met Thr Val Pro Ile Ser Ile
1325                1330                1335

Thr Asn Pro Asp Leu Leu Arg His Ser Thr Glu Leu Phe Met Asp
1340                1345                1350

Ser Gly Phe Ser Pro Leu Cys Gln Arg Met Gly Ala Met Val Ala
1355                1360                1365

Phe Arg Arg Phe Glu Asp Phe Thr Arg Asn Phe Asp Glu Val Ile
1370                1375                1380

Ser Cys Phe Ala Asn Val Pro Lys Asp Thr Pro Leu Phe Ser Glu
1385                1390                1395

Ala Arg Thr Ser Leu Tyr Ser Glu Asp Asp Cys Lys Ser Leu Arg
1400                1405                1410

Glu Glu Pro Ile His Ile Leu Asn Val Ser Ile Gln Cys Ala Asp
1415                1420                1425

His Leu Glu Asp Glu Ala Leu Val Pro Ile Leu Arg Thr Phe Val
1430                1435                1440

Gln Ser Lys Lys Asn Ile Leu Val Asp Tyr Gly Leu Arg Arg Ile
1445                1450                1455

Thr Phe Leu Ile Ala Gln Glu Lys Glu Phe Pro Lys Phe Phe Thr
1460                1465                1470

Phe Arg Ala Arg Asp Glu Phe Ala Glu Asp Arg Ile Tyr Arg His
1475                1480                1485

Leu Glu Pro Ala Leu Ala Phe Gln Leu Glu Leu Asn Arg Met Arg
1490                1495                1500

Asn Phe Asp Leu Thr Ala Val Pro Cys Ala Asn His Lys Met His
1505                1510                1515

Leu Tyr Leu Gly Ala Ala Lys Val Lys Glu Gly Val Glu Val Thr
1520                1525                1530

Asp His Arg Phe Phe Ile Arg Ala Ile Ile Arg His Ser Asp Leu
1535                1540                1545

Ile Thr Lys Glu Ala Ser Phe Glu Tyr Leu Gln Asn Glu Gly Glu
1550                1555                1560

Arg Leu Leu Leu Glu Ala Met Asp Glu Leu Glu Val Ala Phe Asn
1565                1570                1575

Asn Thr Ser Val Arg Thr Asp Cys Asn His Ile Phe Leu Asn Phe
1580                1585                1590

Val Pro Thr Val Ile Met Asp Pro Phe Lys Ile Glu Glu Ser Val
1595                1600                1605

Arg Tyr Met Val Met Arg Tyr Gly Ser Arg Leu Trp Lys Leu Arg
1610                1615                1620
```

```
Val Leu Gln Ala Glu Val Lys Ile Asn Ile Arg Gln Thr Thr Thr
1625                1630                1635

Gly Ser Ala Val Pro Ile Arg Leu Phe Ile Thr Asn Glu Ser Gly
1640                1645                1650

Tyr Tyr Leu Asp Ile Ser Leu Tyr Lys Glu Val Thr Asp Ser Arg
1655                1660                1665

Ser Gly Asn Ile Met Phe His Ser Phe Gly Asn Lys Gln Gly Pro
1670                1675                1680

Gln His Gly Met Leu Ile Asn Thr Pro Tyr Val Thr Lys Asp Leu
1685                1690                1695

Leu Gln Ala Lys Arg Phe Gln Ala Gln Thr Leu Gly Thr Thr Tyr
1700                1705                1710

Ile Tyr Asp Phe Pro Glu Met Phe Arg Gln Ala Leu Phe Lys Leu
1715                1720                1725

Trp Gly Ser Pro Asp Lys Tyr Pro Lys Asp Ile Leu Thr Tyr Thr
1730                1735                1740

Glu Leu Val Leu Asp Ser Gln Gly Leu Val Glu Met Asn Arg
1745                1750                1755

Leu Pro Gly Gly Asn Glu Val Gly Met Val Ala Phe Lys Met Arg
1760                1765                1770

Phe Lys Thr Gln Glu Tyr Pro Glu Gly Arg Asp Val Ile Val Ile
1775                1780                1785

Gly Asn Asp Ile Thr Phe Arg Ile Gly Ser Phe Gly Pro Gly Glu
1790                1795                1800

Asp Leu Leu Tyr Leu Arg Ala Ser Glu Met Ala Arg Ala Glu Gly
1805                1810                1815

Ile Pro Lys Ile Tyr Val Ala Ala Asn Ser Gly Ala Arg Ile Gly
1820                1825                1830

Met Ala Glu Glu Ile Lys His Met Phe His Val Ala Trp Val Asp
1835                1840                1845

Pro Glu Asp Pro His Lys Gly Phe Lys Tyr Leu Tyr Leu Thr Pro
1850                1855                1860

Gln Asp Tyr Thr Arg Ile Ser Ser Leu Asn Ser Val His Cys Lys
1865                1870                1875

His Ile Glu Glu Gly Gly Glu Ser Arg Tyr Met Ile Thr Asp Ile
1880                1885                1890

Ile Gly Lys Asp Asp Gly Leu Gly Val Glu Asn Leu Arg Gly Ser
1895                1900                1905

Gly Met Ile Ala Gly Glu Ser Ser Leu Ala Tyr Glu Glu Ile Val
1910                1915                1920

Thr Ile Ser Leu Val Thr Cys Arg Ala Ile Gly Ile Gly Ala Tyr
1925                1930                1935

Leu Val Arg Leu Gly Gln Arg Val Ile Gln Val Glu Asn Ser His
1940                1945                1950

Ile Ile Leu Thr Gly Ala Ser Ala Leu Asn Lys Val Leu Gly Arg
1955                1960                1965

Glu Val Tyr Thr Ser Asn Asn Gln Leu Gly Gly Val Gln Ile Met
1970                1975                1980

His Tyr Asn Gly Val Ser His Ile Thr Val Pro Asp Asp Phe Glu
1985                1990                1995

Gly Val Tyr Thr Ile Leu Glu Trp Leu Ser Tyr Met Pro Lys Asp
2000                2005                2010

Asn His Ser Pro Val Pro Ile Ile Thr Pro Thr Asp Pro Ile Asp
```

-continued

|  | 2015 |  |  |  | 2020 |  |  |  | 2025 |  |
|---|---|---|---|---|---|---|---|---|---|---|
| Arg | Glu | Ile | Glu | Phe | Leu | Pro | Ser | Arg | Ala | Pro | Tyr | Asp | Pro | Arg |
|  | 2030 |  |  |  | 2035 |  |  |  | 2040 |  |
| Trp | Met | Leu | Ala | Gly | Arg | Pro | His | Pro | Thr | Leu | Lys | Gly | Thr | Trp |
|  | 2045 |  |  |  | 2050 |  |  |  | 2055 |  |
| Gln | Ser | Gly | Phe | Phe | Asp | His | Gly | Ser | Phe | Lys | Glu | Ile | Met | Ala |
|  | 2060 |  |  |  | 2065 |  |  |  | 2070 |  |
| Pro | Trp | Ala | Gln | Thr | Val | Val | Thr | Gly | Arg | Ala | Arg | Leu | Gly | Gly |
|  | 2075 |  |  |  | 2080 |  |  |  | 2085 |  |
| Ile | Pro | Val | Gly | Val | Ile | Ala | Val | Glu | Thr | Arg | Thr | Val | Glu | Val |
|  | 2090 |  |  |  | 2095 |  |  |  | 2100 |  |
| Ala | Val | Pro | Ala | Asp | Pro | Ala | Asn | Leu | Asp | Ser | Glu | Ala | Lys | Ile |
|  | 2105 |  |  |  | 2110 |  |  |  | 2115 |  |
| Ile | Gln | Gln | Ala | Gly | Gln | Val | Trp | Phe | Pro | Asp | Ser | Ala | Tyr | Lys |
|  | 2120 |  |  |  | 2125 |  |  |  | 2130 |  |
| Thr | Ala | Gln | Ala | Val | Lys | Asp | Phe | Asn | Arg | Glu | Lys | Leu | Pro | Leu |
|  | 2135 |  |  |  | 2140 |  |  |  | 2145 |  |
| Met | Ile | Phe | Ala | Asn | Trp | Arg | Gly | Phe | Ser | Gly | Gly | Met | Lys | Asp |
|  | 2150 |  |  |  | 2155 |  |  |  | 2160 |  |
| Met | Tyr | Asp | Gln | Val | Leu | Lys | Phe | Gly | Ala | Tyr | Ile | Val | Asp | Gly |
|  | 2165 |  |  |  | 2170 |  |  |  | 2175 |  |
| Leu | Arg | Gln | Tyr | Lys | Gln | Pro | Ile | Leu | Ile | Tyr | Ile | Pro | Pro | Tyr |
|  | 2180 |  |  |  | 2185 |  |  |  | 2190 |  |
| Ala | Glu | Leu | Arg | Gly | Gly | Ser | Trp | Val | Val | Ile | Asp | Ala | Thr | Ile |
|  | 2195 |  |  |  | 2200 |  |  |  | 2205 |  |
| Asn | Pro | Leu | Cys | Ile | Glu | Met | Tyr | Ala | Asp | Lys | Glu | Ser | Arg | Gly |
|  | 2210 |  |  |  | 2215 |  |  |  | 2220 |  |
| Gly | Val | Leu | Glu | Pro | Glu | Gly | Thr | Val | Glu | Ile | Lys | Phe | Arg | Lys |
|  | 2225 |  |  |  | 2230 |  |  |  | 2235 |  |
| Lys | Asp | Leu | Ile | Lys | Ser | Met | Arg | Arg | Ile | Asp | Pro | Ala | Tyr | Lys |
|  | 2240 |  |  |  | 2245 |  |  |  | 2250 |  |
| Lys | Leu | Met | Glu | Gln | Leu | Gly | Glu | Pro | Asp | Leu | Ser | Asp | Lys | Asp |
|  | 2255 |  |  |  | 2260 |  |  |  | 2265 |  |
| Arg | Lys | Asp | Leu | Glu | Gly | Arg | Leu | Lys | Ala | Arg | Glu | Asp | Leu | Leu |
|  | 2270 |  |  |  | 2275 |  |  |  | 2280 |  |
| Leu | Pro | Ile | Tyr | His | Gln | Val | Ala | Val | Gln | Phe | Ala | Asp | Phe | His |
|  | 2285 |  |  |  | 2290 |  |  |  | 2295 |  |
| Asp | Thr | Pro | Gly | Arg | Met | Leu | Glu | Lys | Gly | Val | Ile | Ser | Asp | Ile |
|  | 2300 |  |  |  | 2305 |  |  |  | 2310 |  |
| Leu | Glu | Trp | Lys | Thr | Ala | Arg | Thr | Phe | Leu | Tyr | Trp | Arg | Leu | Arg |
|  | 2315 |  |  |  | 2320 |  |  |  | 2325 |  |
| Arg | Leu | Leu | Leu | Glu | Asp | Gln | Val | Lys | Gln | Glu | Ile | Leu | Gln | Ala |
|  | 2330 |  |  |  | 2335 |  |  |  | 2340 |  |
| Ser | Gly | Glu | Leu | Ser | His | Val | His | Ile | Gln | Ser | Met | Leu | Arg | Arg |
|  | 2345 |  |  |  | 2350 |  |  |  | 2355 |  |
| Trp | Phe | Val | Glu | Thr | Glu | Gly | Ala | Val | Lys | Ala | Tyr | Leu | Trp | Asp |
|  | 2360 |  |  |  | 2365 |  |  |  | 2370 |  |
| Asn | Asn | Gln | Val | Val | Gln | Trp | Leu | Glu | Gln | His | Trp | Gln | Ala |
|  | 2375 |  |  |  | 2380 |  |  |  | 2385 |  |
| Gly | Asp | Gly | Pro | Arg | Ser | Thr | Ile | Arg | Glu | Asn | Ile | Thr | Tyr | Leu |
|  | 2390 |  |  |  | 2395 |  |  |  | 2400 |  |
| Lys | His | Asp | Ser | Val | Leu | Lys | Thr | Ile | Arg | Gly | Leu | Val | Glu | Glu |
|  | 2405 |  |  |  | 2410 |  |  |  | 2415 |  |

Asn Pro Glu Val Ala Val Asp Cys Val Ile Tyr Leu Ser Gln His
    2420                2425                2430

Ile Ser Pro Ala Glu Arg Ala Gln Val Val His Leu Leu Ser Thr
    2435                2440                2445

Met Asp Ser Pro Ala Ser Thr
    2450                2455

<210> SEQ ID NO 5
<211> LENGTH: 7377
<212> TYPE: DNA
<213> ORGANISM: Homo sapiens
<220> FEATURE:
<221> NAME/KEY: CDS
<222> LOCATION: (1)..(7377)

<400> SEQUENCE: 5

| | | |
|---|---|---|
| atg gtc ttg ctt ctt tgt cta tct cgt ctg att ttc tcc tgt ctg acc<br>Met Val Leu Leu Leu Cys Leu Ser Arg Leu Ile Phe Ser Cys Leu Thr<br>1               5                   10                  15 | 48 |
| ttt tcc tgg tta aaa atc tgg ggg aaa atg acg gac tcc aag ccg atc<br>Phe Ser Trp Leu Lys Ile Trp Gly Lys Met Thr Asp Ser Lys Pro Ile<br>            20                  25                  30 | 96 |
| acc aag agt aaa tca gaa gca aac ctc atc ccg agc cag gag ccc ttt<br>Thr Lys Ser Lys Ser Glu Ala Asn Leu Ile Pro Ser Gln Glu Pro Phe<br>        35                  40                  45 | 144 |
| cca gcc tct gat aac tca ggg gag aca ccg cag aga aat ggg gag ggc<br>Pro Ala Ser Asp Asn Ser Gly Glu Thr Pro Gln Arg Asn Gly Glu Gly<br>    50                  55                  60 | 192 |
| cac act ctg ccc aag aca ccc agc cag gcc gag cca gcc tcc cac aaa<br>His Thr Leu Pro Lys Thr Pro Ser Gln Ala Glu Pro Ala Ser His Lys<br>65                  70                  75                  80 | 240 |
| ggc ccc aaa gat gcc ggt cgg cgg aga aac tcc cta cca ccc tcc cac<br>Gly Pro Lys Asp Ala Gly Arg Arg Arg Asn Ser Leu Pro Pro Ser His<br>                85                  90                  95 | 288 |
| cag aag ccc cca aga aac ccc ctt tct tcc agt gac gca gca ccc tcc<br>Gln Lys Pro Pro Arg Asn Pro Leu Ser Ser Ser Asp Ala Ala Pro Ser<br>            100                 105                 110 | 336 |
| cca gag ctt caa gcc aac ggg act ggg aca caa ggt ctg gag gcc aca<br>Pro Glu Leu Gln Ala Asn Gly Thr Gly Thr Gln Gly Leu Glu Ala Thr<br>        115                 120                 125 | 384 |
| gat acc aat ggc ctg tcc tcc tca gcc agg ccc cag ggc cag caa gct<br>Asp Thr Asn Gly Leu Ser Ser Ser Ala Arg Pro Gln Gly Gln Gln Ala<br>    130                 135                 140 | 432 |
| ggc tcc ccc tcc aaa gaa gac aag aag cag gca aac atc aag agg cag<br>Gly Ser Pro Ser Lys Glu Asp Lys Lys Gln Ala Asn Ile Lys Arg Gln<br>145                 150                 155                 160 | 480 |
| ctg atg acc aac ttc atc ctg ggc tct ttt gat gac tac tcc tct gac<br>Leu Met Thr Asn Phe Ile Leu Gly Ser Phe Asp Asp Tyr Ser Ser Asp<br>                165                 170                 175 | 528 |
| gag gac tct gtt gct ggc tca tct cgt gag tct acc cgg aag ggc agc<br>Glu Asp Ser Val Ala Gly Ser Ser Arg Glu Ser Thr Arg Lys Gly Ser<br>            180                 185                 190 | 576 |
| cgg gcc agc ttg ggg gcc ctg tcc cta gag gct tat ctg acc aca ggt<br>Arg Ala Ser Leu Gly Ala Leu Ser Leu Glu Ala Tyr Leu Thr Thr Gly<br>        195                 200                 205 | 624 |
| gaa gct gag acc cgc gtc ccc act atg agg ccg agc atg tcg gga ctc<br>Glu Ala Glu Thr Arg Val Pro Thr Met Arg Pro Ser Met Ser Gly Leu<br>    210                 215                 220 | 672 |
| cac ctg gtg aag agg gga cgg gaa cac aag aag ctg gac ctg cac aga<br>His Leu Val Lys Arg Gly Arg Glu His Lys Lys Leu Asp Leu His Arg | 720 |

-continued

```
                225                 230                 235                 240
gac ttt acc gtg gct tct ccc gct gag ttt gtc aca cgc tat ggg ggg         768
Asp Phe Thr Val Ala Ser Pro Ala Glu Phe Val Thr Arg Tyr Gly Gly
                245                 250                 255 gat cgg gtc atc gag aag gtg ctt att gcc aac aac ggg att gcc gcc         816
Asp Arg Val Ile Glu Lys Val Leu Ile Ala Asn Asn Gly Ile Ala Ala
                260                 265                 270 gtg aag tgc atg cgc tcc atc cgc agg tgg gcc tat gag atg ttc cgc         864
Val Lys Cys Met Arg Ser Ile Arg Arg Trp Ala Tyr Glu Met Phe Arg
                275                 280                 285 aac gag cgg gcc atc cgg ttt gtt gtg atg gtg acc ccc gag gac ctt         912
Asn Glu Arg Ala Ile Arg Phe Val Val Met Val Thr Pro Glu Asp Leu
                290                 295                 300 aag gcc aac gca gag tac atc aag atg gcg gat cat tac gtc ccc gtc         960
Lys Ala Asn Ala Glu Tyr Ile Lys Met Ala Asp His Tyr Val Pro Val
305                 310                 315                 320 cca gga ggg ccc aat aac aac aac tat gcc aac gtg gag ctg att gtg        1008
Pro Gly Gly Pro Asn Asn Asn Asn Tyr Ala Asn Val Glu Leu Ile Val
                325                 330                 335 gac att gcc aag aga atc ccc gtg cgg gcg gtg tgg gct ggc tgg ggc        1056
Asp Ile Ala Lys Arg Ile Pro Val Arg Ala Val Trp Ala Gly Trp Gly
                340                 345                 350 cat gct tca gaa aac cct aaa ctt ccg gag ctg ctg tgc aag aat gga        1104
His Ala Ser Glu Asn Pro Lys Leu Pro Glu Leu Leu Cys Lys Asn Gly
                355                 360                 365 gtt gct ttc tta ggc cct ccc agt gag gcc atg tgg gcc tta gga gat        1152
Val Ala Phe Leu Gly Pro Pro Ser Glu Ala Met Trp Ala Leu Gly Asp
                370                 375                 380 aag atc gcc tcc acc gtt gtc gcc cag acg cta cag gtc cca acc ctg        1200
Lys Ile Ala Ser Thr Val Val Ala Gln Thr Leu Gln Val Pro Thr Leu
385                 390                 395                 400 ccc tgg agt gga agc ggc ctg aca gtg gag tgg aca gaa gat gat ctg        1248
Pro Trp Ser Gly Ser Gly Leu Thr Val Glu Trp Thr Glu Asp Asp Leu
                405                 410                 415 cag cag gga aaa aga atc agt gtc cca gaa gat gtt tat gac aag ggt        1296
Gln Gln Gly Lys Arg Ile Ser Val Pro Glu Asp Val Tyr Asp Lys Gly
                420                 425                 430 tgc gtg aaa gac gta gat gag ggc ttg gag gca gca gaa aga att ggt        1344
Cys Val Lys Asp Val Asp Glu Gly Leu Glu Ala Ala Glu Arg Ile Gly
                435                 440                 445 ttt cca ttg atg atc aaa gct tct gaa ggt ggc ggg ggg aag gga atc        1392
Phe Pro Leu Met Ile Lys Ala Ser Glu Gly Gly Gly Gly Lys Gly Ile
450                 455                 460 cgg aag gct gag agt gcg gag gac ttc ccg atc ctt ttc aga caa gta        1440
Arg Lys Ala Glu Ser Ala Glu Asp Phe Pro Ile Leu Phe Arg Gln Val
465                 470                 475                 480 cag agt gag atc cca ggc tcg ccc atc ttt ctc atg aag ctg gcc cag        1488
Gln Ser Glu Ile Pro Gly Ser Pro Ile Phe Leu Met Lys Leu Ala Gln
                485                 490                 495 cac gcc cgt cac ctg gaa gtt cag atc ctc gct gac cag tat ggg aat        1536
His Ala Arg His Leu Glu Val Gln Ile Leu Ala Asp Gln Tyr Gly Asn
                500                 505                 510 gct gtg tct ctg ttt ggt cgc gac tgc tcc atc cag cgg cgg cat cag        1584
Ala Val Ser Leu Phe Gly Arg Asp Cys Ser Ile Gln Arg Arg His Gln
                515                 520                 525 aag atc gtt gag gaa gca ccg gcc acc atc gcc ccg ctg gcc ata ttc        1632
Lys Ile Val Glu Glu Ala Pro Ala Thr Ile Ala Pro Leu Ala Ile Phe
530                 535                 540 gag ttc atg gag cag tgt gcc atc cgc ctg gcc aag acc gtg ggc tat        1680
```

```
                    Glu Phe Met Glu Gln Cys Ala Ile Arg Leu Ala Lys Thr Val Gly Tyr
                    545                 550                 555                 560 gtg agt gca ggg gca gtg gaa tac ctc tat agt cag gat ggc agc ttc                    1728
Val Ser Ala Gly Ala Val Glu Tyr Leu Tyr Ser Gln Asp Gly Ser Phe
                565                 570                 575 cac ttc ttg gag ctg aat cct cgc ttg cag gtg gaa cat ccc tgc aca                    1776
His Phe Leu Glu Leu Asn Pro Arg Leu Gln Val Glu His Pro Cys Thr
            580                 585                 590 gaa atg att gct gac gtt aat ctg ccg gcc gcc cag cta cag atc gcc                    1824
Glu Met Ile Ala Asp Val Asn Leu Pro Ala Ala Gln Leu Gln Ile Ala
        595                 600                 605 atg ggc gtg cca ctg cac cgg ctg aag gat atc cgg ctt ctg tat gga                    1872
Met Gly Val Pro Leu His Arg Leu Lys Asp Ile Arg Leu Leu Tyr Gly
    610                 615                 620 gag tca cca tgg gga gtg act ccc att tct ttt gaa acc ccc tca aac                    1920
Glu Ser Pro Trp Gly Val Thr Pro Ile Ser Phe Glu Thr Pro Ser Asn
625                 630                 635                 640 cct ccc ctc gcc cga ggc cac gtc att gcc gcc aga atc acc agc gaa                    1968
Pro Pro Leu Ala Arg Gly His Val Ile Ala Ala Arg Ile Thr Ser Glu
                645                 650                 655 aac cca gac gag ggt ttt aag ccg agc tcc ggg act gtc cag gaa ctg                    2016
Asn Pro Asp Glu Gly Phe Lys Pro Ser Ser Gly Thr Val Gln Glu Leu
            660                 665                 670 aat ttc cgg agc agc aag aac gtg tgg ggt tac ttc agc gtg gcc gct                    2064
Asn Phe Arg Ser Ser Lys Asn Val Trp Gly Tyr Phe Ser Val Ala Ala
        675                 680                 685 act gga ggc ctg cac gag ttt gcg gat tcc caa ttt ggg cac tgc ttc                    2112
Thr Gly Gly Leu His Glu Phe Ala Asp Ser Gln Phe Gly His Cys Phe
    690                 695                 700 tcc tgg gga gag aac cgg gaa gag gcc att tcg aac atg gtg gtg gct                    2160
Ser Trp Gly Glu Asn Arg Glu Glu Ala Ile Ser Asn Met Val Val Ala
705                 710                 715                 720 ttg aag gaa ctg tcc atc cga ggt gac ttt agg act acc gtg gaa tac                    2208
Leu Lys Glu Leu Ser Ile Arg Gly Asp Phe Arg Thr Thr Val Glu Tyr
                725                 730                 735 ctc att aac ctc ctg gag acc gag agc ttc cag aac aac gac atc gac                    2256
Leu Ile Asn Leu Leu Glu Thr Glu Ser Phe Gln Asn Asn Asp Ile Asp
            740                 745                 750 acc ggg tgg ttg gac tac ctc att gct gag aaa gtg cag gcg gag aaa                    2304
Thr Gly Trp Leu Asp Tyr Leu Ile Ala Glu Lys Val Gln Ala Glu Lys
        755                 760                 765 ccg gat atc atg ctt ggg gtg gta tgc ggg gcc ttg aac gtg gcc gat                    2352
Pro Asp Ile Met Leu Gly Val Val Cys Gly Ala Leu Asn Val Ala Asp
    770                 775                 780 gcg atg ttc aga acg tgc atg aca gat ttc tta cac tcc ctg gaa agg                    2400
Ala Met Phe Arg Thr Cys Met Thr Asp Phe Leu His Ser Leu Glu Arg
785                 790                 795                 800 ggc cag gtc ctc cca gcg gat tca cta ctg aac ctt gta gat gtg gaa                    2448
Gly Gln Val Leu Pro Ala Asp Ser Leu Leu Asn Leu Val Asp Val Glu
                805                 810                 815 tta att tac gga ggt gtt aag tac att ctc aag gtg gcc cgg cag tct                    2496
Leu Ile Tyr Gly Gly Val Lys Tyr Ile Leu Lys Val Ala Arg Gln Ser
            820                 825                 830 ctg acc atg ttc gtt ctc atc atg tat ggc tgc cac atc gag att gat                    2544
Leu Thr Met Phe Val Leu Ile Met Tyr Gly Cys His Ile Glu Ile Asp
        835                 840                 845 gcc cac cgg ctg aat gat ggg ggg ctc ctg ctc tcc tac aat ggg aac                    2592
Ala His Arg Leu Asn Asp Gly Gly Leu Leu Leu Ser Tyr Asn Gly Asn
    850                 855                 860
```

-continued

| | |
|---|---|
| agc tac acc acc tac atg aag gaa gag gtt gac agt tac cga att acc<br>Ser Tyr Thr Thr Tyr Met Lys Glu Glu Val Asp Ser Tyr Arg Ile Thr<br>865                       870                   875                880 | 2640 |
| atc ggc aat aag acg tgt gtg ttt gag aag gag aac gat cct aca gtc<br>Ile Gly Asn Lys Thr Cys Val Phe Glu Lys Glu Asn Asp Pro Thr Val<br>                      885                   890                   895 | 2688 |
| ctg aga tcc ccc tcg gct ggg aag ctg aca cag tac aca gtg gag gat<br>Leu Arg Ser Pro Ser Ala Gly Lys Leu Thr Gln Tyr Thr Val Glu Asp<br>          900                   905                   910 | 2736 |
| ggg ggc cac gtt gag gct ggg agc agc tac gct gag atg gag gtg atg<br>Gly Gly His Val Glu Ala Gly Ser Ser Tyr Ala Glu Met Glu Val Met<br>               915                   920                   925 | 2784 |
| aag atg atc atg acc ctg aac gtt cag gaa aga ggc cgg gtg aag tac<br>Lys Met Ile Met Thr Leu Asn Val Gln Glu Arg Gly Arg Val Lys Tyr<br>930                       935                   940 | 2832 |
| atc aag cgt cca ggt gcc gtg ctg gaa gca ggc tgc gtg gtg gcc agg<br>Ile Lys Arg Pro Gly Ala Val Leu Glu Ala Gly Cys Val Val Ala Arg<br>945                       950                   955                960 | 2880 |
| ctg gag ctc gat gac cct tct aaa gtc cac ccg gct gaa ccg ttc aca<br>Leu Glu Leu Asp Asp Pro Ser Lys Val His Pro Ala Glu Pro Phe Thr<br>                       965                   970                   975 | 2928 |
| gga gaa ctc cct gcc cag cag aca ctg ccc atc ctc gga gag aaa ctg<br>Gly Glu Leu Pro Ala Gln Gln Thr Leu Pro Ile Leu Gly Glu Lys Leu<br>          980                   985                   990 | 2976 |
| cac cag gtc ttc cac agc gtc ctg gaa aac ctc acc aac gtc atg agt<br>His Gln Val Phe His Ser Val Leu Glu Asn Leu Thr Asn Val Met Ser<br>               995                  1000               1005 | 3024 |
| ggc ttt tgt ctg cca gag ccc gtt ttt agc ata aag ctg aag gag<br>Gly Phe Cys Leu Pro Glu Pro Val Phe Ser Ile Lys Leu Lys Glu<br>1010                    1015                  1020 | 3069 |
| tgg gtg cag aag ctc atg atg acc ctc cgg cac ccg tca ctg ccg<br>Trp Val Gln Lys Leu Met Met Thr Leu Arg His Pro Ser Leu Pro<br>1025                    1030                  1035 | 3114 |
| ctg ctg gag ctg cag gag atc atg acc agc gtg gca ggc cgc atc<br>Leu Leu Glu Leu Gln Glu Ile Met Thr Ser Val Ala Gly Arg Ile<br>1040                    1045                  1050 | 3159 |
| ccc gcc cct gtg gag aag tct gtc cgc agg gtg atg gcc cag tat<br>Pro Ala Pro Val Glu Lys Ser Val Arg Arg Val Met Ala Gln Tyr<br>1055                    1060                  1065 | 3204 |
| gcc agc aac atc acc tcg gtg ctg tgc cag ttc ccc agc cag cag<br>Ala Ser Asn Ile Thr Ser Val Leu Cys Gln Phe Pro Ser Gln Gln<br>1070                    1075                  1080 | 3249 |
| ata gcc acc atc ctg gac tgc cat gca gcc acc ctg cag cgg aag<br>Ile Ala Thr Ile Leu Asp Cys His Ala Ala Thr Leu Gln Arg Lys<br>1085                    1090                  1095 | 3294 |
| gct gat cga gag gcc ttc ttc atc aac acc cag agc atc gtg cag<br>Ala Asp Arg Glu Ala Phe Phe Ile Asn Thr Gln Ser Ile Val Gln<br>1100                    1105                  1110 | 3339 |
| ttg gtc cag aga tac cgc agc ggg atc cgc ggc tat atg aaa aca<br>Leu Val Gln Arg Tyr Arg Ser Gly Ile Arg Gly Tyr Met Lys Thr<br>1115                    1120                  1125 | 3384 |
| gtg gtg ttg gat ctc ctg aga aga tac ttg cgt gtt gag cac cat<br>Val Val Leu Asp Leu Leu Arg Arg Tyr Leu Arg Val Glu His His<br>1130                    1135                  1140 | 3429 |
| ttt cag caa gcc cac tac gac aag tgt gtg ata aac ctc agg gag<br>Phe Gln Gln Ala His Tyr Asp Lys Cys Val Ile Asn Leu Arg Glu<br>1145                    1150                  1155 | 3474 |
| cag ttc aag cca gac atg tcc cag gtg ctg gac tgc atc ttc tcc<br>Gln Phe Lys Pro Asp Met Ser Gln Val Leu Asp Cys Ile Phe Ser<br>1160                    1165                  1170 | 3519 |

| | | | | | | | | | | | | |
|---|---|---|---|---|---|---|---|---|---|---|---|---|
| cac | gca | cag | gtg | gcc | aag | aag | aac | cag | ctg | gtg | atc | atg | ttg | atc | 3564 |
| His | Ala | Gln | Val | Ala | Lys | Lys | Asn | Gln | Leu | Val | Ile | Met | Leu | Ile | |
| 1175 | | | | 1180 | | | | | 1185 | | | | | | |

| gat | gag | ctg | tgt | ggc | cca | gac | cct | tcc | ctg | tcg | gac | gag | ctg | atc | 3609 |
| Asp | Glu | Leu | Cys | Gly | Pro | Asp | Pro | Ser | Leu | Ser | Asp | Glu | Leu | Ile | |
| 1190 | | | | | 1195 | | | | | 1200 | | | | | |

| tcc | atc | ctc | aac | gag | ctc | act | cag | ctg | agc | aaa | agc | gag | cac | tgc | 3654 |
| Ser | Ile | Leu | Asn | Glu | Leu | Thr | Gln | Leu | Ser | Lys | Ser | Glu | His | Cys | |
| 1205 | | | | | 1210 | | | | | 1215 | | | | | |

| aaa | gtg | gcc | ctc | aga | gcc | cgg | cag | atc | ctg | att | gcc | tcc | cac | ctc | 3699 |
| Lys | Val | Ala | Leu | Arg | Ala | Arg | Gln | Ile | Leu | Ile | Ala | Ser | His | Leu | |
| 1220 | | | | | 1225 | | | | | 1230 | | | | | |

| ccc | tcc | tac | gag | ctg | cgg | cat | aac | cag | gtg | gag | tcc | att | ttc | ctg | 3744 |
| Pro | Ser | Tyr | Glu | Leu | Arg | His | Asn | Gln | Val | Glu | Ser | Ile | Phe | Leu | |
| 1235 | | | | | 1240 | | | | | 1245 | | | | | |

| tct | gcc | att | gac | atg | tac | ggc | cac | cag | ttc | cgc | ccc | gag | aac | ctc | 3789 |
| Ser | Ala | Ile | Asp | Met | Tyr | Gly | His | Gln | Phe | Arg | Pro | Glu | Asn | Leu | |
| 1250 | | | | | 1255 | | | | | 1260 | | | | | |

| aag | aaa | tta | ata | ctt | tcg | gaa | aca | acc | atc | ttc | gac | gtc | ctg | cct | 3834 |
| Lys | Lys | Leu | Ile | Leu | Ser | Glu | Thr | Thr | Ile | Phe | Asp | Val | Leu | Pro | |
| 1265 | | | | | 1270 | | | | | 1275 | | | | | |

| act | ttc | ttc | tat | cac | gca | aac | aaa | gtc | gtg | tgc | atg | gcg | tcc | ttg | 3879 |
| Thr | Phe | Phe | Tyr | His | Ala | Asn | Lys | Val | Val | Cys | Met | Ala | Ser | Leu | |
| 1280 | | | | | 1285 | | | | | 1290 | | | | | |

| gag | gtt | tac | gtg | cgg | agg | ggc | tac | atc | gcc | tat | gag | tta | aac | agc | 3924 |
| Glu | Val | Tyr | Val | Arg | Arg | Gly | Tyr | Ile | Ala | Tyr | Glu | Leu | Asn | Ser | |
| 1295 | | | | | 1300 | | | | | 1305 | | | | | |

| ctg | cag | cac | cgg | cag | ctc | ccg | gac | ggc | acc | tgc | gtg | gta | gaa | ttc | 3969 |
| Leu | Gln | His | Arg | Gln | Leu | Pro | Asp | Gly | Thr | Cys | Val | Val | Glu | Phe | |
| 1310 | | | | | 1315 | | | | | 1320 | | | | | |

| cag | ttc | atg | ctg | ccg | tcc | tcc | cac | cca | aac | cgg | atg | acc | gtg | ccc | 4014 |
| Gln | Phe | Met | Leu | Pro | Ser | Ser | His | Pro | Asn | Arg | Met | Thr | Val | Pro | |
| 1325 | | | | | 1330 | | | | | 1335 | | | | | |

| atc | agc | atc | acc | aac | cct | gac | ctg | ctg | agg | cac | agc | aca | gag | ctc | 4059 |
| Ile | Ser | Ile | Thr | Asn | Pro | Asp | Leu | Leu | Arg | His | Ser | Thr | Glu | Leu | |
| 1340 | | | | | 1345 | | | | | 1350 | | | | | |

| ttc | atg | gac | agc | ggc | ttc | tcc | cca | ctg | tgc | cag | cgc | atg | gga | gcc | 4104 |
| Phe | Met | Asp | Ser | Gly | Phe | Ser | Pro | Leu | Cys | Gln | Arg | Met | Gly | Ala | |
| 1355 | | | | | 1360 | | | | | 1365 | | | | | |

| atg | gta | gcc | ttc | agg | aga | ttc | gag | gac | ttc | acc | aga | aat | ttt | gat | 4149 |
| Met | Val | Ala | Phe | Arg | Arg | Phe | Glu | Asp | Phe | Thr | Arg | Asn | Phe | Asp | |
| 1370 | | | | | 1375 | | | | | 1380 | | | | | |

| gaa | gtc | atc | tct | tgc | ttc | gcc | aac | gtg | ccc | aaa | gac | acc | ccc | ctc | 4194 |
| Glu | Val | Ile | Ser | Cys | Phe | Ala | Asn | Val | Pro | Lys | Asp | Thr | Pro | Leu | |
| 1385 | | | | | 1390 | | | | | 1395 | | | | | |

| ttc | agc | gag | gcc | cgc | acc | tcc | cta | tac | tcc | gag | gat | gac | tgc | aag | 4239 |
| Phe | Ser | Glu | Ala | Arg | Thr | Ser | Leu | Tyr | Ser | Glu | Asp | Asp | Cys | Lys | |
| 1400 | | | | | 1405 | | | | | 1410 | | | | | |

| agc | ctc | aga | gaa | gag | ccc | atc | cac | att | ctg | aat | gtg | tcc | atc | cag | 4284 |
| Ser | Leu | Arg | Glu | Glu | Pro | Ile | His | Ile | Leu | Asn | Val | Ser | Ile | Gln | |
| 1415 | | | | | 1420 | | | | | 1425 | | | | | |

| tgt | gca | gac | cac | ctg | gag | gat | gag | gca | ctg | gtg | ccg | att | tta | cgg | 4329 |
| Cys | Ala | Asp | His | Leu | Glu | Asp | Glu | Ala | Leu | Val | Pro | Ile | Leu | Arg | |
| 1430 | | | | | 1435 | | | | | 1440 | | | | | |

| aca | ttc | gta | cag | tcc | aag | aaa | aat | atc | ctt | gtg | gat | tat | gga | ctc | 4374 |
| Thr | Phe | Val | Gln | Ser | Lys | Lys | Asn | Ile | Leu | Val | Asp | Tyr | Gly | Leu | |
| 1445 | | | | | 1450 | | | | | 1455 | | | | | |

| cga | cga | atc | aca | ttc | ttg | att | gcc | caa | gag | aaa | gaa | ttt | ccc | aag | 4419 |
| Arg | Arg | Ile | Thr | Phe | Leu | Ile | Ala | Gln | Glu | Lys | Glu | Phe | Pro | Lys | |

-continued

| | | | | |
|---|---|---|---|---|
| | 1460 | 1465 | 1470 | |
| ttt ttc aca ttc aga gca aga gat gag ttt gca gaa gat cgc att<br>Phe Phe Thr Phe Arg Ala Arg Asp Glu Phe Ala Glu Asp Arg Ile<br>1475                                      1480                              1485 | | | | 4464 |
| tac cgt cac ttg gaa cct gcc ctg gcc ttc cag ctg gaa ctc aac<br>Tyr Arg His Leu Glu Pro Ala Leu Ala Phe Gln Leu Glu Leu Asn<br>1490                                      1495                             1500 | | | | 4509 |
| cgg atg cgt aac ttc gat ctg acc gcc gtg ccc tgt gcc aac cac<br>Arg Met Arg Asn Phe Asp Leu Thr Ala Val Pro Cys Ala Asn His<br>1505                                    1510                             1515 | | | | 4554 |
| aag atg cac ctt tac ctg ggt gtt gcc aag gtg aag gaa ggt gtg<br>Lys Met His Leu Tyr Leu Gly Val Ala Lys Val Lys Glu Gly Val<br>1520                                    1525                             1530 | | | | 4599 |
| gaa gtg acg gac cat agg ttc ttc atc cgc gcc atc atc agg cac<br>Glu Val Thr Asp His Arg Phe Phe Ile Arg Ala Ile Ile Arg His<br>1535                                    1540                             1545 | | | | 4644 |
| tct gac ctg atc aca aag gaa gcc tcc ttc gaa tac ctg cag aac<br>Ser Asp Leu Ile Thr Lys Glu Ala Ser Phe Glu Tyr Leu Gln Asn<br>1550                                    1555                             1560 | | | | 4689 |
| gag ggt gag cgg ctg ctc ctg gag gcc atg gac gag ctg gag gtg<br>Glu Gly Glu Arg Leu Leu Leu Glu Ala Met Asp Glu Leu Glu Val<br>1565                                    1570                             1575 | | | | 4734 |
| gcg ttc aat aac acc agc gtg cgc acc gac tgc aac cac atc ttc<br>Ala Phe Asn Asn Thr Ser Val Arg Thr Asp Cys Asn His Ile Phe<br>1580                                    1585                             1590 | | | | 4779 |
| ctc aac ttc gtg ccc act gtc atc atg gac ccc ttc aag atc gag<br>Leu Asn Phe Val Pro Thr Val Ile Met Asp Pro Phe Lys Ile Glu<br>1595                                    1600                             1605 | | | | 4824 |
| gag tcc gtg cgc tac atg gtt atg cgc tac ggc agc cgg ctg tgg<br>Glu Ser Val Arg Tyr Met Val Met Arg Tyr Gly Ser Arg Leu Trp<br>1610                                    1615                             1620 | | | | 4869 |
| aaa ctc cgt gtg cta cag gct gag gtc aag atc aac atc cgc cag<br>Lys Leu Arg Val Leu Gln Ala Glu Val Lys Ile Asn Ile Arg Gln<br>1625                                    1630                             1635 | | | | 4914 |
| acc acc acc ggc agt gcc gtt ccc atc cgc ctg ttc atc acc aat<br>Thr Thr Thr Gly Ser Ala Val Pro Ile Arg Leu Phe Ile Thr Asn<br>1640                                    1645                             1650 | | | | 4959 |
| gag tcg ggc tac tac ctg gac atc agc ctc tac aaa gaa gtg act<br>Glu Ser Gly Tyr Tyr Leu Asp Ile Ser Leu Tyr Lys Glu Val Thr<br>1655                                    1660                             1665 | | | | 5004 |
| gac tcc aga tct gga aat atc atg ttt cac tcc ttc ggc aac aag<br>Asp Ser Arg Ser Gly Asn Ile Met Phe His Ser Phe Gly Asn Lys<br>1670                                    1675                             1680 | | | | 5049 |
| caa ggg ccc cag cac ggg atg ctg atc aat act ccc tac gtc acc<br>Gln Gly Pro Gln His Gly Met Leu Ile Asn Thr Pro Tyr Val Thr<br>1685                                    1690                             1695 | | | | 5094 |
| aag gat ctg ctc cag gcc aag cga ttc cag gcc cag acc ctg gga<br>Lys Asp Leu Leu Gln Ala Lys Arg Phe Gln Ala Gln Thr Leu Gly<br>1700                                    1705                             1710 | | | | 5139 |
| acc acc tac gtc tat gac ttc ccg gaa atg ttc agg cag gct ctc<br>Thr Thr Tyr Val Tyr Asp Phe Pro Glu Met Phe Arg Gln Ala Leu<br>1715                                    1720                             1725 | | | | 5184 |
| ttt aaa ctg tgg ggc tcc cca gac aag tat ccc aaa gac atc ctg<br>Phe Lys Leu Trp Gly Ser Pro Asp Lys Tyr Pro Lys Asp Ile Leu<br>1730                                    1735                             1740 | | | | 5229 |
| aca tac act gaa tta gtg ttg gac tct cag ggc cag ctg gtg gag<br>Thr Tyr Thr Glu Leu Val Leu Asp Ser Gln Gly Gln Leu Val Glu<br>1745                                    1750                             1755 | | | | 5274 |
| atg aac cga ctt cct ggt gga aat gag gtg ggc atg gtg gcc ttc | | | | 5319 |

```
                Met Asn Arg Leu Pro Gly Gly Asn Glu Val Gly Met Val Ala Phe
                    1760            1765                1770 aaa atg agg ttt aag acc cag gag tac ccg gaa gga cgg gat gtg        5364
Lys Met Arg Phe Lys Thr Gln Glu Tyr Pro Glu Gly Arg Asp Val
    1775            1780                1785 atc gtc atc ggc aat gac atc acc ttt cgc att gga tcc ttt ggc        5409
Ile Val Ile Gly Asn Asp Ile Thr Phe Arg Ile Gly Ser Phe Gly
    1790            1795                1800 cct gga gag gac ctt ctg tac ctg cgg gca tcc gag atg gcc cgg        5454
Pro Gly Glu Asp Leu Leu Tyr Leu Arg Ala Ser Glu Met Ala Arg
    1805            1810                1815 gca gag ggc att ccc aaa att tac gtg gca gcc aac agt ggc gcc        5499
Ala Glu Gly Ile Pro Lys Ile Tyr Val Ala Ala Asn Ser Gly Ala
    1820            1825                1830 cgt att ggc atg gca gag gag atc aaa cac atg ttc cac gtg gct        5544
Arg Ile Gly Met Ala Glu Glu Ile Lys His Met Phe His Val Ala
    1835            1840                1845 tgg gtg gac cca gaa gac ccc cac aaa gga ttt aaa tac ctg tac        5589
Trp Val Asp Pro Glu Asp Pro His Lys Gly Phe Lys Tyr Leu Tyr
    1850            1855                1860 ctg act ccc caa gac tac acc aga atc agc tcc ctg aac tcc gtc        5634
Leu Thr Pro Gln Asp Tyr Thr Arg Ile Ser Ser Leu Asn Ser Val
    1865            1870                1875 cac tgt aaa cac atc gag gaa gga gga gag tcc aga tac atg atc        5679
His Cys Lys His Ile Glu Glu Gly Gly Glu Ser Arg Tyr Met Ile
    1880            1885                1890 acg gat atc atc ggg aag gat gat ggc ttg ggc gtg gag aat ctg        5724
Thr Asp Ile Ile Gly Lys Asp Asp Gly Leu Gly Val Glu Asn Leu
    1895            1900                1905 agg ggc tca ggc atg att gct ggg gag tcc tct ctg gct tac gaa        5769
Arg Gly Ser Gly Met Ile Ala Gly Glu Ser Ser Leu Ala Tyr Glu
    1910            1915                1920 gag atc gtc acc att agc ttg gtg acc tgc cga gcc att ggg att        5814
Glu Ile Val Thr Ile Ser Leu Val Thr Cys Arg Ala Ile Gly Ile
    1925            1930                1935 ggg gcc tac ttg gtg agg ctg ggc cag cga gtg atc cag gtg gag        5859
Gly Ala Tyr Leu Val Arg Leu Gly Gln Arg Val Ile Gln Val Glu
    1940            1945                1950 aat tcc cac atc atc ctc aca gga gca agt gct ctc aac aag gtc        5904
Asn Ser His Ile Ile Leu Thr Gly Ala Ser Ala Leu Asn Lys Val
    1955            1960                1965 ctg gga aga gag gtc tac aca tcc aac aac cag ctg ggt ggc gtt        5949
Leu Gly Arg Glu Val Tyr Thr Ser Asn Asn Gln Leu Gly Gly Val
    1970            1975                1980 cag atc atg cat tac aat ggt gtc tcc cac atc acc gtg cca gat        5994
Gln Ile Met His Tyr Asn Gly Val Ser His Ile Thr Val Pro Asp
    1985            1990                1995 gac ttt gag ggg gtt tat acc atc ctg gag tgg ctg tcc tat atg        6039
Asp Phe Glu Gly Val Tyr Thr Ile Leu Glu Trp Leu Ser Tyr Met
    2000            2005                2010 cca aag gat aat cac agc cct gtc cct atc atc aca ccc act gac        6084
Pro Lys Asp Asn His Ser Pro Val Pro Ile Ile Thr Pro Thr Asp
    2015            2020                2025 ccc att gac aga gaa att gaa ttc ctc cca tcc aga gct ccc tac        6129
Pro Ile Asp Arg Glu Ile Glu Phe Leu Pro Ser Arg Ala Pro Tyr
    2030            2035                2040 gac ccc cgg tgg atg ctt gca gga agg cct cac cca act ctg aag        6174
Asp Pro Arg Trp Met Leu Ala Gly Arg Pro His Pro Thr Leu Lys
    2045            2050                2055
```

-continued

| | | | | | | | | | | | | | | |
|---|---|---|---|---|---|---|---|---|---|---|---|---|---|---|
| gga | acg | tgg | cag | agc | gga | ttc | ttt | gac | cac | ggc | agt | ttc | aag | gaa | 6219 |
| Gly | Thr | Trp | Gln | Ser | Gly | Phe | Phe | Asp | His | Gly | Ser | Phe | Lys | Glu | |
| | 2060 | | | | 2065 | | | | 2070 | | | | | | |

| atc | atg | gca | ccc | tgg | gcg | cag | acc | gtg | gtg | aca | gga | cga | gca | agg | 6264 |
| Ile | Met | Ala | Pro | Trp | Ala | Gln | Thr | Val | Val | Thr | Gly | Arg | Ala | Arg | |
| | 2075 | | | | 2080 | | | | 2085 | | | | | | |

| ctt | ggg | ggg | att | ccc | gtg | gga | gtg | att | gct | gtg | gag | aca | cgg | act | 6309 |
| Leu | Gly | Gly | Ile | Pro | Val | Gly | Val | Ile | Ala | Val | Glu | Thr | Arg | Thr | |
| | 2090 | | | | 2095 | | | | 2100 | | | | | | |

| gtg | gag | gtg | gca | gtc | cct | gca | gac | cct | gcc | aac | ctg | gat | tct | gag | 6354 |
| Val | Glu | Val | Ala | Val | Pro | Ala | Asp | Pro | Ala | Asn | Leu | Asp | Ser | Glu | |
| | 2105 | | | | 2110 | | | | 2115 | | | | | | |

| gcc | aag | ata | att | cag | cag | gca | gga | cag | gtg | tgg | ttc | cca | gac | tca | 6399 |
| Ala | Lys | Ile | Ile | Gln | Gln | Ala | Gly | Gln | Val | Trp | Phe | Pro | Asp | Ser | |
| | 2120 | | | | 2125 | | | | 2130 | | | | | | |

| gcc | tac | aaa | acc | gcc | cag | gcc | atc | aag | gac | ttc | aac | cgg | gag | aag | 6444 |
| Ala | Tyr | Lys | Thr | Ala | Gln | Ala | Ile | Lys | Asp | Phe | Asn | Arg | Glu | Lys | |
| | 2135 | | | | 2140 | | | | 2145 | | | | | | |

| ttg | ccc | ctg | atg | atc | ttt | gcc | aac | tgg | agg | ggg | ttc | tcc | ggt | ggc | 6489 |
| Leu | Pro | Leu | Met | Ile | Phe | Ala | Asn | Trp | Arg | Gly | Phe | Ser | Gly | Gly | |
| | 2150 | | | | 2155 | | | | 2160 | | | | | | |

| atg | aaa | gac | atg | tat | gac | cag | gtg | ctg | aag | ttt | gga | gcc | tac | atc | 6534 |
| Met | Lys | Asp | Met | Tyr | Asp | Gln | Val | Leu | Lys | Phe | Gly | Ala | Tyr | Ile | |
| | 2165 | | | | 2170 | | | | 2175 | | | | | | |

| gtg | gac | ggc | ctt | aga | caa | tac | aaa | cag | ccc | atc | ctg | atc | tat | atc | 6579 |
| Val | Asp | Gly | Leu | Arg | Gln | Tyr | Lys | Gln | Pro | Ile | Leu | Ile | Tyr | Ile | |
| | 2180 | | | | 2185 | | | | 2190 | | | | | | |

| ccg | ccc | tat | gcg | gag | ctc | cgg | gga | ggc | tcc | tgg | gtg | gtc | ata | gat | 6624 |
| Pro | Pro | Tyr | Ala | Glu | Leu | Arg | Gly | Gly | Ser | Trp | Val | Val | Ile | Asp | |
| | 2195 | | | | 2200 | | | | 2205 | | | | | | |

| gcc | acc | atc | aac | ccg | ctg | tgc | ata | gaa | atg | tat | gca | gac | aaa | gag | 6669 |
| Ala | Thr | Ile | Asn | Pro | Leu | Cys | Ile | Glu | Met | Tyr | Ala | Asp | Lys | Glu | |
| | 2210 | | | | 2215 | | | | 2220 | | | | | | |

| agc | agg | ggt | ggt | gtt | ctg | gaa | cca | gag | ggg | aca | gtg | gag | att | aag | 6714 |
| Ser | Arg | Gly | Gly | Val | Leu | Glu | Pro | Glu | Gly | Thr | Val | Glu | Ile | Lys | |
| | 2225 | | | | 2230 | | | | 2235 | | | | | | |

| ttc | cga | aag | aaa | gat | ctg | ata | aag | tcc | atg | aga | agg | atc | gat | cca | 6759 |
| Phe | Arg | Lys | Lys | Asp | Leu | Ile | Lys | Ser | Met | Arg | Arg | Ile | Asp | Pro | |
| | 2240 | | | | 2245 | | | | 2250 | | | | | | |

| gct | tac | aag | aag | ctc | atg | gaa | cag | cta | ggg | gaa | cct | gat | ctc | tcc | 6804 |
| Ala | Tyr | Lys | Lys | Leu | Met | Glu | Gln | Leu | Gly | Glu | Pro | Asp | Leu | Ser | |
| | 2255 | | | | 2260 | | | | 2265 | | | | | | |

| gac | aag | gac | cga | aag | gac | ctg | gag | ggc | cgg | cta | aag | gct | cgc | gag | 6849 |
| Asp | Lys | Asp | Arg | Lys | Asp | Leu | Glu | Gly | Arg | Leu | Lys | Ala | Arg | Glu | |
| | 2270 | | | | 2275 | | | | 2280 | | | | | | |

| gac | ctg | ctg | ctc | ccc | atc | tac | cac | cag | gtg | gcg | gtg | cag | ttc | gcc | 6894 |
| Asp | Leu | Leu | Leu | Pro | Ile | Tyr | His | Gln | Val | Ala | Val | Gln | Phe | Ala | |
| | 2285 | | | | 2290 | | | | 2295 | | | | | | |

| gac | ttc | cat | gac | aca | ccc | ggc | cgg | atg | ctg | gag | aag | ggc | gtc | ata | 6939 |
| Asp | Phe | His | Asp | Thr | Pro | Gly | Arg | Met | Leu | Glu | Lys | Gly | Val | Ile | |
| | 2300 | | | | 2305 | | | | 2310 | | | | | | |

| tct | gac | atc | ctg | gag | tgg | aag | acc | gca | cgc | acc | ttc | ctg | tat | tgg | 6984 |
| Ser | Asp | Ile | Leu | Glu | Trp | Lys | Thr | Ala | Arg | Thr | Phe | Leu | Tyr | Trp | |
| | 2315 | | | | 2320 | | | | 2325 | | | | | | |

| cgt | ctg | cgc | cgc | ctc | ctc | ctg | gag | gac | cag | gtc | aag | cag | gag | atc | 7029 |
| Arg | Leu | Arg | Arg | Leu | Leu | Leu | Glu | Asp | Gln | Val | Lys | Gln | Glu | Ile | |
| | 2330 | | | | 2335 | | | | 2340 | | | | | | |

| ctg | cag | gcc | agc | ggg | gag | ctg | agt | cac | gtg | cat | atc | cag | tcc | atg | 7074 |
| Leu | Gln | Ala | Ser | Gly | Glu | Leu | Ser | His | Val | His | Ile | Gln | Ser | Met | |
| | 2345 | | | | 2350 | | | | 2355 | | | | | | |

-continued

| | | | | | | | | | | | | | |
|---|---|---|---|---|---|---|---|---|---|---|---|---|---|
| ctg | cgt | cgc | tgg | ttc | gtg | gag | acg | gag | ggg | gct | gtc | aag | gcc | tac | 7119 |
| Leu | Arg | Arg | Trp | Phe | Val | Glu | Thr | Glu | Gly | Ala | Val | Lys | Ala | Tyr | |
| | 2360 | | | | 2365 | | | | | 2370 | | | | | |

```
ctg cgt cgc tgg ttc gtg gag acg gag ggg gct gtc aag gcc tac      7119
Leu Arg Arg Trp Phe Val Glu Thr Glu Gly Ala Val Lys Ala Tyr
    2360                2365                2370 ttg tgg gac aac aac cag gtg gtt gtg cag tgg ctg gaa cag cac      7164
Leu Trp Asp Asn Asn Gln Val Val Val Gln Trp Leu Glu Gln His
2375                2380                2385 tgg cag gca ggg gat ggc ccg cgc tcc acc atc cgt gag aac atc      7209
Trp Gln Ala Gly Asp Gly Pro Arg Ser Thr Ile Arg Glu Asn Ile
    2390                2395                2400 acg tac ctg aag cac gac tct gtc ctc aag acc atc cga ggc ctg      7254
Thr Tyr Leu Lys His Asp Ser Val Leu Lys Thr Ile Arg Gly Leu
    2405                2410                2415 gtt gaa gaa aac ccc gag gtg gcc gtg gac tgt gtg ata tac ctg      7299
Val Glu Glu Asn Pro Glu Val Ala Val Asp Cys Val Ile Tyr Leu
    2420                2425                2430 agc cag cac atc agc cca gct gag cgg gcg cag gtc gtt cac ctg      7344
Ser Gln His Ile Ser Pro Ala Glu Arg Ala Gln Val Val His Leu
    2435                2440                2445 ctg tct acc atg gac agc ccg gcc tcc acc tga                      7377
Leu Ser Thr Met Asp Ser Pro Ala Ser Thr
    2450                2455
```

<210> SEQ ID NO 6
<211> LENGTH: 2458
<212> TYPE: PRT
<213> ORGANISM: Homo sapiens

<400> SEQUENCE: 6

```
Met Val Leu Leu Leu Cys Leu Ser Arg Leu Ile Phe Ser Cys Leu Thr
1               5                   10                  15

Phe Ser Trp Leu Lys Ile Trp Gly Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Ser Asp Ala Ala Pro Ser
            100                 105                 110

Pro Glu Leu Gln Ala Asn Gly Thr Gly Thr Gln Gly Leu Glu Ala Thr
        115                 120                 125

Asp Thr Asn Gly Leu Ser Ser Ser Ala Arg Pro Gln Gly Gln Gln Ala
    130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220
```

-continued

| | | | | | | | | | | | | | |
|---|---|---|---|---|---|---|---|---|---|---|---|---|---|
| His | Leu | Val | Lys | Arg | Gly | Arg | Glu | His | Lys | Lys | Leu | Asp | Leu | His | Arg |
| 225 | | | | 230 | | | | | 235 | | | | 240 |

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Tyr Gly Gly
            245                 250                 255

Asp Arg Val Ile Glu Lys Val Leu Ile Ala Asn Asn Gly Ile Ala Ala
                260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Tyr Ala Asn Val Glu Leu Ile Val
            325                 330                 335

Asp Ile Ala Lys Arg Ile Pro Val Arg Ala Val Trp Ala Gly Trp Gly
                340                 345                 350

His Ala Ser Glu Asn Pro Lys Leu Pro Glu Leu Leu Cys Lys Asn Gly
        355                 360                 365

Val Ala Phe Leu Gly Pro Pro Ser Glu Ala Met Trp Ala Leu Gly Asp
    370                 375                 380

Lys Ile Ala Ser Thr Val Val Ala Gln Thr Leu Gln Val Pro Thr Leu
385                 390                 395                 400

Pro Trp Ser Gly Ser Gly Leu Thr Val Glu Trp Thr Glu Asp Asp Leu
            405                 410                 415

Gln Gln Gly Lys Arg Ile Ser Val Pro Glu Asp Val Tyr Asp Lys Gly
                420                 425                 430

Cys Val Lys Asp Val Asp Glu Gly Leu Glu Ala Ala Glu Arg Ile Gly
        435                 440                 445

Phe Pro Leu Met Ile Lys Ala Ser Glu Gly Gly Gly Gly Lys Gly Ile
    450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
            485                 490                 495

His Ala Arg His Leu Glu Val Gln Ile Leu Ala Asp Gln Tyr Gly Asn
                500                 505                 510

Ala Val Ser Leu Phe Gly Arg Asp Cys Ser Ile Gln Arg Arg His Gln
        515                 520                 525

Lys Ile Val Glu Glu Ala Pro Ala Thr Ile Ala Pro Leu Ala Ile Phe
    530                 535                 540

Glu Phe Met Glu Gln Cys Ala Ile Arg Leu Ala Lys Thr Val Gly Tyr
545                 550                 555                 560

Val Ser Ala Gly Ala Val Glu Tyr Leu Tyr Ser Gln Asp Gly Ser Phe
            565                 570                 575

His Phe Leu Glu Leu Asn Pro Arg Leu Gln Val Glu His Pro Cys Thr
                580                 585                 590

Glu Met Ile Ala Asp Val Asn Leu Pro Ala Ala Gln Leu Gln Ile Ala
        595                 600                 605

Met Gly Val Pro Leu His Arg Leu Lys Asp Ile Arg Leu Leu Tyr Gly
    610                 615                 620

Glu Ser Pro Trp Gly Val Thr Pro Ile Ser Phe Glu Thr Pro Ser Asn
625                 630                 635                 640

Pro Pro Leu Ala Arg Gly His Val Ile Ala Ala Arg Ile Thr Ser Glu

-continued

```
                645                 650                 655
Asn Pro Asp Glu Gly Phe Lys Pro Ser Ser Gly Thr Val Gln Glu Leu
            660                 665                 670

Asn Phe Arg Ser Ser Lys Asn Val Trp Gly Tyr Phe Ser Val Ala Ala
            675                 680                 685

Thr Gly Gly Leu His Glu Phe Ala Asp Ser Gln Phe Gly His Cys Phe
            690                 695                 700

Ser Trp Gly Glu Asn Arg Glu Glu Ala Ile Ser Asn Met Val Val Ala
705                 710                 715                 720

Leu Lys Glu Leu Ser Ile Arg Gly Asp Phe Arg Thr Thr Val Glu Tyr
                725                 730                 735

Leu Ile Asn Leu Leu Glu Thr Glu Ser Phe Gln Asn Asn Asp Ile Asp
            740                 745                 750

Thr Gly Trp Leu Asp Tyr Leu Ile Ala Glu Lys Val Gln Ala Glu Lys
            755                 760                 765

Pro Asp Ile Met Leu Gly Val Val Cys Gly Ala Leu Asn Val Ala Asp
            770                 775                 780

Ala Met Phe Arg Thr Cys Met Thr Asp Phe Leu His Ser Leu Glu Arg
785                 790                 795                 800

Gly Gln Val Leu Pro Ala Asp Ser Leu Leu Asn Leu Val Asp Val Glu
                805                 810                 815

Leu Ile Tyr Gly Gly Val Lys Tyr Ile Leu Lys Val Ala Arg Gln Ser
            820                 825                 830

Leu Thr Met Phe Val Leu Ile Met Tyr Gly Cys His Ile Glu Ile Asp
            835                 840                 845

Ala His Arg Leu Asn Asp Gly Gly Leu Leu Leu Ser Tyr Asn Gly Asn
            850                 855                 860

Ser Tyr Thr Thr Tyr Met Lys Glu Glu Val Asp Ser Tyr Arg Ile Thr
865                 870                 875                 880

Ile Gly Asn Lys Thr Cys Val Phe Glu Lys Glu Asn Asp Pro Thr Val
                885                 890                 895

Leu Arg Ser Pro Ser Ala Gly Lys Leu Thr Gln Tyr Thr Val Glu Asp
                900                 905                 910

Gly Gly His Val Glu Ala Gly Ser Ser Tyr Ala Glu Met Glu Val Met
            915                 920                 925

Lys Met Ile Met Thr Leu Asn Val Gln Glu Arg Gly Arg Val Lys Tyr
930                 935                 940

Ile Lys Arg Pro Gly Ala Val Leu Glu Ala Gly Cys Val Val Ala Arg
945                 950                 955                 960

Leu Glu Leu Asp Asp Pro Ser Lys Val His Pro Ala Glu Pro Phe Thr
                965                 970                 975

Gly Glu Leu Pro Ala Gln Gln Thr Leu Pro Ile Leu Gly Glu Lys Leu
            980                 985                 990

His Gln Val Phe His Ser Val Leu  Glu Asn Leu Thr Asn  Val Met Ser
                995                 1000                1005

Gly Phe Cys Leu Pro Glu Pro  Val Phe Ser Ile Lys  Leu Lys Glu
            1010                1015                1020

Trp Val  Gln Lys Leu Met Met  Thr Leu Arg His Pro  Ser Leu Pro
            1025                1030                1035

Leu Leu  Glu Leu Gln Glu Ile  Met Thr Ser Val Ala  Gly Arg Ile
            1040                1045                1050

Pro Ala  Pro Val Glu Lys Ser  Val Arg Arg Val Met  Ala Gln Tyr
            1055                1060                1065
```

-continued

```
Ala Ser Asn Ile Thr Ser Val Leu Cys Gln Phe Pro Ser Gln Gln
1070                1075                1080

Ile Ala Thr Ile Leu Asp Cys His Ala Ala Thr Leu Gln Arg Lys
    1085                1090                1095

Ala Asp Arg Glu Ala Phe Phe Ile Asn Thr Gln Ser Ile Val Gln
1100                1105                1110

Leu Val Gln Arg Tyr Arg Ser Gly Ile Arg Gly Tyr Met Lys Thr
    1115                1120                1125

Val Val Leu Asp Leu Leu Arg Arg Tyr Leu Arg Val Glu His His
1130                1135                1140

Phe Gln Gln Ala His Tyr Asp Lys Cys Val Ile Asn Leu Arg Glu
    1145                1150                1155

Gln Phe Lys Pro Asp Met Ser Gln Val Leu Asp Cys Ile Phe Ser
1160                1165                1170

His Ala Gln Val Ala Lys Lys Asn Gln Leu Val Ile Met Leu Ile
    1175                1180                1185

Asp Glu Leu Cys Gly Pro Asp Pro Ser Leu Ser Asp Glu Leu Ile
1190                1195                1200

Ser Ile Leu Asn Glu Leu Thr Gln Leu Ser Lys Ser Glu His Cys
    1205                1210                1215

Lys Val Ala Leu Arg Ala Arg Gln Ile Leu Ile Ala Ser His Leu
1220                1225                1230

Pro Ser Tyr Glu Leu Arg His Asn Gln Val Glu Ser Ile Phe Leu
    1235                1240                1245

Ser Ala Ile Asp Met Tyr Gly His Gln Phe Arg Pro Glu Asn Leu
1250                1255                1260

Lys Lys Leu Ile Leu Ser Glu Thr Thr Ile Phe Asp Val Leu Pro
    1265                1270                1275

Thr Phe Phe Tyr His Ala Asn Lys Val Val Cys Met Ala Ser Leu
1280                1285                1290

Glu Val Tyr Val Arg Arg Gly Tyr Ile Ala Tyr Glu Leu Asn Ser
    1295                1300                1305

Leu Gln His Arg Gln Leu Pro Asp Gly Thr Cys Val Val Glu Phe
1310                1315                1320

Gln Phe Met Leu Pro Ser Ser His Pro Asn Arg Met Thr Val Pro
    1325                1330                1335

Ile Ser Ile Thr Asn Pro Asp Leu Leu Arg His Ser Thr Glu Leu
1340                1345                1350

Phe Met Asp Ser Gly Phe Ser Pro Leu Cys Gln Arg Met Gly Ala
    1355                1360                1365

Met Val Ala Phe Arg Arg Phe Glu Asp Phe Thr Arg Asn Phe Asp
1370                1375                1380

Glu Val Ile Ser Cys Phe Ala Asn Val Pro Lys Asp Thr Pro Leu
    1385                1390                1395

Phe Ser Glu Ala Arg Thr Ser Leu Tyr Ser Glu Asp Asp Cys Lys
1400                1405                1410

Ser Leu Arg Glu Glu Pro Ile His Ile Leu Asn Val Ser Ile Gln
    1415                1420                1425

Cys Ala Asp His Leu Glu Asp Glu Ala Leu Val Pro Ile Leu Arg
1430                1435                1440

Thr Phe Val Gln Ser Lys Lys Asn Ile Leu Val Asp Tyr Gly Leu
    1445                1450                1455
```

```
Arg Arg Ile Thr Phe Leu Ile Ala Gln Glu Lys Glu Phe Pro Lys
1460                1465                1470

Phe Phe Thr Phe Arg Ala Arg Asp Glu Phe Ala Glu Asp Arg Ile
1475                1480                1485

Tyr Arg His Leu Glu Pro Ala Leu Ala Phe Gln Leu Glu Leu Asn
1490                1495                1500

Arg Met Arg Asn Phe Asp Leu Thr Ala Val Pro Cys Ala Asn His
1505                1510                1515

Lys Met His Leu Tyr Leu Gly Val Ala Lys Val Lys Glu Gly Val
1520                1525                1530

Glu Val Thr Asp His Arg Phe Phe Ile Arg Ala Ile Ile Arg His
1535                1540                1545

Ser Asp Leu Ile Thr Lys Glu Ala Ser Phe Glu Tyr Leu Gln Asn
1550                1555                1560

Glu Gly Glu Arg Leu Leu Leu Glu Ala Met Asp Glu Leu Glu Val
1565                1570                1575

Ala Phe Asn Asn Thr Ser Val Arg Thr Asp Cys Asn His Ile Phe
1580                1585                1590

Leu Asn Phe Val Pro Thr Val Ile Met Asp Pro Phe Lys Ile Glu
1595                1600                1605

Glu Ser Val Arg Tyr Met Val Met Arg Tyr Gly Ser Arg Leu Trp
1610                1615                1620

Lys Leu Arg Val Leu Gln Ala Glu Val Lys Ile Asn Ile Arg Gln
1625                1630                1635

Thr Thr Thr Gly Ser Ala Val Pro Ile Arg Leu Phe Ile Thr Asn
1640                1645                1650

Glu Ser Gly Tyr Tyr Leu Asp Ile Ser Leu Tyr Lys Glu Val Thr
1655                1660                1665

Asp Ser Arg Ser Gly Asn Ile Met Phe His Ser Phe Gly Asn Lys
1670                1675                1680

Gln Gly Pro Gln His Gly Met Leu Ile Asn Thr Pro Tyr Val Thr
1685                1690                1695

Lys Asp Leu Leu Gln Ala Lys Arg Phe Gln Ala Gln Thr Leu Gly
1700                1705                1710

Thr Thr Tyr Val Tyr Asp Phe Pro Glu Met Phe Arg Gln Ala Leu
1715                1720                1725

Phe Lys Leu Trp Gly Ser Pro Asp Lys Tyr Pro Lys Asp Ile Leu
1730                1735                1740

Thr Tyr Thr Glu Leu Val Leu Asp Ser Gln Gly Gln Leu Val Glu
1745                1750                1755

Met Asn Arg Leu Pro Gly Gly Asn Glu Val Gly Met Val Ala Phe
1760                1765                1770

Lys Met Arg Phe Lys Thr Gln Glu Tyr Pro Glu Gly Arg Asp Val
1775                1780                1785

Ile Val Ile Gly Asn Asp Ile Thr Phe Arg Ile Gly Ser Phe Gly
1790                1795                1800

Pro Gly Glu Asp Leu Leu Tyr Leu Arg Ala Ser Glu Met Ala Arg
1805                1810                1815

Ala Glu Gly Ile Pro Lys Ile Tyr Val Ala Ala Asn Ser Gly Ala
1820                1825                1830

Arg Ile Gly Met Ala Glu Glu Ile Lys His Met Phe His Val Ala
1835                1840                1845

Trp Val Asp Pro Glu Asp Pro His Lys Gly Phe Lys Tyr Leu Tyr
```

-continued

```
                1850                1855                1860
Leu Thr Pro Gln Asp Tyr Thr Arg Ile Ser Ser Leu Asn Ser Val
    1865                1870                1875
His Cys Lys His Ile Glu Glu Gly Gly Glu Ser Arg Tyr Met Ile
    1880                1885                1890
Thr Asp Ile Ile Gly Lys Asp Asp Gly Leu Gly Val Glu Asn Leu
    1895                1900                1905
Arg Gly Ser Gly Met Ile Ala Gly Glu Ser Ser Leu Ala Tyr Glu
    1910                1915                1920
Glu Ile Val Thr Ile Ser Leu Val Thr Cys Arg Ala Ile Gly Ile
    1925                1930                1935
Gly Ala Tyr Leu Val Arg Leu Gly Gln Arg Val Ile Gln Val Glu
    1940                1945                1950
Asn Ser His Ile Ile Leu Thr Gly Ala Ser Ala Leu Asn Lys Val
    1955                1960                1965
Leu Gly Arg Glu Val Tyr Thr Ser Asn Asn Gln Leu Gly Gly Val
    1970                1975                1980
Gln Ile Met His Tyr Asn Gly Val Ser His Ile Thr Val Pro Asp
    1985                1990                1995
Asp Phe Glu Gly Val Tyr Thr Ile Leu Glu Trp Leu Ser Tyr Met
    2000                2005                2010
Pro Lys Asp Asn His Ser Pro Val Pro Ile Ile Thr Pro Thr Asp
    2015                2020                2025
Pro Ile Asp Arg Glu Ile Glu Phe Leu Pro Ser Arg Ala Pro Tyr
    2030                2035                2040
Asp Pro Arg Trp Met Leu Ala Gly Arg Pro His Pro Thr Leu Lys
    2045                2050                2055
Gly Thr Trp Gln Ser Gly Phe Phe Asp His Gly Ser Phe Lys Glu
    2060                2065                2070
Ile Met Ala Pro Trp Ala Gln Thr Val Thr Gly Arg Ala Arg
    2075                2080                2085
Leu Gly Gly Ile Pro Val Gly Val Ile Ala Val Glu Thr Arg Thr
    2090                2095                2100
Val Glu Val Ala Val Pro Ala Asp Pro Ala Asn Leu Asp Ser Glu
    2105                2110                2115
Ala Lys Ile Ile Gln Gln Ala Gly Gln Val Trp Phe Pro Asp Ser
    2120                2125                2130
Ala Tyr Lys Thr Ala Gln Ala Ile Lys Asp Phe Asn Arg Glu Lys
    2135                2140                2145
Leu Pro Leu Met Ile Phe Ala Asn Trp Arg Gly Phe Ser Gly Gly
    2150                2155                2160
Met Lys Asp Met Tyr Asp Gln Val Leu Lys Phe Gly Ala Tyr Ile
    2165                2170                2175
Val Asp Gly Leu Arg Gln Tyr Lys Gln Pro Ile Leu Ile Tyr Ile
    2180                2185                2190
Pro Pro Tyr Ala Glu Leu Arg Gly Gly Ser Trp Val Val Ile Asp
    2195                2200                2205
Ala Thr Ile Asn Pro Leu Cys Ile Glu Met Tyr Ala Asp Lys Glu
    2210                2215                2220
Ser Arg Gly Gly Val Leu Glu Pro Glu Gly Thr Val Glu Ile Lys
    2225                2230                2235
Phe Arg Lys Lys Asp Leu Ile Lys Ser Met Arg Arg Ile Asp Pro
    2240                2245                2250
```

```
Ala Tyr Lys Lys Leu Met Glu Gln Leu Gly Glu Pro Asp Leu Ser
    2255            2260            2265

Asp Lys Asp Arg Lys Asp Leu Glu Gly Arg Leu Lys Ala Arg Glu
    2270            2275            2280

Asp Leu Leu Leu Pro Ile Tyr His Gln Val Ala Val Gln Phe Ala
    2285            2290            2295

Asp Phe His Asp Thr Pro Gly Arg Met Leu Glu Lys Gly Val Ile
    2300            2305            2310

Ser Asp Ile Leu Glu Trp Lys Thr Ala Arg Thr Phe Leu Tyr Trp
    2315            2320            2325

Arg Leu Arg Arg Leu Leu Leu Glu Asp Gln Val Lys Gln Glu Ile
    2330            2335            2340

Leu Gln Ala Ser Gly Glu Leu Ser His Val His Ile Gln Ser Met
    2345            2350            2355

Leu Arg Arg Trp Phe Val Glu Thr Glu Gly Ala Val Lys Ala Tyr
    2360            2365            2370

Leu Trp Asp Asn Asn Gln Val Val Val Gln Trp Leu Glu Gln His
    2375            2380            2385

Trp Gln Ala Gly Asp Gly Pro Arg Ser Thr Ile Arg Glu Asn Ile
    2390            2395            2400

Thr Tyr Leu Lys His Asp Ser Val Leu Lys Thr Ile Arg Gly Leu
    2405            2410            2415

Val Glu Glu Asn Pro Glu Val Ala Val Asp Cys Val Ile Tyr Leu
    2420            2425            2430

Ser Gln His Ile Ser Pro Ala Glu Arg Ala Gln Val Val His Leu
    2435            2440            2445

Leu Ser Thr Met Asp Ser Pro Ala Ser Thr
    2450            2455

<210> SEQ ID NO 7
<211> LENGTH: 7371
<212> TYPE: DNA
<213> ORGANISM: Rattus norvegicus
<220> FEATURE:
<221> NAME/KEY: CDS
<222> LOCATION: (1)..(7371)

<400> SEQUENCE: 7 atg gtc ttg ctt ctc ttt ctg act tac ctg gtt ttc tcc tgc ctg acc     48
Met Val Leu Leu Leu Phe Leu Thr Tyr Leu Val Phe Ser Cys Leu Thr
1               5                   10                  15 att tcc tgg tta aaa atc tgg ggg aag atg aca gac tcg agg ccg ctc     96
Ile Ser Trp Leu Lys Ile Trp Gly Lys Met Thr Asp Ser Arg Pro Leu
            20                  25                  30 agc aac agt aag gtg gat gca agc ctc ctt ccg agc aag gag gag tct    144
Ser Asn Ser Lys Val Asp Ala Ser Leu Leu Pro Ser Lys Glu Glu Ser
        35                  40                  45 ttt gcc tcg gac cag tca gag gag cat ggc gac tgc agc tgt ccg ttg    192
Phe Ala Ser Asp Gln Ser Glu Glu His Gly Asp Cys Ser Cys Pro Leu
    50                  55                  60 aca act cct gac cag gag gag ctg gcc tcc cac gga ggt cct gta gat    240
Thr Thr Pro Asp Gln Glu Glu Leu Ala Ser His Gly Gly Pro Val Asp
65                  70                  75                  80 gcc agt cag cag agg aac tct gta cca acc tca cac cag aag cct ccg    288
Ala Ser Gln Gln Arg Asn Ser Val Pro Thr Ser His Gln Lys Pro Pro
                85                  90                  95 agg aac cca cta tct tcc aat gac acc tgt tcc tcc cca gaa ctc caa    336
```

```
                Arg Asn Pro Leu Ser Ser Asn Asp Thr Cys Ser Ser Pro Glu Leu Gln
                                100                 105                 110 acc aac ggg gta gca gca cct ggc tca gag gtt cca gaa gcc aac ggg          384
Thr Asn Gly Val Ala Ala Pro Gly Ser Glu Val Pro Glu Ala Asn Gly
            115                 120                 125 ttg cct ttc cca gcc agg cct cag acc cag aga acg gga tcc ccc act          432
Leu Pro Phe Pro Ala Arg Pro Gln Thr Gln Arg Thr Gly Ser Pro Thr
130                 135                 140 agg gag gac aag aag cag gca ccc atc aag agg cag ctg atg acc agc          480
Arg Glu Asp Lys Lys Gln Ala Pro Ile Lys Arg Gln Leu Met Thr Ser
145                 150                 155                 160 ttt atc ctg ggc tcc ctc gat gac aac tcc tct gac gag gac cct agt          528
Phe Ile Leu Gly Ser Leu Asp Asp Asn Ser Ser Asp Glu Asp Pro Ser
                165                 170                 175 tct aac tcc ttt cag acc tcc tct cgg aag ggc agc agg gat agc ctg          576
Ser Asn Ser Phe Gln Thr Ser Ser Arg Lys Gly Ser Arg Asp Ser Leu
                180                 185                 190 ggc acc tgt tcc cag gag gct gca ttg aac aca gct gat cct gag tct          624
Gly Thr Cys Ser Gln Glu Ala Ala Leu Asn Thr Ala Asp Pro Glu Ser
            195                 200                 205 cac aca cct act atg agg ccc agc atg tct gga ctc cat ctg gtg aag          672
His Thr Pro Thr Met Arg Pro Ser Met Ser Gly Leu His Leu Val Lys
210                 215                 220 aga ggc cgt gaa cac aag aaa ctg gac ctg cac aga gat ttc act gta          720
Arg Gly Arg Glu His Lys Lys Leu Asp Leu His Arg Asp Phe Thr Val
225                 230                 235                 240 gct tcc cca gcc gaa ttt gtc acc cgc ttt gga ggc aac agg gtt atc          768
Ala Ser Pro Ala Glu Phe Val Thr Arg Phe Gly Gly Asn Arg Val Ile
                245                 250                 255 gag acg gtg ctc atc gcc aat aat ggt atc gct gcg gtc aag tgg atg          816
Glu Thr Val Leu Ile Ala Asn Asn Gly Ile Ala Ala Val Lys Trp Met
                260                 265                 270 cgc tcc atc cgc cgc tgg gcc tat gag atg ttc cgt aat gaa cgc gct          864
Arg Ser Ile Arg Arg Trp Ala Tyr Glu Met Phe Arg Asn Glu Arg Ala
            275                 280                 285 atc cgg ttt gtg gtt atg gtg aca ccc gag gat ctt aag gcc aac gca          912
Ile Arg Phe Val Val Met Val Thr Pro Glu Asp Leu Lys Ala Asn Ala
290                 295                 300 gag tac tac aag atg gcg gac cca gta ctt ccg gtc cca gga gga ccc          960
Glu Tyr Tyr Lys Met Ala Asp Pro Val Leu Pro Val Pro Gly Gly Pro
305                 310                 315                 320 aat aat aac aac tac gcc aac gtt gag ctg atc ata gac att gcc aag         1008
Asn Asn Asn Asn Tyr Ala Asn Val Glu Leu Ile Ile Asp Ile Ala Lys
                325                 330                 335 aga atc cct gtg cag gcc gtg tgg gct ggc tgg ggc cac gct tcg gaa         1056
Arg Ile Pro Val Gln Ala Val Trp Ala Gly Trp Gly His Ala Ser Glu
                340                 345                 350 aac ccc aaa ctt cca gag cta ctg tgc aag cac ggg att gct ttt cta         1104
Asn Pro Lys Leu Pro Glu Leu Leu Cys Lys His Gly Ile Ala Phe Leu
            355                 360                 365 ggt ccc cga gtg agg cca atg ttg ggc ctg gga gac agg ctc tcc tcc         1152
Gly Pro Arg Val Arg Pro Met Leu Gly Leu Gly Asp Arg Leu Ser Ser
370                 375                 380 acc att gta gcc cag aca ttg cag atc cca act cta ccc tgg agc gga         1200
Thr Ile Val Ala Gln Thr Leu Gln Ile Pro Thr Leu Pro Trp Ser Gly
385                 390                 395                 400 agc ggt ctc aca gtg gag tgg acg gag gac agc cag cat cag ggc aaa         1248
Ser Gly Leu Thr Val Glu Trp Thr Glu Asp Ser Gln His Gln Gly Lys
                405                 410                 415
```

|  |  |
|---|---|
| tgc atc agc gtc acg gaa gac gtt tat gaa caa ggc tgt gtg aga gat<br>Cys Ile Ser Val Thr Glu Asp Val Tyr Glu Gln Gly Cys Val Arg Asp<br>420 425 430 | 1296 |
| gtg gac gaa ggc ttg cag gca gca gaa aaa gta gga ttt cct ctg atg<br>Val Asp Glu Gly Leu Gln Ala Ala Glu Lys Val Gly Phe Pro Leu Met<br>435 440 445 | 1344 |
| atc aaa gcc tct gaa ggt gga gga ggg aaa gga atc cgg cag gct gag<br>Ile Lys Ala Ser Glu Gly Gly Gly Gly Lys Gly Ile Arg Gln Ala Glu<br>450 455 460 | 1392 |
| agt gca gag gac ttc cca tgc ttt ttc aga cag gtg cag agt gag atc<br>Ser Ala Glu Asp Phe Pro Cys Phe Phe Arg Gln Val Gln Ser Glu Ile<br>465 470 475 480 | 1440 |
| ccg ggc tcg ccc atc ttt ctc atg aag ctg gcc cag aat gcc cgg cac<br>Pro Gly Ser Pro Ile Phe Leu Met Lys Leu Ala Gln Asn Ala Arg His<br>485 490 495 | 1488 |
| ttg gag gtc cag gtc ttg gca gat cag tat ggg aac gca gtg tcc ctg<br>Leu Glu Val Gln Val Leu Ala Asp Gln Tyr Gly Asn Ala Val Ser Leu<br>500 505 510 | 1536 |
| ttt gga cga gac tgc tcc atc cag agg cgg cac cag aag atc att gag<br>Phe Gly Arg Asp Cys Ser Ile Gln Arg Arg His Gln Lys Ile Ile Glu<br>515 520 525 | 1584 |
| gag gct ccg gcc aac atc gct gct ccg gct gtg ttt gag ttc atg gaa<br>Glu Ala Pro Ala Asn Ile Ala Ala Pro Ala Val Phe Glu Phe Met Glu<br>530 535 540 | 1632 |
| cag tgt gcc gtc ctc ctg gcc aag act gtg gtt tat gtg agc gcg gga<br>Gln Cys Ala Val Leu Leu Ala Lys Thr Val Val Tyr Val Ser Ala Gly<br>545 550 555 560 | 1680 |
| acc gtg ggg tac cta tac agc cag gat ggc agc ttt cac ttc ttg gag<br>Thr Val Gly Tyr Leu Tyr Ser Gln Asp Gly Ser Phe His Phe Leu Glu<br>565 570 575 | 1728 |
| ctg aac cca cgc ctg cag gtg gaa cat ccc tgc act gaa atg att gca<br>Leu Asn Pro Arg Leu Gln Val Glu His Pro Cys Thr Glu Met Ile Ala<br>580 585 590 | 1776 |
| gat gtc aac ctg ccc gct gca cag tta cag atc gcc atg ggc gtg ccc<br>Asp Val Asn Leu Pro Ala Ala Gln Leu Gln Ile Ala Met Gly Val Pro<br>595 600 605 | 1824 |
| ctg cac cgg ctg aag gac ata cgg ctt ctg tac gga gag tcc ccc tgg<br>Leu His Arg Leu Lys Asp Ile Arg Leu Leu Tyr Gly Glu Ser Pro Trp<br>610 615 620 | 1872 |
| gga gtg acc ccc gtt tct ttt gag acc cct ttg agc cct ccc att gcc<br>Gly Val Thr Pro Val Ser Phe Glu Thr Pro Leu Ser Pro Pro Ile Ala<br>625 630 635 640 | 1920 |
| cga ggc cat gtc att gca gcc agg atc acc agc gaa aac cca gac gag<br>Arg Gly His Val Ile Ala Ala Arg Ile Thr Ser Glu Asn Pro Asp Glu<br>645 650 655 | 1968 |
| gcc ttt aag cca agc tca ggg aca gta cag gag ctg aac ttc cgc agc<br>Ala Phe Lys Pro Ser Ser Gly Thr Val Gln Glu Leu Asn Phe Arg Ser<br>660 665 670 | 2016 |
| aac aag aac gtg tgg ggt tac ttc agc gtg gcc gct gct gga ggc ttg<br>Asn Lys Asn Val Trp Gly Tyr Phe Ser Val Ala Ala Ala Gly Gly Leu<br>675 680 685 | 2064 |
| cac gag ttt ccg att tcc cag ttt ggg cac tgc ttc tcc tgg ggc gag<br>His Glu Phe Pro Ile Ser Gln Phe Gly His Cys Phe Ser Trp Gly Glu<br>690 695 700 | 2112 |
| aac cag gaa gag gct att tcg aac atg gtg gtg gct ttg aaa gaa ctg<br>Asn Gln Glu Glu Ala Ile Ser Asn Met Val Val Ala Leu Lys Glu Leu<br>705 710 715 720 | 2160 |
| tct atc cgg ggt gac ttc cgg acc acc gtg gaa tat ctc gtc aac ctt<br>Ser Ile Arg Gly Asp Phe Arg Thr Thr Val Glu Tyr Leu Val Asn Leu<br>725 730 735 | 2208 |

-continued

| | |
|---|---|
| ctg gag acg gag agc tta cag aac aat gat atc gac acg ggg tgg ctg<br>Leu Glu Thr Glu Ser Leu Gln Asn Asn Asp Ile Asp Thr Gly Trp Leu<br>              740                    745                    750 | 2256 |
| gac cac ctc atc gct cag cgg gtg cag gca gag aag ccg gac atc atg<br>Asp His Leu Ile Ala Gln Arg Val Gln Ala Glu Lys Pro Asp Ile Met<br>        755                    760                    765 | 2304 |
| ctc ggg gtg gtg ttt ggg gcc ttg aac gtg gca gac gca atg ttc aga<br>Leu Gly Val Val Phe Gly Ala Leu Asn Val Ala Asp Ala Met Phe Arg<br>770                    775                    780 | 2352 |
| acc tgt att acg gaa ttc ctg cat tcc ttg gaa agg ggt cag gtc ctc<br>Thr Cys Ile Thr Glu Phe Leu His Ser Leu Glu Arg Gly Gln Val Leu<br>785                    790                    795                    800 | 2400 |
| ccg gct gat tct ctg ctg aac atc gtg gac gtt gaa ttg att tac gga<br>Pro Ala Asp Ser Leu Leu Asn Ile Val Asp Val Glu Leu Ile Tyr Gly<br>                        805                    810                    815 | 2448 |
| ggc atc aaa tat gtt ctc aag gtg gcc cgg cag tcc ctg acc atg ttt<br>Gly Ile Lys Tyr Val Leu Lys Val Ala Arg Gln Ser Leu Thr Met Phe<br>        820                    825                    830 | 2496 |
| gtc ctc atc atg aat ggt tgc cac atc gag atc gat gcc cac cgg ccg<br>Val Leu Ile Met Asn Gly Cys His Ile Glu Ile Asp Ala His Arg Pro<br>835                    840                    845 | 2544 |
| aac gat ggg ggc ctg ctc ctg tcc tac aat ggt agc agt tac act aca<br>Asn Asp Gly Gly Leu Leu Leu Ser Tyr Asn Gly Ser Ser Tyr Thr Thr<br>850                    855                    860 | 2592 |
| tac atg aag gaa gag gtg gac agt tac cgg atc act atc ggc aat aag<br>Tyr Met Lys Glu Glu Val Asp Ser Tyr Arg Ile Thr Ile Gly Asn Lys<br>865                    870                    875                    880 | 2640 |
| aca tgc gtg ttt gaa aag gaa aac gac ccc acc gtc ctg aga tcc ccc<br>Thr Cys Val Phe Glu Lys Glu Asn Asp Pro Thr Val Leu Arg Ser Pro<br>                        885                    890                    895 | 2688 |
| tcg gct ggg aag ctg atg cag tac acg gtg gag gat ggc cag cac gtg<br>Ser Ala Gly Lys Leu Met Gln Tyr Thr Val Glu Asp Gly Gln His Val<br>        900                    905                    910 | 2736 |
| gaa gtc ggg agc agc tat gct gag atg gag gtg atg aag atg atc atg<br>Glu Val Gly Ser Ser Tyr Ala Glu Met Glu Val Met Lys Met Ile Met<br>915                    920                    925 | 2784 |
| acc ctg aac gtg caa gag agc ggc cgg gtg aac tac atc aag cga cca<br>Thr Leu Asn Val Gln Glu Ser Gly Arg Val Asn Tyr Ile Lys Arg Pro<br>930                    935                    940 | 2832 |
| ggg gcg gta ttg gag gct ggc tgc gtg gtg gca aag cta gaa ctc gat<br>Gly Ala Val Leu Glu Ala Gly Cys Val Val Ala Lys Leu Glu Leu Asp<br>945                    950                    955                    960 | 2880 |
| gac cct tca aaa gtg cac gcg gca cag ccg ttc aca ggg gag ctc ccc<br>Asp Pro Ser Lys Val His Ala Ala Gln Pro Phe Thr Gly Glu Leu Pro<br>                        965                    970                    975 | 2928 |
| gcc cag cag act ctg ccc atc ctc ggg gag agg ctg cat cag gtg ttc<br>Ala Gln Gln Thr Leu Pro Ile Leu Gly Glu Arg Leu His Gln Val Phe<br>        980                    985                    990 | 2976 |
| cac agc gtc ttg gaa aat ctg acc aat gtc atg aat ggc tac tgc ctg<br>His Ser Val Leu Glu Asn Leu Thr Asn Val Met Asn Gly Tyr Cys Leu<br>        995                    1000                  1005 | 3024 |
| ccc gag ccc ttc ttc agc atg aag ctg aag gac tgg gtg gag aag<br>Pro Glu Pro Phe Phe Ser Met Lys Leu Lys Asp Trp Val Glu Lys<br>1010                    1015                    1020 | 3069 |
| ccc atg atg act ctc cgg cat ccc tcc cta cct ctg ctg gag ctg<br>Pro Met Met Thr Leu Arg His Pro Ser Leu Pro Leu Leu Glu Leu<br>1025                    1030                    1035 | 3114 |
| cag gag atc atg acc agc gtg gca gac cgc atc ccg gtt ccg gtg<br>Gln Glu Ile Met Thr Ser Val Ala Asp Arg Ile Pro Val Pro Val | 3159 |

-continued

| | | | | | | | | | | | | | |
|---|---|---|---|---|---|---|---|---|---|---|---|---|---|
| | | | 1040 | | | | 1045 | | | | 1050 | | |
| gag | aag | gca | gtc | cgc | agg | gtg | ttt | gcg | cag | gac | gcc | agc | aac | atc | 3204 |
| Glu | Lys | Ala | Val | Arg | Arg | Val | Phe | Ala | Gln | Asp | Ala | Ser | Asn | Ile | |
| | 1055 | | | | 1060 | | | | | 1065 | | | | | |
| act | tcg | gtg | ctc | tgc | cag | ttc | ccc | agc | cag | cag | ata | gcc | acc | atc | 3249 |
| Thr | Ser | Val | Leu | Cys | Gln | Phe | Pro | Ser | Gln | Gln | Ile | Ala | Thr | Ile | |
| | 1070 | | | | 1075 | | | | | 1080 | | | | | |
| ctg | gac | tgc | cac | gcc | gcc | acc | ctg | cag | cgt | aag | gtg | gac | cga | gag | 3294 |
| Leu | Asp | Cys | His | Ala | Ala | Thr | Leu | Gln | Arg | Lys | Val | Asp | Arg | Glu | |
| | 1085 | | | | 1090 | | | | | 1095 | | | | | |
| gcc | ttc | ttc | atg | aac | aca | cag | agc | atc | gtg | cag | ctg | atc | cag | aga | 3339 |
| Ala | Phe | Phe | Met | Asn | Thr | Gln | Ser | Ile | Val | Gln | Leu | Ile | Gln | Arg | |
| | 1100 | | | | 1105 | | | | | 1110 | | | | | |
| tac | cgc | agt | ggg | acc | cgt | ggc | atc | atg | aag | gct | gtg | gtg | cta | gac | 3384 |
| Tyr | Arg | Ser | Gly | Thr | Arg | Gly | Ile | Met | Lys | Ala | Val | Val | Leu | Asp | |
| | 1115 | | | | 1120 | | | | | 1125 | | | | | |
| ctc | ctg | agg | aga | tat | ctg | aac | gtg | gag | cat | cat | ttc | cag | caa | gcc | 3429 |
| Leu | Leu | Arg | Arg | Tyr | Leu | Asn | Val | Glu | His | His | Phe | Gln | Gln | Ala | |
| | 1130 | | | | 1135 | | | | | 1140 | | | | | |
| cac | tat | gac | aag | tgt | gtg | atc | aac | ctg | agg | gag | cag | ttc | aag | gcg | 3474 |
| His | Tyr | Asp | Lys | Cys | Val | Ile | Asn | Leu | Arg | Glu | Gln | Phe | Lys | Ala | |
| | 1145 | | | | 1150 | | | | | 1155 | | | | | |
| gac | atg | act | cgg | gtg | ctg | gac | tgc | atc | ttc | tca | cac | tca | caa | gtg | 3519 |
| Asp | Met | Thr | Arg | Val | Leu | Asp | Cys | Ile | Phe | Ser | His | Ser | Gln | Val | |
| | 1160 | | | | 1165 | | | | | 1170 | | | | | |
| gcc | aag | aag | aac | cag | ctg | gtg | acc | atg | ttg | ata | gat | gag | ctg | tgt | 3564 |
| Ala | Lys | Lys | Asn | Gln | Leu | Val | Thr | Met | Leu | Ile | Asp | Glu | Leu | Cys | |
| | 1175 | | | | 1180 | | | | | 1185 | | | | | |
| ggc | cca | gac | ccc | acc | ctg | tca | gaa | gag | ctg | acc | tcc | atc | ctc | aag | 3609 |
| Gly | Pro | Asp | Pro | Thr | Leu | Ser | Glu | Glu | Leu | Thr | Ser | Ile | Leu | Lys | |
| | 1190 | | | | 1195 | | | | | 1200 | | | | | |
| gaa | ctc | acg | cag | ttg | agc | agg | agt | gag | cac | tgc | aag | gtg | gcc | ctg | 3654 |
| Glu | Leu | Thr | Gln | Leu | Ser | Arg | Ser | Glu | His | Cys | Lys | Val | Ala | Leu | |
| | 1205 | | | | 1210 | | | | | 1215 | | | | | |
| aga | gcc | agg | cag | gtc | ctg | att | gcc | tct | cac | ctc | ccc | tcc | tac | gag | 3699 |
| Arg | Ala | Arg | Gln | Val | Leu | Ile | Ala | Ser | His | Leu | Pro | Ser | Tyr | Glu | |
| | 1220 | | | | 1225 | | | | | 1230 | | | | | |
| ctg | cgg | cac | aac | cag | gtg | gag | tca | tct | tcc | tgt | cag | cca | ttg | aca | 3744 |
| Leu | Arg | His | Asn | Gln | Val | Glu | Ser | Ser | Ser | Cys | Gln | Pro | Leu | Thr | |
| | 1235 | | | | 1240 | | | | | 1245 | | | | | |
| tgt | aat | ggc | cac | cag | ttc | tgc | ccg | gaa | aac | ctc | aag | aaa | cta | ata | 3789 |
| Cys | Asn | Gly | His | Gln | Phe | Cys | Pro | Glu | Asn | Leu | Lys | Lys | Leu | Ile | |
| | 1250 | | | | 1255 | | | | | 1260 | | | | | |
| ctt | tcg | gaa | acg | acc | ata | ttc | gat | gtc | ctg | ccc | act | ttc | ttc | tat | 3834 |
| Leu | Ser | Glu | Thr | Thr | Ile | Phe | Asp | Val | Leu | Pro | Thr | Phe | Phe | Tyr | |
| | 1265 | | | | 1270 | | | | | 1275 | | | | | |
| cac | gct | aac | aag | gtc | gtc | tgt | atg | gcg | tcc | ctg | gag | gtt | tat | gtg | 3879 |
| His | Ala | Asn | Lys | Val | Val | Cys | Met | Ala | Ser | Leu | Glu | Val | Tyr | Val | |
| | 1280 | | | | 1285 | | | | | 1290 | | | | | |
| agg | aga | ggt | tac | atc | gcc | tac | gag | tta | aac | agc | cta | cag | cac | cgg | 3924 |
| Arg | Arg | Gly | Tyr | Ile | Ala | Tyr | Glu | Leu | Asn | Ser | Leu | Gln | His | Arg | |
| | 1295 | | | | 1300 | | | | | 1305 | | | | | |
| gag | ctc | cct | gac | ggc | acc | tgc | gtg | gtg | gag | ttc | cag | ttc | atg | ctg | 3969 |
| Glu | Leu | Pro | Asp | Gly | Thr | Cys | Val | Val | Glu | Phe | Gln | Phe | Met | Leu | |
| | 1310 | | | | 1315 | | | | | 1320 | | | | | |
| ccg | tct | tcc | cac | ccc | aac | cgg | atg | gcc | atg | ccc | atc | aat | gtc | tct | 4014 |
| Pro | Ser | Ser | His | Pro | Asn | Arg | Met | Ala | Met | Pro | Ile | Asn | Val | Ser | |
| | 1325 | | | | 1330 | | | | | 1335 | | | | | |
| gac | cct | gac | ctg | ctg | aga | cac | agt | aag | gaa | ctc | ttc | atg | gac | agt | 4059 |

-continued

| | | | | | | | | | | | | |
|---|---|---|---|---|---|---|---|---|---|---|---|---|
| Asp Pro<br>1340 | Asp | Leu | Leu | Arg | His<br>1345 | Ser | Lys | Glu | Leu<br>1350 | Phe | Met | Asp Ser |

```
ggc ttc tcc cca ctg tgt cac cag cgg atg ggg gcc atg gtg gcc       4104
Gly Phe Ser Pro Leu Cys His Gln Arg Met Gly Ala Met Val Ala
    1355                1360                1365 ttc agg aga ttt gag gag ttc acc agg aac ttc gat gaa gtc atc       4149
Phe Arg Arg Phe Glu Glu Phe Thr Arg Asn Phe Asp Glu Val Ile
1370                1375                1380 tcc tgc ttt gcc aac gtg cct aca gac act cct ctc ttc agt aag       4194
Ser Cys Phe Ala Asn Val Pro Thr Asp Thr Pro Leu Phe Ser Lys
    1385                1390                1395 gcg tgc act tcc ctc tac tca gag gag gac agc aag agc ctt caa       4239
Ala Cys Thr Ser Leu Tyr Ser Glu Glu Asp Ser Lys Ser Leu Gln
1400                1405                1410 gag gag ccc atc cac atc ctg aat gtg gcc atc cag tgc gcc gac       4284
Glu Glu Pro Ile His Ile Leu Asn Val Ala Ile Gln Cys Ala Asp
    1415                1420                1425 cac atg gag gac gag aga ctg gtg ccg gtt ttc cgt gcc ttt gta       4329
His Met Glu Asp Glu Arg Leu Val Pro Val Phe Arg Ala Phe Val
1430                1435                1440 cag tcc aag aaa cac atc ctt gtg gat tac gga ctg cga aga atc       4374
Gln Ser Lys Lys His Ile Leu Val Asp Tyr Gly Leu Arg Arg Ile
    1445                1450                1455 aca ttc ctt atc gcc caa gag aag gaa ttt ccc aag ttc ttc acg       4419
Thr Phe Leu Ile Ala Gln Glu Lys Glu Phe Pro Lys Phe Phe Thr
1460                1465                1470 ttc aga gcg aga gat gag ttt gca gaa gac cgg att tac cgc cac       4464
Phe Arg Ala Arg Asp Glu Phe Ala Glu Asp Arg Ile Tyr Arg His
    1475                1480                1485 ttg gag ccg ggc ctg gcc ttc cag ctg gag ctg agc cgg atg cgc       4509
Leu Glu Pro Gly Leu Ala Phe Gln Leu Glu Leu Ser Arg Met Arg
1490                1495                1500 aac ttt gac ttg acg gcc gtg ccc tgt gcc aac cat aag atg cat       4554
Asn Phe Asp Leu Thr Ala Val Pro Cys Ala Asn His Lys Met His
    1505                1510                1515 ctt tac ctg gga gcc gcc aag gtg aag gaa ggg ctg gag gtg act       4599
Leu Tyr Leu Gly Ala Ala Lys Val Lys Glu Gly Leu Glu Val Thr
1520                1525                1530 gac cac agg ttc ttc atc cga gcc atc ata agg cac tca gac ctg       4644
Asp His Arg Phe Phe Ile Arg Ala Ile Ile Arg His Ser Asp Leu
    1535                1540                1545 atc acc aag gaa gcc tcc ttc gag tac ctg cag aat gaa ggg gag       4689
Ile Thr Lys Glu Ala Ser Phe Glu Tyr Leu Gln Asn Glu Gly Glu
1550                1555                1560 cgg ctg ctg ctg gaa gcc atg gac gag ctg gag gtg gcg ttc aac       4734
Arg Leu Leu Leu Glu Ala Met Asp Glu Leu Glu Val Ala Phe Asn
    1565                1570                1575 aac acc agc gtg cgc act gac tgc aac cac atc ttc ctc aac ttc       4779
Asn Thr Ser Val Arg Thr Asp Cys Asn His Ile Phe Leu Asn Phe
1580                1585                1590 gtg gcc cac gtc atc atg gac cca ctc aag atc gag gag tcg gtg       4824
Val Ala His Val Ile Met Asp Pro Leu Lys Ile Glu Glu Ser Val
    1595                1600                1605 cgt gcc atg gtc atg cgt tac ggc agt cgg ctg tgg aag ctc cgt       4869
Arg Ala Met Val Met Arg Tyr Gly Ser Arg Leu Trp Lys Leu Arg
1610                1615                1620 gtg ctg cag gca caa gtt aag atc aac atc cgt cag acg acc tcg       4914
Val Leu Gln Ala Gln Val Lys Ile Asn Ile Arg Gln Thr Thr Ser
    1625                1630                1635
```

```
gac tgc gcc gtc ccc att cgc ctc ttc atc acc aac gag tcc ggc    4959
Asp Cys Ala Val Pro Ile Arg Leu Phe Ile Thr Asn Glu Ser Gly
1640            1645                1650 tac tac ctg gac atc agc ctc tac aaa gaa gtg acc gac tcc aga    5004
Tyr Tyr Leu Asp Ile Ser Leu Tyr Lys Glu Val Thr Asp Ser Arg
     1655                1660                1665 tcc gga aac atc atg ttt cat tcc ttc ggc aac aaa caa ggg agc    5049
Ser Gly Asn Ile Met Phe His Ser Phe Gly Asn Lys Gln Gly Ser
1670                1675                1680 ctg cac ggg atg ctg atc aac acg ccc tac gtc acc aag gat ctg    5094
Leu His Gly Met Leu Ile Asn Thr Pro Tyr Val Thr Lys Asp Leu
     1685                1690                1695 ctc caa gcc aag cga ttc cag gcg cag tcc ctg ggg acc acc tat    5139
Leu Gln Ala Lys Arg Phe Gln Ala Gln Ser Leu Gly Thr Thr Tyr
1700                1705                1710 gtg tac gac ttc cca gag atg ttc agg cag gct ctc ttt aaa ttg    5184
Val Tyr Asp Phe Pro Glu Met Phe Arg Gln Ala Leu Phe Lys Leu
     1715                1720                1725 tgg ggc tcc cca gag aag tac ggg ccc gat atc ctg aca tac aca    5229
Trp Gly Ser Pro Glu Lys Tyr Gly Pro Asp Ile Leu Thr Tyr Thr
1730                1735                1740 gag ctg gtg ttg gac tcc cag ggc cag ctg gtg gag atg aac cgg    5274
Glu Leu Val Leu Asp Ser Gln Gly Gln Leu Val Glu Met Asn Arg
     1745                1750                1755 ctt cct ggt tgt aac gag gtg ggc atg gtg gtt ttc aaa atg agg    5319
Leu Pro Gly Cys Asn Glu Val Gly Met Val Val Phe Lys Met Arg
1760                1765                1770 ttc aag acc ccg gag tat cca gaa ggc cgg gac act atc gtc atc    5364
Phe Lys Thr Pro Glu Tyr Pro Glu Gly Arg Asp Thr Ile Val Ile
     1775                1780                1785 ggc aac gac att acc ttc caa atc ggc tct ttc ggc ata gga gag    5409
Gly Asn Asp Ile Thr Phe Gln Ile Gly Ser Phe Gly Ile Gly Glu
1790                1795                1800 gac ttc ctg tat cta cgg gca tcg gag atg gcc cgg aca gag ggc    5454
Asp Phe Leu Tyr Leu Arg Ala Ser Glu Met Ala Arg Thr Glu Gly
     1805                1810                1815 atc ccc caa atc tat ctg gca gcc aac agc ggc gcc gta ttg ggc    5499
Ile Pro Gln Ile Tyr Leu Ala Ala Asn Ser Gly Ala Val Leu Gly
1820                1825                1830 ctg tcc gag gag atc aag cag ata ttc caa gtg gca tgg gtg gac    5544
Leu Ser Glu Glu Ile Lys Gln Ile Phe Gln Val Ala Trp Val Asp
     1835                1840                1845 cct gag gat ccc tac aaa gga ttt aga tac ctg tac ctg tac ctg    5589
Pro Glu Asp Pro Tyr Lys Gly Phe Arg Tyr Leu Tyr Leu Tyr Leu
1850                1855                1860 acg ccc caa gac tac acc cag atc agc tcc cag aac tcc gtg cac    5634
Thr Pro Gln Asp Tyr Thr Gln Ile Ser Ser Gln Asn Ser Val His
     1865                1870                1875 tgc aaa cac atc gag gac gaa ggc gag tca ggt att atc gtt gat    5679
Cys Lys His Ile Glu Asp Glu Gly Glu Ser Gly Ile Ile Val Asp
1880                1885                1890 gtc atc ggg aag gac agc agc ctg ggt gtg gag aac ctg cgg ggc    5724
Val Ile Gly Lys Asp Ser Ser Leu Gly Val Glu Asn Leu Arg Gly
     1895                1900                1905 tcg ggc atg att gca gga gag gct tct ctg gct tac gaa aaa aat    5769
Ser Gly Met Ile Ala Gly Glu Ala Ser Leu Ala Tyr Glu Lys Asn
1910                1915                1920 gtc acc atc agc atg gtc gac tgc cgc gcc atc gga atc ggg gct    5814
Val Thr Ile Ser Met Val Asp Cys Arg Ala Ile Gly Ile Gly Ala
     1925                1930                1935
```

```
tac ctg gtg agg ctg ggc cag cgg gtg atc cag gtg gaa aac tcc    5859
Tyr Leu Val Arg Leu Gly Gln Arg Val Ile Gln Val Glu Asn Ser
    1940                1945                1950 cac atc atc ctc acg gga gcc ggt gct ctc aac aag gtt ctg gga    5904
His Ile Ile Leu Thr Gly Ala Gly Ala Leu Asn Lys Val Leu Gly
    1955                1960                1965 aga gag gtc tac aca tcc aac aac caa ctg ggc ggt gtg cag atc    5949
Arg Glu Val Tyr Thr Ser Asn Asn Gln Leu Gly Gly Val Gln Ile
    1970                1975                1980 atg cac acc aac ggg gtc tcc cac gtc acg gtg cca gat gac ttc    5994
Met His Thr Asn Gly Val Ser His Val Thr Val Pro Asp Asp Phe
    1985                1990                1995 gag ggg gtc tgc acc att ctg gaa tgg ctg tca tat ata cca aag    6039
Glu Gly Val Cys Thr Ile Leu Glu Trp Leu Ser Tyr Ile Pro Lys
    2000                2005                2010 gac aat caa agc cca gtc ccc atc atc act cct tct gac ccc atc    6084
Asp Asn Gln Ser Pro Val Pro Ile Ile Thr Pro Ser Asp Pro Ile
    2015                2020                2025 gac agg gaa att gaa ttc acc cca acc aaa gct ccc tat gac ccc    6129
Asp Arg Glu Ile Glu Phe Thr Pro Thr Lys Ala Pro Tyr Asp Pro
    2030                2035                2040 agg tgg ctg ctg gca ggg agg cct cac cca act ctg aag ggg acc    6174
Arg Trp Leu Leu Ala Gly Arg Pro His Pro Thr Leu Lys Gly Thr
    2045                2050                2055 tgg cag agt gga ttc ttc gac cat ggc agt ttc aag gaa atc atg    6219
Trp Gln Ser Gly Phe Phe Asp His Gly Ser Phe Lys Glu Ile Met
    2060                2065                2070 gca ccc tgg gac cag act gtg gtg act gga cga gca agg ctg ggg    6264
Ala Pro Trp Asp Gln Thr Val Val Thr Gly Arg Ala Arg Leu Gly
    2075                2080                2085 ggc atc cct gta ggg gtg att gcc gtg gag act cgg tct gtg gag    6309
Gly Ile Pro Val Gly Val Ile Ala Val Glu Thr Arg Ser Val Glu
    2090                2095                2100 gtg gct gtc cct gct cac cca gcc aac ttg gat tct gag gcc aag    6354
Val Ala Val Pro Ala His Pro Ala Asn Leu Asp Ser Glu Ala Lys
    2105                2110                2115 atc atc cag cag gca ggc cag gtg tgg ttc ccg gac tct gcc ttc    6399
Ile Ile Gln Gln Ala Gly Gln Val Trp Phe Pro Asp Ser Ala Phe
    2120                2125                2130 aag acg gct cag gtc atc agg gac ttc aac cag gag cat ctg ctt    6444
Lys Thr Ala Gln Val Ile Arg Asp Phe Asn Gln Glu His Leu Leu
    2135                2140                2145 ctc atg atc ttt gct aac tgg aga ggc ttc tcg ggc ggc atg aaa    6489
Leu Met Ile Phe Ala Asn Trp Arg Gly Phe Ser Gly Gly Met Lys
    2150                2155                2160 gac atg tcc gag cag atg ctg aag ttt ggc gcc tac atc gtg gac    6534
Asp Met Ser Glu Gln Met Leu Lys Phe Gly Ala Tyr Ile Val Asp
    2165                2170                2175 agt ctc cgt ctg tcc aag cag cca gtc ctc atc tat atc cct ccc    6579
Ser Leu Arg Leu Ser Lys Gln Pro Val Leu Ile Tyr Ile Pro Pro
    2180                2185                2190 ggt gcc gaa ctc cga ggg ggc tcc tgg gtt gtc ctc gac tcc agc    6624
Gly Ala Glu Leu Arg Gly Gly Ser Trp Val Val Leu Asp Ser Ser
    2195                2200                2205 atc aac ccc ctg tgc ata gag atg tac gca gac aaa gag agc agg    6669
Ile Asn Pro Leu Cys Ile Glu Met Tyr Ala Asp Lys Glu Ser Arg
    2210                2215                2220 ggg ggt gtt ctg gag ccc gag ggc act gtg gag att aag ttc cgg    6714
Gly Gly Val Leu Glu Pro Glu Gly Thr Val Glu Ile Lys Phe Arg
```

|  |  |
|---|---|
| aag aaa gat ttg gtg aag acc ata agg agg att gac cca gtg tgc<br>Lys Lys Asp Leu Val Lys Thr Ile Arg Arg Ile Asp Pro Val Cys<br>2240                   2245                   2250 | 6759 |
| aag aaa ctc ctg gaa cca gct ggg gac acc cag ctc cct gac aag<br>Lys Lys Leu Leu Glu Pro Ala Gly Asp Thr Gln Leu Pro Asp Lys<br>2255                   2260                   2265 | 6804 |
| gac cgg aaa gag ctg gag agc cag ctg aag gcc cgg gag gac ctg<br>Asp Arg Lys Glu Leu Glu Ser Gln Leu Lys Ala Arg Glu Asp Leu<br>2270                   2275                   2280 | 6849 |
| ctg ctc ccc atc tac cac cag gtg gca gtg cag ttc gcc gac ctg<br>Leu Leu Pro Ile Tyr His Gln Val Ala Val Gln Phe Ala Asp Leu<br>2285                   2290                   2295 | 6894 |
| cat gac acg ccg ggc cac atg ctg aag aag gga atc att tct gat<br>His Asp Thr Pro Gly His Met Leu Lys Lys Gly Ile Ile Ser Asp<br>2300                   2305                   2310 | 6939 |
| gtc ctg gag tgg aag acc aca cgt act tac ttc tac tgg agg ctg<br>Val Leu Glu Trp Lys Thr Thr Arg Thr Tyr Phe Tyr Trp Arg Leu<br>2315                   2320                   2325 | 6984 |
| cgc cgg ctg ctg ctg gag gca cag gtg aag cag gag att ctg cga<br>Arg Arg Leu Leu Leu Glu Ala Gln Val Lys Gln Glu Ile Leu Arg<br>2330                   2335                   2340 | 7029 |
| gcc agc cct gag ctg agc cat gag cac acg cag tcc atg ctg cga<br>Ala Ser Pro Glu Leu Ser His Glu His Thr Gln Ser Met Leu Arg<br>2345                   2350                   2355 | 7074 |
| cgc tgg ttt gtg gag acc gag ggc gcc gtc aag gcc tac ctg tgg<br>Arg Trp Phe Val Glu Thr Glu Gly Ala Val Lys Ala Tyr Leu Trp<br>2360                   2365                   2370 | 7119 |
| gac agc aac cag gtg gta gtc cag tgg ctg gaa cag cac tgg tca<br>Asp Ser Asn Gln Val Val Val Gln Trp Leu Glu Gln His Trp Ser<br>2375                   2380                   2385 | 7164 |
| gcc agg gac aac ctg cgt tcc act atc cga gag aac ctc aat tat<br>Ala Arg Asp Asn Leu Arg Ser Thr Ile Arg Glu Asn Leu Asn Tyr<br>2390                   2395                   2400 | 7209 |
| ctg aag cgg gac tct gtc ctc aag acc atc caa agc cta gtt caa<br>Leu Lys Arg Asp Ser Val Leu Lys Thr Ile Gln Ser Leu Val Gln<br>2405                   2410                   2415 | 7254 |
| gaa cac cca gag gcg acc atg gga ctg tgt gga tac ctg agc cag<br>Glu His Pro Glu Ala Thr Met Gly Leu Cys Gly Tyr Leu Ser Gln<br>2420                   2425                   2430 | 7299 |
| cac ctc acg ccc gct gag cag atg cag gtg gtt cag ctg ctg tcg<br>His Leu Thr Pro Ala Glu Gln Met Gln Val Val Gln Leu Leu Ser<br>2435                   2440                   2445 | 7344 |
| acc acg gag agc cca gct tcc cac tga<br>Thr Thr Glu Ser Pro Ala Ser His<br>2450                   2455 | 7371 |

<210> SEQ ID NO 8
<211> LENGTH: 2456
<212> TYPE: PRT
<213> ORGANISM: Rattus norvegicus

<400> SEQUENCE: 8

Met Val Leu Leu Leu Phe Leu Thr Tyr Leu Val Phe Ser Cys Leu Thr
1               5                   10                 15

Ile Ser Trp Leu Lys Ile Trp Gly Lys Met Thr Asp Ser Arg Pro Leu
               20                   25                   30

Ser Asn Ser Lys Val Asp Ala Ser Leu Leu Pro Ser Lys Glu Glu Ser
        35                   40                   45

```
Phe Ala Ser Asp Gln Ser Glu His Gly Asp Cys Ser Cys Pro Leu
    50                  55                  60

Thr Thr Pro Asp Gln Glu Leu Ala Ser His Gly Gly Pro Val Asp
 65                  70                  75                  80

Ala Ser Gln Gln Arg Asn Ser Val Pro Thr Ser His Gln Lys Pro Pro
             85                  90                  95

Arg Asn Pro Leu Ser Ser Asn Asp Thr Cys Ser Ser Pro Glu Leu Gln
            100                 105                 110

Thr Asn Gly Val Ala Ala Pro Gly Ser Glu Val Pro Glu Ala Asn Gly
            115                 120                 125

Leu Pro Phe Pro Ala Arg Pro Gln Thr Gln Arg Thr Gly Ser Pro Thr
            130                 135                 140

Arg Glu Asp Lys Lys Gln Ala Pro Ile Lys Arg Gln Leu Met Thr Ser
145                 150                 155                 160

Phe Ile Leu Gly Ser Leu Asp Asp Asn Ser Ser Asp Glu Asp Pro Ser
                165                 170                 175

Ser Asn Ser Phe Gln Thr Ser Ser Arg Lys Gly Ser Arg Asp Ser Leu
            180                 185                 190

Gly Thr Cys Ser Gln Glu Ala Ala Leu Asn Thr Ala Asp Pro Glu Ser
            195                 200                 205

His Thr Pro Thr Met Arg Pro Ser Met Ser Gly Leu His Leu Val Lys
    210                 215                 220

Arg Gly Arg Glu His Lys Lys Leu Asp Leu His Arg Asp Phe Thr Val
225                 230                 235                 240

Ala Ser Pro Ala Glu Phe Val Thr Arg Phe Gly Gly Asn Arg Val Ile
                245                 250                 255

Glu Thr Val Leu Ile Ala Asn Asn Gly Ile Ala Ala Val Lys Trp Met
            260                 265                 270

Arg Ser Ile Arg Arg Trp Ala Tyr Glu Met Phe Arg Asn Glu Arg Ala
    275                 280                 285

Ile Arg Phe Val Val Met Val Thr Pro Glu Asp Leu Lys Ala Asn Ala
    290                 295                 300

Glu Tyr Tyr Lys Met Ala Asp Pro Val Leu Val Pro Gly Gly Pro
305                 310                 315                 320

Asn Asn Asn Asn Tyr Ala Asn Val Glu Leu Ile Ile Asp Ile Ala Lys
                325                 330                 335

Arg Ile Pro Val Gln Ala Val Trp Ala Gly Trp Gly His Ala Ser Glu
            340                 345                 350

Asn Pro Lys Leu Pro Glu Leu Leu Cys Lys His Gly Ile Ala Phe Leu
            355                 360                 365

Gly Pro Arg Val Arg Pro Met Leu Gly Leu Gly Asp Arg Leu Ser Ser
            370                 375                 380

Thr Ile Val Ala Gln Thr Leu Gln Ile Pro Thr Leu Pro Trp Ser Gly
385                 390                 395                 400

Ser Gly Leu Thr Val Glu Trp Thr Glu Asp Ser Gln His Gln Gly Lys
            405                 410                 415

Cys Ile Ser Val Thr Glu Asp Val Tyr Glu Gln Gly Cys Val Arg Asp
            420                 425                 430

Val Asp Glu Gly Leu Gln Ala Ala Glu Lys Val Gly Phe Pro Leu Met
            435                 440                 445

Ile Lys Ala Ser Glu Gly Gly Gly Lys Gly Ile Arg Gln Ala Glu
    450                 455                 460

Ser Ala Glu Asp Phe Pro Cys Phe Phe Arg Gln Val Gln Ser Glu Ile
```

-continued

```
            465                 470                 475                 480
    Pro Gly Ser Pro Ile Phe Leu Met Lys Leu Ala Gln Asn Ala Arg His
                    485                 490                 495
    Leu Glu Val Gln Val Leu Ala Asp Gln Tyr Gly Asn Ala Val Ser Leu
                    500                 505                 510
    Phe Gly Arg Asp Cys Ser Ile Gln Arg Arg His Gln Lys Ile Ile Glu
                    515                 520                 525
    Glu Ala Pro Ala Asn Ile Ala Ala Pro Ala Val Phe Glu Phe Met Glu
                    530                 535                 540
    Gln Cys Ala Val Leu Leu Ala Lys Thr Val Val Tyr Val Ser Ala Gly
    545                 550                 555                 560
    Thr Val Gly Tyr Leu Tyr Ser Gln Asp Gly Ser Phe His Phe Leu Glu
                    565                 570                 575
    Leu Asn Pro Arg Leu Gln Val Glu His Pro Cys Thr Glu Met Ile Ala
                    580                 585                 590
    Asp Val Asn Leu Pro Ala Ala Gln Leu Gln Ile Ala Met Gly Val Pro
                    595                 600                 605
    Leu His Arg Leu Lys Asp Ile Arg Leu Leu Tyr Gly Glu Ser Pro Trp
                    610                 615                 620
    Gly Val Thr Pro Val Ser Phe Glu Thr Pro Leu Ser Pro Pro Ile Ala
    625                 630                 635                 640
    Arg Gly His Val Ile Ala Ala Arg Ile Thr Ser Glu Asn Pro Asp Glu
                    645                 650                 655
    Ala Phe Lys Pro Ser Ser Gly Thr Val Gln Glu Leu Asn Phe Arg Ser
                    660                 665                 670
    Asn Lys Asn Val Trp Gly Tyr Phe Ser Val Ala Ala Ala Gly Gly Leu
                    675                 680                 685
    His Glu Phe Pro Ile Ser Gln Phe Gly His Cys Phe Ser Trp Gly Glu
                    690                 695                 700
    Asn Gln Glu Glu Ala Ile Ser Asn Met Val Val Ala Leu Lys Glu Leu
    705                 710                 715                 720
    Ser Ile Arg Gly Asp Phe Arg Thr Thr Val Glu Tyr Leu Val Asn Leu
                    725                 730                 735
    Leu Glu Thr Glu Ser Leu Gln Asn Asn Asp Ile Asp Thr Gly Trp Leu
                    740                 745                 750
    Asp His Leu Ile Ala Gln Arg Val Gln Ala Glu Lys Pro Asp Ile Met
                    755                 760                 765
    Leu Gly Val Val Phe Gly Ala Leu Asn Val Ala Asp Ala Met Phe Arg
                    770                 775                 780
    Thr Cys Ile Thr Glu Phe Leu His Ser Leu Glu Arg Gly Gln Val Leu
    785                 790                 795                 800
    Pro Ala Asp Ser Leu Leu Asn Ile Val Asp Val Glu Leu Ile Tyr Gly
                    805                 810                 815
    Gly Ile Lys Tyr Val Leu Lys Val Ala Arg Gln Ser Leu Thr Met Phe
                    820                 825                 830
    Val Leu Ile Met Asn Gly Cys His Ile Glu Ile Asp Ala His Arg Pro
                    835                 840                 845
    Asn Asp Gly Gly Leu Leu Ser Tyr Asn Gly Ser Ser Tyr Thr Thr
    850                 855                 860
    Tyr Met Lys Glu Glu Val Asp Ser Tyr Arg Ile Thr Ile Gly Asn Lys
    865                 870                 875                 880
    Thr Cys Val Phe Glu Lys Glu Asn Asp Pro Thr Val Leu Arg Ser Pro
                    885                 890                 895
```

-continued

```
Ser Ala Gly Lys Leu Met Gln Tyr Thr Val Glu Asp Gly Gln His Val
            900                 905                 910
Glu Val Gly Ser Ser Tyr Ala Glu Met Glu Val Met Lys Met Ile Met
            915                 920                 925
Thr Leu Asn Val Gln Glu Ser Gly Arg Val Asn Tyr Ile Lys Arg Pro
            930                 935                 940
Gly Ala Val Leu Glu Ala Gly Cys Val Val Ala Lys Leu Glu Leu Asp
945                 950                 955                 960
Asp Pro Ser Lys Val His Ala Ala Gln Pro Phe Thr Gly Glu Leu Pro
                965                 970                 975
Ala Gln Gln Thr Leu Pro Ile Leu Gly Glu Arg Leu His Gln Val Phe
            980                 985                 990
His Ser Val Leu Glu Asn Leu Thr Asn Val Met Asn Gly Tyr Cys Leu
            995                1000                1005
Pro Glu Pro Phe Phe Ser Met Lys Leu Lys Asp Trp Val Glu Lys
    1010                1015                1020
Pro Met Met Thr Leu Arg His Pro Ser Leu Pro Leu Leu Glu Leu
    1025                1030                1035
Gln Glu Ile Met Thr Ser Val Ala Asp Arg Ile Pro Val Pro Val
    1040                1045                1050
Glu Lys Ala Val Arg Arg Val Phe Ala Gln Asp Ala Ser Asn Ile
    1055                1060                1065
Thr Ser Val Leu Cys Gln Phe Pro Ser Gln Gln Ile Ala Thr Ile
    1070                1075                1080
Leu Asp Cys His Ala Ala Thr Leu Gln Arg Lys Val Asp Arg Glu
    1085                1090                1095
Ala Phe Phe Met Asn Thr Gln Ser Ile Val Gln Leu Ile Gln Arg
    1100                1105                1110
Tyr Arg Ser Gly Thr Arg Gly Ile Met Lys Ala Val Val Leu Asp
    1115                1120                1125
Leu Leu Arg Arg Tyr Leu Asn Val Glu His His Phe Gln Gln Ala
    1130                1135                1140
His Tyr Asp Lys Cys Val Ile Asn Leu Arg Glu Gln Phe Lys Ala
    1145                1150                1155
Asp Met Thr Arg Val Leu Asp Cys Ile Phe Ser His Ser Gln Val
    1160                1165                1170
Ala Lys Lys Asn Gln Leu Val Thr Met Leu Ile Asp Glu Leu Cys
    1175                1180                1185
Gly Pro Asp Pro Thr Leu Ser Glu Glu Leu Thr Ser Ile Leu Lys
    1190                1195                1200
Glu Leu Thr Gln Leu Ser Arg Ser Glu His Cys Lys Val Ala Leu
    1205                1210                1215
Arg Ala Arg Gln Val Leu Ile Ala Ser His Leu Pro Ser Tyr Glu
    1220                1225                1230
Leu Arg His Asn Gln Val Glu Ser Ser Ser Cys Gln Pro Leu Thr
    1235                1240                1245
Cys Asn Gly His Gln Phe Cys Pro Glu Asn Leu Lys Lys Leu Ile
    1250                1255                1260
Leu Ser Glu Thr Thr Ile Phe Asp Val Leu Pro Thr Phe Phe Tyr
    1265                1270                1275
His Ala Asn Lys Val Val Cys Met Ala Ser Leu Glu Val Tyr Val
    1280                1285                1290
```

-continued

```
Arg Arg Gly Tyr Ile Ala Tyr Glu Leu Asn Ser Leu Gln His Arg
    1295               1300              1305

Glu Leu Pro Asp Gly Thr Cys Val Val Glu Phe Gln Phe Met Leu
    1310              1315              1320

Pro Ser Ser His Pro Asn Arg Met Ala Met Pro Ile Asn Val Ser
    1325              1330              1335

Asp Pro Asp Leu Leu Arg His Ser Lys Glu Leu Phe Met Asp Ser
    1340              1345              1350

Gly Phe Ser Pro Leu Cys His Gln Arg Met Gly Ala Met Val Ala
    1355              1360              1365

Phe Arg Arg Phe Glu Glu Phe Thr Arg Asn Phe Asp Glu Val Ile
    1370              1375              1380

Ser Cys Phe Ala Asn Val Pro Thr Asp Thr Pro Leu Phe Ser Lys
    1385              1390              1395

Ala Cys Thr Ser Leu Tyr Ser Glu Glu Asp Ser Lys Ser Leu Gln
    1400              1405              1410

Glu Glu Pro Ile His Ile Leu Asn Val Ala Ile Gln Cys Ala Asp
    1415              1420              1425

His Met Glu Asp Glu Arg Leu Val Pro Val Phe Arg Ala Phe Val
    1430              1435              1440

Gln Ser Lys Lys His Ile Leu Val Asp Tyr Gly Leu Arg Arg Ile
    1445              1450              1455

Thr Phe Leu Ile Ala Gln Glu Lys Glu Phe Pro Lys Phe Phe Thr
    1460              1465              1470

Phe Arg Ala Arg Asp Glu Phe Ala Glu Asp Arg Ile Tyr Arg His
    1475              1480              1485

Leu Glu Pro Gly Leu Ala Phe Gln Leu Glu Leu Ser Arg Met Arg
    1490              1495              1500

Asn Phe Asp Leu Thr Ala Val Pro Cys Ala Asn His Lys Met His
    1505              1510              1515

Leu Tyr Leu Gly Ala Ala Lys Val Lys Glu Gly Leu Glu Val Thr
    1520              1525              1530

Asp His Arg Phe Phe Ile Arg Ala Ile Ile Arg His Ser Asp Leu
    1535              1540              1545

Ile Thr Lys Glu Ala Ser Phe Glu Tyr Leu Gln Asn Glu Gly Glu
    1550              1555              1560

Arg Leu Leu Leu Glu Ala Met Asp Glu Leu Glu Val Ala Phe Asn
    1565              1570              1575

Asn Thr Ser Val Arg Thr Asp Cys Asn His Ile Phe Leu Asn Phe
    1580              1585              1590

Val Ala His Val Ile Met Asp Pro Leu Lys Ile Glu Glu Ser Val
    1595              1600              1605

Arg Ala Met Val Met Arg Tyr Gly Ser Arg Leu Trp Lys Leu Arg
    1610              1615              1620

Val Leu Gln Ala Gln Val Lys Ile Asn Ile Arg Gln Thr Thr Ser
    1625              1630              1635

Asp Cys Ala Val Pro Ile Arg Leu Phe Ile Thr Asn Glu Ser Gly
    1640              1645              1650

Tyr Tyr Leu Asp Ile Ser Leu Tyr Lys Glu Val Thr Asp Ser Arg
    1655              1660              1665

Ser Gly Asn Ile Met Phe His Ser Phe Gly Asn Lys Gln Gly Ser
    1670              1675              1680

Leu His Gly Met Leu Ile Asn Thr Pro Tyr Val Thr Lys Asp Leu
```

```
                1685                1690                1695

Leu Gln Ala Lys Arg Phe Gln Ala Gln Ser Leu Gly Thr Thr Tyr
    1700                1705                1710

Val Tyr Asp Phe Pro Glu Met Phe Arg Gln Ala Leu Phe Lys Leu
    1715                1720                1725

Trp Gly Ser Pro Glu Lys Tyr Gly Pro Asp Ile Leu Thr Tyr Thr
    1730                1735                1740

Glu Leu Val Leu Asp Ser Gln Gly Gln Leu Val Glu Met Asn Arg
    1745                1750                1755

Leu Pro Gly Cys Asn Glu Val Gly Met Val Val Phe Lys Met Arg
    1760                1765                1770

Phe Lys Thr Pro Glu Tyr Pro Glu Gly Arg Asp Thr Ile Val Ile
    1775                1780                1785

Gly Asn Asp Ile Thr Phe Gln Ile Gly Ser Phe Gly Ile Gly Glu
    1790                1795                1800

Asp Phe Leu Tyr Leu Arg Ala Ser Glu Met Ala Arg Thr Glu Gly
    1805                1810                1815

Ile Pro Gln Ile Tyr Leu Ala Ala Asn Ser Gly Ala Val Leu Gly
    1820                1825                1830

Leu Ser Glu Glu Ile Lys Gln Ile Phe Gln Val Ala Trp Val Asp
    1835                1840                1845

Pro Glu Asp Pro Tyr Lys Gly Phe Arg Tyr Leu Tyr Leu Tyr Leu
    1850                1855                1860

Thr Pro Gln Asp Tyr Thr Gln Ile Ser Ser Gln Asn Ser Val His
    1865                1870                1875

Cys Lys His Ile Glu Asp Glu Gly Glu Ser Gly Ile Ile Val Asp
    1880                1885                1890

Val Ile Gly Lys Asp Ser Ser Leu Gly Val Glu Asn Leu Arg Gly
    1895                1900                1905

Ser Gly Met Ile Ala Gly Glu Ala Ser Leu Ala Tyr Glu Lys Asn
    1910                1915                1920

Val Thr Ile Ser Met Val Asp Cys Arg Ala Ile Gly Ile Gly Ala
    1925                1930                1935

Tyr Leu Val Arg Leu Gly Gln Arg Val Ile Gln Val Glu Asn Ser
    1940                1945                1950

His Ile Ile Leu Thr Gly Ala Gly Ala Leu Asn Lys Val Leu Gly
    1955                1960                1965

Arg Glu Val Tyr Thr Ser Asn Asn Gln Leu Gly Gly Val Gln Ile
    1970                1975                1980

Met His Thr Asn Gly Val Ser His Val Thr Val Pro Asp Asp Phe
    1985                1990                1995

Glu Gly Val Cys Thr Ile Leu Glu Trp Leu Ser Tyr Ile Pro Lys
    2000                2005                2010

Asp Asn Gln Ser Pro Val Pro Ile Ile Thr Pro Ser Asp Pro Ile
    2015                2020                2025

Asp Arg Glu Ile Glu Phe Thr Pro Thr Lys Ala Pro Tyr Asp Pro
    2030                2035                2040

Arg Trp Leu Leu Ala Gly Arg Pro His Pro Thr Leu Lys Gly Thr
    2045                2050                2055

Trp Gln Ser Gly Phe Phe Asp His Gly Ser Phe Lys Glu Ile Met
    2060                2065                2070

Ala Pro Trp Asp Gln Thr Val Val Thr Gly Arg Ala Arg Leu Gly
    2075                2080                2085
```

-continued

| | | | | | | | | | | | |
|---|---|---|---|---|---|---|---|---|---|---|---|
| Gly | Ile | Pro | Val | Gly | Val | Ile | Ala | Val | Glu | Thr | Arg | Ser | Val | Glu |
| | 2090 | | | | 2095 | | | | 2100 | | | | | |
| Val | Ala | Val | Pro | Ala | His | Pro | Ala | Asn | Leu | Asp | Ser | Glu | Ala | Lys |
| | 2105 | | | | 2110 | | | | 2115 | | | | | |
| Ile | Ile | Gln | Gln | Ala | Gly | Gln | Val | Trp | Phe | Pro | Asp | Ser | Ala | Phe |
| | 2120 | | | | 2125 | | | | 2130 | | | | | |
| Lys | Thr | Ala | Gln | Val | Ile | Arg | Asp | Phe | Asn | Gln | Glu | His | Leu | Leu |
| | 2135 | | | | 2140 | | | | 2145 | | | | | |
| Leu | Met | Ile | Phe | Ala | Asn | Trp | Arg | Gly | Phe | Ser | Gly | Gly | Met | Lys |
| | 2150 | | | | 2155 | | | | 2160 | | | | | |
| Asp | Met | Ser | Glu | Gln | Met | Leu | Lys | Phe | Gly | Ala | Tyr | Ile | Val | Asp |
| | 2165 | | | | 2170 | | | | 2175 | | | | | |
| Ser | Leu | Arg | Leu | Ser | Lys | Gln | Pro | Val | Leu | Ile | Tyr | Ile | Pro | Pro |
| | 2180 | | | | 2185 | | | | 2190 | | | | | |
| Gly | Ala | Glu | Leu | Arg | Gly | Gly | Ser | Trp | Val | Val | Leu | Asp | Ser | Ser |
| | 2195 | | | | 2200 | | | | 2205 | | | | | |
| Ile | Asn | Pro | Leu | Cys | Ile | Glu | Met | Tyr | Ala | Asp | Lys | Glu | Ser | Arg |
| | 2210 | | | | 2215 | | | | 2220 | | | | | |
| Gly | Gly | Val | Leu | Glu | Pro | Glu | Gly | Thr | Val | Glu | Ile | Lys | Phe | Arg |
| | 2225 | | | | 2230 | | | | 2235 | | | | | |
| Lys | Lys | Asp | Leu | Val | Lys | Thr | Ile | Arg | Arg | Ile | Asp | Pro | Val | Cys |
| | 2240 | | | | 2245 | | | | 2250 | | | | | |
| Lys | Lys | Leu | Leu | Glu | Pro | Ala | Gly | Asp | Thr | Gln | Leu | Pro | Asp | Lys |
| | 2255 | | | | 2260 | | | | 2265 | | | | | |
| Asp | Arg | Lys | Glu | Leu | Glu | Ser | Gln | Leu | Lys | Ala | Arg | Glu | Asp | Leu |
| | 2270 | | | | 2275 | | | | 2280 | | | | | |
| Leu | Leu | Pro | Ile | Tyr | His | Gln | Val | Ala | Val | Gln | Phe | Ala | Asp | Leu |
| | 2285 | | | | 2290 | | | | 2295 | | | | | |
| His | Asp | Thr | Pro | Gly | His | Met | Leu | Lys | Lys | Gly | Ile | Ile | Ser | Asp |
| | 2300 | | | | 2305 | | | | 2310 | | | | | |
| Val | Leu | Glu | Trp | Lys | Thr | Thr | Arg | Thr | Tyr | Phe | Tyr | Trp | Arg | Leu |
| | 2315 | | | | 2320 | | | | 2325 | | | | | |
| Arg | Arg | Leu | Leu | Leu | Glu | Ala | Gln | Val | Lys | Gln | Glu | Ile | Leu | Arg |
| | 2330 | | | | 2335 | | | | 2340 | | | | | |
| Ala | Ser | Pro | Glu | Leu | Ser | His | Glu | His | Thr | Gln | Ser | Met | Leu | Arg |
| | 2345 | | | | 2350 | | | | 2355 | | | | | |
| Arg | Trp | Phe | Val | Glu | Thr | Glu | Gly | Ala | Val | Lys | Ala | Tyr | Leu | Trp |
| | 2360 | | | | 2365 | | | | 2370 | | | | | |
| Asp | Ser | Asn | Gln | Val | Val | Val | Gln | Trp | Leu | Glu | Gln | His | Trp | Ser |
| | 2375 | | | | 2380 | | | | 2385 | | | | | |
| Ala | Arg | Asp | Asn | Leu | Arg | Ser | Thr | Ile | Arg | Glu | Asn | Leu | Asn | Tyr |
| | 2390 | | | | 2395 | | | | 2400 | | | | | |
| Leu | Lys | Arg | Asp | Ser | Val | Leu | Lys | Thr | Ile | Gln | Ser | Leu | Val | Gln |
| | 2405 | | | | 2410 | | | | 2415 | | | | | |
| Glu | His | Pro | Glu | Ala | Thr | Met | Gly | Leu | Cys | Gly | Tyr | Leu | Ser | Gln |
| | 2420 | | | | 2425 | | | | 2430 | | | | | |
| His | Leu | Thr | Pro | Ala | Glu | Gln | Met | Gln | Val | Val | Gln | Leu | Leu | Ser |
| | 2435 | | | | 2440 | | | | 2445 | | | | | |
| Thr | Thr | Glu | Ser | Pro | Ala | Ser | His | | | | | | | |
| | 2450 | | | | 2455 | | | | | | | | | |

<210> SEQ ID NO 9
<211> LENGTH: 7371

```
<212> TYPE: DNA
<213> ORGANISM: Rattus norvegicus
<220> FEATURE:
<221> NAME/KEY: CDS
<222> LOCATION: (1)..(7371)

<400> SEQUENCE: 9 atg gtc ttg ctt ctc ttt ctg act tac ctg gtt ttc tcc tgc ctg acc        48
Met Val Leu Leu Leu Phe Leu Thr Tyr Leu Val Phe Ser Cys Leu Thr
1               5                   10                  15 att tcc tgg tta aaa atc tgg ggg aag atg aca gac tcg agg ccg ctc        96
Ile Ser Trp Leu Lys Ile Trp Gly Lys Met Thr Asp Ser Arg Pro Leu
            20                  25                  30 agc aac agt aag gtg gat gca agc ctc ctt ccg agc aag gag gag tct        144
Ser Asn Ser Lys Val Asp Ala Ser Leu Leu Pro Ser Lys Glu Glu Ser
        35                  40                  45 ttt gcc tcg gac cag tca gag gag cat ggc gac tgc agc tgt ccg ttg        192
Phe Ala Ser Asp Gln Ser Glu Glu His Gly Asp Cys Ser Cys Pro Leu
    50                  55                  60 aca act cct gac cag gag gag ctg gcc tcc cac gga ggt cct gta gat        240
Thr Thr Pro Asp Gln Glu Glu Leu Ala Ser His Gly Gly Pro Val Asp
65                  70                  75                  80 gcc agt cag cag agg aac tct gta cca acc tca cac cag aag cct ccg        288
Ala Ser Gln Gln Arg Asn Ser Val Pro Thr Ser His Gln Lys Pro Pro
                85                  90                  95 agg aac cca cta tct tcc aat gac acc tgt tcc tcc cca gaa ctc caa        336
Arg Asn Pro Leu Ser Ser Asn Asp Thr Cys Ser Ser Pro Glu Leu Gln
            100                 105                 110 acc aac ggg gta gca gca cct ggc tca gag gtt cca gaa gcc aac ggg        384
Thr Asn Gly Val Ala Ala Pro Gly Ser Glu Val Pro Glu Ala Asn Gly
        115                 120                 125 ttg cct ttc cca gcc agg cct cag acc cag aga acg gga tcc ccc act        432
Leu Pro Phe Pro Ala Arg Pro Gln Thr Gln Arg Thr Gly Ser Pro Thr
    130                 135                 140 agg gag gac aag aag cag gca ccc atc aag agg cag ctg atg acc agc        480
Arg Glu Asp Lys Lys Gln Ala Pro Ile Lys Arg Gln Leu Met Thr Ser
145                 150                 155                 160 ttt atc ctg ggc tcc ctc gat gac aac tcc tct gac gag gac cct agt        528
Phe Ile Leu Gly Ser Leu Asp Asp Asn Ser Ser Asp Glu Asp Pro Ser
                165                 170                 175 tct aac tcc ttt cag acc tcc tct cgg aag ggc agc agg gat agc ctg        576
Ser Asn Ser Phe Gln Thr Ser Ser Arg Lys Gly Ser Arg Asp Ser Leu
            180                 185                 190 ggc acc tgt tcc cag gag gct gca ttg aac aca gct gat cct gag tct        624
Gly Thr Cys Ser Gln Glu Ala Ala Leu Asn Thr Ala Asp Pro Glu Ser
        195                 200                 205 cac aca cct act atg agg ccc agc atg tct gga ctc cat ctg gtg aag        672
His Thr Pro Thr Met Arg Pro Ser Met Ser Gly Leu His Leu Val Lys
    210                 215                 220 aga ggc cgt gaa cac aag aaa ctg gac ctg cac aga gat ttc act gta        720
Arg Gly Arg Glu His Lys Lys Leu Asp Leu His Arg Asp Phe Thr Val
225                 230                 235                 240 gct tcc cca gcc gaa ttt gtc acc cgc ttt gga ggc aac agg gtt atc        768
Ala Ser Pro Ala Glu Phe Val Thr Arg Phe Gly Gly Asn Arg Val Ile
                245                 250                 255 gag acg gtg ctc atc gcc aat aat ggt atc gct gcg gtc aag tgg atg        816
Glu Thr Val Leu Ile Ala Asn Asn Gly Ile Ala Ala Val Lys Trp Met
            260                 265                 270 cgc tcc atc cgc cgc tgg gcc tat gag atg ttc cgt aat gaa cgc gct        864
Arg Ser Ile Arg Arg Trp Ala Tyr Glu Met Phe Arg Asn Glu Arg Ala
        275                 280                 285
```

```
atc cgg ttt gtg gtt atg gtg aca ccc gag gat ctt aag gcc aac gca     912
Ile Arg Phe Val Val Met Val Thr Pro Glu Asp Leu Lys Ala Asn Ala
    290                 295                 300 gag tac tac aag atg gcg gac cca gta ctt ccg gtc cca gga gga ccc     960
Glu Tyr Tyr Lys Met Ala Asp Pro Val Leu Pro Val Pro Gly Gly Pro
305                 310                 315                 320 aat aat aac aac tac gcc aac gtt gag ctg atc ata gac att gcc aag    1008
Asn Asn Asn Asn Tyr Ala Asn Val Glu Leu Ile Ile Asp Ile Ala Lys
                325                 330                 335 aga atc cct gtg cag gcc gtg tgg gct ggc tgg ggc cac gct tcg gaa    1056
Arg Ile Pro Val Gln Ala Val Trp Ala Gly Trp Gly His Ala Ser Glu
            340                 345                 350 aac ccc aaa ctt cca gag cta ctg tgc aag cac ggg att gct ttt cta    1104
Asn Pro Lys Leu Pro Glu Leu Leu Cys Lys His Gly Ile Ala Phe Leu
        355                 360                 365 ggt ccc cga gtg agg cca atg ttg ggc ctg gga gac agg ctc tcc tcc    1152
Gly Pro Arg Val Arg Pro Met Leu Gly Leu Gly Asp Arg Leu Ser Ser
    370                 375                 380 acc att gta gcc cag aca ttg cag atc cca act cta ccc tgg agc gga    1200
Thr Ile Val Ala Gln Thr Leu Gln Ile Pro Thr Leu Pro Trp Ser Gly
385                 390                 395                 400 agc ggt ctc aca gtg gag tgg acg gag gac agc cag cat cag ggc aaa    1248
Ser Gly Leu Thr Val Glu Trp Thr Glu Asp Ser Gln His Gln Gly Lys
                405                 410                 415 tgc atc agc gtc acg gaa gac gtt tat gaa caa ggc tgt gtg aga gat    1296
Cys Ile Ser Val Thr Glu Asp Val Tyr Glu Gln Gly Cys Val Arg Asp
            420                 425                 430 gtg gac gaa ggc ttg cag gca gca gaa aaa gta gga ttt cct ctg atg    1344
Val Asp Glu Gly Leu Gln Ala Ala Glu Lys Val Gly Phe Pro Leu Met
        435                 440                 445 atc aaa gcc tct gaa ggt gga gga ggg aaa gga atc cgg cag gct gag    1392
Ile Lys Ala Ser Glu Gly Gly Gly Gly Lys Gly Ile Arg Gln Ala Glu
    450                 455                 460 agt gca gag gac ttc cca tgc ttt ttc aga cag gtg cag agt gag atc    1440
Ser Ala Glu Asp Phe Pro Cys Phe Phe Arg Gln Val Gln Ser Glu Ile
465                 470                 475                 480 ccg ggc tcg ccc atc ttt ctc atg aag ctg gcc cag aat gcc cgg cac    1488
Pro Gly Ser Pro Ile Phe Leu Met Lys Leu Ala Gln Asn Ala Arg His
                485                 490                 495 ttg gag gtc cag gtc ttg gca gat cag tat ggg aac gca gtg tcc ctg    1536
Leu Glu Val Gln Val Leu Ala Asp Gln Tyr Gly Asn Ala Val Ser Leu
            500                 505                 510 ttt gga cga gac tgc tcc atc cag agg cgg cac cag aag atc att gag    1584
Phe Gly Arg Asp Cys Ser Ile Gln Arg Arg His Gln Lys Ile Ile Glu
        515                 520                 525 gag gct ccg gcc aac atc gct gct ccg gct gtg ttt gag ttc atg gaa    1632
Glu Ala Pro Ala Asn Ile Ala Ala Pro Ala Val Phe Glu Phe Met Glu
    530                 535                 540 cag tgt gcc gtc ctc ctg gcc aag act gtg gtt tat gtg agc gcg gga    1680
Gln Cys Ala Val Leu Leu Ala Lys Thr Val Val Tyr Val Ser Ala Gly
545                 550                 555                 560 acc gtg ggg tac cta tac agc cag gat ggc agc ttt cac ttc ttg gag    1728
Thr Val Gly Tyr Leu Tyr Ser Gln Asp Gly Ser Phe His Phe Leu Glu
                565                 570                 575 ctg aac cca cgc ctg cag gtg gaa cat ccc tgc act gaa atg att gca    1776
Leu Asn Pro Arg Leu Gln Val Glu His Pro Cys Thr Glu Met Ile Ala
            580                 585                 590 gat gtc aac ctg ccc gct gca cag tta cag atc gcc atg ggc gtg ccc    1824
Asp Val Asn Leu Pro Ala Ala Gln Leu Gln Ile Ala Met Gly Val Pro
```

-continued

```
              595                 600                 605
ctg cac cgg ctg aag gac ata cgg ctt ctg tac gga gag tcc ccc tgg    1872
Leu His Arg Leu Lys Asp Ile Arg Leu Leu Tyr Gly Glu Ser Pro Trp
610                 615                 620 gga gtg acc ccc gtt tct ttt gag acc cct ttg agc cct ccc att gcc    1920
Gly Val Thr Pro Val Ser Phe Glu Thr Pro Leu Ser Pro Pro Ile Ala
625                 630                 635                 640 cga ggc cat gtc att gca gcc agg atc acc agc gaa aac cca gac gag    1968
Arg Gly His Val Ile Ala Ala Arg Ile Thr Ser Glu Asn Pro Asp Glu
                645                 650                 655 gcc ttt aag cca agc tca ggg aca gta cag gag ctg aac ttc cgc agc    2016
Ala Phe Lys Pro Ser Ser Gly Thr Val Gln Glu Leu Asn Phe Arg Ser
            660                 665                 670 aac aag aac gtg tgg ggt tac ttc agc gtg gcc gct gct gga ggc ttg    2064
Asn Lys Asn Val Trp Gly Tyr Phe Ser Val Ala Ala Ala Gly Gly Leu
        675                 680                 685 cac gag ttt ccg att tcc cag ttt ggg cac tgc ttc tcc tgg ggc gag    2112
His Glu Phe Pro Ile Ser Gln Phe Gly His Cys Phe Ser Trp Gly Glu
690                 695                 700 aac cag gaa gag gct att tcg aac atg gtg gtg gct ttg aaa gaa ctg    2160
Asn Gln Glu Glu Ala Ile Ser Asn Met Val Val Ala Leu Lys Glu Leu
705                 710                 715                 720 tct atc cgg ggt gac ttc cgg acc acc gtg gaa tat ctc gtc aac ctt    2208
Ser Ile Arg Gly Asp Phe Arg Thr Thr Val Glu Tyr Leu Val Asn Leu
                725                 730                 735 ctg gag acg gag agc tta cag aac aat gat atc gac acg ggg tgg ctg    2256
Leu Glu Thr Glu Ser Leu Gln Asn Asn Asp Ile Asp Thr Gly Trp Leu
            740                 745                 750 gac cac ctc atc gct cag cgg gtg cag gca gag aag ccg gac atc atg    2304
Asp His Leu Ile Ala Gln Arg Val Gln Ala Glu Lys Pro Asp Ile Met
        755                 760                 765 ctc ggg gtg gtg ttt ggg gcc ttg aac gtg gca gac gca atg ttc aga    2352
Leu Gly Val Val Phe Gly Ala Leu Asn Val Ala Asp Ala Met Phe Arg
770                 775                 780 acc tgt att acg gaa ttc ctg cat tcc ttg gaa agg ggt cag gtc ctc    2400
Thr Cys Ile Thr Glu Phe Leu His Ser Leu Glu Arg Gly Gln Val Leu
785                 790                 795                 800 ccg gct gat tct ctg ctg aac atc gtg gac gtt gaa ttg att tac gga    2448
Pro Ala Asp Ser Leu Leu Asn Ile Val Asp Val Glu Leu Ile Tyr Gly
                805                 810                 815 ggc atc aaa tat gtt ctc aag gtg gcc cgg cag tcc ctg acc atg ttt    2496
Gly Ile Lys Tyr Val Leu Lys Val Ala Arg Gln Ser Leu Thr Met Phe
            820                 825                 830 gtc ctc atc atg aat ggt tgc cac atc gag atc gat gcc cac cgg ccg    2544
Val Leu Ile Met Asn Gly Cys His Ile Glu Ile Asp Ala His Arg Pro
        835                 840                 845 aac gat ggg ggc ctg ctc ctg tcc tac aat ggt agc agt tac act aca    2592
Asn Asp Gly Gly Leu Leu Leu Ser Tyr Asn Gly Ser Ser Tyr Thr Thr
850                 855                 860 tac atg aag gaa gag gtg gac agt tac cgg atc act atc ggc aat aag    2640
Tyr Met Lys Glu Glu Val Asp Ser Tyr Arg Ile Thr Ile Gly Asn Lys
865                 870                 875                 880 aca tgc gtg ttt gaa aag gaa aac gac ccc acc gtc ctg aga tcc ccc    2688
Thr Cys Val Phe Glu Lys Glu Asn Asp Pro Thr Val Leu Arg Ser Pro
                885                 890                 895 tcg gct ggg aag ctg atg cag tac acg gtg gag gat ggc cag cac gtg    2736
Ser Ala Gly Lys Leu Met Gln Tyr Thr Val Glu Asp Gly Gln His Val
            900                 905                 910 gaa gtc ggg agc agc tat gct gag atg gag gtg atg aag atg atc atg    2784
```

```
                                                                -continued

Glu Val Gly Ser Ser Tyr Ala Glu Met Glu Val Met Lys Met Ile Met
        915                 920                 925 acc ctg aac gtg caa gag agc ggc cgg gtg aac tac atc aag cga cca    2832
Thr Leu Asn Val Gln Glu Ser Gly Arg Val Asn Tyr Ile Lys Arg Pro
930                 935                 940 ggg gcg gta ttg gag gct ggc tgc gtg gtg gca aag cta gaa ctc gat    2880
Gly Ala Val Leu Glu Ala Gly Cys Val Val Ala Lys Leu Glu Leu Asp
945                 950                 955                 960 gac cct tca aaa gtg cac gcg gca cag ccg ttc aca ggg gag ctc ccc    2928
Asp Pro Ser Lys Val His Ala Ala Gln Pro Phe Thr Gly Glu Leu Pro
                965                 970                 975 gcc cag cag act ctg ccc atc ctc ggg gag agg ctg cat cag gtg ttc    2976
Ala Gln Gln Thr Leu Pro Ile Leu Gly Glu Arg Leu His Gln Val Phe
            980                 985                 990 cac agc gtc ttg gaa aat ctg acc  aat gtc atg aat ggc tac tgc ctg   3024
His Ser Val Leu Glu Asn Leu Thr  Asn Val Met Asn Gly Tyr Cys Leu
            995             1000                1005 ccc gag ccc ttc ttc agc atg  aag ctg aag gac tgg  gtg gag aag      3069
Pro Glu Pro Phe Phe Ser Met  Lys Leu Lys Asp Trp  Val Glu Lys
        1010                1015                1020 ccc atg  atg act ctc cgg cat  ccc tcc cta cct ctg  ctg gag ctg     3114
Pro Met  Met Thr Leu Arg His  Pro Ser Leu Pro Leu  Leu Glu Leu
    1025                1030                1035 cag gag  atc atg acc agc gtg  gca gac cgc atc ccg  gtt ccg gtg     3159
Gln Glu  Ile Met Thr Ser Val  Ala Asp Arg Ile Pro  Val Pro Val
    1040                1045                1050 gag aag  gca gtc cgc agg gtg  ttt gcg cag gac gcc  agc aac atc     3204
Glu Lys  Ala Val Arg Arg Val  Phe Ala Gln Asp Ala  Ser Asn Ile
    1055                1060                1065 act tcg  gtg ctc tgc cag ttc  ccc agc cag cag ata  gcc acc atc     3249
Thr Ser  Val Leu Cys Gln Phe  Pro Ser Gln Gln Ile  Ala Thr Ile
    1070                1075                1080 ctg gac  tgc cac gcc gcc acc  ctg cag cgt aag gtg  gac cga gag     3294
Leu Asp  Cys His Ala Ala Thr  Leu Gln Arg Lys Val  Asp Arg Glu
    1085                1090                1095 gcc ttc  ttc atg aac aca cag  agc atc gtg cag ctg  atc cag aga     3339
Ala Phe  Phe Met Asn Thr Gln  Ser Ile Val Gln Leu  Ile Gln Arg
    1100                1105                1110 tac cgc  agt ggg acc cgt ggc  atc atg aag gct gtg  gtg cta gac     3384
Tyr Arg  Ser Gly Thr Arg Gly  Ile Met Lys Ala Val  Val Leu Asp
    1115                1120                1125 ctc ctg  agg aga tat ctg aac  gtg gag cat cat ttc  cag caa gcc     3429
Leu Leu  Arg Arg Tyr Leu Asn  Val Glu His His Phe  Gln Gln Ala
    1130                1135                1140 cac tat  gac aag tgt gtg atc  aac ctg agg gag cag  ttc aag gcg     3474
His Tyr  Asp Lys Cys Val Ile  Asn Leu Arg Glu Gln  Phe Lys Ala
    1145                1150                1155 gac atg  act cgg gtg ctg gac  tgc atc ttc tca cac  tca caa gtg     3519
Asp Met  Thr Arg Val Leu Asp  Cys Ile Phe Ser His  Ser Gln Val
    1160                1165                1170 gcc aag  aag aac cag ctg gtg  acc atg ttg ata gat  gag ctg tgt     3564
Ala Lys  Lys Asn Gln Leu Val  Thr Met Leu Ile Asp  Glu Leu Cys
    1175                1180                1185 ggc cca  gac ccc acc ctg tca  gaa gag ctg acc tcc  atc ctc aag     3609
Gly Pro  Asp Pro Thr Leu Ser  Glu Glu Leu Thr Ser  Ile Leu Lys
    1190                1195                1200 gaa ctc  acg cag ttg agc agg  agt gag cac tgc aag  gtg gcc ctc     3654
Glu Leu  Thr Gln Leu Ser Arg  Ser Glu His Cys Lys  Val Ala Leu
    1205                1210                1215
```

```
-continued aga gcc agg cag gtc ctg att gcc tct cac ctc ccc tcc tac gag    3699
Arg Ala Arg Gln Val Leu Ile Ala Ser His Leu Pro Ser Tyr Glu
    1220            1225                1230 ctg cgg cac aac cag gtg gag tca tct tcc tgt cag cca ttg aca    3744
Leu Arg His Asn Gln Val Glu Ser Ser Ser Cys Gln Pro Leu Thr
1235                1240                1245 tgt aat ggc cac cag ttc tgc ccg gaa aac ctc aag aaa cta ata    3789
Cys Asn Gly His Gln Phe Cys Pro Glu Asn Leu Lys Lys Leu Ile
        1250                1255                1260 ctt tcg gaa acg acc ata ttc gat gtc ctg ccc act ttc ttc tat    3834
Leu Ser Glu Thr Thr Ile Phe Asp Val Leu Pro Thr Phe Phe Tyr
    1265                1270                1275 cac gct aac aag gtc gtc tgt atg gcg tcc ctg gag gtt tat gtg    3879
His Ala Asn Lys Val Val Cys Met Ala Ser Leu Glu Val Tyr Val
1280                1285                1290 agg aga ggt tac atc gcc tac gag tta aac agc cta cag cac cgg    3924
Arg Arg Gly Tyr Ile Ala Tyr Glu Leu Asn Ser Leu Gln His Arg
        1295                1300                1305 gag ctc cct gac ggc acc tgc gtg gtg gag ttc cag ttc atg ctg    3969
Glu Leu Pro Asp Gly Thr Cys Val Val Glu Phe Gln Phe Met Leu
    1310                1315                1320 ccg tct tcc cac ccc aac cgg atg gcc atg ccc atc aat gtc tct    4014
Pro Ser Ser His Pro Asn Arg Met Ala Met Pro Ile Asn Val Ser
1325                1330                1335 gac cct gac ctg ctg aga cac agt aag gaa ctc ttc atg gac agt    4059
Asp Pro Asp Leu Leu Arg His Ser Lys Glu Leu Phe Met Asp Ser
        1340                1345                1350 ggc ttc tcc cca ctg tgt cac cag cgg atg ggg gcc atg gtg gcc    4104
Gly Phe Ser Pro Leu Cys His Gln Arg Met Gly Ala Met Val Ala
    1355                1360                1365 ttc agg aga ttt gag gag ttc acc agg aac ttc gat gaa gtc atc    4149
Phe Arg Arg Phe Glu Glu Phe Thr Arg Asn Phe Asp Glu Val Ile
1370                1375                1380 tcc tgc ttt gcc aac gtg cct aca gac act cct ctc ttc agt aag    4194
Ser Cys Phe Ala Asn Val Pro Thr Asp Thr Pro Leu Phe Ser Lys
        1385                1390                1395 gcg tgc act tcc ctc tac tca gag gag gac agc aag agc ctt caa    4239
Ala Cys Thr Ser Leu Tyr Ser Glu Glu Asp Ser Lys Ser Leu Gln
    1400                1405                1410 gag gag ccc atc cac atc ctg aat gtg gcc atc cag tgc gcc gac    4284
Glu Glu Pro Ile His Ile Leu Asn Val Ala Ile Gln Cys Ala Asp
1415                1420                1425 cac atg gag gac gag aga ctg gtg ccg gtt ttc cgt gcc ttt gta    4329
His Met Glu Asp Glu Arg Leu Val Pro Val Phe Arg Ala Phe Val
        1430                1435                1440 cag tcc aag aaa cac atc ctt gtg gat tac gga ctg cga aga atc    4374
Gln Ser Lys Lys His Ile Leu Val Asp Tyr Gly Leu Arg Arg Ile
    1445                1450                1455 aca ttc ctt atc gcc caa gag aag gaa ttt ccc aag ttc ttc acg    4419
Thr Phe Leu Ile Ala Gln Glu Lys Glu Phe Pro Lys Phe Phe Thr
1460                1465                1470 ttc aga gcg aga gat gag ttt gca gaa gac cgg att tac cgc cac    4464
Phe Arg Ala Arg Asp Glu Phe Ala Glu Asp Arg Ile Tyr Arg His
        1475                1480                1485 ttg gag ccg ggc ctg gcc ttc cag ctg gag ctg agc cgg atg cgc    4509
Leu Glu Pro Gly Leu Ala Phe Gln Leu Glu Leu Ser Arg Met Arg
    1490                1495                1500 aac ttt gac ttg acg gcc gtg ccc tgt gcc aac cat aag atg cat    4554
Asn Phe Asp Leu Thr Ala Val Pro Cys Ala Asn His Lys Met His
1505                1510                1515
```

-continued

| | | |
|---|---|---|
| ctt tac ctg gga gcc gcc aag gtg aag gaa ggg ctg gag gtg act<br>Leu Tyr Leu Gly Ala Ala Lys Val Lys Glu Gly Leu Glu Val Thr<br>1520                        1525                     1530 | 4599 |
| gac cac agg ttc ttc atc cga gcc atc ata agg cac tca gac ctg<br>Asp His Arg Phe Phe Ile Arg Ala Ile Ile Arg His Ser Asp Leu<br>1535                        1540                     1545 | 4644 |
| atc acc aag gaa gcc tcc ttc gag tac ctg cag aat gaa ggg gag<br>Ile Thr Lys Glu Ala Ser Phe Glu Tyr Leu Gln Asn Glu Gly Glu<br>1550                        1555                     1560 | 4689 |
| cgg ctg ctg ctg gaa gcc atg gac gag ctg gag gtg gcg ttc aac<br>Arg Leu Leu Leu Glu Ala Met Asp Glu Leu Glu Val Ala Phe Asn<br>1565                        1570                     1575 | 4734 |
| aac acc agc gtg cgc act gac tgc aac cac atc ttc ctc aac ttc<br>Asn Thr Ser Val Arg Thr Asp Cys Asn His Ile Phe Leu Asn Phe<br>1580                        1585                     1590 | 4779 |
| gtg gcc cac gtc atc atg gac cca ctc aag atc gag gag tcg gtg<br>Val Ala His Val Ile Met Asp Pro Leu Lys Ile Glu Glu Ser Val<br>1595                        1600                     1605 | 4824 |
| cgt gcc atg gtc atg cgt tac ggc agt cgg ctg tgg aag ctc cgt<br>Arg Ala Met Val Met Arg Tyr Gly Ser Arg Leu Trp Lys Leu Arg<br>1610                        1615                     1620 | 4869 |
| gtg ctg cag gca caa gtt aag atc aac atc cgt cag acg acc tcg<br>Val Leu Gln Ala Gln Val Lys Ile Asn Ile Arg Gln Thr Thr Ser<br>1625                        1630                     1635 | 4914 |
| gac tgc gcc gtc ccc att cgc ctc ttc atc acc aac gag tcc ggc<br>Asp Cys Ala Val Pro Ile Arg Leu Phe Ile Thr Asn Glu Ser Gly<br>1640                        1645                     1650 | 4959 |
| tac tac ctg gac atc agc ctc tac aaa gaa gtg acc gac tcc aga<br>Tyr Tyr Leu Asp Ile Ser Leu Tyr Lys Glu Val Thr Asp Ser Arg<br>1655                        1660                     1665 | 5004 |
| tcc gga aac atc atg ttt cat tcc ttc ggc aac aaa caa ggg agc<br>Ser Gly Asn Ile Met Phe His Ser Phe Gly Asn Lys Gln Gly Ser<br>1670                        1675                     1680 | 5049 |
| ctg cac ggg atg ctg atc aac acg ccc tac gtc acc aag gat ctg<br>Leu His Gly Met Leu Ile Asn Thr Pro Tyr Val Thr Lys Asp Leu<br>1685                        1690                     1695 | 5094 |
| ctc caa gcc aag cga ttc cag gcg cag tcc ctg ggg acc acc tat<br>Leu Gln Ala Lys Arg Phe Gln Ala Gln Ser Leu Gly Thr Thr Tyr<br>1700                        1705                     1710 | 5139 |
| gtg tac gac ttc cca gag atg ttc agg cag gct ctc ttt aaa ttg<br>Val Tyr Asp Phe Pro Glu Met Phe Arg Gln Ala Leu Phe Lys Leu<br>1715                        1720                     1725 | 5184 |
| tgg ggc tcc cca gag aag tac ggg ccc gat atc ctg aca tac aca<br>Trp Gly Ser Pro Glu Lys Tyr Gly Pro Asp Ile Leu Thr Tyr Thr<br>1730                        1735                     1740 | 5229 |
| gag ctg gtg ttg gac tcc cag ggc cag ctg gtg gag atg aac cgg<br>Glu Leu Val Leu Asp Ser Gln Gly Gln Leu Val Glu Met Asn Arg<br>1745                        1750                     1755 | 5274 |
| ctt cct ggt tgt aac gag gtg ggc atg gtg gtt ttc aaa atg agg<br>Leu Pro Gly Cys Asn Glu Val Gly Met Val Val Phe Lys Met Arg<br>1760                        1765                     1770 | 5319 |
| ttc aag acc ccg gag tat cca gaa ggc cgg gac act atc gtc atc<br>Phe Lys Thr Pro Glu Tyr Pro Glu Gly Arg Asp Thr Ile Val Ile<br>1775                        1780                     1785 | 5364 |
| ggc aac gac att acc ttc caa atc ggc tct ttc ggc ata gga gag<br>Gly Asn Asp Ile Thr Phe Gln Ile Gly Ser Phe Gly Ile Gly Glu<br>1790                        1795                     1800 | 5409 |
| gac ttc ctg tat cta cgg gca tcg gag atg gcc cgg aca gag ggc<br>Asp Phe Leu Tyr Leu Arg Ala Ser Glu Met Ala Arg Thr Glu Gly | 5454 |

-continued

|  |  |  |  |
|---|---|---|---|
| | 1805 | 1810 | 1815 |
| atc ccc caa atc tat ctg gca gcc aac agc ggc gcc gta ttg ggc<br>Ile Pro Gln Ile Tyr Leu Ala Ala Asn Ser Gly Ala Val Leu Gly<br>1820                                   1825                                   1830 | | 5499 |
| ctg tcc gag gag atc aag cag ata ttc caa gtg gca tgg gtg gac<br>Leu Ser Glu Glu Ile Lys Gln Ile Phe Gln Val Ala Trp Val Asp<br>1835                                   1840                                   1845 | | 5544 |
| cct gag gat ccc tac aaa gga ttt aga tac ctg tac ctg tac ctg<br>Pro Glu Asp Pro Tyr Lys Gly Phe Arg Tyr Leu Tyr Leu Tyr Leu<br>1850                                   1855                                   1860 | | 5589 |
| acg ccc caa gac tac acc cag atc agc tcc cag aac tcc gtg cac<br>Thr Pro Gln Asp Tyr Thr Gln Ile Ser Ser Gln Asn Ser Val His<br>1865                                   1870                                   1875 | | 5634 |
| tgc aaa cac atc gag gac gaa ggc gag tca ggt att atc gtt gat<br>Cys Lys His Ile Glu Asp Glu Gly Glu Ser Gly Ile Ile Val Asp<br>1880                                   1885                                   1890 | | 5679 |
| gtc atc ggg aag gac agc agc ctg ggt gtg gag aac ctg cgg ggc<br>Val Ile Gly Lys Asp Ser Ser Leu Gly Val Glu Asn Leu Arg Gly<br>1895                                   1900                                   1905 | | 5724 |
| tcg ggc atg att gca gga gag gct tct ctg gct tac gaa aaa aat<br>Ser Gly Met Ile Ala Gly Glu Ala Ser Leu Ala Tyr Glu Lys Asn<br>1910                                   1915                                   1920 | | 5769 |
| gtc acc atc agc atg gtc gac tgc cgc gcc atc gga atc ggg gct<br>Val Thr Ile Ser Met Val Asp Cys Arg Ala Ile Gly Ile Gly Ala<br>1925                                   1930                                   1935 | | 5814 |
| tac ctg gtg agg ctg ggc cag cgg gtg atc cag gtg gaa aac tcc<br>Tyr Leu Val Arg Leu Gly Gln Arg Val Ile Gln Val Glu Asn Ser<br>1940                                   1945                                   1950 | | 5859 |
| cac atc atc ctc acg gga gcc ggt gct ctc aac aag gtt ctg gga<br>His Ile Ile Leu Thr Gly Ala Gly Ala Leu Asn Lys Val Leu Gly<br>1955                                   1960                                   1965 | | 5904 |
| aga gag gtc tac aca tcc aac aac caa ctg ggc ggt gtg cag atc<br>Arg Glu Val Tyr Thr Ser Asn Asn Gln Leu Gly Gly Val Gln Ile<br>1970                                   1975                                   1980 | | 5949 |
| atg cac acc aac ggg gtc tcc cac gtc acg gtg cca gat gac ttc<br>Met His Thr Asn Gly Val Ser His Val Thr Val Pro Asp Asp Phe<br>1985                                   1990                                   1995 | | 5994 |
| gag ggg gtc tgc acc att ctg gaa tgg ctg tca tat ata cca aag<br>Glu Gly Val Cys Thr Ile Leu Glu Trp Leu Ser Tyr Ile Pro Lys<br>2000                                   2005                                   2010 | | 6039 |
| gac aat caa agc cca gtc ccc atc atc act cct tct gac ccc atc<br>Asp Asn Gln Ser Pro Val Pro Ile Ile Thr Pro Ser Asp Pro Ile<br>2015                                   2020                                   2025 | | 6084 |
| gac agg gaa att gaa ttc acc cca acc aaa gct ccc tat gac ccc<br>Asp Arg Glu Ile Glu Phe Thr Pro Thr Lys Ala Pro Tyr Asp Pro<br>2030                                   2035                                   2040 | | 6129 |
| agg tgg ctg ctg gca ggg agg cct cac cca act ctg aag ggg acc<br>Arg Trp Leu Leu Ala Gly Arg Pro His Pro Thr Leu Lys Gly Thr<br>2045                                   2050                                   2055 | | 6174 |
| tgg cag agt gga ttc ttc gac cat ggc agt ttc aag gaa atc atg<br>Trp Gln Ser Gly Phe Phe Asp His Gly Ser Phe Lys Glu Ile Met<br>2060                                   2065                                   2070 | | 6219 |
| gca ccc tgg gac cag act gtg gtg act gga cga gca agg ctg ggg<br>Ala Pro Trp Asp Gln Thr Val Val Thr Gly Arg Ala Arg Leu Gly<br>2075                                   2080                                   2085 | | 6264 |
| ggc atc cct gta ggg gtg att gcc gtg gag act cgg tct gtg gag<br>Gly Ile Pro Val Gly Val Ile Ala Val Glu Thr Arg Ser Val Glu<br>2090                                   2095                                   2100 | | 6309 |
| gtg gct gtc cct gct cac cca gcc aac ttg gat tct gag gcc aag | | 6354 |

```
                                            -continued

Val Ala Val Pro Ala His Pro Ala Asn Leu Asp Ser Glu Ala Lys
    2105            2110            2115 atc atc cag cag gca ggc cag gtg tgg ttc ccg gac tct gcc ttc      6399
Ile Ile Gln Gln Ala Gly Gln Val Trp Phe Pro Asp Ser Ala Phe
    2120            2125            2130 aag acg gct cag gtc atc agg gac ttc aac cag gag cat ctg ctt      6444
Lys Thr Ala Gln Val Ile Arg Asp Phe Asn Gln Glu His Leu Leu
    2135            2140            2145 ctc atg atc ttt gct aac tgg aga ggc ttc tcg ggc ggc atg aaa      6489
Leu Met Ile Phe Ala Asn Trp Arg Gly Phe Ser Gly Gly Met Lys
    2150            2155            2160 gac atg tcc gag cag atg ctg aag ttt ggc gcc tac atc gtg gac      6534
Asp Met Ser Glu Gln Met Leu Lys Phe Gly Ala Tyr Ile Val Asp
    2165            2170            2175 agt ctc cgt ctg tcc aag cag cca gtc ctc atc tat atc cct ccc      6579
Ser Leu Arg Leu Ser Lys Gln Pro Val Leu Ile Tyr Ile Pro Pro
    2180            2185            2190 ggt gcc gaa ctc cga ggg ggc tcc tgg gtt gtc ctc gac tcc agc      6624
Gly Ala Glu Leu Arg Gly Gly Ser Trp Val Val Leu Asp Ser Ser
    2195            2200            2205 atc aac ccc ctg tgc ata gag atg tac gca gac aaa gag agc agg      6669
Ile Asn Pro Leu Cys Ile Glu Met Tyr Ala Asp Lys Glu Ser Arg
    2210            2215            2220 ggg ggt gtt ctg gag ccc gag ggc act gtg gag att aag ttc cgg      6714
Gly Gly Val Leu Glu Pro Glu Gly Thr Val Glu Ile Lys Phe Arg
    2225            2230            2235 aag aaa gat ttg gtg aag acc ata agg agg att gac cca gtg tgc      6759
Lys Lys Asp Leu Val Lys Thr Ile Arg Arg Ile Asp Pro Val Cys
    2240            2245            2250 aag aaa ctc ctg gaa cca gct ggg gac acc cag ctc cct gac aag      6804
Lys Lys Leu Leu Glu Pro Ala Gly Asp Thr Gln Leu Pro Asp Lys
    2255            2260            2265 gac cgg aaa gag ctg gag agc cag ctg aag gcc cgg gag gac ctg      6849
Asp Arg Lys Glu Leu Glu Ser Gln Leu Lys Ala Arg Glu Asp Leu
    2270            2275            2280 ctg ctc ccc atc tac cac cag gtg gca gtg cag ttc gcc gac ctg      6894
Leu Leu Pro Ile Tyr His Gln Val Ala Val Gln Phe Ala Asp Leu
    2285            2290            2295 cat gac acg ccg ggc cac atg ctg aag aag gga atc att tct gat      6939
His Asp Thr Pro Gly His Met Leu Lys Lys Gly Ile Ile Ser Asp
    2300            2305            2310 gtc ctg gag tgg aag acc aca cgt act tac ttc tac tgg agg ctg      6984
Val Leu Glu Trp Lys Thr Thr Arg Thr Tyr Phe Tyr Trp Arg Leu
    2315            2320            2325 cgc cgg ctg ctg ctg gag gca cag gtg aag cag gag att ctg cga      7029
Arg Arg Leu Leu Leu Glu Ala Gln Val Lys Gln Glu Ile Leu Arg
    2330            2335            2340 gcc agc cct gag ctg agc cat gag cac acg cag tcc atg ctg cga      7074
Ala Ser Pro Glu Leu Ser His Glu His Thr Gln Ser Met Leu Arg
    2345            2350            2355 cgc tgg ttt gtg gag acc gag ggc gcc gtc aag gcc tac ctg tgg      7119
Arg Trp Phe Val Glu Thr Glu Gly Ala Val Lys Ala Tyr Leu Trp
    2360            2365            2370 gac agc aac cag gtg gta gtc cag tgg ctg gaa cag cac tgg tca      7164
Asp Ser Asn Gln Val Val Val Gln Trp Leu Glu Gln His Trp Ser
    2375            2380            2385 gcc agg gac aac ctg cgt tcc act atc cga gag aac ctc aat tat      7209
Ala Arg Asp Asn Leu Arg Ser Thr Ile Arg Glu Asn Leu Asn Tyr
    2390            2395            2400
```

-continued

| | | | | | | | | | | | | | | |
|---|---|---|---|---|---|---|---|---|---|---|---|---|---|---|
| ctg | aag | cgg | gac | tct | gtc | ctc | aag | acc | atc | caa | agc | cta | gtt | caa | 7254 |
| Leu | Lys | Arg | Asp | Ser | Val | Leu | Lys | Thr | Ile | Gln | Ser | Leu | Val | Gln | |
| | 2405 | | | | 2410 | | | | | 2415 | | | | | |
| gaa | cac | cca | gag | gcg | acc | atg | gga | ctg | tgt | gga | tac | ctg | agc | cag | 7299 |
| Glu | His | Pro | Glu | Ala | Thr | Met | Gly | Leu | Cys | Gly | Tyr | Leu | Ser | Gln | |
| | 2420 | | | | 2425 | | | | | 2430 | | | | | |
| cac | ctc | acg | ccc | gct | gag | cag | atg | cag | gtg | gtt | cag | ctg | ctg | tcg | 7344 |
| His | Leu | Thr | Pro | Ala | Glu | Gln | Met | Gln | Val | Val | Gln | Leu | Leu | Ser | |
| | 2435 | | | | 2440 | | | | | 2445 | | | | | |
| acc | acg | gag | agc | cca | gct | tcc | cac | tga | | | | | | | 7371 |
| Thr | Thr | Glu | Ser | Pro | Ala | Ser | His | | | | | | | | |
| | 2450 | | | | 2455 | | | | | | | | | | |

<210> SEQ ID NO 10
<211> LENGTH: 2456
<212> TYPE: PRT
<213> ORGANISM: Rattus norvegicus

<400> SEQUENCE: 10

Met Val Leu Leu Leu Phe Leu Thr Tyr Leu Val Phe Ser Cys Leu Thr
1               5                   10                  15

Ile Ser Trp Leu Lys Ile Trp Gly Lys Met Thr Asp Ser Arg Pro Leu
            20                  25                  30

Ser Asn Ser Lys Val Asp Ala Ser Leu Leu Pro Ser Lys Glu Glu Ser
        35                  40                  45

Phe Ala Ser Asp Gln Ser Glu Glu His Gly Asp Cys Ser Cys Pro Leu
    50                  55                  60

Thr Thr Pro Asp Gln Glu Glu Leu Ala Ser His Gly Gly Pro Val Asp
65                  70                  75                  80

Ala Ser Gln Gln Arg Asn Ser Val Pro Thr Ser His Gln Lys Pro Pro
                85                  90                  95

Arg Asn Pro Leu Ser Ser Asn Asp Thr Cys Ser Ser Pro Glu Leu Gln
            100                 105                 110

Thr Asn Gly Val Ala Ala Pro Gly Ser Glu Val Pro Glu Ala Asn Gly
        115                 120                 125

Leu Pro Phe Pro Ala Arg Pro Gln Thr Gln Arg Thr Gly Ser Pro Thr
    130                 135                 140

Arg Glu Asp Lys Lys Gln Ala Pro Ile Lys Arg Gln Leu Met Thr Ser
145                 150                 155                 160

Phe Ile Leu Gly Ser Leu Asp Asp Asn Ser Asp Glu Asp Pro Ser
                165                 170                 175

Ser Asn Ser Phe Gln Thr Ser Ser Arg Lys Gly Ser Arg Asp Ser Leu
            180                 185                 190

Gly Thr Cys Ser Gln Glu Ala Ala Leu Asn Thr Ala Asp Pro Glu Ser
        195                 200                 205

His Thr Pro Thr Met Arg Pro Ser Met Ser Gly Leu His Leu Val Lys
    210                 215                 220

Arg Gly Arg Glu His Lys Lys Leu Asp Leu His Arg Asp Phe Thr Val
225                 230                 235                 240

Ala Ser Pro Ala Glu Phe Val Thr Arg Phe Gly Gly Asn Arg Val Ile
                245                 250                 255

Glu Thr Val Leu Ile Ala Asn Asn Gly Ile Ala Ala Val Lys Trp Met
            260                 265                 270

Arg Ser Ile Arg Arg Trp Ala Tyr Glu Met Phe Arg Asn Glu Arg Ala
        275                 280                 285

Ile Arg Phe Val Val Met Val Thr Pro Glu Asp Leu Lys Ala Asn Ala

-continued

```
            290                 295                 300
Glu Tyr Tyr Lys Met Ala Asp Pro Val Leu Pro Val Pro Gly Gly Pro
305                 310                 315                 320

Asn Asn Asn Asn Tyr Ala Asn Val Glu Leu Ile Ile Asp Ile Ala Lys
                325                 330                 335

Arg Ile Pro Val Gln Ala Val Trp Ala Gly Trp Gly His Ala Ser Glu
            340                 345                 350

Asn Pro Lys Leu Pro Glu Leu Leu Cys Lys His Gly Ile Ala Phe Leu
            355                 360                 365

Gly Pro Arg Val Arg Pro Met Leu Gly Leu Gly Asp Arg Leu Ser Ser
370                 375                 380

Thr Ile Ala Gln Thr Leu Gln Ile Pro Thr Leu Pro Trp Ser Gly
385                 390                 395                 400

Ser Gly Leu Thr Val Glu Trp Thr Glu Asp Ser Gln His Gln Gly Lys
                405                 410                 415

Cys Ile Ser Val Thr Glu Asp Val Tyr Glu Gln Gly Cys Val Arg Asp
            420                 425                 430

Val Asp Glu Gly Leu Gln Ala Ala Glu Lys Val Gly Phe Pro Leu Met
            435                 440                 445

Ile Lys Ala Ser Glu Gly Gly Gly Lys Gly Ile Arg Gln Ala Glu
    450                 455                 460

Ser Ala Glu Asp Phe Pro Cys Phe Phe Arg Gln Val Gln Ser Glu Ile
465                 470                 475                 480

Pro Gly Ser Pro Ile Phe Leu Met Lys Leu Ala Gln Asn Ala Arg His
                485                 490                 495

Leu Glu Val Gln Val Leu Ala Asp Gln Tyr Gly Asn Ala Val Ser Leu
            500                 505                 510

Phe Gly Arg Asp Cys Ser Ile Gln Arg Arg His Gln Lys Ile Ile Glu
            515                 520                 525

Glu Ala Pro Ala Asn Ile Ala Ala Pro Ala Val Phe Glu Phe Met Glu
            530                 535                 540

Gln Cys Ala Val Leu Leu Ala Lys Thr Val Val Tyr Val Ser Ala Gly
545                 550                 555                 560

Thr Val Gly Tyr Leu Tyr Ser Gln Asp Gly Ser Phe His Phe Leu Glu
                565                 570                 575

Leu Asn Pro Arg Leu Gln Val Glu His Pro Cys Thr Glu Met Ile Ala
            580                 585                 590

Asp Val Asn Leu Pro Ala Ala Gln Leu Gln Ile Ala Met Gly Val Pro
            595                 600                 605

Leu His Arg Leu Lys Asp Ile Arg Leu Leu Tyr Gly Glu Ser Pro Trp
            610                 615                 620

Gly Val Thr Pro Val Ser Phe Glu Thr Pro Leu Ser Pro Pro Ile Ala
625                 630                 635                 640

Arg Gly His Val Ile Ala Ala Arg Ile Thr Ser Glu Asn Pro Asp Glu
                645                 650                 655

Ala Phe Lys Pro Ser Ser Gly Thr Val Gln Glu Leu Asn Phe Arg Ser
            660                 665                 670

Asn Lys Asn Val Trp Gly Tyr Phe Ser Val Ala Ala Gly Gly Leu
            675                 680                 685

His Glu Phe Pro Ile Ser Gln Phe Gly His Cys Phe Ser Trp Gly Glu
            690                 695                 700

Asn Gln Glu Glu Ala Ile Ser Asn Met Val Val Ala Leu Lys Glu Leu
705                 710                 715                 720
```

```
Ser Ile Arg Gly Asp Phe Arg Thr Thr Val Glu Tyr Leu Val Asn Leu
            725                 730                 735

Leu Glu Thr Glu Ser Leu Gln Asn Asn Asp Ile Asp Thr Gly Trp Leu
            740                 745                 750

Asp His Leu Ile Ala Gln Arg Val Gln Ala Glu Lys Pro Asp Ile Met
            755                 760                 765

Leu Gly Val Val Phe Gly Ala Leu Asn Val Ala Asp Ala Met Phe Arg
            770                 775                 780

Thr Cys Ile Thr Glu Phe Leu His Ser Leu Glu Arg Gly Gln Val Leu
785                 790                 795                 800

Pro Ala Asp Ser Leu Leu Asn Ile Val Asp Val Glu Leu Ile Tyr Gly
            805                 810                 815

Gly Ile Lys Tyr Val Leu Lys Val Ala Arg Gln Ser Leu Thr Met Phe
            820                 825                 830

Val Leu Ile Met Asn Gly Cys His Ile Glu Ile Asp Ala His Arg Pro
            835                 840                 845

Asn Asp Gly Gly Leu Leu Leu Ser Tyr Asn Gly Ser Ser Tyr Thr Thr
850                 855                 860

Tyr Met Lys Glu Glu Val Asp Ser Tyr Arg Ile Thr Ile Gly Asn Lys
865                 870                 875                 880

Thr Cys Val Phe Glu Lys Glu Asn Asp Pro Thr Val Leu Arg Ser Pro
            885                 890                 895

Ser Ala Gly Lys Leu Met Gln Tyr Thr Val Glu Asp Gly Gln His Val
            900                 905                 910

Glu Val Gly Ser Ser Tyr Ala Glu Met Glu Val Met Lys Met Ile Met
            915                 920                 925

Thr Leu Asn Val Gln Glu Ser Gly Arg Val Asn Tyr Ile Lys Arg Pro
            930                 935                 940

Gly Ala Val Leu Glu Ala Gly Cys Val Val Ala Lys Leu Glu Leu Asp
945                 950                 955                 960

Asp Pro Ser Lys Val His Ala Ala Gln Pro Phe Thr Gly Glu Leu Pro
            965                 970                 975

Ala Gln Gln Thr Leu Pro Ile Leu Gly Glu Arg Leu His Gln Val Phe
            980                 985                 990

His Ser Val Leu Glu Asn Leu Thr Asn Val Met Asn Gly Tyr Cys Leu
            995                 1000                1005

Pro Glu Pro Phe Phe Ser Met Lys Leu Lys Asp Trp Val Glu Lys
    1010            1015                1020

Pro Met Met Thr Leu Arg His Pro Ser Leu Pro Leu Leu Glu Leu
    1025            1030                1035

Gln Glu Ile Met Thr Ser Val Ala Asp Arg Ile Pro Val Pro Val
    1040            1045                1050

Glu Lys Ala Val Arg Arg Val Phe Ala Gln Asp Ala Ser Asn Ile
    1055            1060                1065

Thr Ser Val Leu Cys Gln Phe Pro Ser Gln Gln Ile Ala Thr Ile
    1070            1075                1080

Leu Asp Cys His Ala Ala Thr Leu Gln Arg Lys Val Asp Arg Glu
    1085            1090                1095

Ala Phe Phe Met Asn Thr Gln Ser Ile Val Gln Leu Ile Gln Arg
    1100            1105                1110

Tyr Arg Ser Gly Thr Arg Gly Ile Met Lys Ala Val Val Leu Asp
    1115            1120                1125
```

-continued

```
Leu Leu Arg Arg Tyr Leu Asn  Val Glu His  His Phe  Gln Gln Ala
    1130             1135              1140

His Tyr Asp Lys Cys Val Ile  Asn Leu Arg  Glu Gln  Phe Lys Ala
    1145             1150              1155

Asp Met Thr Arg Val Leu Asp  Cys Ile Phe  Ser His  Ser Gln Val
    1160             1165              1170

Ala Lys Lys Asn Gln Leu Val  Thr Met Leu  Ile Asp  Glu Leu Cys
    1175             1180              1185

Gly Pro Asp Pro Thr Leu Ser  Glu Glu Leu  Thr Ser  Ile Leu Lys
    1190             1195              1200

Glu Leu Thr Gln Leu Ser Arg  Ser Glu His  Cys Lys  Val Ala Leu
    1205             1210              1215

Arg Ala Arg Gln Val Leu Ile  Ala Ser His  Leu Pro  Ser Tyr Glu
    1220             1225              1230

Leu Arg His Asn Gln Val Glu  Ser Ser Ser  Cys Gln  Pro Leu Thr
    1235             1240              1245

Cys Asn Gly His Gln Phe Cys  Pro Glu Asn  Leu Lys  Lys Leu Ile
    1250             1255              1260

Leu Ser Glu Thr Thr Ile Phe  Asp Val Leu  Pro Thr  Phe Phe Tyr
    1265             1270              1275

His Ala Asn Lys Val Val Cys  Met Ala Ser  Leu Glu  Val Tyr Val
    1280             1285              1290

Arg Arg Gly Tyr Ile Ala Tyr  Glu Leu Asn  Ser Leu  Gln His Arg
    1295             1300              1305

Glu Leu Pro Asp Gly Thr Cys  Val Val Glu  Phe Gln  Phe Met Leu
    1310             1315              1320

Pro Ser Ser His Pro Asn Arg  Met Ala Met  Pro Ile  Asn Val Ser
    1325             1330              1335

Asp Pro Asp Leu Leu Arg His  Ser Lys Glu  Leu Phe  Met Asp Ser
    1340             1345              1350

Gly Phe Ser Pro Leu Cys His  Gln Arg Met  Gly Ala  Met Val Ala
    1355             1360              1365

Phe Arg Arg Phe Glu Glu Phe  Thr Arg Asn  Phe Asp  Glu Val Ile
    1370             1375              1380

Ser Cys Phe Ala Asn Val Pro  Thr Asp Thr  Pro Leu  Phe Ser Lys
    1385             1390              1395

Ala Cys Thr Ser Leu Tyr Ser  Glu Glu Asp  Ser Lys  Ser Leu Gln
    1400             1405              1410

Glu Glu Pro Ile His Ile Leu  Asn Val Ala  Ile Gln  Cys Ala Asp
    1415             1420              1425

His Met Glu Asp Glu Arg Leu  Val Pro Val  Phe Arg  Ala Phe Val
    1430             1435              1440

Gln Ser Lys Lys His Ile Leu  Val Asp Tyr  Gly Leu  Arg Arg Ile
    1445             1450              1455

Thr Phe Leu Ile Ala Gln Glu  Lys Glu Phe  Pro Lys  Phe Phe Thr
    1460             1465              1470

Phe Arg Ala Arg Asp Glu Phe  Ala Glu Asp  Arg Ile  Tyr Arg His
    1475             1480              1485

Leu Glu Pro Gly Leu Ala Phe  Gln Leu Glu  Leu Ser  Arg Met Arg
    1490             1495              1500

Asn Phe Asp Leu Thr Ala Val  Pro Cys Ala  Asn His  Lys Met His
    1505             1510              1515

Leu Tyr Leu Gly Ala Ala Lys  Val Lys Glu  Gly Leu  Glu Val Thr
```

|  |  |  |  |  |  |  |  |  |  |
|---|---|---|---|---|---|---|---|---|---|
| | 1520 | | | | 1525 | | | | 1530 |
| Asp | His | Arg | Phe | Phe | Ile | Arg | Ala | Ile | Ile | Arg | His | Ser | Asp | Leu |
| 1535 | | | | | 1540 | | | | | 1545 | | | | |
| Ile | Thr | Lys | Glu | Ala | Ser | Phe | Glu | Tyr | Leu | Gln | Asn | Glu | Gly | Glu |
| 1550 | | | | | 1555 | | | | | 1560 | | | | |
| Arg | Leu | Leu | Leu | Glu | Ala | Met | Asp | Glu | Leu | Glu | Val | Ala | Phe | Asn |
| 1565 | | | | | 1570 | | | | | 1575 | | | | |
| Asn | Thr | Ser | Val | Arg | Thr | Asp | Cys | Asn | His | Ile | Phe | Leu | Asn | Phe |
| 1580 | | | | | 1585 | | | | | 1590 | | | | |
| Val | Ala | His | Val | Ile | Met | Asp | Pro | Leu | Lys | Ile | Glu | Glu | Ser | Val |
| 1595 | | | | | 1600 | | | | | 1605 | | | | |
| Arg | Ala | Met | Val | Met | Arg | Tyr | Gly | Ser | Arg | Leu | Trp | Lys | Leu | Arg |
| 1610 | | | | | 1615 | | | | | 1620 | | | | |
| Val | Leu | Gln | Ala | Gln | Val | Lys | Ile | Asn | Ile | Arg | Gln | Thr | Thr | Ser |
| 1625 | | | | | 1630 | | | | | 1635 | | | | |
| Asp | Cys | Ala | Val | Pro | Ile | Arg | Leu | Phe | Ile | Thr | Asn | Glu | Ser | Gly |
| 1640 | | | | | 1645 | | | | | 1650 | | | | |
| Tyr | Tyr | Leu | Asp | Ile | Ser | Leu | Tyr | Lys | Glu | Val | Thr | Asp | Ser | Arg |
| 1655 | | | | | 1660 | | | | | 1665 | | | | |
| Ser | Gly | Asn | Ile | Met | Phe | His | Ser | Phe | Gly | Asn | Lys | Gln | Gly | Ser |
| 1670 | | | | | 1675 | | | | | 1680 | | | | |
| Leu | His | Gly | Met | Leu | Ile | Asn | Thr | Pro | Tyr | Val | Thr | Lys | Asp | Leu |
| 1685 | | | | | 1690 | | | | | 1695 | | | | |
| Leu | Gln | Ala | Lys | Arg | Phe | Gln | Ala | Gln | Ser | Leu | Gly | Thr | Thr | Tyr |
| 1700 | | | | | 1705 | | | | | 1710 | | | | |
| Val | Tyr | Asp | Phe | Pro | Glu | Met | Phe | Arg | Gln | Ala | Leu | Phe | Lys | Leu |
| 1715 | | | | | 1720 | | | | | 1725 | | | | |
| Trp | Gly | Ser | Pro | Glu | Lys | Tyr | Gly | Pro | Asp | Ile | Leu | Thr | Tyr | Thr |
| 1730 | | | | | 1735 | | | | | 1740 | | | | |
| Glu | Leu | Val | Leu | Asp | Ser | Gln | Gly | Gln | Leu | Val | Glu | Met | Asn | Arg |
| 1745 | | | | | 1750 | | | | | 1755 | | | | |
| Leu | Pro | Gly | Cys | Asn | Glu | Val | Gly | Met | Val | Val | Phe | Lys | Met | Arg |
| 1760 | | | | | 1765 | | | | | 1770 | | | | |
| Phe | Lys | Thr | Pro | Glu | Tyr | Pro | Glu | Gly | Arg | Asp | Thr | Ile | Val | Ile |
| 1775 | | | | | 1780 | | | | | 1785 | | | | |
| Gly | Asn | Asp | Ile | Thr | Phe | Gln | Ile | Gly | Ser | Phe | Gly | Ile | Gly | Glu |
| 1790 | | | | | 1795 | | | | | 1800 | | | | |
| Asp | Phe | Leu | Tyr | Leu | Arg | Ala | Ser | Glu | Met | Ala | Arg | Thr | Glu | Gly |
| 1805 | | | | | 1810 | | | | | 1815 | | | | |
| Ile | Pro | Gln | Ile | Tyr | Leu | Ala | Ala | Asn | Ser | Gly | Ala | Val | Leu | Gly |
| 1820 | | | | | 1825 | | | | | 1830 | | | | |
| Leu | Ser | Glu | Glu | Ile | Lys | Gln | Ile | Phe | Gln | Val | Ala | Trp | Val | Asp |
| 1835 | | | | | 1840 | | | | | 1845 | | | | |
| Pro | Glu | Asp | Pro | Tyr | Lys | Gly | Phe | Arg | Tyr | Leu | Tyr | Leu | Tyr | Leu |
| 1850 | | | | | 1855 | | | | | 1860 | | | | |
| Thr | Pro | Gln | Asp | Tyr | Thr | Gln | Ile | Ser | Ser | Gln | Asn | Ser | Val | His |
| 1865 | | | | | 1870 | | | | | 1875 | | | | |
| Cys | Lys | His | Ile | Glu | Asp | Glu | Gly | Glu | Ser | Gly | Ile | Ile | Val | Asp |
| 1880 | | | | | 1885 | | | | | 1890 | | | | |
| Val | Ile | Gly | Lys | Asp | Ser | Ser | Leu | Gly | Val | Glu | Asn | Leu | Arg | Gly |
| 1895 | | | | | 1900 | | | | | 1905 | | | | |
| Ser | Gly | Met | Ile | Ala | Gly | Glu | Ala | Ser | Leu | Ala | Tyr | Glu | Lys | Asn |
| 1910 | | | | | 1915 | | | | | 1920 | | | | |

-continued

```
Val Thr Ile Ser Met Val Asp Cys Arg Ala Ile Gly Ile Gly Ala
    1925             1930             1935

Tyr Leu Val Arg Leu Gly Gln Arg Val Ile Gln Val Glu Asn Ser
    1940             1945             1950

His Ile Ile Leu Thr Gly Ala Gly Ala Leu Asn Lys Val Leu Gly
    1955             1960             1965

Arg Glu Val Tyr Thr Ser Asn Asn Gln Leu Gly Gly Val Gln Ile
    1970             1975             1980

Met His Thr Asn Gly Val Ser His Val Thr Val Pro Asp Asp Phe
    1985             1990             1995

Glu Gly Val Cys Thr Ile Leu Glu Trp Leu Ser Tyr Ile Pro Lys
    2000             2005             2010

Asp Asn Gln Ser Pro Val Pro Ile Ile Thr Pro Ser Asp Pro Ile
    2015             2020             2025

Asp Arg Glu Ile Glu Phe Thr Pro Thr Lys Ala Pro Tyr Asp Pro
    2030             2035             2040

Arg Trp Leu Leu Ala Gly Arg Pro His Pro Thr Leu Lys Gly Thr
    2045             2050             2055

Trp Gln Ser Gly Phe Phe Asp His Gly Ser Phe Lys Glu Ile Met
    2060             2065             2070

Ala Pro Trp Asp Gln Thr Val Val Thr Gly Arg Ala Arg Leu Gly
    2075             2080             2085

Gly Ile Pro Val Gly Val Ile Ala Val Glu Thr Arg Ser Val Glu
    2090             2095             2100

Val Ala Val Pro Ala His Pro Ala Asn Leu Asp Ser Glu Ala Lys
    2105             2110             2115

Ile Ile Gln Gln Ala Gly Gln Val Trp Phe Pro Asp Ser Ala Phe
    2120             2125             2130

Lys Thr Ala Gln Val Ile Arg Asp Phe Asn Gln Glu His Leu Leu
    2135             2140             2145

Leu Met Ile Phe Ala Asn Trp Arg Gly Phe Ser Gly Gly Met Lys
    2150             2155             2160

Asp Met Ser Glu Gln Met Leu Lys Phe Gly Ala Tyr Ile Val Asp
    2165             2170             2175

Ser Leu Arg Leu Ser Lys Gln Pro Val Leu Ile Tyr Ile Pro Pro
    2180             2185             2190

Gly Ala Glu Leu Arg Gly Gly Ser Trp Val Val Leu Asp Ser Ser
    2195             2200             2205

Ile Asn Pro Leu Cys Ile Glu Met Tyr Ala Asp Lys Glu Ser Arg
    2210             2215             2220

Gly Gly Val Leu Glu Pro Glu Gly Thr Val Glu Ile Lys Phe Arg
    2225             2230             2235

Lys Lys Asp Leu Val Lys Thr Ile Arg Arg Ile Asp Pro Val Cys
    2240             2245             2250

Lys Lys Leu Leu Glu Pro Ala Gly Asp Thr Gln Leu Pro Asp Lys
    2255             2260             2265

Asp Arg Lys Glu Leu Glu Ser Gln Leu Lys Ala Arg Glu Asp Leu
    2270             2275             2280

Leu Leu Pro Ile Tyr His Gln Val Ala Val Gln Phe Ala Asp Leu
    2285             2290             2295

His Asp Thr Pro Gly His Met Leu Lys Lys Gly Ile Ile Ser Asp
    2300             2305             2310
```

```
Val Leu Glu Trp Lys Thr Arg Thr Tyr Phe Tyr Trp Arg Leu
    2315                2320            2325

Arg Arg Leu Leu Leu Glu Ala Gln Val Lys Gln Glu Ile Leu Arg
    2330                2335            2340

Ala Ser Pro Glu Leu Ser His Glu His Thr Gln Ser Met Leu Arg
    2345                2350            2355

Arg Trp Phe Val Glu Thr Glu Gly Ala Val Lys Ala Tyr Leu Trp
    2360                2365            2370

Asp Ser Asn Gln Val Val Val Gln Trp Leu Glu Gln His Trp Ser
    2375                2380            2385

Ala Arg Asp Asn Leu Arg Ser Thr Ile Arg Glu Asn Leu Asn Tyr
    2390                2395            2400

Leu Lys Arg Asp Ser Val Leu Lys Thr Ile Gln Ser Leu Val Gln
    2405                2410            2415

Glu His Pro Glu Ala Thr Met Gly Leu Cys Gly Tyr Leu Ser Gln
    2420                2425            2430

His Leu Thr Pro Ala Glu Gln Met Gln Val Val Gln Leu Leu Ser
    2435                2440            2445

Thr Thr Glu Ser Pro Ala Ser His
    2450                2455

<210> SEQ ID NO 11
<211> LENGTH: 2458
<212> TYPE: PRT
<213> ORGANISM: Homo sapiens
<220> FEATURE:
<221> NAME/KEY: MISC_FEATURE
<222> LOCATION: (1)..(2458)
<223> OTHER INFORMATION: Xaa is any amino acid

<400> SEQUENCE: 11

Met Val Leu Leu Leu Cys Leu Ser Xaa Leu Ile Phe Ser Cys Leu Thr
1               5                   10                  15

Phe Ser Trp Leu Lys Ile Trp Gly Lys Met Thr Asp Ser Lys Pro Ile
                20                  25                  30

Thr Lys Ser Lys Ser Glu Ala Asn Leu Ile Pro Ser Gln Glu Pro Phe
            35                  40                  45

Pro Ala Ser Asp Asn Ser Gly Glu Thr Pro Gln Arg Asn Gly Glu Gly
        50                  55                  60

His Thr Leu Pro Lys Thr Pro Ser Gln Ala Glu Pro Ala Ser His Lys
65                  70                  75                  80

Gly Pro Lys Asp Ala Gly Arg Arg Arg Asn Ser Leu Pro Pro Ser His
                    85                  90                  95

Gln Lys Pro Pro Arg Asn Pro Leu Ser Ser Ser Asp Ala Ala Xaa Ser
                100                 105                 110

Pro Glu Leu Gln Ala Asn Gly Thr Gly Thr Gln Gly Leu Glu Xaa Thr
            115                 120                 125

Asp Thr Asn Gly Leu Ser Ser Ser Ala Arg Pro Gln Gly Gln Gln Ala
        130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                    165                 170                 175

Glu Asp Ser Val Ala Gly Ser Ser Arg Glu Ser Thr Arg Lys Gly Ser
                180                 185                 190

Arg Ala Ser Leu Gly Ala Leu Ser Leu Glu Ala Tyr Leu Thr Thr Gly
```

```
                195                 200                 205
Glu Ala Glu Thr Arg Val Pro Thr Met Arg Pro Ser Met Ser Gly Leu
    210                 215                 220

His Leu Val Lys Arg Gly Arg Glu His Lys Leu Asp Leu His Arg
225                 230                 235                 240

Asp Phe Thr Val Ala Ser Pro Ala Glu Phe Val Thr Arg Xaa Gly Gly
                245                 250                 255

Asp Arg Val Ile Glu Lys Val Leu Ile Ala Asn Asn Gly Ile Ala Ala
                260                 265                 270

Val Lys Cys Met Arg Ser Ile Arg Arg Trp Ala Tyr Glu Met Phe Arg
                275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Asn Tyr Ala Asn Val Glu Leu Ile Val
                325                 330                 335

Asp Ile Ala Lys Arg Ile Pro Val Xaa Ala Xaa Trp Xaa Xaa Xaa Xaa
            340                 345                 350

His Ala Ser Glu Asn Pro Lys Leu Pro Glu Leu Leu Cys Lys Asn Gly
            355                 360                 365

Val Ala Phe Leu Gly Pro Pro Ser Glu Ala Met Trp Ala Leu Gly Asp
    370                 375                 380

Lys Ile Ala Ser Thr Val Val Ala Gln Thr Leu Gln Val Pro Thr Leu
385                 390                 395                 400

Pro Trp Ser Gly Ser Gly Leu Thr Val Glu Trp Thr Glu Asp Asp Leu
                405                 410                 415

Gln Gln Gly Lys Arg Ile Ser Val Pro Glu Asp Val Tyr Asp Lys Gly
                420                 425                 430

Cys Val Lys Asp Val Asp Glu Gly Leu Glu Ala Ala Glu Arg Ile Gly
            435                 440                 445

Phe Xaa Leu Met Ile Lys Ala Ser Glu Gly Gly Gly Gly Lys Gly Ile
    450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                485                 490                 495

His Ala Arg His Leu Glu Val Gln Ile Leu Ala Asp Gln Tyr Gly Asn
            500                 505                 510

Ala Val Ser Leu Phe Gly Arg Asp Cys Ser Ile Gln Arg Arg His Gln
    515                 520                 525

Lys Ile Val Glu Glu Ala Pro Ala Thr Ile Ala Pro Leu Ala Ile Phe
    530                 535                 540

Glu Phe Met Glu Gln Cys Ala Ile Arg Leu Ala Lys Thr Val Gly Tyr
545                 550                 555                 560

Val Ser Ala Gly Xaa Val Glu Tyr Leu Tyr Ser Gln Asp Gly Ser Phe
                565                 570                 575

His Phe Leu Glu Leu Asn Pro Arg Leu Gln Val Glu His Pro Cys Thr
            580                 585                 590

Glu Met Ile Ala Asp Val Asn Leu Pro Ala Ala Gln Leu Gln Ile Ala
        595                 600                 605

Met Gly Val Pro Leu Xaa Arg Leu Lys Asp Ile Arg Leu Leu Tyr Gly
610                 615                 620
```

-continued

Glu Ser Pro Trp Gly Val Thr Pro Ile Ser Phe Glu Thr Pro Ser Asn
625                 630                 635                 640

Pro Pro Leu Ala Arg Gly His Val Ile Ala Arg Ile Thr Ser Xaa
        645                 650                 655

Asn Pro Asp Glu Gly Xaa Lys Pro Ser Ser Gly Thr Val Gln Glu Leu
        660                 665                 670

Asn Phe Arg Ser Ser Lys Asn Val Trp Gly Tyr Phe Ser Val Ala Ala
        675                 680                 685

Thr Gly Gly Leu His Glu Phe Ala Asp Ser Gln Phe Gly His Cys Phe
        690                 695                 700

Ser Trp Gly Glu Asn Arg Glu Glu Ala Ile Ser Asn Met Val Val Ala
705                 710                 715                 720

Leu Lys Glu Leu Ser Ile Arg Gly Asp Phe Arg Thr Thr Val Glu Tyr
                725                 730                 735

Leu Ile Asn Leu Leu Xaa Xaa Glu Ser Phe Gln Asn Asn Asp Ile Asp
                740                 745                 750

Thr Gly Trp Leu Asp Tyr Leu Ile Ala Glu Lys Val Gln Ala Glu Lys
        755                 760                 765

Pro Asp Ile Met Leu Gly Val Val Cys Gly Ala Leu Asn Val Ala Asp
        770                 775                 780

Ala Met Phe Arg Thr Cys Met Thr Asp Phe Leu His Ser Leu Xaa Arg
785                 790                 795                 800

Gly Gln Val Leu Pro Ala Asp Ser Leu Leu Asn Leu Val Asp Val Glu
                805                 810                 815

Leu Ile Tyr Gly Gly Val Lys Tyr Ile Leu Lys Val Ala Arg Gln Ser
                820                 825                 830

Leu Thr Met Phe Val Leu Ile Met Xaa Gly Cys His Ile Glu Ile Asp
        835                 840                 845

Ala His Arg Leu Asn Asp Gly Gly Leu Leu Ser Tyr Asn Gly Asn
850                 855                 860

Ser Tyr Thr Thr Tyr Met Lys Glu Val Asp Ser Tyr Arg Ile Thr
865                 870                 875                 880

Ile Gly Asn Lys Thr Cys Val Phe Glu Lys Glu Asn Asp Pro Thr Val
                885                 890                 895

Leu Arg Ser Pro Ser Ala Gly Lys Leu Thr Gln Tyr Thr Val Glu Asp
                900                 905                 910

Gly Gly His Val Glu Ala Gly Ser Ser Tyr Ala Glu Met Glu Val Met
        915                 920                 925

Lys Met Ile Met Thr Leu Asn Val Gln Glu Arg Gly Arg Val Lys Tyr
930                 935                 940

Ile Lys Arg Pro Gly Ala Val Leu Glu Ala Gly Cys Val Val Ala Arg
945                 950                 955                 960

Leu Glu Leu Asp Asp Pro Ser Lys Val His Pro Ala Glu Pro Phe Thr
                965                 970                 975

Gly Glu Leu Pro Ala Gln Gln Thr Leu Pro Ile Leu Gly Glu Lys Leu
        980                 985                 990

His Gln Val Phe His Ser Val Leu Glu Asn Leu Thr Asn Val Met Ser
        995                 1000                1005

Gly Phe Cys Leu Pro Glu Pro Val Phe Ser Ile Lys Leu Lys Glu
        1010                1015                1020

Trp Xaa Gln Lys Leu Met Met Thr Leu Arg His Pro Ser Leu Pro
        1025                1030                1035

-continued

```
Leu Leu Glu Leu Gln Glu Ile Met Thr Ser Val Ala Gly Arg Ile
    1040                1045                1050

Pro Ala Pro Val Glu Lys Ser Val Arg Arg Xaa Met Ala Gln Tyr
    1055                1060                1065

Ala Ser Asn Ile Thr Ser Val Leu Cys Gln Phe Pro Ser Gln Gln
    1070                1075                1080

Ile Ala Thr Ile Leu Asp Cys His Ala Ala Thr Leu Gln Arg Lys
    1085                1090                1095

Ala Asp Arg Glu Xaa Phe Phe Ile Asn Thr Gln Ser Ile Val Gln
    1100                1105                1110

Leu Val Gln Arg Tyr Arg Ser Gly Ile Arg Gly Tyr Met Lys Thr
    1115                1120                1125

Val Val Leu Asp Leu Leu Arg Arg Tyr Leu Arg Val Glu His His
    1130                1135                1140

Phe Gln Gln Ala His Tyr Asp Lys Cys Val Ile Asn Leu Arg Glu
    1145                1150                1155

Gln Phe Lys Pro Asp Met Ser Gln Val Leu Asp Cys Ile Phe Ser
    1160                1165                1170

His Ala Gln Val Ala Lys Lys Asn Gln Leu Val Ile Met Leu Ile
    1175                1180                1185

Asp Glu Leu Cys Gly Pro Asp Pro Ser Leu Ser Asp Glu Leu Ile
    1190                1195                1200

Ser Ile Leu Asn Glu Leu Thr Gln Leu Ser Lys Ser Glu His Cys
    1205                1210                1215

Lys Val Ala Leu Arg Ala Arg Gln Ile Leu Ile Ala Ser His Leu
    1220                1225                1230

Pro Ser Tyr Glu Leu Arg His Asn Gln Val Glu Ser Ile Phe Leu
    1235                1240                1245

Ser Ala Ile Asp Met Tyr Gly His Gln Phe Xaa Pro Glu Asn Leu
    1250                1255                1260

Lys Lys Leu Ile Leu Ser Glu Thr Thr Ile Phe Asp Val Leu Pro
    1265                1270                1275

Thr Phe Phe Tyr His Ala Asn Lys Val Val Cys Met Ala Ser Leu
    1280                1285                1290

Glu Val Tyr Val Arg Arg Gly Tyr Ile Ala Tyr Glu Leu Asn Ser
    1295                1300                1305

Leu Gln His Arg Gln Leu Pro Asp Gly Thr Cys Val Val Glu Phe
    1310                1315                1320

Gln Phe Met Leu Pro Ser Ser His Pro Asn Arg Met Thr Val Pro
    1325                1330                1335

Ile Ser Ile Thr Asn Pro Asp Leu Leu Arg His Ser Thr Glu Leu
    1340                1345                1350

Phe Met Asp Ser Gly Phe Ser Pro Leu Cys Gln Arg Met Gly Ala
    1355                1360                1365

Met Val Ala Phe Arg Arg Phe Glu Asp Phe Thr Arg Asn Phe Asp
    1370                1375                1380

Glu Val Ile Ser Cys Phe Ala Asn Val Pro Lys Asp Thr Pro Leu
    1385                1390                1395

Phe Ser Glu Ala Arg Thr Ser Leu Tyr Ser Glu Asp Asp Cys Lys
    1400                1405                1410

Ser Leu Arg Glu Glu Pro Ile His Ile Leu Asn Val Ser Ile Gln
    1415                1420                1425

Cys Ala Asp His Leu Glu Asp Glu Ala Leu Val Pro Ile Leu Arg
```

-continued

```
                1430                1435                1440
Thr Phe Val Gln Ser Lys Lys Asn Ile Leu Val Asp Tyr Gly Leu
            1445                1450                1455
Arg Arg Ile Thr Phe Leu Ile Ala Gln Glu Lys Glu Phe Pro Lys
            1460                1465                1470
Phe Phe Thr Phe Arg Ala Xaa Asp Glu Phe Ala Glu Asp Arg Ile
            1475                1480                1485
Tyr Arg His Leu Glu Pro Ala Leu Ala Phe Gln Leu Glu Leu Asn
            1490                1495                1500
Arg Met Arg Asn Phe Asp Leu Thr Ala Val Pro Cys Ala Asn His
            1505                1510                1515
Lys Met His Leu Tyr Leu Gly Xaa Ala Lys Val Lys Glu Gly Val
            1520                1525                1530
Glu Val Thr Asp His Arg Phe Phe Ile Arg Ala Ile Ile Xaa His
            1535                1540                1545
Ser Asp Leu Ile Thr Lys Glu Ala Ser Phe Glu Tyr Leu Gln Asn
            1550                1555                1560
Glu Gly Glu Arg Leu Leu Leu Glu Ala Met Asp Glu Leu Glu Val
            1565                1570                1575
Ala Phe Asn Asn Thr Ser Val Arg Thr Asp Cys Asn His Ile Phe
            1580                1585                1590
Leu Asn Phe Val Pro Thr Val Ile Met Asp Pro Phe Lys Ile Glu
            1595                1600                1605
Glu Ser Val Arg Tyr Met Val Met Arg Tyr Gly Ser Arg Leu Trp
            1610                1615                1620
Lys Leu Arg Val Leu Gln Ala Glu Val Lys Ile Asn Ile Arg Gln
            1625                1630                1635
Thr Thr Thr Gly Ser Ala Val Pro Ile Arg Leu Phe Ile Thr Asn
            1640                1645                1650
Glu Ser Gly Tyr Tyr Leu Asp Ile Ser Leu Tyr Lys Glu Val Thr
            1655                1660                1665
Asp Ser Arg Ser Gly Asn Ile Met Phe His Ser Phe Gly Asn Lys
            1670                1675                1680
Gln Gly Pro Gln His Gly Met Leu Ile Asn Thr Pro Tyr Val Thr
            1685                1690                1695
Lys Asp Leu Leu Gln Ala Lys Arg Phe Gln Ala Gln Thr Leu Gly
            1700                1705                1710
Thr Thr Tyr Xaa Tyr Asp Phe Pro Glu Met Phe Arg Gln Ala Leu
            1715                1720                1725
Phe Lys Leu Trp Gly Ser Pro Asp Lys Tyr Pro Lys Asp Ile Leu
            1730                1735                1740
Thr Tyr Thr Glu Leu Val Leu Asp Ser Gln Gly Gln Leu Val Glu
            1745                1750                1755
Met Asn Arg Leu Pro Gly Gly Asn Glu Val Gly Met Val Ala Phe
            1760                1765                1770
Lys Met Arg Phe Lys Thr Gln Glu Tyr Pro Glu Gly Arg Asp Val
            1775                1780                1785
Ile Val Ile Gly Asn Asp Ile Thr Phe Arg Ile Gly Ser Phe Gly
            1790                1795                1800
Pro Gly Glu Asp Leu Leu Tyr Leu Arg Ala Ser Glu Met Ala Arg
            1805                1810                1815
Ala Glu Xaa Ile Pro Lys Ile Tyr Val Ala Ala Asn Ser Gly Ala
            1820                1825                1830
```

-continued

Arg Ile Gly Met Ala Glu Glu Ile Lys His Met Phe His Val Ala
1835                1840                1845

Trp Val Asp Pro Glu Asp Pro His Lys Gly Phe Lys Tyr Leu Tyr
1850                1855                1860

Leu Thr Pro Gln Asp Tyr Thr Arg Ile Ser Ser Leu Asn Ser Val
1865                1870                1875

His Cys Lys His Ile Glu Glu Gly Gly Glu Ser Arg Tyr Met Ile
1880                1885                1890

Thr Asp Ile Ile Gly Lys Asp Asp Gly Leu Gly Val Glu Asn Leu
1895                1900                1905

Arg Gly Ser Gly Met Ile Ala Gly Glu Ser Ser Leu Ala Tyr Glu
1910                1915                1920

Glu Ile Val Thr Ile Ser Leu Val Thr Cys Arg Ala Ile Gly Ile
1925                1930                1935

Gly Ala Tyr Leu Val Arg Leu Gly Gln Arg Val Ile Gln Val Glu
1940                1945                1950

Asn Ser His Ile Ile Leu Thr Gly Ala Ser Ala Leu Asn Lys Val
1955                1960                1965

Leu Gly Arg Glu Val Tyr Thr Ser Asn Asn Gln Leu Gly Gly Val
1970                1975                1980

Gln Ile Met His Tyr Asn Gly Val Ser His Ile Thr Val Pro Asp
1985                1990                1995

Asp Phe Glu Gly Val Tyr Thr Ile Leu Glu Trp Leu Ser Tyr Met
2000                2005                2010

Pro Lys Asp Asn His Ser Pro Val Pro Ile Ile Thr Pro Thr Asp
2015                2020                2025

Pro Ile Asp Arg Glu Ile Glu Phe Leu Pro Ser Arg Ala Pro Tyr
2030                2035                2040

Asp Pro Arg Trp Met Leu Ala Gly Arg Pro His Pro Thr Leu Lys
2045                2050                2055

Gly Thr Trp Gln Ser Gly Phe Phe Asp His Gly Ser Phe Lys Glu
2060                2065                2070

Ile Met Ala Pro Trp Ala Gln Thr Val Val Thr Gly Arg Ala Arg
2075                2080                2085

Leu Gly Gly Ile Pro Val Gly Val Ile Ala Val Glu Thr Arg Thr
2090                2095                2100

Val Glu Val Ala Val Pro Ala Asp Pro Ala Asn Leu Asp Ser Glu
2105                2110                2115

Ala Lys Ile Ile Gln Gln Ala Gly Gln Val Trp Phe Pro Asp Ser
2120                2125                2130

Ala Tyr Lys Thr Ala Gln Ala Xaa Lys Asp Phe Asn Arg Glu Lys
2135                2140                2145

Leu Pro Leu Met Ile Phe Ala Asn Trp Arg Gly Phe Ser Gly Gly
2150                2155                2160

Met Lys Asp Met Tyr Asp Gln Val Leu Lys Phe Gly Ala Tyr Ile
2165                2170                2175

Val Asp Gly Leu Arg Gln Tyr Lys Gln Pro Ile Leu Ile Tyr Ile
2180                2185                2190

Xaa Xaa Xaa Xaa Glu Leu Arg Gly Gly Ser Trp Val Val Ile Asp
2195                2200                2205

Ala Thr Ile Asn Pro Leu Cys Ile Glu Met Tyr Ala Asp Lys Glu
2210                2215                2220

```
Ser Arg Gly Gly Val Leu Glu Pro Glu Gly Thr Val Glu Ile Lys
    2225                2230                2235

Phe Arg Lys Xaa Asp Leu Ile Lys Ser Met Arg Arg Ile Asp Pro
    2240                2245                2250

Ala Tyr Lys Lys Leu Met Glu Gln Leu Gly Glu Pro Asp Leu Ser
    2255                2260                2265

Asp Lys Asp Arg Lys Asp Leu Glu Gly Arg Leu Lys Ala Arg Glu
    2270                2275                2280

Asp Leu Leu Leu Pro Ile Tyr His Gln Val Ala Val Gln Phe Ala
    2285                2290                2295

Asp Phe His Asp Thr Pro Gly Arg Met Leu Glu Lys Gly Val Ile
    2300                2305                2310

Ser Asp Ile Leu Glu Trp Lys Thr Ala Arg Thr Phe Leu Tyr Trp
    2315                2320                2325

Arg Leu Arg Arg Leu Leu Leu Glu Asp Gln Val Lys Gln Glu Ile
    2330                2335                2340

Leu Gln Ala Ser Gly Glu Leu Ser His Val His Ile Gln Ser Met
    2345                2350                2355

Leu Arg Arg Trp Phe Val Glu Thr Glu Gly Ala Val Lys Ala Tyr
    2360                2365                2370

Leu Trp Asp Asn Asn Gln Val Val Val Gln Trp Leu Glu Gln His
    2375                2380                2385

Trp Gln Ala Gly Asp Gly Pro Arg Ser Thr Ile Arg Glu Asn Ile
    2390                2395                2400

Thr Tyr Leu Lys His Asp Ser Val Leu Lys Thr Ile Arg Gly Leu
    2405                2410                2415

Val Glu Glu Asn Pro Glu Val Ala Val Asp Cys Val Ile Tyr Leu
    2420                2425                2430

Ser Gln His Ile Ser Pro Ala Glu Arg Ala Gln Val Val His Leu
    2435                2440                2445

Leu Ser Thr Met Asp Ser Pro Ala Ser Thr
    2450                2455

<210> SEQ ID NO 12
<211> LENGTH: 7377
<212> TYPE: DNA
<213> ORGANISM: Homo sapiens
<220> FEATURE:
<221> NAME/KEY: CDS
<222> LOCATION: (1)..(7377)

<400> SEQUENCE: 12 atg gtc ttg ctt ctt tgt cta tct cgt ctg att ttc tcc tgt ctg acc      48
Met Val Leu Leu Leu Cys Leu Ser Arg Leu Ile Phe Ser Cys Leu Thr
1               5                   10                  15 ttt tcc tgg tta aaa atc tgg ggg aaa atg acg gac tcc aag ccg atc      96
Phe Ser Trp Leu Lys Ile Trp Gly Lys Met Thr Asp Ser Lys Pro Ile
            20                  25                  30 acc aag agt aaa tca gaa gca aac ctc atc ccg agc cag gag ccc ttt     144
Thr Lys Ser Lys Ser Glu Ala Asn Leu Ile Pro Ser Gln Glu Pro Phe
        35                  40                  45 cca gcc tct gat aac tca ggg gag aca ccg cag aga aat ggg gag ggc     192
Pro Ala Ser Asp Asn Ser Gly Glu Thr Pro Gln Arg Asn Gly Glu Gly
    50                  55                  60 cac act ctg ccc aag aca ccc agc cag gcc gag cca gcc tcc cac aaa     240
His Thr Leu Pro Lys Thr Pro Ser Gln Ala Glu Pro Ala Ser His Lys
65                  70                  75                  80
```

```
ggc ccc aaa gat gcc ggt cgg cgg aga aac tcc cta cca ccc tcc cac      288
Gly Pro Lys Asp Ala Gly Arg Arg Arg Asn Ser Leu Pro Pro Ser His
                85                  90                  95 cag aag ccc cca aga aac ccc ctt tct tcc agt gac gca gca ccc tcc      336
Gln Lys Pro Pro Arg Asn Pro Leu Ser Ser Ser Asp Ala Ala Pro Ser
            100                 105                 110 cca gag ctt caa gcc aac ggg act ggg aca caa ggt ctg gag gcc aca      384
Pro Glu Leu Gln Ala Asn Gly Thr Gly Thr Gln Gly Leu Glu Ala Thr
        115                 120                 125 gat acc aat ggc ctg tcc tcc tca gcc agg ccc cag ggc cag caa gct      432
Asp Thr Asn Gly Leu Ser Ser Ser Ala Arg Pro Gln Gly Gln Gln Ala
    130                 135                 140 ggc tcc ccc tcc aaa gaa gac aag aag cag gca aac atc aag agg cag      480
Gly Ser Pro Ser Lys Glu Asp Lys Lys Gln Ala Asn Ile Lys Arg Gln
145                 150                 155                 160 ctg atg acc aac ttc atc ctg ggc tct ttt gat gac tac tcc tct gac      528
Leu Met Thr Asn Phe Ile Leu Gly Ser Phe Asp Asp Tyr Ser Ser Asp
                165                 170                 175 gag gac tct gtt gct ggc tca tct cgt gag tct acc cgg aag ggc agc      576
Glu Asp Ser Val Ala Gly Ser Ser Arg Glu Ser Thr Arg Lys Gly Ser
            180                 185                 190 cgg gcc agc ttg ggg gcc ctg tcc cta gag gct tat ctg acc aca ggt      624
Arg Ala Ser Leu Gly Ala Leu Ser Leu Glu Ala Tyr Leu Thr Thr Gly
        195                 200                 205 gaa gct gag acc cgc gtc ccc act atg agg ccg agc atg tcg gga ctc      672
Glu Ala Glu Thr Arg Val Pro Thr Met Arg Pro Ser Met Ser Gly Leu
    210                 215                 220 cac ctg gtg aag agg gga cgg gaa cac aag aag ctg gac ctg cac aga      720
His Leu Val Lys Arg Gly Arg Glu His Lys Lys Leu Asp Leu His Arg
225                 230                 235                 240 gac ttt acc gtg gct tct ccc gct gag ttt gtc aca cgc ttt ggg ggg      768
Asp Phe Thr Val Ala Ser Pro Ala Glu Phe Val Thr Arg Phe Gly Gly
                245                 250                 255 gat cgg gtc atc gag aag gtg ctt att gcc aac aac ggg att gcc gcc      816
Asp Arg Val Ile Glu Lys Val Leu Ile Ala Asn Asn Gly Ile Ala Ala
            260                 265                 270 gtg aag tgc atg cgc tcc atc cgc agg tgg gcc tat gag atg ttc cgc      864
Val Lys Cys Met Arg Ser Ile Arg Arg Trp Ala Tyr Glu Met Phe Arg
        275                 280                 285 aac gag cgg gcc atc cgg ttt gtt gtg atg gtg acc ccc gag gac ctt      912
Asn Glu Arg Ala Ile Arg Phe Val Val Met Val Thr Pro Glu Asp Leu
    290                 295                 300 aag gcc aac gca gag tac atc aag atg gcg gat cat tac gtc ccc gtc      960
Lys Ala Asn Ala Glu Tyr Ile Lys Met Ala Asp His Tyr Val Pro Val
305                 310                 315                 320 cca gga ggg ccc aat aac aac aac tat gcc aac gtg gag ctg att gtg     1008
Pro Gly Gly Pro Asn Asn Asn Asn Tyr Ala Asn Val Glu Leu Ile Val
                325                 330                 335 gac att gcc aag aga atc ccc gtg cag gcg gtg tgg gct ggc tgg ggc     1056
Asp Ile Ala Lys Arg Ile Pro Val Gln Ala Val Trp Ala Gly Trp Gly
            340                 345                 350 cat gct tca gaa aac cct aaa ctt ccg gag ctg ctg tgc aag aat gga     1104
His Ala Ser Glu Asn Pro Lys Leu Pro Glu Leu Leu Cys Lys Asn Gly
        355                 360                 365 gtt gct ttc tta ggc cct ccc agt gag gcc atg tgg gcc tta gga gat     1152
Val Ala Phe Leu Gly Pro Pro Ser Glu Ala Met Trp Ala Leu Gly Asp
    370                 375                 380 aag atc gcc tcc acc gtt gtc gcc cag acg cta cag gtc cca acc ctg     1200
Lys Ile Ala Ser Thr Val Val Ala Gln Thr Leu Gln Val Pro Thr Leu
385                 390                 395                 400
```

-continued

```
ccc tgg agt gga agc ggc ctg aca gtg gag tgg aca gaa gat gat ctg    1248
Pro Trp Ser Gly Ser Gly Leu Thr Val Glu Trp Thr Glu Asp Asp Leu
            405                 410                 415 cag cag gga aaa aga atc agt gtc cca gaa gat gtt tat gac aag ggt    1296
Gln Gln Gly Lys Arg Ile Ser Val Pro Glu Asp Val Tyr Asp Lys Gly
        420                 425                 430 tgc gtg aaa gac gta gat gag ggc ttg gag gca gca gaa aga att ggt    1344
Cys Val Lys Asp Val Asp Glu Gly Leu Glu Ala Ala Glu Arg Ile Gly
    435                 440                 445 ttt cca ttg atg atc aaa gct tct gaa ggt ggc ggg ggg aag gga atc    1392
Phe Pro Leu Met Ile Lys Ala Ser Glu Gly Gly Gly Gly Lys Gly Ile
450                 455                 460 cgg aag gct gag agt gcg gag gac ttc ccg atc ctt ttc aga caa gta    1440
Arg Lys Ala Glu Ser Ala Glu Asp Phe Pro Ile Leu Phe Arg Gln Val
465                 470                 475                 480 cag agt gag atc cca ggc tcg ccc atc ttt ctc atg aag ctg gcc cag    1488
Gln Ser Glu Ile Pro Gly Ser Pro Ile Phe Leu Met Lys Leu Ala Gln
            485                 490                 495 cac gcc cgt cac ctg gaa gtt cag atc ctc gct gac cag tat ggg aat    1536
His Ala Arg His Leu Glu Val Gln Ile Leu Ala Asp Gln Tyr Gly Asn
        500                 505                 510 gct gtg tct ctg ttt ggt cgc gac tgc tcc atc cag cgg cgg cat cag    1584
Ala Val Ser Leu Phe Gly Arg Asp Cys Ser Ile Gln Arg Arg His Gln
    515                 520                 525 aag atc gtt gag gaa gca ccg gcc acc atc gcc ccg ctg gcc ata ttc    1632
Lys Ile Val Glu Glu Ala Pro Ala Thr Ile Ala Pro Leu Ala Ile Phe
530                 535                 540 gag ttc atg gag cag tgt gcc atc cgc ctg gcc aag acc gtg ggc tat    1680
Glu Phe Met Glu Gln Cys Ala Ile Arg Leu Ala Lys Thr Val Gly Tyr
545                 550                 555                 560 gtg agt gca ggg aca gtg gaa tac ctc tat agt cag gat ggc agc ttc    1728
Val Ser Ala Gly Thr Val Glu Tyr Leu Tyr Ser Gln Asp Gly Ser Phe
            565                 570                 575 cac ttc ttg gag ctg aat cct cgc ttg cag gtg gaa cat ccc tgc aca    1776
His Phe Leu Glu Leu Asn Pro Arg Leu Gln Val Glu His Pro Cys Thr
        580                 585                 590 gaa atg att gct gac gtt aat ctg ccg gcc gcc cag cta cag atc gcc    1824
Glu Met Ile Ala Asp Val Asn Leu Pro Ala Ala Gln Leu Gln Ile Ala
    595                 600                 605 atg ggc gtg cca ctg cac cgg ctg aag gat atc cgg ctt ctg tat gga    1872
Met Gly Val Pro Leu His Arg Leu Lys Asp Ile Arg Leu Leu Tyr Gly
610                 615                 620 gag tca cca tgg gga gtg act ccc att tct ttt gaa acc ccc tca aac    1920
Glu Ser Pro Trp Gly Val Thr Pro Ile Ser Phe Glu Thr Pro Ser Asn
625                 630                 635                 640 cct ccc ctc gcc cga ggc cac gtc att gcc gcc aga atc acc agc gaa    1968
Pro Pro Leu Ala Arg Gly His Val Ile Ala Ala Arg Ile Thr Ser Glu
            645                 650                 655 aac cca gac gag ggt ttt aag ccg agc tcc ggg act gtc cag gaa ctg    2016
Asn Pro Asp Glu Gly Phe Lys Pro Ser Ser Gly Thr Val Gln Glu Leu
        660                 665                 670 aat ttc cgg agc agc aag aac gtg tgg ggt tac ttc agc gtg gcc gct    2064
Asn Phe Arg Ser Ser Lys Asn Val Trp Gly Tyr Phe Ser Val Ala Ala
    675                 680                 685 act gga ggc ctg cac gag ttt gcg gat tcc caa ttt ggg cac tgc ttc    2112
Thr Gly Gly Leu His Glu Phe Ala Asp Ser Gln Phe Gly His Cys Phe
690                 695                 700 tcc tgg gga gag aac cgg gaa gag gcc att tcg aac atg gtg gtg gct    2160
Ser Trp Gly Glu Asn Arg Glu Glu Ala Ile Ser Asn Met Val Val Ala
```

```
                    705             710               715                 720
ttg aag gaa ctg tcc atc cga ggt gac ttt agg act acc gtg gaa tac         2208
Leu Lys Glu Leu Ser Ile Arg Gly Asp Phe Arg Thr Thr Val Glu Tyr
                725                 730                 735 ctc att aac ctc ctg gag acc gag agc ttc cag aac aac gac atc gac         2256
Leu Ile Asn Leu Leu Glu Thr Glu Ser Phe Gln Asn Asn Asp Ile Asp
            740                 745                 750 acc ggg tgg ttg gac tac ctc att gct gag aaa gtg cag gcg gag aaa         2304
Thr Gly Trp Leu Asp Tyr Leu Ile Ala Glu Lys Val Gln Ala Glu Lys
        755                 760                 765 ccg gat atc atg ctt ggg gtg gta tgc ggg gcc ttg aac gtg gcc gat         2352
Pro Asp Ile Met Leu Gly Val Val Cys Gly Ala Leu Asn Val Ala Asp
    770                 775                 780 gcg atg ttc aga acg tgc atg aca gat ttc tta cac tcc ctg gaa agg         2400
Ala Met Phe Arg Thr Cys Met Thr Asp Phe Leu His Ser Leu Glu Arg
785                 790                 795                 800 ggc cag gtc ctc cca gcg gat tca cta ctg aac ctt gta gat gtg gaa         2448
Gly Gln Val Leu Pro Ala Asp Ser Leu Leu Asn Leu Val Asp Val Glu
                805                 810                 815 tta att tac gga ggt gtt aag tac att ctc aag gtg gcc cgg cag tct         2496
Leu Ile Tyr Gly Gly Val Lys Tyr Ile Leu Lys Val Ala Arg Gln Ser
            820                 825                 830 ctg acc atg ttc gtt ctc atc atg aat ggc tgc cac atc gag att gat         2544
Leu Thr Met Phe Val Leu Ile Met Asn Gly Cys His Ile Glu Ile Asp
        835                 840                 845 gcc cac cgg ctg aat gat ggg ggg ctc ctg ctc tcc tac aat ggg aac         2592
Ala His Arg Leu Asn Asp Gly Gly Leu Leu Leu Ser Tyr Asn Gly Asn
    850                 855                 860 agc tac acc acc tac atg aag gaa gag gtt gac agt tac cga att acc         2640
Ser Tyr Thr Thr Tyr Met Lys Glu Glu Val Asp Ser Tyr Arg Ile Thr
865                 870                 875                 880 atc ggc aat aag acg tgt gtg ttt gag aag gag aac gat cct aca gtc         2688
Ile Gly Asn Lys Thr Cys Val Phe Glu Lys Glu Asn Asp Pro Thr Val
                885                 890                 895 ctg aga tcc ccc tcg gct ggg aag ctg aca cag tac aca gtg gag gat         2736
Leu Arg Ser Pro Ser Ala Gly Lys Leu Thr Gln Tyr Thr Val Glu Asp
            900                 905                 910 ggg ggc cac gtt gag gct ggg agc agc tac gct gag atg gag gtg atg         2784
Gly Gly His Val Glu Ala Gly Ser Ser Tyr Ala Glu Met Glu Val Met
        915                 920                 925 aag atg atc atg acc ctg aac gtt cag gaa aga ggc cgg gtg aag tac         2832
Lys Met Ile Met Thr Leu Asn Val Gln Glu Arg Gly Arg Val Lys Tyr
    930                 935                 940 atc aag cgt cca ggt gcc gtg ctg gaa gca ggc tgc gtg gtg gcc agg         2880
Ile Lys Arg Pro Gly Ala Val Leu Glu Ala Gly Cys Val Val Ala Arg
945                 950                 955                 960 ctg gag ctc gat gac cct tct aaa gtc cac ccg gct gaa ccg ttc aca         2928
Leu Glu Leu Asp Asp Pro Ser Lys Val His Pro Ala Glu Pro Phe Thr
                965                 970                 975 gga gaa ctc cct gcc cag cag aca ctg ccc atc ctc gga gag aaa ctg         2976
Gly Glu Leu Pro Ala Gln Gln Thr Leu Pro Ile Leu Gly Glu Lys Leu
            980                 985                 990 cac cag gtc ttc cac agc gtc ctg  gaa aac ctc acc aac  gtc atg agt       3024
His Gln Val Phe His Ser Val Leu  Glu Asn Leu Thr Asn  Val Met Ser
        995                 1000                 1005 ggc ttt tgt ctg cca gag ccc  gtt ttt agc ata aag  ctg aag gag           3069
Gly Phe Cys Leu Pro Glu Pro  Val Phe Ser Ile Lys  Leu Lys Glu
    1010                 1015                 1020 tgg gtg cag aag ctc atg atg  acc ctc cgg cac ccg  tca ctg ccg           3114
```

```
    Trp Val Gln Lys Leu Met Met Thr Leu Arg His Pro Ser Leu Pro
        1025            1030            1035 ctg ctg gag ctg cag gag atc atg acc agc gtg gca ggc cgc atc        3159
Leu Leu Glu Leu Gln Glu Ile Met Thr Ser Val Ala Gly Arg Ile
    1040            1045            1050 ccc gcc cct gtg gag aag tct gtc cgc agg gtg atg gcc cag tat        3204
Pro Ala Pro Val Glu Lys Ser Val Arg Arg Val Met Ala Gln Tyr
    1055            1060            1065 gcc agc aac atc acc tcg gtg ctg tgc cag ttc ccc agc cag cag        3249
Ala Ser Asn Ile Thr Ser Val Leu Cys Gln Phe Pro Ser Gln Gln
    1070            1075            1080 ata gcc acc atc ctg gac tgc cat gca gcc acc ctg cag cgg aag        3294
Ile Ala Thr Ile Leu Asp Cys His Ala Ala Thr Leu Gln Arg Lys
    1085            1090            1095 gct gat cga gag gtc ttc ttc atc aac acc cag agc atc gtg cag        3339
Ala Asp Arg Glu Val Phe Phe Ile Asn Thr Gln Ser Ile Val Gln
    1100            1105            1110 ttg gtc cag aga tac cgc agc ggg atc cgc ggc tat atg aaa aca        3384
Leu Val Gln Arg Tyr Arg Ser Gly Ile Arg Gly Tyr Met Lys Thr
    1115            1120            1125 gtg gtg ttg gat ctc ctg aga aga tac ttg cgt gtt gag cac cat        3429
Val Val Leu Asp Leu Leu Arg Arg Tyr Leu Arg Val Glu His His
    1130            1135            1140 ttt cag caa gcc cac tac gac aag tgt gtg ata aac ctc agg gag        3474
Phe Gln Gln Ala His Tyr Asp Lys Cys Val Ile Asn Leu Arg Glu
    1145            1150            1155 cag ttc aag cca gac atg tcc cag gtg ctg gac tgc atc ttc tcc        3519
Gln Phe Lys Pro Asp Met Ser Gln Val Leu Asp Cys Ile Phe Ser
    1160            1165            1170 cac gca cag gtg gcc aag aag aac cag ctg gtg atc atg ttg atc        3564
His Ala Gln Val Ala Lys Lys Asn Gln Leu Val Ile Met Leu Ile
    1175            1180            1185 gat gag ctg tgt ggc cca gac cct tcc ctg tcg gac gag ctg atc        3609
Asp Glu Leu Cys Gly Pro Asp Pro Ser Leu Ser Asp Glu Leu Ile
    1190            1195            1200 tcc atc ctc aac gag ctc act cag ctg agc aaa agc gag cac tgc        3654
Ser Ile Leu Asn Glu Leu Thr Gln Leu Ser Lys Ser Glu His Cys
    1205            1210            1215 aaa gtg gcc ctc aga gcc cgg cag atc ctg att gcc tcc cac ctc        3699
Lys Val Ala Leu Arg Ala Arg Gln Ile Leu Ile Ala Ser His Leu
    1220            1225            1230 ccc tcc tac gag ctg cgg cat aac cag gtg gag tcc att ttc ctg        3744
Pro Ser Tyr Glu Leu Arg His Asn Gln Val Glu Ser Ile Phe Leu
    1235            1240            1245 tct gcc att gac atg tac ggc cac cag ttc tgc ccc gag aac ctc        3789
Ser Ala Ile Asp Met Tyr Gly His Gln Phe Cys Pro Glu Asn Leu
    1250            1255            1260 aag aaa tta ata ctt tcg gaa aca acc atc ttc gac gtc ctg cct        3834
Lys Lys Leu Ile Leu Ser Glu Thr Thr Ile Phe Asp Val Leu Pro
    1265            1270            1275 act ttc ttc tat cac gca aac aaa gtc gtg tgc atg gcg tcc ttg        3879
Thr Phe Phe Tyr His Ala Asn Lys Val Val Cys Met Ala Ser Leu
    1280            1285            1290 gag gtt tac gtg cgg agg ggc tac atc gcc tat gag tta aac agc        3924
Glu Val Tyr Val Arg Arg Gly Tyr Ile Ala Tyr Glu Leu Asn Ser
    1295            1300            1305 ctg cag cac cgg cag ctc ccg gac ggc acc tgc gtg gta gaa ttc        3969
Leu Gln His Arg Gln Leu Pro Asp Gly Thr Cys Val Val Glu Phe
    1310            1315            1320
```

-continued

| | | |
|---|---|---|
| cag ttc atg ctg ccg tcc tcc cac cca aac cgg atg acc gtg ccc<br>Gln Phe Met Leu Pro Ser Ser His Pro Asn Arg Met Thr Val Pro<br>1325                          1330                       1335 | 4014 |
| atc agc atc acc aac cct gac ctg ctg agg cac agc aca gag ctc<br>Ile Ser Ile Thr Asn Pro Asp Leu Leu Arg His Ser Thr Glu Leu<br>1340                       1345                    1350 | 4059 |
| ttc atg gac agc ggc ttc tcc cca ctg tgc cag cgc atg gga gcc<br>Phe Met Asp Ser Gly Phe Ser Pro Leu Cys Gln Arg Met Gly Ala<br>1355                       1360                    1365 | 4104 |
| atg gta gcc ttc agg aga ttc gag gac ttc acc aga aat ttt gat<br>Met Val Ala Phe Arg Arg Phe Glu Asp Phe Thr Arg Asn Phe Asp<br>1370                       1375                    1380 | 4149 |
| gaa gtc atc tct tgc ttc gcc aac gtg ccc aaa gac acc ccc ctc<br>Glu Val Ile Ser Cys Phe Ala Asn Val Pro Lys Asp Thr Pro Leu<br>1385                       1390                    1395 | 4194 |
| ttc agc gag gcc cgc acc tcc cta tac tcc gag gat gac tgc aag<br>Phe Ser Glu Ala Arg Thr Ser Leu Tyr Ser Glu Asp Asp Cys Lys<br>1400                       1405                    1410 | 4239 |
| agc ctc aga gaa gag ccc atc cac att ctg aat gtg tcc atc cag<br>Ser Leu Arg Glu Glu Pro Ile His Ile Leu Asn Val Ser Ile Gln<br>1415                       1420                    1425 | 4284 |
| tgt gca gac cac ctg gag gat gag gca ctg gtg ccg att tta cgg<br>Cys Ala Asp His Leu Glu Asp Glu Ala Leu Val Pro Ile Leu Arg<br>1430                       1435                    1440 | 4329 |
| aca ttc gta cag tcc aag aaa aat atc ctt gtg gat tat gga ctc<br>Thr Phe Val Gln Ser Lys Lys Asn Ile Leu Val Asp Tyr Gly Leu<br>1445                       1450                    1455 | 4374 |
| cga cga atc aca ttc ttg att gcc caa gag aaa gaa ttt ccc aag<br>Arg Arg Ile Thr Phe Leu Ile Ala Gln Glu Lys Glu Phe Pro Lys<br>1460                       1465                    1470 | 4419 |
| ttt ttc aca ttc aga gca aga gat gag ttt gca gaa gat cgc att<br>Phe Phe Thr Phe Arg Ala Arg Asp Glu Phe Ala Glu Asp Arg Ile<br>1475                       1480                    1485 | 4464 |
| tac cgt cac ttg gaa cct gcc ctg gcc ttc cag ctg gaa ctc aac<br>Tyr Arg His Leu Glu Pro Ala Leu Ala Phe Gln Leu Glu Leu Asn<br>1490                       1495                    1500 | 4509 |
| cgg atg cgt aac ttc gat ctg acc gcc gtg ccc tgt gcc aac cac<br>Arg Met Arg Asn Phe Asp Leu Thr Ala Val Pro Cys Ala Asn His<br>1505                       1510                    1515 | 4554 |
| aag atg cac ctt tac ctg ggt gct gcc aag gtg aag gaa ggt gtg<br>Lys Met His Leu Tyr Leu Gly Ala Ala Lys Val Lys Glu Gly Val<br>1520                       1525                    1530 | 4599 |
| gaa gtg acg gac cat agg ttc ttc atc cgc gcc atc atc agg cac<br>Glu Val Thr Asp His Arg Phe Phe Ile Arg Ala Ile Ile Arg His<br>1535                       1540                    1545 | 4644 |
| tct gac ctg atc aca aag gaa gcc tcc ttc gaa tac ctg cag aac<br>Ser Asp Leu Ile Thr Lys Glu Ala Ser Phe Glu Tyr Leu Gln Asn<br>1550                       1555                    1560 | 4689 |
| gag ggt gag cgg ctg ctc ctg gag gcc atg gac gag ctg gag gtg<br>Glu Gly Glu Arg Leu Leu Leu Glu Ala Met Asp Glu Leu Glu Val<br>1565                       1570                    1575 | 4734 |
| gcg ttc aat aac acc agc gtg cgc acc gac tgc aac cac atc ttc<br>Ala Phe Asn Asn Thr Ser Val Arg Thr Asp Cys Asn His Ile Phe<br>1580                       1585                    1590 | 4779 |
| ctc aac ttc gtg ccc act gtc atc atg gac ccc ttc aag atc gag<br>Leu Asn Phe Val Pro Thr Val Ile Met Asp Pro Phe Lys Ile Glu<br>1595                       1600                    1605 | 4824 |
| gag tcc gtg cgc tac atg gtt atg cgc tac ggc agc cgg ctg tgg<br>Glu Ser Val Arg Tyr Met Val Met Arg Tyr Gly Ser Arg Leu Trp<br>1610                       1615                    1620 | 4869 |

| | | | | | | | | | | | | |
|---|---|---|---|---|---|---|---|---|---|---|---|---|
| aaa | ctc | cgt | gtg | cta | cag | gct | gag | gtc | aag | atc | aac | atc cgc cag | 4914 |
| Lys | Leu | Arg | Val | Leu | Gln | Ala | Glu | Val | Lys | Ile | Asn | Ile Arg Gln |
| | 1625 | | | | 1630 | | | | 1635 | | | |
| acc | acc | acc | ggc | agt | gcc | gtt | ccc | atc | cgc | ctg | ttc | atc acc aat | 4959 |
| Thr | Thr | Thr | Gly | Ser | Ala | Val | Pro | Ile | Arg | Leu | Phe | Ile Thr Asn |
| | 1640 | | | | 1645 | | | | 1650 | | | |
| gag | tcg | ggc | tac | tac | ctg | gac | atc | agc | ctc | tac | aaa | gaa gtg act | 5004 |
| Glu | Ser | Gly | Tyr | Tyr | Leu | Asp | Ile | Ser | Leu | Tyr | Lys | Glu Val Thr |
| | 1655 | | | | 1660 | | | | 1665 | | | |
| gac | tcc | aga | tct | gga | aat | atc | atg | ttt | cac | tcc | ttc | ggc aac aag | 5049 |
| Asp | Ser | Arg | Ser | Gly | Asn | Ile | Met | Phe | His | Ser | Phe | Gly Asn Lys |
| | 1670 | | | | 1675 | | | | 1680 | | | |
| caa | ggg | ccc | cag | cac | ggg | atg | ctg | atc | aat | act | ccc | tac gtc acc | 5094 |
| Gln | Gly | Pro | Gln | His | Gly | Met | Leu | Ile | Asn | Thr | Pro | Tyr Val Thr |
| | 1685 | | | | 1690 | | | | 1695 | | | |
| aag | gat | ctg | ctc | cag | gcc | aag | cga | ttc | cag | gcc | cag | acc ctg gga | 5139 |
| Lys | Asp | Leu | Leu | Gln | Ala | Lys | Arg | Phe | Gln | Ala | Gln | Thr Leu Gly |
| | 1700 | | | | 1705 | | | | 1710 | | | |
| acc | acc | tac | atc | tat | gac | ttc | ccg | gaa | atg | ttc | agg | cag gct ctc | 5184 |
| Thr | Thr | Tyr | Ile | Tyr | Asp | Phe | Pro | Glu | Met | Phe | Arg | Gln Ala Leu |
| | 1715 | | | | 1720 | | | | 1725 | | | |
| ttt | aaa | ctg | tgg | ggc | tcc | cca | gac | aag | tat | ccc | aaa | gac atc ctg | 5229 |
| Phe | Lys | Leu | Trp | Gly | Ser | Pro | Asp | Lys | Tyr | Pro | Lys | Asp Ile Leu |
| | 1730 | | | | 1735 | | | | 1740 | | | |
| aca | tac | act | gaa | tta | gtg | ttg | gac | tct | cag | ggc | cag | ctg gtg gag | 5274 |
| Thr | Tyr | Thr | Glu | Leu | Val | Leu | Asp | Ser | Gln | Gly | Gln | Leu Val Glu |
| | 1745 | | | | 1750 | | | | 1755 | | | |
| atg | aac | cga | ctt | cct | ggt | gga | aat | gag | gtg | ggc | atg | gtg gcc ttc | 5319 |
| Met | Asn | Arg | Leu | Pro | Gly | Gly | Asn | Glu | Val | Gly | Met | Val Ala Phe |
| | 1760 | | | | 1765 | | | | 1770 | | | |
| aaa | atg | agg | ttt | aag | acc | cag | gag | tac | ccg | gaa | gga | cgg gat gtg | 5364 |
| Lys | Met | Arg | Phe | Lys | Thr | Gln | Glu | Tyr | Pro | Glu | Gly | Arg Asp Val |
| | 1775 | | | | 1780 | | | | 1785 | | | |
| atc | gtc | atc | ggc | aat | gac | atc | acc | ttt | cgc | att | gga | tcc ttt ggc | 5409 |
| Ile | Val | Ile | Gly | Asn | Asp | Ile | Thr | Phe | Arg | Ile | Gly | Ser Phe Gly |
| | 1790 | | | | 1795 | | | | 1800 | | | |
| cct | gga | gag | gac | ctt | ctg | tac | ctg | cgg | gca | tcc | gag | atg gcc cgg | 5454 |
| Pro | Gly | Glu | Asp | Leu | Leu | Tyr | Leu | Arg | Ala | Ser | Glu | Met Ala Arg |
| | 1805 | | | | 1810 | | | | 1815 | | | |
| gca | gag | ggc | att | ccc | aaa | att | tac | gtg | gca | gcc | aac | agt ggc gcc | 5499 |
| Ala | Glu | Gly | Ile | Pro | Lys | Ile | Tyr | Val | Ala | Ala | Asn | Ser Gly Ala |
| | 1820 | | | | 1825 | | | | 1830 | | | |
| cgt | att | ggc | atg | gca | gag | gag | atc | aaa | cac | atg | ttc | cac gtg gct | 5544 |
| Arg | Ile | Gly | Met | Ala | Glu | Glu | Ile | Lys | His | Met | Phe | His Val Ala |
| | 1835 | | | | 1840 | | | | 1845 | | | |
| tgg | gtg | gac | cca | gaa | gac | ccc | cac | aaa | gga | ttt | aaa | tac ctg tac | 5589 |
| Trp | Val | Asp | Pro | Glu | Asp | Pro | His | Lys | Gly | Phe | Lys | Tyr Leu Tyr |
| | 1850 | | | | 1855 | | | | 1860 | | | |
| ctg | act | ccc | caa | gac | tac | acc | aga | atc | agc | tcc | ctg | aac tcc gtc | 5634 |
| Leu | Thr | Pro | Gln | Asp | Tyr | Thr | Arg | Ile | Ser | Ser | Leu | Asn Ser Val |
| | 1865 | | | | 1870 | | | | 1875 | | | |
| cac | tgt | aaa | cac | atc | gag | gaa | gga | gga | gag | tcc | aga | tac atg atc | 5679 |
| His | Cys | Lys | His | Ile | Glu | Glu | Gly | Gly | Glu | Ser | Arg | Tyr Met Ile |
| | 1880 | | | | 1885 | | | | 1890 | | | |
| acg | gat | atc | atc | ggg | aag | gat | gat | ggc | ttg | ggc | gtg | gag aat ctg | 5724 |
| Thr | Asp | Ile | Ile | Gly | Lys | Asp | Asp | Gly | Leu | Gly | Val | Glu Asn Leu |
| | 1895 | | | | 1900 | | | | 1905 | | | |
| agg | ggc | tca | ggc | atg | att | gct | ggg | gag | tcc | tct | ctg | gct tac gaa | 5769 |
| Arg | Gly | Ser | Gly | Met | Ile | Ala | Gly | Glu | Ser | Ser | Leu | Ala Tyr Glu |

-continued

|  | 1910 |  |  |  | 1915 |  |  |  |  | 1920 |  |  |  |
|---|---|---|---|---|---|---|---|---|---|---|---|---|---|
| gag | atc | gtc | acc | att | agc | ttg | gtg | acc | tgc | cga | gcc | att | ggg | att | 5814 |
| Glu | Ile | Val | Thr | Ile | Ser | Leu | Val | Thr | Cys | Arg | Ala | Ile | Gly | Ile |  |
| 1925 |  |  |  |  | 1930 |  |  |  |  | 1935 |  |  |  |  |

| ggg | gcc | tac | ttg | gtg | agg | ctg | ggc | cag | cga | gtg | atc | cag | gtg | gag | 5859 |
| Gly | Ala | Tyr | Leu | Val | Arg | Leu | Gly | Gln | Arg | Val | Ile | Gln | Val | Glu |  |
| 1940 |  |  |  |  | 1945 |  |  |  |  | 1950 |  |  |  |  |

| aat | tcc | cac | atc | atc | ctc | aca | gga | gca | agt | gct | ctc | aac | aag | gtc | 5904 |
| Asn | Ser | His | Ile | Ile | Leu | Thr | Gly | Ala | Ser | Ala | Leu | Asn | Lys | Val |  |
| 1955 |  |  |  |  | 1960 |  |  |  |  | 1965 |  |  |  |  |

| ctg | gga | aga | gag | gtc | tac | aca | tcc | aac | aac | cag | ctg | ggt | ggc | gtt | 5949 |
| Leu | Gly | Arg | Glu | Val | Tyr | Thr | Ser | Asn | Asn | Gln | Leu | Gly | Gly | Val |  |
| 1970 |  |  |  |  | 1975 |  |  |  |  | 1980 |  |  |  |  |

| cag | atc | atg | cat | tac | aat | ggt | gtc | tcc | cac | atc | acc | gtg | cca | gat | 5994 |
| Gln | Ile | Met | His | Tyr | Asn | Gly | Val | Ser | His | Ile | Thr | Val | Pro | Asp |  |
| 1985 |  |  |  |  | 1990 |  |  |  |  | 1995 |  |  |  |  |

| gac | ttt | gag | ggg | gtt | tat | acc | atc | ctg | gag | tgg | ctg | tcc | tat | atg | 6039 |
| Asp | Phe | Glu | Gly | Val | Tyr | Thr | Ile | Leu | Glu | Trp | Leu | Ser | Tyr | Met |  |
| 2000 |  |  |  |  | 2005 |  |  |  |  | 2010 |  |  |  |  |

| cca | aag | gat | aat | cac | agc | cct | gtc | cct | atc | atc | aca | ccc | act | gac | 6084 |
| Pro | Lys | Asp | Asn | His | Ser | Pro | Val | Pro | Ile | Ile | Thr | Pro | Thr | Asp |  |
| 2015 |  |  |  |  | 2020 |  |  |  |  | 2025 |  |  |  |  |

| ccc | att | gac | aga | gaa | att | gaa | ttc | ctc | cca | tcc | aga | gct | ccc | tac | 6129 |
| Pro | Ile | Asp | Arg | Glu | Ile | Glu | Phe | Leu | Pro | Ser | Arg | Ala | Pro | Tyr |  |
| 2030 |  |  |  |  | 2035 |  |  |  |  | 2040 |  |  |  |  |

| gac | ccc | cgg | tgg | atg | ctt | gca | gga | agg | cct | cac | cca | act | ctg | aag | 6174 |
| Asp | Pro | Arg | Trp | Met | Leu | Ala | Gly | Arg | Pro | His | Pro | Thr | Leu | Lys |  |
| 2045 |  |  |  |  | 2050 |  |  |  |  | 2055 |  |  |  |  |

| gga | acg | tgg | cag | agc | gga | ttc | ttt | gac | cac | ggc | agt | ttc | aag | gaa | 6219 |
| Gly | Thr | Trp | Gln | Ser | Gly | Phe | Phe | Asp | His | Gly | Ser | Phe | Lys | Glu |  |
| 2060 |  |  |  |  | 2065 |  |  |  |  | 2070 |  |  |  |  |

| atc | atg | gca | ccc | tgg | gcg | cag | acc | gtg | gtg | aca | gga | cga | gca | agg | 6264 |
| Ile | Met | Ala | Pro | Trp | Ala | Gln | Thr | Val | Val | Thr | Gly | Arg | Ala | Arg |  |
| 2075 |  |  |  |  | 2080 |  |  |  |  | 2085 |  |  |  |  |

| ctt | ggg | ggg | att | ccc | gtg | gga | gtg | att | gct | gtg | gag | aca | cgg | act | 6309 |
| Leu | Gly | Gly | Ile | Pro | Val | Gly | Val | Ile | Ala | Val | Glu | Thr | Arg | Thr |  |
| 2090 |  |  |  |  | 2095 |  |  |  |  | 2100 |  |  |  |  |

| gtg | gag | gtg | gca | gtc | cct | gca | gac | cct | gcc | aac | ctg | gat | tct | gag | 6354 |
| Val | Glu | Val | Ala | Val | Pro | Ala | Asp | Pro | Ala | Asn | Leu | Asp | Ser | Glu |  |
| 2105 |  |  |  |  | 2110 |  |  |  |  | 2115 |  |  |  |  |

| gcc | aag | ata | att | cag | cag | gca | gga | cag | gtg | tgg | ttc | cca | gac | tca | 6399 |
| Ala | Lys | Ile | Ile | Gln | Gln | Ala | Gly | Gln | Val | Trp | Phe | Pro | Asp | Ser |  |
| 2120 |  |  |  |  | 2125 |  |  |  |  | 2130 |  |  |  |  |

| gcc | tac | aaa | acc | gcc | cag | gcc | atc | aag | gac | ttc | aac | cgg | gag | aag | 6444 |
| Ala | Tyr | Lys | Thr | Ala | Gln | Ala | Ile | Lys | Asp | Phe | Asn | Arg | Glu | Lys |  |
| 2135 |  |  |  |  | 2140 |  |  |  |  | 2145 |  |  |  |  |

| ttg | ccc | ctg | atg | atc | ttt | gcc | aac | tgg | agg | ggg | ttc | tcc | ggt | ggc | 6489 |
| Leu | Pro | Leu | Met | Ile | Phe | Ala | Asn | Trp | Arg | Gly | Phe | Ser | Gly | Gly |  |
| 2150 |  |  |  |  | 2155 |  |  |  |  | 2160 |  |  |  |  |

| atg | aaa | gac | atg | tat | gac | cag | gtg | ctg | aag | ttt | gga | gcc | tac | atc | 6534 |
| Met | Lys | Asp | Met | Tyr | Asp | Gln | Val | Leu | Lys | Phe | Gly | Ala | Tyr | Ile |  |
| 2165 |  |  |  |  | 2170 |  |  |  |  | 2175 |  |  |  |  |

| gtg | gac | ggc | ctt | aga | caa | tac | aaa | cag | ccc | atc | ctg | atc | tat | atc | 6579 |
| Val | Asp | Gly | Leu | Arg | Gln | Tyr | Lys | Gln | Pro | Ile | Leu | Ile | Tyr | Ile |  |
| 2180 |  |  |  |  | 2185 |  |  |  |  | 2190 |  |  |  |  |

| ccg | ccc | tat | gcg | gag | ctc | cgg | gga | ggc | tcc | tgg | gtg | gtc | ata | gat | 6624 |
| Pro | Pro | Tyr | Ala | Glu | Leu | Arg | Gly | Gly | Ser | Trp | Val | Val | Ile | Asp |  |
| 2195 |  |  |  |  | 2200 |  |  |  |  | 2205 |  |  |  |  |

| gcc | acc | atc | aac | ccg | ctg | tgc | ata | gaa | atg | tat | gca | gac | aaa | gag | 6669 |

| | | | | | | | | | | |
|---|---|---|---|---|---|---|---|---|---|---|
| Ala | Thr | Ile | Asn | Pro | Leu | Cys | Ile | Glu | Met | Tyr | Ala | Asp | Lys | Glu |
| | 2210 | | | | 2215 | | | | 2220 | | | | | |

```
agc agg ggt ggt gtt ctg gaa cca gag ggg aca gtg gag att aag    6714
Ser Arg Gly Gly Val Leu Glu Pro Glu Gly Thr Val Glu Ile Lys
    2225                2230                2235 ttc cga aag aaa gat ctg ata aag tcc atg aga agg atc gat cca    6759
Phe Arg Lys Lys Asp Leu Ile Lys Ser Met Arg Arg Ile Asp Pro
    2240                2245                2250 gct tac aag aag ctc atg gaa cag cta ggg gaa cct gat ctc tcc    6804
Ala Tyr Lys Lys Leu Met Glu Gln Leu Gly Glu Pro Asp Leu Ser
    2255                2260                2265 gac aag gac cga aag gac ctg gag ggc cgg cta aag gct cgc gag    6849
Asp Lys Asp Arg Lys Asp Leu Glu Gly Arg Leu Lys Ala Arg Glu
    2270                2275                2280 gac ctg ctg ctc ccc atc tac cac cag gtg gcg gtg cag ttc gcc    6894
Asp Leu Leu Leu Pro Ile Tyr His Gln Val Ala Val Gln Phe Ala
    2285                2290                2295 gac ttc cat gac aca ccc ggc cgg atg ctg gag aag ggc gtc ata    6939
Asp Phe His Asp Thr Pro Gly Arg Met Leu Glu Lys Gly Val Ile
    2300                2305                2310 tct gac atc ctg gag tgg aag acc gca cgc acc ttc ctg tat tgg    6984
Ser Asp Ile Leu Glu Trp Lys Thr Ala Arg Thr Phe Leu Tyr Trp
    2315                2320                2325 cgt ctg cgc cgc ctc ctc ctg gag gac cag gtc aag cag gag atc    7029
Arg Leu Arg Arg Leu Leu Leu Glu Asp Gln Val Lys Gln Glu Ile
    2330                2335                2340 ctg cag gcc agc ggg gag ctg agt cac gtg cat atc cag tcc atg    7074
Leu Gln Ala Ser Gly Glu Leu Ser His Val His Ile Gln Ser Met
    2345                2350                2355 ctg cgt cgc tgg ttc gtg gag acg gag ggg gct gtc aag gcc tac    7119
Leu Arg Arg Trp Phe Val Glu Thr Glu Gly Ala Val Lys Ala Tyr
    2360                2365                2370 ttg tgg gac aac aac cag gtg gtt gtg cag tgg ctg gaa cag cac    7164
Leu Trp Asp Asn Asn Gln Val Val Val Gln Trp Leu Glu Gln His
    2375                2380                2385 tgg cag gca ggg gat ggc ccg cgc tcc acc atc cgt gag aac atc    7209
Trp Gln Ala Gly Asp Gly Pro Arg Ser Thr Ile Arg Glu Asn Ile
    2390                2395                2400 acg tac ctg aag cac gac tct gtc ctc aag acc atc cga ggc ctg    7254
Thr Tyr Leu Lys His Asp Ser Val Leu Lys Thr Ile Arg Gly Leu
    2405                2410                2415 gtt gaa gaa aac ccc gag gtg gcc gtg gac tgt gtg ata tac ctg    7299
Val Glu Glu Asn Pro Glu Val Ala Val Asp Cys Val Ile Tyr Leu
    2420                2425                2430 agc cag cac atc agc cca gct gag cgg gcg cag gtc gtt cac ctg    7344
Ser Gln His Ile Ser Pro Ala Glu Arg Ala Gln Val Val His Leu
    2435                2440                2445 ctg tct acc atg gac agc ccg gcc tcc acc tga                    7377
Leu Ser Thr Met Asp Ser Pro Ala Ser Thr
    2450                2455

<210> SEQ ID NO 13
<211> LENGTH: 2458
<212> TYPE: PRT
<213> ORGANISM: Homo sapiens

<400> SEQUENCE: 13

Met Val Leu Leu Leu Cys Leu Ser Arg Leu Ile Phe Ser Cys Leu Thr
1               5                   10                  15

Phe Ser Trp Leu Lys Ile Trp Gly Lys Met Thr Asp Ser Lys Pro Ile
```

-continued

```
                20                  25                  30
Thr Lys Ser Lys Ser Glu Ala Asn Leu Ile Pro Ser Gln Glu Pro Phe
            35                  40                  45
Pro Ala Ser Asp Asn Ser Gly Glu Thr Pro Gln Arg Asn Gly Glu Gly
        50                  55                  60
His Thr Leu Pro Lys Thr Pro Ser Gln Ala Glu Pro Ala Ser His Lys
65                  70                  75                  80
Gly Pro Lys Asp Ala Gly Arg Arg Arg Asn Ser Leu Pro Pro Ser His
                85                  90                  95
Gln Lys Pro Pro Arg Asn Pro Leu Ser Ser Ser Asp Ala Ala Pro Ser
            100                 105                 110
Pro Glu Leu Gln Ala Asn Gly Thr Gly Thr Gln Gly Leu Glu Ala Thr
        115                 120                 125
Asp Thr Asn Gly Leu Ser Ser Ser Ala Arg Pro Gln Gly Gln Gln Ala
    130                 135                 140
Gly Ser Pro Ser Lys Glu Asp Lys Lys Gln Ala Asn Ile Lys Arg Gln
145                 150                 155                 160
Leu Met Thr Asn Phe Ile Leu Gly Ser Phe Asp Asp Tyr Ser Ser Asp
                165                 170                 175
Glu Asp Ser Val Ala Gly Ser Ser Arg Glu Ser Thr Arg Lys Gly Ser
            180                 185                 190
Arg Ala Ser Leu Gly Ala Leu Ser Leu Glu Ala Tyr Leu Thr Thr Gly
        195                 200                 205
Glu Ala Glu Thr Arg Val Pro Thr Met Arg Pro Ser Met Ser Gly Leu
    210                 215                 220
His Leu Val Lys Arg Gly Arg Glu His Lys Lys Leu Asp Leu His Arg
225                 230                 235                 240
Asp Phe Thr Val Ala Ser Pro Ala Glu Phe Val Thr Arg Phe Gly Gly
                245                 250                 255
Asp Arg Val Ile Glu Lys Val Leu Ile Ala Asn Asn Gly Ile Ala Ala
            260                 265                 270
Val Lys Cys Met Arg Ser Ile Arg Arg Trp Ala Tyr Glu Met Phe Arg
        275                 280                 285
Asn Glu Arg Ala Ile Arg Phe Val Val Met Val Thr Pro Glu Asp Leu
    290                 295                 300
Lys Ala Asn Ala Glu Tyr Ile Lys Met Ala Asp His Tyr Val Pro Val
305                 310                 315                 320
Pro Gly Gly Pro Asn Asn Asn Tyr Ala Asn Val Glu Leu Ile Val
                325                 330                 335
Asp Ile Ala Lys Arg Ile Pro Val Gln Ala Val Trp Ala Gly Trp Gly
            340                 345                 350
His Ala Ser Glu Asn Pro Lys Leu Pro Glu Leu Leu Cys Lys Asn Gly
        355                 360                 365
Val Ala Phe Leu Gly Pro Pro Ser Glu Ala Met Trp Ala Leu Gly Asp
    370                 375                 380
Lys Ile Ala Ser Thr Val Val Ala Gln Thr Leu Gln Val Pro Thr Leu
385                 390                 395                 400
Pro Trp Ser Gly Ser Gly Leu Thr Val Glu Trp Thr Glu Asp Asp Leu
                405                 410                 415
Gln Gln Gly Lys Arg Ile Ser Val Pro Glu Asp Val Tyr Asp Lys Gly
            420                 425                 430
Cys Val Lys Asp Val Asp Glu Gly Leu Glu Ala Ala Glu Arg Ile Gly
        435                 440                 445
```

-continued

```
Phe Pro Leu Met Ile Lys Ala Ser Glu Gly Gly Gly Lys Gly Ile
    450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
            485                 490                 495

His Ala Arg His Leu Glu Val Gln Ile Leu Ala Asp Gln Tyr Gly Asn
        500                 505                 510

Ala Val Ser Leu Phe Gly Arg Asp Cys Ser Ile Gln Arg Arg His Gln
    515                 520                 525

Lys Ile Val Glu Glu Ala Pro Ala Thr Ile Ala Pro Leu Ala Ile Phe
530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
            565                 570                 575

His Phe Leu Glu Leu Asn Pro Arg Leu Gln Val Glu His Pro Cys Thr
        580                 585                 590

Glu Met Ile Ala Asp Val Asn Leu Pro Ala Ala Gln Leu Gln Ile Ala
    595                 600                 605

Met Gly Val Pro Leu His Arg Leu Lys Asp Ile Arg Leu Leu Tyr Gly
    610                 615                 620

Glu Ser Pro Trp Gly Val Thr Pro Ile Ser Phe Glu Thr Pro Ser Asn
625                 630                 635                 640

Pro Pro Leu Ala Arg Gly His Val Ile Ala Ala Arg Ile Thr Ser Glu
            645                 650                 655

Asn Pro Asp Glu Gly Phe Lys Pro Ser Ser Gly Thr Val Gln Glu Leu
        660                 665                 670

Asn Phe Arg Ser Ser Lys Asn Val Trp Gly Tyr Phe Ser Val Ala Ala
    675                 680                 685

Thr Gly Gly Leu His Glu Phe Ala Asp Ser Gln Phe Gly His Cys Phe
    690                 695                 700

Ser Trp Gly Glu Asn Arg Glu Glu Ala Ile Ser Asn Met Val Val Ala
705                 710                 715                 720

Leu Lys Glu Leu Ser Ile Arg Gly Asp Phe Arg Thr Thr Val Glu Tyr
            725                 730                 735

Leu Ile Asn Leu Leu Glu Thr Glu Ser Phe Gln Asn Asn Asp Ile Asp
        740                 745                 750

Thr Gly Trp Leu Asp Tyr Leu Ile Ala Glu Lys Val Gln Ala Glu Lys
    755                 760                 765

Pro Asp Ile Met Leu Gly Val Val Cys Gly Ala Leu Asn Val Ala Asp
770                 775                 780

Ala Met Phe Arg Thr Cys Met Thr Asp Phe Leu His Ser Leu Glu Arg
785                 790                 795                 800

Gly Gln Val Leu Pro Ala Asp Ser Leu Leu Asn Leu Val Asp Val Glu
            805                 810                 815

Leu Ile Tyr Gly Gly Val Lys Tyr Ile Leu Lys Val Ala Arg Gln Ser
        820                 825                 830

Leu Thr Met Phe Val Leu Ile Met Asn Gly Cys His Ile Glu Ile Asp
    835                 840                 845

Ala His Arg Leu Asn Asp Gly Gly Leu Leu Leu Ser Tyr Asn Gly Asn
    850                 855                 860
```

-continued

```
Ser Tyr Thr Thr Tyr Met Lys Glu Glu Val Asp Ser Tyr Arg Ile Thr
865                 870                 875                 880

Ile Gly Asn Lys Thr Cys Val Phe Glu Lys Glu Asn Asp Pro Thr Val
                885                 890                 895

Leu Arg Ser Pro Ser Ala Gly Lys Leu Thr Gln Tyr Thr Val Glu Asp
            900                 905                 910

Gly Gly His Val Glu Ala Gly Ser Ser Tyr Ala Glu Met Glu Val Met
        915                 920                 925

Lys Met Ile Met Thr Leu Asn Val Gln Glu Arg Gly Arg Val Lys Tyr
    930                 935                 940

Ile Lys Arg Pro Gly Ala Val Leu Glu Ala Gly Cys Val Val Ala Arg
945                 950                 955                 960

Leu Glu Leu Asp Asp Pro Ser Lys Val His Pro Ala Glu Pro Phe Thr
                965                 970                 975

Gly Glu Leu Pro Ala Gln Gln Thr Leu Pro Ile Leu Gly Glu Lys Leu
            980                 985                 990

His Gln Val Phe His Ser Val Leu Glu Asn Leu Thr Asn Val Met Ser
        995                 1000                1005

Gly Phe Cys Leu Pro Glu Pro Val Phe Ser Ile Lys Leu Lys Glu
    1010                1015                1020

Trp Val Gln Lys Leu Met Met Thr Leu Arg His Pro Ser Leu Pro
    1025                1030                1035

Leu Leu Glu Leu Gln Glu Ile Met Thr Ser Val Ala Gly Arg Ile
    1040                1045                1050

Pro Ala Pro Val Glu Lys Ser Val Arg Arg Val Met Ala Gln Tyr
    1055                1060                1065

Ala Ser Asn Ile Thr Ser Val Leu Cys Gln Phe Pro Ser Gln Gln
    1070                1075                1080

Ile Ala Thr Ile Leu Asp Cys His Ala Ala Thr Leu Gln Arg Lys
    1085                1090                1095

Ala Asp Arg Glu Val Phe Phe Ile Asn Thr Gln Ser Ile Val Gln
    1100                1105                1110

Leu Val Gln Arg Tyr Arg Ser Gly Ile Arg Gly Tyr Met Lys Thr
    1115                1120                1125

Val Val Leu Asp Leu Leu Arg Arg Tyr Leu Arg Val Glu His His
    1130                1135                1140

Phe Gln Gln Ala His Tyr Asp Lys Cys Val Ile Asn Leu Arg Glu
    1145                1150                1155

Gln Phe Lys Pro Asp Met Ser Gln Val Leu Asp Cys Ile Phe Ser
    1160                1165                1170

His Ala Gln Val Ala Lys Lys Asn Gln Leu Val Ile Met Leu Ile
    1175                1180                1185

Asp Glu Leu Cys Gly Pro Asp Pro Ser Leu Ser Asp Glu Leu Ile
    1190                1195                1200

Ser Ile Leu Asn Glu Leu Thr Gln Leu Ser Lys Ser Glu His Cys
    1205                1210                1215

Lys Val Ala Leu Arg Ala Arg Gln Ile Leu Ile Ala Ser His Leu
    1220                1225                1230

Pro Ser Tyr Glu Leu Arg His Asn Gln Val Glu Ser Ile Phe Leu
    1235                1240                1245

Ser Ala Ile Asp Met Tyr Gly His Gln Phe Cys Pro Glu Asn Leu
    1250                1255                1260

Lys Lys Leu Ile Leu Ser Glu Thr Thr Ile Phe Asp Val Leu Pro
```

-continued

```
            1265                1270                1275

Thr Phe Phe Tyr His Ala Asn Lys Val Val Cys Met Ala Ser Leu
    1280                1285                1290

Glu Val Tyr Val Arg Arg Gly Tyr Ile Ala Tyr Glu Leu Asn Ser
    1295                1300                1305

Leu Gln His Arg Gln Leu Pro Asp Gly Thr Cys Val Val Glu Phe
    1310                1315                1320

Gln Phe Met Leu Pro Ser Ser His Pro Asn Arg Met Thr Val Pro
    1325                1330                1335

Ile Ser Ile Thr Asn Pro Asp Leu Leu Arg His Ser Thr Glu Leu
    1340                1345                1350

Phe Met Asp Ser Gly Phe Ser Pro Leu Cys Gln Arg Met Gly Ala
    1355                1360                1365

Met Val Ala Phe Arg Arg Phe Glu Asp Phe Thr Arg Asn Phe Asp
    1370                1375                1380

Glu Val Ile Ser Cys Phe Ala Asn Val Pro Lys Asp Thr Pro Leu
    1385                1390                1395

Phe Ser Glu Ala Arg Thr Ser Leu Tyr Ser Glu Asp Asp Cys Lys
    1400                1405                1410

Ser Leu Arg Glu Glu Pro Ile His Ile Leu Asn Val Ser Ile Gln
    1415                1420                1425

Cys Ala Asp His Leu Glu Asp Glu Ala Leu Val Pro Ile Leu Arg
    1430                1435                1440

Thr Phe Val Gln Ser Lys Lys Asn Ile Leu Val Asp Tyr Gly Leu
    1445                1450                1455

Arg Arg Ile Thr Phe Leu Ile Ala Gln Glu Lys Glu Phe Pro Lys
    1460                1465                1470

Phe Phe Thr Phe Arg Ala Arg Asp Glu Phe Ala Glu Asp Arg Ile
    1475                1480                1485

Tyr Arg His Leu Glu Pro Ala Leu Ala Phe Gln Leu Glu Leu Asn
    1490                1495                1500

Arg Met Arg Asn Phe Asp Leu Thr Ala Val Pro Cys Ala Asn His
    1505                1510                1515

Lys Met His Leu Tyr Leu Gly Ala Ala Lys Val Lys Glu Gly Val
    1520                1525                1530

Glu Val Thr Asp His Arg Phe Phe Ile Arg Ala Ile Ile Arg His
    1535                1540                1545

Ser Asp Leu Ile Thr Lys Glu Ala Ser Phe Glu Tyr Leu Gln Asn
    1550                1555                1560

Glu Gly Glu Arg Leu Leu Leu Glu Ala Met Asp Glu Leu Glu Val
    1565                1570                1575

Ala Phe Asn Asn Thr Ser Val Arg Thr Asp Cys Asn His Ile Phe
    1580                1585                1590

Leu Asn Phe Val Pro Thr Val Ile Met Asp Pro Phe Lys Ile Glu
    1595                1600                1605

Glu Ser Val Arg Tyr Met Val Met Arg Tyr Gly Ser Arg Leu Trp
    1610                1615                1620

Lys Leu Arg Val Leu Gln Ala Glu Val Lys Ile Asn Ile Arg Gln
    1625                1630                1635

Thr Thr Thr Gly Ser Ala Val Pro Ile Arg Leu Phe Ile Thr Asn
    1640                1645                1650

Glu Ser Gly Tyr Tyr Leu Asp Ile Ser Leu Tyr Lys Glu Val Thr
    1655                1660                1665
```

-continued

```
Asp Ser Arg Ser Gly Asn Ile Met Phe His Ser Phe Gly Asn Lys
    1670                1675                1680

Gln Gly Pro Gln His Gly Met Leu Ile Asn Thr Pro Tyr Val Thr
    1685                1690                1695

Lys Asp Leu Leu Gln Ala Lys Arg Phe Gln Ala Gln Thr Leu Gly
    1700                1705                1710

Thr Thr Tyr Ile Tyr Asp Phe Pro Glu Met Phe Arg Gln Ala Leu
    1715                1720                1725

Phe Lys Leu Trp Gly Ser Pro Asp Lys Tyr Pro Lys Asp Ile Leu
    1730                1735                1740

Thr Tyr Thr Glu Leu Val Leu Asp Ser Gln Gly Gln Leu Val Glu
    1745                1750                1755

Met Asn Arg Leu Pro Gly Gly Asn Glu Val Gly Met Val Ala Phe
    1760                1765                1770

Lys Met Arg Phe Lys Thr Gln Glu Tyr Pro Glu Gly Arg Asp Val
    1775                1780                1785

Ile Val Ile Gly Asn Asp Ile Thr Phe Arg Ile Gly Ser Phe Gly
    1790                1795                1800

Pro Gly Glu Asp Leu Leu Tyr Leu Arg Ala Ser Glu Met Ala Arg
    1805                1810                1815

Ala Glu Gly Ile Pro Lys Ile Tyr Val Ala Ala Asn Ser Gly Ala
    1820                1825                1830

Arg Ile Gly Met Ala Glu Glu Ile Lys His Met Phe His Val Ala
    1835                1840                1845

Trp Val Asp Pro Glu Asp Pro His Lys Gly Phe Lys Tyr Leu Tyr
    1850                1855                1860

Leu Thr Pro Gln Asp Tyr Thr Arg Ile Ser Ser Leu Asn Ser Val
    1865                1870                1875

His Cys Lys His Ile Glu Glu Gly Gly Glu Ser Arg Tyr Met Ile
    1880                1885                1890

Thr Asp Ile Ile Gly Lys Asp Asp Gly Leu Gly Val Glu Asn Leu
    1895                1900                1905

Arg Gly Ser Gly Met Ile Ala Gly Glu Ser Ser Leu Ala Tyr Glu
    1910                1915                1920

Glu Ile Val Thr Ile Ser Leu Val Thr Cys Arg Ala Ile Gly Ile
    1925                1930                1935

Gly Ala Tyr Leu Val Arg Leu Gly Gln Arg Val Ile Gln Val Glu
    1940                1945                1950

Asn Ser His Ile Ile Leu Thr Gly Ala Ser Ala Leu Asn Lys Val
    1955                1960                1965

Leu Gly Arg Glu Val Tyr Thr Ser Asn Asn Gln Leu Gly Gly Val
    1970                1975                1980

Gln Ile Met His Tyr Asn Gly Val Ser His Ile Thr Val Pro Asp
    1985                1990                1995

Asp Phe Glu Gly Val Tyr Thr Ile Leu Glu Trp Leu Ser Tyr Met
    2000                2005                2010

Pro Lys Asp Asn His Ser Pro Val Pro Ile Ile Thr Pro Thr Asp
    2015                2020                2025

Pro Ile Asp Arg Glu Ile Glu Phe Leu Pro Ser Arg Ala Pro Tyr
    2030                2035                2040

Asp Pro Arg Trp Met Leu Ala Gly Arg Pro His Pro Thr Leu Lys
    2045                2050                2055
```

-continued

```
Gly Thr Trp Gln Ser Gly Phe Phe Asp His Gly Ser Phe Lys Glu
    2060            2065            2070

Ile Met Ala Pro Trp Ala Gln Thr Val Val Thr Gly Arg Ala Arg
    2075            2080            2085

Leu Gly Gly Ile Pro Val Gly Val Ile Ala Val Glu Thr Arg Thr
    2090            2095            2100

Val Glu Val Ala Val Pro Ala Asp Pro Ala Asn Leu Asp Ser Glu
    2105            2110            2115

Ala Lys Ile Ile Gln Gln Ala Gly Gln Val Trp Phe Pro Asp Ser
    2120            2125            2130

Ala Tyr Lys Thr Ala Gln Ala Ile Lys Asp Phe Asn Arg Glu Lys
    2135            2140            2145

Leu Pro Leu Met Ile Phe Ala Asn Trp Arg Gly Phe Ser Gly Gly
    2150            2155            2160

Met Lys Asp Met Tyr Asp Gln Val Leu Lys Phe Gly Ala Tyr Ile
    2165            2170            2175

Val Asp Gly Leu Arg Gln Tyr Lys Gln Pro Ile Leu Ile Tyr Ile
    2180            2185            2190

Pro Pro Tyr Ala Glu Leu Arg Gly Gly Ser Trp Val Val Ile Asp
    2195            2200            2205

Ala Thr Ile Asn Pro Leu Cys Ile Glu Met Tyr Ala Asp Lys Glu
    2210            2215            2220

Ser Arg Gly Gly Val Leu Glu Pro Glu Gly Thr Val Glu Ile Lys
    2225            2230            2235

Phe Arg Lys Lys Asp Leu Ile Lys Ser Met Arg Arg Ile Asp Pro
    2240            2245            2250

Ala Tyr Lys Lys Leu Met Glu Gln Leu Gly Glu Pro Asp Leu Ser
    2255            2260            2265

Asp Lys Asp Arg Lys Asp Leu Glu Gly Arg Leu Lys Ala Arg Glu
    2270            2275            2280

Asp Leu Leu Leu Pro Ile Tyr His Gln Val Ala Val Gln Phe Ala
    2285            2290            2295

Asp Phe His Asp Thr Pro Gly Arg Met Leu Glu Lys Gly Val Ile
    2300            2305            2310

Ser Asp Ile Leu Glu Trp Lys Thr Ala Arg Thr Phe Leu Tyr Trp
    2315            2320            2325

Arg Leu Arg Arg Leu Leu Leu Glu Asp Gln Val Lys Gln Glu Ile
    2330            2335            2340

Leu Gln Ala Ser Gly Glu Leu Ser His Val His Ile Gln Ser Met
    2345            2350            2355

Leu Arg Arg Trp Phe Val Glu Thr Glu Gly Ala Val Lys Ala Tyr
    2360            2365            2370

Leu Trp Asp Asn Asn Gln Val Val Val Gln Trp Leu Glu Gln His
    2375            2380            2385

Trp Gln Ala Gly Asp Gly Pro Arg Ser Thr Ile Arg Glu Asn Ile
    2390            2395            2400

Thr Tyr Leu Lys His Asp Ser Val Leu Lys Thr Ile Arg Gly Leu
    2405            2410            2415

Val Glu Glu Asn Pro Glu Val Ala Val Asp Cys Val Ile Tyr Leu
    2420            2425            2430

Ser Gln His Ile Ser Pro Ala Glu Arg Ala Gln Val Val His Leu
    2435            2440            2445

Leu Ser Thr Met Asp Ser Pro Ala Ser Thr
```

-continued

<210> SEQ ID NO 14
<211> LENGTH: 2455
<212> TYPE: PRT
<213> ORGANISM: Rattus norvegicus

<400> SEQUENCE: 14

Met Val Leu Leu Leu Phe Leu Thr Cys Leu Val Phe Ser Cys Leu Thr
1               5                   10                  15

Ile Ser Trp Leu Lys Ile Trp Gly Lys Met Thr Asp Ser Lys Pro Leu
            20                  25                  30

Ser Asn Ser Lys Val Asp Ala Ser Leu Leu Ser Ser Lys Glu Glu Ser
            35                  40                  45

Phe Ser Ala Ser Asp Gln Ser Glu Glu His Gly Asp Cys Ser Cys Pro
    50                  55                  60

Leu Thr Thr Pro Asp Gln Glu Glu Leu Ala Ser His Gly Gly Pro Val
65                  70                  75                  80

Asp Ala Ser Gln Gln Arg Asn Ser Val Pro Ser Ser His Gln Lys Pro
                85                  90                  95

Pro Arg Asn Pro Leu Ser Ser Asn Asp Thr Cys Ser Ser Pro Glu Leu
            100                 105                 110

Gln Thr Asn Gly Val Ala Ala Pro Gly Ser Glu Val Pro Glu Ala Asn
            115                 120                 125

Gly Leu Pro Phe Pro Ala Arg Pro Gln Thr Gln Arg Thr Gly Ser Pro
    130                 135                 140

Thr Arg Glu Asp Lys Lys Gln Ala His Ile Lys Arg Gln Leu Met Thr
145                 150                 155                 160

Ser Phe Ile Leu Gly Ser Leu Asp Asp Asn Ser Ser Asp Glu Asp Pro
                165                 170                 175

Ser Ala Ser Ser Phe Gln Thr Ser Ser Arg Lys Gly Ser Arg Ala Ser
            180                 185                 190

Leu Gly Thr Leu Ser Gln Glu Ala Ala Leu Asn Thr Ala Asp Pro Glu
            195                 200                 205

Ser His Thr Pro Thr Met Arg Pro Ser Met Ser Gly Leu His Leu Val
    210                 215                 220

Lys Arg Gly Arg Glu His Lys Lys Leu Asp Leu His Arg Asp Phe Thr
225                 230                 235                 240

Val Ala Ser Pro Ala Glu Phe Val Thr Arg Phe Gly Gly Asn Arg Val
                245                 250                 255

Ile Glu Thr Val Leu Ile Ala Asn Asn Gly Ile Ala Ala Val Lys Cys
            260                 265                 270

Met Arg Ser Ile Arg Arg Trp Ala Tyr Glu Met Phe Arg Asn Glu Arg
            275                 280                 285

Ala Ile Arg Phe Val Val Met Val Thr Pro Glu Asp Leu Lys Ala Asn
    290                 295                 300

Ala Glu Tyr Ile Lys Met Ala Asp Gln Tyr Val Pro Val Pro Gly Gly
305                 310                 315                 320

Pro Asn Asn Asn Asn Tyr Ala Asn Val Glu Leu Ile Ile Asp Ile Ala
                325                 330                 335

Lys Arg Ile Pro Val Gln Ala Val Trp Ala Gly Trp Gly His Ala Ser
            340                 345                 350

Glu Asn Pro Lys Leu Pro Glu Leu Leu Cys Lys His Glu Ile Ala Phe
            355                 360                 365

```
Leu Gly Pro Pro Ser Glu Ala Met Trp Ala Leu Gly Asp Lys Ile Ser
    370                 375                 380

Ser Thr Ile Val Ala Gln Thr Leu Gln Ile Pro Thr Leu Pro Trp Ser
385                 390                 395                 400

Gly Ser Gly Leu Thr Val Glu Trp Thr Glu Asp Ser Gln His Gln Gly
                405                 410                 415

Lys Cys Ile Ser Val Pro Glu Asp Val Tyr Glu Gln Gly Cys Val Arg
            420                 425                 430

Asp Val Asp Glu Gly Leu Gln Ala Ala Glu Lys Val Gly Phe Pro Leu
        435                 440                 445

Met Ile Lys Ala Ser Glu Gly Gly Gly Lys Gly Ile Arg Arg Ala
    450                 455                 460

Glu Ser Ala Glu Asp Phe Pro Met Leu Phe Arg Gln Val Gln Ser Glu
465                 470                 475                 480

Ile Pro Gly Ser Pro Ile Phe Leu Met Lys Leu Ala Gln Asn Ala Arg
                485                 490                 495

His Leu Glu Val Gln Val Leu Ala Asp Gln Tyr Gly Asn Ala Val Ser
            500                 505                 510

Leu Phe Gly Arg Asp Cys Ser Ile Gln Arg Arg His Gln Lys Ile Ile
        515                 520                 525

Glu Glu Ala Pro Ala Thr Ile Ala Ala Pro Ala Val Phe Glu Phe Met
530                 535                 540

Glu Gln Cys Ala Val Leu Leu Ala Lys Thr Val Gly Tyr Val Ser Ala
545                 550                 555                 560

Gly Thr Val Glu Tyr Leu Tyr Ser Gln Asp Gly Ser Phe His Phe Leu
                565                 570                 575

Glu Leu Asn Pro Arg Leu Gln Val Glu His Pro Cys Thr Glu Met Ile
            580                 585                 590

Ala Asp Val Asn Leu Pro Ala Ala Gln Leu Gln Ile Ala Met Gly Val
        595                 600                 605

Pro Leu His Arg Leu Lys Asp Ile Arg Leu Leu Tyr Gly Glu Ser Pro
610                 615                 620

Trp Gly Val Thr Pro Val Ser Phe Glu Thr Pro Leu Ser Pro Pro Ile
625                 630                 635                 640

Ala Arg Gly His Val Ile Ala Ala Arg Ile Thr Ser Glu Asn Pro Asp
                645                 650                 655

Glu Gly Phe Lys Pro Ser Ser Gly Thr Val Gln Glu Leu Asn Phe Arg
            660                 665                 670

Ser Asn Lys Asn Val Trp Gly Tyr Phe Ser Val Ala Ala Ala Gly Gly
        675                 680                 685

Leu His Glu Phe Ala Asp Ser Gln Phe Gly His Cys Phe Ser Trp Gly
690                 695                 700

Glu Asn Arg Glu Glu Ala Ile Ser Asn Met Val Val Ala Leu Lys Glu
705                 710                 715                 720

Leu Ser Ile Arg Gly Asp Phe Arg Thr Val Glu Tyr Leu Val Asn
                725                 730                 735

Leu Leu Glu Thr Glu Ser Phe Gln Asn Asn Asp Ile Asp Thr Gly Trp
            740                 745                 750

Leu Asp His Leu Ile Ala Gln Arg Val Gln Ala Glu Lys Pro Asp Ile
        755                 760                 765

Met Leu Gly Val Val Cys Gly Ala Leu Asn Val Ala Asp Ala Met Phe
770                 775                 780

Arg Thr Cys Met Thr Glu Phe Leu His Ser Leu Glu Arg Gly Gln Val
```

```
                     785                 790                 795                 800
Leu Pro Ala Asp Ser Leu Leu Asn Ile Val Asp Val Glu Leu Ile Tyr
                805                 810                 815
Gly Gly Ile Lys Tyr Val Leu Lys Val Ala Arg Gln Ser Leu Thr Met
                820                 825                 830
Phe Val Leu Ile Met Asn Gly Cys His Ile Glu Ile Asp Ala His Arg
                835                 840                 845
Leu Asn Asp Gly Gly Leu Leu Ser Tyr Asn Gly Ser Ser Tyr Thr
850                 855                 860
Thr Tyr Met Lys Glu Glu Val Asp Ser Tyr Arg Ile Thr Ile Gly Asn
865                 870                 875                 880
Lys Thr Cys Val Phe Glu Lys Glu Asn Asp Pro Thr Val Leu Arg Ser
                885                 890                 895
Pro Ser Ala Gly Lys Leu Met Gln Tyr Thr Val Glu Asp Gly Gln His
                900                 905                 910
Val Glu Val Gly Ser Ser Tyr Ala Glu Met Glu Val Met Lys Met Ile
                915                 920                 925
Met Thr Leu Asn Val Gln Glu Ser Gly Arg Val Lys Tyr Ile Lys Arg
                930                 935                 940
Pro Gly Ala Val Leu Glu Ala Gly Cys Val Val Ala Lys Leu Glu Leu
945                 950                 955                 960
Asp Asp Pro Ser Lys Val His Ala Ala Gln Pro Phe Thr Gly Glu Leu
                965                 970                 975
Pro Ala Gln Gln Thr Leu Pro Ile Leu Gly Arg Leu His Gln Val
                980                 985                 990
Phe His Ser Val Leu Glu Asn Leu Thr Asn Val Met Asn Gly Tyr Cys
                995                 1000                1005
Leu Pro Glu Pro Phe Phe Ser Met Lys Leu Lys Asp Trp Val Glu
     1010                1015                1020
Lys Leu Met Met Thr Leu Arg His Pro Ser Leu Pro Leu Leu Glu
     1025                1030                1035
Leu Gln Glu Ile Met Thr Ser Val Ala Gly Arg Ile Pro Val Pro
     1040                1045                1050
Val Glu Lys Ala Val Arg Arg Val Met Ala Gln Tyr Ala Ser Asn
     1055                1060                1065
Ile Thr Ser Val Leu Cys Gln Phe Pro Ser Gln Ile Ala Thr
     1070                1075                1080
Ile Leu Asp Cys His Ala Ala Thr Leu Gln Arg Lys Val Asp Arg
     1085                1090                1095
Glu Ala Phe Phe Met Asn Thr Gln Ser Ile Val Gln Leu Ile Gln
     1100                1105                1110
Arg Tyr Arg Ser Gly Thr Arg Gly Tyr Met Lys Ala Val Val Leu
     1115                1120                1125
Asp Leu Leu Arg Arg Tyr Leu Asn Val Glu His His Phe Gln Gln
     1130                1135                1140
Ala His Tyr Asp Lys Cys Val Ile Asn Leu Arg Glu Gln Phe Lys
     1145                1150                1155
Pro Asp Met Thr Arg Val Leu Asp Cys Ile Phe Ser His Ser Gln
     1160                1165                1170
Val Ala Lys Lys Asn Gln Leu Val Thr Met Leu Ile Asp Glu Leu
     1175                1180                1185
Cys Gly Pro Asp Pro Thr Leu Ser Glu Glu Leu Thr Ser Ile Leu
     1190                1195                1200
```

-continued

```
Lys Glu Leu Thr Gln Leu Ser Arg Ser Glu His Cys Lys Val Ala
1205                1210                1215

Leu Arg Ala Arg Gln Val Leu Ile Ala Ser His Leu Pro Ser Tyr
1220                1225                1230

Glu Leu Arg His Asn Gln Val Glu Ser Ile Phe Leu Ser Ala Ile
1235                1240                1245

Asp Met Tyr Gly His Gln Phe Cys Pro Glu Asn Leu Lys Lys Leu
1250                1255                1260

Ile Leu Ser Glu Thr Thr Ile Phe Asp Val Leu Pro Thr Phe Phe
1265                1270                1275

Tyr His Ala Asn Lys Val Val Cys Met Ala Ser Leu Glu Val Tyr
1280                1285                1290

Val Arg Arg Gly Tyr Ile Ala Tyr Glu Leu Asn Ser Leu Gln His
1295                1300                1305

Arg Glu Leu Pro Asp Gly Thr Cys Val Val Glu Phe Gln Phe Met
1310                1315                1320

Leu Pro Ser Ser His Pro Asn Arg Met Ala Met Pro Ile Asn Val
1325                1330                1335

Ser Asp Pro Asp Leu Leu Arg His Ser Lys Glu Leu Phe Met Asp
1340                1345                1350

Ser Gly Phe Ser Pro Leu Cys Gln Arg Met Gly Ala Met Val Ala
1355                1360                1365

Phe Arg Arg Phe Glu Glu Phe Thr Arg Asn Phe Asp Glu Val Ile
1370                1375                1380

Ser Cys Phe Ala Asn Val Pro Thr Asp Thr Pro Leu Phe Ser Lys
1385                1390                1395

Ala Cys Thr Ser Leu Tyr Ser Glu Glu Asp Ser Lys Ser Leu Gln
1400                1405                1410

Glu Glu Pro Ile His Ile Leu Asn Val Ala Ile Gln Cys Ala Asp
1415                1420                1425

His Met Glu Asp Glu Arg Leu Val Pro Val Phe Arg Ala Phe Val
1430                1435                1440

Gln Ser Lys Lys His Ile Leu Val Asp Tyr Gly Leu Arg Arg Ile
1445                1450                1455

Thr Phe Leu Ile Ala Gln Glu Arg Glu Phe Pro Lys Phe Phe Thr
1460                1465                1470

Phe Arg Ala Arg Asp Glu Phe Ala Glu Asp Arg Ile Tyr Arg His
1475                1480                1485

Leu Glu Pro Ala Leu Ala Phe Gln Leu Glu Leu Ser Arg Met Arg
1490                1495                1500

Asn Phe Asp Leu Thr Ala Val Pro Cys Ala Asn His Lys Met His
1505                1510                1515

Leu Tyr Leu Gly Ala Ala Lys Val Lys Glu Gly Leu Glu Val Thr
1520                1525                1530

Asp His Arg Phe Phe Ile Arg Ala Ile Ile Arg His Ser Asp Leu
1535                1540                1545

Ile Thr Lys Glu Ala Ser Phe Glu Tyr Leu Gln Asn Glu Gly Glu
1550                1555                1560

Arg Leu Leu Leu Glu Ala Met Asp Glu Leu Glu Val Ala Phe Asn
1565                1570                1575

Asn Thr Ser Val Arg Thr Asp Cys Asn His Ile Phe Leu Asn Phe
1580                1585                1590
```

-continued

```
Val Pro Thr Val Ile Met Asp Pro Leu Lys Ile Glu Glu Ser Val
1595                1600                1605

Arg Ala Met Val Met Arg Tyr Gly Ser Arg Leu Trp Lys Leu Arg
1610                1615                1620

Val Leu Gln Ala Glu Val Lys Ile Asn Ile Arg Gln Thr Thr Ser
1625                1630                1635

Asp Cys Ala Val Pro Ile Arg Leu Phe Ile Thr Asn Glu Ser Gly
1640                1645                1650

Tyr Tyr Leu Asp Ile Ser Leu Tyr Lys Glu Val Thr Asp Ser Arg
1655                1660                1665

Ser Gly Asn Ile Met Phe His Ser Phe Gly Asn Lys Gln Gly Ser
1670                1675                1680

Leu His Gly Met Leu Ile Asn Thr Pro Tyr Val Thr Lys Asp Leu
1685                1690                1695

Leu Gln Ala Lys Arg Phe Gln Ala Gln Ser Leu Gly Thr Thr Tyr
1700                1705                1710

Val Tyr Asp Phe Pro Glu Met Phe Arg Gln Ala Leu Phe Lys Leu
1715                1720                1725

Trp Gly Ser Pro Glu Lys Tyr Pro Lys Asp Ile Leu Thr Tyr Thr
1730                1735                1740

Glu Leu Val Leu Asp Ser Gln Gly Gln Leu Val Glu Met Asn Arg
1745                1750                1755

Leu Pro Gly Cys Asn Glu Val Gly Met Val Val Phe Lys Met Arg
1760                1765                1770

Phe Lys Thr Pro Glu Tyr Pro Glu Gly Arg Asp Thr Ile Val Ile
1775                1780                1785

Gly Asn Asp Ile Thr Phe Gln Ile Gly Ser Phe Gly Ile Gly Glu
1790                1795                1800

Asp Phe Leu Tyr Leu Arg Ala Ser Glu Met Ala Arg Thr Glu Gly
1805                1810                1815

Ile Pro Gln Ile Tyr Leu Ala Ala Asn Ser Gly Ala Arg Met Gly
1820                1825                1830

Leu Ser Glu Glu Ile Lys Gln Ile Phe Gln Val Ala Trp Val Asp
1835                1840                1845

Pro Glu Asp Pro Tyr Lys Gly Phe Arg Tyr Leu Tyr Leu Thr Pro
1850                1855                1860

Gln Asp Tyr Thr Gln Ile Ser Ser Gln Asn Ser Val His Cys Lys
1865                1870                1875

His Ile Glu Asp Glu Gly Glu Ser Arg Tyr Val Ile Val Asp Val
1880                1885                1890

Ile Gly Lys Asp Ser Ser Leu Gly Val Glu Asn Leu Arg Gly Ser
1895                1900                1905

Gly Met Ile Ala Gly Glu Ala Ser Leu Ala Tyr Glu Lys Asn Val
1910                1915                1920

Thr Ile Ser Met Val Thr Cys Arg Ala Ile Gly Ile Gly Ala Tyr
1925                1930                1935

Leu Val Arg Leu Gly Gln Arg Val Ile Gln Val Glu Asn Ser His
1940                1945                1950

Ile Ile Leu Thr Gly Ala Gly Ala Leu Asn Lys Val Leu Gly Arg
1955                1960                1965

Glu Val Tyr Thr Ser Asn Asn Gln Leu Gly Gly Val Gln Ile Met
1970                1975                1980

His Thr Asn Gly Val Ser His Val Thr Val Pro Asp Asp Phe Glu
```

-continued

```
               1985                1990                1995
Gly Val Cys Thr Ile Leu Glu Trp Leu Ser Tyr Ile Pro Lys Asp
        2000                2005                2010

Asn Gln Ser Pro Val Pro Ile Ile Thr Pro Ser Asp Pro Ile Asp
        2015                2020                2025

Arg Glu Ile Glu Phe Thr Pro Thr Lys Ala Pro Tyr Asp Pro Arg
        2030                2035                2040

Trp Leu Leu Ala Gly Arg Pro His Pro Thr Leu Lys Gly Thr Trp
        2045                2050                2055

Gln Ser Gly Phe Phe Asp His Gly Ser Phe Lys Glu Ile Met Ala
        2060                2065                2070

Pro Trp Ala Gln Thr Val Val Thr Gly Arg Ala Arg Leu Gly Gly
        2075                2080                2085

Ile Pro Val Gly Val Ile Ala Val Glu Thr Arg Ser Val Glu Val
        2090                2095                2100

Ala Val Pro Ala Asp Pro Ala Asn Leu Asp Ser Glu Ala Lys Ile
        2105                2110                2115

Ile Gln Gln Ala Gly Gln Val Trp Phe Pro Asp Ser Ala Phe Lys
        2120                2125                2130

Thr Ala Gln Val Ile Arg Asp Phe Asn Gln Glu His Leu Pro Leu
        2135                2140                2145

Met Ile Phe Ala Asn Trp Arg Gly Phe Ser Gly Gly Met Lys Asp
        2150                2155                2160

Met Tyr Glu Gln Met Leu Lys Phe Gly Ala Tyr Ile Val Asp Ser
        2165                2170                2175

Leu Arg Leu Phe Lys Gln Pro Val Leu Ile Tyr Ile Pro Pro Gly
        2180                2185                2190

Ala Glu Leu Arg Gly Gly Ala Trp Val Val Leu Asp Ser Ser Ile
        2195                2200                2205

Asn Pro Leu Cys Ile Glu Met Tyr Ala Asp Lys Glu Ser Arg Gly
        2210                2215                2220

Gly Val Leu Glu Pro Glu Gly Thr Val Glu Ile Lys Phe Arg Lys
        2225                2230                2235

Lys Asp Leu Val Lys Thr Ile Arg Arg Ile Asp Pro Val Cys Lys
        2240                2245                2250

Lys Leu Leu Gly Gln Leu Gly Thr Ala Gln Leu Pro Asp Lys Asp
        2255                2260                2265

Arg Lys Glu Leu Glu Ser Gln Leu Lys Ala Arg Glu Asp Leu Leu
        2270                2275                2280

Leu Pro Ile Tyr His Gln Val Ala Val Gln Phe Ala Asp Leu His
        2285                2290                2295

Asp Thr Pro Gly His Met Leu Glu Lys Gly Ile Ile Ser Asp Val
        2300                2305                2310

Leu Glu Trp Lys Thr Thr Arg Thr Tyr Phe Tyr Trp Arg Leu Arg
        2315                2320                2325

Arg Leu Leu Leu Glu Ala Gln Val Lys Gln Glu Ile Leu Arg Ala
        2330                2335                2340

Ser Pro Glu Leu Ser His Glu His Thr Gln Ser Met Leu Arg Arg
        2345                2350                2355

Trp Phe Val Glu Thr Glu Gly Ala Val Lys Ala Tyr Leu Trp Asp
        2360                2365                2370

Ser Asn Gln Val Val Val Gln Trp Leu Glu Gln His Trp Ser Ala
        2375                2380                2385
```

```
Arg Asp Asn Leu Arg Ser Thr Ile Arg Glu Asn Ile Asn Tyr Leu
    2390            2395                2400

Lys Arg Asp Ser Val Leu Lys Thr Ile Gln Ser Leu Val Gln Glu
2405                2410                2415

His Pro Glu Ala Thr Met Asp Cys Val Ala Tyr Leu Ser Gln His
    2420            2425                2430

Leu Thr Pro Ala Glu Gln Met Gln Val Val Gln Leu Leu Ser Thr
    2435            2440                2445

Thr Glu Ser Pro Ala Ser His
    2450            2455

<210> SEQ ID NO 15
<211> LENGTH: 7388
<212> TYPE: DNA
<213> ORGANISM: Rattus norvegicus
<220> FEATURE:
<221> NAME/KEY: CDS
<222> LOCATION: (21)..(7388)

<400> SEQUENCE: 15
```

| | | | | | | | |
|---|---|---|---|---|---|---|---|
| tcccttgaca ggttgtctga atg gtc ttg ctt ctc ttt ctg act tgc ctg gtt | | | | | | | 53 |
| | Met Val Leu Leu Leu Phe Leu Thr Cys Leu Val | | | | | | |
| | 1 5 10 | | | | | | |
| ttc tcc tgc ctg acc att tcc tgg tta aaa atc tgg ggg aag atg aca | | | | | | | 101 |
| Phe Ser Cys Leu Thr Ile Ser Trp Leu Lys Ile Trp Gly Lys Met Thr | | | | | | | |
| 15 20 25 | | | | | | | |
| gac tcg aag ccg ctc agc aac agt aag gtg gat gca agc ctc ctt tcg | | | | | | | 149 |
| Asp Ser Lys Pro Leu Ser Asn Ser Lys Val Asp Ala Ser Leu Leu Ser | | | | | | | |
| 30 35 40 | | | | | | | |
| agc aag gag gag tcc ttt tca gcc tcg gac cag tca gag gag cat ggc | | | | | | | 197 |
| Ser Lys Glu Glu Ser Phe Ser Ala Ser Asp Gln Ser Glu Glu His Gly | | | | | | | |
| 45 50 55 | | | | | | | |
| gac tgc agc tgt ccg ttg aca act cct gac cag gag gag ctg gcc tcc | | | | | | | 245 |
| Asp Cys Ser Cys Pro Leu Thr Thr Pro Asp Gln Glu Glu Leu Ala Ser | | | | | | | |
| 60 65 70 75 | | | | | | | |
| cac gga ggt cct gta gat gcc agt cag cag agg aac tct gtg cca agc | | | | | | | 293 |
| His Gly Gly Pro Val Asp Ala Ser Gln Gln Arg Asn Ser Val Pro Ser | | | | | | | |
| 80 85 90 | | | | | | | |
| tca cac cag aag cct ccg agg aac cca cta tct tcc aat gac acc tgt | | | | | | | 341 |
| Ser His Gln Lys Pro Pro Arg Asn Pro Leu Ser Ser Asn Asp Thr Cys | | | | | | | |
| 95 100 105 | | | | | | | |
| tcc tcc cca gaa ctc caa acc aac ggg gta gca gcc cct ggc tca gag | | | | | | | 389 |
| Ser Ser Pro Glu Leu Gln Thr Asn Gly Val Ala Ala Pro Gly Ser Glu | | | | | | | |
| 110 115 120 | | | | | | | |
| gtt cca gaa gcc aac ggg ttg cct ttc cca gcc agg cct cag acc cag | | | | | | | 437 |
| Val Pro Glu Ala Asn Gly Leu Pro Phe Pro Ala Arg Pro Gln Thr Gln | | | | | | | |
| 125 130 135 | | | | | | | |
| aga acg gga tcc ccc act agg gag gac aag aag cag gca cac atc aag | | | | | | | 485 |
| Arg Thr Gly Ser Pro Thr Arg Glu Asp Lys Lys Gln Ala His Ile Lys | | | | | | | |
| 140 145 150 155 | | | | | | | |
| agg cag ctg atg acc agc ttt atc ctg ggc tcc ctc gat gac aac tcc | | | | | | | 533 |
| Arg Gln Leu Met Thr Ser Phe Ile Leu Gly Ser Leu Asp Asp Asn Ser | | | | | | | |
| 160 165 170 | | | | | | | |
| tct gac gag gac cct agt gct agc tcc ttc cag acc tcc tct cgg aag | | | | | | | 581 |
| Ser Asp Glu Asp Pro Ser Ala Ser Ser Phe Gln Thr Ser Ser Arg Lys | | | | | | | |
| 175 180 185 | | | | | | | |
| ggc agc agg gct agc ctg ggc acc ctg tcc cag gag gct gca ttg aac | | | | | | | 629 |
| Gly Ser Arg Ala Ser Leu Gly Thr Leu Ser Gln Glu Ala Ala Leu Asn | | | | | | | |
| 190 195 200 | | | | | | | |

-continued

```
aca gct gat cct gag tct cac aca cct act atg agg ccc agc atg tct     677
Thr Ala Asp Pro Glu Ser His Thr Pro Thr Met Arg Pro Ser Met Ser
    205                 210                 215 gga ctc cat ctg gtg aag aga ggc cgt gaa cac aag aaa ctg gac ctg     725
Gly Leu His Leu Val Lys Arg Gly Arg Glu His Lys Lys Leu Asp Leu
220                 225                 230                 235 cac aga gat ttc act gta gct tcc cca gcc gaa ttt gtc acc cgc ttt     773
His Arg Asp Phe Thr Val Ala Ser Pro Ala Glu Phe Val Thr Arg Phe
                240                 245                 250 gga ggc aac agg gtt atc gag acg gtg ctc atc gcc aat aat ggt atc     821
Gly Gly Asn Arg Val Ile Glu Thr Val Leu Ile Ala Asn Asn Gly Ile
                    255                 260                 265 gct gcg gtc aag tgt atg cgc tcc atc cgc cgc tgg gcc tat gag atg     869
Ala Ala Val Lys Cys Met Arg Ser Ile Arg Arg Trp Ala Tyr Glu Met
            270                 275                 280 ttc cgt aat gaa cgc gcc atc cgg ttt gtg gtt atg gtg aca ccc gag     917
Phe Arg Asn Glu Arg Ala Ile Arg Phe Val Val Met Val Thr Pro Glu
        285                 290                 295 gat ctt aag gcc aac gca gag tac atc aag atg gcg gac cag tac gtt     965
Asp Leu Lys Ala Asn Ala Glu Tyr Ile Lys Met Ala Asp Gln Tyr Val
300                 305                 310                 315 ccg gtc cca gga gga ccc aat aat aac aac tac gcc aac gtt gag ctg    1013
Pro Val Pro Gly Gly Pro Asn Asn Asn Asn Tyr Ala Asn Val Glu Leu
                320                 325                 330 atc ata gac att gcc aag aga atc cct gtg cag gcc gtg tgg gct ggc    1061
Ile Ile Asp Ile Ala Lys Arg Ile Pro Val Gln Ala Val Trp Ala Gly
                    335                 340                 345 tgg ggc cac gct tcg gaa aac ccc aaa ctt cca gag cta ctg tgc aag    1109
Trp Gly His Ala Ser Glu Asn Pro Lys Leu Pro Glu Leu Leu Cys Lys
            350                 355                 360 cac gag att gct ttc cta ggt ccc ccg agt gag gcc atg tgg gcc ctg    1157
His Glu Ile Ala Phe Leu Gly Pro Pro Ser Glu Ala Met Trp Ala Leu
        365                 370                 375 gga gac aag atc tcc tcc acc att gta gcc cag aca ttg cag atc cca    1205
Gly Asp Lys Ile Ser Ser Thr Ile Val Ala Gln Thr Leu Gln Ile Pro
380                 385                 390                 395 act cta ccc tgg agc gga agc ggt ctc aca gtg gag tgg acg gag gac    1253
Thr Leu Pro Trp Ser Gly Ser Gly Leu Thr Val Glu Trp Thr Glu Asp
                400                 405                 410 agc cag cat cag ggc aaa tgc atc agc gtc ccg gaa gac gtt tat gaa    1301
Ser Gln His Gln Gly Lys Cys Ile Ser Val Pro Glu Asp Val Tyr Glu
                    415                 420                 425 caa ggc tgt gtg aga gat gtg gac gaa ggc ttg cag gca gca gaa aaa    1349
Gln Gly Cys Val Arg Asp Val Asp Glu Gly Leu Gln Ala Ala Glu Lys
            430                 435                 440 gta gga ttt cct ctg atg atc aaa gcc tct gaa ggt gga gga ggg aaa    1397
Val Gly Phe Pro Leu Met Ile Lys Ala Ser Glu Gly Gly Gly Gly Lys
        445                 450                 455 gga atc cgc agg gct gag agt gca gag gac ttc ccg atg ctt ttc aga    1445
Gly Ile Arg Arg Ala Glu Ser Ala Glu Asp Phe Pro Met Leu Phe Arg
460                 465                 470                 475 cag gtg cag agt gag atc ccg ggc tcg ccc atc ttt ctc atg aag ctg    1493
Gln Val Gln Ser Glu Ile Pro Gly Ser Pro Ile Phe Leu Met Lys Leu
                480                 485                 490 gcc cag aat gct cgg cac ttg gag gtc cag gtc ttg gca gat cag tat    1541
Ala Gln Asn Ala Arg His Leu Glu Val Gln Val Leu Ala Asp Gln Tyr
                    495                 500                 505 ggg aac gca gtg tcc ctg ttt gga cga gac tgc tcc atc cag agg cgg    1589
Gly Asn Ala Val Ser Leu Phe Gly Arg Asp Cys Ser Ile Gln Arg Arg
            510                 515                 520
```

-continued

| | |
|---|---|
| cac cag aag atc att gag gag gct ccg gcc acc atc gct gct ccg gct<br>His Gln Lys Ile Ile Glu Glu Ala Pro Ala Thr Ile Ala Ala Pro Ala<br>525                         530                    535 | 1637 |
| gtg ttt gag ttc atg gaa cag tgt gcc gtc ctc ctg gcc aag act gtg<br>Val Phe Glu Phe Met Glu Gln Cys Ala Val Leu Leu Ala Lys Thr Val<br>540                         545                    550                    555 | 1685 |
| ggt tat gtg agc gcg gga acc gtg gag tac cta tac agc cag gat ggc<br>Gly Tyr Val Ser Ala Gly Thr Val Glu Tyr Leu Tyr Ser Gln Asp Gly<br>               560                    565                    570 | 1733 |
| agc ttt cac ttc ttg gag ctg aac cca cgc ctg cag gtg gaa cat ccc<br>Ser Phe His Phe Leu Glu Leu Asn Pro Arg Leu Gln Val Glu His Pro<br>          575                    580                    585 | 1781 |
| tgc act gaa atg atc gca gat gtc aac ctg ccc gct gca cag tta cag<br>Cys Thr Glu Met Ile Ala Asp Val Asn Leu Pro Ala Ala Gln Leu Gln<br>590                         595                    600 | 1829 |
| atc gcc atg ggc gtg ccc ctg cac cgg ctg aag gac ata cgg ctt ctg<br>Ile Ala Met Gly Val Pro Leu His Arg Leu Lys Asp Ile Arg Leu Leu<br>605                         610                    615 | 1877 |
| tac gga gag tcc ccc tgg gga gtg acc ccc gtt tct ttt gag acc cct<br>Tyr Gly Glu Ser Pro Trp Gly Val Thr Pro Val Ser Phe Glu Thr Pro<br>620                         625                    630                    635 | 1925 |
| ttg agc cct ccc att gcc cga ggc cat gtc att gca gcc agg atc acc<br>Leu Ser Pro Pro Ile Ala Arg Gly His Val Ile Ala Ala Arg Ile Thr<br>               640                    645                    650 | 1973 |
| agc gaa aac cca gac gag ggc ttt aag cca agc tca ggg aca gtg cag<br>Ser Glu Asn Pro Asp Glu Gly Phe Lys Pro Ser Ser Gly Thr Val Gln<br>          655                    660                    665 | 2021 |
| gag ctg aac ttc cgc agc aac aag aac gtg tgg ggt tac ttc agc gtg<br>Glu Leu Asn Phe Arg Ser Asn Lys Asn Val Trp Gly Tyr Phe Ser Val<br>670                         675                    680 | 2069 |
| gcc gct gct ggg ggc ttg cac gag ttt gcc gat tcc cag ttt ggg cac<br>Ala Ala Ala Gly Gly Leu His Glu Phe Ala Asp Ser Gln Phe Gly His<br>685                         690                    695 | 2117 |
| tgc ttc tcc tgg ggc gag aac cgt gaa gag gct att tcg aac atg gtg<br>Cys Phe Ser Trp Gly Glu Asn Arg Glu Glu Ala Ile Ser Asn Met Val<br>700                         705                    710                    715 | 2165 |
| gtg gct ttg aaa gaa ctg tct atc cgg ggt gac ttc cgg acc acc gtg<br>Val Ala Leu Lys Glu Leu Ser Ile Arg Gly Asp Phe Arg Thr Thr Val<br>               720                    725                    730 | 2213 |
| gaa tat ctc gtc aac ctt ctg gag acg gag agc ttc cag aac aat gat<br>Glu Tyr Leu Val Asn Leu Leu Glu Thr Glu Ser Phe Gln Asn Asn Asp<br>          735                    740                    745 | 2261 |
| atc gac acg ggg tgg ctg gac cac ctc atc gct cag cgg gtg cag gca<br>Ile Asp Thr Gly Trp Leu Asp His Leu Ile Ala Gln Arg Val Gln Ala<br>750                         755                    760 | 2309 |
| gag aag ccg gac atc atg ctc ggg gtg gtg tgt ggg gcc ttg aac gtg<br>Glu Lys Pro Asp Ile Met Leu Gly Val Val Cys Gly Ala Leu Asn Val<br>765                         770                    775 | 2357 |
| gca gac gcg atg ttc aga acc tgt atg acg gaa ttc ctg cat tcc ttg<br>Ala Asp Ala Met Phe Arg Thr Cys Met Thr Glu Phe Leu His Ser Leu<br>780                         785                    790                    795 | 2405 |
| gaa agg ggt cag gtc ctc ccg gct gat tct ctg ctg aac atc gtg gac<br>Glu Arg Gly Gln Val Leu Pro Ala Asp Ser Leu Leu Asn Ile Val Asp<br>               800                    805                    810 | 2453 |
| gtt gag ttg att tac gga ggc atc aaa tat gtt ctc aag gtg gcc cgg<br>Val Glu Leu Ile Tyr Gly Gly Ile Lys Tyr Val Leu Lys Val Ala Arg<br>          815                    820                    825 | 2501 |
| cag tcc ctg acc atg ttt gtc ctc atc atg aat ggt tgc cac atc gag<br>Gln Ser Leu Thr Met Phe Val Leu Ile Met Asn Gly Cys His Ile Glu | 2549 |

-continued

|  |  |
|---|---|
| atc gat gcc cac cgg ctg aac gat ggg ggc ctg ctc ctg tcc tac aat<br>Ile Asp Ala His Arg Leu Asn Asp Gly Gly Leu Leu Leu Ser Tyr Asn<br>845                    850                    855 | 2597 |
| ggt agc agt tac act aca tac atg aag gaa gag gtg gac agt tac cgg<br>Gly Ser Ser Tyr Thr Thr Tyr Met Lys Glu Glu Val Asp Ser Tyr Arg<br>860                    865                    870                    875 | 2645 |
| atc act atc ggc aat aag aca tgc gtg ttt gaa aag gaa aac gac ccc<br>Ile Thr Ile Gly Asn Lys Thr Cys Val Phe Glu Lys Glu Asn Asp Pro<br>                  880                    885                    890 | 2693 |
| acc gtc ctg aga tcc ccc tcg gct ggg aag ctg atg cag tac acg gtg<br>Thr Val Leu Arg Ser Pro Ser Ala Gly Lys Leu Met Gln Tyr Thr Val<br>              895                    900                    905 | 2741 |
| gag gat ggc cag cac gtg gaa gtc ggg agc agc tat gct gag atg gag<br>Glu Asp Gly Gln His Val Glu Val Gly Ser Ser Tyr Ala Glu Met Glu<br>910                    915                    920 | 2789 |
| gtg atg aag atg atc atg acc ctg aac gtg caa gag agc ggc cgg gtg<br>Val Met Lys Met Ile Met Thr Leu Asn Val Gln Glu Ser Gly Arg Val<br>925                    930                    935 | 2837 |
| aag tac atc aag cga cca ggg gcg gta ttg gag gct ggc tgc gtg gtg<br>Lys Tyr Ile Lys Arg Pro Gly Ala Val Leu Glu Ala Gly Cys Val Val<br>940                    945                    950                    955 | 2885 |
| gca aag cta gaa ctc gat gac cct tca aaa gtg cac gcg gca cag ccg<br>Ala Lys Leu Glu Leu Asp Asp Pro Ser Lys Val His Ala Ala Gln Pro<br>              960                    965                    970 | 2933 |
| ttc aca ggg gag ctc ccc gcc cag cag act ctg ccc atc ctc ggg gag<br>Phe Thr Gly Glu Leu Pro Ala Gln Gln Thr Leu Pro Ile Leu Gly Glu<br>975                    980                    985 | 2981 |
| agg ctg cat cag gtg ttc cac agc gtc ttg gaa aat ctg  acc aat gtc<br>Arg Leu His Gln Val Phe His Ser Val Leu Glu Asn Leu  Thr Asn Val<br>990                    995                    1000 | 3029 |
| atg aat ggc tac tgc ctg ccc  gag ccc ttc ttc agc  atg aag ctg<br>Met Asn Gly Tyr Cys Leu Pro  Glu Pro Phe Phe Ser  Met Lys Leu<br>1005                    1010                    1015 | 3074 |
| aag gac tgg gtg gag aag ctc  atg atg act ctc cgg  cat ccc tcc<br>Lys Asp Trp Val Glu Lys Leu  Met Met Thr Leu Arg  His Pro Ser<br>1020                    1025                    1030 | 3119 |
| cta cct ctg ctg gag ctg cag  gag atc atg acc agc  gtg gca ggc<br>Leu Pro Leu Leu Glu Leu Gln  Glu Ile Met Thr Ser  Val Ala Gly<br>1035                    1040                    1045 | 3164 |
| cgc atc ccg gtt ccg gtg gag  aag gca gtc cgc agg  gtg atg gcg<br>Arg Ile Pro Val Pro Val Glu  Lys Ala Val Arg Arg  Val Met Ala<br>1050                    1055                    1060 | 3209 |
| cag tac gcc agc aac atc act  tcg gtg ctc tgc cag  ttc ccc agc<br>Gln Tyr Ala Ser Asn Ile Thr  Ser Val Leu Cys Gln  Phe Pro Ser<br>1065                    1070                    1075 | 3254 |
| cag cag ata gcc acc atc ctg  gac tgc cac gcc gcc  acc ctg cag<br>Gln Gln Ile Ala Thr Ile Leu  Asp Cys His Ala Ala  Thr Leu Gln<br>1080                    1085                    1090 | 3299 |
| cgt aag gtg gac cga gag gcc  ttc ttc atg aac aca  cag agc atc<br>Arg Lys Val Asp Arg Glu Ala  Phe Phe Met Asn Thr  Gln Ser Ile<br>1095                    1100                    1105 | 3344 |
| gtg cag ctg atc cag aga tac  cgc agt ggg acc cgt  ggc tac atg<br>Val Gln Leu Ile Gln Arg Tyr  Arg Ser Gly Thr Arg  Gly Tyr Met<br>1110                    1115                    1120 | 3389 |
| aag gct gtg gtg cta gac ctc  ctg agg aga tat ctg  aac gtg gag<br>Lys Ala Val Val Leu Asp Leu  Leu Arg Arg Tyr Leu  Asn Val Glu<br>1125                    1130                    1135 | 3434 |
| cat cat ttc cag caa gcc cac  tat gac aag tgt gtg  atc aac ctg | 3479 |

```
His His Phe Gln Gln Ala His Tyr Asp Lys Cys Val Ile Asn Leu
    1140            1145            1150 agg gag cag ttc aag ccg gac atg act cgg gtg ctg gac tgc atc          3524
Arg Glu Gln Phe Lys Pro Asp Met Thr Arg Val Leu Asp Cys Ile
    1155            1160            1165 ttc tca cac tca caa gtg gcc aag aag aac cag ctg gtg acc atg          3569
Phe Ser His Ser Gln Val Ala Lys Lys Asn Gln Leu Val Thr Met
    1170            1175            1180 ttg ata gat gag ctg tgt ggc cca gac ccc acc ctg tca gaa gag          3614
Leu Ile Asp Glu Leu Cys Gly Pro Asp Pro Thr Leu Ser Glu Glu
    1185            1190            1195 ctg acc tcc atc ctc aag gaa ctc acg cag ttg agc agg agt gag          3659
Leu Thr Ser Ile Leu Lys Glu Leu Thr Gln Leu Ser Arg Ser Glu
    1200            1205            1210 cac tgc aag gtg gcc ctc aga gcc agg cag gtc ctg att gcc tct          3704
His Cys Lys Val Ala Leu Arg Ala Arg Gln Val Leu Ile Ala Ser
    1215            1220            1225 cac ctc ccc tcc tac gag ctg cgg cac aac cag gtg gag tcc atc          3749
His Leu Pro Ser Tyr Glu Leu Arg His Asn Gln Val Glu Ser Ile
    1230            1235            1240 ttc ctg tca gcc att gac atg tat ggc cac cag ttc tgc ccg gaa          3794
Phe Leu Ser Ala Ile Asp Met Tyr Gly His Gln Phe Cys Pro Glu
    1245            1250            1255 aac ctc aag aaa cta ata ctt tcg gaa acg acc ata ttc gat gtc          3839
Asn Leu Lys Lys Leu Ile Leu Ser Glu Thr Thr Ile Phe Asp Val
    1260            1265            1270 ctg ccc act ttc ttc tat cac gct aac aag gtc gtc tgt atg gcg          3884
Leu Pro Thr Phe Phe Tyr His Ala Asn Lys Val Val Cys Met Ala
    1275            1280            1285 tcc ctg gag gtt tat gtg agg aga ggt tac atc gcc tac gag tta          3929
Ser Leu Glu Val Tyr Val Arg Arg Gly Tyr Ile Ala Tyr Glu Leu
    1290            1295            1300 aac agc cta cag cac cgg gag ctc cct gac ggc acc tgc gtg gtg          3974
Asn Ser Leu Gln His Arg Glu Leu Pro Asp Gly Thr Cys Val Val
    1305            1310            1315 gag ttc cag ttc atg ctg ccg tct tcc cac ccc aac cgg atg gcc          4019
Glu Phe Gln Phe Met Leu Pro Ser Ser His Pro Asn Arg Met Ala
    1320            1325            1330 atg ccc atc aat gtc tct gac cct gac ctg ctg aga cac agt aag          4064
Met Pro Ile Asn Val Ser Asp Pro Asp Leu Leu Arg His Ser Lys
    1335            1340            1345 gaa ctc ttc atg gac agt ggc ttc tcc cca ctg tgc cag cgg atg          4109
Glu Leu Phe Met Asp Ser Gly Phe Ser Pro Leu Cys Gln Arg Met
    1350            1355            1360 ggg gcc atg gtg gcc ttc agg aga ttt gag gag ttc acc agg aac          4154
Gly Ala Met Val Ala Phe Arg Arg Phe Glu Glu Phe Thr Arg Asn
    1365            1370            1375 ttc gat gaa gtc atc tcc tgc ttt gcc aac gtg cct aca gac act          4199
Phe Asp Glu Val Ile Ser Cys Phe Ala Asn Val Pro Thr Asp Thr
    1380            1385            1390 cct ctc ttc agt aag gcg tgc act tcc ctc tac tca gag gag gac          4244
Pro Leu Phe Ser Lys Ala Cys Thr Ser Leu Tyr Ser Glu Glu Asp
    1395            1400            1405 agc aag agc ctt caa gag gag ccc atc cac atc ctg aat gtg gcc          4289
Ser Lys Ser Leu Gln Glu Glu Pro Ile His Ile Leu Asn Val Ala
    1410            1415            1420 atc cag tgc gcc gac cac atg gag gac gag aga ctg gtg ccg gtt          4334
Ile Gln Cys Ala Asp His Met Glu Asp Glu Arg Leu Val Pro Val
    1425            1430            1435
```

```
ttc cgt gcc ttt gta cag tcc aag aaa cac atc ctt gtg gat tac       4379
Phe Arg Ala Phe Val Gln Ser Lys Lys His Ile Leu Val Asp Tyr
    1440            1445                1450 gga ctg cga aga atc aca ttc ctt atc gcc caa gag aga gaa ttt       4424
Gly Leu Arg Arg Ile Thr Phe Leu Ile Ala Gln Glu Arg Glu Phe
1455            1460                1465 ccc aag ttc ttc acg ttc aga gcg aga gat gag ttt gca gaa gac       4469
Pro Lys Phe Phe Thr Phe Arg Ala Arg Asp Glu Phe Ala Glu Asp
1470            1475                1480 cgg att tac cgc cac ttg gag ccg gcc ctg gcc ttc cag ctg gag       4514
Arg Ile Tyr Arg His Leu Glu Pro Ala Leu Ala Phe Gln Leu Glu
        1485            1490                1495 ctg agc cgg atg cgc aac ttt gac ctg acg gcc gtg ccc tgt gcc       4559
Leu Ser Arg Met Arg Asn Phe Asp Leu Thr Ala Val Pro Cys Ala
1500            1505                1510 aac cat aag atg cat ctt tac ctg gga gcc gcc aag gtg aag gaa       4604
Asn His Lys Met His Leu Tyr Leu Gly Ala Ala Lys Val Lys Glu
    1515            1520                1525 ggg ctg gag gtg act gac cac agg ttc ttc atc cga gcc atc ata       4649
Gly Leu Glu Val Thr Asp His Arg Phe Phe Ile Arg Ala Ile Ile
1530            1535                1540 agg cac tca gac ctg atc acc aag gaa gcc tcc ttc gag tac ctg       4694
Arg His Ser Asp Leu Ile Thr Lys Glu Ala Ser Phe Glu Tyr Leu
    1545            1550                1555 cag aat gaa ggg gag cgg ctg ctg ctg gaa gcc atg gat gag ctg       4739
Gln Asn Glu Gly Glu Arg Leu Leu Leu Glu Ala Met Asp Glu Leu
1560            1565                1570 gag gtg gcg ttc aac aac acc agc gtg cgc act gac tgc aac cac       4784
Glu Val Ala Phe Asn Asn Thr Ser Val Arg Thr Asp Cys Asn His
    1575            1580                1585 atc ttc ctc aac ttc gtg ccc acg gtc atc atg gac cca ctc aag       4829
Ile Phe Leu Asn Phe Val Pro Thr Val Ile Met Asp Pro Leu Lys
1590            1595                1600 atc gag gag tcg gtg cgt gcc atg gtc atg cgt tac ggc agt cgg       4874
Ile Glu Glu Ser Val Arg Ala Met Val Met Arg Tyr Gly Ser Arg
        1605            1610                1615 ctg tgg aag ctc cgt gtg ctg cag gca gaa gtt aag atc aac atc       4919
Leu Trp Lys Leu Arg Val Leu Gln Ala Glu Val Lys Ile Asn Ile
1620            1625                1630 cgt cag acg acc tcg gac tgc gcc gtc ccc att cgc ctc ttc atc       4964
Arg Gln Thr Thr Ser Asp Cys Ala Val Pro Ile Arg Leu Phe Ile
    1635            1640                1645 acc aac gag tcc ggc tac tac ctg gac atc agc ctc tac aaa gaa       5009
Thr Asn Glu Ser Gly Tyr Tyr Leu Asp Ile Ser Leu Tyr Lys Glu
1650            1655                1660 gtg acc gac tcc aga tcc gga aac atc atg ttt cat tcc ttc ggc       5054
Val Thr Asp Ser Arg Ser Gly Asn Ile Met Phe His Ser Phe Gly
    1665            1670                1675 aac aaa caa ggg agc ctg cac ggg atg ctg atc aac acg ccc tac       5099
Asn Lys Gln Gly Ser Leu His Gly Met Leu Ile Asn Thr Pro Tyr
1680            1685                1690 gtc acc aag gat ctg ctc caa gcc aag cga ttc cag gcg cag tcc       5144
Val Thr Lys Asp Leu Leu Gln Ala Lys Arg Phe Gln Ala Gln Ser
        1695            1700                1705 ctg ggg acc acc tat gtg tac gac ttc cca gag atg ttc agg cag       5189
Leu Gly Thr Thr Tyr Val Tyr Asp Phe Pro Glu Met Phe Arg Gln
1710            1715                1720 gct ctc ttt aaa ttg tgg ggc tcc cca gag aag tac ccc aaa gat       5234
Ala Leu Phe Lys Leu Trp Gly Ser Pro Glu Lys Tyr Pro Lys Asp
    1725            1730                1735
```

```
atc ctg aca tac aca gag ctg gtg ttg gac tcc cag ggc cag ctg        5279
Ile Leu Thr Tyr Thr Glu Leu Val Leu Asp Ser Gln Gly Gln Leu
    1740            1745                1750 gtg gag atg aac cgg ctt cct ggt tgt aac gag gtg ggc atg gtg        5324
Val Glu Met Asn Arg Leu Pro Gly Cys Asn Glu Val Gly Met Val
1755            1760                1765 gtt ttc aaa atg agg ttc aag acc ccg gag tat cca gaa ggc cgg        5369
Val Phe Lys Met Arg Phe Lys Thr Pro Glu Tyr Pro Glu Gly Arg
    1770            1775                1780 gac act atc gtc atc ggc aac gac att acc ttc caa atc ggc tct        5414
Asp Thr Ile Val Ile Gly Asn Asp Ile Thr Phe Gln Ile Gly Ser
    1785            1790                1795 ttc ggc ata gga gag gac ttc ctg tat cta cgg gca tcg gag atg        5459
Phe Gly Ile Gly Glu Asp Phe Leu Tyr Leu Arg Ala Ser Glu Met
    1800            1805                1810 gcc cgg aca gag ggc atc ccc caa atc tat ctg gca gcc aac agc        5504
Ala Arg Thr Glu Gly Ile Pro Gln Ile Tyr Leu Ala Ala Asn Ser
    1815            1820                1825 ggg gcc cgt atg ggc ctg tcc gag gag atc aag cag ata ttc caa        5549
Gly Ala Arg Met Gly Leu Ser Glu Glu Ile Lys Gln Ile Phe Gln
    1830            1835                1840 gtg gca tgg gtg gac cct gag gat ccc tac aaa gga ttt aga tac        5594
Val Ala Trp Val Asp Pro Glu Asp Pro Tyr Lys Gly Phe Arg Tyr
    1845            1850                1855 ctg tac ctg acg ccc caa gac tac acc cag atc agc tcc cag aac        5639
Leu Tyr Leu Thr Pro Gln Asp Tyr Thr Gln Ile Ser Ser Gln Asn
    1860            1865                1870 tcc gtg cac tgc aaa cac atc gag gac gaa ggc gag tcc agg tat        5684
Ser Val His Cys Lys His Ile Glu Asp Glu Gly Glu Ser Arg Tyr
    1875            1880                1885 gtc atc gtt gat gtc atc ggg aag gac agc agc ctg ggt gtg gag        5729
Val Ile Val Asp Val Ile Gly Lys Asp Ser Ser Leu Gly Val Glu
    1890            1895                1900 aac ctg cgg ggc tcg ggc atg att gca gga gag gct tct ctg gct        5774
Asn Leu Arg Gly Ser Gly Met Ile Ala Gly Glu Ala Ser Leu Ala
    1905            1910                1915 tac gaa aaa aat gtc acc atc agc atg gtg acc tgc cgc gcc atc        5819
Tyr Glu Lys Asn Val Thr Ile Ser Met Val Thr Cys Arg Ala Ile
    1920            1925                1930 gga atc ggg gct tac ctg gtg agg ctg ggc cag cgg gtg atc cag        5864
Gly Ile Gly Ala Tyr Leu Val Arg Leu Gly Gln Arg Val Ile Gln
    1935            1940                1945 gtg gaa aac tcc cac atc atc ctc acg gga gcc ggt gct ctc aac        5909
Val Glu Asn Ser His Ile Ile Leu Thr Gly Ala Gly Ala Leu Asn
    1950            1955                1960 aag gtc ctg gga aga gag gtc tac aca tcc aac aac caa ctg ggc        5954
Lys Val Leu Gly Arg Glu Val Tyr Thr Ser Asn Asn Gln Leu Gly
    1965            1970                1975 ggt gtg cag atc atg cac acc aac ggg gtc tcc cac gtc acg gtg        5999
Gly Val Gln Ile Met His Thr Asn Gly Val Ser His Val Thr Val
    1980            1985                1990 cca gat gac ttc gag ggg gtc tgc acc att ctg gaa tgg ctg tca        6044
Pro Asp Asp Phe Glu Gly Val Cys Thr Ile Leu Glu Trp Leu Ser
    1995            2000                2005 tat ata cca aag gac aat caa agc cca gtc ccc atc atc act cct        6089
Tyr Ile Pro Lys Asp Asn Gln Ser Pro Val Pro Ile Ile Thr Pro
    2010            2015                2020 tct gac ccc atc gac agg gaa att gaa ttc acc cca acc aaa gct        6134
Ser Asp Pro Ile Asp Arg Glu Ile Glu Phe Thr Pro Thr Lys Ala
```

-continued

| | | |
|---|---|---|
| ccc tat gac ccc agg tgg ctg ctt gca ggg agg cct cac cca act<br>Pro Tyr Asp Pro Arg Trp Leu Leu Ala Gly Arg Pro His Pro Thr<br>2040                        2045                        2050 | 6179 |
| ctg aag ggg acc tgg cag agt gga ttc ttc gac cat ggc agt ttc<br>Leu Lys Gly Thr Trp Gln Ser Gly Phe Phe Asp His Gly Ser Phe<br>2055                        2060                        2065 | 6224 |
| aag gaa atc atg gca ccc tgg gcc cag acc gtg gtg act gga cga<br>Lys Glu Ile Met Ala Pro Trp Ala Gln Thr Val Val Thr Gly Arg<br>2070                        2075                        2080 | 6269 |
| gca agg ctg ggg ggc atc cct gta ggg gtg att gcc gtg gag act<br>Ala Arg Leu Gly Gly Ile Pro Val Gly Val Ile Ala Val Glu Thr<br>2085                        2090                        2095 | 6314 |
| cgg tct gtg gag gtg gct gtc cct gct gac cct gcc aac ttg gat<br>Arg Ser Val Glu Val Ala Val Pro Ala Asp Pro Ala Asn Leu Asp<br>2100                        2105                        2110 | 6359 |
| tct gag gcc aag atc atc cag cag gca ggc cag gtg tgg ttc ccg<br>Ser Glu Ala Lys Ile Ile Gln Gln Ala Gly Gln Val Trp Phe Pro<br>2115                        2120                        2125 | 6404 |
| gac tct gcc ttc aag acg gct cag gtc atc agg gac ttc aac cag<br>Asp Ser Ala Phe Lys Thr Ala Gln Val Ile Arg Asp Phe Asn Gln<br>2130                        2135                        2140 | 6449 |
| gag cat ctg cct ctc atg atc ttt gcc aac tgg aga ggc ttc tcg<br>Glu His Leu Pro Leu Met Ile Phe Ala Asn Trp Arg Gly Phe Ser<br>2145                        2150                        2155 | 6494 |
| ggt ggc atg aaa gac atg tac gag cag atg ctg aag ttt ggc gcc<br>Gly Gly Met Lys Asp Met Tyr Glu Gln Met Leu Lys Phe Gly Ala<br>2160                        2165                        2170 | 6539 |
| tac atc gtg gac agt ctc cgt ctg ttc aag cag cca gtt ctc atc<br>Tyr Ile Val Asp Ser Leu Arg Leu Phe Lys Gln Pro Val Leu Ile<br>2175                        2180                        2185 | 6584 |
| tat atc cct cct ggt gcc gaa ctc cga ggg ggc gcc tgg gtt gtc<br>Tyr Ile Pro Pro Gly Ala Glu Leu Arg Gly Gly Ala Trp Val Val<br>2190                        2195                        2200 | 6629 |
| ctc gac tcc agc atc aac ccc ctg tgc ata gag atg tac gca gac<br>Leu Asp Ser Ser Ile Asn Pro Leu Cys Ile Glu Met Tyr Ala Asp<br>2205                        2210                        2215 | 6674 |
| aaa gag agc agg ggg ggt gtc ctg gag ccc gag ggc act gtg gag<br>Lys Glu Ser Arg Gly Gly Val Leu Glu Pro Glu Gly Thr Val Glu<br>2220                        2225                        2230 | 6719 |
| att aag ttc cgg aag aaa gat ttg gtg aag acc ata agg agg att<br>Ile Lys Phe Arg Lys Lys Asp Leu Val Lys Thr Ile Arg Arg Ile<br>2235                        2240                        2245 | 6764 |
| gac cca gtg tgc aag aaa ctc ctg ggg cag ctg ggg aca gcc cag<br>Asp Pro Val Cys Lys Lys Leu Leu Gly Gln Leu Gly Thr Ala Gln<br>2250                        2255                        2260 | 6809 |
| ctc cct gac aag gac cgg aaa gag ctg gag agc cag ctg aag gcc<br>Leu Pro Asp Lys Asp Arg Lys Glu Leu Glu Ser Gln Leu Lys Ala<br>2265                        2270                        2275 | 6854 |
| cgg gag gac ctg ctc ctc ccc atc tac cac cag gtg gca gtg cag<br>Arg Glu Asp Leu Leu Leu Pro Ile Tyr His Gln Val Ala Val Gln<br>2280                        2285                        2290 | 6899 |
| ttc gcc gac ctg cat gac acg ccg ggc cac atg ctg gag aag gga<br>Phe Ala Asp Leu His Asp Thr Pro Gly His Met Leu Glu Lys Gly<br>2295                        2300                        2305 | 6944 |
| atc att tct gat gtg ctg gag tgg aag acc aca cgt acc tac ttc<br>Ile Ile Ser Asp Val Leu Glu Trp Lys Thr Thr Arg Thr Tyr Phe<br>2310                        2315                        2320 | 6989 |
| tac tgg agg ctg cgc cgg ctg ctg ctg gag gca cag gtg aag cag | 7034 |

-continued

| | | | | | | | | | | | | | | |
|---|---|---|---|---|---|---|---|---|---|---|---|---|---|---|
|Tyr|Trp|Arg|Leu|Arg|Arg|Leu|Leu|Leu|Glu|Ala|Gln|Val|Lys|Gln|
|2325| | | |2330| | | | |2335| | | | | |

```
gag att ctg cga gcc agc cct gag ctg agc cat gag cac acg cag      7079
Glu Ile Leu Arg Ala Ser Pro Glu Leu Ser His Glu His Thr Gln
    2340            2345            2350 tcc atg ctg cga cgc tgg ttt gtg gag acc gag ggc gcc gtc aag      7124
Ser Met Leu Arg Arg Trp Phe Val Glu Thr Glu Gly Ala Val Lys
    2355            2360            2365 gcc tac ctg tgg gac agc aac cag gtg gta gtc cag tgg ctg gaa      7169
Ala Tyr Leu Trp Asp Ser Asn Gln Val Val Val Gln Trp Leu Glu
    2370            2375            2380 cag cac tgg tca gcc agg gac aac ctg cgt tcc act atc cga gag      7214
Gln His Trp Ser Ala Arg Asp Asn Leu Arg Ser Thr Ile Arg Glu
    2385            2390            2395 aac atc aat tat ctg aag cgg gac tct gtc ctc aag acc atc caa      7259
Asn Ile Asn Tyr Leu Lys Arg Asp Ser Val Leu Lys Thr Ile Gln
    2400            2405            2410 agc cta gtt caa gaa cac cca gag gcg acc atg gac tgt gtg gca      7304
Ser Leu Val Gln Glu His Pro Glu Ala Thr Met Asp Cys Val Ala
    2415            2420            2425 tac ctg agc cag cac ctc acg ccc gct gag cag atg cag gtg gtt      7349
Tyr Leu Ser Gln His Leu Thr Pro Ala Glu Gln Met Gln Val Val
    2430            2435            2440 cag ctg ctg tct acc acg gag agc cca gct tcc cac tga              7388
Gln Leu Leu Ser Thr Thr Glu Ser Pro Ala Ser His
    2445            2450            2455
```

<210> SEQ ID NO 16
<211> LENGTH: 2455
<212> TYPE: PRT
<213> ORGANISM: Rattus norvegicus

<400> SEQUENCE: 16

```
Met Val Leu Leu Leu Phe Leu Thr Cys Leu Val Phe Ser Cys Leu Thr
1               5                   10                  15

Ile Ser Trp Leu Lys Ile Trp Gly Lys Met Thr Asp Ser Lys Pro Leu
            20                  25                  30

Ser Asn Ser Lys Val Asp Ala Ser Leu Leu Ser Ser Lys Glu Glu Ser
        35                  40                  45

Phe Ser Ala Ser Asp Gln Ser Glu Glu His Gly Asp Cys Ser Cys Pro
    50                  55                  60

Leu Thr Thr Pro Asp Gln Glu Glu Leu Ala Ser His Gly Gly Pro Val
65                  70                  75                  80

Asp Ala Ser Gln Gln Arg Asn Ser Val Pro Ser Ser His Gln Lys Pro
                85                  90                  95

Pro Arg Asn Pro Leu Ser Ser Asn Asp Thr Cys Ser Ser Pro Glu Leu
            100                 105                 110

Gln Thr Asn Gly Val Ala Ala Pro Gly Ser Glu Val Pro Glu Ala Asn
        115                 120                 125

Gly Leu Pro Phe Pro Ala Arg Pro Gln Thr Gln Arg Thr Gly Ser Pro
    130                 135                 140

Thr Arg Glu Asp Lys Lys Gln Ala His Ile Lys Arg Gln Leu Met Thr
145                 150                 155                 160

Ser Phe Ile Leu Gly Ser Leu Asp Asp Asn Ser Ser Asp Glu Asp Pro
                165                 170                 175

Ser Ala Ser Ser Phe Gln Thr Ser Ser Arg Lys Gly Ser Arg Ala Ser
            180                 185                 190
```

```
Leu Gly Thr Leu Ser Gln Glu Ala Ala Leu Asn Thr Ala Asp Pro Glu
        195                 200                 205

Ser His Thr Pro Thr Met Arg Pro Ser Met Ser Gly Leu His Leu Val
    210                 215                 220

Lys Arg Gly Arg Glu His Lys Lys Leu Asp Leu His Arg Asp Phe Thr
225                 230                 235                 240

Val Ala Ser Pro Ala Glu Phe Val Thr Arg Phe Gly Gly Asn Arg Val
                245                 250                 255

Ile Glu Thr Val Leu Ile Ala Asn Asn Gly Ile Ala Ala Val Lys Cys
            260                 265                 270

Met Arg Ser Ile Arg Arg Trp Ala Tyr Glu Met Phe Arg Asn Glu Arg
    275                 280                 285

Ala Ile Arg Phe Val Val Met Val Thr Pro Glu Asp Leu Lys Ala Asn
290                 295                 300

Ala Glu Tyr Ile Lys Met Ala Asp Gln Tyr Val Pro Val Pro Gly Gly
305                 310                 315                 320

Pro Asn Asn Asn Tyr Ala Asn Val Glu Leu Ile Ile Asp Ile Ala
                325                 330                 335

Lys Arg Ile Pro Val Gln Ala Val Trp Ala Gly Trp Gly His Ala Ser
            340                 345                 350

Glu Asn Pro Lys Leu Pro Glu Leu Leu Cys Lys His Glu Ile Ala Phe
    355                 360                 365

Leu Gly Pro Pro Ser Glu Ala Met Trp Ala Leu Gly Asp Lys Ile Ser
    370                 375                 380

Ser Thr Ile Val Ala Gln Thr Leu Gln Ile Pro Thr Leu Pro Trp Ser
385                 390                 395                 400

Gly Ser Gly Leu Thr Val Glu Trp Thr Glu Asp Ser Gln His Gln Gly
                405                 410                 415

Lys Cys Ile Ser Val Pro Glu Asp Val Tyr Glu Gln Gly Cys Val Arg
            420                 425                 430

Asp Val Asp Glu Gly Leu Gln Ala Ala Glu Lys Val Gly Phe Pro Leu
        435                 440                 445

Met Ile Lys Ala Ser Glu Gly Gly Gly Gly Lys Gly Ile Arg Arg Ala
    450                 455                 460

Glu Ser Ala Glu Asp Phe Pro Met Leu Phe Arg Gln Val Gln Ser Glu
465                 470                 475                 480

Ile Pro Gly Ser Pro Ile Phe Leu Met Lys Leu Ala Gln Asn Ala Arg
                485                 490                 495

His Leu Glu Val Gln Val Leu Ala Asp Gln Tyr Gly Asn Ala Val Ser
            500                 505                 510

Leu Phe Gly Arg Asp Cys Ser Ile Gln Arg Arg His Gln Lys Ile Ile
    515                 520                 525

Glu Glu Ala Pro Ala Thr Ile Ala Ala Pro Ala Val Phe Glu Phe Met
530                 535                 540

Glu Gln Cys Ala Val Leu Leu Ala Lys Thr Val Gly Tyr Val Ser Ala
545                 550                 555                 560

Gly Thr Val Glu Tyr Leu Tyr Ser Gln Asp Gly Ser Phe His Phe Leu
                565                 570                 575

Glu Leu Asn Pro Arg Leu Gln Val Glu His Pro Cys Thr Glu Met Ile
            580                 585                 590

Ala Asp Val Asn Leu Pro Ala Ala Gln Leu Gln Ile Ala Met Gly Val
    595                 600                 605

Pro Leu His Arg Leu Lys Asp Ile Arg Leu Leu Tyr Gly Glu Ser Pro
```

-continued

```
            610                 615                 620
Trp Gly Val Thr Pro Val Ser Phe Glu Thr Pro Leu Ser Pro Pro Ile
625                 630                 635                 640

Ala Arg Gly His Val Ile Ala Ala Arg Ile Thr Ser Glu Asn Pro Asp
                645                 650                 655

Glu Gly Phe Lys Pro Ser Ser Gly Thr Val Gln Glu Leu Asn Phe Arg
                660                 665                 670

Ser Asn Lys Asn Val Trp Gly Tyr Phe Ser Val Ala Ala Ala Gly Gly
                675                 680                 685

Leu His Glu Phe Ala Asp Ser Gln Phe Gly His Cys Phe Ser Trp Gly
            690                 695                 700

Glu Asn Arg Glu Glu Ala Ile Ser Asn Met Val Val Ala Leu Lys Glu
705                 710                 715                 720

Leu Ser Ile Arg Gly Asp Phe Arg Thr Thr Val Glu Tyr Leu Val Asn
                725                 730                 735

Leu Leu Glu Thr Glu Ser Phe Gln Asn Asn Asp Ile Asp Thr Gly Trp
                740                 745                 750

Leu Asp His Leu Ile Ala Gln Arg Val Gln Ala Glu Lys Pro Asp Ile
            755                 760                 765

Met Leu Gly Val Val Cys Gly Ala Leu Asn Val Ala Asp Ala Met Phe
770                 775                 780

Arg Thr Cys Met Thr Glu Phe Leu His Ser Leu Glu Arg Gly Gln Val
785                 790                 795                 800

Leu Pro Ala Asp Ser Leu Leu Asn Ile Val Asp Val Glu Leu Ile Tyr
                805                 810                 815

Gly Gly Ile Lys Tyr Val Leu Lys Val Ala Arg Gln Ser Leu Thr Met
                820                 825                 830

Phe Val Leu Ile Met Asn Gly Cys His Ile Glu Ile Asp Ala His Arg
            835                 840                 845

Leu Asn Asp Gly Gly Leu Leu Ser Tyr Asn Gly Ser Ser Tyr Thr
            850                 855                 860

Thr Tyr Met Lys Glu Glu Val Asp Ser Tyr Arg Ile Thr Ile Gly Asn
865                 870                 875                 880

Lys Thr Cys Val Phe Glu Lys Glu Asn Asp Pro Thr Val Leu Arg Ser
                885                 890                 895

Pro Ser Ala Gly Lys Leu Met Gln Tyr Thr Val Glu Asp Gly Gln His
                900                 905                 910

Val Glu Val Gly Ser Ser Tyr Ala Glu Met Glu Val Met Lys Met Ile
            915                 920                 925

Met Thr Leu Asn Val Gln Glu Ser Gly Arg Val Lys Tyr Ile Lys Arg
930                 935                 940

Pro Gly Ala Val Leu Glu Ala Gly Cys Val Val Ala Lys Leu Glu Leu
945                 950                 955                 960

Asp Asp Pro Ser Lys Val His Ala Ala Gln Pro Phe Thr Gly Glu Leu
                965                 970                 975

Pro Ala Gln Gln Thr Leu Pro Ile Leu Gly Glu Arg Leu His Gln Val
                980                 985                 990

Phe His Ser Val Leu Glu Asn Leu  Thr Asn Val Met Asn  Gly Tyr Cys
            995                 1000                1005

Leu Pro  Glu Pro Phe Phe Ser  Met Lys Leu Lys Asp  Trp Val Glu
        1010                 1015                1020

Lys Leu  Met Met Thr Leu Arg  His Pro Ser Leu Pro  Leu Leu Glu
        1025                 1030                1035
```

-continued

Leu Gln Glu Ile Met Thr Ser Val Ala Gly Arg Ile Pro Val Pro
1040            1045                1050

Val Glu Lys Ala Val Arg Arg Val Met Ala Gln Tyr Ala Ser Asn
1055            1060                1065

Ile Thr Ser Val Leu Cys Gln Phe Pro Ser Gln Gln Ile Ala Thr
1070            1075                1080

Ile Leu Asp Cys His Ala Ala Thr Leu Gln Arg Lys Val Asp Arg
1085            1090                1095

Glu Ala Phe Phe Met Asn Thr Gln Ser Ile Val Gln Leu Ile Gln
1100            1105                1110

Arg Tyr Arg Ser Gly Thr Arg Gly Tyr Met Lys Ala Val Val Leu
1115            1120                1125

Asp Leu Leu Arg Arg Tyr Leu Asn Val Glu His His Phe Gln Gln
1130            1135                1140

Ala His Tyr Asp Lys Cys Val Ile Asn Leu Arg Glu Gln Phe Lys
1145            1150                1155

Pro Asp Met Thr Arg Val Leu Asp Cys Ile Phe Ser His Ser Gln
1160            1165                1170

Val Ala Lys Lys Asn Gln Leu Val Thr Met Leu Ile Asp Glu Leu
1175            1180                1185

Cys Gly Pro Asp Pro Thr Leu Ser Glu Glu Leu Thr Ser Ile Leu
1190            1195                1200

Lys Glu Leu Thr Gln Leu Ser Arg Ser Glu His Cys Lys Val Ala
1205            1210                1215

Leu Arg Ala Arg Gln Val Leu Ile Ala Ser His Leu Pro Ser Tyr
1220            1225                1230

Glu Leu Arg His Asn Gln Val Glu Ser Ile Phe Leu Ser Ala Ile
1235            1240                1245

Asp Met Tyr Gly His Gln Phe Cys Pro Glu Asn Leu Lys Lys Leu
1250            1255                1260

Ile Leu Ser Glu Thr Thr Ile Phe Asp Val Leu Pro Thr Phe Phe
1265            1270                1275

Tyr His Ala Asn Lys Val Val Cys Met Ala Ser Leu Glu Val Tyr
1280            1285                1290

Val Arg Arg Gly Tyr Ile Ala Tyr Glu Leu Asn Ser Leu Gln His
1295            1300                1305

Arg Glu Leu Pro Asp Gly Thr Cys Val Val Glu Phe Gln Phe Met
1310            1315                1320

Leu Pro Ser Ser His Pro Asn Arg Met Ala Met Pro Ile Asn Val
1325            1330                1335

Ser Asp Pro Asp Leu Leu Arg His Ser Lys Glu Leu Phe Met Asp
1340            1345                1350

Ser Gly Phe Ser Pro Leu Cys Gln Arg Met Gly Ala Met Val Ala
1355            1360                1365

Phe Arg Arg Phe Glu Glu Phe Thr Arg Asn Phe Asp Glu Val Ile
1370            1375                1380

Ser Cys Phe Ala Asn Val Pro Thr Asp Thr Pro Leu Phe Ser Lys
1385            1390                1395

Ala Cys Thr Ser Leu Tyr Ser Glu Glu Asp Ser Lys Ser Leu Gln
1400            1405                1410

Glu Glu Pro Ile His Ile Leu Asn Val Ala Ile Gln Cys Ala Asp
1415            1420                1425

-continued

```
His Met Glu Asp Glu Arg Leu Val Pro Val Phe Arg Ala Phe Val
    1430                1435                1440

Gln Ser Lys Lys His Ile Leu Val Asp Tyr Gly Leu Arg Arg Ile
    1445                1450                1455

Thr Phe Leu Ile Ala Gln Arg Glu Phe Pro Lys Phe Phe Thr
    1460                1465                1470

Phe Arg Ala Arg Asp Glu Phe Ala Glu Asp Arg Ile Tyr Arg His
    1475                1480                1485

Leu Glu Pro Ala Leu Ala Phe Gln Leu Glu Leu Ser Arg Met Arg
    1490                1495                1500

Asn Phe Asp Leu Thr Ala Val Pro Cys Ala Asn His Lys Met His
    1505                1510                1515

Leu Tyr Leu Gly Ala Ala Lys Val Lys Glu Gly Leu Glu Val Thr
    1520                1525                1530

Asp His Arg Phe Phe Ile Arg Ala Ile Ile Arg His Ser Asp Leu
    1535                1540                1545

Ile Thr Lys Glu Ala Ser Phe Glu Tyr Leu Gln Asn Glu Gly Glu
    1550                1555                1560

Arg Leu Leu Leu Glu Ala Met Asp Glu Leu Glu Val Ala Phe Asn
    1565                1570                1575

Asn Thr Ser Val Arg Thr Asp Cys Asn His Ile Phe Leu Asn Phe
    1580                1585                1590

Val Pro Thr Val Ile Met Asp Pro Leu Lys Ile Glu Glu Ser Val
    1595                1600                1605

Arg Ala Met Val Met Arg Tyr Gly Ser Arg Leu Trp Lys Leu Arg
    1610                1615                1620

Val Leu Gln Ala Glu Val Lys Ile Asn Ile Arg Gln Thr Thr Ser
    1625                1630                1635

Asp Cys Ala Val Pro Ile Arg Leu Phe Ile Thr Asn Glu Ser Gly
    1640                1645                1650

Tyr Tyr Leu Asp Ile Ser Leu Tyr Lys Glu Val Thr Asp Ser Arg
    1655                1660                1665

Ser Gly Asn Ile Met Phe His Ser Phe Gly Asn Lys Gln Gly Ser
    1670                1675                1680

Leu His Gly Met Leu Ile Asn Thr Pro Tyr Val Thr Lys Asp Leu
    1685                1690                1695

Leu Gln Ala Lys Arg Phe Gln Ala Gln Ser Leu Gly Thr Thr Tyr
    1700                1705                1710

Val Tyr Asp Phe Pro Glu Met Phe Arg Gln Ala Leu Phe Lys Leu
    1715                1720                1725

Trp Gly Ser Pro Glu Lys Tyr Pro Lys Asp Ile Leu Thr Tyr Thr
    1730                1735                1740

Glu Leu Val Leu Asp Ser Gln Gly Gln Leu Val Glu Met Asn Arg
    1745                1750                1755

Leu Pro Gly Cys Asn Glu Val Gly Met Val Val Phe Lys Met Arg
    1760                1765                1770

Phe Lys Thr Pro Glu Tyr Pro Glu Gly Arg Asp Thr Ile Val Ile
    1775                1780                1785

Gly Asn Asp Ile Thr Phe Gln Ile Gly Ser Phe Gly Ile Gly Glu
    1790                1795                1800

Asp Phe Leu Tyr Leu Arg Ala Ser Glu Met Ala Arg Thr Glu Gly
    1805                1810                1815

Ile Pro Gln Ile Tyr Leu Ala Ala Asn Ser Gly Ala Arg Met Gly
```

-continued

```
                1820                1825                1830

Leu Ser Glu Glu Ile Lys Gln Ile Phe Gln Val Ala Trp Val Asp
    1835                1840                1845

Pro Glu Asp Pro Tyr Lys Gly Phe Arg Tyr Leu Tyr Leu Thr Pro
    1850                1855                1860

Gln Asp Tyr Thr Gln Ile Ser Ser Gln Asn Ser Val His Cys Lys
    1865                1870                1875

His Ile Glu Asp Glu Gly Glu Ser Arg Tyr Val Ile Val Asp Val
    1880                1885                1890

Ile Gly Lys Asp Ser Ser Leu Gly Val Glu Asn Leu Arg Gly Ser
    1895                1900                1905

Gly Met Ile Ala Gly Glu Ala Ser Leu Ala Tyr Glu Lys Asn Val
    1910                1915                1920

Thr Ile Ser Met Val Thr Cys Arg Ala Ile Gly Ile Gly Ala Tyr
    1925                1930                1935

Leu Val Arg Leu Gly Gln Arg Val Ile Gln Val Glu Asn Ser His
    1940                1945                1950

Ile Ile Leu Thr Gly Ala Gly Ala Leu Asn Lys Val Leu Gly Arg
    1955                1960                1965

Glu Val Tyr Thr Ser Asn Asn Gln Leu Gly Gly Val Gln Ile Met
    1970                1975                1980

His Thr Asn Gly Val Ser His Val Thr Val Pro Asp Asp Phe Glu
    1985                1990                1995

Gly Val Cys Thr Ile Leu Glu Trp Leu Ser Tyr Ile Pro Lys Asp
    2000                2005                2010

Asn Gln Ser Pro Val Pro Ile Ile Thr Pro Ser Asp Pro Ile Asp
    2015                2020                2025

Arg Glu Ile Glu Phe Thr Pro Thr Lys Ala Pro Tyr Asp Pro Arg
    2030                2035                2040

Trp Leu Leu Ala Gly Arg Pro His Pro Thr Leu Lys Gly Thr Trp
    2045                2050                2055

Gln Ser Gly Phe Phe Asp His Gly Ser Phe Lys Glu Ile Met Ala
    2060                2065                2070

Pro Trp Ala Gln Thr Val Val Thr Gly Arg Ala Arg Leu Gly Gly
    2075                2080                2085

Ile Pro Val Gly Val Ile Ala Val Glu Thr Arg Ser Val Glu Val
    2090                2095                2100

Ala Val Pro Ala Asp Pro Ala Asn Leu Asp Ser Glu Ala Lys Ile
    2105                2110                2115

Ile Gln Gln Ala Gly Gln Val Trp Phe Pro Asp Ser Ala Phe Lys
    2120                2125                2130

Thr Ala Gln Val Ile Arg Asp Phe Asn Gln Glu His Leu Pro Leu
    2135                2140                2145

Met Ile Phe Ala Asn Trp Arg Gly Phe Ser Gly Gly Met Lys Asp
    2150                2155                2160

Met Tyr Glu Gln Met Leu Lys Phe Gly Ala Tyr Ile Val Asp Ser
    2165                2170                2175

Leu Arg Leu Phe Lys Gln Pro Val Leu Ile Tyr Ile Pro Pro Gly
    2180                2185                2190

Ala Glu Leu Arg Gly Gly Ala Trp Val Val Leu Asp Ser Ser Ile
    2195                2200                2205

Asn Pro Leu Cys Ile Glu Met Tyr Ala Asp Lys Glu Ser Arg Gly
    2210                2215                2220
```

| | | | | | | | | | | |
|---|---|---|---|---|---|---|---|---|---|---|
| Gly | Val | Leu | Glu | Pro | Glu | Gly | Thr | Val | Glu | Ile | Lys | Phe | Arg | Lys |
| | 2225 | | | | 2230 | | | | 2235 | |

Gly Val Leu Glu Pro Glu Gly Thr Val Glu Ile Lys Phe Arg Lys
    2225                2230                2235

Lys Asp Leu Val Lys Thr Ile Arg Arg Ile Asp Pro Val Cys Lys
    2240                2245                2250

Lys Leu Leu Gly Gln Leu Gly Thr Ala Gln Leu Pro Asp Lys Asp
    2255                2260                2265

Arg Lys Glu Leu Glu Ser Gln Leu Lys Ala Arg Glu Asp Leu Leu
    2270                2275                2280

Leu Pro Ile Tyr His Gln Val Ala Val Gln Phe Ala Asp Leu His
    2285                2290                2295

Asp Thr Pro Gly His Met Leu Glu Lys Gly Ile Ile Ser Asp Val
    2300                2305                2310

Leu Glu Trp Lys Thr Thr Arg Thr Tyr Phe Tyr Trp Arg Leu Arg
    2315                2320                2325

Arg Leu Leu Glu Ala Gln Val Lys Gln Glu Ile Leu Arg Ala
    2330                2335                2340

Ser Pro Glu Leu Ser His Glu His Thr Gln Ser Met Leu Arg Arg
    2345                2350                2355

Trp Phe Val Glu Thr Glu Gly Ala Val Lys Ala Tyr Leu Trp Asp
    2360                2365                2370

Ser Asn Gln Val Val Gln Trp Leu Glu Gln His Trp Ser Ala
    2375                2380                2385

Arg Asp Asn Leu Arg Ser Thr Ile Arg Glu Asn Ile Asn Tyr Leu
    2390                2395                2400

Lys Arg Asp Ser Val Leu Lys Thr Ile Gln Ser Leu Val Gln Glu
    2405                2410                2415

His Pro Glu Ala Thr Met Asp Cys Val Ala Tyr Leu Ser Gln His
    2420                2425                2430

Leu Thr Pro Ala Glu Gln Met Gln Val Val Gln Leu Leu Ser Thr
    2435                2440                2445

Thr Glu Ser Pro Ala Ser His
    2450                2455

<210> SEQ ID NO 17
<211> LENGTH: 7328
<212> TYPE: DNA
<213> ORGANISM: Rattus norvegicus

<400> SEQUENCE: 17

```
tcccttgaca ggttgtctga atggtcttgc ttctctttct gacttgcctg gttttctcct    60
gcctgaccat ttcctggtta aaatctgggg ggaagatgac agactcgaag ccgctcagca   120
acagtaaggt ggatgcaagc ctccttttcga gcaaggagga gtccttttca gcctcggacc   180
agtcagagga gcatggcgac tgcagctgtc cgttgacaac tcctgaccag gaggagctgg   240
cctcccacgg aggtcctgta gatgccagtc agcagaggaa ctctgtgcca agctcacacc   300
agaagcctcc gaggaaccca ctatcttcca atgacacctg ttcctcccca gaactccaaa   360
ccaacggggt agcagcccct ggctcagagg ttccagaagc aacgggttg cctttcccag   420
ccaggcctca gacccagaga acgggatccc ccactaggga ggacaagaag caggcacaca   480
tcaagaggca gctgatgacc agctttatcc tgggctccct cgatgacaac tcctctgacg   540
aggaccctag tgctagctcc ttccagacct cctctcggaa gggcagcagg gctagcctgg   600
gcaccctgtc ccaggaggct gcattgaaca cagctgatcc tgagtctcac acacctacta   660
```

-continued

```
tgaggcccag catgtctgga ctccatctgg tgaagagagg ccgtgaacac aagaaactgg    720
acctgcacag agatttcact gtagcttccc cagccgaatt tgtcaccgc tttggaggca     780
acagggttat cgagacggtg ctcatcgcca ataatggtat cgctgcggtc aagtgtatgc    840
gctccatccg ccgctgggcc tatgagatgt tccgtaatga acgcgccatc cggtttgtgg    900
ttatggtgac acccgaggat cttaaggcca acgcagagta catcaagatg gcggaccagt    960
acgttccggt cccaggagga cccaataata acaactacgc caacgttgag ctgatcatag   1020
acattgccaa gagaatccct gtgcaggccg tgtgggctgg ctgggccac gcttcggaaa    1080
accccaaact tccagagcta ctgtgcaagc acgagattgc tttcctaggt cccccgagtg   1140
aggccatgtg ggccctggga gacaagatct cctccaccat tgtagcccag acattgcaga   1200
tcccaactct accctggagc ggaagcggtc tcacagtgga gtggacggag gacagccagc   1260
atcagggcaa atgcatcagc gtcccggaag acgtttatga acaaggctgt gtgagagatg   1320
tggacgaagg cttgcaggca gcagaaaaag taggatttcc tctgatgatc aaagcctctg   1380
aaggtggagg agggaaagga atccgcaggg ctgagagtgc agaggacttc ccgatgcttt   1440
tcagacaggt gcagagtgag atcccgggct cgcccatctt tctcatgaag ctggcccaga   1500
atgctcggca cttggaggtc caggtcttgg cagatcagta tgggaacgca gtgtccctgt   1560
ttggacgaga ctgctccatc cagaggcggc accagaagat cattgaggag ctccggcca   1620
ccatcgctgc tccggctgtg tttgagttca tggaacagtg tgccgtcctc ctggccaaga   1680
ctgtgggtta tgtgagcgcg ggaaccgtgg agtacctata cagccaggat ggcagctttc   1740
acttcttgga gctgaaccca cgcctgcagg tggaacatcc ctgcactgaa atgatcgcag   1800
aggacatacg gcttctgtac ggagagtccc cctggggagt gaccccgtt tcttttgaga    1860
ccccctttgag ccctcccatt gcccgaggcc atgtcattgc agccaggatc accagcgaaa   1920
acccagacga gggcttttaag ccaagctcag ggacagtgca ggagctgaac ttccgcagca    1980
acaagaacgt gtggggttac ttcagcgtgg ccgctgctgg gggcttgcac gagtttgccg   2040
attcccagtt tgggcactgc ttctcctggg gcgagaaccg tgaagaggct atttcgaaca   2100
tggtggtggc tttgaaagaa ctgtctatcc ggggtgactt ccggaccacc gtggaatatc   2160
tcgtcaacct tctggagacg gagagcttcc agaacaatga tatcgacacg gggtggctgg   2220
accacctcat cgctcagcgg gtgcaggcag agaagccgga catcatgctc ggggtggtgt   2280
gtggggcctt gaacgtggca gacgcgatgt tcagaacctg tatgacgaa ttcctgcatt     2340
ccttggaaag gggtcaggtc ctcccggctg attctctgct gaacatcgtg gacgttgagt   2400
tgatttacgg aggcatcaaa tatgttctca aggtggcccg gcagtccctg accatgtttg   2460
tcctcatcat gaatggttgc cacatcgaga tcgatgccca ccggctgaac gatggggcc    2520
tgctcctgtc ctacaatggt agcagttaca ctacatacat gaaggaagag gtggacagtt   2580
accgatcac tatcggcaat aagacatgcg tgtttgaaaa ggaaaacgac cccaccgtcc    2640
tgagatcccc ctcggctggg aagctgatgc agtacacggt ggaggatggc cagcacgtgg   2700
aagtcgggag cagctatgct gagatggagg tgatgaagat gatcatgacc ctgaacgtgc   2760
aagagagcgg ccgggtgaag tacatcaagc gaccagggc ggtattggag ctggctgcg    2820
tggtggcaaa gctagaactc gatgacccctt caaaagtgca cgcggcacag ccgttcacag   2880
gggagctccc cgcccagcag actctgccca tcctcgggga gaggctgcat caggtgttcc   2940
acagcgtctt ggaaaatctg accaatgtca tgaatggcta ctgcctgccc gagcccttct   3000
tcagcatgaa gctgaaggac tgggtggaga agctcatgat gactctccgg catccctccc   3060
```

-continued

```
tacctctgct ggagctgcag gagatcatga ccagcgtggc aggccgcatc ccggttccgg    3120
tggagaaggc agtccgcagg gtgatggcgc agtacgccag caacatcact tcggtgctct    3180
gccagttccc cagccagcag atagccacca tcctggactg ccacgccgcc accctgcagc    3240
gtaaggtgga ccgagaggcc ttcttcatga acacacagag catcgtgcag ctgatccaga    3300
gataccgcag tgggacccgt ggctacatga aggctgtggt gctagacctc ctgaggagat    3360
atctgaacgt ggagcatcat ttccagcaag cccactatga caagtgtgtg atcaacctga    3420
gggagcagtt caagccggac atgactcggg tgctggactg catcttctca cactcacaag    3480
tggccaagaa gaaccagctg gtgaccatgt tgatagatga gctgtgtggc ccagacccca    3540
ccctgtcaga gagctgacc tccatcctca aggaactcac gcagttgagc aggagtgagc    3600
actgcaaggt ggccctcaga gccaggcagg tcctgattgc ctctcacctc ccctcctacg    3660
agctgcggca caaccaggtg gagtccatct tcctgtcagc cattgacatg tatggccacc    3720
agttctgccc ggaaaacctc aagaaactaa tactttcgga aacgaccata ttcgatgtcc    3780
tgcccacttt cttctatcac gctaacaagg tcgtctgtat ggcgtccctg gaggtttatg    3840
tgaggagagg ttacatcgcc tacgagttaa acagcctaca gcaccgggag ctccctgacg    3900
gcacctgcgt ggtggagttc cagttcatgc tgccgtcttc ccaccccaac cggatggcca    3960
tgcccatcaa tgtctctgac cctgacctgc tgagacacag taaggaactc ttcatggaca    4020
gtggcttctc cccactgtgc cagcggatgg gggccatggt ggccttcagg agatttgagg    4080
agttcaccag gaacttcgat gaagtcatct cctgctttgc caacgtgcct acagacactc    4140
ctctcttcag taaggcgtgc acttccctct actcagagga ggacagcaag agccttcaag    4200
aggagcccat ccacatcctg aatgtggcca tccagtgcgc cgaccacatg gaggacgaga    4260
gactggtgcc ggttttccgt gcctttgtac agtccaagaa acacatcctt gtggattacg    4320
gactgcgaag aatcacattc cttatcgccc aagagagaga atttcccaag ttcttcacgt    4380
tcagagcgag agatgagttt gcagaagacc ggatttaccg ccacttggag ccggccctgg    4440
ccttccagct ggagctgagc cggatgcgca actttgacct gacggccgtg ccctgtgcca    4500
accataagat gcatctttac ctgggagccg ccaaggtgaa ggaagggctg gaggtgactg    4560
accacaggtt cttcatccga gccatcataa ggcactcaga cctgatcacc aaggaagcct    4620
ccttcgagta cctgcagaat gaaggggagc ggctgctgct ggaagccatg gatgagctgg    4680
aggtggcgtt caacaacacc agcgtgcgca ctgactgcaa ccacatcttc ctcaacttcg    4740
tgcccacggt catcatggac ccactcaaga tcgaggagtc ggtgcgtgcc atggtcatgc    4800 gttacgcag tcggctgtgg aagctccgtg tgctgcaggc agaagttaag atcaacatcc    4860
gtcagacgac ctcggactgc gccgtcccca ttcgcctctt catcaccaac gagtccggct    4920
actacctgga catcagcctc tacaaagaag tgaccgactc cagatccgga acatcatgt    4980 ttcattcctt cggcaacaaa caagggagcc tgcacgggat gctgatcaac acgccctacg    5040
tcaccaagga tctgctccaa gccaagcgat tccaggcgca gtccctgggg accacctatg    5100
tgtacgactt cccagagatg ttcaggcagg ctctctttaa attgtggggc tccccagaga    5160
agtaccccaa agatatcctg acatacacag agctggtgtt ggactccag ggccagctgg    5220 tggagatgaa ccggcttcct ggttgtaacg aggtgggcat ggtggttttc aaaatgaggt    5280
tcaagacccc ggagtatcca gaaggccggg acactatcgt catcggcaac gacattacct    5340
tccaaatcgg ctctttcggc ataggagagg acttcctgta tctacgggca tcggagatgg    5400
```

```
cccggacaga gggcatcccc caaatctatc tggcagccaa cagcggggcc cgtatgggcc    5460
tgtccgagga gatcaagcag atattccaag tggcatgggt ggaccctgag gatccctaca    5520
aaggatttag atacctgtac ctgacgcccc aagactacac ccagatcagc tcccagaact    5580
ccgtgcactg caaacacatc gaggacgaag gcgagtccag gtatgtcatc gttgatgtca    5640
tcggaaggga cagcagcctg ggtgtggaga acctgcgggg ctcgggcatg attgcaggag    5700
aggcttctct ggcttacgaa aaaaatgtca ccatcagcat ggtgacctgc cgcgccatcg    5760
gaatcggggc ttacctggtg aggctgggcc agcgggtgat ccaggtggaa aactcccaca    5820
tcatcctcac gggagccggt gctctcaaca aggtcctggg aagagaggtc tacacatcca    5880
acaaccaact gggcggtgtg cagatcatgc acaccaacgg ggtctcccac gtcacggtgc    5940
cagatgactt cgagggggtc tgcaccattc tggaatggct gtcatatata ccaaaggaca    6000
atcaaagccc agtccccatc atcactcctt ctgaccccat cgacagggaa attgaattca    6060
ccccaaccaa agctccctat gaccccaggt ggctgcttgc agggaggcct cacccaactc    6120
tgaaggggac ctggcagagt ggattcttcg accatggcag tttcaaggaa atcatggcac    6180
cctgggccca gaccgtggtg actggacgag caaggctggg gggcatccct gtaggggtga    6240
ttgccgtgga gactcggtct gtggaggtgg ctgtccctgc tgaccctgcc aacttggatt    6300
ctgaggccaa gatcatccag caggcaggcc aggtgtggtt cccggactct gccttcaaga    6360
cggctcaggt catcagggac ttcaaccagg agcatctgcc tctcatgatc tttgccaact    6420
ggagaggctt ctcgggtggc atgaaagaca tgtacgagca gatgctgaag tttgcgcct    6480
acatcgtgga cagtctccgt ctgttcaagc agccagttct catctatatc cctcctggtg    6540
ccgaactccg aggggggcgcc tgggttgtcc tcgactccag catcaacccc ctgtgcatag    6600
agatgtacgc agacaaagag agcagggggg gtgtcctgga gcccgagggc actgtggaga    6660
ttaagttccg gaagaaagat ttggtgaaga ccataaggag gattgaccca gtgtgcaaga    6720
aactcctggg gcagctgggg acagcccagc tccctgacaa ggaccggaaa gagctggaga    6780
gccagctgaa ggcccgggag gacctgctgc tccccatcta ccaccaggtg gcagtgcagt    6840
tcgccgacct gcatgacacg ccgggccaca tgctggagaa gggaatcatt tctgatgtgc    6900
tggagtggaa gaccacacgt acctacttct actggaggct gcgccggctg ctgctggagg    6960
cacaggtgaa gcaggagatt ctgcgagcca gccctgagct gagccatgag cacacgcagt    7020
ccatgctgcg acgctggttt gtggagaccg agggcgccgt caaggcctac ctgtgggaca    7080
gcaaccaggt ggtagtccag tggctggaac agcactggtc agcagggac aacctgcgtt    7140
ccactatccg agagaacatc aattatctga agcgggactc tgtcctcaag accatccaaa    7200
gcctagttca agaacaccca gaggcgacca tggactgtgt ggcataccctg agccagcacc    7260
tcacgcccgc tgagcagatg caggtggttc agctgctgtc taccacggag agcccagctt    7320
cccactga                                                            7328
```

<210> SEQ ID NO 18
<211> LENGTH: 10
<212> TYPE: PRT
<213> ORGANISM: Artificial
<220> FEATURE:
<223> OTHER INFORMATION: Synthesized peptide

<400> SEQUENCE: 18

Glu Gln Lys Leu Ile Ser Glu Glu Asp Leu
1               5                   10

```
<210> SEQ ID NO 19
<211> LENGTH: 23
<212> TYPE: DNA
<213> ORGANISM: Artificial
<220> FEATURE:
<223> OTHER INFORMATION: Synthesized primer

<400> SEQUENCE: 19
tcctgtattg gcgtctgcgc cgc                                        23

<210> SEQ ID NO 20
<211> LENGTH: 27
<212> TYPE: DNA
<213> ORGANISM: Artificial
<220> FEATURE:
<223> OTHER INFORMATION: Synthesized primer

<400> SEQUENCE: 20
cgaattcacg gtggaggccg ggctgtc                                    27

<210> SEQ ID NO 21
<211> LENGTH: 64
<212> TYPE: DNA
<213> ORGANISM: Artificial
<220> FEATURE:
<223> OTHER INFORMATION: Synthesized primer

<400> SEQUENCE: 21
ggccgaagcc ggtaccgcca tgggcaaaga agacaagaag caggcaaaca tcaagaggca  60
gctg                                                              64

<210> SEQ ID NO 22
<211> LENGTH: 21
<212> TYPE: DNA
<213> ORGANISM: Artificial
<220> FEATURE:
<223> OTHER INFORMATION: Synthesized primer

<400> SEQUENCE: 22
cgtctgggcg acaacggtgg a                                          21

<210> SEQ ID NO 23
<211> LENGTH: 23
<212> TYPE: DNA
<213> ORGANISM: Artificial
<220> FEATURE:
<223> OTHER INFORMATION: Synthesized primer

<400> SEQUENCE: 23
tcctgtattg gcgtctgcgc cgc                                        23

<210> SEQ ID NO 24
<211> LENGTH: 75
<212> TYPE: DNA
<213> ORGANISM: Artificial
<220> FEATURE:
<223> OTHER INFORMATION: Synthesized primer

<400> SEQUENCE: 24
ggccgaagcc accggtgccc agatcctctt ctgagatgag ttttgttcg cccgtagaat  60 cgagaccgag gagag                                                 75

<210> SEQ ID NO 25
<211> LENGTH: 26
```

<212> TYPE: DNA
<213> ORGANISM: Artificial
<220> FEATURE:
<223> OTHER INFORMATION: Synthesized Primer

<400> SEQUENCE: 25
cgatcccccc caaagcgtgt gacaaa                                          26

<210> SEQ ID NO 26
<211> LENGTH: 23
<212> TYPE: DNA
<213> ORGANISM: Artificial
<220> FEATURE:
<223> OTHER INFORMATION: Synthesized primer

<400> SEQUENCE: 26
ccacaccgcc tgcacgggga ttc                                             23

<210> SEQ ID NO 27
<211> LENGTH: 27
<212> TYPE: DNA
<213> ORGANISM: Artificial
<220> FEATURE:
<223> OTHER INFORMATION: Synthesized primer

<400> SEQUENCE: 27
gaggtattcc actgtccctg cactcac                                         27

<210> SEQ ID NO 28
<211> LENGTH: 29
<212> TYPE: DNA
<213> ORGANISM: Artificial
<220> FEATURE:
<223> OTHER INFORMATION: Synthesized primer

<400> SEQUENCE: 28
cgatgtggca gccattcatg atgagaacg                                       29

<210> SEQ ID NO 29
<211> LENGTH: 30
<212> TYPE: DNA
<213> ORGANISM: Artificial
<220> FEATURE:
<223> OTHER INFORMATION: Synthesized primer

<400> SEQUENCE: 29
tgttgatgaa gaagacctct cgatcagcct                                      30

<210> SEQ ID NO 30
<211> LENGTH: 23
<212> TYPE: DNA
<213> ORGANISM: Artificial
<220> FEATURE:
<223> OTHER INFORMATION: Synthesized primer

<400> SEQUENCE: 30
gttctcgggg cagaactggt ggc                                             23

<210> SEQ ID NO 31
<211> LENGTH: 28
<212> TYPE: DNA
<213> ORGANISM: Artificial
<220> FEATURE:
<223> OTHER INFORMATION: Synthesized primer

<400> SEQUENCE: 31

-continued

```
ccttcacctt ggcagcaccc aggtaaag                                    28

<210> SEQ ID NO 32
<211> LENGTH: 27
<212> TYPE: DNA
<213> ORGANISM: Artificial
<220> FEATURE:
<223> OTHER INFORMATION: Synthesized primer

<400> SEQUENCE: 32
gggaagtcat agatgtaggt ggttccc                                     27

<210> SEQ ID NO 33
<211> LENGTH: 4
<212> TYPE: PRT
<213> ORGANISM: Artificial
<220> FEATURE:
<223> OTHER INFORMATION: Core sequence of commercially available FLAG
      peptide

<400> SEQUENCE: 33

Asp Tyr Lys Asp
1

<210> SEQ ID NO 34
<211> LENGTH: 8
<212> TYPE: PRT
<213> ORGANISM: Artificial
<220> FEATURE:
<223> OTHER INFORMATION: Commerically available FLAG sequence

<400> SEQUENCE: 34

Asp Tyr Lys Asp Asp Asp Asp Lys
1               5
```